United States Patent
Thompson et al.

(10) Patent No.: US 6,569,851 B1
(45) Date of Patent: May 27, 2003

(54) CYCLOALKYL, LACTAM, LACTONE AND RELATED COMPOUNDS, PHARMACEUTICAL COMPOSITIONS COMPRISING SAME, AND METHODS FOR INHIBITING β-AMYLOID PEPTIDE RELEASE AND/OR ITS SYNTHESIS BY USE OF SUCH COMPOUNDS

(75) Inventors: Richard C. Thompson, Frankfort, IN (US); Stephen Wilkie, Indianapolis, IN (US); Douglas R. Stack, Fishers, IN (US); Eldon E. VanMeter, Greenwood, IN (US); Qing Shi, Carmel, IN (US); Thomas C. Britton, Carmel, IN (US); James E. Audia, Indianapolis, IN (US); Jon K. Reel, Carmel, IN (US); Thomas E. Mabry, Indianapolis, IN (US); Bruce A. Dressman, Indianapolis, IN (US); Cynthia L. Cwi, Indianapolis, IN (US); Steven S. Henry, New Palestine, IN (US); Stacey L. McDaniel, Martinsville, IN (US); Russell D. Stucky, Indianapolis, IN (US); Warren J. Porter, Indianapolis, IN (US)

(73) Assignees: Elan Pharmaceutials, Inc., South San Francisco, CA (US); Eli Lilly & Company, Indianapolis, IN (US)

( * ) Notice: Subject to any disclaimer, the term of this patent is extended or adjusted under 35 U.S.C. 154(b) by 0 days.

(21) Appl. No.: 09/338,191

(22) Filed: Jun. 22, 1999

Related U.S. Application Data

(60) Provisional application No. 60/160,067, filed on Jun. 22, 1998.

(51) Int. Cl.[7] ............... C07D 243/24; C07D 223/18; C07D 223/16; C07D 243/14; A61K 31/55
(52) U.S. Cl. ............... 514/219; 514/220; 514/221; 540/509; 540/517; 540/518; 540/558; 540/559; 540/560; 540/561
(58) Field of Search ............... 540/509, 558, 540/559, 560, 561, 517, 518; 514/221, 219, 220

(56) References Cited

U.S. PATENT DOCUMENTS

| | | | |
|---|---|---|---|
| 3,598,859 A | 8/1971 | Yates et al. | 260/471 |
| 3,657,341 A | 4/1972 | Thorne | 260/558 |
| 4,080,449 A | 3/1978 | Croisier et al. | 424/244 |
| 4,410,520 A | 10/1983 | Watthey | 424/244 |
| 4,473,575 A | 9/1984 | Watthey | 424/263 |
| 4,477,464 A | 10/1984 | Slade et al. | 424/275 |
| 4,666,829 A | 5/1987 | Glenner et al. | 435/6 |
| 4,977,168 A | 12/1990 | Bernat et al. | 514/330 |
| 5,015,639 A | 5/1991 | Berger et al. | 514/213 |
| 5,206,235 A | 4/1993 | Fisher et al. | 514/213 |
| 5,238,932 A | 8/1993 | Flynn et al. | 514/214 |
| 5,247,080 A | 9/1993 | Berger et al. | 540/523 |
| 5,264,433 A | 11/1993 | Sato et al. | 514/221 |
| 5,283,241 A | 2/1994 | Bochis et al. | 514/183 |
| 5,284,841 A | 2/1994 | Chu et al. | 514/183 |
| 5,324,726 A | 6/1994 | Bock et al. | 514/221 |
| 5,360,802 A | 11/1994 | Chambers et al. | 514/221 |
| 5,382,664 A | 1/1995 | Sato et al. | 540/509 |
| 5,420,271 A | 5/1995 | Warshawsky et al. | 540/521 |
| 5,478,857 A | 12/1995 | Clemens et al. | 514/381 |
| 5,486,541 A | 1/1996 | Sterling et al. | 514/657 |
| 5,502,048 A | 3/1996 | Chapdelaire et al. | 514/213 |
| 5,519,061 A | 5/1996 | Youdim et al. | 514/647 |
| 5,532,415 A | 7/1996 | Youdim et al. | 564/308 |
| 5,541,182 A | 7/1996 | Satoh et al. | 514/221 |
| 5,556,969 A | 9/1996 | Chambers et al. | 540/509 |
| 5,618,812 A | 4/1997 | Castro Pineiro et al. | 514/221 |
| 5,631,251 A * | 5/1997 | Butcher et al. | 514/221 |
| 5,633,251 A | 5/1997 | Claremon et al. | 514/221 |
| 5,656,626 A | 8/1997 | Chapdelaine et al. | 514/213 |

(List continued on next page.)

FOREIGN PATENT DOCUMENTS

| | | |
|---|---|---|
| EP | 0 061 187 | 9/1982 |
| EP | 0 167 919 | 1/1986 |
| EP | 0 284 256 | 9/1988 |
| EP | 0 349 949 | 1/1990 |
| EP | 0 376 849 | 7/1990 |
| EP | 0 434 360 | 6/1991 |
| EP | 0 434 364 | 6/1991 |
| EP | 0 434 369 | 6/1991 |
| EP | 0 490 590 | 6/1992 |
| EP | 0 514 133 | 11/1992 |
| EP | 514 133 | * 12/1992 |
| EP | 0 523 845 | 1/1993 |

(List continued on next page.)

OTHER PUBLICATIONS

Shinozaki et al. (WO 98/25911). Abstract.*
Butcher et al.(WO 96/40146). Abstract.*
Chambers et al. (US 5,556,969). Abstract.*
Donati et al. (WO 95/03285). Abstract.*
Tranquillini et al. (WO 94/25445). Abstract.*
Hagishita et al. (JP 06211812). Abstract.*
Chambers et al. (US 5,360,802). Abstract.*
Satoh et al. (WO 94/00438). Abstract.*
JP 05247033. Abstract.*
Satoh et al. (WO 92/11246). Abstract.*
Sato et al. (WO 92/01683). Abstract.*

(List continued on next page.)

Primary Examiner—Bruck Kifle
(74) Attorney, Agent, or Firm—Burns, Doane, Swecker & Mathis LLP

(57) ABSTRACT

Disclosed are compounds which inhibit β-amyloid peptide release and/or its synthesis, and, accordingly, have utility in treating Alzheimer's disease. Also disclosed are pharmaceutical compositions that include a compound which inhibits β-amyloid peptide release and/or its synthesis as well as methods for treating Alzheimer's disease both prophylactically and therapeutically with such pharmaceutical compositions.

76 Claims, No Drawings

U.S. PATENT DOCUMENTS

| | | | |
|---|---|---|---|
| 5,658,901 A | 8/1997 | Claremon et al. | 514/221 |
| 5,672,598 A | 9/1997 | De et al. | 514/212 |
| 5,681,833 A | 10/1997 | Castro Pineiro et al. | 514/215 |
| 5,686,449 A | 11/1997 | Tranquillini et al. | 514/221 |
| 5,712,397 A | 1/1998 | Esser et al. | 546/90 |
| 5,716,953 A | 2/1998 | Donati et al. | 514/221 |
| 5,770,573 A | 6/1998 | Arrhenius et al. | 514/18 |
| 6,239,131 B1 | 5/2001 | Sinozaki et al. | 514/221 |

FOREIGN PATENT DOCUMENTS

| | | |
|---|---|---|
| EP | 0 549 039 | 6/1993 |
| EP | 0 591 529 | 4/1994 |
| EP | 0 647 632 | 4/1995 |
| EP | 0 652 009 | 8/1995 |
| EP | 0 667 344 | 8/1995 |
| EP | 0 677 517 | 10/1995 |
| EP | 0 732 399 | 9/1996 |
| EP | 0 778 266 | 11/1997 |
| EP | 0 945 445 | 9/1999 |
| GB | 1 519 495 | 7/1978 |
| GB | 1 573 931 | 8/1980 |
| GB | 2 272 439 | 5/1994 |
| GB | 2 290 788 | 1/1996 |
| JP | 05247033 | 9/1993 |
| JP | 06145148 | 5/1994 |
| JP | 04210967 | 8/1994 |
| JP | 06211812 | 8/1994 |
| JP | 07304770 | 11/1995 |
| JP | 10072444 | 3/1998 |
| WO | 92/01683 | 2/1992 |
| WO | WO 92/01683 | 2/1992 |
| WO | WO 92/11246 | 9/1992 |
| WO | 92/16524 | 10/1992 |
| WO | 93/19052 | 9/1993 |
| WO | 93/19063 | 9/1993 |
| WO | 94/04531 | 3/1994 |
| WO | 94/05693 | 3/1994 |
| WO | 94/07486 | 4/1994 |
| WO | 94/10569 | 5/1994 |
| WO | WO 94/00438 | 6/1994 |
| WO | WO 94/25445 | 11/1994 |
| WO | WO 95/03285 | 2/1995 |
| WO | 95/03289 | 2/1995 |
| WO | 95/03290 | 2/1995 |
| WO | 95/09838 | 4/1995 |
| WO | 95/14671 | 6/1995 |
| WO | 95/21840 | 8/1995 |
| WO | 95/23810 | 9/1995 |
| WO | 95/25118 | 9/1995 |
| WO | 95/32191 | 11/1995 |
| WO | 96/05839 | 2/1996 |
| WO | 96/16981 | 6/1996 |
| WO | 96/20725 | 7/1996 |
| WO | 96/22966 | 8/1996 |
| WO | WO 96/40146 | 12/1996 |
| WO | 96/40146 | 12/1996 |
| WO | 96/40653 | 12/1996 |
| WO | 96/40654 | 12/1996 |
| WO | 96/40655 | 12/1996 |
| WO | 96/40656 | 12/1996 |
| WO | WO 97/16410 | 5/1997 |
| WO | 97/30072 | 8/1997 |
| WO | 97/38705 | 10/1997 |
| WO | 98/00405 | 1/1998 |
| WO | WO 98/22433 | 5/1998 |
| WO | WO 98/22494 | 5/1998 |
| WO | WO 98/25911 | 6/1998 |
| WO | 98/25930 | 6/1998 |
| WO | 98/28268 | 7/1998 |
| WO | 98/38177 | 9/1998 |

OTHER PUBLICATIONS

Aquino, et al. "Discovery of 1,5–Benzodiazepines with Peripheral Cholecystokinin (CCK–A) Receptor Agonist Activity. 1. Optimization of the Agonist Trigger." *J. Med. Chem.* 39: 562–569 (1996).

Bock, et al. "Selective Non–Peptide Ligands for an Accommodating Peptide Receptor. Imidazobenzodiazepines as Potent Cholecystokinin Type B Receptor Antagonists." *Bioorg. and Med. Chem. Lets.* 2(9):987–998 (1994).

Bock, et al. "Synthesis and Resolution of 3–Amino–1, 3–dihydro–5–phenyl–2H–1,4–benzodiazepin–2–ones." *J. Org. Chem.* 52:3232–3239 (1987).

Bock, et al. "An Expedient Synthesis of 3–Amino–1, 3–Dihydro–5–Phenyl–2H–1,4–Benzodiazepin–2–one." *Tet. Lets.* 28(9): 939–942 (1987).

Chambers, et al. L–708,474: the C5–Cyclohexyl Analogue of L–365,260, A Selective High Affinity Ligand for the CCKB/Gastrin Receptor. *Bioorg. and Med. Chem. Letts.* 3(10):1919–1924 (1993).

Chartier–Harlin, et al. "Early–onset Alzheimer's disease caused by mutations at codon 717 of the β–Amyloid precursor protein gene." *Nature.* 353: 844–846 (1991).

Citron, et al. "Mutation of the β–amyloid precursor protein in familial Alzheimer's disease increases β–amyloid protein production." *Nature* 360:672–674 (1992).

Cordell. "B–Amyloid Formation as a Potential Therapeutic Target for Alzheimer's Disease." *Ann. Rev. Pharmacol. Toxicol.* 34:69–89 (1994).

Evans, et al. "Methods for Drug Discovery: Development of Potent, Selective Orally Effective Cholecystokinin Antagonists." *J. Med. Chem.* 31:2235–2246 (1988).

Evans, et al. "Molecular Mimicry and the Design of Peptidomimetrics." *Molecular Mimicry in Health and Disease.* (A. Lernmark, et al., eds.) Elsevier Science Publishers B.v. (Biomedical Division) (1988) pp. 23–34.

Finizia, et al. "Synthesis and Evaluation of Novel 1,5–Benzodiazepines as potent and selective CCK–B Ligands, Effect of the Substitution of the N–5 Phenyl with Alkyl Groups." *Bioorg. & Medicinal Chemistry Letters.* 6(24):2957–2962 (1996).

Glenner, et al. "Alzheimer's disease: Initial Report of the Purification and Characterization of a Novel Cerebrovascular Amyloid Protein." *Biochem. Biophys. Res. Commun.* 120(3): 885–890 (1984).

Goate, et al. "Segregation of a missense mutation in the amyloid precursor protein gene with familial Alzheimer's disease." *Nature.* 349: 704–706 (1991).

Hirst, et al. "Discovery of 1,5–Benzodiazepines with Peripheral Cholecystokinin (CCK–A) Receptor Agonists Activity (II): Optimization of the C3 Amino Substituent." *J. Med. Chem.* 39:5236–5245 (1996).

Hofmann, et al. "Interactions of Benzodiazepine Derivatives with Annexins." *J. Biol. Chem.* 273(5):2885–2894 (1998).

Johnson–Wood, et al. "Amyloid precursor protein processing and $A\beta_{42}$ deposition in a transgenic mouse model of Alzheimer's disease." *PNAS USA.* 94: 1550–1555 (1997).

Ksander, G.M., et al. "Dual Angiotensin Converting Enzyme/Thromboxane Synthase Inhibitors." *J. Med. Chem.* 37: 1823–1832 (1994).

Lowe, et al. "A Water Soluble Benzazepine Cholecystokinin–B–Receptor Antagonist." *Bioorg. and Med. Chem. Lets.* 5(17): 1993–1936 (1995).

Lowe, et al. "5–Phenyl–3–ureidobenzzazepin–2–ones as Cholecystokinin–B Receptor Antagonists." *J. Med. Chem.* 37: 3789–3811 (1994).

Mullan, et al. "A pathogenic mutation for probable Alzheimer's disease in the APP gene at the N–terminus of β–amyloid." *Nature Genet.* 1: 345–347 (1992).

Murrell, et al. "A Mutation in the Amyloid Precursor Protein Associate with Hereditary Alzheimer's Disease." *Science.* 254: 97–99 (1991).

Papadopoulos, et al. Anodic Oxidation of N–Acyl and N–Alkoxylcarbonyl Dipeptide Esters as a Key Steop for the Formation of Chiral Heterocyclic Synthetic Building Blocks. *Tetrahedron* 47(4/5):563–572 (1991).

Patel, et al. "Biological Preperties of the Benzodiazepine Amidine Derivative L–740,093, a Choleycystokinin–B/Gastrin Receptor Antagonist with High Affinity in vitro and High Potency in vivo." *Molecular Pharmacology.* 46:943–948 (1994).

Rittle, et al. "A New Amine Resolution Method and its Application to 3–Aminobenzodiazepines." *Tet. Lets.* 28(5):521–522 (1987).

Satoh, et al. "New 1,4–Benzodiazepine–2–one Derivatives as Gastrin/Cholecystokinin–B Antagonists." *Chem. Pharm. Bull.* 43(12): 2159–2167 (1995).

Selkoe, et al. "Amyloid Protein and Alzheimer's Disease." *Scientific American.* 68–78 (1991).

Selkoe, et al. "The Molecular Pathology of Alzheimer's Disease." *Neuron.* 6:487–498 (1991).

Semple, et al. "Design, Synthesis, and Evolution of a Novel, Selective, and Orally Bioavailable Class of Thrombin Inhibitors: P1–Argininal Derivatives Incorporating P3–P4 Lactam Sulfoamide Moieties." *J. Med. Chem.* 39: 4531–4536 (1996).

Semple, et al. "A Facile Large Scale Synthesis of Optically Active 3–Amino–5–(2–Pyridyl)–1, 4–Benzodiazepin–2–One Derivatives." *Synthetic Communications.* 26(4): 721–727 (1996).

Seubert, et al. "Isolation and quantification of soluble Alzheimer's peptide from biological fluids." *Nature.* 359: 325–327 (1992).

Sherrill, et al. "An Improved Synthesis and Resolution of 3–Amino–1,3 dihydro–5–phenyl–2H–1, 4–benzodiazepinn–2–ones." *J. Org. Chem.* 60:730–734 (1995).

Showell, et al. "High Affinity and Potent, Water–Soluble 5–Amino–1,4–Benzodiazepine CCKB/Gastrin Receptor Antagonists Containing a Cationic Solubilizing Group." *J. Med. Chem.* 37:719–721 (1994).

Smith, et al. "β–APP Processing as a Therapeutic Target for Alzheimer's Disease." *Current Pharmaceutical Design.* 3:439–445 (1997).

Van Niel, et al. "CCKB Selective Receptor Ligands: Novel 1,3,5–Trisubstituted Benzazepin–2–ones." *Bioorganic & Medicinal Chemistry Letters.* 5(13):1421–1426 (1995).

Varnavas, et al. "Synthesis of New Benzodiazepine Derivatives as Potential Cholecystokinin Antagonists." *Il Farmaco.* 46(2):391–401 (1991).

* cited by examiner

CYCLOALKYL, LACTAM, LACTONE AND RELATED COMPOUNDS, PHARMACEUTICAL COMPOSITIONS COMPRISING SAME, AND METHODS FOR INHIBITING β-AMYLOID PEPTIDE RELEASE AND/OR ITS SYNTHESIS BY USE OF SUCH COMPOUNDS

CROSS-REFERENCE TO RELATED APPLICATIONS

This application claims the benefit of U.S. Provisional application No. 60/160,067, which was converted pursuant to 37 C.F.R. § 1.53(b) from U.S. Ser. No. 09/102,507, filed Jun. 22, 1998; the disclosure of which is incorporated herein by reference in its entirety.

BACKGROUND OF THE INVENTION

1. Field of the Invention

This invention relates to compounds which inhibit β-amyloid peptide release and/or its synthesis, and, accordingly, have utility in treating Alzheimer's disease.

2. References

The following publications, patents and patent applications are cited in this application as superscript numbers:

---

1 Glenner, et al., Biochem. Biophys. Res. Commun., 120: 885–890 (1984)
2 U.S. Pat. No. 4,666,829
3 Selkoe, Neuron, 6: 487–498 (1991)
4 Goate, et al., Nature, 349: 704–706 (1990)
5 Chartier Harlan, et al., Nature, 353: 844–846 (1989)
6 Murrell, et al., Science 254: 97–99 (1991)
7 Mullan, et al., Nature Genet., 1: 345–347 (1992)
8 Schenk, et al., International Patent Application Publication No. WO 94/10569, "Methods and Compositions for the Detection of Soluble B-Amyloid Peptide", published 11 May 1994
9 Selkoe, Scientific American, "Amyloid Protein and Alzheimer's Disease", pp. 2–8, November, 1991
10 Tetrahedron Letters, 34(48), 7685 (1993)
11 Losse, et al., Tetrahedron, 27: 1423–1434 (1971)
12 Citron, et al., Nature, 360: 672–674 (1992)
13 Hansen, et al., J. Immun. Meth., 119: 203–210 (1989)
14 U.S. Pat. No. 3,598,859
15 Ogliaruso and Wolfe, Synthesis of Lactones and Lactams, Patai, et al. Editor, J. Wiley & Sons, New York, New York, U.S.A., pp. 1085 et seq. (1993).
16 Ugi, et al., Tetrahedron, 52(35): 11657–11664 (1996)
17 Blade-Font, Tetrahedron Lett., 21: 2443 (1980).
18 Freidinger, et al., J. Org. Chem., 47: 104–109 (1982)
19 Semple, et al., J. Med. Chem., 39: 4531–4536 (1996).
20 Holladay, et al., J. Org. Chem., 56: 3900–3905 (1991).
21 Donaruma, et al., Organic Reactions, 11: 1–156 (1960)
22 Wolff, Organic Reactions 3: 307–336 (1946)
23 Krow, et al., J. Org. Chem., 61: 5574–5580 (1996)
24 Tetrahedron, 35: 2433 (1979)
25 Gracias, et al., J. Am. Chem. Soc., 117: 8047–8048 (1995)
26 Milligan, et al., J. Am. Chem. Soc., 117: 10449–10459 (1995)
27 Miller, et al., J. Am. Chem. Soc., 118: 9606–9614 (1996)
28 March, Advanced Organic Chemistry, Reaction Mechanisms and Structure, 2nd Edition, McGraw-Hill Book Company, New York, New York, U.S.A. (1977)
29 Colombo, et al., Tetrahedron Lett., 35(23): 4031–4034 (1994)
30 Rogriguez, et al., Tetrahedron, 52: 7727–1736 (1996)
31 Parsons, et al., Biochem. Biophys. Res. Comm., 117: 108–113 (1983)
32 Watthey, et al., J. Med. Chem., 28: 1511–1516 (1985)
33 Armstrong, et al., Tetrahedron Lett., 35: 3239 (1994)
34 King, et al., J. Org. Chem., 58: 3384 (1993).
35 Hu, et al., Tetrahedron Lett., 36(21): 3659–3662 (1995).
36 Wada, et al., Bull. Chem. Soc. Japan, 46: 2833–2835 (1973)
37 Gaetzi, Chem. Abs., 66: 28690m
38 Wheeler, et al., Organic Syntheses, Coll. Vol. VI, p. 840
39 J. Med. Chem., 28(12): 1886 (1985)
40 Brenner, et al., U.S. Pat. No. 2,938,029
41 Evans, et al., J. Am. Chem. Soc., 112: 4011–4030 (1990)
42 Micouin, et al., Tetrahedron, 52: 7719–7726 (1996)
43 Butcher, et al., Tetrahedron Lett., 37(37): 6685–6688 (1996)
44 M.L. Reupple, et al., J. Am. Chem. Soc., 93: 7021 et seq. (1971)
45 P.A.S. Smith, Organic Reactions, 3: 337–449 (1946)
46 K. Orito, et al., Tetrahedron, 36: 1017–1021 (1980)
47 Krimm, Chem. Ber., 91: 1057 (1958)
48 Suda, et al., J. Chem. Soc. Chem Comm., 949–950, (1994)
49 Barton, et al., J. Chem. Soc., 1764–1767 (1975)
50 Kitagawa, et al., J. Am. Chem. Soc., 117: 5169–5178 (1975)
51 Akhatar, et al., J. Org. Chem. 55: 5222–5225 (1990)
52 Nedenskov, et al., Acta Chem. Scand., 12: 1405–1410 (1958)
53 Sakakida, et al., Bull. Chem. Soc. Japan, 44: 478–480 (1971)
54 Hoffman, et al., Tet. Lett., 30: 4207–4210 (1989)
55 Vedejs, et al., Tet. Lett., 33: 3261–3264 (1992)
56 van der Steen, et al., Tetrahedron, 47: 7503–7524 (1991)
57 Hart, et al., Chem Rev., 89: 1447–1465 (1989)
58 Lowe, et al., Bioorg. Med. Chem. Lett., 4: 2877–2882 (1994)
59 McKennis, Jr., et al., J. Org. Chem., 28: 383–387 (1963)
60 Shirota, et al., J. Med. Chem., 20: 1623–1627 (1977)
61 Overberger, et al., J. Am. Chem. Soc., 85: 3431 (1963)
62 Herschmann, Helv. Chim. Acta, 32: 2537 (1949)
63 Overberger, et al., Macromolecules, 1: 1 (1968)
64 Busacca, et al., Tet. Lett., 33: 165–168 (1992)
65 Croisier, et al., U.S. Pat. No. 4,080,449
66 J.A. Robl, et al., Tetrahedron Lett., 36(10): 1593–1596 (1995)
67 Flynn, et al., J. Med. Chem., 36: 2420–2423 (1993)
68 Orito, et al., Tetrahedron, 36: 1017–1021 (1980)
69 Kawase, et al., J. Org. Chem., 54: 3394–3403 (1989)
70 Lowe, et al., J. Med. Chem., 37: 3789–3811 (1994)
71 Robl, et al., Bioorg. Med. Chem. Lett., 4: 1789–1794 (1994)
72 Skiles, et al., Bioorg. Med. Chem Lett., 3: 773–778 (1993)
73 Grunewald, et al., J. Med. Chem., 39(18): 3539 (1996)
74 Thomas, et al., J. Chem. Soc., Perkin II, 747 (1986)
75 Warshawsky, et al., Bioorg. Med. Chem. Lett., 6: 957–962 (1996)
76 Ben-Ishai, et al., Tetrahedron, 43: 439–450 (1987)
77 van Niel et al., Bioorg. Med. Chem. Lett., 5: 1421–1426 (1995)
78 Kawase, et al., J. Org. Chem., 54: 3394–3403 (1989)
79 Edwards, et al., Can. J. Chem., 49: 1648–1658 (1971)
80 Milligan, et al., J. Am. Chem. Soc., 117: 10449–10459 (1995)
81 Curran et al., Tet. Lett., 36: 191–194 (1995)
82 Slusarchyk, et al., Bioorg. Med. Chem. Lett., 5: 753–758 (1995)
83 Wyvratt, et al., Eur. Pat. Appl. 61187 (1982)
84 Cornille, et al., J. Am. Chem. Soc., 117: 909–917 (1995)
85 Kolc, Coll. Czech. Chem. Comm., 34: 630 (1969)
86 Dickerman, et al., J. Org. Chem., 14: 530 (1949)
87 Dickerman, et al., J. Org. Chem., 20: 206 (1955)
88 Dickerman, et al., J. Org. Chem., 19: 1855 (1954)
89 Hoffman, et al., J. Org. Chem., 27: 3565 (1962)
90 Wasserman, et al., J. Am. Chem. Soc., 103: 461–2 (1981)
91 Crombie, et al., Tetrahedron Lett., 27(42): 5151–5154 (1986)
92 Yokoo, et al., Bull, Chem. Soc. Jap., 29: 631 (1956)
93 Burkholder, et al., Biog. Med. Chem. Lett., 2: 231 (1993)
94 Karanewsky, U.S. Pat. No. 4,460,579
95 Kametani, et al., Heterocycles, 9: 831–840 (1978)
96 Yanganasawa, et al., J. Med. Chem., 30: 1984–1991 (1987)
97 J. Das et al., Biorg. Med. Chem. Lett., 4: 2193–2198 (1994)

---

All of the above publications, patents and patent applications are herein incorporated by reference in their entirety to the same extent as if each individual publication, patent or patent application was specifically and individually indicated to be incorporated by reference in its entirety.

3. State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (AP) or sometimes A, AP or /A4. B-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine[595]-methionine[596] to asparagine[595]-leucine[596] (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs that are capable of inhibiting β-amyloid peptide release and/or its synthesis in vivo.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition. The class of compounds having the described properties are defined by Formulas I–VI below:

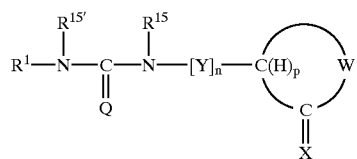

Formula I

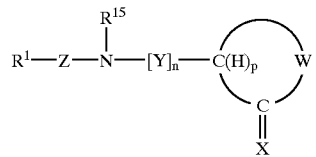

Formula II

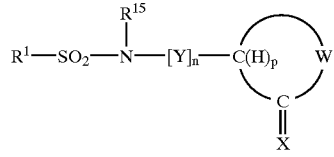

Formula III

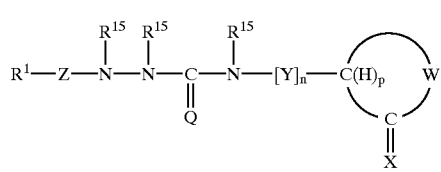

Formula IV

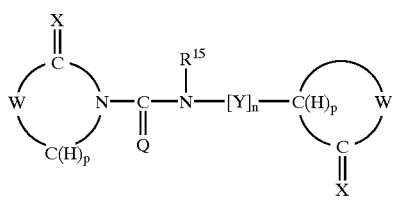

Formula V

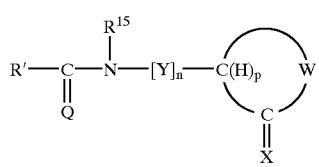

Formula VI wherein R¹ is selected from the group consisting of aryl, alkyl, alkenyl, alkynyl, cycloalkyl, cycloalkenyl, substituted alkyl, substituted alkenyl, substituted alkynyl, substituted cycloalkyl, substituted cycloalkenyl, aryl, heteroaryl and heterocyclic;

R' is selected from the group consisting of aryl, cycloalkyl, substituted cycloalkyl, cycloalkenyl, substituted cycloalkenyl, heterocyclic, heteroaryl, heterocyclooxy, —CH₃, —CH=CH₂, —CH=CHR¹, —CH=CR¹R¹, —CR¹=CH₂, —CR¹=CHR¹, —CR¹=CR¹R¹, —C≡CH and —C≡CR¹; with the proviso that when R' is heteroaryl or heterocyclic, there is no N in R' at a position beta to the C=Q group;

Q is S or O;

R¹⁵ is selected from the group consisting of hydrogen, alkyl, substituted alkyl, aryl, heterocyclic and heteroaryl;

R¹⁵' is selected from the group consisting of hydrogen, hydroxyl, alkyl, substituted alkyl, aryl, heterocyclic and heteroaryl;

W, together with —C(H)ₚC(=X)—, forms a cycloalkyl, cycloalkenyl, heterocyclic, substituted cycloalkyl, or substituted cycloalkenyl group wherein each of said cycloalkyl, cycloalkenyl, heterocyclic, substituted cycloalkyl or substituted cycloalkenyl group is optionally fused to form a bi- or multi-fused ring system (preferably no more than 5 fused rings) with one or more ring structures selected from the group consisting of cycloalkyl, cycloalkenyl, heterocyclic, aryl and heteroaryl group which, in turn, each of such ring structures are optionally substituted with 1 to 4 substituents selected from the group consisting of hydroxyl, keto, thioketo, halo, alkoxy, substituted alkoxy, thioalkoxy, substituted thioalkoxy, nitro, cyano, carboxyl, carboxyl esters, alkyl, substituted alkyl, alkenyl, substituted alkenyl, alkynyl, substituted alkynyl, amino, substituted amino, —NHC(O)R⁴, —NHSO₂R⁴, —C(O)NH₂, —C(O)NHR⁴, —C(O)NR⁴R⁴, —S(O)R⁴, —S(O)₂R⁴, —S(O)₂NHR and —S(O)₂NR⁴R⁴, where each R⁴ is independently selected from the group consisting of alkyl, substituted alkyl, aryl and heteroaryl;

X is selected from the group consisting of oxo (=O), thiooxo (=S), hydroxyl (—H,—OH), thiol (H,—SH) and hydro (H,H);

Y is represented by the formula:

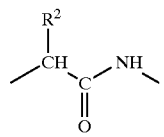

wherein each R² is independently selected from the group consisting of alkyl, substituted alkyl, alkenyl, substituted alkenyl, alkynyl, substituted alkynyl, cycloalkyl, aryl, heteroaryl and heterocyclic;

Z is represented by the formula —T—C(X')(X")C(O)— where T is selected from the group consisting of a bond covalently linking R¹ to —C(X')(X")—, oxygen, sulfur, and —NR⁵ where R⁵ is hydrogen, acyl, alkyl, substituted alkyl, aryl, heterocyclic or heteroaryl group;

R⁵' is hydrogen, alkyl, substituted alkyl, aryl, heterocyclic or heteroaryl group;

X' and X" are independently selected from the group consisting of hydrogen, fluoro, alkyl, substituted alkyl; aryl, heteroaryl, heterocyclic, —OR⁵', —SR⁵, —N(R⁵)₂, —N(CO)OR¹⁵ and —N₃, with the proviso that at least one of X' or X" is other than hydrogen, hydroxy or fluoro, and with the further proviso that both X' and X" cannot both be —OR⁵', —SR⁵, —N(R⁵)₂, —N(CO)OR¹⁵ and —N₃; further, neither X' and X" can be —OR⁵', —SR⁵, —N(R⁵)₂, —N(CO)OR¹⁵ or —N₃ when T is other than a bond covalently linking R¹ to —C(X')(X")—;

n is an integer equal to 1 or 2;

p is an integer equal to 0 or 1 such that when p is zero, the ring defined by W and —C(H)ₚC(=X)— is unsaturated at the carbon atom of ring attachment to Y and when p is one, the ring is saturated at the carbon atom of ring attachment to Y, with the following provisos:

when R1 is 2-propylpentanoyl, R2 is methyl, and R15 is hydrogen, then W, together with >CH and >C=X, does not form a 2,3-dihydro-1-methyl-5-phenyl-1H-1,4-benzodiazepin-2-one when R1 is 3,5-difluorobenzoyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is trans-cinnamyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is 2-(4-chlorophenoxy)-2-methylpropionyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is α-methoxyphenylacetyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is diphenylacetyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is α-methoxyphenylacetyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is α-hydroxy-diphenylacetyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is diphenylacetyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is 2-(chlorophenoxy)-2-methylpropionyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is diphenylacetyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1 is 3,5-difluorobenzoyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1 is trans-cinnamyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1 is 2-(4-chlorophenoxy)-2-methylpropionyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1—N($R^{15}$) is (2,5-dimethoxyphenyl)ureylenyl and R2 is methyl, then W, together with >CH and >C=X, does not form a 2,3-dihydro-1-methyl-5-phenyl-1H-1,4-benzodiazepin-2-one when R1 is D,L-2-pyrrolidinone-5-yl, R2 is methyl, and R15 is hydrogen, then W, together with >CH and >C=X, does not form a 7-methyl-5,7-dihydro-6H-dibenz[b,d]azepin-6-one.

Accordingly, in one of its method aspects, this invention is directed to a method for inhibiting β-amyloid peptide release and/or its synthesis in a cell which method comprises administering to such a cell an amount of a compound or a mixture of compounds as described herein effective in inhibiting the cellular release and/or synthesis of β-amyloid peptide.

Because the in vivo generation of β-amyloid peptide is associated with the pathogenesis of $AD^{8,9}$, the compounds described herein can also be employed in conjunction with a pharmaceutical composition to prophylactically and/or therapeutically prevent and/or treat AD. Accordingly, in another of its method aspects, this invention is directed to a prophylactic method for preventing the onset of AD in a patient at risk for developing AD by administering to the patient a pharmaceutical composition comprising a pharmaceutically inert carrier and an effective amount of one or more of the compounds described herein.

In yet another of its method aspects, this invention is directed to a therapeutic method for treating a patient with AD in order to inhibit further deterioration in the condition of that patient which method comprises administering to said patient a pharmaceutical composition comprising a pharmaceutically inert carrier and an effective amount of a compound or a mixture of compounds as described herein.

Preferred R' groups include, by way of example, all of the aryl (including substituted aryl), cycloalkyl, and substituted cycloalkyl groups defined for R' above as well as the following additional groups:

thiophene-2-yl, 2-furanyl, cyclopropyl, cyclobutyl, 1-phenylcyclopropyl, cyclopentyl, cyclohexyl, cycloheptyl, 2-benzofuranyl, 5-chloro-benzofuran-2-yl, 5,5-dimethyl-butyrolactone-4-yl, 4-methylsulfonyl-phenyl, cis-2-phenyl-cyclopropyl, 5-methylsulfonylthiophen-2-yl, 1,8 dimethyl-6-hydroxy-bicyclo[2.2.2]oct-2-yl, 1,4-benzodioxan-2-yl, tetrahydrofuran-2-yl, tetrahydrofuran-3-yl, cyclohex-3-enyl, 3,5-difluorophenyl, 4-methylphenyl, 2-naphthyl, 1-naphthyl, 4-chlorothiophene-yl, 4-cyanophenyl, tetrahydrofuran-2-yl, cyclohex-3-ene-yl, 1,2,3,4-tetrahydronaphth-2-yl, 1,2,3,4-tetrahydronaphth-3-yl, 4-trifluoromethyl-cyclohexyl, bicyclo[2.2.1]hept-2-yl, bicyclo[2.2.1]hept-5-ene-2-yl, 2,2 dichloropropyl, 2,4-dichlorophenyl, cis-2-methyl-cyclopropyl, 1-(4-chlorophenyl)cyclobutyl, 2-phenylphenyl, 1,2-dihydro-1-oxo-2-phenyl-bicyclo[3.3.1]non-6-ene-3-yl and —CH=CH(φ)).

Preferred $R^1$ groups include unsubstituted aryl groups such as phenyl, 1-naphthyl, 2-naphthyl, etc.; substituted aryl groups such as monosubstituted phenyls (preferably substituents at 3 or 5 positions); disubstituted phenyls (preferably substituents at 3 and 5 positions); and trisubstituted phenyls (preferably substituents at the 3,4,5 positions). Preferably, the substituted phenyl groups do not include more than 3 substituents. Examples of substituted phenyls include, for instance, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 3-(trifluoromethyl)-4-chlorophenyl, 3-chloro-4-cyanophenyl, 3-chloro-4-iodophenyl, 3,4-methylenedioxyphenyl, 4-azidophenyl, 4-cyanophenyl, 4-ethylphenyl, 4-iodophenyl, 4-(phenylcarbonyl)phenyl, 4-(1-othoxy)ethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl)phenyl, 3,5-dimethoxyphenyl, 2,4-dichlorophenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5,6-pentafluorophenyl, 2,5-dimethylphenyl, 4-phenylphenyl, 2-fluoro-3-trifluoromethylphenyl.

Other preferred $R^1$ groups include, by way of example, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH₂-cyclopropyl, —CH₂-cyclobutyl, —CH₂-cyclohexyl, —CH₂-cyclopentyl, —CH₂CH₂-cyclopropyl, —CH₂CH₂-cyclobutyl, —CH₂CH₂-cyclohexyl, —CH₂CH₂—cyclopentyl, pyrid-2-yl, pyrid-3-yl, pyrid-4-yl, fluoropyridyls (including 5-fluoropyrid-3-yl), chloropyridyls (including 5-chloropyrid-3-yl), thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetrazol-5-yl, allyl, 2-(cyclohexyl)ethyl, (CH₃)₂CH=CHCH₂CH₂CH(CH₃)—, phenyl-C(O)CH₂—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl)methyl, (2-methoxyphenyl)methyl, (3-methoxyphenyl)methyl, (3-hydroxyphenyl)methyl, (4-hydroxyphenyl)methyl, (4-methoxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH₃OC(O)CH₂—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH₃CH=CH—, CH₃CH₂CH=CH—, (4-chlorophenyl)C(O)CH₂—, (4-fluorophenyl)C(O)CH₂—, (4-methoxyphenyl)C(O)CH₂—, 4-(fluorophenyl)-NHC(O)CH₂—, 1-phenyl-n-butyl, (phenyl)₂-CHNHC(O)CH₂CH₂—, (CH₃)₂NC(O)CH₂—, (phenyl)₂CHNHC(O)CH₂CH₂—, methylcarbonylmethyl, (2,4-dimethylphenyl)C(O)CH₂—, 4-methoxyphenyl-C(O)CH₂—, phenyl-C(O)CH₂—, CH₃C(O)N(phenyl)-, ethenyl, methylthiomethyl, (CH₃)₃CNHC(O)CH₂—, 4-fluorophenyl-C(O)CH₂—, diphenylmethyl, phenoxymethyl, 3,4-methylenedioxyphenyl-CH₂—, benzo[b]thiophen-3-yl, (CH₃)₃COC(O)NHCH₂—, trans-styryl, H₂NC(O)CH₂CH₂—, 2-trifluoromethylphenyl-C(O)CH₂, C(O)NHCH(phenyl)CH₂—, mesityl, CH₃CH(=NHOH)CH₂—, 4-CH₃-phenyl-NHC(O)CH₂CH₂—, C(O)CH(phenyl)CH₂—, (CH₃)₂CHC(O)NHCH(phenyl)-, CH₃CH₂OCH₂—, CH₃OC(O)CH(CH₃)(CH₂)₃—, 2,2,2-trifluoroethyl, 1-(trifluoromethyl)ethyl, 2-CH₃-benzofuran-3-yl, 2-(2,4-dichlorophenoxy)ethyl, phenyl-SO₂CH₂—, 3-cyclohexyl-n-propyl, CF₃CH₂CH₂CH₂— and N-pyrrolidinyl.

Still other preferred R¹ groups include those set forth in the Tables below.

Each R² is preferably (and independently for n=2) selected from the group consisting of alkyl, substituted alkyl, alkenyl, cycloalkyl, aryl, heteroaryl and heterocyclic.

Particularly preferred R² substituents include, by way of example, methyl, ethyl, n-propyl, iso-propyl, n-butyl, iso-butyl, sec-butyl, tert-butyl, —CH₂CH(CH₂CH₃)₂, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH₂-cyclopropyl, —CH₂-cyclohexyl, —CH₂CH₂-cyclopropyl, —CH₂CH₂-cyclohexyl, —CH₂-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH₃)₂NCH₂CH₂CH₂O-benzyl, p-(CH₃)₃COC(O)CH₂O-benzyl, p-(HOOCCH₂O)-benzyl, 2-aminopyrid-6-yl, p-(N-morpholino-CH₂CH₂O)-benzyl, —CH₂CH₂C(O)NH₂, —CH₂-imidazol-4-yl, —CH₂-(3-tetrahydrofuranyl), —CH₂-thiophen-2-yl, —CH₂(1-methyl)cyclopropyl, —CH₂-thiophen-3-yl, thiophen-3-yl, thiophen-2-yl, —CH₂-C(O)O-t-butyl, —CH₂—C(CH₃)₃, —CH₂CH(CH₂CH₃)₂, -2-methylcyclopentyl, -cyclohex-2-enyl, —CH[CH(CH₃)₂]COOCH₃, —CH₂CH₂N(CH₃)₂, —CH₂C(CH₃)=C , —CH₂CH=CHCH₃ (cis and trans), —CH₂OH, —CH(OH)CH₃, —CH(O-t-butyl)CH₃, —CH₂OCH₃, —(CH₂)₄NH-Boc, —(CH₂)₄NH₂, —CH₂-pyridyl (e.g., 2-pyridyl, 3-pyridyl and 4-pyridyl), pyridyl (2-pyridyl, 3-pyridyl and 4-pyridyl), —CH₂-naphthyl (e.g., 1-naphthyl and 2-naphthyl), —CH₂-(N-morpholino), p-(N-morpholino-CH₂CH₂O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH₂CH₂SCH₃, thien-2-yl, and thien-3-yl.

Compounds of this invention include, by way of example,

3-[(N'-(4-methylbenzoyl)-D-phenylglycinyl)]amino-2,3-dihydro-1-methyl-5-phenyl-1H-1,4-benzodiazepin-2-one 3-[(N'-(4-methylbenzoyl)-L-alaninyl)]amino-2,3-dihydro-1-methyl-5-phenyl-1H-1,4-benzodiazepin-2-one 3-[(N'-(Diphenylacetyl)-L-alaninyl)]amino-2,3-dihydro-1-methyl-5-phenyl-1H-1,4-benzodiazepin-2-one 3-[(N'-(2-Naphthoyl)-L-alaninyl)]amino-2,3-dihydro-1-methyl-5-phenyl-1H-1,4-benzodiazepin-2-one 3-[(N'-(1-Naphthoyl)-L-alaninyl)]amino-2,3-dihydro-1-methyl-5-phenyl-1H-1,4-benzodiazepin-2-one 3-[(N'-(5-Chloro-2-thiophenecarboxyl)-L-alaninyl)]amino-2,3-dihydro-1-methyl-5-phenyl-1H-1,4-benzodiazepin-2-one 3-[(N'-(4-Cyanobenzoyl)-L-alaninyl)]amino-2,3-dihydro-1-methyl-5-phenyl-1H-1,4-benzodiazepin-2-one 3-[(N'-(Tetrahydro-2-furoyl)-L-alaninyl)]amino-2,3-dihydro-1-methyl-5-phenyl-1H-1,4-benzodiazepin-2-one 3-[(N'-(3,5-Difluorobenzoyl)-L-alaninyl)]amino-2,3-dihydro-1-methyl-5-phenyl-1H-1,4-benzodiazepin-2-one 3-[(N'-(3-Cyclohexenecarboxyl)-L-alaninyl)]amino-2,3-dihydro-1-methyl-5-phenyl-1H-1,4-benzodiazepin-2-one 3-[(N'-(Acetyl)-L-alaninyl)]amino-2,3-dihydro-1-methyl-5-phenyl-1H-1,4-benzodiazepin-2-one 3-[(N'-(1,2,3,4-Tetrahydro-2-naphthoyl)-L-alaninyl)]amino-2,3-dihydro-1-methyl-5-phenyl-1H-1,4-benzodiazepin-2-one 3-[(N'-(Cyclopentanecarboxyl)-L-alaninyl)]amino-2,3-dihydro-1-methyl-5-phenyl-1H-1,4-benzodiazepin-2-one (S)-3-[(N'-(2-phenoxybutyryl)-L-alaninyl)]amino-2,3-dihydro-1-methyl-5-phenyl-1H-1,4-benzodiazepin-2-one (S)-3-[(N'-(2-Thiophenecarboxyl)-L-alaninyl)]amino-2,3-dihydro-1-methyl-5-phenyl-1H-1,4-benzodiazepin-2-one (S)-3-[(N'-(2,3-Diphenylpropionyl)-L-alaninyl)]amino-2,3-dihydro-1-methyl-5-phenyl-1H-1,4-benzodiazepin-2-one (S)-3-[(N'-((R,S)-(−)-α-Methoxyphenylacetyl)-L-alaninyl]amino-2,3-dihydro-1-methyl-5-phenyl-1H-1,4-benzodiazepin-2-one (S)-3-[(N'-(2-Furoyl)-L-alaninyl)]amino-2,3-dihydro-1-methyl-5-phenyl-1H-1,4-benzodiazepin-2-one (S)-3-[(N'-(2-Phenoxypropionyl)-L-alaninyl)]amino-2,3-dihydro-1-methyl-5-phenyl-1H-1,4-benzodiazepin-2-one (S)-3-[(N'-(Cyclohexanecarboxyl)-L-alaninyl)]amino-2,3-dihydro-1-methyl-5-phenyl-1H-1,4-benzodiazepin-2-one (S)-3-[(N'-(2-(4-Chlorophenoxy)-2-methylpropionyl)-L-alaninyl)]amino-2,3-dihydro-1-methyl-5-phenyl-1H-1,4-benzodiazepin-2-one (S)-3-[(N'-(Cyclobutanecarboxyl)-L-alaninyl)]amino-2,3-dihydro-1-methyl-5-phenyl-1H-1,4-benzodiazepin-2-one (S)-3-[(N'-(1-Phenyl-1-cyclopropanecarboxyl)-L-alaninyl)]amino-2,3-dihydro-1-methyl-5-phenyl-1H-1,4-benzodiazepin-2-one (S)-3-[(N'-(2-Benzofurancarboxyl)-L-alaninyl)]amino-2,3-dihydro-1-methyl-5-phenyl-1H-1,4-benzodiazepin-2-one (S)-3-[(N'-(2-Isopropyl-2-phenylacetyl)-L-alaninyl)]amino-2,3-dihydro-1-methyl-5-phenyl-1H-1,4-benzodiazepin-2-one (S)-3-[(N'-(5-Chlorobenzofuran-2-carboxyl)-L-alaninyl)]amino-2,3-dihydro-1-methyl-5-phenyl-1H-1,4-benzodiazepin-2-one (S)-3-[(N'-(2-Ethylhexanoyl)-L-alaninyl)]amino-2,3-dihydro-1-methyl-5-phenyl-1H-1,4-benzodiazepin-2-one (S)-3-[(N'-(2-Methylbutyryl)-L-alaninyl)]amino-2,3-dihydro-1-methyl-5-phenyl-1H-1,4-benzodiazepin-2-one (S)-3-[(N'-((R,S)-2-Phenoxypropionyl)-L-alaninyl)]amino-2,3-dihydro-1-methyl-5-phenyl-1H-1,4-benzodiazepin-2-one (S)-3-[(N'-(5,5-dimethyl-butyrolactone-4-yl)-L-alaninyl)]amino-2,3-dihydro-1-methyl-5-phenyl-1H-1,4-benzodiazepin-2-one (S)-3-[(N'-(2-Methyl-4,4,4-trifluorobutyryl)-L-alaninyl)]amino-2,3-dihydro-1-methyl-5-phenyl-1H-1,4-benzodiazepin-2-one 5-{N'-(2-phenylpropionyl)-L-alaninyl}-amino-7-methyl-5,7-dihydro-6H-dibenz[b,d]azepin-6-one 5-{N'-(tetrahydro-3-furoyl)-L-alaninyl}-amino-7-methyl-5,7-dihydro-6H-dibenz[b,d]azepin-6-one 3-[N'-(3,5-difluorophenyl-α-methoxyacetyl)-L-alaninyl]-amino-2,3-dihydro-1-methyl-5-phenyl-1H-1,4-Benzodiazepin-2-one 3-[N'-(3,5-difluorophenyl-α-methoxyacetyl)-L-alaninyl]-amino-2,3-dihydro-1-methyl-5-phenyl-1H-1,4-Benzodiazepin-2-one (S)-3-[(N'-(4-(Trifluoromethyl)cyclohexane carboxyl)-L-alaninyl)]amino-2,3-dihydro-1-methyl-5-phenyl-1H-1,4-benzodiazepin-2-one (S)-3-[(N'-(Bicyclo[2.2.1]heptane-2-carboxyl)-L-alaninyl)]amino-2,3-dihydro-1-methyl-5-phenyl-1H-1,4-benzodiazepin-2-one (S)-3-[(N'-(Bicyclo(2.2.1)hept-5-ene-2-carboxyl)-L-alaninyl)]amino-2,3-dihydro-1-methyl-5-phenyl-1H-1,4-benzodiazepin-2-one (S)-3-[(N'-(2,2-Dichlorocyclopropane carboxyl)-L-alaninyl)]amino-2,3-dihydro-1-methyl-5-phenyl-1H-1,4-benzodiazepin-2-one (S)-3-[(N'-(Cycloheptanecarboxyl)-L-alaninyl)]amino-2,3-dihydro-1-methyl-5-phenyl-1H-1,4-benzodiazepin-2-one (S)-3-[(N'-(2-Methylvaleryl)-L-alaninyl)]amino-2,3-dihydro-1-methyl-5-phenyl-1H-1,4-benzodiazepin-2-one 3-[(N'-(2-(4-hydroxyphenoxy)propionyl)-L-alaninyl)]amino-2,3-dihydro-1-methyl-5-phenyl-1H-1,4-benzodiazepin-2-one (S)-3-[(N'-(α-(Hydroxymethyl)phenylacetyl)-L-alaninyl)]amino-2,3-dihydro-1-methyl-5-phenyl-1H-1,4-benzodiazepin-2-one (S)-3-[(N'-(1-(2,4-Dichlorophenyl)cyclopropanecarboxyl)-L-alaninyl)]amino-2,3-dihydro-1-methyl-5-phenyl-1H-1,4-benzodiazepin-2-one (S)-3-[(N'-(2-Ethylbutyryl)-L-alaninyl)]amino-2,3-dihydro-1-methyl-5-phenyl-1H-1,4-benzodiazepin-2-one (S)-3-[(N'-(2-Methylcyclopropanecarboxyl)-L-alaninyl)]amino-2,3-dihydro-1-methyl-5-phenyl-1H-1,4-benzodiazepin-2-one (S)-3-[(N'-(1-(4-Chlorophenyl)-1-cyclobutanecarboxyl)-L-alaninyl)]amino-2,3-dihydro-1-methyl-5-phenyl-1H-1,4-benzodiazepin-2-one (S)-3-[(N'-(2-Biphenylcarboxyl)-L-alaninyl)]amino-2,3-dihydro-1-methyl-5-phenyl-1H-1,4-benzodiazepin-2-one (S)-3-[(N'-(Pivalyl)-L-alaninyl)]amino-2,3-dihydro-1-methyl-5-phenyl-1H-1,4-benzodiazepin-2-one (S)-3-[(N'-(trans-Cinnamyl)-L-alaninyl)]amino-2,3-dihydro-1-methyl-5-phenyl-1H-1,4-benzodiazepin-2-one (S)-3-[(N'-(1,2-Dihydro-1-oxo-2-phenyl-4-isoquinolinecarboxyl)-L-alaninyl)]amino-2,3-dihydro-1-methyl-5-phenyl-1H-1,4-benzodiazepin-2-one (S)-3-[(N'-(Bicyclo(3.3.1)non-6-ene-3-carboxyl)-L-alaninyl)]amino-2,3-dihydro-1-methyl-5-phenyl-1H-1,4-benzodiazepin-2-one (S)-3-[(N'-(Cyclopropanecarboxyl)-L-alaninyl)]amino-2,3-dihydro-1-methyl-5-phenyl-1H-1,4-benzodiazepin-2-one (S)-3-[(N'-(3-furoyl)-L-alaninyl)]amino-2,3-dihydro-1-methyl-5-phenyl-1H-1,4-benzodiazepin-2-one (S)-3-[(N'-(2-(4-Cyanophenoxy)-2-methylpropionyl)-L-alaninyl)]amino-2,3-dihydro-1-methyl-5-phenyl-1H-1,4-benzodiazepin-2-one (S)-3-[(N'-(Diphenylacetyl)-L-alaninyl)]amino-2,3-dihydro-1-methyl-5-phenyl-1H-1,4-benzodiazepin-2-one (S)-3-[(N'-(Tetrahydro-2-ftiroyl)-L-alaninyl)]amino-2,3-dihydro-1-methyl-5-phenyl-1H-1,4-benzodiazepin-2-one (S)-3-[(N'-(3,5-Difluorobenzoyl)-L-alaninyl)]amino-2,3-dihydro-1-methyl-5-phenyl-1H-1,4-benzodiazepin-2-one (S)-3-[(N'-(3-Cyclohexenecarboxyl)-L-alaninyl)]amino-2,3-dihydro-1-methyl-5-phenyl-1H-1,4-benzodiazepin-2-one (S)-3-[(N'-(1,2,3,4-Tetrahydro-2-naphthoyl)-L-alaninyl)]amino-2,3-dihydro-1-methyl-5-phenyl-1H-1,4-benzodiazepin-2-one (S)-3-[(N'-(Cyclopentanecarboxyl)-L-alaninyl)]amino-2,3-dihydro-1-methyl-5-phenyl-1H-1,4-benzodiazepin-2-one (S)-3-[(N'-(2-(4-trifluorophenyoxy)propionyl)-L-alaninyl)]amino-2,3-dihydro-1-methyl-5-phenyl-1H-1,4-benzodiazepin-2-one (S)-3-[(N'-(2-(4-Biphenylyloxy)propionyl)-L-alaninyl)]
amino-2,3-dihydro-1-methyl-5-phenyl-1H-1,4-
benzodiazepin-2-one (S)-3-[(N'-(Diphenylacetyl)-L-phenylglycinyl)]amino-2,
3-dihydro-1-methyl-5-phenyl-1H-1,4-benzodiazepin-
2-one (S)-3-[(N'-(4-(methylsulfonyl)benzoyl)-L-alaninyl)]
amino-2,3-dihydro-1-methyl-5-phenyl-1H-1,4-
benzodiazepin-2-one (S)-3-[(N'-(4-chloro-α-methylphenylacetyl)-L-alaninyl)]
amino-2,3-dihydro-1-methyl-5-phenyl-1H-1,4-
benzodiazepin-2-one (S)-3-[(N'-(trans-2-Phenyl-1-cyclopropanecarboxyl)-L-
alaninyl)]amino-2,3-dihydro-1-methyl-5-phenyl-1H-1,
4-benzodiazepin-2-one (S)-3-[(N'-(4-chloro-(α,α-dimethylphenylacetyl)-L-
alaninyl)]amino-2,3-dihydro-1-methyl-5-phenyl-1H-1,
4-benzodiazepin-2-one (S)-3-[(N'-(5-methylsulfonyl)thiophene-2-carboxyl)-L-
alaninyl)]amino-2,3-dihydro-1-methyl-5-phenyl-1H-1,
4-benzodiazepin-2-one (S)-3-[(N'-(1,8-dimethyl-6-Hydroxy-bicyclo(2.2.2)
octane-2-carboxyl)-L-alaninyl)]amino-2,3-dihydro-1-
methyl-5-phenyl-1H-1,4-benzodiazepin-2-one (S)-3-[(N'-((S)-(+)-2-hydroxy-2-phenylpropionyl)-L-
alaninyl)]amino-2,3-dihydro-1-methyl-5-phenyl-1H-1,
4-benzodiazepin-2-one (S)-3-[(N'-(1,4-Benzodioxan-2-carboxyl)-L-alaninyl)]
amino-2,3-dihydro-1-methyl-5-phenyl-1H-1,4-
benzodiazepin-2-one (S)-3-[(N'-(Tetrahydro-3-furoyl)-L-alaninyl)]amino-2,3-
dihydro-1-methyl-5-phenyl-1H-1,4-benzodiazepin-2-
one (S)-3-[(N'-(Acetyl)-L-phenylglycinyl)]amino-2,3-
dihydro-1-methyl-5-phenyl-1H-1,4-benzodiazepin-2-
one (S)-3-[(N'-(3-Cyclohexenecarboxyl)-L-phenylglycinyl)]
amino-2,3-dihydro-1-methyl-5-phenyl-1H-1,4-
benzodiazepin-2-one (S)-3-[(N'-(Cyclopropanecarboxyl)-L-phenylglycinyl)]
amino-2,3-dihydro-1-methyl-5-phenyl-1H-1,4-
benzodiazepin-2-one (S)-3-[(N'-(3,5-Difluorobenzoyl)-L-phenylglycinyl)]
amino-2,3-dihydro-1-methyl-5-phenyl-1H-1,4-
benzodiazepin-2-one 3-[(N'-(L-2-pyrrolidinone-5-yl)-L-alaninyl)]amino]-2,3-
dihydro-1-methyl-5-(2-pyridyl)-1H-1,4-
benzodiazepin-2-one 3-[(N'-(trans-cinnamyl)-L-alaninyl)]amino]-2,3-dihydro-
1-methyl-5-(2-pyridyl)-1H-1,4-benzodiazepin-2-one 3-[(N'-(1-phenyl-1-cyclopropanecarboxyl)-L-alaninyl)]
amino]-2,3-dihydro-1-methyl-5-(2-pyridyl)-1H-1,4-
benzodiazepin-2-one 3-[(N'-(1-phenyl-1-cyclopropanecarboxyl)-L-alaninyl)]
amino]-2,3-dihydro-1-(3,3-dimethyl-2-oxobutyl)-5-(2-
pyridyl)-1H-1,4-benzodiazepin-2-one (S)-3-[(N'-(α-hydroxy-diphenylacetyl)-L-alaninyl)]
amino-2,3-dihydro-1-methyl-5-(2-pyridyl)-1H-1,4-
benzodiazepin-2-one 3-[(N'-(3,5-difluorobenzoyl)-L-alaninyl)]amino]-2,3-
dihydro-1-(3,3-dimethyl-2-oxobutyl)-5-(2-pyridyl)-
1H-1,4-benzodiazepin-2-one 3-[(N'-(L-2-pyrrolidinone-5-yl)-L-alaninyl)]amino]-2,3-
dihydro-1-(3,3-dimethyl-2-oxobutyl)-5-(2-pyridyl)-
1H-1,4-benzodiazepin-2-one (S)-3-[(N'-(α-hydroxy-diphenylacetyl)-L-alaninyl)]
amino-2,3-dihydro-1-2-(diethylamino)ethyl-5-(2-
pyridyl)-1H-1,4-benzodiazepin-2-one 3-[(N'-(1-phenyl-1-cyclopropanecarboxyl)-L-alaninyl)]
amino]-2,3-dihydro-1-(2-N,N-diethylaminoethyl)-5-
(2-pyridyl)-1H-1,4-benzodiazepin-2-one 3-[(N'-(α-methoxyphenylacetyl)-L-alaninyl)]amino]-2,3-
dihydro-1-(2-N,N-diethylaminoethyl)-5-(2-pyridyl)-
1H-1,4-benzodiazepin-2-one 3-(S)-[2-((1H)-isoquinoline-3,4-dihydro-3-oxo)-2-
methyl-acetyl]-amino-2,3-dihydro-1-methyl-5-phenyl-
1H-1,4-benzodiazepin-2-one 3-(S)-[2-((1H)-isoquinoline-3,4-dihydro-3-oxo)-2-
methyl-acetyl]-amino-2,3-dihydro-1-methyl-5-phenyl-
1H-1,4-benzodiazepin-2-one (S)-3-[(N'-((trans-2-Phenylcyclopropyl)ureylenyl)-L-
alaninyl)]amino-2,3-dihydro-1-methyl-5-phenyl-1H-1,
4-benzodiazepin-2-one (S)-3-[(N'-((3,4-Dichlorophenyl)ureylenyl)-L-alaninyl)]
amino-2,3-dihydro-1-methyl-5-phenyl-1H-1,4-
benzodiazepin-2-one (S)-3-[(N'-((2-propenyl)ureylenyl)-L-alaninyl)]amino-2,
3-dihydro-1-methyl-5-phenyl-1H-1,4-benzodiazepin-
2-one (S)-3-[(N'-((R)-(−)-1-(1-Naphthyl)ethyl)ureylenyl)-L-
alaninyl)]amino-2,3-dihydro-1-methyl-5-phenyl-1H-1,
4-benzodiazepin-2-one (S)-3-[(N'-((2,6-Diisopropylphenyl)ureylenyl)-L-
alaninyl)]amino-2,3-dihydro-1-methyl-5-phenyl-1H-1,
4-benzodiazepin-2-one (S)-3-[(N'-((3-[(Trifluoromethyl)phenyl)ureylenyl)-L-
alaninyl)]amino-2,3-dihydro-1-methyl-5-phenyl-1H-1,
4-benzodiazepin-2-one (S)-3-[(N'-((Phenyl)ureylenyl)-L-alaninyl)]amino-2,3-
dihydro-1-methyl-5-phenyl-1H-1,4-benzodiazepin-2-
one (S)-3-[(N'-((4-ethoxycarbonylphenyl)ureylenyl)-L-
alaninyl)]amino-2,3-dihydro-1-methyl-5-phenyl-1H-1,
4-benzodiazepin-2-one (S)-3-[(N'-((2-Bromophenyl)ureylenyl)-L-alaninyl)]
amino-2,3-dihydro-1-methyl-5-phenyl-1H-1,4-
benzodiazepin-2-one (S)-3-[(N'-((o-Tolyl)ureylenyl)-L-alaninyl)]amino-2,3-
dihydro-1-methyl-5-phenyl-1H-1,4-benzodiazepin-2-
one (S)-3-[(N'-((2-Ethyl-6-methylphenyl)ureylenyl)-L-
alaninyl)]amino-2,3-dihydro-1-methyl-5-phenyl-1H-1,
4-benzodiazepin-2-one (S)-3-[(N'-((2-Fluorophenyl)ureylenyl)-L-alaninyl)]
amino-2,3-dihydro-1-methyl-5-phenyl-1H-1,4-
benzodiazepin-2-one (S)-3-[(N'-((2,4-difluorophenyl)ureylenyl)-L-alaninyl)]
amino-2,3-dihydro-1-methyl-5-phenyl-1H-1,4-
benzodiazepin-2-one (S)-3-[(N'-((2-Ethoxyphenyl)ureylenyl)-L-alaninyl)]
amino-2,3-dihydro-1-methyl-5-phenyl-1H-1,4-
benzodiazepin-2-one (S)-3-[(N'-((3-Acetylphenyl)ureylenyl)-L-alaninyl)]
amino-2,3-dihydro-1-methyl-5-phenyl-1H-1,4-
benzodiazepin-2-one (S)-3-[(N'-((3-[(cyano)phenyl)ureylenyl)-L-alaninyl)]
amino-2,3-dihydro-1-methyl-5-phenyl-1H-1,4-
benzodiazepin-2-one (S)-3-[(N'-((Phenethyl)ureylenyl)-L-alaninyl)]amino-2,3-dihydro-1-methyl-5-phenyl-1H-1,4-benzodiazepin-2-one (S)-3-[(N'-((4-n-Butylphenyl)ureylenyl)]amino-2,3-dihydro-1-methyl-5-phenyl-1H-1,4-benzodiazepin-2-one (S)-3-[(N'-((Octyl)ureylenyl)-L-alaninyl)]amino-2,3-dihydro-1-methyl-5-phenyl-1H-1,4-benzodiazepin-2-one (S)-3-[(N'-((4-Biphenyl)ureylenyl)-L-alaninyl)]amino-2,3-dihydro-1-methyl-5-phenyl-1H-1,4-benzodiazepin-2-one (S)-3-[(N'-((4-Isopropylphenyl)ureylenyl)-L-alaninyl)]amino-2,3-dihydro-1-methyl-5-phenyl-1H-1,4-benzodiazepin-2-one (S)-3-[(N'-((Hexyl)ureylenyl)-L-alaninyl)]amino-2,3-dihydro-1-methyl-5-phenyl-1H-1,4-benzodiazepin-2-one (S)-3-[(N'-((2-Isopropylphenyl)ureylenyl)-L-alaninyl)]amino-2,3-dihydro-1-methyl-5-phenyl-1H-1,4-benzodiazepin-2-one (S)-3-[(N'-((2,6-Difluorophenyl)ureylenyl)-L-alaninyl)]amino-2,3-dihydro-1-methyl-5-phenyl-1H-1,4-benzodiazepin-2-one (S)-3-[(N'-((Octadecyl)ureylenyl)-L-alaninyl)]amino-2,3-dihydro-1-methyl-5-phenyl-1H-1,4-benzodiazepin-2-one (S)-3-[(N'-((4-(Trifluoromethoxy)phenyl)ureylenyl)-L-alaninyl)]amino-2,3-dihydro-1-methyl-5-phenyl-1H-1,4-benzodiazepin-2-one (S)-3-[(N'-((2,4-Dichlorophenyl)ureylenyl)-L-alaninyl)]amino-2,3-dihydro-1-methyl-5-phenyl-1H-1,4-benzodiazepin-2-one (S)-3-[(N'-((3-Ethoxycarbonylphenyl)ureylenyl)-L-alaninyl)]amino-2,3-dihydro-1-methyl-5-phenyl-1H-1,4-benzodiazepin-2-one (S)-3-[(N'-((4-Chlorophenyl)ureylenyl)-L-alaninyl)]amino-2,3-dihydro-1-methyl-5-phenyl-1H-1,4-benzodiazepin-2-one (S)-3-[(N'-((4-butoxyphenyl)ureylenyl)-L-alaninyl)]amino-2,3-dihydro-1-methyl-5-phenyl-1H-1,4-benzodiazepin-2-one (S)-3-[(N'-((4-Phenoxyphenyl)ureylenyl)-L-alaninyl)]amino-2,3-dihydro-1-methyl-5-phenyl-1H-1,4-benzodiazepin-2-one (S)-3-[(N'-((1-Naphthyl)ureylenyl)-L-alaninyl)]amino-2,3-dihydro-1-methyl-5-phenyl-1H-1,4-benzodiazepin-2-one (S)-3-[(N'-((2-Biphenyl)ureylenyl)-L-alaninyl)]amino-2,3-dihydro-1-methyl-5-phenyl-1H-1,4-benzodiazepin-2-one (S)-3-[(N'-((2-(Methylthio)phenyl)ureylenyl)-L-alaninyl)]amino-2,3-dihydro-1-methyl-5-phenyl-1H-1,4-benzodiazepin-2-one (S)-3-[(N'-((2-Ethylphenyl)ureylenyl)-L-alaninyl)]amino-2,3-dihydro-1-methyl-5-phenyl-1H-1,4-benzodiazepin-2-one (S)-3-[(N'-((3-Methoxyphenyl)ureylenyl)-L-alaninyl)]amino-2,3-dihydro-1-methyl-5-phenyl-1H-1,4-benzodiazepin-2-one (S)-3-[(N'-((3,4,5-Trimethoxyphenyl)ureylenyl)-L-alaninyl)]amino-2,3-dihydro-1-methyl-5-phenyl-1H-1,4-benzodiazepin-2-one (S)-3-[(N'-((2,4,6-Trimethylphenyl)ureylenyl)-L-alaninyl)]amino-2,3-dihydro-1-methyl-5-phenyl-1H-1,4-benzodiazepin-2-one (S)-3-[(N'-((2-methyl-6-t-butylphenyl)ureylenyl)-L-alaninyl)]amino-2,3-dihydro-1-methyl-5-phenyl-1H-1,4-benzodiazepin-2-one (S)-3-[(N'-((2-(2-thiophene-yl)ethyl)ureylenyl)-L-alaninyl)]amino-2,3-dihydro-1-methyl-5-phenyl-1H-1,4-benzodiazepin-2-one 3-[N'-3,5-difluorophenyl-acetamido)-L-alaninyl]-3-amino-2,3-dihydro1-methyl-5-phenyl-1H-1,4-benzodiazepine 3-[N'-3,5-difluorophenyl-α-azidoacetyl)-L-alaninyl]-3-amino-2,3-dihydro1-methyl-5-phenyl-1H-1,4-benzodiazepine 5-{N'-(cyclopropane carboxyl)-L-alaninyl}-amino-7-methyl-5,7-dihydro-6H-dibenz[b,d]azepin-6-one 5-{N'-(2-methylhexanoyl)-L-alaninyl}-amino-7-methyl-5,7-dihydro-6H-dibenz[b,d]azepin-6-one 5-{N'-(bicyclo[2.2.1]heptane-2-carboxyl)-L-alaninyl}-amino-7-methyl-5,7-dihydro-6H-dibenz[b,d]azepin-6-one 5-{N'-(N-acetyl-N-phenylglycinyl)-L-alaninyl}-amino-7-methyl-5,7-dihydro-6H-dibenz[b,d]azepin-6-one 5-{N'-((aminoacetoxy)-3,5-difluorophenylacetyl)-L-alaninyl}-amino-7-methyl-5,7-dihydro-6H-dibenz[b,d]azepin-6-one 3-[N'-(3,5-difluorophenyl-α-(2-aminoacetoxy)acetyl)-L-alaninyl]-amino-2,3-dihydro-1-methyl-5-phenyl-1H-1,4-Benzodiazepin-2-one 5-{N'-(diphenylacetyl)-L-alaninyl}-amino-7-methyl-5,7-dihydro-6H-dibenz[b,d]azepin-6-one 5-{N'-(acetyl)-L-alaninyl}-amino-7-methyl-5,7-dihydro-6H-dibenz[b,d]azepin-6-one 5-{N'-(2-phenoxyphenylacetyl)-L-alaninyl}-amino-7-methyl-5,7-dihydro-6H-dibenz[b,d]azepin-6-one 5-{N'-(trans-cinnamyl)-L-alaninyl}-amino-7-methyl-5,7-dihydro-6H-dibenz[b,d]azepin-6-one 5-{N'-(tetrahydro-2-furoyl)-L-alaninyl}-amino-7-methyl-5,7-dihydro-6H-dibenz[b,d]azepin-6-one 5-{N'-(cyclopentanecarboxyl)L-alaninyl}-amino-7-methyl-5,7-dihydro-6H-dibenz[b,d]azepin-6-one 5-{N'-(2-thiophenecarboxyl)-L-alaninyl}-amino-7-methyl-5,7-dihydro-6H-dibenz[b,d]azepin-6-one 5-{N'-((S)-(+)-2-hydroxy-2-phenylpropionyl)-L-alaninyl}-amino-7-methyl-5,7-dihydro-6H-dibenz[b,d]azepin-6-one 5-{N'-((R)-(−)-2-hydroxy-2-phenylpropionyl)-L-alaninyl}-amino-7-methyl-5,7-dihydro-6H-dibenz[b,d]azepin-6-one 3-[N'-(3,5-difluorophenyl-α-hydroxy-α-methylacetyl)-L-alaninyl]-amino-2,3-dihydro-1-methyl-5-(2-fluorophenyl)-1H-1,4-Benzodiazepin-2-one 5-{N'-(benzenesulfonyl)-L-alaninyl}-amino-7-methyl-5,7-dihydro-6H-dibenz[b,d]azepin-6-one 3-[N'-(3,5-difluorophenyl-α-hydroxy-α-methylacetyl)-L-alaninyl]-amino-2,3-dihydro-1-methyl-5-(2-fluorophenyl)-1H-1,4-Benzodiazepin-2-one 5-{N'-(3-fluorobenzenesulfonyl)-L-alaninyl}-amino-7-methyl-5,7-dihydro-6H-dibenz[b,d]azepin-6-one 5-(S)-(N'-((Butylureylenyl)-L-alaninyl)-amino-7-methyl-5,7-dihydro-6H-dibenz[b,d]azepin-6-one 5-(S)-(N'-((Benzylureylenyl)-L-alaninyl)-amino-7-methyl-5,7-dihydro-6H-dibenz[b,d]azepin-6-one 5-{N'-(benzylsulfonyl)-L-alaninyl}-amino-7-methyl-5,7-dihydro-6H-dibenz[b,d]azepin-6-one 5-(S)-(N'-((Ethylureylenyl)-L-alaninyl)-amino-7-methyl-5,7-dihydro-6H-dibenz[b,d]azepin-6-one 5-(S)-(N'-((Phenethylureylenyl)-L-alaninyl)-amino-7-methyl-5,7-dihydro-6H-dibenz[b,d]azepin-6-one 5-(S)-(N'-(3,5-difluorophenyl-α-aminoacetyl)-L-valinyl]-amino-7-methyl-5,7-dihydro-6H-dibenz[b,d]azepin-6-one -(S)-(N'-(3,5-difluorophenyl-α-aminoacetyl)-L-tert-leucinyl-amino-7-methyl-5,7-dihydro-6H-dibenz[b,d]azepin-6-one 5-{N'-(butylsulfonyl)-L-alaninyl}-amino-7-methyl-5,7-dihydro-6H-dibenz[b,d]azepin-6-one 5-{N'-(octylsulfonyl)-L-alaninyl}-amino-7-methyl-5,7-dihydro-6H-dibenz[b,d]azepin-6-one 5-(S)-(N'-((2-(thiophen-2-yl)ethylureylenyl)-L-alaninyl)-amino-7-methyl-5,7-dihydro-6H-dibenz[b,d]azepin-6-one 5-(S)-(N'-(3,5-difluorophenyl-α-aminoacetyl)-L-alaninyl-amino-7-methyl-5,7-dihydro-6H-dibenz[b,d]azepin-6-one 5-(S)-(N'-(L-valinyl)-L-alaninyl-)]amino-2,3-dihydro-1-methyl-5-phenyl-1H-1,4-benzodiazepin-2-one 5-(R/S)-(N'-(2-hydroxy-2-phenethylureylenyl)-L-alaninyl)-amino-7-methyl-5,7-dihydro-6H-dibenz[b,d]azepin-6-one 5-(S)-(N'-((hexylureylenyl)-L-alaninyl)-amino-7-methyl-5,7-dihydro-6H-dibenz[b,d]azepin-6-one 5-(S)-(N'-((cyclohexylureylenyl)-L-alaninyl)-amino-7-methyl-5,7-dihydro-6H-dibenz[b,d]azepin-6-one 5-(S)-(N'-((isopropylureylenyl)-L-alaninyl)-amino-7-methyl-5,7-dihydro-6H-dibenz[b,d]azepin-6-one 5-(S)-(N'-((tert-butylureylenyl)-L-alaninyl)-amino-7-methyl-5,7-dihydro-6H-dibenz[b,d]azepin-6-one 5-(S)-(N'-((1-adamantylureylenyl)-L-alaninyl)-amino-7-methyl-5,7-dihydro-6H-dibenz[b,d]azepin-6-one 5-(S)-(N'-((2-methylpropylureylenyl)-L-alaninyl)-amino-7-methyl-5,7-dihydro-6H-dibenz[b,d]azepin-6-one 5-(S)-(N'-(R/S)-3-hydroxy-3-phenylethylureylenyl)-L-alaninyl)-amino-7-methyl-5,7-dihydro-6H-dibenz[b,d]azepin-6-one 5-(S)-(N'-((3-methylbutylureylenyl)-L-alaninyl)-amino-7-methyl-5,7-dihydro-6H-dibenz[b,d]azepin-6-one 5-(S)-((N'-(S)-1-hydroxymethyl-3-methylbutylureylenyl)-L-alaninyl)-amino-7-methyl-5,7-dihydro-6H-dibenz[b,d]azepin-6-one 5-(S)-((N'-(1S)-(2S)-1-hydroxymethyl-2-methylbutylureylenyl)-L-alaninyl)-amino-7-methyl-5,7-dihydro-6H-dibenz[b,d]azepin-6-one 5-(S)-(N'-(3chloropropylureylenyl)-L-alaninyl)-amino-7-methyl-5,7-dihydro-6H-dibenz[b,d]azepin-6-one 5-(S)-(N'-octylureylenyl)-L-alaninyl)-amino-7-methyl-5,7-dihydro-6H-dibenz[b,d]azepin-6-one 5-(S)-(N'-1,1,3,3-tetramethylbutylureylenyl)-L-alaninyl)-amino-7-methyl-5,7-dihydro-6H-dibenz[b,d]azepin-6-one 5-(S)-(N'-(R/S)-1-methylbutylureylenyl)-L-alaninyl)-amino-7-methyl-5,7-dihydro-6H-dibenz[b,d]azepin-6-one 5-(S)-((N'-(R/S)-1-hydroxymethylbutylureylenyl)-L-alaninyl)-amino-7-methyl-5,7-dihydro-6H-dibenz[b,d]azepin-6-one 5-(S)-((N'-(R/S)-1,3-dimethylbutylureylenyl)-L-alaninyl)-amino-7-methyl-5,7-dihydro-6H-dibenz[b,d]azepin-6-one 5-(S)-((N'-(R)-1-hydroxymethyl-3-methylbutylureylenyl)-L-alaninyl)-amino-7-methyl-5,7-dihydro-6H-dibenz[b,d]azepin-6-one 5-(S)-((N'-(R/S)-2-methylbutylureylenyl)-L-alaninyl)-amino-7-methyl-5,7-dihydro-6H-dibenz[b,d]azepin-6-one 5-(S)-(N'-morpholinoureylenyl)-L-alaninyl)-amino-7-methyl-5,7-dihydro-6H-dibenz[b,d]azepin-6-one 5-(S)-(N'-(2-(2-hydroxyethoxy)-ethylureylenyl)-L-alaninyl)-amino-7-methyl-5,7-dihydro-6H-dibenz[b,d]azepin-6-one 5-(S)-(N'-piperidinylureylenyl)-L-alaninyl)-amino-7-methyl-5,7-dihydro-6H-dibenz[b,d]azepin-6-one 5-(S)-(N'-(N"-methyl-N"-butylureylenyl)-L-alaninyl)-amino-7-methyl-5,7-dihydro-6H-dibenz[b,d]azepin-6-one 5-(S)-(N'-(1-(R/S)-hydroxymethylcyclopentylureylenyl)-L-alaninyl)-amino-7-methyl-5,7-dihydro-6H-dibenz[b,d]azepin-6-one 5-(S)-(N'-(4-hydroxybutylureylenyl)-L-alaninyl)-amino-7-methyl-5,7-dihydro-6H-dibenz[b,d]azepin-6-one 5-(S)-(N-(1-(R/S)-hydroxymethyl-2-methylpropylureylenyl)-L-alaninyl)-amino-7-methyl-5,7-dihydro-6H-dibenz[b,d]azepin-6-one 5-(S)-(N'-(2-(R/S)-hydroxycyclohexylureylenyl)-L-alaninyl)-amino-7-methyl-5,7-dihydro-6H-dibenz[b,d]azepin-6-one 5-(S)-(N'-(isopropyl-hydroxyureylenyl)-L-alaninyl)-amino-7-methyl-5,7-dihydro-6H-dibenz[b,d]azepin-6-one 5-(S)-(N'-(benzyl-hydroxyureylenyl)-L-alaninyl)-amino-7-methyl-5,7-dihydro-6H-dibenz[b,d]azepin-6-one 5-(S)-(N'-(valinyl)-L-alaninyl-amino-7-methyl-5,7-dihydro-6H-dibenz[b,d]azepin-6-one 5-(S)-(N'-(phenylglycinyl)-L-alaninyl-amino-7-methyl-5,7-dihydro-6H-dibenz[b,d]azepin-6-one 5-(S)-(N'-(3,5-difluorophenyl-α-aminoacetyl)-L-alaninyl-amino-7-methyl-5,7-dihydro-6H-dibenz[b,d]azepin-6-one 5-(S)-(N'-(3,5-difluoro phenylglycinyl)-L-alaninyl-amino-7-methyl-5,7-dihydro-6H-dibenz[b,d]azepin-6-one 5-(S)-(N'-(threonine)-L-alaninyl-amino-7-methyl-5,7-dihydro-6H-dibenz[b,d]azepin-6-one 5-(S)-(N'-(D-valinyl)-L-alaninyl-amino-7-methyl-5,7-dihydro-6H-dibenz[b,d]azepin-6-one 5-(S)-(N'-(phenylglycinyl)-L-alaninyl-amino-7-methyl-5,7-dihydro-6H-dibenz[b,d]azepin-6-one 5-(S)-(N"-(S)-phenylglycinyl)-N'-L-alaninyl]amino-1-methyl-5-phenyl-1,3,4,5-tetrahydro-2H-1,5-benzodiazepin-2-one 5-(S)-[(N"-L-valinyl)-N'-L-alaninyl]amino-1-methyl-5-phenyl-1,3,4,5-tetrahydro-2H-1,5-benzodiazepin-2-one 5-(S)-(N'-(thiomorpholinylureylenyl)-L-alaninyl)-amino-7-methyl-5,7-dihydro-6H-dibenz[b,d]azepin-6-one 5-(S)-(N'-(2(R/S)-hydroxybutylureylenyl)-L-alaninyl)-amino-7-methyl-5,7-dihydro-6H-dibenz[b,d]azepin-6-one 5-(S)-(N'-2,2,2-trifluoroethylureylenyl)-L-alaninyl)-amino-7-methyl-5,7-dihydro-6H-dibenz[b,d]azepin-6-one 5-(S)-(N'-(4R/S)-cyclohexylureylenyl)-L-alaninyl)-amino-7-methyl-5,7-dihydro-6H-dibenz[b,d]azepin-6-one 5-(S)-(N'-(1R)-hydroxymethyl-3-methylthiopropylureylenyl)-L-alaninyl)-amino-7-methyl-5,7-dihydro-6H-dibenz[b,d]azepin-6-one 5-{N'-(2-hydroxy-2-methylpropionyl)-L-alaninyl}-amino-7-methyl-5,7-dihydro-6H-dibenz[b,d]azepin-6-one 5-{N'-(2-hydroxy-2-methylbutanoyl)-L-alaninyl}-amino-7-methyl-5,7-dihydro-6H-dibenz[b,d]azepin-6-one 3-[N'-(2-thioacetyl-3-methyl-butanoyl)-L-alaninyl]-amino-2,3-dihydro-1-methyl-5-phenyl-1H-1,4-benzodiazepin-2-one 5-(S)-[N'-(2-thioacetyl-3-methyl-butanoyl)-L-alaninyl]-amino-7-methyl-5,7-dihydro-6H-dibenz[b,d]azepin-6-one 5-(S)-[N'-(L-Trifluoromethylphenylglycinyl)-L-alaninyl]-amino-7-methyl-5,7-dihydro-6H-dibenz[b,d]azepin-6-one 5-(S)-[N'-(L-N-methyl-valinyl)-L-alaninyl]-amino-7-methyl-5,7-dihydro-6H-dibenz[b,d]azepin-6-one 5-(S)-(N''-(3,5-difluorophenylglycinyl)-N'-L-alaninyl]amino-2,4-dioxo-1-methyl-5-phenyl-2,3,4,5-tetrahydro-2H-1,5-benzodiazepine hydrochloride 5-(S)-(N''-(3,5-difluorophenylglycinyl)-N'-L-alaninyl]amino-2,4-dioxo-1-methyl-5-phenyl-2,3,4,5-tetrahydro-2H-1,5-benzodiazepine hydrochloride 5-(S)-[N'-(Hexafluorovalinyl)-L-alaninyl]-amino-7-methyl-5,7-dihydro-6H-dibenz[b,d]azepin-6-one 3-[N'-(2-mercapto-3-methyl-butanoyl)-L-alaninyl]-amino-2,3-dihydro-1-methyl-5-phenyl-1H-1,4-benzodiazepin-2-one 5-(S)-[N'-(2-mercapto-3-methylbutanoyl)-L-alaninyl]-amino-7-methyl-5,7-dihydro-6H-dibenz[b,d]azepin-6-one Additional examples of suitable compounds include:

5-(S)-[N'-(2-Amino-3,3,3-trifluoromethylbutyryl)-L-alaninyl]-amino-7-methyl-5,7-dihydro-6H-dibenz[b,d]azepin-6-one 5-(S)-[N'-(2-amino-5,5,5-trifluoropentanyl)-L-alaninyl]-amino-7-methyl-5,7-dihydro-6H-dibenz[b,d]azepin-6-one 5-(S)-[N'-(2-amino-4,4,4-trifluorobutyryl)-L-alaninyl]-amino-7-methyl-5,7-dihydro-6H-dibenz[b,d]azepin-6-one 1-(S)-[N'-(2-Amino-3,3,3-trifluorobutyryl)-L-alaninyl]-amino-3-methyl-4,5,6,7-tetrahydro-2H-3-benzazepin-2-one 1-(S)-[N'-(2-Amino-5,5,5-trifluoropentanoyl)-L-alaninyl]-amino-3-methyl-4,5,6,7-tetrahydro-2H-3-benzazepin-2-one 1-(S)-[N'-(2-Amino-4,4,4-trifluorobutyryl)-L-alaninyl]-amino-3-methyl-4,5,6,7-tetrahydro-2H-3-benzazepin-2-one 1-(S)-[N'-(2-Aminobutyryl)-L-alaninyl]-amino-3-methyl-4,5,6,7-tetrahydro-2H-3-benzazepin-2-one 1-(S)-[N'-(Hexafluorovalinyl)-L-alaninyl]-amino-3-methyl-4,5,6,7-tetrahydro-2H-3-benzazepin-2-one 1-(S)-[N'-(L-2-Aminobutyryl)-L-alaninyl]-amino-3-(2-methylpropyl)-4,5,6,7-tetrahydro-2H-3-benzazepin-2-one Preferred cyclic groups defined by W and —C(H)$_p$C(=X)— include cycloalkyl, lactone, lactam, benzepinone, dibenzazepinone and benzodiazepine groups. In one preferred embodiment, the cyclic group defined by W and —C(H)$_p$C(=X)—, forms a cycloalkyl group of the formula:

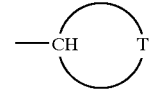

wherein T is selected from the group consisting of alkylene and substituted alkylene.

A preferred cycloalkyl group is represented by the formula:

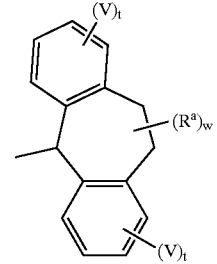

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, alkaryl, aryl, aryloxy, carboxyl, carboxylalkyl, cyano, halo, nitro, heteroaryl, thioalkoxy, substituted thioalkoxy, trihalomethyl and the like; each R$^a$ is independently selected from the group consisting of alkyl, substituted alkyl, alkoxy, substituted alkoxy, amino, substituted amino carboxyl, carboxyl alkyl, cyano, halo, and the like; t is an integer from 0 to 4; and w is an integer from 0 to 3.

Preferably t is an integer from 0 to 2 and, more preferably, is an integer equal to 0 or 1.

In another preferred embodiment, the cyclic group defined by W, together with —C(H)$_p$C(=X)— is a ring of the formula:

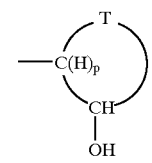

or

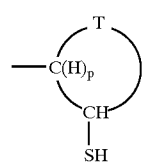

wherein p is zero or one, T is selected from the group consisting of alkylene, substituted alkylene, alkenylene, substituted alkenylene, —(R$^{21}$Z)$_q$R$^{21}$— and —ZR$^{21}$—, where Z is a substituent selected from the group consisting of —O—, —S— and >NR$^{20}$, each R$^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each R$^{21}$ is independently alkylene, substituted alkylene, alkenylene and substituted alkenylene with the proviso that when Z is —O— or —S—, any unsaturation in the alkenylene and substituted alkenylene does not involve participation of the —O— or —S—, and q is an integer of from 1 to 3.

Particularly preferred alcohol or thiol substituted groups include

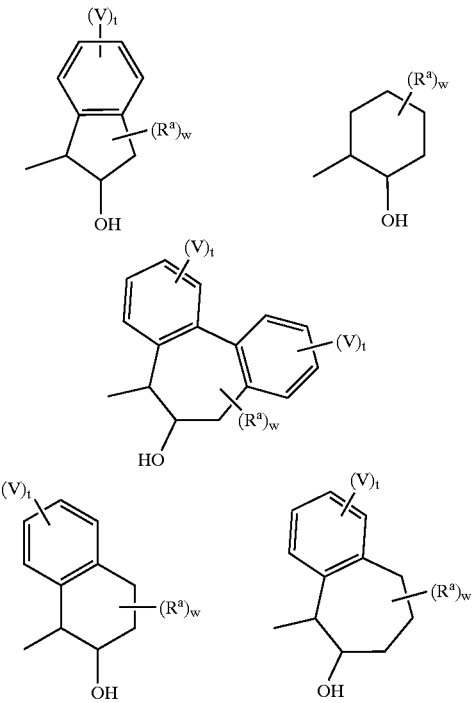

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, alkaryl, aryl, aryloxy, carboxyl, carboxyalkyl, cyano, halo, nitro, heteroaryl, thioalkoxy, substituted thioalkoxy, trihalomethyl and the like; each $R^a$ is independently selected from the group consisting of alkyl, substituted alkyl, alkoxy, substituted alkoxy, amino, substituted amino, carboxyl, carboxyalkyl, cyano, halo, and the like; t is an integer from 0 to 4; and w is an integer from 0 to 3.

Preferably t is an integer from 0 to 2 and, more preferably, is an integer equal to 0 or 1.

Yet another preferred embodiment of the cyclic group defined by W, together with —C(H)$_p$C(=X)—, is a ring of the formula:

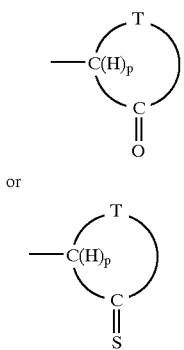

wherein p is zero or one, T is selected from the group consisting of alkylene, substituted alkylene, alkenylene, substituted alkenylene, —(R$^{21}$Z)$_q$R$^{21}$— and —ZR$^{21}$—, where Z is a substituent selected from the group consisting of —O—, —S— and >NR$^{20}$, each R$^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each R$^{21}$ is independently alkylene, substituted alkylene, alkenylene and substituted alkenylene with the proviso that when Z is —O— or —S—, any unsaturation in the alkenylene and substituted alkenylene does not involve participation of the —O— or —S—, and q is an integer of from 1 to 3.

Particularly preferred cyclic ketone and thioketone groups include:

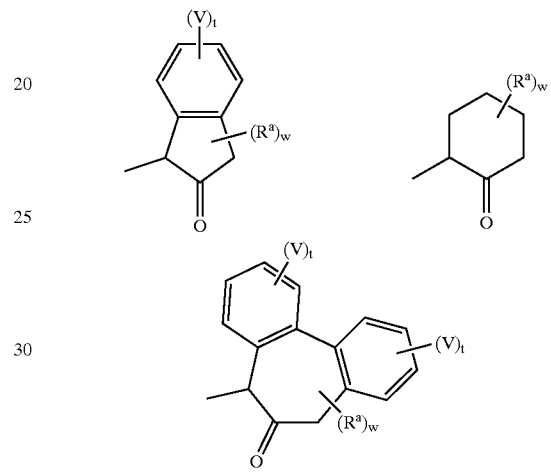

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino aminoacyl, alkaryl, aryl, aryloxy, carboxyl, carboxylalkyl, cyano, halo, nitro, heteroaryl, thioalkoxy, substituted thioalkoxy, trihalomethyl and the like; each $R^a$ is independently selected from the group consisting of alkyl, substituted alkyl, alkoxy, substituted alkoxy, amino, substituted amino carboxyl, carboxyl alkyl, cyano, halo, and the like; t is an integer from 0 to 4; and w is an integer from 0 to 3.

Preferably t is an integer from 0 to 2 and, more preferably, is an integer equal to 0 or 1.

In another preferred embodiment, the cyclic group defined by W, together with —C(H)$_p$C(=X)—, forms a ring of the formula:

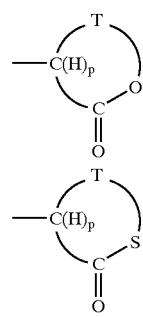

-continued

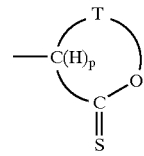

or

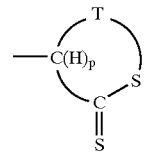

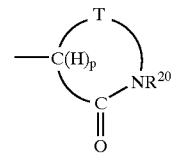

or a thiolactam ring of the formula:

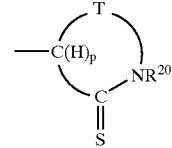

wherein p is zero or one, T is selected from the group consisting of alkylene, substituted alkylene, alkenylene, substituted alkenylene, $-(R^{21}Z)_q R^{21}-$ and $-ZR^{21}-$, where Z is a substituent selected from the group consisting of $-O-$, $-S-$ and $>NR^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when Z is $-O-$ or $-S-$, any unsaturation in the alkenylene and substituted alkenylene does not involve participation of the $-O-$ or $-S-$, and q is an integer of from 1 to 3.

Particularly preferred lactone and thiolactone groups include:

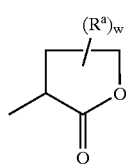 and 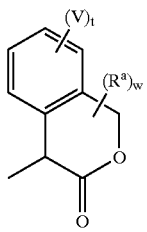

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino aminoacyl, alkaryl, aryl, aryloxy, carboxyl, carboxylalkyl, cyano, halo, nitro, heteroaryl, thioalkoxy, substituted thioalkoxy, trihalomethyl and the like; each $R^a$ is independently selected from the group consisting of alkyl, substituted alkyl, alkoxy, substituted alkoxy, amino, substituted amino carboxyl, carboxyl alkyl, cyano, halo, and the like; t is an integer from 0 to 4; and w is an integer from 0 to 3.

Preferably t is an integer from 0 to 2 and, more preferably, is an integer equal to 0 or 1.

In another preferred embodiment, the cyclic group defined by W and $-C(H)_p C(=X)-$, forms a lactam ring of the formula:

wherein p is zero or one, T is selected from the group consisting of alkylene, substituted alkylene, alkenylene, substituted alkenylene, $-(R^{21}Z)_q R^{21}-$ and $-ZR^{21}-$, where Z is a substituent selected from the group consisting of $-O-$, $-S-$ and $>NR^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when Z is $-O-$ or $-S-$, any unsaturation in the alkenylene and substituted alkenylene does not involve participation of the $-O-$ or $-S-$, and q is an integer of from 1 to 3.

Particularly preferred lactam and thiolactam groups include:

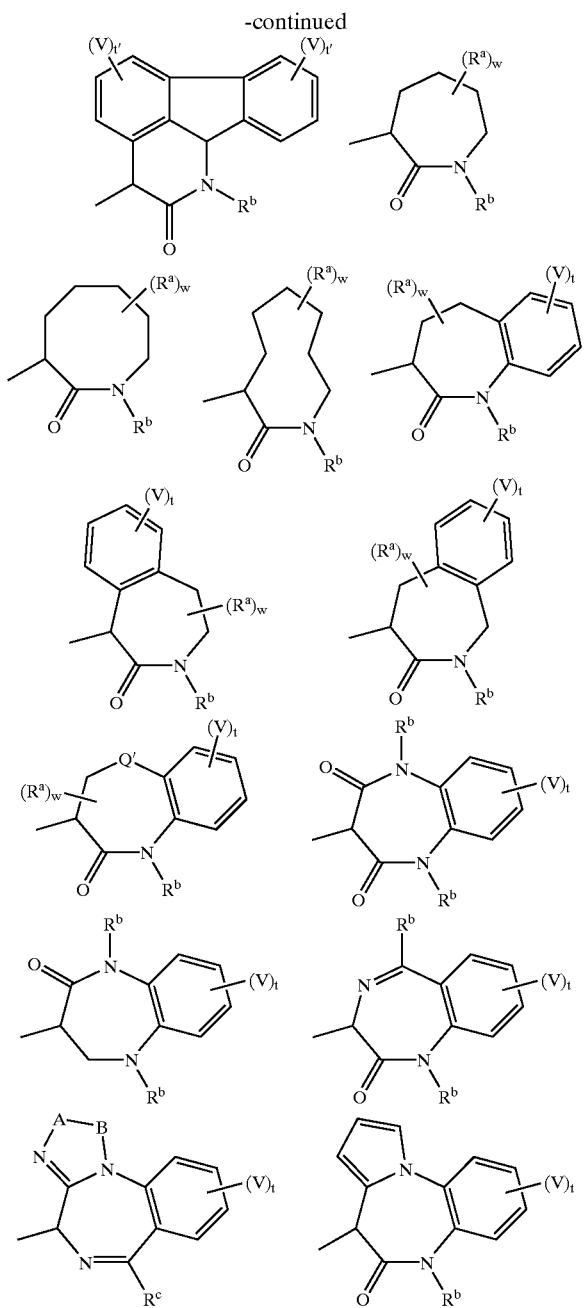

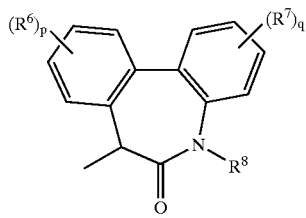

wherein A—B is selected from the group consisting of alkylene, alkenylene, substituted alkylene, substituted alkenylene and —N=CH—; Q is oxygen or sulfur; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino aminoacyl, alkaryl, aryl, aryloxy, carboxyl, carboxylalkyl, cyano, halo, nitro, heteroaryl, thioalkoxy, substituted thioalkoxy, trihalomethyl and the like; each $R^a$ is independently selected from the group consisting of alkyl, substituted alkyl, alkoxy, substituted alkoxy, amino, substituted amino carboxyl, carboxyl alkyl, cyano, halo, and the like; $R^b$ is selected from the group consisting of hydrogen, alkyl, substituted alkyl, alkenyl, substituted alkenyl, alkynyl, substituted alkynyl, acyl, aryl, heteroaryl, heterocyclic, and the like; $R^c$ is selected from the group consisting of alkyl, substituted alkyl, alkenyl, substituted alkenyl, aryl, heteroaryl, heterocyclic, thioalkoxy, substituted amino, cycloalkyl, and substituted cycloalkyl; t is an integer from 0 to 4; t is an integer from 0 to 3; and w is an integer from 0 to 3.

Preferably t is an integer from 0 to 2 and, more preferably, is an integer equal to 0 or 1.

In one preferred embodiment of this invention, W is a cyclic group of the formula:

wherein
each $R^6$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;

each $R^7$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;

$R^8$ is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;

p is an integer from 0 to 4; q is an integer from 0 to 4.

Preferably, $R^6$ and $R^7$ are independently selected from the group consisting of alkoxy, substituted alkoxy, alkyl, substituted alkyl, amino, substituted amino, carboxyl, carboxyalkyl, cyano, halo, nitro, thioalkoxy and substituted thioalkoxy. More preferably, when present, $R^6$ and $R^7$ are fluoro.

$R^8$ is preferably selected from the group consisting of hydrogen, alkyl, substituted alkyl, acyl, aryl, cycloalkyl and substituted cycloalkyl. More preferably, $R^8$ is selected from the group consisting of hydrogen, alkyl, substituted alkyl and cycloalkyl.

Particularly preferred $R^8$ substituents include, by way of example, hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, cyclohexyl, and the like.

In another preferred embodiment of this invention, W is a cyclic group of the formula:

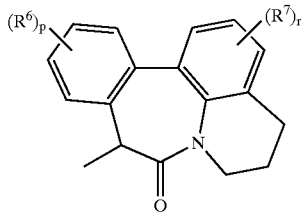

wherein $R^6$, $R^7$, and p are as defined herein and r is an integer from 0 to 3.

In still another preferred embodiment of this invention, W is a cyclic group of the formula:

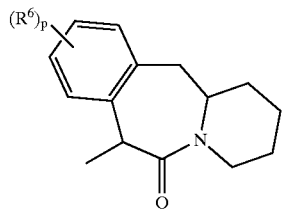

wherein $R^6$ and p are as defined herein.

In yet another preferred embodiment of this invention, W is a cyclic ring of the formula:

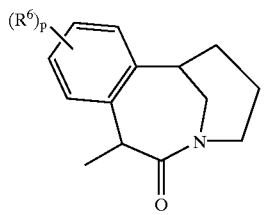

wherein $R^6$ and p are as defined herein.

In still another preferred embodiment of this invention, W is a cyclic ring of the formula:

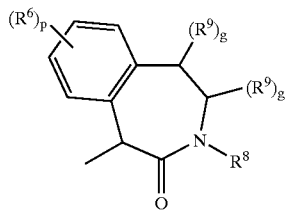

wherein $R^6$, $R^8$ and p are as defined herein; and each $R^9$ is independently selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic; and g is an integer from 0 to 2.

When present, $R^9$ is preferably alkyl or substituted alkyl.

In another preferred embodiment of this invention, W is a cyclic ring of the formula:

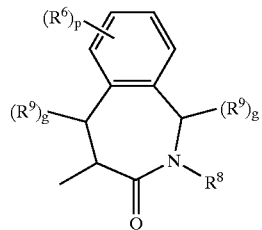

wherein $R^6$, $R^8$, $R^9$, g and p are as defined herein.

In yet another preferred embodiment of this invention, W is a cyclic ring of the formula:

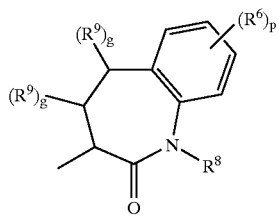

wherein $R^6$, $R^8$, $R^9$, g and p are as defined herein.

In still another preferred embodiment of this invention, W is a cyclic ring of the formula:

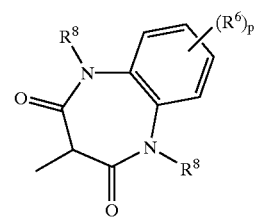

wherein $R^6$, each $R^8$ and p are as defined herein.

In another preferred embodiment of this invention, W is a cyclic ring of the formula:

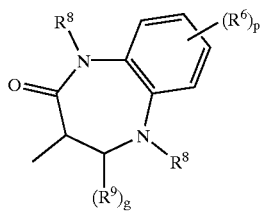

wherein $R^6$, each $R^8$, $R^9$, g and p are as defined herein.

In another preferred embodiment of this invention, W is a cyclic ring of the formula:

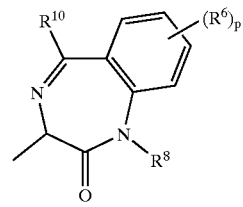

wherein $R^6$, $R^8$ and p are as defined herein; and
$R^{10}$ is selected from the group consisting of alkyl, substituted alkyl, alkenyl, substituted alkenyl, alkynyl, substituted alkynyl, substituted amino, aryl, cycloalkyl, substituted cycloalkyl, cycloalkenyl, substituted cycloalkenyl, heteroaryl, heterocyclic, thioalkoxy and substituted thioalkoxy.

In another preferred embodiment of this invention, W is a cyclic ring of the formula:

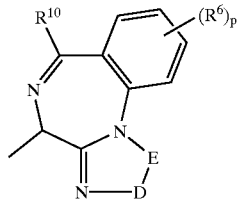

wherein $R^6$, $R^{10}$ and p are as defined herein; and
D—E is selected from the group consisting of alkylene, alkenylene, substituted alkylene, substituted alkenylene and —N=CH—.

In another preferred embodiment of this invention, W is a cyclic ring of the formula:

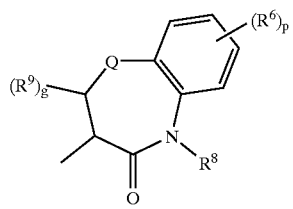

wherein $R^6$, $R^8$, $R^9$, g and p are as defined herein; and
Q is oxygen, sulfur, —S(O)— or —S(O)—.

In another preferred embodiment of this invention, W is a cyclic ring of the formula:

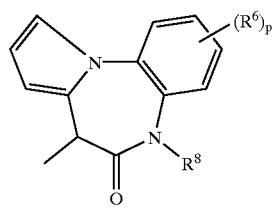

wherein $R^6$, $R^8$ and p are as defined herein.

In another preferred embodiment of this invention, W is a cyclic ring of the formula:

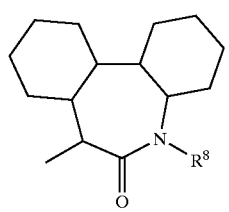

wherein $R^8$ is as defined herein.

In the above formulae, preferably each $R^6$ is independently selected from the group consisting of alkyl, substituted alkyl, alkoxy and halo; each $R^7$ is independently selected from the group consisting of alkyl, substituted alkyl, alkoxy and halo; each $R^8$ is independently selected from the group consisting of alkyl, substituted alkyl, cycloalkyl and aryl; each $R^9$ is independently selected from the group consisting of alkyl, substituted alkyl, cycloalkyl and aryl; and g, p, q and r are 0 or 1. More preferably, g, p, q and r are 0.

In another preferred embodiment, the cyclic group defined by W, together with —C(H)$_p$C(=X)—, forms a ring of the formula:

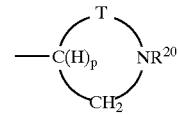

wherein p is zero or one, T is selected from the group consisting of alkylene, substituted alkylene, alkenylene, substituted alkenylene, —(R$^{21}$Z)$_q$R$^{21}$— and —ZR$^{21}$—, where Z is a substituent selected from the group consisting of —O—, —S— and >NR$^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when Z is —O— or —S—, any unsaturation in the alkenylene and substituted alkenylene does not involve participation of the —O— or —S—, and q is an integer of from 1 to 3.

A still further preferred embodiment is directed to a ring group defined by W, together with —C(H)$_p$C(=X)—, of the formula:

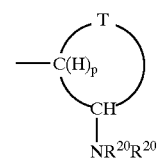

wherein p is zero or one, T is selected from the group consisting of alkylene, substituted alkylene, alkenylene, substituted alkenylene, —(R$^{21}$Z)$_q$R$^{21}$— and —ZR$^{21}$—, where Z is a substituent selected from the group consisting of —O—, —S— and >NR$^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when Z is —O— or —S—, any unsaturation in the alkenylene and substituted alkenylene does not involve participation of the —O— or —S—, and q is an integer of from 1 to 3.

In another preferred embodiment, $R^{15}$ is H, $R^1$ is alkyl or aryl, Rb is alkyl, substituted alkyl, cycloalkyl or aryl, $R^2$ is methyl, and the compound is a compound of Formulas I, II or VI.

This invention also provides for novel pharmaceutical compositions comprising a pharmaceutically inert carrier and one or more of the compounds described in Formulas I–VI above.

Still further, this invention provides for novel compounds of Formulas I–VI:

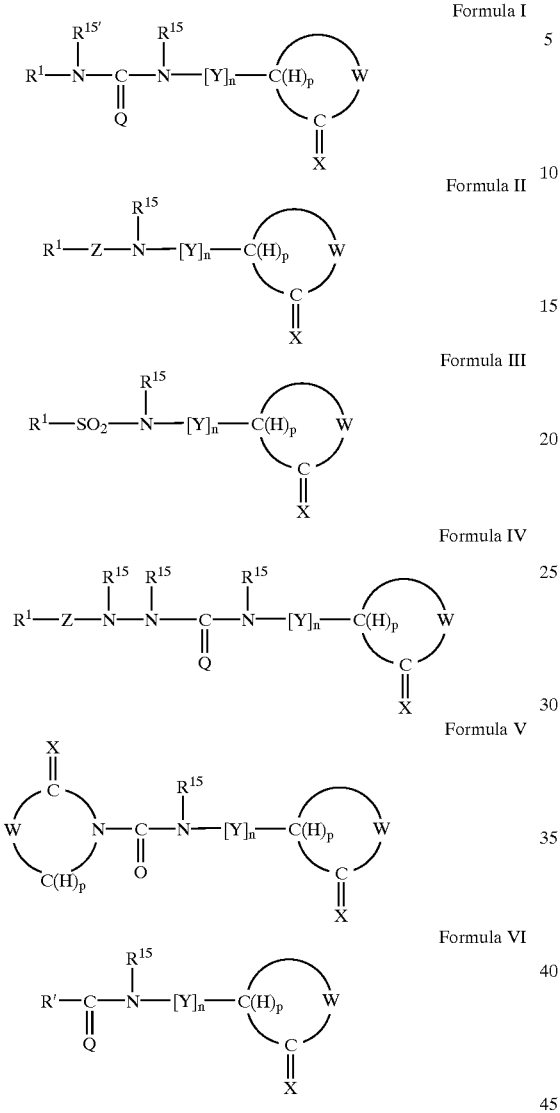

Formula I

Formula II

Formula III

Formula IV

Formula V

Formula VI wherein R$^1$ is selected from the group consisting of alkyl, alkenyl, alkynyl, cycloalkyl, cycloalkenyl, substituted alkyl, substituted alkenyl, substituted alkynyl, substituted cycloalkyl, substituted cycloalkenyl, aryl, heteroaryl and heterocyclic;

R' is selected from the group consisting of aryl, cycloalkyl, substituted cycloalkyl, cycloalkenyl, substituted cycloalkenyl, heteroaryl, heterocyclic, —CH$_3$, —CH=CH$_2$, —CH=CHR$^1$, —CH=CR$^1$R$^1$, —CR$^1$=CH$_2$, —CR$^1$=CHR$^1$, —CR$^1$=CR$^1$R$^1$, —C=CH and —C=CR$^1$; with the proviso that when R' is heteroaryl or heterocyclic, there is no N in R' at a position beta to the C=Q group;

Q is S or O;

R$^{15}$ is selected from the group consisting of hydrogen, alkyl, substituted alkyl, aryl, heterocyclic and heteroaryl;

R$^{15'}$ is selected from the group consisting of hydrogen, hydroxyl, alkyl, substituted alkyl, aryl, heterocyclic and heteroaryl;

W, together with —C(H)$_p$C(=X)—, forms a cycloalkyl, cycloalkenyl, heterocyclic, substituted cycloalkyl, or substituted cycloalkenyl group wherein each of said cycloalkyl, cycloalkenyl, heterocyclic, substituted cycloalkyl or substituted cycloalkenyl group is optionally fused to form a bi- or multi-fused ring system (preferably no more than 5 fused rings) with one or more ring structures selected from the group consisting of cycloalkyl, cycloalkenyl, heterocyclic, aryl and heteroaryl group which, in turn, each of such ring structures are optionally substituted with 1 to 4 substituents selected from the group consisting of hydroxyl, keto, thioketo, halo, alkoxy, substituted alkoxy, thioalkoxy, substituted thioalkoxy, nitro, cyano, carboxyl, carboxyl esters, alkyl, substituted alkyl, alkenyl, substituted alkenyl, alkynyl, substituted alkynyl, amino, substituted amino, —NHC(O)R$^4$, —NHSO$_2$R$^4$, —C(O)NH$_2$, —C(O)NHR$^4$, —C(O)NR$^4$R$^4$, —S(O)R$^4$, —S(O)$_2$R$^4$, —S(O)$_2$NHR$^4$ and —S(O)$_2$NR$^4$R$^4$, where each R is independently selected from the group consisting of alkyl, substituted alkyl, aryl and heteroaryl;

X is selected from the group consisting of oxo (=O), thiooxo (=), hydroxyl (—H, —OH), thiol (H, —SH) and hydro (H,H);

Y is represented by the formula:

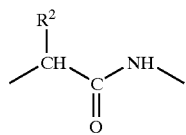

wherein each R$^2$ is independently selected from the group consisting of alkyl, substituted alkyl, alkenyl, substituted alkenyl, alkynyl, substituted alkynyl, cycloalkyl, aryl, heteroaryl and heterocyclic;

Z is represented by the formula —T—C(X')(X")C(O)— where T is selected from the group consisting of a bond covalently linking R$^1$ to —C(X')(X")—, oxygen, sulfur, and —NR$^5$ where R$^5$ is hydrogen, acyl, alkyl, substituted alkyl, aryl, heterocyclic or heteroaryl group;

R$^{5'}$ is hydrogen, alkyl, substituted alkyl, aryl, heterocyclic or heteroaryl group;

X' and X" are independently selected from the group consisting of hydrogen, fluoro, alkyl, substituted alkyl, aryl, heteroaryl, heterocyclic, —OR$^{5'}$, —SR$^5$, —N(R$^5$)$_2$, —N(CO)OR$^{15}$ and —N$_3$, with the proviso that at least one of X' or X" is other than hydrogen, hydroxy or fluoro, and with the further proviso that both X' and X" cannot both be —OR$^{5'}$, —SR$^5$, —N(R$^5$)$_2$, —N(CO)OR$^{15}$ and —N$_3$; further, neither X' and X" can be —OR$^{5'}$, —SR$^5$, —N(R$^5$)$_2$, —N(CO)OR$^{15}$ or —N$_3$ when T is other than a bond covalently linking R$^1$ to —C(X')(X")—;

n is an integer equal to 1 or 2;

p is an integer equal to 0 or 1 such that when p is zero, the ring defined by W and —C(H)$_p$C(=X)— is unsaturated at the carbon atom of ring attachment to Y and when p is one, the ring is saturated at the carbon atom of ring attachment to Y, with the following provisos:

when R1 is 2-propylpentanoyl, R2 is methyl, and R15 is hydrogen, then W, together with >CH and >C=X, does not form a 2,3-dihydro-1-methyl-5-phenyl-1H-1,4-benzodiazepin-2-one when R1 is 3,5-difluorobenzoyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is trans-cinnamyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is 2-(4-chlorophenoxy)-2-methylpropionyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is α-methoxyphenylacetyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is diphenylacetyl, R2 is methyl, and R15 is hydrogen, then W, together with >CH and >C=X, does not form a 2,3-dihydro-1-methyl-5-(2-pyridyl)-1H-1,4-benzodiazepin-2-one when R1 is α-methoxyphenylacetyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is α-hydroxy-diphenylacetyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is diphenylacetyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is 2-(chlorophenoxy)-2-methylpropionyl, R2 is methyl, and R15 is hydrogen, then W, together with >CH and >C=X, does not form a 2,3-dihydro-1-(3,3-dimethyl-2-oxobutyl)-5-(2-pyridyl)-1H-1,4-benzodiazepin-2-one when R1 is diphenylacetyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1 is 3,5-difluorobenzoyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1 is trans-cinnamyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1 is 2-(4-chlorophenoxy)-2-methylpropionyl, R2 is methyl, and R15 is hydrogen, then W, together with >CH and >C=X, does not form a 2,3-dihydro-1-(2-N,N-diethylaminoethyl)-5-(2-pyridyl)-1H-1,4-benzodiazepin-2-one when R1—N(R15) is (2,5-dimethoxyphenyl)ureylenyl and R2 is methyl, then W, together with >CH and >C=X, does not form a 2,3-dihydro-1-methyl-5-phenyl-1H-1,4-benzodiazepin-2-one when R1 is D,L-2-pyrrolidinone-5-yl, R2 is methyl, and R15 is hydrogen, then W, together with >CH and >C=X, does not form a 7-methyl-5,7-dihydro-6H-dibenz[b,d]azepin-6-one.

As is appreciated by the skilled person, compounds of the present invention exist as isomers. Herein, the Cahn-Prelog-Ingold designations of (R)- and (S)- and, for amino acid derived portions of the compounds, the L- and D- designations of stereochemistry relative to the isomers of glyceraldehyde are used to refer to specific isomers where designated. The specific isomers can be prepared by stereospecific synthesis or can be resolved and recovered by techniques known in the art, such as, chromatography on chiral stationary phases, and fractional recrystallization of addition salts formed by reagents used for that purpose. Useful methods of resolving and recovering specific stereoisomers are known in the art and described, for example, in Stereochemistry of Organic Compounds, E. L. Eliel and S. H. Wilen (Wiley-Interscience 1994), Enantiomers, Racemates and Resolutions, J. Jacques, A. Collet and S. J. Wilen (Wiley-Interscience 1981), and European Patent Application No. EP-A-838448, published Apr. 29, 1998. It is to be understood that the invention extends to all of the isomeric forms of the compounds of the present invention, including the diastereomeric, enantiomeric and racemic forms of the compounds.

Preferred compounds described herein include those set forth in the tables below:

TABLE 1-1

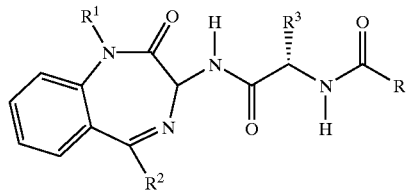

| Ex. | R | $R^1$ | $R^2$ | $R^3$ |
|---|---|---|---|---|
| 1-1 | 2-thiophene-yl | methyl | phenyl | methyl |
| 1-2 | 2-furanyl | methyl | phenyl | methyl |
| 1-3 | cyclobutyl | methyl | phenyl | methyl |
| 1-4 | 1-phenyl cyclopropyl | methyl | phenyl | methyl |
| 1-5 | cyclohexyl | methyl | phenyl | methyl |
| 1-6 | 2-benzofuranyl | methyl | phenyl | methyl |
| 1-7 | 5-chloro benzofuran-2-yl | methyl | phenyl | methyl |
| 1-8 | 5,5-dimethyl-butyrolactone-4-yl | methyl | phenyl | methyl |
| 1-9 | 3-furoyl | methyl | phenyl | methyl |
| 1-10 | 4-methyl sulfonyl phenyl | methyl | phenyl | methyl |
| 1-11 | cis-2-phenyl | methyl | phenyl | methyl |
| 1-12 | 5-methyl sulfonyl thiophen-2-yl | methyl | phenyl | methyl |
| 1-13 | 1,8-dimethyl-6-hydroxy-bicyclo[2.2.2]-oct-2-yl | methyl | phenyl | methyl |
| 1-14 | 1,4-benzo dioxan-2-yl | methyl | phenyl | methyl |
| 1-15 | tetrahydro furan-3-yl | methyl | phenyl | methyl |
| 1-16 | cyclohex-3-ene-yl | methyl | phenyl | phenyl |
| 1-17 | cyclopropyl | methyl | phenyl | phenyl |
| 1-18 | 3,5-difluoro phenyl | methyl | phenyl | phenyl |
| 1-19 | 2-pyrrolidinone- | methyl | 2-pyridyl | methyl |
| 1-21 | 1-phenyl | methyl | 2-pyridyl | methyl |
| 1-22 | 1-phenyl cyclopropyl | 2-oxo-3,3-dimethylbutyl | 2-pyridyl | methyl |
| 1-23 | 3,5-difluorophenyl | 2-oxo-3,3-dimethylbutyl | 2-pyridyl | methyl |

TABLE 1-1-continued

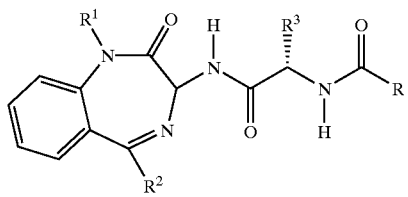

| Ex. | R | R¹ | R² | R³ |
|---|---|---|---|---|
| 1-24 | 2-pyrrolidinone-5-yl | 2-oxo-3,3-dimethylbutyl | 2-pyridyl | methyl |
| 1-26 | 1-phenyl cyclopropyl | 2-diethyl aminoethyl | 2-pyridyl | methyl |
| 1-27 | 4-methylphenyl | methyl | phenyl | phenyl |
| 1-28 | 4-methylphenyl | methyl | phenyl | methyl |
| 1-29 | 3-pyridyl | methyl | phenyl | methyl |
| 1-30 | 2-naphthyl | methyl | phenyl | methyl |
| 1-31 | 1-naphthyl | methyl | phenyl | methyl |
| 1-32 | 4-chloro-thiophene-yl | methyl | phenyl | methyl |
| 1-33 | 4-cyanophenyl | methyl | phenyl | methyl |
| 1-34 | tetrahydrofuran-2-yl | methyl | phenyl | methyl |
| 1-35 | 3,5-difluoro phenyl | methyl | phenyl | methyl |
| 1-36 | cyclohex-3-ene-yl | methyl | phenyl | methyl |
| 1-37 | 1,2,3,4-tetrahydro naphth-2-yl | methyl | phenyl | methyl |
| 1-38 | cyclopentyl | methyl | phenyl | methyl |
| 1-39 | 4-trifluoro methyl cyclohexyl | methyl | phenyl | methyl |
| 1-40 | bicyclo[2.2.1]hept-2-yl | methyl | phenyl | methyl |
| 1-41 | bicyclo[2.2.1]hept-5-ene-2-yl | methyl | phenyl | methyl |
| 1-42 | 2,2-dichloro cyclopropyl | methyl | phenyl | methyl |
| 1-43 | cycloheptyl | methyl | phenyl | methyl |
| 1-44 | 1-(2,4-dichloro phenyl)-cyclopropyl | methyl | phenyl | methyl |
| 1-45 | cis-2-methyl cyclopropyl | methyl | phenyl | methyl |
| 1-46 | 1-(4-chloro phenyl) cyclobutyl | methyl | phenyl | methyl |
| 1-47 | 2-phenylphenyl | methyl | phenyl | methyl |
| 1-48 | 1,2-dihydro-1-oxo-2-phenyl-4-isoquinolinyl | methyl | phenyl | methyl |
| 1-49 | bicyclo[3.3.1]non-6-ene-3-yl | methyl | phenyl | methyl |
| 1-50 | cyclopropyl | methyl | phenyl | methyl |
| 1-51 | tetrahydro furan-2-yl | methyl | phenyl | methyl |
| 1-52 | 3,5-difluoro phenyl | methyl | phenyl | methyl |
| 1-53 | cyclohex-3-ene-yl | methyl | phenyl | methyl |
| 1-54 | 1,2,3,4-tetrahydro naphth-3-yl | methyl | phenyl | methyl |
| 1-55 | cyclopentyl | methyl | phenyl | methyl |

TABLE 1-2

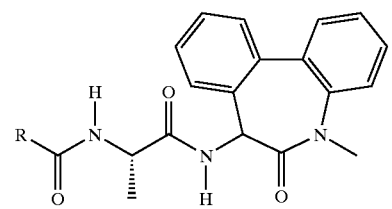

| Ex. | R |
|---|---|
| 1-56 | tetrahydrofuran-3-yl |
| 1-57 | cyclopropyl |
| 1-59 | bicyclo[2.2.1]heptan-2-yl |
| 1-60 | tetrahydrofuran-2-yl |
| 1-61 | cyclopentyl |
| 1-62 | thiophene-2-yl |

TABLE 2-1

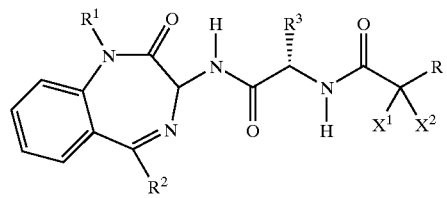

| Ex. | R | X¹ | X² | R¹ | R² | R³ |
|---|---|---|---|---|---|---|
| 2-1 | benzyl | phenyl | H | methyl | phenyl | methyl |
| 2-2 | phenyl | ethyl | H | methyl | phenyl | methyl |
| 2-4 | phenyl | isopropyl | H | methyl | phenyl | methyl |
| 2-5 | butyl | ethyl | H | methyl | phenyl | methyl |
| 2-6 | ethyl | methyl | H | methyl | phenyl | methyl |
| 2-7 | 2,2,2-trifluoro ethyl | methyl | H | methyl | phenyl | methyl |
| 2-8 | phenyl | phenyl | H | methyl | phenyl | phenyl |
| 2-9 | 4-chloro phenyl | methyl | H | methyl | phenyl | methyl |
| 2-10 | 4-chloro phenyl | methyl | methyl | methyl | phenyl | methyl |
| 2-11 | phenyl | methyl | hydroxyl | methyl | phenyl | methyl |
| 2-12 | phenyl | phenyl | hydroxyl | methyl | 2-pyridyl | methyl |
| 2-15 | phenyl | phenyl | hydroxyl | 2-oxo-3,3- | 2-pyridyl | methyl |
| 2-17 | phenyl | phenyl | hydroxyl | 2-diethyl amino ethyl | 2-pyridyl | methyl |
| 2-18 | 3,5-difluoro phenyl | methyl | hydroxyl | methyl | phenyl | methyl |
| 2-19 | 3,5-difluoro phenyl | methyl | hydroxyl | methyl | phenyl | methyl |

TABLE 2-2

| Ex | R | R¹ | X¹ | X² |
|---|---|---|---|---|
| 2-20 | phenyl | methyl | phenyl | H |
| 2-21 | H | methyl | H | H |
| 2-22 | propyl | methyl | methyl | H |
| 2-23 | phenyl | methyl | hydroxymethyl | H |
| 2-24 | ethyl | methyl | ethyl | H |
| 2-25 | methyl | methyl | methyl | methyl |
| 2-26 | phenyl | methyl | phenyl | H |
| 2-27 | H | phenyl | H | H |
| 2-28 | isopropyl | methyl | thioacetyl | H |
| 2-29 | isopropyl | methyl | thio | H |

TABLE 2-3

| Ex. | R | X¹ | X² |
|---|---|---|---|
| 2-30 | phenyl | methyl | H |
| 2-31 | butyl | methyl | H |
| 2-32 | phenyl | phenyl | H |
| 2-33 | phenyl | methyl | hydroxyl |
| 2-34 | phenyl | hydroxyl | methyl |
| 2-35 | methyl | hydroxyl | methyl |
| 2-36 | ethyl | hydroxyl | methyl |
| 2-37 | isopropyl | thioacetyl | H |
| 2-38 | H | H | H |
| 2-39 | isopropyl | thiol | H |

TABLE 3-1

| Ex. | R¹ | R² |
|---|---|---|
| 3-1 | phenyl | methyl |
| 3-2 | 2-pyridyl | methyl |

TABLE 3-2

| Ex. | R |
|---|---|
| 3-5 | Methyl |

TABLE 4-1

| Ex. | R | R¹ | R² | R³ | R⁴ |
|---|---|---|---|---|---|
| 4-1 | phenyl | methyl | ethyl | H | phenoxy |
| 4-2 | phenyl | methyl | phenyl | H | methoxy |
| 4-3 | phenyl | methyl | methyl | methyl | 4-chlorophenoxy |
| 4-4 | phenyl | methyl | methyl | H | phenoxy |
| 4-5 | phenyl | methyl | 3,5-difluoro phenyl | H | methoxy |
| 4-6 | phenyl | methyl | 3,5-difluoro phenyl | H | methoxy |
| 4-7 | phenyl | methyl | methyl | H | 4-hydroxyphenoxy |
| 4-8 | phenyl | methyl | methyl | H | 4-trifluoromethoxy phenoxy |
| 4-9 | phenyl | methyl | methyl | H | 4-phenylphenoxy |
| 4-10 | 2-pyridyl | 2-(diethyl amino) ethyl | phenyl | H | methoxy |
| 4-16 | phenyl | methyl | methyl | methyl | 4-cyano phenoxy |

TABLE 5-1

| Ex. | R | R' | X |
|---|---|---|---|
| 5-1 | trans-2-phenylcyclopropyl | H | O |
| 5-2 | 3,4-dichlorophenyl | H | O |
| 5-3 | 2-propenyl | H | O |
| 5-4 | (1-naphthyl)ethyl | H | O |
| 5-5 | 2,6-diisopropylphenyl | H | O |
| 5-6 | 3-[(trifluoromethyl)phenyl | H | O |
| 5-7 | phenyl | H | O |

TABLE 5-1-continued

| Ex. | R | R' | X |
|---|---|---|---|
| 5-8 | (4-ethoxycarbonyl)phenyl | H | O |
| 5-9 | 2-bromophenyl | H | O |
| 5-10 | o-tolyl | H | O |
| 5-11 | 2-ethyl-6-methylphenyl | H | O |
| 5-12 | 2-fluorophenyl | H | O |
| 5-13 | 2,4-difluorophenyl | H | O |
| 5-14 | 2-ethoxyphenyl | H | O |
| 5-15 | 3-acetylphenyl | H | O |
| 5-16 | 3-[(cyano)phenyl | H | O |
| 5-18 | phenethyl | H | O |
| 5-19 | 4-n-butylphenyl | H | O |
| 5-20 | octyl | H | O |
| 5-21 | 4-biphenyl | H | O |
| 5-22 | 4-isopropylphenyl | H | O |
| 5-23 | hexyl | H | O |
| 5-24 | 2-isopropylphenyl | H | S |
| 5-25 | 2,6-difluorophenyl | H | O |
| 5-26 | octadecyl | H | O |
| 5-27 | 4-(trifluoromethoxy)phenyl | H | O |
| 5-28 | 2,4-dichlorophenyl | H | O |
| 5-29 | 3-ethoxycarbonylphenyl | H | O |
| 5-30 | 4-chlorophenyl | H | O |
| 5-31 | 4-butoxyphenyl | H | O |
| 5-32 | 4-phenoxyphenyl | H | O |
| 5-33 | 1-naphthyl | H | O |
| 5-34 | 2-biphenyl | H | O |
| 5-35 | 2-(methylthio)phenyl | H | O |
| 5-36 | 2-ethylphenyl | H | O |
| 5-37 | 3-methoxyphenyl | H | O |
| 5-38 | 3,4,5-trimethoxyphenyl | H | O |
| 5-39 | 2,4,6-trimethylphenyl | H | O |
| 5-40 | 2-methyl-6-t-butylphenyl | H | O |
| 5-41 | 2-(2-thiophene-yl | H | O |

TABLE 5-2

| Ex. | R | R' |
|---|---|---|
| 5-43 | (2-thiophene-yl)ethyl | H |
| 5-44 | phenethyl | H |
| 5-45 | butyl | H |
| 5-46 | benzyl | H |
| 5-47 | ethyl | H |
| 5-48 | 2-hydroxy-2-phenethyl | H |
| 5-49 | hexyl | H |
| 5-50 | cyclohexyl | H |
| 5-51 | isopropyl | H |
| 5-52 | t-butyl | H |
| 5-53 | 1-adamantyl | H |
| 5-54 | 2-methylpropyl | H |

TABLE 5-2-continued

| Ex. | R | R' |
|---|---|---|
| 5-55 | 3-hydroxy-3-phenylethyl | H |
| 5-56 | 3-methylbutyl | H |
| 5-57 | (S)-1-hydroxymethyl-3-methylbutyl | H |
| 5-58 | (1S)-(2S)-1-hydroxymethyl-2-methylbutyl | H |
| 5-59 | 3-chloropropyl | H |
| 5-60 | octyl | H |
| 5-61 | 1,1,3,3-tetramethylbutyl | H |
| 5-62 | (R/S)-1-methylbutyl | H |
| 5-63 | 5-(S)-((N'-(R/S)-1-hydroxymethylbutyl | H |
| 5-64 | (R/S)-1,3-dimethylbutyl | H |
| 5-65 | (R)-1-hydroxymethyl-3-methylbutyl | H |
| 5-66 | (R/S)-2-methylbutyl | H |
| 5-67 | morpholino | H |
| 5-68 | 2-(2-hydroxyethoxy)-ethyl | H |
| 5-69 | piperidinyl | H |
| 5-70 | N"-methyl-N"-butyl | H |
| 5-71 | 1-(R/S)-hydroxymethylcyclopentyl | H |
| 5-72 | 4-hydroxybutyl | H |
| 5-73 | 1-(R/S)-hydroxymethyl-2- | H |
| 5-74 | 2-(R/S)-hydroxycyclohexyl | H |
| 5-75 | isopropyl | OH |
| 5-76 | 1-(benzyl) | OH |
| 5-77 | thiomorpholinyl | H |
| 5-78 | 2(R/S)-hydroxybutyl | H |
| 5-79 | 2,2,2-trifluoroethyl | H |
| 5-80 | (4R/S)-cyclohexyl | H |
| 5-81 | hydroxymethyl-3-methylthiopropyl | H |

TABLE 6-1

| Ex. | R | R' |
|---|---|---|
| 6-1 | phenyl | H |
| 6-2 | 3-fluorophenyl | H |
| 6-3 | benzyl | H |
| 6-4 | butyl | H |
| 6-5 | octyl | H |

TABLE 7-1

| Ex. | R | R' | R" |
|---|---|---|---|
| 7-1 | 3,5-difluorophenyl | NH$_2$ | isopropyl |
| 7-2 | 3,5-difluorophenyl | NH$_2$ | t-butyl |
| 7-3 | isopropyl | NH$_2$ | methyl |
| 7-4 | phenyl | NH$_2$ | methyl |
| 7-5 (Isomer A) | 3,5-difluoro phenyl | NH$_2$ | methyl |
| 7-6 (Isomer B) | 3,5-difluoro phenyl | NH$_2$ | methyl |
| 7-8 | isopropyl | NH$_2$ | methyl |
| 7-9 | phenyl | NH$_2$ | methyl |
| 7-10 (Mixture of isomers) | 3,5-difluorophenyl | NH$_2$ | methyl |
| 7-11 | phenyl | CF$_3$C(O)NH— | methyl |
| 7-12 | isopropyl | NHCH$_3$ | methyl |
| 7-13 | 1-trifluoro methyl-2,2,2-trifluoroethyl | NH$_2$ | methyl |

TABLE 7-2

| Ex. | R | R' |
|---|---|---|
| 7-15 | isopropyl | —NH$_2$ |

TABLE 7-3

| Ex. | R | R' |
|---|---|---|
| 7-17 | phenyl | NH$_2$ |
| 7-18 | isopropyl | NH$_2$ |

TABLE 7-4

| Ex. | R | R' |
|---|---|---|
| 7-19 | 3,5-difluoro phenyl | NH$_2$—HCl |
| 7-20 | 3,5-difluoro phenyl | NH$_2$—HCl |

TABLE 7-5

| Ex. | R |
|---|---|
| 36361 | 1-trifluoromethyl ethyl |
| 36362 | 3,3,3-trifluoropropyl |
| 36363 | 2,2,2-trifluoroethyl |

TABLE 7-6

| Ex. | R | R$^1$ |
|---|---|---|
| 36364 | 1-trifluoromethyl ethyl | methyl |
| 36365 | 3,3,3-trifluoropropyl | methyl |
| 36366 | 2,2,2-trifluoroethyl | methyl |
| 36367 | ethyl | methyl |
| 36368 | 1-(trifluoromethyl)-2,2,2-trifluoroethyl | methyl |
| 36369 | ethyl | isobutyl |

TABLE 8-1

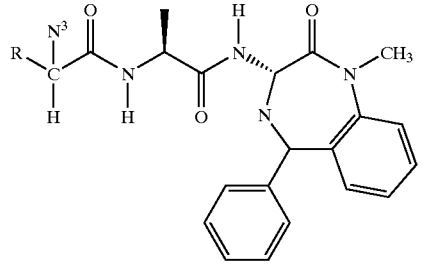

| Ex. | R |
|---|---|
| 8-1 | 3,5-difluorophenyl |

TABLE 9-1

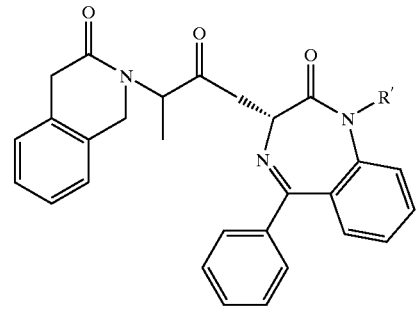

| Ex. | R' |
|---|---|
| 9-1 | methyl |

TABLE 9-2

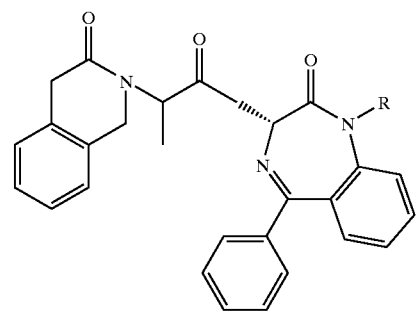

| Ex. | R |
|---|---|
| 9-2 | methyl |

TABLE 10-1

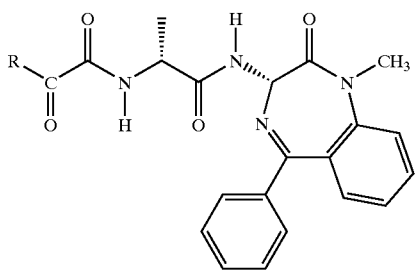

| Ex. | R |
|---|---|
| 10-1 | 3,5-difluorophenylmethyl |

TABLE 10-2

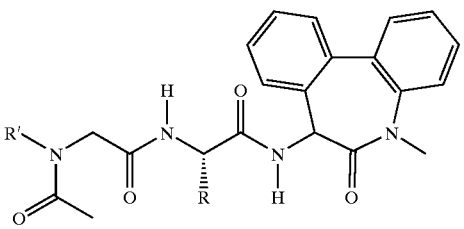

| Ex. | R | R' |
|---|---|---|
| 10-2 | methyl | phenyl |

Also included within the scope of this invention are prodrugs of the compounds of Formulas I–VI described above including acylated forms of alcohols and thiols, aminals of one or more amines, and the like, as well as acid addition salts of amines. This invention is not intended to encompass subject matter disclosed and claimed in co-pending U.S. Ser. No. 08/996,422, the contents of which are hereby incorporated by reference in its entirety.

DETAILED DESCRIPTION OF THE INVENTION

As above, this invention relates to compounds that inhibit β-amyloid peptide release and/or its synthesis, and, accordingly, have utility in treating Alzheimer's disease. However, prior to describing this invention in further detail, the following terms will first be defined.

Definitions

The term "β-amyloid peptide" refers to a 39–43 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is an approximate 39–43 amino acid fragment of a large membrane-spanning glycoprotein, referred to as the β-amyloid precursor protein (APP). Its 43-amino acid sequence is:

1
  Asp Ala Glu Phe Arg His Asp Ser Gly Tyr
11
  Glu Val His His Gln Lys Leu Val Phe Phe
21
  Ala Glu Asp Val Gly Ser Asn Lys Gly Ala
31
  Ile Ile Gly Leu Met Val Gly Gly Val Val
41
  Ile Ala Thr (SEQ ID NO: 1)
or a sequence which is substantially homologous thereto.

"Alkyl" refers to monovalent alkyl groups preferably having from 1 to 20 carbon atoms, more preferably 1 to 10 carbon atoms and most preferably 1 to 6 carbon atoms. This term is exemplified by groups such as methyl, ethyl, n-propyl, iso-propyl, n-butyl, iso-butyl, n-hexyl, and the like.

"Substituted alkyl" refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, keto, thioketo, carboxyl, carboxyalkyl, thiol, thioalkoxy, substituted thioalkoxy, aryl, aryloxy, heteroaryl, heteroaryloxy, heterocyclic, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Alkylene" refers to divalent alkylene groups preferably having from 1 to 10 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to an alkylene group, preferably of from 1 to 10 carbon atoms, having from 1 to 3 substituents selected from the group consisting of alkoxy, substituted alkoxy, acyl, acylamino, acyloxy, amino, substituted amino, aminoacyl, aminoacyloxy, oxyacylamino, cyano, halogen, hydroxyl, keto, thioketo, carboxyl, carboxyalkyl, thiol, thioalkoxy, substituted thioalkoxy, aryl, heteroaryl, heterocyclic, heterocyclooxy, heterocyclooxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic. Additionally, such substituted alkylene groups include those where 2 substituents on the alkylene group are fused to form one or more cycloalkyl, aryl, heterocyclic or heteroaryl groups fused to the alkylene group. Preferably, such fused cycloalkyl groups contain from 1 to 3 fused ring structures.

"Alkenylene" refers to divalent alkenylene groups preferably having from 2 to 10 carbon atoms and more preferably 2 to 6 carbon atoms. This term is exemplified by groups such as ethenylene (—CH=CH—), the propenylene isomers (e.g., —CH$_2$CH=CH— and —C(CH$_3$)=CH—) and the like.

"Substituted alkenylene" refers to an alkenylene group, preferably of from 2 to 10 carbon atoms, having from 1 to 3 substituents selected from the group consisting of alkoxy, substituted alkoxy, acyl, acylamino, acyloxy, amino, substituted amino, aminoacyl, aminoacyloxy, oxyacylamino, cyano, halogen, hydroxyl, keto, thioketo, carboxyl, carboxyalkyl, thiol, thioalkoxy, substituted thioalkoxy, aryl, heteroaryl, heterocyclic, heterocyclooxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic. Additionally, such substituted alkylene groups include those where 2 substituents on the alkylene group are fused to form one or more cycloalkyl, aryl, heterocyclic or heteroaryl groups fused to the alkylene group.

"Alkaryl" refers to -alkylene-aryl groups where alkylene and aryl are as defined herein. Such alkaryl groups are exemplified by benzyl, phenethyl and the like.

"Alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—" where substituted alkyl is as defined above.

"Alkylalkoxy" refers to the group "-alkylene-O-alkyl" where alkylene and alkyl are as defined above. Such groups include methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$-O-C(CH$_3$)$_3$) and the like.

"Alkylthioalkoxy" refers to the group "-alkylene-S-alkyl" where alkylene and alkyl are as defined above. Such groups include methylenethiomethoxy (—CH$_2$SCH$_3$), ethylenethiomethoxy (—CH$_2$CH$_2$SCH$_3$), n-propylene-thio-iso-propoxy (—CH$_2$CH$_2$CH$_2$SCH(CH$_3$)$_2$), methylenethio-t-butoxy (—CH$_2$SC(CH$_3$)$_3$) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

"Substituted alkenyl" refers to an alkenyl group as defined above having from 1 to 3 substituents selected from the group consisting of alkoxy, substituted alkoxy, acyl, acylamino, acyloxy, amino, substituted amino, aminoacyl, aminoacyloxy, oxyacylamino, cyano, halogen, hydroxyl, keto, thioketo, carboxyl, carboxyalkyl, thiol, thioalkoxy, substituted thioalkoxy, aryl, heteroaryl, heterocyclic, heterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—CH≡CH$_2$), propargyl (—CH$_2$C≡CH) and the like.

"Substituted alkynyl" refers to an alkynyl group as defined above having from 1 to 3 substituents selected from the group consisting of alkoxy, substituted alkoxy, acyl, acylamino, acyloxy, amino, substituted amino, aminoacyl, aminoacyloxy, oxyacylamino, cyano, halogen, hydroxyl, keto, thioketo, carboxyl, carboxyalkyl, thiol, thioalkoxy, substituted thioalkoxy, aryl, heteroaryl, heterocyclic, heterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

"Acylamino" refers to the group —C(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Substituted amino" refers to the group —N(R)2, where each R is independently selected from the group consisting of hydrogen, alkyl, substituted alkyl, alkenyl, substituted alkenyl, alkynyl, substituted alkynyl, aryl, cycloalkyl, substituted cycloalkyl, heteroaryl, heterocyclic and where both R groups are joined to form a heterocyclic group. When both R groups are hydrogen, —N(R)2 is an amino group. Examples of substituted amino groups include, by way of example, mono- and di-alkylamino, mono- and di-(substituted alkyl)amino, mono- and di-arylamino, mono- and diheteroarylamino, mono and di-heterocyclic amino, and unsymmetric di-substituted amines having different substituents selected from the group consisting of alkyl, substituted alkyl, aryl, heteroaryl, heterocyclic and the like.

"Aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

"Aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

"Acyloxy" refers to the groups alkyl-C(O)O—, substituted alkyl-C(O)O—, cycloalkyl-C(O)O—, aryl-C(O)O—, heteroaryl-C(O)O—, and heterocyclic-C(O)O— wherein alkyl, substituted alkyl, cycloalkyl, aryl, heteroaryl, and heterocyclic are as defined herein.

"Aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of acyloxy, 1 to 5 and preferably 1 to 3 substituents selected from the group consisting of hydroxy, acyl, alkyl, alkoxy, alkenyl, alkynyl, substituted alkyl, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

"Carboxyalkyl" refers to the group "—C(O)O-alkyl" and "—C(O)O-substituted alkyl" where alkyl and substituted alkyl are as defined above.

"Cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclohexyl, cycloheptyl, cyclooctyl, and the like, or multiple ring structures such as adamantanyl, bicyclo[2.2.1]heptyl, bicyclo(2.2.1)hept-5-ene-yl, bicyclo(3.3.1)non-6-ene-3-carboxyl) and the like.

"Substituted cycloalkyl" refers to cycloalkyl groups having from 1 to 5 (preferably 1 to 3) substituents selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, alkaryl, aryl, aryloxy, carboxyl, carboxyalkyl, cyano, halo, nitro, heteroaryl, thioalkoxy, substituted thioalkoxy, trihalomethyl and the like.

"Cycloalkenyl" refers to cyclic alkenyl groups of from 4 to 12 carbon atoms having at least one cyclic ring and preferably no more than four rings, which rings are optionally fused, and which include at least one point of internal unsaturation. Examples of suitable cycloalkenyl groups include, for instance, cyclobut-2-enyl, cyclopent-3-enyl, cyclooct-3-enyl and the like.

"Substituted cycloalkenyl" refers to cycloalkenyl groups having from 1 to 5 substituents selected from the group consisting of hydroxy, acyl, acyloxy, alkyl, substitute d alkyl, alkoxy, substituted alkoxy, alkenyl, substituted alkenyl, alkynyl, substituted alkynyl, amino, substituted amino, aminoacyl, alkaryl, aryl, aryloxy, carboxyl, carboxyalkyl, cyano, halo, nitro, heteroaryl, thioalkoxy, substituted thioalkoxy, trihalomethyl and the like.

"Halo" or "halogen" refers to fluoro, chloro, bromo and iodo and preferably is either fluoro or chloro.

"Heteroaryl" refers to an aromatic carbocyclic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of acyloxy, 1 to 5 and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroaryloxy" refers to "O-heteroaryl", where heteroaryl is as defined herein.

"Heterocyclooxy" refers to "O-heterocyclic", where heterocyclic is as defined herein.

"Heterocycle" or "heterocyclic" refers to a monovalent saturated or unsaturated group having a single ring or multiple condensed rings, from 1 to 15 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioalkoxy" refers to the group —S-alkyl.

"Substituted thioalkoxy" refers to the group —S-substituted alkyl.

"Thioaryloxy" refers to the group aryl-S— wherein the aryl group is as defined above including optionally substituted aryl groups also defined above.

"Thioheteroaryloxy" refers to the group heteroaryl-S— wherein the heteroaryl group is as defined above including optionally substituted aryl groups as also defined above.

As to any of the above groups that contain 1 or more substituents, it is understood, of course, that such groups do not contain any substitution or substitution patterns which are sterically impractical and/or synthetically non-feasible.

"Pharmaceutically acceptable salts" refers to pharmaceutically acceptable salts of a compound of Formulas I–VI which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable amino blocking groups include conventional substituents such as t-butyoxycarbonyl (t-BOC), benzyloxycarbonyl (CBZ), and the like which can be removed by conventional conditions compatible with the nature of the product.

Preferred carboxyl protecting groups include esters such as methyl, ethyl, propyl, t-butyl etc. which can be removed by mild hydrolysis conditions compatible with the nature of the product.

Compound Preparation

Amidation Chemistry

Compounds including amide linkages can be readily prepared by conventional amidation of a carboxyl acid as shown in reaction (1) below where, for the sake of illustration, n is one:

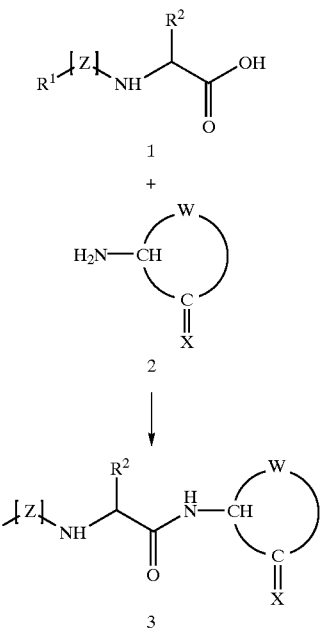

Reaction 1 wherein $R^1$, $R^2$, W, X, and Z are as defined above. The reaction is conventionally conducted by using at least a stoichiometric amount of carboxylic acid 1 and amine 2. This reaction is conventionally conducted for peptide synthesis and synthetic methods used therein can also be employed to prepare compound 3 which is a compound of formula I above. For example, well known coupling reagents such as carbodiimides with or without the use of well known additives such as N-hydroxysuccinimide, 1-hydroxybenzotriazole, etc. can be used to facilitate coupling. The reaction is conventionally conducted in an inert aprotic polar diluent such as dimethylformamide, dichloromethane, chloroform, acetonitrile, tetrahydrofuran and the like. Alternatively, the acid halide of compound 1 can be employed in reaction (1) and, when so employed, it is typically employed in the presence of a suitable base to scavenge the acid generated during the reaction. Suitable bases include, by way of example, triethylamine, diisopropylethylamine, N-methylmorpholine and the like.

Various compounds as described herein can be prepared by N-substitution reactions of compound 2. Reaction of compound 2 with an carboxylic acid derivative can also lead to various compounds as described herein. Both reactions are described below.

Synthesis of Carboxylic Acid Starting Materials

Carboxylic acids 1 can be prepared by several divergent synthetic routes with the particular route selected relative to the ease of compound preparation, commercial availability of starting materials, whether n is one or two.

A. Synthesis of Carboxylic Acids

When n is one, a first synthetic method involves the introduction of the $R^1$ group to the amino acid $NH_2CH(R^2)$COOH or ester thereof.

The introduction of the $R^1$ group onto the amino acid $NH_2CH(R^2)COOH$ or ester thereof can be accomplished in several methods. For example, conventional coupling of a halo acetic acid with a primary amine forms an amino acid as shown in reaction (2) below:

Reaction 2

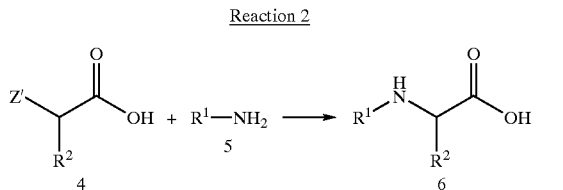

wherein $R^1$ and $R^2$ are as defined above and Z is a halo group such as chloro or bromo. Alternatively, leaving groups other than halo may be employed such as triflate and the like. Additionally, suitable esters of 4 may be employed in this reaction.

As above, reaction (2) involves coupling of a suitable haloacetic acid derivative 4 with a primary amine 5 under conditions that provide for amino acid 6. This reaction is described by, for example, Yates, et al.[14] and proceeds by combining approximately stoichiometric equivalents of haloacetic acid 4 with primary amine 5 in a suitable inert diluent such as, water, dimethylsulfoxide (DMSO) and the like. The reaction employs an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, N-substituted amino acid 6 is recovered by conventional methods including precipitation, chromatography, filtration and the like.

In reaction (2), each of the reagents (haloacetic acid 4, primary amine 5 and alcohol 6) are well known in the art with a plurality of each being commercially available.

In an alternative embodiment, the $R^1$ group can be coupled to an alanine ester (or other suitable amino acid ester) by conventional N-arylation. For example, a stoichiometric equivalent or slight excess of the amino acid ester can be dissolved in a suitable diluent such as DMSO and coupled with a halo-$R^1$ compound, $Z—R^1$ where Z is a halo group such as chloro or bromo and $R^1$ is as defined above. The reaction is conducted in the presence of an excess of base such as sodium hydroxide to scavenge the acid generated by the reaction. The reaction typically proceeds at from 15° C. to about 250° C. and is complete in about 1 to 24 hours. Upon reaction completion, N-substituted amino acid ester is recovered by conventional methods including chromatography, filtration and the like. This ester is then hydrolyzed by conventional methods to provide for carboxylic acid 1 for use in reaction (1).

In still another alternative embodiment, the esterified amino acids described above can be prepared by reductive amination of a suitable pyruvate ester in the manner illustrated in reaction (3) below:

Reaction 3

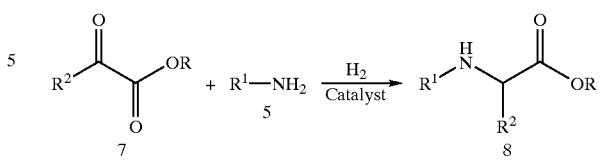

wherein $R^1$ is typically an alkyl group and $R^1$ and $R^2$ are as defined above.

In reaction (3), approximately stoichiometric equivalents of pyruvate ester 7 and amine 5 are combined in an inert diluent such as methanol, ethanol and the like and the reaction solution treated under conditions that provide for imine formation (not shown). The imine formed is then reduced under conventional conditions by a suitable reducing agent such as sodium cyanoborohydride, $H_2$/palladium on carbon and the like to form the N-substituted amino acid ester 8. In a particularly preferred embodiment, the reducing agent is $H_2$/palladium on carbon which is incorporated into the initial reaction medium which permits imine reduction in situ in a one pot procedure to provide for the N-substituted amino acid ester 8.

The reaction is preferably conducted at from about 20° C. to about 80° C. at a pressure of from 1 to 10 atmospheres until the reaction is complete, which typically occurs within 1 to about 24 hours. Upon reaction completion, N-substituted amino acid ester 8 is recovered by conventional methods including chromatography, filtration and the like.

Subsequent hydrolysis of the ester 8 leads to the corresponding carboxylic acid derivative 1 which can be employed in reaction (1) above.

For compounds where n is two, conventional coupling of a second amino acid (e.g., $NH_2CH(R^2)C(O)OR$ where R is typically an alkyl group) to the amino acid produced above (i.e., $R^1NHCH(R^2)COOH$) provides for esters of an analogue of carboxylic acid 1 which are then conventionally de-esterified to provide for an analogue of compound 1.

Alternatively, an ester such as $H_2NCH(R^2)C(O)NHCH(R^2)COOR$ where each $R^2$ is independently as defined above and R is typically an alkyl group can first be formed by conventional peptide synthetic procedures, N-substitution can be conducted in the manner described above followed by de-esterification to provide for analogues of carboxylic acids 1 where n is two.

When n is one, a first synthetic method involves conventional coupling of an carboxylic acid derivative with a primary amine of an esterified amino acid as shown in reaction (4) below:

Reaction 4

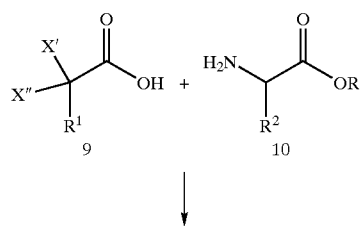

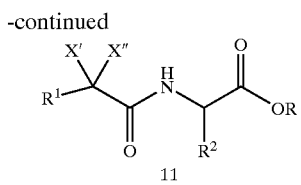

wherein R is typically an alkyl group and $R^1$, $R^2$, $X'$ and $X''$ are as defined above.

Reaction (4) merely involves coupling of a suitable carboxylic acid derivative 9 with the primary amine of amino acid ester 10 under conditions that provide for the N-acetyl derivative 11. Alternatively, the carboxylic acid R'COOH can be used in place of compound 9 to provide intermediates useful for preparing compounds of Formula VI above. This reaction is conventionally conducted for peptide synthesis and synthetic methods used therein can also be employed to prepare the N-acetyl amino acid esters 11 of this invention. For example, well known coupling reagents such as carbodiimides with or without the use of well known additives such as N-hydroxysuccinimide, 1-hydroxybenzotriazole, etc. can be used to facilitate coupling. The reaction is conventionally conducted in an inert aprotic polar diluent such as dimethylformamide, dichloromethane, chloroform, acetonitrile, or tetrahydrofuran. Alternatively, the acid halide of compound 9 can be employed in reaction (4) and, when so employed, it is typically employed in the presence of a suitable base to scavenge the acid generated during the reaction. Suitable bases include, by way of example, triethylamine, diisopropylethylamine, and N-methylmorpholine.

Reaction (4) is preferably conducted at from about 0° C. to about 60° C. until the reaction is complete, which typically occurs within 1 to about 24 hours. Upon reaction completion, N-acetyl amino acid ester 11 is recovered by conventional methods including precipitation, chromatography, and filtration or alternatively is hydrolyzed to the corresponding acid without purification and/or isolation other than conventional work-up (e.g., aqueous extraction, etc.).

In reaction (4), each of the reagents (carboxylic acid derivative 9 and amino acid ester 10) are well known in the art with a plurality of each being commercially available.

When n is two, a further amino acid ester is coupled to the amino acid ester 11 by first de-esterifying 11 and then using well known peptide coupling chemistry with well known coupling reagents such as carbodiimides with or without the use of well known additives such as N-hydroxysuccinimide and 1-hydroxybenzotriazole, which can be used to facilitate coupling. The reaction is conventionally conducted in an inert aprotic polar diluent such as dimethylformamide, dichloromethane, chloroform, acetonitrile, or tetrahydrofuran. De-esterification of the resulting ester provides for carboxylic acids 1 having n equal to 2.

Alternatively, carboxylic acids 1 having n equal to 2 can be prepared by first forming the ester, N-acetylating these esters and then de-esterifying the resulting product.

Carboxylic acids 1 having n equal to 1 or 2 can also be prepared by using polymer-supported forms of carbodiimide peptide coupling reagents. A polymer-supported form of EDC, for example, has been described (*Tetrahedron Letters*, 34(48), 7685 (1993))[10]. Additionally, a new carbodiimide coupling reagent, PEPC, and its corresponding polymer-supported forms have been discovered and are very useful for preparing such compounds.

Polymers suitable for use in making a polymer-supported coupling reagent are either commercially available or may be prepared by methods well known to those of skill in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer backbone must be inert to both the carbodiimide and reaction conditions under which the ultimate polymer-bound coupling reagents will be used.

Certain hydroxymethylated resins may be converted into chloromethylated resins useful for the preparation of polymer-supported coupling reagents. Examples of these hydroxylated resins include the 4-hydroxymethylphenylacetamidomethyl resin (Pam Resin) and 4-benzyloxybenzyl alcohol resin (Wang Resin) available from Advanced Chemtech of Louisville, Ky., USA (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis., USA (see Aldrich 1994–1995 catalog, page 899). Methods for the preparation of PEPC and its polymer-supported forms are outlined in the following scheme.

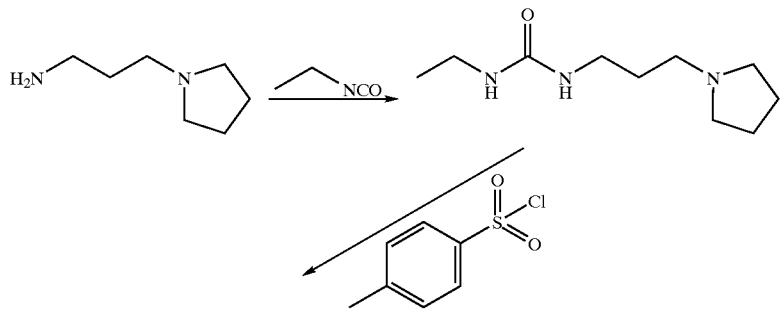

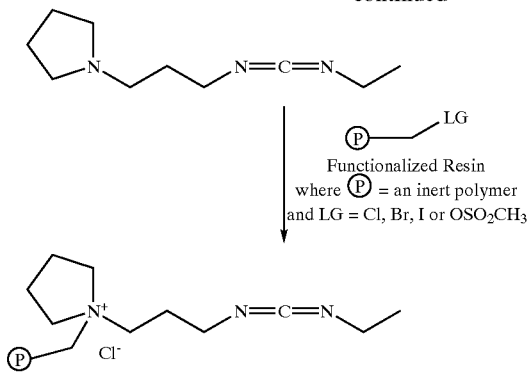

Such methods are described more fully in PCT Application PCT/US97/22986, which application is incorporated herein by reference in its entirety. Briefly, PEPC is prepared by first reacting ethyl isocyanate with 1-(3-aminopropyl) pyrrolidine. The resulting urea is treated with 4-toluenesulfonyl chloride to provide PEPC. The polymer-supported form is prepared by reaction of PEPC with an appropriate resin under standard conditions to give the desired reagent.

The carboxylic acid coupling reactions employing these reagents are performed at about ambient temperature to about 45° C., for from about 3 to 120 hours. Typically, the product is isolated by washing the reaction mixture with $CHCl_3$ and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

Sulfonamidation Chemistry

Sulfonamides, such as those in Formula III, can be readily prepared using known sulfonamidation reactions. These typically involve the reaction of sulfonyl chlorides with primary or secondary amines in the presence of a tertiary amine or other suitable acid scavenger (See, for Example, page 923, Morrison and Boyd, Organic Chemistry, fourth edition).

Synthesis of Sulfonic Acid Starting Materials

Suitable sulfonic acids can be prepared by several divergent synthetic routes with the particular route selected relative to the ease of compound preparation, and commercial availability of starting materials.

A. Synthesis of Sulfonic Acids

Alkyl sulfonic acids can be prepared using means well known to those of skill in the art, as described, for example, in U.S. Pat. Nos. 2,493,038 and 2,697,722, the contents of which are hereby incorporated by reference. One method for preparing alkyl sulfonic acids is by the oxidation of disulfides, which can themselves be prepared by the oxidation of thiols. Aromatic sulfonic acids can be produced by the sulfonating action of sulfuric acid, $SO_3$, oleum or alkyl sulfonic acids on aromatic compounds using techniques well known to those of skill in the art.

Activation of Sulfonic Acids

Suitable sulfonic acid derivatives can be prepared, for example, by reacting a sulfonic acid with a chlorinating reagent such as phosphorous pentachloride or sulfonyl chloride.

Preparation of Ureas

Ureas can be prepared by any known methodology, but preferably are prepared by reacting an amine with an isocyanate, as described on page 844 of Morrison and Boyd, Organic Chemistry, Fourth Edition, Allyn and Bacon, ed., Boston (1983). Suitable isocyanates can be prepared using methods known to those of skill in the art.

Preparation of Cyclic Amino Compounds

Cyclic amino compounds 2 employed in reaction (1) above are generally aminolactams, aminolactones, aminothiolactones and aminocycloalkyl compounds which can be represented by the formula:

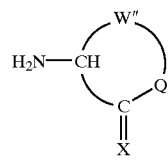

wherein X is as defined above, Q is preferably selected from the group consisting of —O—, —S—, >$NR^6$, and >$CR^7R^8$ where each of $R^6$, $R^7$ and $R^8$ are independently selected from the group consisting of hydrogen, alkyl, substituted alkyl, alkenyl, substituted alkenyl, alkynyl, substituted alkynyl, aryl, heteroaryl and heterocyclic with the proviso that if Q is —O—, —S— or >$NR^6$, then X is oxo or dihydro, and W together with Q, C=X and CH forms a lactone, thiolactone, lactam, cyclic ketone, cyclic alcohol, a heterocycle, and the like.

The aminolactams, aminolactones and aminothiolactones of the formulas above can be prepared by use or adaptation of known chemical syntheses which syntheses are well described in the literature. See, e.g., Ogliaruso and Wolfe, *Synthesis of Lactones and Lactams*, Patai, et al. Editor, J. Wiley & Sons, New York, N.Y., USA, pp. 1085 et seq. (1993)[15].

Specifically, 3-amino substituted lactams 13 with 5, 6 or 7 ring atoms may be prepared by the direct cyclization of a suitable α, omega-diamino acid ester 12 as shown in reaction (5) below:

Reaction 5

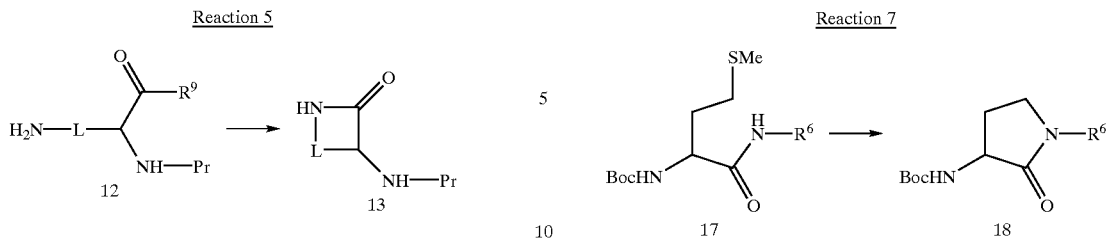

wherein L is a linking group (typically an alkylene group) of from 2–4 atoms, Pr is a suitable protecting group such as t-butoxycarbonyl, carbobenzyloxy, or the like and $R^9$ is an alkoxy or aryloxy group such as methoxy, ethoxy, p-nitrophenoxy, N-succinimidoxy, and the like. The reaction may be carried out in a solvent such as water, methanol, ethanol, pyridine, and the like. Such reactions are exemplified by cyclization of a lysine ester to a caprolactam as described by Ugi, et al., *Tetrahedron*, 52(35):11657–11664 (1996)[16]. Alternatively, such a cyclization can also be conducted in the presence of dehydrating agents such as alumina or silica to form lactams as described by Blade-Font, *Tetrahedron Lett.*, 21:2443 (1980)[17].

The preparation of aminolactams alkylated on the amino group of the cyclic lactam is described by Freidinger, et al., *J. Org. Chem.*, 47:104–109 (1982)[18] and illustrated in reaction (6) below:

Reaction 6

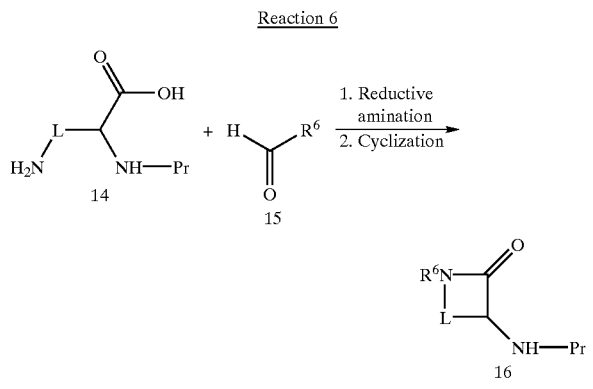

wherein L and $R^6$ are as defined above.

In reaction (6), reductive amination of 14 with aldehyde 15 and subsequent ring closure by methods using, for example, EDC provides for aminolactam 16. The preparation of 6 membered lactams using this general procedure is described by Semple, et al., *J. Med. Chem.*, 39:4531–4536 (1996)[19].

The internal cyclization of an amide anion with a halide or equivalent thereof can sometimes be used to particular advantage in the synthesis of smaller ring lactams where the stereochemistry of the amino-lactam center is available from the standard amino-acid pool. This approach is illustrated in reaction (7) below:

Reaction 7

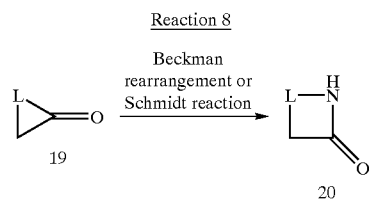

where $R^6$ is as defined above.

The approach of reaction (7) is presented by Semple, et al., supra.[19], and Freidinger, et al., *J. Org. Chem.*, 47:104–109 (1982)[18] where a dimethylsulfonium leaving group is generated from methyl iodide treatment of an alkyl methyl sulfide 17 to provide for lactam 18. A similar approach using a Mitsunobu reaction on an omega alcohol is found Holladay, et al., *J. Org. Chem.*, 56:3900–3905 (1991)[20].

In another method, lactams 20 can be prepared from cyclic ketones 19 using either the well known Beckmann rearrangement (e.g., Donaruma, et al., *Organic Reactions*, 11:1–156 (1960))[21] or the well known Schmidt reaction (Wolff, *Organic Reactions*, 3:307–336 (1946))[22] as shown in reaction (8) below:

Reaction 8

Beckman rearrangement or Schmidt reaction

19 → 20 wherein L is as defined above.

Application of these two reactions leads to a wide variety of lactams especially lactams having two hydrogen atoms on the carbon α to the lactam carbonyl which lactams form a preferred group of lactams in the synthesis of the compounds described above. In these reactions, the L group can be highly variable including, for example, alkylene, substituted alkylene and hetero containing alkylene with the proviso that a heteroatom is not adjacent to the carbonyl group of compound 19. Additionally, the Beckmann rearrangement can be applied to bicyclic ketones as described in Krow, et al., *J. Org. Chem.*, 61:5574–5580 (1996)[23].

The preparation of lactones can be similarly conducted using peracids in a Baeyer-Villiger reaction on ketones. Alternatively, thiolactones can be prepared by cyclization of an omega —SH group to a carboxylic acid and thiolactams can be prepared by conversion of the oxo group to the thiooxo group by $P_2S_5$ or by use of the commercially available Lawesson's Reagent, *Tetrahedron*, 35:2433 (1979)[24].

One recently reported route for lactam synthesis is a variation of the Schmidt reaction through the use of an alkylazide, either intermolecularly or intramolecularly, through a tethered alkylazide function that attacks a ketone under acidic conditions. Gracias, et al., *J. Am. Chem. Soc.*, 117:8047–8048 (1995)[25] describes the intermolecular version whereas Milligan, et al., *J. Am. Chem. Soc.*, 117:10449–10459 (1995)[26] describes the intramolecular version. One example of the intramolecular version is illustrated in reaction (9) below:

Reaction 9

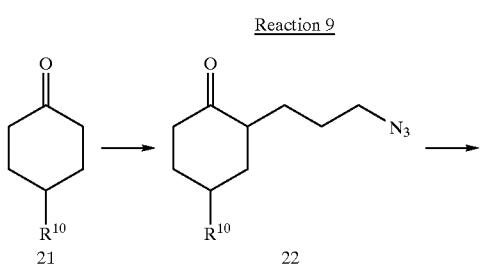

where $R^{10}$ is exemplified by alkyl, substituted alkyl, alkoxy, substituted alkoxy, aryl, heteroaryl, cycloalkyl and heterocyclic.

In this reaction, ketone 21 is converted to an α-(w-alkyl) ketone 22 which is cyclized to form bicyclic lactam 23. Such intramolecular reactions are useful in forming bicyclic lactams having 5–7 members and the lactam ring of 6–13 members. The use of heteroatoms at non-reactive sites in these rings is feasible in preparing heterobicyclic lactams.

Still another recent approach to the synthesis of lactams is described by Miller, et al., *J. Am. Chem. Soc.*, 118:9606–9614 (1996)[27] and references cited and is illustrated in reaction (10) below:

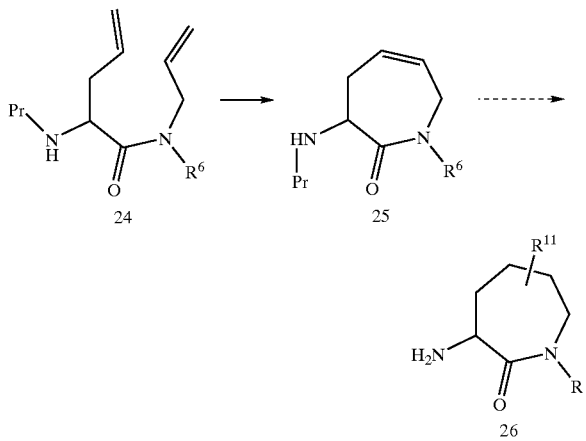

where $R^6$ and Pr are as defined above and $R^{11}$ is exemplified by halo, alkyl, substituted alkyl, alkoxy, substituted alkoxy, aryl, heteroaryl, cycloalkyl and heterocyclic wherein the aryl, heteroaryl, cycloalkyl and heterocyclic group is optionally fused to the lactam ring structure.

Specifically, in reaction (10), lactam 26 is formed from an appropriate unsaturated amide (e.g., 24) through a ruthenium or molybdenum complexes catalyzed olefin metathesis reaction to form unsaturated lactam 25 which can be used herein without further modification. However, the unsaturation in 25 permits a myriad of techniques such as hydroboration, Sharpless or Jacobsen epoxidations, Sharpless dihydroxylations, Diels-Alder additions, dipolar cycloaddition reactions and many more chemistries to provide for a wide range of substituents on the lactam ring.

Moreover, subsequent transformations of the formed substitution leads to other additional substituents (e.g., mesylation of an alcohol followed by nucleophilic substitution reactions). See, for example, March, et al. for a recitation of numerous such possible reactions.[28] Saturated amides used in this reaction are conventional with amide 24 being commercially available.

Related chemistry to cyclize amides to form lactams is disclosed by Colombo, et al., *Tetrahedron Lett.*, 35(23):4031–4034 (1994)[29] and is illustrated in reaction (11) below:

(Reaction 11)

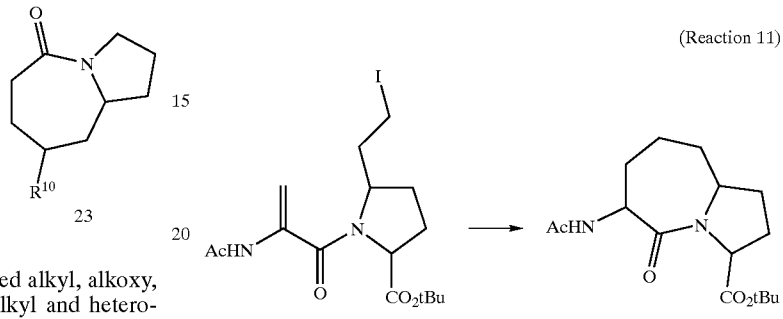

In this reaction, proline derivative 27 is cyclized via a tributyltin-radical cyclization to provide for lactam 28.

Some of the lactams described above contain the requisite amino group a to the lactam carbonyl whereas others did not. However, the introduction of the required amino group can be achieved by any of several routes delineated below which merely catalogue several recent literature references for this synthesis.

For example, in a first general synthetic procedure, azide or amine displacement of a leaving group a to the carbonyl group of the lactam leads to the α-aminolactams. Such general synthetic procedures are exemplified by the introduction of a halogen atom followed by displacement with phthalimide anion or azide and subsequent conversion to the amine typically by hydrogenation for the azide as described in Rogriguez, et al., *Tetrahedron*, 52:7727–7736 (1996)[30], Parsons, et al., *Biochem. Biophys. Res. Comm.*, 117:108–113 (1983)[31] and Watthey, et al., *J. Med. Chem.*, 28:1511–1516 (1985)[32]. One particular method involves iodination and azide displacement on, for example, benzyllactams as described by Armstrong, et al., *Tetrahedron Lett.*, 35:3239 (1994)[33] and by King, et al., *J. Org. Chem.*, 58:3384 (1993)[34].

Another example of this first general procedure for the synthesis of α-aminolactams from the corresponding lactam involves displacement of a triflate group by an azido group as described by Hu, et al., *Tetrahedron Lett.*, 36(21):3659–3662 (1995)[35].

Still another example of this first general procedure uses a Mitsunobu reaction of an alcohol and a nitrogen equivalent (either —NH₂ or a phthalimido group) in the presence of an azodicarboxylate and a triarylphosphine as described in Wada, et al., *Bull. Chem. Soc. Japan*, 46:2833–2835 (1973)[36] using an open chain reagent.

Yet another example of this first general procedure involves reaction of α-chlorolactams with anilines or alkyl amines in a neat mixture at 120° C. to provide for 2-(N-aryl or N-alkyl)lactams as described by Gaetzi, *Chem. Abs.*, 66:28690m.[37]

In a second general synthetic procedure, reaction of an enolate with an alkyl nitrite ester to prepare the a oxime followed by reduction yields the α-aminolactam compound.

This general synthetic procedure is exemplified by Wheeler, et al., *Organic Syntheses*, Coll. Vol. VI, p. 840[38] which describes the reaction of isoamyl nitrite with a ketone to prepare the desired oxime. The reduction of the oxime methyl ester (prepared from the oxime by reaction with methyl iodide) is described in the *J. Med. Chem.*, 28(12):1886 (1985)[39] and the reduction of α-oximino caprolactams by Raney-nickel and palladium catalysts is described by Brenner, et al., U.S. Pat. No. 2,938,029.[40]

In a third general synthetic procedure, direct reaction of an enolate with an electrophilic nitrogen transfer agent can be used. The original reaction employed toluenesulfonyl azide but was improved as described by Evans, et al., *J. Am. Chem. Soc.*, 112:4011–4030 (1990)[41]. Specifically, direct introduction of an azido group which can be reduced to the amine by hydrogenation is described by Micouin, et al., *Tetrahedron*, 52:7719–7726 (1996)[42]. Likewise, the use of triisopropylbenzenesulfonyl azide as the azide transferring agent for reaction with an enolate is described by Evans, et al., supra. The use of triphenylphosphine to reduce the α-azidolactams to the corresponding aminolactams in the benzodiazepine series is disclosed by Butcher, et al., *Tetrahedron Lett.*, 37(37):6685–6688 (1996)[43]. Lastly, diazo transfer of β-diketones and subsequent reduction of the diazo group to the amino group is exemplified by Hu, et al., *Tetrahedron Lett.*, 36(21):3659–3662 (1995)[35] who used Raney-nickel and hydrogen in acetic acid and acetic anhydride as the solvent.

In a fourth general procedure, N-substituted lactams are first converted to the 3-alkoxycarbonyl derivatives by reaction with a dialkyl carbonate and a base such as sodium hydride. See, for example, M. L. Reupple, et al., *J. Am. Chem. Soc.*, 93:7021 et seq. (1971)[44] The resulting esters serve as starting materials for conversion to the 3-amino derivatives. This conversion is achieved via the Curtius reaction as shown in reaction (12) below:

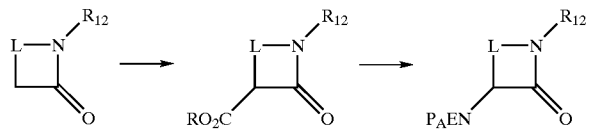

where Pr is as defined above and $R^{12}$ is typically hydrogen, an alkyl or an aryl group.

The Curtius reaction is described by P. A. S. Smith, *Organic Reactions*, 3:337–449 (1946).[45] Depending on the reaction conditions chosen, Pr=H or a protecting group such as Boc. For example, when R=H, treatment of the acid with diphenylphosphoryl azide in the presence of t-butanol provides the product wherein Pr=Boc.

The α-aminolactams employed as the cyclic amino compounds 2 in reaction (1) above include ring N-substituted lactams in addition to ring N—H lactams. Some methods for preparing ring N-substituted lactams have been described above. More generally, however, the preparation of these compounds range from the direct introduction of the substituent after lactam formation to essentially introduction before lactam formation. The former methods typically employ a base and an primary alkyl halide although it is contemplated that a secondary alkyl halide can also be employed although yields may suffer.

Accordingly, a first general method for preparing N-substituted lactams is achieved via reaction of the lactam with base and alkyl halide (or acrylates in some cases). This reaction is quite well known and bases such as sodamide, sodium hydride, LDA, LiHMDS in appropriate solvents such as THF, DMF, etc. are employed provided that the selected base is compatible with the solvent. See for example: K. Orito, et al., *Tetrahedron*, 36:1017–1021 (1980)[46] and J. E. Semple, et al., *J. Med. Chem.*, 39:4531–4536 (1996)[19] (use of LiHMDS with either R—X or acrylates as electrophiles).

A second general method employs reductive amination on an amino function that is then cyclized to an appropriate ester or other carbonyl function.

A third general method achieves production of the N-substitution during lactam formation. Literature citations report such production from either photolytic or thermal rearrangement of oxaziridines, particularly of N-aryl compounds. See, for example, Krimm, *Chem. Ber.*, 91:1057 (1958)[47] and Suda, et al., *J. Chem. Soc. Chem Comm.*, 949–950, (1994).[48] Also, the use of methyl hydroxylamine for the formation of nitrones and their rearrangement to the N-methyl derivatives is reported by Barton, et al., *J. Chem. Soc.*, 1764–1767 (1975).[49] Additionally, the use of the oxaziridine process in chiral synthesis has been reported by Kitagawa, et al., *J. Am. Chem. Soc.*, 117:5169–5178 (1975).[50]

A more direct route to obtain N-phenyl substituted lactams from the corresponding NH lactams through the use of t-butyltetramethylguanidine and triphenylbismuth dichloride is disclosed by Akhatar, et al., *J. Org. Chem.*, 55:5222–5225 (1990)[51] as shown in reaction (13) below.

(Reaction 13)

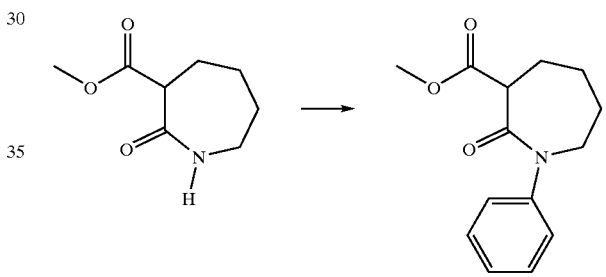

Given that numerous methods are available to introduce an α-amino group onto a lactam (or lactone) ring, the following lactams (and appropriate corresponding lactones) are contemplated for use in the synthesis of compounds described above. Similar alcohol functions at the carbonyl position are derivative of either amine ring opening of cyclic epoxides, ring opening of aziridines, displacement of appropriate halides with amine or alcohol nucleophiles, or most likely reduction of appropriate ketones. These ketones are also of interest to the present invention.

Monocyclic lactams as described by Nedenskov, et al., *Acta Chem. Scand.*, 12:1405–1410 (1958)[52] are represented by the formula:

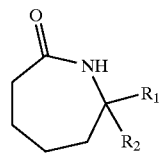

where $R_1$ and $R_2$ are exemplified by alkyl, aryl or alkenyl (e.g., allyl).

Monocyclic lactams containing a second nitrogen ring atom as described by Sakakida, et al., *Bull. Chem. Soc. Japan*, 44:478–480 (1971)[53] are represented by the formula:

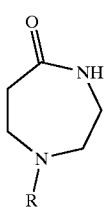

where R is exemplified by CH$_3$— or PhCH$_2$—.

Monocyclic lactams having hydroxyl substitution on the ring as described by Hu, et al., *Tetrahedron Lett.*, 36(21):3659–3662 (1995)[35] are represented by the formula:

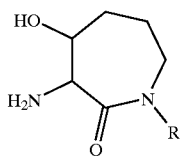

where R is exemplified by benzyl (includes both the cis and trans hydroxy lactams).

The direct preparation N-substituted lactams of 5–8 members from the corresponding ketones is described by Hoffman, et al., *Tet. Lett.*, 30:4207–4210 (1989). These lactams are represented by the formula:

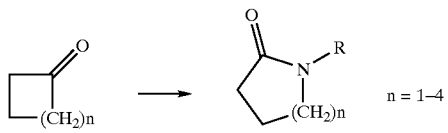

wherein R is alkyl, alkenyl, alkynyl, cycloalkyl, or benzyl.

N-Methoxylactams prepared from cyclohexanone and dimethoxyamine are described by Vedejs, et al., *Tet. Lett.*, 33:3261–3264 (1992).[55] These structures are represented by the formula:

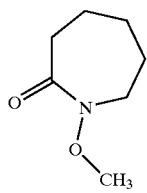

Substituted 3-aminoazetidinone derivatives prepared by a variety of routes including those described by van der Steen, et al., *Tetrahedron*, 47, 7503–7524 (1991)[56], Hart, et al., *Chem Rev.*, 89:1447–1465 (1989)[57] and references cited therein are represented by the formula:

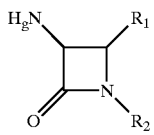

where R$_1$ and R$_2$ are independently selected from alkyl, substituted alkyl, alkenyl, substituted alkenyl, aryl, heteroaryl, heterocyclic or are fused to form a cyclic group.

Ring substituted lactams are described by Lowe, et al., *Bioorg. Med. Chem. Lett.*, 4:2877–2882 (1994)[58] and are represented by the formula:

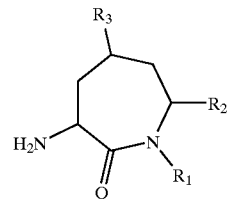

wherein R$_2$ and R$_3$ are exemplified by aryl and substituted aryl and R$_1$ is exemplified by alkyl or hydrogen.

The synthesis of substituted 3-aminopyrrolidones from α-bromoketones is described by McKennis, Jr., et al.,*J. Org. Chem.*, 28:383–387 (1963)[59]. These compounds are represented by the formula:

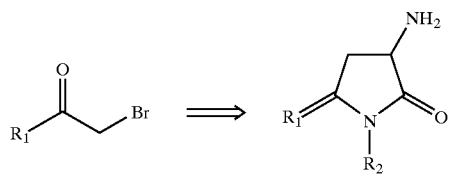

where R$^1$ is aryl or heteroaryl and R$^2$ corresponds to any substituent for which the corresponding amine R$^2$—NH$_2$ exists.

Additional references for the synthesis of α aminolactams are as follows:

1. Shirota, et al., *J. Med. Chem.*, 1623–1627 (1977)[60] which describes the synthesis of

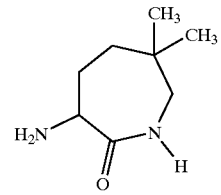

2. Overberger, et al.,*J. Am. Chem. Soc.*, 85:3431 (1963)[61] which describes the preparation of optically active-methylcaprolactam of the formula:

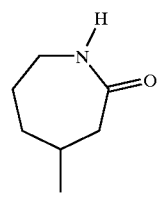

3. Herschmann, *Helv. Chim. Acta*, 32:2537 (1949)[62] describes the synthesis of a disubstituted caprolactam from the Beckman rearrangement of menthone which is represented by the formula:

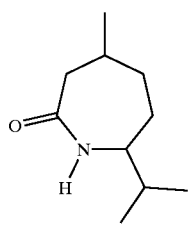

4. Overberger, et al., *Macromolecules*, 1:1 (1968)[63] describes the synthesis of eight-membered lactams from 3-methylcycloheptanone as shown below:

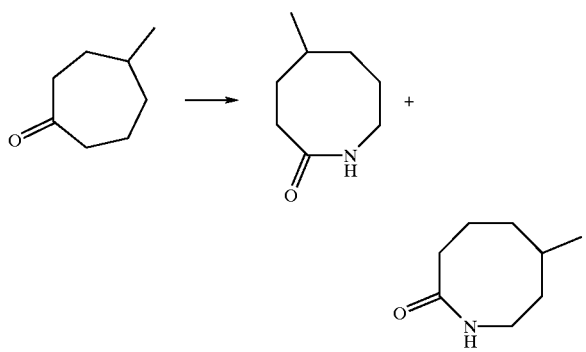

5. The synthesis of benzolactams (benzazepinones) has been reported by Busacca, et al., *Tet. Lett.*, 33:165–168 (1992)[64].

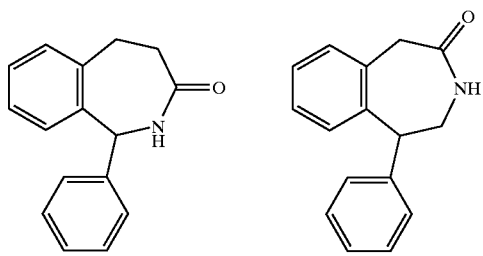

by Croisier, et al., U.S. Pat. No. 4,080,449[65]:

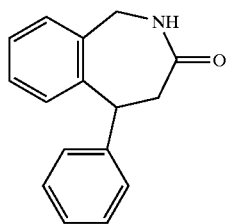

and by J. A. Robl, et al., *Tetrahedron Lett.*, 36(10):1593–1596 (1995)[66] who employed an internal Friedel-Crafts like cyclization to prepare the tricyclic benzyllactams shown below where Pht is the phthalimido protecting group:

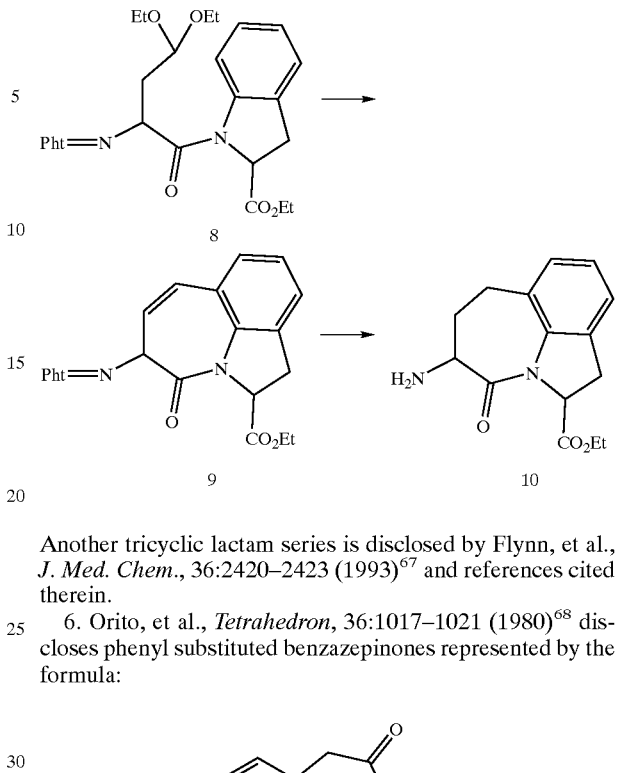

Another tricyclic lactam series is disclosed by Flynn, et al., *J. Med. Chem.*, 36:2420–2423 (1993)[67] and references cited therein.

6. Orito, et al., *Tetrahedron*, 36:1017–1021 (1980)[68] discloses phenyl substituted benzazepinones represented by the formula:

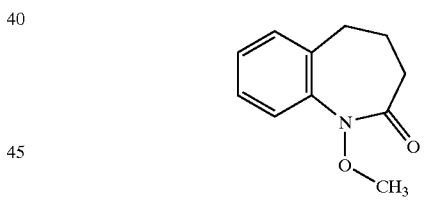

wherein R=H or $CH_3$—;

Kawase, et al., *J. Org. Chem.*, 54:3394–3403 (1989)[69] discloses a N-methoxy benzazepinone represented by the formula:

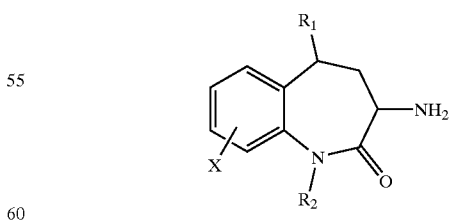

7. Lowe, et al., *J. Med. Chem.*, 37:3789–3811 (1994)[70] describes several synthetic pathways to substituted benzazepinones of the formula:

where $R_1$ is substituted aryl or cyclohexyl, X is a suitable substituent and $R_2$ can be H or alkyl. The syntheses described in Lowe are, however, adaptable to form numerous $R^1$ substituents.

8. Robl, et al., *Bioorg. Med. Chem. Lett.*, 4:1789–1794 (1994)[71] and references cited therein as well as Skiles, et al.,

*Bioorg. Med. Chem. Lett.*, 3:773–778 (1993)[72] disclose benzofused lactams which contain additional heteroatoms in the lactam ring. These compounds are represented by the formula:

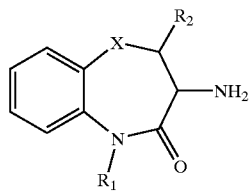

where X is O and $R_2$=H or $CH_3$ or X=S and $R_2$=H. In either case, $R_1$=H or alkyl. Also, in Skiles, the thio group of the thiolactam can be oxidized to the $SO_2$ group. These structures are also presented from Beckmann rearrangement in Grunewald, et al., *J. Med. Chem.*, 39(18):3539 (1996).[73]

9. Also syntheses for the benzoheterolactam series is presented in Thomas, et al., *J. Chem. Soc.*, Perkin II, 747 (1986)[74] which could lead to compounds of the formula:

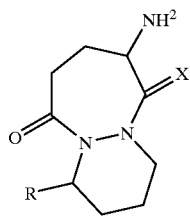

where X is O or $H_2$ and $R^1$ is $CO_2R$.

10. Further examples of benzazepinones are found in Warshawsky, et al., *Bioorg. Med. Chem. Lett.*, 6:957–962 (1996)[75] which discloses

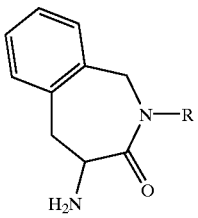

The synthesis can be generalized to produce R=alkyl or aryl.

11. Ben-Ishai, et al., *Tetrahedron*, 43:439–450 (1987)[76] describes syntheses which could lead to several benzolactams of the formula

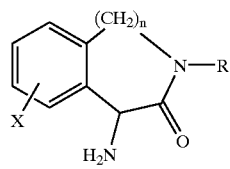

wherein n=0,1,2 and R=—$CH_3$, $PhCH_2$— and H.

12. van Niel et al., *Bioorg. Med. Chem. Lett.*, 5:1421–1426 (1995)[77] reports the synthesis of

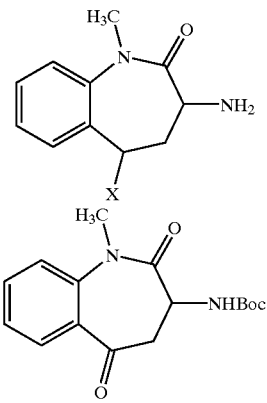

wherein X is —OH, —$NH_2$ or —$NR^6R^6$ where $R^6$ is as defined above. The reported ketone is a versatile synthetic intermediate which can be modified by conventional methods such as reductive amination, reduction, etc.

13. Kawase, et al., *J. Org. Chem.*, 54:3394–3403 (1989)[78] describes a synthetic method for the preparation of:

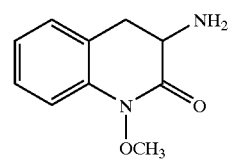

In addition to the above, saturated bicyclic α-aminolactams are also contemplated for use in the synthesis of compounds of formulas I–VI. Such saturated bicyclic α-aminolactams are well known in the art. For example, Edwards, et al., *Can. J. Chem.*, 49:1648–1658 (1971)[79] describes several syntheses of bicyclic lactams of the formula:

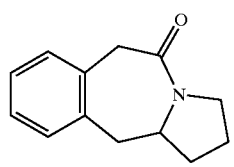

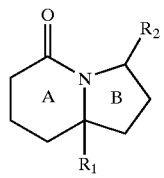

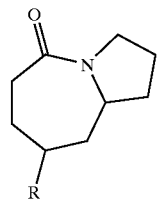

Similarly, Milligan, et al., *J. Am. Chem. Soc.*, 117:10449–10459 (1995)[80] and references cited therein report the synthesis of lactams of the formula:

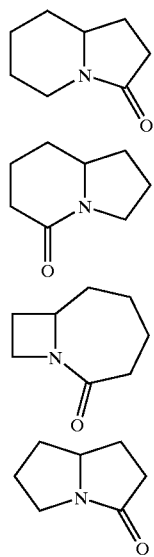

wherein R1 and R2 are H or —CH₃, ring A can have from 6–13 members and ring B can have from 5–7 members. R can be alkyl, aryl, cycloalkyl, and the like.

The introduction of a heteroatom into the saturated cyclic structure fused to the lactam ring is disclosed by Curran et al., *Tet. Lett.*, 36:191–194 (1995)[81] who describe a synthetic method which can be used to obtain a lactam of the formula:

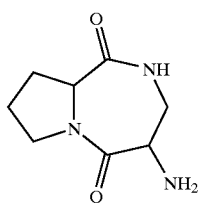

by Slusarchyk, et al., *Bioorg. Med. Chem. Lett.*, 5:753–758 (1995)[82] who describe syntheses which could lead to a lactam of the formula:

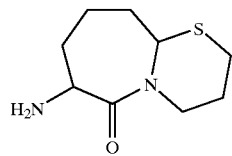

and by Wyvratt, et al., Eur. Pat. Appl. 61187 (1982)[83] who describe a lactam of the formula:

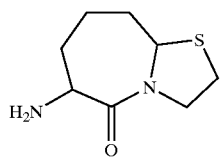

Lactams having further heteroatom(s) in the cyclic lactam structure (in addition to the nitrogen of the amido group of the lactam) are described by Cornille, et al., *J. Am. Chem. Soc.*, 117:909–917 (1995)[84] who describe lactams of the formula:

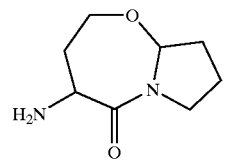

J. Kolc, *Coll. Czech. Chem. Comm.*, 34:630 (1969)[85] who describes lysines suitable for cyclization to lactams which have a hetero lactam ring atom as shown by the formula:

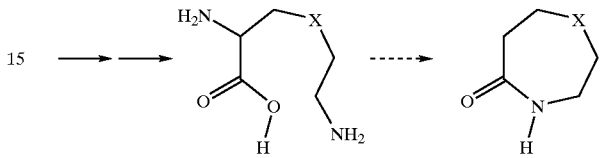

wherein X=O, S and NR where R is, for example, alkyl, substituted alkyl, aryl, heteroaryl, heterocyclic, heterocyclooxy, and the like.

Similarly, each of Dickerman, et al., *J. Org. Chem.*, 14:530 (1949)[86], Dickerman, et al., *J. Org. Chem.*, 20:206 (1955)[87], and Dickerman, et al., *J. Org. Chem.*, 19:1855 (1954)[88] used the Schmidt and Beckmann reactions on substituted 4-piperidones to provide for lactams of the formula:

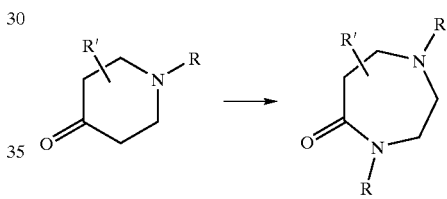

where R is acyl, alkyl, substituted alkyl, aryl, heteroaryl or heterocyclic provided that R is not an acid labile group such as t-Boc; and R' is hydrogen, alkyl, substituted alkyl, alkoxy, substituted alkoxy, aryl, aryloxy, heteroaryl, heteroaryloxy, heterocyclic, heterocyclooxy, halo, cyano, nitro, trihalomethyl, and the like.

An internal cyclization of appropriate ethylenediamine amides onto a ketone or aldehyde is described by Hoffman, et al., *J. Org. Chem.*, 27:356–589 (1962)[89] as follows:

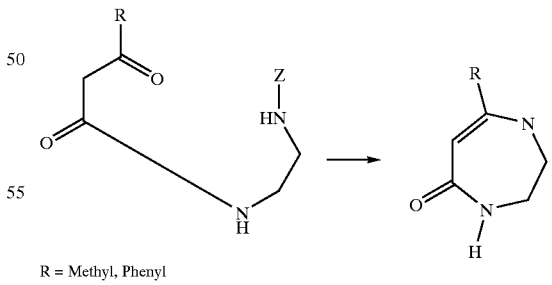

R = Methyl, Phenyl

Ring expansion methodology based on β lactams to provide for larger ring lactams containing an aza group has twice been reported in Wasserman, et al., *J. Am. Chem. Soc.*, 103:461–2 (1981)[90] and in Crombie, et al., *Tetrahedron Lett.*, 27(42):5151–5154 (1986).[91]

Dieckmann methodology has been used to prepare aza caprolactams from unsymmetrical amines such as shown below by Yokoo, et al., *Bull, Chem. Soc. Jap.*, 29:631 (1956).[92]

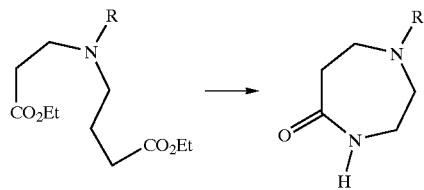

wherein R is as defined in this reference. The disclosure of Yokoo, et al. can be extended to cover R being alkyl, substituted alkyl, aryl, alkoxy, substituted alkoxy, heteroaryl, cycloalkyl, heterocyclic, heterocyclooxy, alkenyl, substituted alkenyl, and the like.

The synthesis of various members of the oxalactam series has been reported by Burkholder, et al., *Bioorg. Med. Chem. Lett.*, 2:231 (1993)[93] and references cited therein which oxalactams are represented by the formula:

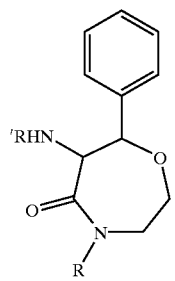

wherein R' is as defined in the reference and R can be alkyl, substituted alkyl, aryl, alkoxy, substituted alkoxy, heteroaryl, cycloalkyl, heterocyclic, heterocyclooxy, alkenyl, substituted alkenyl, and the like.

The synthesis of thialactams (generally oxalactams can be made by the same methodology) has been reported by Freidinger, et al., *J. Org. Chem.*, 47:104–109 (1982)[18] who prepared thialactams of the formula:

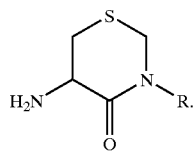

This reference provides a series of procedures having broad application for synthesis of lactams, permitting R in the above formula to be derived from any amine (alkyl, aryl, heteroaryl, etc.) with the restriction being that the R-group does not contain any functional groups reactive with form- aldehyde (e.g., primary and secondary amines). The general synthetic scheme provided by Freidlinger, et al. is:

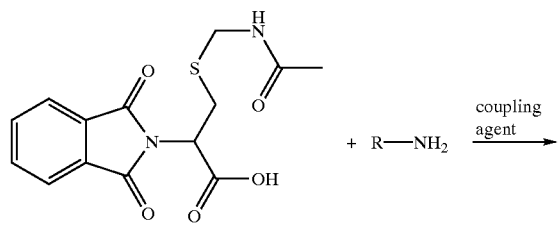

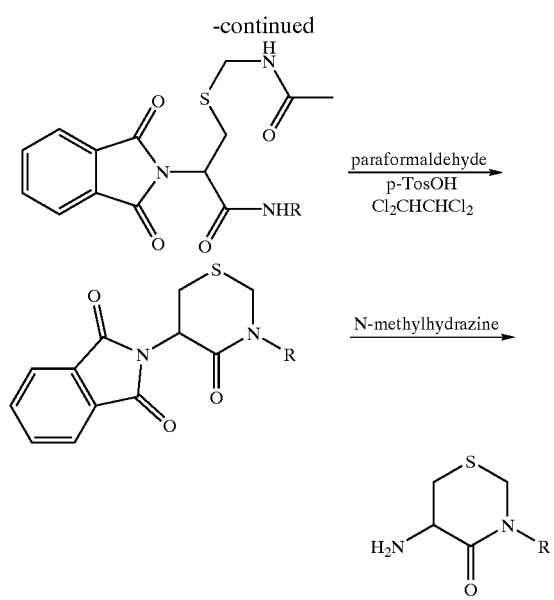

The coupling agent is any standard reagent used in the formation of typical peptide or amide bonds, for example, carbodiimide reagents. See, also, Karanewsky, U.S. Pat. No. 4,460,579 and Kametani, et al., *Heterocycles*, 9:831–840 (1978).[95]

The Friedinger procedure can be extended to afford disubstituted thialactams of the following structure:

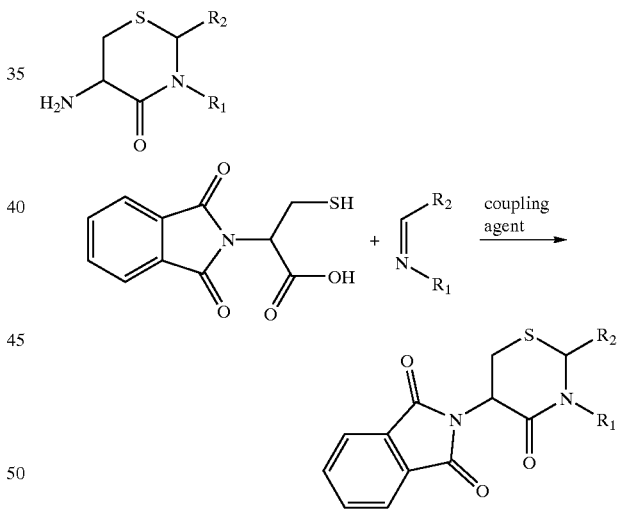

In practical terms, $R_2$ will be limited to aryl and heteroaryl groups and sterically hindered alkyl groups such as t-butyl. $R_1$ can be highly variable and is limited only by subsequent reaction steps.

Still further is the Kametani procedure which provides for lactams as follows:

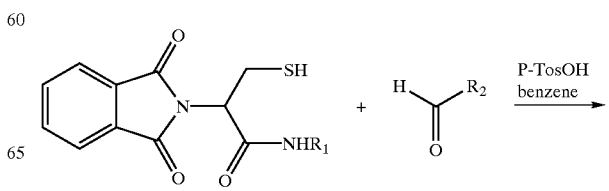

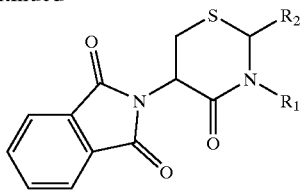

In principle, the Kametani procedure allows for a wide selection of R1 and R2 groups limited primarily by stability to the reaction conditions.

See, for example, Yanganasawa, et al., *J. Med. Chem.*, 30: 1984–1991 (1987)[96] and J. Das et al., *Biorg. Med. Chem. Lett.*, 4:2193–2198 (1994)[97] which describes general methods for the synthesis of isomeric 7-membered thialactams of the following structure:

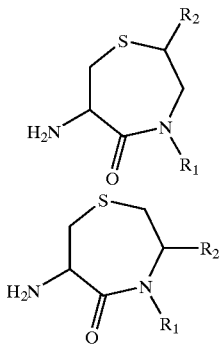

The first synthetic route is:

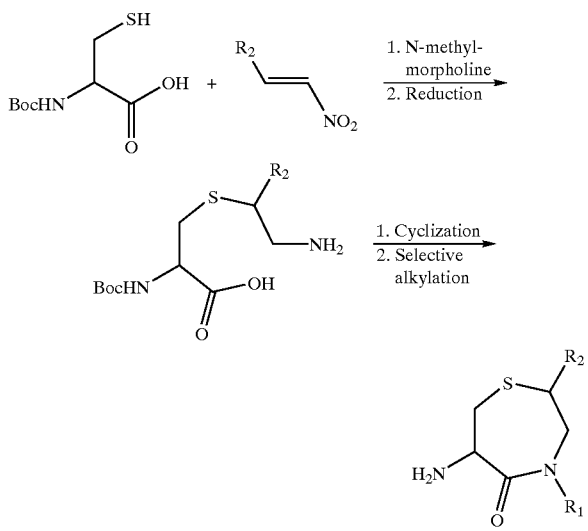

$R_2$ can be highly variable (e.g., alkyl, substituted alkyl, aryl, heteroaryl, heterocyclic and the like) since a number of well documented routes exist for the synthesis of nitroethylene derivatives from aldehydes and nitromethane (Henry reaction) followed by dehydration. $R_1$ is limited to groups that can undergo alkylation reactions.

The second compound series can be prepared as follows:

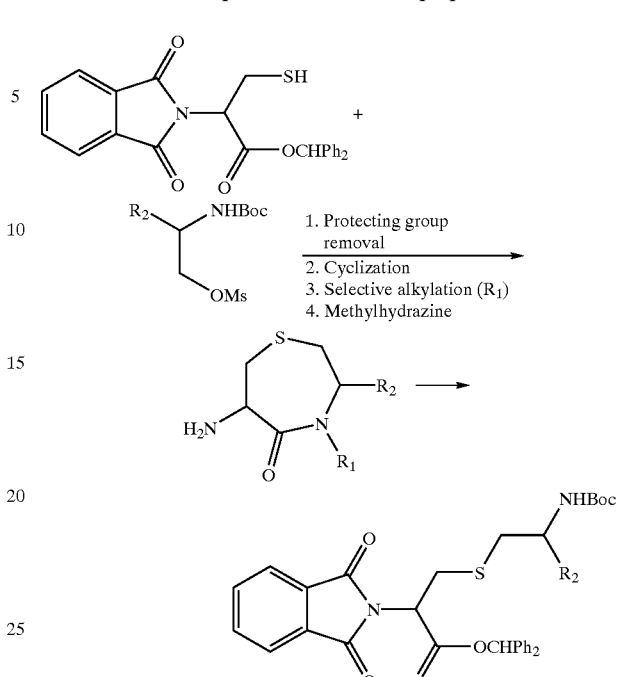

In this synthesis, $R_2$ can be highly variable. The starting component required to introduce $R_2$ can be readily derived by the reduction of any known α-BOC-amino acid to the alcohol derivative followed by formation of the mesylate.

As noted above, the primary approaches to the preparation of lactams is the Beckmann/Schmidt ring expansion reaction using either inter- or intramolecular approaches serves to prepare lactams of various ring sizes. The intramolecular approach generates bicyclic materials with the lactam nitrogen incorporated into the ring fusion. Additional approaches set forth above involve the internal cyclization of omega-amino acids/esters where the construction of the substituent pattern takes place prior to cyclization, and internal cyclization of an electrophilic center onto a nucleophilic functional group as in the Friedel Crafts type cyclization used in the Ben-Ishal procedure for making benzazepinones. This latter procedure is applicable to a wide variety of heteroaromatics as well as benzenoid rings, and may also be applied to non-aromatic double or triple bonds to generate a wide array of substituents or ring fusions.

Deoxygenation of the lactam by reagents such as diborane, $LiAlH_4$, and the like leads to azaheterocycles (=X is dihydro).

Similarly, for X=H, OH, such compounds can be prepared by epoxidation of cycloalkenyl groups followed by oxirane opening by, e.g., ammonia. After formation of compounds of Formulas I–VI, =X being H, OH can be oxidized to provide for cycloalkylones (=X being oxo).

Additionally, the 5,7-dihydro-6H-dibenz[b,d]azepin-6-one derivatives employed in this invention can be prepared using conventional procedures and reagents. For example, an appropriately substituted N-tert-Boc-2-amino-2'-methylbiphenyl compound can be cyclized to form the corresponding 5,7-dihydro-6H-dibenz[b,d]azepin-6-one derivative by first treating the biphenyl compound with about 2.1 to about 2.5 equivalents of a strong base, such as sec-butyl lithium. This reaction is typically conducted at a temperature ranging from about −80° C. to about −60° C. in an inert diluent such as THF. The resulting dianion is then treated with dry carbon dioxide at a temperature of about −78° C. to afford the 5,7-dihydro-6H-diben[b,d]azepin-6-one. This procedure is described further in R. D. Clark et al., *Tetrahedron*, 49(7), 1351–1356 (1993) and references cited therein.

After forming the 5,7-dihydro-6H-dibenz[b,d]azepin-6-one, the amide nitrogen can be readily alkylated by first treating the dibenazepinone with about 1.1 to about 1.5 equivalents of a strong base, such as sodium hydride, in an inert diluent, such as DMF. This reaction is typically conducted at a temperature ranging from about −10° C. to about 80° C. for about 0.5 to about 6 hours. The resulting anion is then contacted with an excess, preferably about 1.1 to about 3.0 equivalents, of an alkyl halide, typically an alkyl chloride, bromide or iodide. Generally, this reaction is conducted at a temperature of about 0° C. to about 100° C. for about 1 to about 48 hours.

An amino group can then be introduced at the 5-position of the 7-alkyl-5,7-dihydro-6H-diben[b,d]azepin-6-one using conventional procedures and reagents. For example, treatment of 7-methyl-5,7-dihydro-6H-diben[b,d]azepin-6-one with an excess of butyl nitrite in the presence of a strong base, such as potassium 1,1,1,3,3,3-hexamethyldisilazane (KHMDS), affords 5-oximo-7-methyl-5,7-dihydro-6H-diben[b,d]azepin-6-one. Subsequent reduction of the oximo group by hydrogenation in the presence of a catalyst, such as palladium on carbon, then provides 5-amino-7-methyl-5,7-dihydro-6H-diben[b,d]azepin-6-one. Other conventional amination procedures, such as azide transfer followed by reduction of the azido group, may also be employed.

Similarly, various benzodiazepine derivatives suitable for use in this invention can be prepared using conventional procedures and reagents. For example, a 2-aminobenzophenone can be readily coupled to α-(isopropylthio)-N-(benzyloxycarbonyl)glycine by first forming the acid chloride of the glycine derivative with oxalyl chloride, and then coupling the acid chloride with the 2-aminobenzophenone in the presence of a base, such as 4-methylmorpholine, to afford the 2-[-(isopropylthio)-N-(benzyloxycarbonyl)glycinyl]-aminobenzophenone. Treatment of this compound with ammonia gas in the presence of an excess, preferably about 1.1 to about 1.5 equivalents, of mercury (II) chloride then affords the 2-[N-(α-amino)-N-(benzyloxycarbonyl)-glycinyl]aminobenzophenone. This intermediate can then be readily cyclized by treatment with glacial acetic acid and ammonium acetate to provide the 3-(benzyloxycarbonyl)amino-2,3-dihydro-5-phenyl-1H-1,4-benzodiazepin-2-one 1. Subsequent removal of the Cbz group affords the 3-amino-2,3-dihydro-5-phenyl-1H-1,4-benzodiazepin-2-one.

Alternatively, 2,3-dihydro-5-phenyl-1H-1,4-benzodiazepin-2-ones can be readily aminated at the 3-position using conventional azide transfer reactions followed by reduction of the resulting azido group to form the corresponding amino group. The conditions for these and related reactions are described in the examples set forth below. Additionally, 2,3-dihydro-5-phenyl-1H-1,4-benzodiazepin-2-ones are readily alkylated at the 1-position using conventional procedures and reagents. For example, this reaction is typically conducted by first treating the benzodiazepinone with about 1.1 to about 1.5 equivalents of a base, such as sodium hydride, potassium tert-butoxide, potassium 1,1,1,3,3,3-hexamethyldisilazane, cesium carbonate, in an inert diluent, such as DMF. This reaction is typically conducted at a temperature ranging from about −78° C. to about 80° C. for about 0.5 to about 6 hours. The resulting anion is then contacted with an excess, preferably about 1.1 to about 3.0 equivalents, of an alkyl halide, typically an alkyl chloride, bromide or iodide. Generally, this reaction is conducted at a temperature of about 0° C. to about 100° C. for about 1 to about 48 hours.

Additionally, the 3-amino-2,4-dioxo-2,3,4,5-tetrahydro-1H-1,5-benzodiazepines employed in this invention are typically prepared by first coupling malonic acid with a 1,2-phenylenediamine. Conditions for this reaction are well known in the art and are described, for example, in PCT Application WO 96-US8400 960603. Subsequent alkylation and amination using conventional procedures and reagents affords various 3-amino-1,5-bis(alkyl)-2,4-dioxo-2,3,4,5-tetrahydro-1H-1,5-benzodiazepines. Such procedures are described in further detail in the example set forth below.

Accordingly, a vast number of lactams, lactones and thiolactones are available by art recognized procedures. Similarly, the art is replete with examples of aminocycloalkyl compounds for use in the synthesis of compounds of Formulas I–VI above.

In the synthesis of the compounds described herein using the synthetic methods described above, the starting materials can contain a chiral center (e.g., alanine) and, when a racemic starting material is employed, the resulting product is a mixture of R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Pharmaceutical Formulations

When employed as pharmaceuticals, the compounds described herein are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The pharmaceutical compositions contain, as the active ingredient, one or more of the compounds described above, associated with pharmaceutically acceptable carriers. The pharmaceutical compositions can be prepared, for example, by mixing the active ingredient with an excipient, diluting the active ingredient with an excipient, or enclosing the active ingredient within a carrier such as a capsule (including microparticles, nanoparticles, and liposomes), sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of Formulas I–VI above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, and the severity of the patient's symptoms.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50 to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 560 mg quantities.

FORMULATION EXAMPLE 9

A subcutaneous formulation may be prepared as follows:

| Ingredient | Quantity |
| --- | --- |
| Active Ingredient | 1.0 mg |
| corn oil | 1 ml |

(Depending on the solubility of the active ingredient in corn oil, up to about 5.0 mg or more of the active ingredient may be employed in this formulation, if desired).

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in diagnosing and treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028, the contents of each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as a "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 1 to about 500 mg/kg/day.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The compounds described herein are also suitable for use in the administration of the compounds to a cell for diagnostic and drug discovery purposes. Specifically, the compounds may be used in the diagnosis of cells releasing and/or synthesizing β-amyloid peptide. In addition the compounds described herein are useful for the measurement and evaluation of the activity of other candidate drugs on the inhibition of the cellular release and/or synthesis of β-amyloid peptide.

The following synthetic and biological examples are offered to illustrate this invention and are not to be construed in any way as limiting the scope of this invention.

EXAMPLES

In the examples below, the following abbreviations have the following meanings. If an abbreviation is not defined, it has its generally accepted meaning.

| | |
|---|---|
| BEMP | = 2-tert-butylimino-2-diethylamino-1,3-dimethylperhydro-1,3,2-diazaphosphorine |
| Boc | = t-butoxycarbonyl |
| BOP | = benzotriazol-1-yloxy-tris (dimethylamino) phosphonium hexafluorophosphate |
| bd | = broad doublet |
| bs | = broad singlet |
| d | = doublet |
| dd | = doublet of doublets |
| DIC | = diisopropylcarbodiimide |
| DMF | = dimethylformamide |
| DMAP | = dimethylaminopyridine |
| DMSO | = dimethylsulfoxide |
| EDC | = ethyl-1-(3-dimethyaminopropyl)carbodiimide |
| eq. | = equivalents |
| EtOAc | = ethyl acetate |
| g | = grams |

-continued

| | | |
|---|---|---|
| HOBT | = | 1-hydroxybenzotriazole hydrate |
| Hunig's base | = | diisopropylethylamine |
| L | = | liter |
| m | = | multiplet |
| M | = | molar |
| max | = | maximum |
| meq | = | milliequivalent |
| mg | = | milligram |
| mL | = | milliliter |
| mm | = | millimeter |
| mmol | = | millimole |
| MOC | = | methoxyoxycarbonyl |
| N | = | normal |
| N/A | = | not available |
| ng | = | nanogram |
| nm | = | nanometers |
| OD | = | optical density |
| PEPC | = | 1-(3-(1-pyrrolidinyl)propyl)-3-ethylcarbodiimide |
| PP-HOBT | = | piperidine-piperidine-1-hydroxybenzotrizole |
| psi | = | pounds per square inch |
| | = | phenyl |
| q | = | quartet |
| quint. | = | quintet |
| rpm | = | rotations per minute |
| s | = | singlet |
| t | = | triplet |
| TFA | = | trifluoroacetic acid |
| THF | = | tetrahydrofuran |
| tlc | = | thin layer chromatography |
| L | = | microliter |
| UV | = | ultra-violet |

In the examples below, all temperatures are in degrees Celcius (unless otherwise indicated). The compounds set forth in the examples below were prepared using the following general procedures as indicated.

The term "Aldrich" indicates that the compound or reagent used in the procedure is commercially available from Aldrich Chemical Company, Inc., 1001 West Saint Paul Avenue, Milwaukee, Wis. 53233 USA.

The term "Fluka" indicates that the-compound or reagent is commercially available from Fluka Chemical Corp., 980 South 2nd Street, Ronkonkoma N.Y. 11779 USA.

The term "Lancaster" indicates that the compound or reagent is commercially available from Lancaster Synthesis, Inc., P.O. Box 100 Windham, N.H. 03087 USA.

The term "Sigma" indicates that the compound or reagent is commercially available from Sigma, P.O. Box 14508, St. Louis Mo. 63178 USA;

The term "Chemservice" indicates that the compound or reagent is commercially available from Chemservice, Inc., Westchester, Pa.

The term "Bachem" indicates that the compound or reagent is commercially available from Bachem Biosciences Inc., 3700 Horizon Drive, Renaissance at Gulph Mills, King of Prussia, Pa. 19406 USA.

The term "Maybridge" indicates that the compound or reagent is commercially available from Maybridge Chemical Co. Trevillett, Tintagel, Cornwall PL34 OHW United Kingdom.

The term "TCI" indicates that the compound or reagent is commercially available from TCI America, 9211 North Harborgate Street, Portland Oreg. 97203.

The term "Alfa" indicates that the compound or reagent is commercially available from Johnson Matthey Catalog Company, Inc. 30 Bond Street, Ward Hill, Mass. 01835-0747.

The term "Novabiochem" indicates that the compound or reagent is commercially available from Calbiochem-Novabiochem Corp. 10933 North Torrey Pines Road, P.O. Box 12087, La Jolla Calif. 92039-2087.

The term "Oakwood" indicates that the compound or reagent is commercially available from Oakwood, Columbia, S.C.

The term "Advanced Chemtech" indicates that the compound or reagent is commercially available from Advanced Chemtech, Louisville, Ky.

The term "Pfaltz & Bauer" indicates that the compound or reagent is commercially available from Pfaltz & Bauer, Waterbury, Conn., USA.

I. COUPLING PROCEDURES

General Procedure A

First EDC Coupling Procedure

To a 1:1 mixture of the corresponding carboxylic acid and the corresponding amino acid ester or amide in $CH_2Cl_2$ at 0° C. was added 1.5 equivalents triethylamine, followed by 2.0 equivalents hydroxybenzotriazole monohydrate and then 1.25 equivalents of ethyl-3-(3-dimethylamino)propyl carbodiimide HCl. The reaction mixture was stirred overnight at room temperature and then transferred to a separatory funnel. The mixture was washed with water, saturated aqueous $NaHCO_3$, 1N HCl and saturated aqueous NaCl, and then dried over $MgSO_4$. The resulting solution was stripped free of solvent on a rotary evaporator to yield the crude product.

General Procedure B

Second EDC Coupling Procedure

A mixture of the corresponding acid (1 eqv), N-1-hydroxybenzotriazole (1.6 eqv), the corresponding amine (1 eqv), N-methylmorpholine (3 eqv) and dichloromethane (or DMF for insoluble substrates) was cooled in an ice-water bath and stirred until a clear solution was obtained. EDC (1.3 eqv) was then added to the reaction mixture. The cooling bath was then allowed to warm to ambient temperature over 1–2 h and the reaction mixture was stirred overnight. The reaction mixture was then evaporated to dryness under vacuum. To the residue was added 20% aqueous potassium carbonate and the mixture was shaken throughly and then allowed to stand until the oily product solidified (overnight if necessary). The solid product was then collected by filtration, washed thoroughly with 20% aqueous potassium carbonate, water, 10% HCl, and water to give the product, usually in pure state. No racemization was observed.

General Procedure C

Third EDC Coupling Procedure

The carboxylic acid was dissolved in methylene chloride. The corresponding amino acid ester or amide (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product.

General Procedure D

Fourth EDC Coupling Procedure

A round bottom flask was charged with the corresponding carboxylic acid (1.0 eq.), hydroxybenzotriazole hydrate (1.1 eq.) and the corresponding amine (1.0 eq.) in THF under nitrogen atmosphere. An appropriate amount (1.1 eq for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in ethyl acetate (or similar solvent) and water, washed with saturated aqueous sodium bicarbonate solution, 1 N HCl, brine, dried over anhydrous sodium sulfate and the solvent removed at reduced pressure to provide the product.

General Procedure E

BOP Coupling Procedure

To a stirred solution of N-(3,5-difluorophenylacetyl) alanine (2 mmol) in DMF, cooled in an ice-water bath, was added BOP (2.4 mmol) and N-methylmorpholine (6 mmol). The reaction mixture was stirred for 50 min. and then a solution of α-amino-α-lactam (2 mmol) in DMF cooled at 0° C. was added. The cooling bath was allowed to warm to ambient temperature over 1–2 h and the reaction mixture was then stirred overnight. A 20% aqueous potassium carbonate solution (60 mL) was added and this mixture shaken throughly. No solid formed. The mixture was then washed with ethyl acetate (150 mL) and evaporated to dryness under vacuum to give a white solid. Water (50 mL) was then added and this mixture was shaken throughly. The precipitate that formed was collected by filtration, then washed thoroughly with water, followed by 1 mL of diethyl ether to give the product (51 mg, 0.16 mmol, 7.8%).

General Procedure F

Coupling of an Acid Chloride with an Amino Acid Ester

To a stirred solution of (D,L)-alanine isobutyl ester hydrochloride (4.6 mmol) in 5 ml of pyridine was added 4.6 mmol of the acid chloride. Precipitation occurred immediately. The mixture was stirred for 3.5 h, dissolved in 100 mL of diethyl ether, washed with 10% HCl three times, brine once, 20% potassium carbonate once and brine once. The solution was dried over magnesium sulfate, filtered, and evaporated to yield the product. Other amino acid esters may also be employed in this procedure.

General Procedure G

Coupling of a Carboxylic Acid with an Amino Acid Ester

A solution of the carboxylic acid (3.3 mmol) and 1,1'-carbodiimidazole (CDI) in 20 mL THF was stirred for 2 h. (D,L)-alanine isobutyl ester hydrochloride (3.6 mmol) was added, followed by 1.5 mL (10.8 mmol) of triethylamine. The reaction mixture was stirred overnight. The reaction mixture was dissolved in 100 mL of diethyl ether, washed with 10% HCl three times, brine once, 20% potassium carbonate once and brine once. The solution was dried over magnesium sulfate, filtered, and evaporated to yield the product. Other amino acid esters may also be employed in this procedure.

General Procedure H

Fifth EDC Coupling Procedure

In a round bottom flask was added a carboxylic acid (1.1 eq.) in THF, an amine hydrochloride (1.0 eq.), 1-hydroxybenzotriazole hydrate (1.1 eq.), N,N-diisopropylethylamine (2.1 eq.), followed by 1-(3-dimethylaminopropyl)-3-ethylcarbodiimide hydrochloride (EDC) (1.1 eq.). The reaction mixture stirred at room temperature for 10–20 hours under an atmosphere of nitrogen. The mixture was diluted with EtOAc and washed with 0.1 M HCl (1×10 mL), saturated NaHCO$_3$ (1×10 mL), H$_2$O (1×10 mL), and brine and dried over MgSO$_4$. The drying agent was removed by filtration and the filtrate was concentrated in vacuo. The residue was purified by flash column chromatography on silica gel followed by trituration from EtOAc and hexanes.

General Procedure I

Sixth EDC Coupling Procedure

To a solution or suspension of the amine or amine hydrochloride (1.0 eq.) in THF (0.05–0.1 M) under N$_2$ at 0° C. was added the carboxylic acid (1.0–1.1 eq.), hydroxybenzotriazole monohydrate (1.1–1.15 eq.), Hunig's base (1.1 eq. for free amines and 1.1–2.3 eq. for hydrochloride amine salts), followed by 1-(3-dimethylaminopropyl)-3-ethylcarbodiimide hydrochloride (1.1–1.15 eq.). The cooling bath was removed and the mixture allowed to warm to room temperature for 10–24 hours. The solution or mixture was diluted with EtOAc, in a 3–5 volume multiple of the initial THF volume, and washed with 0.1–1.0 M aq. HCl (1 or 2×), dilute NaHCO$_3$ (1 or 2×), and brine (1×). Then, the organic phase was dried over either MgSO$_4$ or Na$_2$SO$_4$, filtered, concentrated to provide the crude product, which was either further purified or utilized without further purification.

General Procedure J

EEDQ Coupling Procedure

To a solution of the amine in THF (1.0 eq., 0.05–0.08 M, final molarity) under N$_2$ at room temperature was added the N-t-Boc protected amino acid (1.1 eq., either as a solid or in THF via cannula), followed by EEDQ (Aldrich, 1.1 eq.). The pale yellow solution was stirred at room temperature for 16–16.5 hours, then diluted with EtOAc (in a 3–5 volume multiple of the initial THF volume), and washed with 1M aq. HCl (2×), dilute aq. NaHCO$_3$ (2×), and brine (1×). The organic phase was dried over either Na$_2$SO$_4$ or MgSO$_4$, filtered, and concentrated.

II. CARBOXYLIC ACIDS

General Procedure II-A

Ester Hydrolysis to Free Acid

Ester hydrolysis to the free acid was conducted by conventional methods. Below are two examples of such conventional de-esterification methods.

Method A: To a carboxylic ester compound in a 1:1 mixture of CH$_3$OH/H$_2$O was added 2–5 equivalents of K$_2$CO$_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over MgSO$_4$. The solution was stripped free of solvent on a rotary evaporator to yield the product.

Method B: The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was dissolved in water and washed with ether. The layers were separated and the aqueous layer was acidified to pH 2. The aqueous layer was extracted with ethyl acetate. The ethyl acetate extracts were dried over $Na_2SO_4$ and the solvent was removed under reduced pressure after filtration. The residue was purified by conventional methods (e.g., recrystallization).

General Procedure II-B

Acid Chloride Preparation

A carboxylic acid is dissolved in dichloromethane and this solution is cooled to 0° C. DMF (0.5 mL, catalytic) is added, followed by the dropwise addition of oxalyl chloride (18 mL, 0.20 mol) over a 5 minute period. The reaction is stirred for 3 h and then rotoevaporated at reduced pressure to give an oil which is placed on a high vacuum pump for 1 h to afford the acid chlorides.

General Procedure II-C

Schotten-Baumann Procedure

The acid chloride (from General Procedure II-B) is added dropwise to a 0° C. solution of L-alanine (Aldrich) (16.7 g, 0.187 mol) in 2 N sodium hydroxide (215 mL, 0.43 mol) or another amino acid such as tert-leucine or phenyl glycine. The reaction is stirred for 1 h at 0° C. and then overnight at room temperature. The reaction is diluted with water (100 mL), then extracted with ethyl acetate (3×150 mL). The organic layer is then washed with brine (200 mL), dried over $MgSO_4$, and rotoevaporated at reduced pressure to a residue. Recrystallization of the residue from ethyl acetate/hexanes affords the desired product in high yield.

General Procedure II-D

Reductive Amination

To a solution of an arylamine in ethanol in a hydrogenation flask is added 1 equivalent of a 2-oxocarboxylic acid ester (e.g., pyruvate ester), followed by 10% palladium on carbon (25 weight percent based on the arylamine). The reaction mixture is hydrogenated at 20 psi $H_2$ on a Parr shaker until complete reaction is indicated by tlc (30 minutes to 16 hours). The reaction mixture is then filtered through a pad of Celite 545 (available from Aldrich Chemical Company, Inc.) and stripped free of solvent on a rotary evaporator. The crude product residue can then be further purified via chromatography.

3. Cyclic Ketone Derivatives

General Procedure 3-A

Jones Oxidation Procedure

The compound to be oxidized is stirred in acetone and the Jones reagent is added in portions until the starting material is consumed. The reaction mixture is quenched with isopropanol and the mixture is filtered through Celite and concentrated under reduced pressure. The residue is partitioned between ethyl acetate and water and the organic portion is dried over sodium sulfate and then concentrated under reduced pressure. The crude product is purified by silica gel chromatography and/or recrystallization.

General Procedure 3-B

Swern Oxidation Procedure

To a stirred mixture of oxalyl chloride (0.1.5 mL, 1.2 mmol) in 10 mL of dichloromethane cooled to −78° C. is added DMSO (0.106 mL, 1.5 mmol) and the mixture is stirred for 10 minutes. A solution of the alcohol (0.1828 g, 0.60 mmol) in 20 mL of chloroform is added dropwise. The reaction mixture is stirred at −78° C. for 2 hours, and then 0.5 mL (3.6 mmol) of triethylamine is added. Stirring is continued for 1 hour and then the mixture is allowed to warm to room temperature and stirring is continued at ambient temperature overnight. The mixture is then diluted with 50 mL of dichloromethane, washed with brine (3×), dried over magnesium sulfate, filtered and evaporated to dryness to give a crude product that is typically purified by column chromatography.

5. Lactams

General Procedure 5-A

N-Alkylation of Lactams

To a stirred solution of a BOC-protected α-aminocaprolactam (6.87 g, 30 mmol) in DMF (150 mL) was added in portions 97% NaH (1.08 g, 45 mmol). Bubbling occurred immediately and followed by heavy precipitation. After 10 min., benzyl bromide (3.93 mL, 33 mmol) was added. The precipitate dissolved quickly and in about 10 min. a clear solution was obtained. The reaction mixture was stirred overnight and then evaporated as completely as possible on a rotovap at 30° C. Ethyl acetate (100 mL) was added to the residue and this mixture was washed with water, brine, and dried over magnesium sulfate. After filtration and concentration, a thick liquid (10 g) was obtained which was then chromatographed over silica gel with 1:3 ethyl acetate/hexane as the eluant to provide 5.51 g (58%) of the N-benzylated product as an oil. Other lactams and alkylating agents may be used in this procedure to obtain a wide variety of N-alkylated lactams. Various bases, such as $LiN(SiMe_3)$, may also be employed.

General Procedure 5-B

BOC Removal Procedure

The BOC-protected compound in a 1:1–2:1 mixture of $CH_2Cl_2$ and trifluoroacetic acid was stirred until tlc indicated complete conversion, typically 2 hours. The solution was then stripped to dryness and the residue was taken up in ethyl acetate or $CH_2Cl_2$. The solution was washed with saturated aqueous $NaHCO_3$ and the aqueous phase was adjusted to a basic pH, then extracted with ethyl acetate or $CH_2Cl_2$. The organic phase was washed with saturated aqueous NaCl and dried over $MgSO_4$. The solution was stripped free of solvent on a rotary evaporator to yield the product.

General Procedure 5-C

Synthesis of A-Aminolactams

The Schmidt reaction was conducted on 4-ethylcyclohexanone using hydroxyamine sulfonic acid as described in Olah, Org. Synth. Collective, Vol. VII, page 254, to provide 5-ethylcaprolactam in 76% yield. Using the procedure described in Watthey, et al., J. Med. Chem., 1985, 28, 1511–1516, this lactam was then dichlorinated with $PCl_5$ at the α position and reduced by hydrogenation to provide four isomeric monochlorides (two racemic mixtures). The two racemic mixtures were separated from each other by column chromatography using silica gel and each racemic mixture was reacted with sodium azide to yield the corresponding azide, which was hydrogenated to provide the corresponding α-aminolactams. Other cycloalkanones may be employed in this procedure to provide a wide variety of α-aminolactams. In some cases, such as when preparing the 9-membered ring α-aminolactam, longer reaction times, higher reaction temperatures and an excess of sodium azide may be required. For example, the 9-membered ring α-aminolactam required 5 equivalents of sodium azide, a reaction temperature of 120° C. and a reaction time of 4 days. Such conditions can be readily determined by those of ordinary skill in the art.

General Procedure 5-D

Synthesis of 4-Amino-1,2,3,4-tetrahydroisoquinoline-3-ones

The 4-amino-1,2,3,4-tetrahydroisoquinoline-3-one derivatives employed in this invention can be prepared by the following art-recognized procedures. The conditions for these reactions are further described in D. Ben-Ishai, et al., *Tetrahedron*, 43, 439450 (1987). The following intermediates were prepared via this procedure:

3-amino-1,2,3,4-tetrahydroisoquinolin-3-one 4-amino-7-benzyl-1,2,3,4-tetrahydroisoquinolin-3-one 4-amino-1-phenyl-1,2,3,4-tetrahydroisoquinolin-3-one cis and trans-4-amino-1-phenyl-1,2,3,4-tetrahydroisoquinolin-3-one 4-amino-2-phenethyl-1,2,3,4-tetrahydroisoquinolin-3-one 4-amino-2-methyl-1,2,3,4-tetrahydroisoquinolin-3-one 9-amino(fluoren-1-yl)glycine d-lactam-1,2,3,4-tetrahydroisoquinolin-3-one.

Step A—Preparation of N-Bismethoxycarbonylaminoacetic Acid: To one mole equivalent of glyoxylic acid in 2 liters of ethanol-free chloroform was added two mole equivalents of methyl carbamate and 0.1 mole equivalent of naphthalene sulfonic acid. The reaction mixture was then brought to a reflux for 6 hours. Water was removed using an inverse Dean Stark trap. The reaction was then cooled and the product filtered and washed with chloroform. The white solid was recrystallized from ethyl acetate/hexanes to give a white powder in 65% yield.

Step B—Coupling Procedure: To 0.0291 moles of N-bismethoxycarbonylaminoacetic acid (or the appropriate carbocyclic acid) in 200 mL of THF was added one mole equivalent of EDCCHCl, a benzylamine, HOBT, and diisopropylethylamine. The reaction was allowed to stir at room temperature for 18 hours and then poured into a separatory funnel and extracted into ethyl acetate. The ethyl acetate solution was washed with 1 molar $K_2CO_3$ and then 1 molar HCl. The organic layer was dried over $Na_2SO_4$, filtered and solvent removed to give the crystalline benzylamide of N-bismethoxycarbonylaminoacetic acid. This material was used without further purification. Typical yields range from 40–55%.

Step C—Cyclization Procedure: The benzylamide of N-bismethoxycarbonylaminoacetic acid (0.008 moles) was dissolved in 75 mL of methanesulfonic acid and allowed to stir over night at room temperature. The reaction mixture was poured over ice and extracted into ethyl acetate. The ethyl acetate extract was washed with 1 molar $K_2CO_3$ and then 1 N HCl. The organic layer was dried over $Na_2SO_4$, filtered and the solvent removed to give the crystalline 4-methoxycarbonylamino-1,2,3,4-tetrahydroisoquinoline-3-one in 50–90% yield. This material was used without further purification.

Step D—Removal of the Methoxyoxycarbonyl Group (MOC): To the 4-methoxycarbonylamino-1,2,3,4-tetrahydroisoquinoline-3-one (3.4 mmoles) in 30 ML of acetonitrile was added 2 mole equivalents of trimethylsilyliodide (TMSI). The reaction mixture was heated to 50–80° C. for 3 hrs and then cooled and poured into a separatory funnel. The reaction mixture was diluted with ethyl acetate and washed with 1 molar $K_2CO_3$ and then with 5% $NaHSO_3$. The organic layer was dried over $Na_2SO_4$ and filtered. The solvent was removed under reduced pressure to give the 4-amino-1,2,3,4-tetrahydroisoquinoline-3-one derivative. Typical yields range from 50–87%.

Step E—Alternative Procedure for Removal of the Methoxyoxycarbonyl Group: To 3.8 mmoles of the MOC-protected compound was added 10 mL of 30% HBr in acetic acid and this reaction mixture was heated to 60° C. for 3 hrs. The mixture was then cooled and hexanes were added. The hexanes layer was decanted off and the residue as placed under reduced pressure to give a tan solid. This solid was slurried in ether and filtered to give the 4-amino-1,2,3,4-tetrahydroisoquinoline-3-one hydrobromide salt. Typical yields range from 57–88%.

Example 5-A

Synthesis of 3-Amino-1,2,3,4-tetrahydroquinolin-2-one

Step A: Sodium (0.30 g, 110M %) was added to anhydrous ethanol (45 mL) and the reaction mixture was stirred until homogenous. Diethyl N-acetylaminomalonate (2.51 g, 100 M %) was added in one portion and this mixture was stirred for 1 h. 2-Nitrobenzyl bromide (2.5 g, 100M %) was then added in one portion and the reaction mixture was stirred for 3 h. The reaction was poured into water and extracted with ethyl acetate (3x) and then backwashed with water (3x) and brine (1x). Treatment with $MgSO_4$, rotoevaporation, and chromatography (30% EtOAc/hexanes) yielded diethyl N-acetylamino-2-nitrobenzylmalonate in 82% yield.

Step B: Diethyl N-acetylamino-2-nitrobenzylmalonate (1 g, 100M %) was dissolved in a minimum amount of EtOH. Pd/C (10%, 0.05 g) was added and the reaction mixture was subjected to 50 psi of $H_2$ for 3 hours. The reaction was then filtered thru a pad of celite. Additional EtOH (25 mL) and TsOH (catalytic amount, 0.01 g) were added and this mixture was refluxed for 2 hours. The reaction was rotoevaporated to a residue and then partitioned between water and ethyl acetate. The water layer was extracted with ethyl acetate (3x) and the combined ethyl acetate extracts were washed with water (3x) and then brine (1x). Treatment with $MgSO_4$ and rotoevaporation yielded pure 3-(N-acetylamino)-3-carboethoxy-1,2,3,4-tetrahydroquinolin-2-one (89% yield).

Step C: 3-(N-Acetylamino)-3-carboethoxy-1,2,3,4-tetrahydroquinolin-2-one (0.75 g, 100M %) was suspended in 6N HCl (25 mL) and the mixture was heated to 100° C. for 3 hours. The reaction was cooled, rotoevaporated to a residue and then partitioned between water and ethyl acetate. The water was extracted with ethyl acetate (3x) and the combined ethyl acetate extracts were then washed with water (3x) and then brine (1x). Treatment with $MgSO_4$ followed by rotoevaporation yielded 3-(R,S)-amino-1,2,3,4-tetrahydroquinolin-2-one (72% yield).

Example 5-B

Synthesis of 4-Amino-1-(pyrid-4-yl)-1,2,3,4-tetrahydroisoquinolin-3-one

Step A: To a solution of 4-cyanopyridine (Aldrich) (0.150 moles) in 300 mL of dry ether was added 1.1 eq. of phenylmagnesium bromide (Aldrich) dropwise. The reaction was refluxed for 2 hours and then stirred overnight at room temperature. Sodium borohydride (1.0 eq.) was added dropwise as a solution in 200 mL of methanol (CAUTION—very exothermic). The reaction was then heated to reflux for 6 hours, cooled and quenched with a saturated solution of ammonium chloride. The solution was decanted from the salt in the reaction mixture and acidified with 1N HCl. After washing the aqueous layer with ethyl acetate, the pH of aqueous layer was adjusted to about 9.0 with 1N sodium hydroxide (cold). The aqueous layer was then extracted with ethyl acetate and the organic extracts washed with brine, dried over $Na_2SO_4$, filtered and concentrated to give 4-pyridyl-a-benzyl amine as a thick yellow oil.

Step B: Following General Procedure 5-D and using 4-pyridyl-a-benzyl amine, the title compound was prepared.

Example 5-C

Synthesis of 4-Amino-1-(pyrid-2-yl)-1,2,3,4-tetrahydroisoquinolin-3-one

Step A: 2-Pyridyl-a-benzyl amine was prepared by substituting 2-cyanopyridine (Aldrich) for 4-cyanopyridine in the procedure described in Example 5-B.

Step B: Following General Procedure 5-D and using 4-pyridyl-a-benzyl amine, the title compound was prepared.

Example 5-D

Synthesis of 4-Amino-1-(pyrid-3-yl)-1,2,3,4-tetrahydroisoquinolin-3-one

Step A: Following the procedure described in *J. Med. Chem.*, 1982, 25, 1248, and using 3-benzoyl-pyridine (Aldrich), 3-pyridyl-a-benzyl amine was prepared.

Step B: Following General Procedure 5-D and using 3-pyridyl-a-benzyl amine, the title compound was prepared.

Example 5-E

Synthesis of 4-Amino-7-benzyl-1,2,3,4-tetrahydroisoquinolin-3-one

Step A: To a Parr bottle containing 3-benzoylbenzoic acid (0.044 moles) (Aldrich) in 150 mL of ethyl acetate and 4.5 mL of concentrated $H_2SO_4$ was added 10 grams of 5% Pd/C. The mixture was hydrogenated on a Parr apparatus under hydrogen (45 psi) overnight. The reaction mixture was then filtered through Hyflo, washing with ethyl acetate. The filtrate was dried over $Na_2SO_4$, filtered and concentrated to give an oil. The oil was slurried in hexane and the resulting white solid was collected by filtration to afford 3-benzylbenzoic acid, which was used without further purification.

Step B: To the product from Step A (0.0119 moles) was added 150 mL of $CH_2Cl_2$, one drop of DMF, 10 mL of oxalyl chloride, and the mixture was stirred at room temperature for 3 hours. After cooling to 10° C., 30 mL of $NH_4OH$ (exothermic) was added and the mixture was stirred for 30 min. The reaction mixture was then concentrated and the resulting residue diluted with ethyl acetate. The organic layer was washed with 1N NaOH, brine, dried over $Na_2SO_4$, and concentrated to give the 3-(benzyl)benzamide as a white solid, which was used without further purification.

Step C: To a solution of 3-(benzyl)benzamide (0.0094 moles) from Step B in 70 of toluene was added 8 mL of Red-A17 (65+wt. % solution of sodium bis(2-methoxyethoxy)aluminum hydride in toluene, Aldrich) (CAUTION—reaction very exothermic). The reaction mixture was then heated at 60° C. for 2 hours and then poured over ice. The resulting mixture was extracted with ethyl acetate and the combined extracts were washed with water and brine. The organic layer was extracted with 1N HCl and the aqueous layer washed with ethyl acetate. The pH of the aqueous layer was then adjusted to about 9.0 with 1N NaOH and extracted with ethyl acetate. The organic extracts were washed with water and brine and then concentrated to give 3-(benzyl)benzyl amine.

Step D: Following General Procedure 5-D and using 3-(benzyl)benzyl amine, the title compound was prepared.

Example 5-F

Synthesis of 4-Amino-6-phenyl-1,2,3,4-tetrahydroisoquinolin-3-one

Step A: To a solution of 4-biphenylcarboxamide (Aldrich) (0.025 mole) in 150 mL of THF cooled to 10° C. was added a solution of 1.5 eq of LAH (1M in THF) dropwise. The reaction mixture turned from a white slurry to a green homogenous solution and then to a yellow homogeneous solution. The reaction was then quenched with 2.5 mL of 1N NaOH. The mixture was then filtered through Hyflo and extracted with ethyl acetate. The organic layer was then washed with 1N HCl. The pH of the resulting aqueous layer was adjusted to about 9 with 1N NaOH and extracted with ethyl acetate. The organic extracts were washed with water and brine, and then dried over $Na_2SO_4$, filtered and concentrated to give 4-(phenyl)benzyl amine as a white solid.

Step B: Following General Procedure 5-D and using 4-(phenyl)benzyl amine, the title compound was prepared.

Example 5-G

Synthesis of cis- and trans-4-Amino-1-phenyl-1,2,3,4-tetrahydroisoquinolin-3-one Step A: Following General Procedure 5-D and using a-phenylbenzylamine (Aldrich), 4-amino-1-phenyl-1,2,3,4-tetrahydroisoquinolin-3-one was prepared.

Step B: To a solution of 4-amino-1-phenyl-1,2,3,4-tetrahydroisoquinolin-3-one (0.00158 moles) from Step A in 20 mL of $CH_2Cl_2$ was added 2.0 eq. of triethylamine and Boc anhydride (1.1 eq.). The reaction was stirred overnight at room temperature and then concentrated. The residue was diluted with ethyl acetate and water. The pH of the aqueous layer was adjusted to 3.0 with sodium bisulfate and the layers were separated. The organic layer was dried over $Na_2SO_4$, filtered and concentrated. The residue was purified by LC 2000, eluting with ethyl acetate/hexanes (70:30) to give a white solid containing a 1:1 mixture of cis- and trans4-(N-Boc-amino)-1-phenyl-1,2,3,4-tetrahydroisoquinolin-3-one isomers. This mixture was recrystallized from ethyl acetate to give the pure trans isomer and a cis isomer-enriched mixture of cis and trans isomers. This mixture was recrystallized again from ethyl acetate/hexanes (70:30) to give the pure cis isomer.

Step C: The cis isomer and the trans isomer from Step B were separately deprotected using General Procedure 8-J to give cis4-amino-1-phenyl-1,2,3,4-tetrahydroisoquinolin-3- one and trans4-amino-1-phenyl-1,2,3,4-tetrahydroisoquinolin-3-one.

Example 5-H

Synthesis of 4-Amino-7-phenyl-1,2,3,4-tetrahydroisoquinolin-3-one

Step A: To a solution of 1-bromo-3-phenylbenzene (Aldrich) (0.0858 moles) in 300 mL of dry THF cooled to −78° C. was added tert-butyl lithium (2 eq.) (1.7M in hexane) dropwise. The reaction mixture was stirred for 40 min. at −78° C. and then quenched with 2 eq. of DMF (13.24 mL). The resulting mixture was stirred for 20 min. and then poured into a separatory funnel and extracted with $CH_2Cl_2$. The organic extracts were washed with water, dried over $Na_2SO_4$, filtered and concentrated to give a brown oil. This oil was purified by LC 2000 chromatography, eluting with ethyl acetate/hexanes (5:95) to give 3-biphenylcarboxaldehyde.

Step B: To a solution of 3-biphenylcarboxaldehyde (0.011 eq.) in 30 mL of methanol was added 10 eq. of 7N $NH_3$/MeOH and $NaCNBH_4$ (2 eq.). A yellow gum precipitated from solution. The solution was then heated at 60° C. until gum dissolved and the solution was stirred at room temperature overnight. The reaction mixture was then concentrated and the resulting residue diluted with ice water and ethyl acetate. The organic layer was then washed with brine and extracted with 5N HCl. The pH of the aqueous layer was then adjusted to 12 and the aqueous layer was extracted with cold ethyl acetate. The organic layer was dried over $Na_2SO_4$, filtered and concentrated to give 3-(phenyl)benzyl amine as an oil.

Step C: Following General Procedure 5-D and using 3-(phenyl)benzyl amine, the title compound was prepared.

Example 5-I

Synthesis of 4-Amino-1-benzyl-1,2,3,4-tetrahydroisoquinolin-3-one

Step A: To a solution of benzoyl chloride (0.123 moles) (Aldrich) in 600 mL of $CH_2Cl_2$ was added 2.0 eq. of phenethylamine (Aldrich) dropwise. The reaction mixture was stirred at room temperature for 3 hours and then poured into a separatory and extracted with $CH_2Cl_2$. The organic extracts were washed with water and 1N HCl, and then dried over $Na_2SO_4$, filtered and concentrated to give N-phenethyl benzamide.

Step B: Reduction of N-phenethyl benzamide using the procedure of Example 5-E, Step C afforded N-benzyl-N-phenethylamine as an oil.

Step C: Following General Procedure 5-D and using N-benzyl-N-phenethylamine, the title compound was prepared.

Example 5-J

Synthesis of 3-Amino-1-methyl-2-indolinone Monohydrochloride

Step A: (2,3-Dihydro-1-methyl-2-oxo-1H-indol-3-yl) carbamic acid methyl ester (CAS No. 110599-56-9) was prepared using the procedure described in Ben-Ishai, D.; Sataty, I.; Peled, N.; Goldshare, R. *Tetrahedron* 1987, 43, 439–450. The starting materials for this preparation were N-methylaniline (CAS #100-61-8, Eastman Kodak Co.), glyoxylic acid (CAS #298-12-4, Aldrich), and methyl carbamate (CAS #598-55-0, Aldrich).

Step B: The product from Step A (333.5 mg) in 31% HBr in AcOH (10 mL) was heated to 50–60° C. for 2 hours. The resulting orange solution was concentrated to a thick orange oil which was dissolved in EtOAc (15 mL) and the product extracted into 1 M aq. HCl (10 mL). The aqueous acid was neutralized with aq. $NaHCO_3$ and the product extracted into $CH_2Cl_2$ (10×10 mL). HCl (gas) was passed through the combined $CH_2Cl_2$ extracts to form a purple solution. The solution was concentrated to provide the title compound (262.8 mg) as a purple solid.

Example 5-K

Synthesis of 3-Amino-1-methyl-4-phenyl-3,4-trans-dihydrocarbostyril/Tin Complex

Step A:—Synthesis of 4-Phenyl-3,4-dihydrocarbostyril
4-Phenyl-3,4-dihydrocarbostyril (CAS #4888-33-9) was prepared in two steps using the procedure described by Conley, R. T.; Knopka, W. N. *J. Org. Chem.* 1964, 29, 496–497. The starting materials for this preparation were cinnamoyl chloride (Aldrich) and aniline (Aldrich). The title compound was purified by flash chromatography eluting with $CH_2Cl_2$/EtOAc (4:1).

Step B:—Synthesis of 1-Methyl-4-phenyl-3,4-dihydrocarbostyril
To a suspension of NaH (1.2 eq., 0.537 g of 60% dispersion in mineral oil) in THF (50 mL) under $N_2$ at 0° C. was added the product from Step A (1.0 eq., 2.50 g) in THF (50 mL) via cannula over a period of 5 minutes. The resulting pale yellow mixture was stirred at 0° C. for 10 minutes, then MeI (2.0 eq., 1.39 mL) was added. The opaque yellow mixture was allowed to slowly (ice bath not removed) warm to ambient temperature with stirring for 15 hours. 1M Aq. HCl (50 mL) and EtOAc (250 mL) were added and the phases partitioned. The organic phase was washed with dilute $NaHCO_3$ (1×100 mL), brine (1×100 mL), then dried over $MgSO_4$, filtered, concentrated, and the residue purified by flash chromatography eluting with $CH_2Cl_2$/EtOAc (19:1 gradient to 15:1) to provide 1-methyl-4-phenyl-3,4-dihydrocarbostyril.

Step C:—Synthesis of 3-Azido-1-methyl-4phenyl-3,4-trans-dihydrocarbostyril
Following General Procedure 8-K, 3-azido-1-methyl-4-phenyl-3,4-trans-dihydrocarbostyril was prepared as a white solid. The product was purified by flash chromatography eluting with $CH_2Cl_2$/hexanes/EtOAc 15:15:1.
Selected $^1$H-NMR data for the title compound ($CDCl_3$): d=4.46 (d, 1H, J=10.57 Hz), 4.18 (d, 1H, J=10.63 Hz).

Step D:—Synthesis of 3-Amino-1-methyl-4-phenyl-3,4-trans-dihydrocarbostyril/Tin Complex
To a mixture of $SnCl_2$ (350.7 mg) in MeOH (7 mL) under $N_2$ at 0° C. was added the product from Step C (257.4 mg) in MeOH/THF (5 mL/5 mL) via cannula over a period of 1 minute. The cooling bath was removed the solution allowed to warm to ambient temperature for 8 hours (No starting material by TLC). The solution was concentrated to a yellow foam, THF (10 mL) was added and the mixture was reconcentrated and used without further purification.

Example 5-L

Synthesis of 3-Amino-1-methyl-4-phenyl-3,4-cis-dihydrocarbostyril

Step A:—Synthesis of 3-Amino-1-methyl-4-phenyl-3,4-trans-dihydrocarbostyril
3-Amino-1-methyl-4-phenyl-3,4-trans-dihydrocarbostyril was prepared following General Procedure 8-F using 3-azido-1-methyl-4-phenyl-3,4-transdihydrocarbostyril from Example 5-K, Step C. The product was purified by L.C. 2000 eluting with EtOAc/hexanes (4:1) to yield a white solid.

Selected $^1$H-NMR data for the title compound (CDCl$_3$): d=4.03 (d, 1H, J=12.8 Hz), 3.92 (d, 1H, J=12.7 Hz).

Step B:—Synthesis of 3-(4-Chlorobenzylimine)-1-methyl-4-phenyl-3,4-trans-dihydrocarbostyril To a solution of the product from Step A (1 eq., 239.6 mg) in CH$_2$Cl$_2$ (10 mL) under N$_2$ at ambient temperature was added 4-chlorobenzaldehyde (1.05 eq., 140 mg, Aldrich), Et$_3$N (1.4 eq., 185 mL), and MgSO$_4$ (3.6 eq., 411 mg). The resultant mixture was stirred at room temperature for 73 hours. The solids were removed by filtration through a plug of Celite, rinsing with CH$_2$Cl$_2$, and the filtrate concentrated to provide 3-(4-chlorobenzylimine)-1-methyl-4-phenyl-3,4-trans-dihydrocarbostyril as a thick white foam.

Step C:—Synthesis of 3-Amino-1-methyl-4-phenyl-3,4-cis-dihydrocarbostyril

To a solution of diisopropylamine (1.05 eq., 0.132 mL) in THF (5 mL) under N$_2$ at −78° C. was added a solution of n-BuLi (1.05 eq., 0.588 ml of a. 1.6 M solution in hexanes) and the result solution was stirred for 30 minutes. To this solution was added the product from Step B (1.0 eq., 336 mg) in THF (2 mL) via cannula. The solution was allowed to warm to 0° C., then quenched with 1 M aq. HCl (3 mL) and allowed to warm to room temperature with stirring overnight. The product was extracted into H$_2$O and washed with EtOAc (1×), then the aqueous acid was basified with 1 M aq. K$_2$CO$_3$ and the product extracted into EtOAc. The EtOAc extract was dried over Na$_2$SO$_4$, filtered, and concentrated to give 3-amino-1-methyl-4-phenyl-3,4-cis-dihydrocarbostyril.

Selected $^1$H-NMR data for the title compound (CDCl$_3$): d=4.31 (d, 1H, J=6.6 Hz).

Example 5-M

Synthesis of 3-Amino-1-tert-butoxycarbonyl-4-phenyl-3,4-trans-dihydrocarbostyril/Tin Complex Step A:—Synthesis of 1-tert-Butoxycarbonyl-4-phenyl-3,4-dihydrocarbostyril 1-tert-Butoxycarbonyl-4-phenyl-3,4-dihydrocarbostyril was prepared from the product of Example 5-K, Step A (CAS #4888-33-9) by the Boc procedure for aryl amides described by Grehn, L.; Gunnarsson, K.; Ragnarsson, U. *Acta Chemica Scandinavica B* 1986, 40, 745–750; employing (Boc)$_2$O (Aldrich) and catalytic DMAP (Aldrich) in acetonitrile. The product was purified by flash chromatography eluting with CH$_2$Cl$_2$ gradient to CH$_2$Cl$_2$/EtOAc (19:1) and isolated as a pale yellow oil.

Step B—Synthesis of 3-Azido-1-tert-butoxycarbonyl-4-phenyl-3,4-tans-dihydrocarbostyril Following General Procedure 8-K using the product from Step A, the title compound was prepared as a 12.4:1 mixture of trans/cis isomers which were separated by flash chromatography eluting with hexanes/Et$_2$O (6:1 gradient to 4:1) in the first column and hexanes/EtOAc (12:1) in a second column. The pure trans isomer was used in Step C.

Selected $^1$H-NMR data for the title compound (CDCl$_3$): d=4.45 (d, 1H, J=11.1 Hz), 4.24 (d, 1H, J=11.2 Hz).

Step C:—Synthesis of 3-Amino-1-tert-butoxycarbonyl-4-phenyl-3,4-trans-dihydrocarbostyril/Tin Complex To a mixture of SnCl$_2$ (450.6 mg) in MeOH (9 mL) under N$_2$ at 0° C. was added the product from Part D (433.0 mg) in MeOH (15 mL) via cannula over a period of 1 minute. The cooling bath was removed the solution allowed to warm to ambient temperature for 17 hours. The solution was concentrated to an amorphous yellow solid and used without further purification.

Example 5-N

Synthesis of (S)-3-Amino-1-benzyl-d-valerolactam

Step A:—Synthesis of L-(+)-Ornithine Methyl Ester Hydrochloride

Into a stirred suspension of L-(+)-ornithine hydrochloride (Aldrich) in methanol was bubbled anhydrous hydrochloric acid gas until the solution was saturated. The reaction mixture was capped with a rubber septum and stirring was continued overnight at room temperature. The solvent was then stripped under reduced pressure and the residue triturated with ether. The resulting solid was dried under reduced pressure to afford L-(+)-ornithine methyl ester hydrochloride as a white solid (97% yield).

Step B:—Synthesis of (S)-3-Amino-d-valerolactam

Sodium spheres in oil (2.0 eq.) (Aldrich) were washed with hexanes (2×) and methanol (2.3 mL/mmol) was slowly added. The reaction mixture was stirred under nitrogen until the sodium dissolved and then L-(+)-ornithine methyl ester hydrochloride (1 eq.) in methanol (2.3 mL/mmol) was added dropwise. The reaction mixture was stirred for 16 hours and then diluted with diethyl ether (5 mL/mmol) and filtered to remove the solids. The solvent was then removed under reduced pressure and the residue was heated at 70° C. for 3 hours under reduced pressure. The residue was then triturated with dichloromethane/ether, the solvent decanted and the resulting residue dried under reduced pressure to afford (S)-3-amino-d-valerolactam (44% yield).

Step C:—Synthesis of N-Boc-(S)-3-Amino-d-valerolactam (S)-3-Amino-d-valerolactam (1 eq.) was dissolved in dioxane and the solution was chilled to 0° C. BOC-anhydride (1.3 eq.) was added and the ice bath was removed allowing the solution to come to room temperature and stirring was continued for 16 hours. The solution was rotary evaporated to afford N-Boc-(S)-3-amino-d-valerolactam.

Step D:—Synthesis of (S)-3-Amino-1-benzyl-d-valerolactam

Following General Procedure 5-A and using N-Boc-(S)-3-amino-d-valerolactam and benzyl bromide provided N-Boc-(S)-3-amino-1-benzyl-d-valerolactam. Removal of the Boc group using General Procedure 5-B afford the title compound.

Example 5-O

Synthesis of 4-Amino-2-aza-2-benzyl-3-oxo-bicyclo [3,2,1]octane Hydrochloride

Step A:—Synthesis of 2-aza-3-oxo-Bicyclo[3,2,1]octane and 3-aza-2-oxo-Bicyclo[3,2,1]octane (9:1 Mixture)

To (")-norcamphor (Aldrich) in 1 mL/mmole of acetic acid was added 1.5 eq. of hydroxylamine-O-sulfonic acid. The reaction mixture was heated to reflux under nitrogen for 1 hour and then saturated sodium carbonate and dilute sodium hydroxide were added. The resulting mixture was extracted with dichloromethane and the organic extracts washed with brine, dried over sodium sulfate, and the solvent removed under reduced pressure. Purification of the residue by column chromatography afforded a 9:1 mixture of 2-aza-3-oxo-bicyclo[3,2,1]octane and 3-aza-2-oxo-bicyclo[3,2,1]octane.

Step B:—Synthesis of 2-aza-2-Benzyl-3-oxo-bicyclo[3,2,1] octane Following General Procedure 5-A and using the product for Step A and benzyl bromide, 2-aza-2-benzyl-3-oxo-bicyclo[3,2,1]octane was prepared.

Step C:—Synthesis of 2-aza-2-Benzyl-4-oximino-3-oxo-bicyclo[3,2,1]octane

To a solution of 2-aza-2-benzyl-3-oxo-bicyclo[3,2,1] octane in THF was added 2.5 eq. of 1M t-BuOK/THF (Aldrich) and the resulting mixture was stirred for 30 minutes. Isoamyl nitrite (1.5 eq.) was then added dropwise and the reaction mixture was stirred overnight. To the reaction mixture was added 3N HCl and this mixture was extracted with ethyl acetate and the organic extracts washed with water, dried, and concentrated under reduced pressure. The residue was triturated with ether/hexanes, the solvents decanted and the residue dried under reduced pressure to afford 2-aza-2-benzyl-4-oximino-3-oxo-bicyclo[3,2,1] octane as a tan liquid (41% yield). This procedure is further described in Y. Kim, *Tetrahedron Lett.* 30(21), 2833–2636 (1989).

Step D:—Synthesis of 2-aza-2-Benzyl-4-amino-3-oxo-bicyclo[3,2,1]octane

A solution of 2-aza-2-benzyl-4-oximino-3-oxo-bicyclo[3,2,1]octane in 10 mL/mmole of ethanol and 5.8 mL/mmole of 3N HCl containing 0.5 g/mmole of 10% Pd/C was saturated with hydrogen gas to 45 psi. The mixture was shaken for 3 hours and then filtered through a layer of Celite. The filtrate was dried over sodium sulfate and concentrated under reduced pressure to afford the title compound as a solid (86% yield). This procedure is further described in E. Reimann, *Arch. Pharm.* 310, 102–109 (1977).

6. Benzazepinone Derivatives and Related Compounds

General Procedure 6-A

Alkylation of 1-Amino-1,3,4,5-tetrahydro-2H-3-benzazepin-2-one

Step A: 1-Ethoxycarbonylamino-1,3,4,5-tetrahydro-2H-3-benzazepin-2-one was prepared according to the procedure of Ben-Ishai et al., *Tetrahedron*, 1987, 43, 430.

Step B: 1-Ethoxycarbonylamino-1,3,4,5-tetrahydro-2H-3-benzazepin-2-one (2.0 g, 100 M %) was dissolved in DMF (30 mL) and NaH (95%, 0.17 g, 100M %) was added in one portion. The reaction mixture was stirred for 1 hour and then the appropriate alkyl iodide (300M %) was added and the mixture was stirred for 12 hours. The reaction was poured into water and extracted with ethyl acetate (3x). The ethyl acetate extracts were then washed with water (3x) and brine (1x). Treatment with MgSO$_4$, rotoevaporation, and chromatography (30% EtOAc/hexanes) yielded 1-ethoxycarbonylamino-3-alkyl-1,3,4,5-tetrahydro-2H-3-benzazepin-2-one in 87% yield.

Step C: 1-Ethoxycarbonylamino-3-alkyl-1,3,4,5-tetrahydro-2H-3-benzazepin-2-one (1.0 g, 100M %) was suspended in 30 mL of 30% HBr/HOAc and heated to 100° C. The reaction mixture was stirred for 5 hours at this temperature and then the reaction was cooled and rotoevaporated to yield 1-amino-3-alkyl-1,3,4,5-tetrahydro-2H-3-benzazepin-2-one as the hydrobromide salt (100% yield).

General Procedure 6-B

Alkylation of 3-Amino-1,3,4,5-tetrahydro-2H-1-benzazepin-2-one

Step A: 3-Amino-1,3,4,5-tetrahydro-2H-1-benzazepin-2-one was prepared from α-tetralone using the methods described in Armstrong et al. *Tetrahedron Letters*, 1994, 35, 3239. The following compounds were as prepared by this procedure for use in the following steps:

5-methyl-3-amino-1,3,4,5-tetrahydro-2H-1-benzazepin-2-one (from 4-methyl-α-tetralone (Aldrich)); and 5,5-dimethyl-3-amino-1,3,4,5-tetrahydro-2H-1-benzazepin-2-one (from 4,4-dimethyl-α-tetralone (Aldrich)).

Step B: 3-Amino-1,3,4,5-tetrahydro-2H-1-benzazepin-2-one (4.43 g, 100M %) was suspended in t-butanol (30 mL) and BOC-anhydride (7.5 mL, 130M %) was added dropwise. The reaction mixture was stirred for 2 hours and then it was rotoevaporated to a residue which was chromatographed with 60% ethyl acetate/hexanes to yield BOC-protected 3-amino-1,3,4,5-tetrahydro-2H-1-benzazepin-2-one in 87% yield.

Step C: BOC-protected 3-amino-1,3,4,5-tetrahydro-2H-1-benzazepin-2-one (1.5 g, 100M %) was dissolved in DMF (20 mL) and NaH (95%, 0.13 g, 100M %) was added in one portion. The reaction mixture was stirred for 1 hour and then the appropriate alkyl iodide (300M %) was added and stirring was continued for 12 hours. The reaction was poured into water and extracted with ethyl acetate (3x). The ethyl acetate extracts were washed with water (3x) and then brine (1x). Treatment with MgSO$_4$, rotoevaporation, and chromatography (30% EtOAc/hexanes) yielded a BOC-protected 3-amino-1-alkyl-1,3,4,5-tetrahydro-2H-1-benzazepin-2-one in 80% yield.

Step D: The BOC-protected 3-amino-1-alkyl-1,3,4,5-tetrahydro-2H-1-benzazepin-2-one (1.0 g, 100M %) was suspended in 30 mL of 1:1 CH$_2$Cl$_2$/triflouroacetic acid and the mixture was stirred for 4 hours. The reaction was then rotoevaporated to yield the 3-amino-1-alkyl-1,3,4,5-tetrahydro-2H-1-benzazepin-2-one (100% yield).

Example 6-A

Synthesis of 3-Amino-1,5-dimethyl-1,3,4,5-tetrahydro-2H-1-benzazepin-2-one

Step A: 3-Amino-5-methyl-1,3,4,5-tetrahydro-2H-1-benzazepin-2-one was prepared from 4-methyl-α-tetralone using the methods described in Armstrong et al. *Tetrahedron Letters*, 1994, 35, 3239.

Step B: 3-Amino-5-methyl-1,3,4,5-tetrahydro-2H-1-benzazepin-2-one (9.3 g 100M %) was dissolved in dioxane (300 mL) and the solution was chilled to 0° C. BOC-anhydride (13.89 g 130M %) was added and the ice bath was removed allowing the solution to come to room temperature and stirring was continued for. 16 hours. The solution was rotary evaporated to remove dioxane to provide an off white solid. This solid was recrystallized from CHCl$_3$ to yield BOC-protected 3-amino-5-methyl-1,3,4,5-tetrahydro-2H-1-benzazepin-2-one in 55% yield.

Step C: BOC-protected 3-amino-5-methyl-1,3,4,5-tetrahydro-2H-1-benzazepin-2-one (100 M %) was dissolved in DMF (20 mL) and NaH (95%, 100 M %) was added in one portion and the reaction mixture was stirred for 1 hour. Methyl iodide (300 M %) was added and this mixture was stirred for 12 hours. The reaction was then poured into water and extracted with ethyl acetate (3x) then backwashed with water (3x) and then brine (1x). Treatment with MgSO$_4$, rotoevaporation, and chromatography (5% MeOH/CH$_2$Cl$_2$) yielded BOC-protected 3-amino-1,5-dimethyl-1,3,4,5-tetrahydro-2H-1-benzazepin-2-one in 75% yield.

Step D: BOC-protected 3-amino-1,5-dimethyl-1,3,4,5-tetrahydro-2H-1-benzazepin-2-one (100 M %) was suspended in 30 mL of 1:1 CH$_2$Cl$_2$/triflouroacetic acid. The reaction mixture was stirred for 4 hours. The reaction was then rotoevaporated to yield 3-amino-1,5-dimethyl-1,3,4,5-tetrahydro-2H-1-benzazepin-2-one (100% yield).

Example 6-B

Synthesis of 5-(L-Alaninyl)-amino-3,3,7-trimethyl-5,7-dihydro-6H-benz[b]azepin-6-one Hydrochloride Following the procedure of Example 7-I and using 5-amino-3,3,7-trimethyl-5,7-dihydro-6H-benz[b]azepin-6-one hydrochloride (Example 6-C), the title compound was prepared.

Example 6-C

Synthesis of 5-Amino-3,3,7-trimethyl-5,7-dihydro-6H-benz[b]azepin-6-one Hydrochloride Step A: Following General Procedure 5-A and using N-t-Boc-5-amino-3,3-dimethyl-5,7-dihydro-6H-benz[b]azepin-6-one (General Procedure 6-B, followed by Boc protection) and methyl iodide, N-t-Boc-5-amino-3,3,7-trimethyl-5,7-dihydro-6H-benz[b]azepin-6-one was prepared.

Step B: Following General Procedure 8-N and using N-t-Boc-5-amino-3,3,7-trimethyl-5,7-dihydro-6H-benz[b]azepin-6-one, the title compound was prepared.

Example 6-D

Synthesis of 3-(S)-Amino-1-methyl-5-oxa-1,3,4,5-tetrahydro-2H-1-benzazepin-2-one Step A: 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286.

Step B: Following General Procedure 5-A and using the product from Step A, the title compound was prepared.

Example 6-E

Synthesis of 3-(S)-Amino-1-ethyl-5-oxa-1,3,4,5-tetrahydro-2H-1-benzazepin-2-one

Step A: 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286.

Step B: Following General Procedure 5-A and using the product from Step A, the title compound was prepared.

Example 6-F

Synthesis of 3-(S)-Amino-1-methyl-5-thia-1,3,4,5-tetrahydro-2H-1-benzazepin-2-one The title compound was prepared from N-Boc-cystine (Novabio) and 2-fluoro-1-nitrobenzene (Aldrich) using the method of R. J. DeVita et al., *Bioorganic and Medicinal Chemistry Lett.* 1995, 5(12) 1281–1286, followed by General Procedure 5-A.

7. Dibenzazepinone Derivatives and Related Compounds

General Procedure 7-A

Preparation of 5-Amino-7-alkyl-5,7-dihydro-6H-dibenz[b,d]azepin-6-one Derivatives Step A: Following General Procedure 5-A and using 5,7-dihydro-6H-dibenz[b,d]azepin-6-one and an alkyl halide, the 7-alkyl-5,7-dihydro-6H-dibenz[b,d]azepin-6-one was prepared.

Step B: The 7-alkyl-5,7-dihydro-6H-dibenz[b,d]azepin-6-one (1 eq.) was dissolved in THF and isoamylnitrite (1.2 eq.) was added. The mixture was cooled to 0° C. in an ice bath. NaHMDS (1.1 eq., 1M in THF) was added dropwise. After stirring for 1 hour or until the reaction was complete, the mixture was concentrated then acidified with 1N HCl and extracted with EtOAc. The organic portion was dried and concentrated to yield a crude product which was purified by silica gel chromatography.

Step C: The resulting oxime was dissolved in EtOH/NH$_3$ (20:1) and hydrogenated in a bomb using Raney nickel and hydrogen (500 psi) at 100° C. for 10 hours. The resulting mixture was filtered and concentrated to provide an oil which was purified by silica gel chromatography to yield the title compound.

General Procedure 7-B

Preparation of Fluoro-substituted 5,7-dihydro-6H-dibenz[b,d]azepin-6-one Derivatives A modification of the procedure of Robin D. Clark and Jahangir, *Tetrahedron*, Vol. 49, No. 7, pp. 1351–1356, 1993 was used. Specifically, an appropriately substituted N-t-Boc-2-amino-2'-methylbiphenyl was dissolved in THF and cooled to −78° C. s-Butyl lithium (1.3M in cyclohexane, 2.2 eq.) was added slowly so that the temperature remained below −65° C. The resulting mixture was allowed to warm to −25° C. and was stirred at that temperature for 1 hour. The mixture was cooled to −78° C. Dry $CO_2$ was bubbled through the mixture for 30 seconds. The mixture was allowed to warm to ambient temperature then was carefully quenched with water. The mixture was concentrated under reduced pressure then was adjusted to pH 3 with 1N HCl. The mixture was extracted with EtOAc and the organic portion was dried and concentrated to yield a crude material. The crude material was dissolved in methanol and the solution was saturated with HCl. The mixture was heated at reflux for 12 hours then was allowed to cool. The mixture was concentrated to provide crude lactam which was purified by chromatography or crystallization.

General Procedure 7-C

Resolution of 5-Amino-7-methyl-5,7-dihydro-6H-dibenz[b,d]azepin-6-one

In a round bottom flask was added the racemic freebase amine (1.0 eq.) in methanol followed by di-p-toluoyl-D-tartaric acid monohydrate (1.0 eq.). The mixture was concentrated in vacuo to a residue and redissolved in a moderate volume of methanol and allowed to stir at room temperature open to the atmosphere (8–72 hours). The solid was removed by filtration. The enantiomeric excess was determined by chiral HPLC (Chiracel ODR) using 15% acetonitrile and 85% $H_2O$ with 0.1% trifluoroacetic acid and a flow rate of 1.0 mL/min at 35° C. The resolved di-p-toluoyl-D-tartaric salt was then dissolved in EtOAc and saturated $NaHCO_3$ until pH 9–10 was reached. The layers were separated and the organic layer was washed again with saturated $NaHCO_3$, $H_2O$, and brine. The organic layer was dried over $MgSO_4$ and the drying agent was removed by filtration. The filtrate was concentrated in vacuo. The free amine was dissolved in MeOH and HCl (12M, 1.0 eq.) was added. The salt was concentrated in vacuo and the resulting film was triturated with EtOAc. The HCl salt was filtered and rinsed with EtOAc. The ee was determined by chiral HPLC.

Example 7-A

Synthesis of 5-Amino-7-methyl-5,7-dihydro-6H-dibenz[b,d]azepin-6-one Hydrochloride Step A—Synthesis of 7-Methyl-5,7-dihydro-6H-dibenz[b,d]azepin-6-one A round bottom flask was charged with sodium hydride (0.295 g, 7.46 mmol) in 9.0 ml of DMF and treated with 5,7-dihydro-6H-dibenz[b,d]azepin-6-one (1.3 g, 6.22 mmol) (CAS #20011-90-9, prepared as described in Brown, et. al., *Tetrahedron Letters*, No. 8, 667–670, (1971) and references cited therein). After stirring at 60° C. for 1 h, the solution was treated with methyl iodide (1.16 ml, 18.6 mmol) and stirring continued for 17 h with the exclusion of light. After cooling, the reaction was diluted with $CH_2Cl_2/H_2O$, washed with $NaHSO_4$ solution, $H_2O$, and dried over $Na_2SO_4$. Evaporation and flash chromatography ($SiO_2$, $CHCl_3$) gave 0.885 g (63%) of the title compound as a colorless solid.

NMR data was as follows:

$^1$H-nmr ($CDCl_3$): d=7.62 (d, 2H), 7.26–7.47 (m, 6H), 3.51 (m, 2H), 3.32 (s, 3H). $C_{15}H_{13}NO$ (MW=223.27); mass spectroscopy (MH+) 223. Anal. Calcd for $C_{15}H_{13}NO$; C, 80.69; H, 5.87; N, 6.27. Found: C, 80.11; H, 5.95; N, 6.23.

Step B—Synthesis of 7-Methyl-5-oximo-5,7-dihydro-6H-dibenz[b,d]azepin-6-one

The compound isolated above (0.700 g, 3.14 mmol) was dissolved in 20 ml of toluene and treated with butyl nitrite (0.733 ml, 6.28 mmol). The reaction temperature was lowered to 0° C. and the solution was treated with KHMDS (9.42 ml, 0.5 M) under $N_2$ atmosphere. After stirring for 1 h the reaction was quenched with a saturated solution of $NaHSO_4$, diluted with $CH_2Cl_2$ and separated. The organic layer was dried over $Na_2SO_4$ and the title compound purified by chromatography ($SiO_2$, 98:2 $CHCl_3$/MeOH) giving 0.59 g (80%) as a colorless solid.

$C_{15}H_{12}N_2O_2$ (MW=252.275); mass spectroscopy (MH+) 252. Anal. Calcd for $C_{15}H_{12}N_2O_2$; C, 71.42; H, 4.79; N, 11.10. Found: C, 71.24; H, 4.69; N, 10.87.

Step C—Synthesis of 5-Amino-7-Methyl-5,7-dihydro-6H-dibenz[b,d]azepin-6-one Hydrochloride The oxime isolated above (0.99 g, 3.92 mmol) was hydrogenated in a Parr apparatus at 35 psi over 10% Pd/C (0.46 g) in 3A ethanol. After 32 h the reaction mixture was filtered through a plug of celite, the filtrate evaporated to a foam and treated with a saturated solution of HCl (g) in $Et_2O$. The resulting colorless solid was filtered, rinsed with cold $Et_2O$ and vacuum dried to give 0.66 g (61%), of the title compound.

NMR data was as follows:

$^1$H-nmr (DNSOd): d=9.11 (bs, 3H), 7.78–7.41(m, 8H), 4.83 (s, 1H), 3.25 (s, 3H). $C_{15}H_{14}N_2O$ HCl (MW=274.753); mass spectroscopy (MH+ free base) 238. Anal. Calcd for $C_{15}H_{14}N_2O$ HCl; C, 65.57; H, 5.50; N, 10.19 Found: C, 65.27; H, 5.67; N, 10.13.

Example 7-B

Synthesis of (S)- and (R)-5-(L-Alaninyl)-amino-7-methyl-5,7-dihydro-6H-dibenz[b,d]azepin-6-one Step A—Synthesis of (S)- and (R)-5-(N-boc-L-Alaninyl-amino-7-methyl-5,7-dihydro-6H-dibenz[b,d]azepin-6-one Boc-L-Alanine (0.429 g, 2.26 mmol) (Aldrich) was dissolved in THF and treated with HOBt hydrate (0.305 g, 2.26 mmol), and 5-amino-7-methyl-5,7-dihydro-6H-dibenz[b,d]azepin-6-one (0.45 g, 1.89 mmol) (Example 7-A). The temperature was lowered to 0° C. and the reaction mixture treated with EDC (0.449 g, 2.26 mmol) (Aldrich) and stirred 17 hours under $N_2$. The reaction mixture was evaporated, the residue diluted with $EtOAc/H_2O$, washed 1.0 N HCl, sat. $NaHCO_3$, brine and dried over $Na_2SO_4$. The diastereomers were separated on a Chiralcel OD column using 10% IPA/heptane at 1.5 ml/minute.

Isomer 1: Retention time 3.37 minutes.

NMR data was as follows:

$^1$H-nmr ($CDCl_3$): d=7.62–7.33 (m, 9H), 5.26 (d, 1H), 5.08 (m, 1H), 4.34 (m, 1H), 3.35 (s, 3H), 1.49 (s, 9H), 1.40 (d, 3H). Optical Rotation: $[a]_{20}$=–96 @589 nm (c=1, MeOH). $C_{23}H_{27}N_3O_4$ (MW=409.489); mass spectroscopy (MH+) 409. Anal. Calcd for $C_{23}H_{27}N_3O_4$; C, 67.46; H, 6.64; N, 10.26. Found: C, 68.42; H, 7.02; N, 9.81.

Isomer 2: Retention time 6.08 minutes.

NMR data was as follows:

$^1$H-nmr ($CDCl_3$): d=7.74 (bd, 1H), 7.62–7.32 (m, 8H), 5.28 (d, 1H), 4.99 (m, 1H), 4.36 (m, 1H), 3.35 (s, 3H), 1.49 (s, 9H), 1.46 (d, 3H). Optical Rotation: $[a]_{20}$=69 @589 nm (c=1, MeOH). $C_{23}H_{27}N_3O_4$ (MW=409.489); mass spectroscopy (MH+) 409. Anal. Calcd for $C_{23}H_{27}N_3O_4$; C, 67.46; H, 6.64; N, 10.26. Found: C, 67.40; H, 6.62; N, 10.02.

Step B—Synthesis of (S)- and (R)-5-(L-Alaninyl)-amino-7-methyl-4,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:

$C_{18}H_{19}N_3O_2$·HCl (MW=345.832); mass spectroscopy (MH+ free base) 309. Optical Rotation: $[a]_{20}$=–55 @589 nm (c=1, MeOH).

Isomer 2:

$C_{18}H_{19}N_3O_2$·HCl (MW=345.832); mass spectroscopy (MH+ free base) 309. Optical Rotation: $[a]_{20}$=80 @589 nm (c=1, MeOH).

Example 7-C

Synthesis of (S)- and (R)-5-(L-Valinyl)-amino-7-methyl-5,7-dihydro-6H-dibenz[b,d]azepin-6-one Step A—Synthesis of (S)- and (R)-5-(N-boc-L-Valinyl)-amino-7-methyl-5,7-dihydro-6H-dibenz[b,d]azepin-6-one Boc-L-Valine (0.656 g, 3.02 mmol) (Aldrich) was dissolved in THF and treated with HOBt hydrate (0.408, 3.02 mmol), Dipea (1.05 mmol, 6.05 mmol) and 5-amino-7-methyl-5,7-dihydro-6H-dibenz[b,d]azepin-6-one hydrochloride (0.75 g, 2.75 mmol)(Example 7-A). The temperature was lowered to 0° C. and the reaction mixture treated with EDC (0.601 g, 3.02 mmol)(Alrich) and stirred 17 hours under $N_2$. The reaction mixture was evaporated, the residue diluted with $EtOAc/H_2O$, washed 1.0 N HCl, sat. $NaHCO_3$, brine and dried over $Na_2SO_4$. The diastereomers were separated on a Chiralcel OD column using 10% IPA/heptane at 1.5 ml/minute.

Isomer 1: Retention time 3.23 minutes.

Optical Rotation: $[a]_{20}$=–120 @589 nm (c=1, MeOH). $C_{25}H_{31}N_3O_4$ (MW=437.544); mass spectroscopy (MH+) 438.

Isomer 2: Retention time 6.64 minutes.

Optical Rotation: $[a]_{20}$=50 @589 nm (c=1, MeOH). $C_{25}H_{31}N_3O_4$ (MW=437.544); mass spectroscopy (MH+) 438.

Step B—Synthesis of (S)- and (R)-5-(L-Valinyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:

$C_{20}H_{23}N_3O_2$·HCl (MW=373.88); mass spectroscopy (MH+ free base) 338. Optical Rotation: $[a]_{20}$=–38 @589 nm (c=1, MeOH).

Isomer 2:

$C_{20}H_{23}N_3O_2 \cdot HCl$ (MW=373.88); mass spectroscopy (MH+ free base) 338. Optical Rotation: $[a]_{20}$=97 @589 nm (c=1, MeOH).

Example 7-D

Synthesis of (S)- and (R)-5-(L-tert-Leucine)-amino-7-methyl-5,7-dihydro-6H-dibenz[b,d]azepin-6-one Step A—Synthesis of (S)- and (R)-5-(N-boc-L-tert-Leucinyl)-amino-7-methyl-5,7-dihydro-6H-dibenz[b,d]azepin-6-one Boc-L-tert-Leucine (0.698 g, 3.02 mmol) (Fluka) was dissolved in THF and treated with HOBt hydrate (0.408, 3.02 mmol), Dipea (1.05 ml, 6.05 mmol) and 5-amino-7-methyl-5,7-dihydro-6H-dibenz[b,d]azepin-6-one hydrochloride (0.75 g, 2.75 mmol)(Example 7-A). The temperature was lowered to 0° C. and the reaction mixture treated with EDC (0.601 g, 3.02 mmol) (Alrich) and stirred 17 hours under $N_2$. The reaction mixture was evaporated, the residue diluted with $EtOAc/H_2O$, washed 1.0 N HCl, sat. $NaHCO_3$, brine and dried over $Na_2SO_4$. The diastereomers were separated on a Chiralcel OD column using 10% IPA/heptane at 1.5 ml/minute.

Isomer 1: Retention time 3.28 minutes.

Optical Rotation: $[a]_{20}$=−128 @589 nm (c=1, MeOH). $C_{26}H_{33}N_3O_4$ (MW=451.571); mass spectroscopy (MH+) 452.

Isomer 2: Retention time 5.52 minutes.

Optical Rotation: $[a]_{20}$=26 @589 nm (c=1, MeOH). $C_{26}H_{33}N_3O_4$ (MW=451.571); mass spectroscopy (MH+) 452.

Step B—Synthesis of (S)- and (R)-5-(L-tert-Leucinyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:

$C_{21}H_{25}N_3O_2 \cdot HCl$ (MW=387.91); mass spectroscopy (MH+ free base) 352. Optical Rotation: $[a]_{20}$=−34 @589 nm (c=1, MeOH).

Isomer 2:

$C_{21}H_{25}N_3O_2 \cdot HCl$ (MW=387.91); mass spectroscopy (MH+ free base) 352. Optical Rotation: $[a]_{20}$=108 @589 nm (c=1, MeOH).

Example 7-E

Synthesis of 5-(N-boc-Amino)-5,7-dihydro-6H,7H-dibenz[b,d]azepin-6-one

Step A—Synthesis of 5-Iodo-5,7-dihydro-6H-dibenz[b,d]azepin-6-one

A solution of 5,7-dihydro-6H-dibenz[b,d]azepin-6-one (1.0 g, 4.77 mmol) (Example 7-A) and $Et_3N$ (2.66 ml, 19.12 mmol) were stirred for 5.0 minutes at −15° C. in $CH_2Cl_2$ and treated with TMSI (1.36 ml, 9.54 mmol). After stirring for 15 minutes $I_2$ (1.81 g, 7.16 mmol) was added in a single portion and the reaction allowed to warm to 5–10° C. over 3 h. The reaction was quenched with sat. $Na_2SO_3$, diluted with $CH_2Cl_2$ and separated. The organics were washed with $Na_2SO_3$ and $NaHSO_3$ and dried over $MgSO_4$. After filtration, the organics were concentrated to approximately 20 ml and diluted with an additional 20 ml of hexanes. The title compound was isolated as a tan precipitate by filtration.

Step B—Synthesis of 5-Azido-5,7-dihydro-6H-dibenz[b,d]azepin-6-one

The iodide isolate above was dissolved in DMF and treated with 1.2 equivalents of $NaN_3$. After stirring 17 h at 23° C. the mixture was diluted with $EtOAc/H_2O$, separated, washed with brine and dried over $MgSO_4$. The title compound was triturated from hot EtOAc as a tan powder.

Step C—Synthesis of 5-(N-boc-Amino)-5,7-dihydro-6H,7H-dibenz[b,d]azepin-6-one

The azide was dissolved in $THF/H_2O$ and stirred at 23° C. for 17 h in the presence of 3.0 equivalents of $Ph_3P$. The reaction was diluted with 50% HOAc/toluene, separated, the aqueous layer extracted with toluene and evaporated to an oily residue. This was taken to pH 7.0 by the addition of 1 N NaOH, the resulting HOAc salt was collected and vacuum dried. Finally, the compound was treated with Boc anhydride (1.05 equivalents) and $Et_3N$ (2.1 equivalents) in THF. After stirring for 5 h at 23° C. the reaction was filtered and the title compound isolated as a colorless powder.

Example 7-F

Synthesis of 5-Amino-7-(2-methylpropyl)-5,7-dihydro-6H-dibenz[b,d]azepin-6-one Hydrochloride Step A—Synthesis of 5-(N-boc-Amino)-7-(2-methylpropyl-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 7-E) in DMF was treated with $Cs_2CO_3$ (0.22 g, 0.678 mmol) and warmed to 60° C. To the reaction mixture was added 1-iodo-2-methylpropane (0.078 ml, 0.678 mmol) and stirring continued for 17 h. After cooling to 23° C. the mixture was diluted with $CH_2Cl_2$, washed with several portions of brine and dried over $Na_2SO_4$. The title compound was purified by chromatography ($SiO_2$, $CHCl_3/MeOH$ 9:1).

$C_{23}H_{28}N_2O_3$ (MW=380.41); mass spectroscopy (MH+) 381 Anal. Calcd for $C_{23}H_{28}N_2O_3$; C, 72.61; H, 7.42; N, 7.36. Found: C, 72.31; H, 7.64; N, 7.17.

Step B—Synthesis of 5-Amino-7-(2-methylpropyl)-5,7-dihydro-6H-dibenz[b,d]azepin-6-one Hydrochloride The compound isolated in Part A was deprotected in dioxane saturated with gaseous HCl. The title compound was isolated as a slightly colored solid after evaporation and vacuum drying.

Example 7-G

Synthesis of 5-Amino-7-(methoxyacetyl)-5,7-dihydro-6H-dibenz[b,d]azepin-6-one Hydrochloride Step A—Synthesis of 5-(N-boc-Amino)-7-(methoxyacetyl)-5,7-dihydro-6H-dibenz[b,d]azepin-6-one A solution of 5-(N-Boc-amino)-5,7-dihydro-6H-dibenz[b,d]azepin-6-one (1.03, 3.08 mmol) (Example 7-E) in DMF was treated with $Cs_2CO_3$ (1.10 g, 3.39 mmol) and warmed to 60° C. To the reaction mixture was added bromomethyl acetate (0.321 ml, 3.39 mmol) (Aldrich) and stirring continued for 17 h. After cooling to 23° C. the mixture was diluted with $CH_2Cl_2$, washed with several portions of brine and dried over $Na_2SO_4$. The title compound was purified by chromatography ($SiO_2$, $CHCl_3$).

$C_{22}H_{24}N_2O_5$ (MW=396.44); mass spectroscopy (MH+) 397; Anal. Calcd for $C_{22}H_{24}N_2O_5$; C, 66.65; H, 6.10; N, 7.07. Found: C, 66.28; H, 5.72; N, 6.50.

Step B—Synthesis of 5-Amino-7-(methoxyacetyl)-5,7-dihydro-6H-dibenz[b,d]azepin-6-one Hydrochloride The compound isolated in Part A was deprotected in dioxane saturated with gaseous HCl. The title compound was isolated as a colorless solid after evaporation and vacuum drying.

$C_{17}H_{16}N_2O_3$ HCl (MW=332.78); mass spectroscopy (MH+ free base) 297.

Example 7-H

Synthesis of 5-Amino-7-(3,3-dimethyl-2-butanonyl)-5,7-dihydro-6H-dibenz[b,d]azepin-6-one Hydrochloride Step A—Synthesis of 5-(N-boc-Amino)-7-(3,3-dimethyl-butanonyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 7-E) in DMF was treated with $Cs_2CO_3$ (0.3 g, 0.925 mmol) and warmed to 60° C. To the reaction mixture was added 1-chloro-3,3-dimethyl-2-butanone (0.096 ml, 0.74 mmol) (Aldrich) and stirring continued for 17 h. After cooling to 23° C., the mixture was diluted with $CH_2Cl_2$, washed with several portions of brine and dried over $Na_2SO_4$. The title compound was isolated as a colorless solid.

$C_{25}H_{30}N_2O_4$ (MW=422.522); mass spectroscopy (MH+) 423.

Step B—Synthesis of 5-Amino-7-(3,3-dimethyl-2-butanonyl)-5,7-dihydro-6H-dibenz[b,d]azepin-6-one Hydrochloride The compound isolated in Part A was deprotected in dioxane saturated with gaseous HCl. The title compound was isolated as a colorless solid after evaporation and vacuum drying.

Example 7-I

Synthesis of L-Alaninyl-5-amino-7-methyl-5,7-dihydro-6H-dibenz[b,d]azepin-6-one Hydrochloride Step A: Following General Procedure D and using N-t-Boc-L-alanine and 5-amino-7-methyl-5,7-dihydro-6H-dibenz[b,d]azepin-6-one, N-t-Boc-L-alaninyl-5-amino-7-methyl-5,7-dihydro-6H-dibenz[b,d]azepin-6-one was prepared.

Step B: Following General Procedure 8-N and using the N-t-Boc-L-alaninyl-5-amino-7-methyl-5,7-dihydro-6H-dibenz[b,d]azepin-6-one, the title compound was prepared. Other substituted N-t-Boc-L-alaninyl-5-amino-7-methyl-5,7-dihydro-6H-dibenz[b,d]azepin-6-ones can also be prepared by this procedure.

Example 7-J

Synthesis of L-Valinyl-5-amino-7-methyl-5,7-dihydro-6H-dibenz[b,d]azepin-6-one Hydrochloride Step A: Following General Procedure D and using N-t-Boc-L-valine and 5-amino-7-methyl-5,7-dihydro-6H-dibenz[b,d]azepin-6-one, N-t-Boc-L-valinyl-5-amino-7-methyl-5,7-dihydro-6H-dibenz[b,d]azepin-6-one was prepared.

Step B: Following General Procedure 8-N and using the N-t-Boc-L-valinyl-5-amino-7-methyl-5,7-dihydro-6H-dibenz[b,d]azepin-6-one, the title compound was prepared. Other substituted N-t-Boc-L-valinyl-5-amino-7-methyl-5,7-dihydro-6H-dibenz[b,d]azepin-6-ones can also be prepared by this procedure.

Example 7-K

Synthesis of 5-Amino-7-phenbutyl-5,7-dihydro-6H-dibenz[b,d]azepin-6-one

Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and 1-chloro-4-phenylbutane (Aldrich), the title compound was prepared.

Example 7-L

Synthesis of 5-Amino-7-cyclopropymethyl-5,7-dihydro-6H-dibenz[b,d]azepin-6-one

Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and (bromomethyl)cyclopropane (Aldrich), the title compound was prepared.

Example 7-M

Synthesis of 5-Amino-7-(2,2,2-trifluoroethyl)-5,7-dihydro-6H-dibenz[b,d]azepin-6-one Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and 1-bromo-2,2,2-trifluoroethane (Aldrich), the title compound was prepared.

Example 7-N

Synthesis of 5-Amino-7-cyclohexyl-5,7-dihydro-6H-dibenz[b,d]azepin-6-one

Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and bromocyclohexane (Aldrich), the title compound was prepared.

Example 7-O

Synthesis of 5-(L-Alaninyl)amino9-fluoro-7-methyl-5,7-dihydro-6H-dibenz[b,d]azepin-6-one Hydrochloride Step 1: 2-Bromo-5-fluorotoluene was stirred in THF at −78° C. s-BuLi (1.05 eq., 1.3 M in cyclohexane) was slowly added and the mixture was stirred for 45 minutes. Trimethylborate (1.5 eq) was added and the mixture was allowed to warm to ambient temperature. After stirring for 1 hour, pinacol (2 eq.) was added. The mixture was stirred for 16 hours then was concentrated under reduced pressure. The resulting residue was slurried in $CH_2Cl_2$ and filtered through Celite. The filtrate was concentrated to yield an oil which was purified by chromatography on deactivated silica gel ($Et_3N$) to yield the arylboronate ester.

Step 2: 2-Bromoaniline (1 eq.) and di-t-butyl-dicarbonate (1.1 eq.) were stirred at 80° C. for 20 hours. The resulting mixture was allowed to cool and was directly distilled using house vacuum to provide N-t-Boc-2-bromoaniline.

Step 3: N-t-Boc-2-bromoaniline (Step 2, 1 eq.), the arylboronate ester (Step 1, 1.1 eq.), $K_2CO_3$ (1.1 eq.) and tetrakis(triphenylphosphine)palladium(0) (0.02 eq) were stirred in 20% water/dioxane under nitrogen. The solution was heated at reflux for 10 hours. The mixture was allowed to cool then was concentrated. The resulting residue was partitioned between water and chloroform. The organic portion was dried and concentrated to yield an oil which was purified by silica gel chromatography using 1:1 $CH_2Cl_2$/hexanes.

Step 4: Following General Procedure 7-B and using the substituted biphenyl from step 3, the 9-fluoro-5,7-dihydro-6H-dibenz[b,d]azepin-6-one was prepared.

Step 5: 9-Fluoro-5,7-dihydro-6H-dibenz[b,d]azepin-6-one (1 eq., Step 4), cesium carbonate (1.1 eq., Aldrich) and methyl iodide (1.1 eq., Aldrich) were stirred in dry DMF at ambient temperature for 16 hours. The mixture was concentrated under reduced pressure to provide a residue which was partitioned between EtOAc and water. The organic portion was dried and concentrated to yield an oil which was purified by silica gel chromatography to 9-fluoro-7-methyl-5,7-dihydro-6H-dibenz[b,d]azepin-6-one.

Step 6: Following General Procedure 7-A, Step B and 9-fluoro-7-methyl-5,7-dihydro-6H-dibenz[b,d]azepin-6-one from Step 5,5-amino-9-fluoro-7-methyl-5,7-dihydro-6H-dibenz[b,d]azepin-6-one was prepared.

Step 7: Following the procedure of Example 7-I and using 5-amino-9-fluoro-7-methyl-5,7-dihydro-6H-dibenz[b,d]azepin-6-one from Step 6, the title compound was prepared.

Example 7-P

Synthesis of 5-(L-Alaninyl)amino-1,3-fluoro-7-methyl-5,7-dihydro-6H-dibenz[b,d]azepin-6-one Hydrochloride Following the procedure of Example 7-O and using 2-bromo-4-fluoroaniline (Step 2, Lancaster) and o-tolylboronic acid (Step 3, Aldrich), the title compound was prepared.

Example 7-Q

Synthesis of 5-(L-Alaninyl)amino-10-fluoro-7-methyl-5,7-dihydro-6H-dibenz[b,d]azepin-6-one Hydrochloride Following the procedure of Example 7-O and using 2-bromo-4-fluorotoluene (Step 1), the title compound was prepared.

Example 7-R

Synthesis of 5-(L-Alanyl)-amino-7-cyclopropylmethyl-5,7-dihydro-6H-dibenz[b,d]azepin-6-one Hydrochloride Following the procedure of Example 7-I and using 5-amino-7-cyclopropylmethyl-5,7-dihydro-6H-dibenz[b,d]azepin-6-one (Example 7-L), the title compound was prepared.

Example 7-S

Synthesis of 5-(L-Alaninyl)amino-7-phenbutyl-5,7-dihydro-6H-dibenz[b,d]azepin-6-one Hydrochloride Following the procedure of Example 7-I and using 5-amino-7-phenbutyl-5,7-dihydro-6H-dibenz[b,d]azepin-6-one (Example 7-K), the title compound was prepared.

Example 7-T

Synthesis of 5-(L-Valinyl)amino-7-cyclopropylmethyl-5,7-dihydro-6H-dibenz[b,d]azepin-6-one Hydrochloride Following the procedure of Example 7-J and using 5-amino-7-cyclopropylmethyl-5,7-dihydro-6H-dibenz[b,d]azepin-6-one (Example 7-L), the title compound was prepared.

Example 7-U

Synthesis of 5-(L-Valinyl)amino-7-phenbutyl-5,7-dihydro-6H-dibenz[b,d]azepin-6-one Hydrochloride Following the procedure of Example 7-J and using 5-amino-7-phenbutyl-5,7-dihydro-6H-dibenz[b,d]azepin-6-one (Example 7-U), the title compound was prepared.

Example 7-V

Synthesis of 5-(L-Valinyl)amino-7-hexyl-5,7-dihydro-6H-dibenz[b,d]azepin-6-one Hydrochloride Step A: Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and 1-bromohexane (Aldrich), 5-amino-7-hexyl-5,7-dihydro-6H-dibenz[b,d]azepin-6-one was prepared.

Step B: Following the procedure of Example 7-J and using 5-amino-7-hexyl-5,7-dihydro-6H-dibenz[b,d]azepin-6-one, the title compound was prepared.

Example 7-W

Synthesis of 5-(L-Valinyl)amino-10-fluoro-7-methyl-5,7-dihydro-6H-dibenz[b,d]azepin-6-one Hydrochloride Following the procedure of Example 7-J and using 5-amino-10-fluoro-7-methyl-5,7-dihydro-6H-dibenz[b,d]azepin-6-one (as prepared in Example 7-Q), the title compound was prepared.

Example 7-X

Synthesis of 5-(L-Valinyl)amino-1,3-fluoro-7-methyl-5,7-dihydro-6H-dibenz[b,d]azepin-6-one Hydrochloride Following the procedure of Example 7-J and using the 5-amino-1,3-fluoro-7-methyl-5,7-dihydro-6H-dibenz[b,d]azepin-6-one (as prepared in Example 7-P), the title compound was prepared.

Example 7-Y

Synthesis of 5-(L-Valinyl)amino-1,3-fluoro-7-methyl-5,7-dihydro-6H-dibenz[b,d]azepin-6-one Hydrochloride Following the procedure of Example 7-J and using the 5-amino-9-fluoro-7-methyl-5,7-dihydro-6H-dibenz[b,d]azepin-6-one (as prepared in Example 7-O), the title compound was prepared.

Example 7-Z

Synthesis of (5-Amino-7-methyl-1,2,3,4,5,7-hexahydro-6H-dicyclohexyl[b,d]azepin-6-one The 5-amino-7-methyl-5,7-dihydro-6H-dibenz[b,d]azepin-6-one hydrochloride (Example 7-A) was dissolved in a 1:1 mixture of EtOAc/HOAc. 5% Rh/C was added and the mixture was stirred at 60° C. under 60 psi of hydrogen. After 3 days, the mixture was filtered and the filtrate was concentrated to provide an oil which was purified by SCX-cation exchange chromatography to yield the title compound.

Example 7-AA

Synthesis of 5-(S)-Amino-7-methyl-5,7-dihydro-6H-dibenz[b,d]azepin-6-one Hydrochloride Following General Procedure 7-C using racemic 5-amino-7-methyl-5,7-dihydro-6H-dibenz[b,d]azepin-6-one (1.0 eq.) and di-p-toluoyl-D-tartaric acid monohydrate (1.0 eq.) in methanol, the title compound was prepared as a solid. The product was collected by filtration. Enantiomeric excess was determined by chiral HPLC.

Desired enantiomer 1: retention time of 9.97 minutes.

Undesired enantiomer 2: retention time of 8.62 minutes.

NMR data was as follows:

$^1$H-nmr (CDCl$_3$): d=9.39 (s, 2H), 7.75–7.42 (m, 8H), 4.80 (s, 1H), 3.30 (s, 3H). C$_{15}$H$_{15}$ClN$_2$O (MW 274.75); mass spectroscopy (MH+) 239.1. Anal Calcd for C$_{15}$H$_{15}$ClN$_2$O$_3$; C, 65.57; H, 5.50; N, 10.20; Found: C, 65.51, H, 5.61; N, 10.01.

8. Benzodiazepine Derivatives and Related Compounds

General Procedure 8-A

N-1-Methylation of Benzodiazepines

A solution of benzodiazepine (1 eq.) in DMF (0.1 M concentration) at 0° C. was treated with potassium tert-butoxide (1.0 eq., 1.0 M solution in THF). After stirring for 30 minutes at 0° C., iodomethane (1.3 eq.) was added and stirring continued for 25 minutes. The mixture was diluted with methylene chloride and washed with water and brine. The organic phase was dried over Na$_2$SO$_4$, filtered, and concentrated. The crude product was then either purified by trituration with 1:1 ether/hexanes or chromatographed via HPLC using ethyl acetate/hexanes as the eluent.

General Procedure 8-B

Cbz Removal Procedure

A flask was charged with the Cbz-protected 3-aminobenzodiazepine (1 eq.). To this was added HBr (34 eq.; 30% solution in acetic acid). Within 20 minutes all of the starting material dissolves. The reaction was stirred for 5 hours at ambient temperature. Ether was added to the orange solution causing the HBr amine salt to precipitate. The mixture was decanted. This process of adding ether and decanting was repeated thrice in an effort to remove acetic acid and benzyl bromide. Toluene was added and the mixture concentrated in vacuo. This step was also repeated. The HBr salt was partitioned between ethyl acetate and 1 M K$_2$CO$_3$. The aqueous layer was back-extracted with ethyl acetate. The combined organics were washed with brine, dried over Na$_2$SO$_4$, filtered, and concentrated.

General Procedure 8-C

Boc Removal Procedure

A solution of Boc-protected amine (1 eq.) in methylene chloride (0.15 M concentration) was cooled to 0° C. and treated with trifluoroacetic acid (30 eq.). After 10 minutes at 0° C., the cooling bath was removed and stirring continued at ambient for 20 minutes to 1 hour. The mixture was concentrated in vacuo to remove excess trifluoroacetic acid. The residue was dissolved in methylene chloride and washed with saturated aqueous NaHCO$_3$ or 1 M K$_2$CO$_3$ and brine. The organic layer was dried over Na$_2$SO$_4$, filtered, and concentrated.

General Procedure 8-D

Azide Transfer Reaction Using KHMDS

The azido derivative was prepared using the procedure described in John W. Butcher et al., Tet. Lett., 37, 6685–6688 (1996).

General Procedure 8-E

Azide Transfer Reaction Using LDA

To a solution of diisopropylamine (1.1 eq.) in 1 mL of dry THF cooled to −78° C. was added n-butyl lithium (1.6M in hexane) (1.1 eq.) dropwise maintaining the reaction temperature at −78° C. The reaction mixture was stirred for 30 min. at −78° C. and then the lactam (0.471 mM) was added dropwise as a solution in 1 mL of dry THF. The reaction mixture was stirred at −78° C. for 30 min. and then a pre-cooled solution of trisyl azide (1.2 eq.) was added as a solution in 1 mL of dry THF. The reaction mixture was stirred at −78° C. for 20 min. and then quenched with acetic acid (4.0 eq.). The reaction mixture was then stirred at 40° C. for 2 hrs. The reaction was then poured into EtOAc and washed with water, sodium bicarbonate and brine, and then dried over sodium sulfate, filtered and concentrated. The residue was purified by LC 2000 chromatography.

General Procedure 8-F

Azido Group Reduction

The azido group was reduced to the corresponding primary amine using the procedure described in John W. Butcher et al., Tet. Lett., 37, 6685–6688 (1996).

General Procedure 8-G

N-Alkylation of Amides or Lactams Using Sodium Hydride or Potassium tert-Butoxide To a slurry of sodium hydride or potassium tert-butoxide (1.1 eq) in 15 mL of dry DMF was added the appropriate amide (0.0042 moles) as a solution in 10 mL of DMF. The alkyl iodide was then added and a thick slurry resulted. The reaction became less thick as time elapsed and when complete by TLC the reaction had become homogeneous. The reaction mixture was poured over ice and extracted into ethyl acetate. The organic layer was washed with water, followed by brine. The organic layer was then dried over sodium sulfate, filtered and concentrated under reduced pressure. The residue was purified by HPLC (LC 2000), eluting with an ethyl acetate/hexane system.

General Procedure 8-H

N-Alkylation of Amides or Lactams Using KHMDS

To the appropriate amide or lactam in THF cooled to −78° C. was added KHMDS dropwise and the reaction mixture was stirred for 30 min. at −78° C. The alkyl iodide was then added dropwise while maintaining the temperature at −70° C. The cooling bath was then removed and reaction was allowed to warm to room temperature and stirring was continued for 2 hours. The reaction mixture was then poured over ice and extracted into ethyl acetate. The organic extracts were washed with water, followed by brine. The organic layer was then dried over sodium sulfate, filtered and concentrated under reduced pressure. The residue was purified by HPLC (LC 2000), eluting with an ethyl acetate/hexane system.

General Procedure 8-I

N-Alkylation of Amides or Lactams Using Cesium Carbonate

To a solution of the amide or lactam in DMF was added cesium carbonate (1.05 eq) and an alkyl iodide (1.1 eq). The mixture was allowed to stir overnight at room temperature and then the reaction mixture was diluted with ethyl acetate and washed with water, followed by brine. The organic layer was dried over sodium sulfate, filtered and concentrated under reduced pressure. The residue was purified by HPLC (LC 2000), eluting with an ethyl acetate/hexane system.

General Procedure 8-J

BOC Removal Procedure

To an N-Boc protected compound was added $CH_2Cl_2$/TFA (4:1) at room temperature. The reaction mixture was stirred at room temperature for 3 hours and then concentrated. The residue was extracted into dichloromethane and washed with water, saturated sodium bicarbonate, dried over $Na_2SO_4$, filtered and concentrated to give the free amine.

General Procedure 8-K

Azide Transfer Procedure

This azide transfer procedure is a modification of the procedure described in Evans, D. A.; Britton, T. C.; Ellman, J. A.; Dorow, R. L. *J. Am. Chem. Soc.* 1990, 112, 4011–4030. To a solution of the lactam substrate (1.0 eq.) in THF (~0.1 M) under $N_2$ at −78° C. was added a solution of $KN(TMS)_2$ (1.1 eq. of 0.5 M in Toluene, Aldrich) dropwise over a period of 2–10 minutes. A slight exotherm was often observed by an internal thermometer, and the resulting solution was stirred for 5–15 minutes, while re-cooling to −78° C. Then, trisyl azide (1.1–1.5 eq., CAS No. 36982-84-0, prepared as described by references in the Evans reference above) in THF (~0.5 M), either precooled to −78° C. or at room temperature, was added via cannula over a period of 0.5–5 minutes. Again, a slight exotherm was generally noted. The resulting solution was stirred for from 5–10 minutes, while re-cooling to −78° C. Then, AcOH (4.5–4.6 eq., glacial) was added, the cooling bath removed and the mixture allowed to warm to room temperature with stirring for 12–16 hours. The mixture was diluted with EtOAc, in a 2–5 volume multiple of the initial THF volume, and washed with dilute aq. $NaHCO_3$ (1–2×), 0.1–1.0 M aq. HCl (0–2×), and brine (1×). The organic phase was then dried over $MgSO_4$, filtered, concentrated to provide the crude product.

General Procedure 8-L

Azide Reduction to an Amine

A mixture of the azide in absolute EtOH (0.03–0.07 M) and 10% Pd/C (~⅓ by weight of the azide) was shaken in a Parr apparatus under H2 (35–45 psi) at room temperature for 3–6 hours. The catalyst was removed by filtration through a plug of Celite, rinsing with absolute EtOH, and the filtrate concentrated to provide the crude amine product.

General Procedure 8-M

Amide Alkylation Using Cesium Carbonate

This procedure is a modification of the procedure described in Claremon, D. A.; et al, PCT Application: WO 96-US8400 960603. To a mixture of 2,4-dioxo-2,3,4,5-tetrahydro-1H-1,5-benzodiazepine (CAS No. 49799-48-6) in DMF (1.0 eq., 0.7 M) under $N_2$ at room temperature was added $Cs_2CO_3$ (2.2 eq.) and the appropriate alkyl halide (2.2 eq.). The mixture was stirred at room temperature for 5.5–16 hours. The mixture was partitioned between EtOAc and sat. $NaHCO_3$. The aqueous layer was extracted with EtOAc (1–2×) and the combined EtOAc extracts were dried over $Na_2SO_4$, filtered, and concentrated to provide the crude product.

General Procedure 8-N

BOC Removal Procedure

A stream of anhydrous HCl gas was passed through a stirred solution of the N-t-Boc protected amino acid in 1,4-dioxane (0.03–0.09 M), chilled in a ice bath to 10° C. under $N_2$, for 10–15 minutes. The solution was capped, the cooling bath removed, and the solution was allowed to warm to room temperature with stirring for 2–8 hours, monitoring by TLC for the consumption of starting material. The solution was concentrated (and in some instances dissolved in $CH_2Cl_2$ then re-concentrated and placed in vacuum oven at 60–70° C. to remove most of the residual dioxane) and used without further purification.

Example 8-A

Synthesis of 3-Amino-1,3-dihydro-5-(1-piperidinyl)-2H-1,4-benzodiazepin-2-one Step A—Preparation of 1,2-Dihydro-3H-1-methyl-5-(1-piperidinyl)-1,4-benzodiazepin-2-one A solution of phosphorous pentachloride (1.2 eq) in methylene chloride was added dropwise to a solution of 1-methyl-1,2,3,4-tetrahydro-3H-1,4-benzodiazepin-2,5-dione (Showell, G. A.; Bourrain, S.; Neduvelil, J. G.; Fletcher, S. R.; Baker, R.; Watt, A. P.; Fletcher, A. E.; Freedman, S. B.; Kemp, J. A.; Marshall, G. R.; Patel, S.; Smith, A. J.; Matassa, V. G. *J. Med. Chem.* 1994, 37, 719.) in methylene chloride. The resultant yellowish-orange solution was stirred at ambient temperature for 2.5 hours; the solvent was removed in vacuo. The orange residue was redissolved in methylene chloride, cooled to 0 EC, and treated with a solution of piperidine (2 eq) and triethylamine (2 eq) in methylene chloride. The cooling bath was removed and the reaction stirred for 18 hours. The reaction mixture was washed with saturated aqueous $NaHCO_3$ (back-extracted with methylene chloride) and brine. The organic phase was dried over $Na_2SO_4$, filtered, and concentrated. The residue was purified via HPLC eluting with a gradient of 4 to 10% methanol/methylene chloride affording the title intermediate as a yellow solid having a melting point of 103–105° C.

$C_{15}H_{19}N_3O$ (MW 257.37); mass spectroscopy 257. Anal. Calcd for $C_{15}H_{19}N_3O$: C, 70.01; H, 7.44; N, 16.33. Found: C, 69.94; H, 7.58; N, 16.23.

Step B—Preparation of 1,2-Dihydro-3H-1-methyl-3-oximido-5-(1-piperidinyl)-1,4-benzodiazepin-2-one Potassium tert-butoxide (2.5 eq) was added in two portions to a −20° C. solution of 1,2-dihydro-3H-1-methyl-5-(1-piperidinyl)-1,4-benzodiazepin-2-one (1 eq) in toluene). After stirring at −20° C. for 20 min, isoamyl nitrite (1.2 eq.; Aldrich) was added to the red reaction mixture. The reaction was stirred at −20° C. for 5 hours at which time the reaction was done by TLC. The cooling bath was removed and the reaction quenched with 0.5 M citric acid. After stirring for 10 minutes, diethyl ether was added. The suspension was stirred at ambient temperature overnight then filtered washing with ether. The resultant cream colored solid had a melting point of 197–200° C.

$^1$H NMR data of the E/Z isomers was as follows:

$^1$H NMR (300 MHz, $CDCl_3$): d=7.64 (1H, bs), 7.48 (2H, d, J=7.4 Hz), 7.35–7.20 (6H, m), 6.75 (1H, bs), 3.8–3.2 (8H, m), 3.46 (3H, s), 3.42 (3H, s), 1.90–1.40 (12H, m). $C_{15}H_{18}N_4O_2$ (MW=286.37); mass spectroscopy 286.

Step C—Preparation of 1,2-Dihydro-3H-1-methyl-3-[O-(ethylaminocarbonyl)oximido]-5-(1-piperidinyl)-14-benzodiazepin-2-one A mixture of 1,2-dihydro-3H-1-methyl-3-oximido-5-(1-piperidinyl)-1,4-benzodiazepin-2-one (1 eq) in THF was treated with ethyl isocyanate (1.7 eq) and triethylamine (0.6 eq). The mixture was heated to 64° C. for 4 hours. The mixture was concentrated and the residue purified by HPLC eluting with 5% methanol/methylene chloride.

¹H NMR data of the E/Z isomers was as follows:
¹H NMR (300 MHz, CDCl₃): d=7.50 (2H, dd, J=8.4, 1.5 Hz), 7.35–7.22 (6H, m), 6.42 (1H, bt), 6.20 (1H, bt), 3.7–3.4 (8H, m), 3.46 (3H, s), 3.44 (3H, s), 3.25 (4H, m), 1.9–1.4 (12H, m), 1.12 (3H, t, J=6.3 Hz), 1.10 (3H, t, J=6.3 Hz). C$_{18}$H$_{23}$N$_5$O$_3$ (MW=357.46); mass spectroscopy 357.

Step D—Preparation of 3-Amino-1,3-dihydro-2H-1-methyl-5-(1-piperidinyl)-1,4-benzodiazepin-2-one The 1,2-dihydro-3H-1-methyl-3-[O-(ethylaminocarbonyl)oximido]-5-(1-piperidinyl)-1,4-benzodiazepin-2-one (1 eq) was hydrogenated in methanol over 5% palladium on carbon (0.15 eq) at 43 psi for 3.25 hours. The reaction was filtered through celite and concentrated in vacuo. The residue was taken up in methylene chloride and filtered a second time through celite. The filtrate was concentrated and the resultant foam was used immediately.

Example 8-B

Synthesis of 3-(L-Alaninyl)-amino-2,3-dihydro-1-methyl-5-phenyl-1H-1,4-benzodiazepin-2-one Step A—Preparation of (S)-3-Amino-1,3-dihydro-1-methyl-5-phenyl-2H-1,4-benzodiazepin-2-one, (1S)-7,7-Dimethyl-2-oxobicyclo[2.2.1]heptane-1-methanesulfonate The title intermediate was prepared according to Reider, P. J.; Davis, P.; Hughes, D. L.; Grabowski, E. J. J. *J. Org. Chem.* 1987, 52, 955 using 3-amino-1,3-dihydro-1-methyl-5-phenyl-2H-1,4-benzodiazepin-2-one (Bock M. G.; DiPardo, R. M.; Evans, B. E.; Rittle, K. E.; Veber, D. F.; Freidinger, R. M.; Hirshfield, J.; Springer, J. P. *J. Org. Chem.* 1987, 52, 3232.) as the starting material.

Step B—Preparation of 3-[N'-(tert-Butylcarbamate)-L-alaninyl]-amino-2,3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2.2.1]heptane-1-methanesulfonate was free based by partitioning between methylene chloride and 1M potassium carbonate. The free amine was then coupled with N-Boc-alanine following General Procedure D.

C$_{24}$H$_{28}$N$_4$O$_4$ (MW=436.56); mass spectroscopy 436. Anal. Calc. for C$_{24}$H$_{28}$N$_4$O$_4$: C, 66.03; H, 6.47; N, 12.84. Found: C, 65.79; H, 6.68; N, 12.80.

Step C—Preparation of 3-(L-Alaninyl)-amino-2,3-dihydro-1-methyl-5-phenyl-1H-1,4-benzodiazepin-2-one Following General Procedure 8-C using 3-[N'-(tert-butylcarbamate)-L-alaninyl]-amino-2,3-dihydro-1-methyl-5-phenyl-1H-1,4-benzodiazepin-2-one, the title compound was prepared as a white foam.

Anal. Calc. for C$_{19}$H$_{19}$N$_4$O$_2$: C, 69.21; H, 6.64; N, 15.37. Found: C, 70.11; H, 6.85; N, 15.01.

Example 8-C

Synthesis of 3-(L-Alaninyl)-amino-7-chloro-2,3-dihydro-1-methyl-5-phenyl-1H-1,4-benzodiazepin-2-one Step A—Preparation of 3-(Benzyloxycarbonyl)-amino-7-chloro-2,3-dihydro-1-methyl-5-phenyl-1H-1,4-benzodiazepin-2-one A solution of 3-(benzyloxycarbonyl)-amino-7-chloro-2,3-dihydro-5-phenyl-1H-1,4-Benzodiazepin-2-one (1 eq; Neosystem) in DMF was cooled to 0° C. and treated with potassium tert-butoxide (1 eq; 1.0M solution in THF). The resultant yellow solution was stirred at 0° C. for 30 minutes then quenched with methyl iodide (1.3 eq). After stirring an addition 25 minutes the reaction was diluted with methylene chloride and washed with water and brine. The organic phase was dried over Na$_2$SO$_4$, filtered, and concentrated. The residue was purified via HPLC chromatography eluting with a gradient of 20630% ethyl acetate/hexanes.

C$_{24}$H$_{20}$ClN$_3$O$_3$ (MW=433.92); mass spectroscopy 433. Anal. calcd for C$_{24}$H$_{20}$ClN$_3$O$_3$: C, 66.44; H, 4.65; N, 9.68. Found: C, 66.16; H, 4.50; N, 9.46.

Step B—Preparation of 3-Amino-7-chloro-1,3-dihydro-1-methyl-5-phenyl-2H-1,4-benzodiazepin-2-one Following General Procedure 8-B using 3-(benzyloxycarbonyl)-amino-7-chloro-2,3-dihydro-1-methyl-5-phenyl-1H-1,4-benzodiazepin-2-one, the title intermediate was prepared as a white foam which was used immediately in Step C.

Step C—Preparation of 3-[N-tert-Butylcarbamate)-L-alaninyl]-amino-7-chloro-1,3-dihydro-1-methyl-5-phenyl-2H-1,4-benzodiazepin-2-one Following General Procedure D using N-Boc-L-alanine and 3-amino-7-chloro-1,3-dihydro-1-methyl-5-phenyl-2H-1,4-benzodiazepin-2-one, the title intermediate was prepared as a white foam.

C$_{24}$H$_{28}$ClN$_4$O$_4$ (MW=471.18); mass spectroscopy 471; Anal. calcd for C$_{24}$H$_{28}$ClN$_4$O$_4$: C, 61.21; H, 5.78; N, 11.90. Found: C, 61.24; H, 5.59; N, 11.67.

Step D—Preparation of 3-(L-Alaninyl)amino-7-chloro-1,3-dihydro-1-methyl-5-phenyl-2H-1,4-benzodiazepin-2-one Following General Procedure 8-C using 3-[N-tert-butylcarbamate)-L-alaninyl]-amino-7-chloro-1,3-dihydro-1-methyl-5-phenyl-2H-1,4-benzodiazepin-2-one, the title intermediate was prepared as a white foam. The crude material was used immediately.

Example 8-D

Synthesis of 3-(L-Alaninyl)amino-7-bromo-2,3-dihydro-1-methyl-5-(2-fluorophenyl)-1H-1,4-benzodiazepin-2-one Step A—Preparation of 3-(Benzyloxycarbonyl)-amino-7-bromo-2,3-dihydro-1-methyl-5-(2-fluorophenyl)-1H-1,4-benzodiazepin-2-one Following General Procedure 8-A using 3-(benzyloxycarbonyl)-amino-7-bromo-2,3-dihydro-5-(2-fluorophenyl)-1H-1,4-benzodiazepin-2-one (Neosystem), the title intermediate was prepared as a white foam.

C$_{24}$H$_{19}$BrFN$_3$O$_3$ (MW=496.36); mass spectroscopy 497. Anal. calcd for C$_{24}$H$_{19}$BrFN$_3$O$_3$: C, 58.08; H, 3.86; N, 8.47. Found: C, 57.90; H, 4.15; N, 8.20.

Step B—Preparation of 3-Amino-7-bromo-1,3-dihydro-1-methyl-5-(2-fluorophenyl)-2H-1,4-benzodiazepin-2-one Following General Procedure 8-B using 3-(benzyloxycarbonyl)-amino-7-bromo-2,3-dihydro-1-methyl-5-(2-fluorophenyl)-1H-1,4-benzodiazepin-2-one, the title intermediate was prepared as a white foam which was used immediately in Step C.

Step C—Preparation of 3-[N'-(tert-Butylcarbamate)-L-alaninyl]-amino-7-bromo-1,3-dihydro-1-methyl-5-(2-fluorophenyl)-2H-1,4-benzodiazepin-2-one Following General Procedure D using N-Boc-L-alanine (Novo) and 3-amino-7-bromo-1,3-dihydro-1-methyl-5-(2-fluorophenyl)-2H-1,4-benzodiazepin-2-one, the title intermediate was prepared as a white foam.

C$_{24}$H$_{26}$BrFN$_4$O$_4$, (MW=533.12); mass spectroscopy 533.2. Anal. calcd for C$_{24}$H$_{26}$BrFN$_4$O$_4$: C, 54.04; H, 4.91; N, 10.50. Found: C, 53.75; H, 4.92; N, 10.41.

Step D—Preparation of 3-(L-Alaninyl)-amino-7-bromo-1,3-dihydro-1-methyl-5-(2-fluorophenyl)-2H-1,4-benzodiazepin-2-one Following General Procedure 8-C using 3-[N'-(tert-butylcarbamate)-L-alaninyl]-amino-7-bromo-1,3-dihydro- 1-methyl-5-(2-fluorophenyl)-2H-1,4-benzodiazepin-2-one, the title intermediate was prepared as a white foam. The crude material was used immediately.

Example 8-E

Synthesis of 3-(N-Methyl-L-alaninyl)-amino-2,3-dihydro-1-methyl-5-phenyl-1H-1,4-benzodiazepin-2-one Step A—Preparation of 3-[N'-(tert-Butylcarbamate)-N'-methyl-L-alaninyl]-amino-2,3-dihydro-1-methyl-5-phenyl-1H-1,4-benzodiazepin-2-one Following General Procedure D and using (S)-3-amino-1,3-dihydro-1-methyl-5-phenyl-2H-1,4-benzodiazepin-2-one (Example 8-B) and N-tert-Boc-N-methyl-alanine (Sigma), the title intermediate was obtained as a white solid.

$C_{25}H_{30}N_4O_4$ (MW=450.2); mass spectroscopy (M+1) 451.2. Anal. calcd for $C_{25}H_{30}N_4O_4$: C, 66.65; H, 6.71; N, 12.44. Found: C, 66.66; H, 6.89; N, 12.21.

Step A—Preparation of 3-(N'-Methyl-L-alaninyl)-amino-2,3-dihydro-1-methyl-5-phenyl-1H-1,4-benzodiazepin-2-one Following General Procedure 8-C and using 3-[N'-(tert-butylcarbamate)-N-methyl-L-alaninyl]-amino-2,3-dihydro-1-methyl-5-phenyl-1H-1,4-benzodiazepin-2-one, the title intermediate was prepared as a white foam.

$C_{20}H_{22}N_4O_2$ (MW=350.46); mass spectroscopy (M+1) 351.4. Anal. calcd for $C_{20}H_{22}N_4O_2$: C, 68.55; H, 6.33; N, 15.99. Found, C, 68.36; H, 6.20; N, 15.79.

Example 8-F

Synthesis of 3-(L-Alaninyl)amino-7-chloro-2,3-dihydro-1-methyl-5-(2-chlorophenyl)-1H-1,4-benzodiazepin-2-one Step A—Preparation of 3-(Benzyloxycarbonyl)-amino-7-chloro-2,3-dihydro-1-methyl-5-(2-chlorophenyl)-1H-1,4-benzodiazepin-2-one Following General Procedure 8-A using 3-(benzyloxycarbonyl)-amino-7-chloro-2,3-dihydro-5-(2-chlorophenyl)-1H-1,4-benzodiazepin-2-one (Neosystem), the title intermediate was prepared as a white solid having a melting point of 232–233° C.

$C_{24}H_{19}Cl_2N_3O_3$ (MW=468.36); mass spectroscopy 468. $^1$H NMR (300 MHz, CDCl$_3$): d=7.67 (1H, m), 7.52 (1H, dd, J=2.4, 8.7 Hz), 7.42–7.26 (9H, m), 7.07 (1H, d, J=2.4 Hz), 6.70 (1H, d, J=8.3 Hz), 5.35 (1H, d, J=8.4 Hz), 5.14 (2H, ABq, J=19.6 Hz), 3.47 (3H, s). $^{13}$C NMR (75 MHz, CDCl$_3$): d=166.66, 165.65, 155.72, 140.52, 136.99, 136.0, 132.87, 131.99, 131.47, 131.40, 131.38, 131.16, 130.54, 130.06, 128.45, 128.08, 128.03, 127.72, 127.22, 123.28, 122.01, 68.95, 67.02, 35.32.

Step B—Preparation of 3-Amino-7-chloro-1,3-dihydro-1-methyl-5-(2-chlorophenyl)-2H-1,4-benzodiazepin-2-one Following General Procedure 8-B using 3-(benzyloxycarbonyl)-amino-7-chloro-2,3-dihydro-1-methyl-5-(2-chlorophenyl)-1H-1,4-benzodiazepin-2-one, the title intermediate was prepared as a white foam which was used immediately in Step C.

Step C—Preparation of 3-[N'-(tert-Butylcarbamate)-L-alaninyl]-amino-7-chloro-1,3-dihydro-1-methyl-5-(2-chlorophenyl)-2H-1,4-benzodiazepin-2-one Following General Procedure D using N-Boc-L-alanine and 3-amino-7-chloro-1,3-dihydro-1-methyl-5-(2-chlorophenyl)-2H-1,4-benzodiazepin-2-one, the title intermediate was prepared as a white foam.

$C_{24}H_{26}Cl_2N_4O_4$ (MW=505.44); mass spectroscopy 505.2.

Step D—Preparation of 3-(L-Alaninyl)-amino-7-chloro-1,3-dihydro-1-methyl-5-(2-chlorophenyl)-2H-1,4-benzodiazepin-2-one Following General Procedure 8-C using 3-[N'-(tert-butylcarbamate)-L-alaninyl]-amino-7-chloro-1,3-dihydro-1-methyl-5-(2-chlorophenyl)-2H-1,4-benzodiazepin-2-one, the title intermediate was prepared as a white foam. The crude material was used immediately.

Example 8-G

Synthesis of 3-(L-Alaninyl)amino-5-cyclohexyl-2,3-dihydro-1-methyl-1H-1,4-Benzodiazepin-2-one Step A—Preparation of 3-(Benzyloxycarbonyl)-amino-5-cyclohexyl-2,3-dihydro-1-methyl-1H-1,4-benzodiazepin-2-one Following General Procedure 8-A using 3-(benzyloxycarbonyl)-amino-5-cyclohexyl-2,3-dihydro-1H-1,4-benzodiazepin-2-one (Neosystem), the title intermediate was prepared as a white solid having a melting point of 205–206° C.

$C_{24}H_{27}N_3O_3$ (MW=405.54); mass spectroscopy 405. $^1$H NMR (300 MHz, CDCl$_3$): d=7.54 (1H, d, J=7.9 Hz), 7.48 (1H, d, J=7.7 Hz), 7.36–7.26 (7H, m), 6.54 (1H, d, J=8.3 Hz), 5.15 (1H, d, J=8.0 Hz), 5.09 (2H, ABq, J=17.1 Hz), 3.39 (3H, s), 2.77 (1H, m), 2.01 (1H, bd, J=13.6 Hz), 1.85 (1H, bd, J=12.4 Hz), 1.68–1.49 (4H, m), 1.34–1.02 (4H, m).

Step B—Preparation of 3-Amino-5-cyclohexyl-1,3-dihydro-1-methyl-2H-1,4-benzodiazepin-2-one Following General Procedure 8-B using 3-(benzyloxycarbonyl)-amino-5-cyclohexyl-2,3-dihydro-1-methyl-1H-1,4-benzodiazepin-2-one, the title intermediate was prepared as a white foam which was used immediately in Step C.

$C_{16}H_{21}N_3O$ (MW+H=272.1763); mass spectroscopy 272.1766.

Step C—Preparation of 3-[N'-(tert-Butylcarbamate)-L-alaninyl]-amino-5-cyclohexyl-1,3-dihydro-1-methyl-2H-1,4-benzodiazepin-2-one Following General Procedure D using N-Boc-L-alanine and 3-amino-5-cyclohexyl-1,3-dihydro-1-methyl-2H-1,4-benzodiazepin-2-one, the title intermediate was prepared as a white foam.

$C_{24}H_{34}N_4O_4$ (MW=442.62); mass spectroscopy (M+H) 443.2.

Step D—Preparation of 3-(L-Alaninyl)amino-5-cyclohexyl-1,3-dihydro-1-methyl-2H-1,4-benzodiazepin-2-one Following General Procedure 8-C using 3-[N'-(tert-butylcarbamate)-L-alaninyl]-amino-5-cyclohexyl-1,3-dihydro-1-methyl-2H-1,4-benzodiazepin-2-one, the title intermediate was prepared as a white foam. The crude material was used immediately.

$C_{19}H_{26}N_4O_2$ (M+H=343.2136); mass spectroscopy found 343.2139.

Example 8-H

Synthesis of 3-(L-Alaninyl)amino-2,3-dihydro-1-methyl-7-nitro-5-phenyl-1H-1,4-benzodiazepin-2-one Step A—Preparation of 2-[N-(a-Isopropylthio)-N-(benzyloxycarbonyl)-glycinyl]-amino-5-nitrobenzophenone A solution of α-(isopropylthio)-N-(benzyloxycarbonyl) glycine (1 eq; prepared according to Zoller, V.; Ben-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-5-nitrobenzophenone (0.9 eq.; Acros) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous NaHCO$_3$, and brine. The organic phase was dried over Na$_2$SO$_4$, filtered, and concentrated. The residue was purified via preparative LC2000 eluting with a gradient of 15620% ethyl acetate/hexanes giving an off-white foam.

$C_{26}H_{25}N_3O_6S$ (MW=507.61); mass spectroscopy found 507.9. Anal. calcd for $C_{26}H_{25}N_3O_6S$: C, 61.53; H, 4.96; N, 8.28. Found: C, 61.70; H, 4.99; N, 8.22.

Step B—Preparation of 2-[N-(α-Amino)-N'-(benzyloxycarbonyl)-glycinyl]-amino-5-nitrobenzophenone Ammonia gas was bubbled into a solution 2-[N-(α-isopropylthio)-N'-(benzyloxycarbonyl)-glycinyl]-amino-5-nitrobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step C without further purification.

Step C—Preparation of 3-(Benzyloxycarboyl)-amino-2,3-dihydro-7-nitro-5-phenyl-1H-1,4-benzodiazepin-2-one 2-[N-(α-Amino)-N'-(benzyloxycarbonyl)-glycinyl]-amino-5-nitrobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over Na$_2$SO$_4$, filtered, and concentrated. The residue was purified via flash chromatography eluting with a gradient of 263% isopropyl alcohol/methylene chloride.

$C_{23}H_{18}N_4O_5$ (MW=430.45); mass spectroscopy found (M+H) 431.2. Anal. calcd for $C_{23}H_{18}N_4O_5$: C, 64.18; H, 4.22; N, 13.02. Found: C, 64.39; H, 4.30; N, 13.07.

Step D—Preparation of 3-(Benzyloxycarbonyl)-amino-2,3-dihydro-1-methyl-7-nitro-5-phenyl-1H-1,4-benzodiazepin-2-one Following General Procedure 8-A and using 3-(benzyloxycarbonyl)-amino-2,3-dihydro-7-nitro-5-phenyl-1H-1,4-benzodiazepin-2-one, the title intermediate was prepared as a yellow foam.

$C_{24}H_{20}N_4O_5$ (MW=444.48); mass spectroscopy found (M+H) 445.2. Anal. calcd for $C_{24}H_{20}N_4O_5$: C, 64.86; H, 4.54; N, 12.60. Found: C, 65.07; H, 4.55; N, 12.46.

Step E—Preparation of 3-Amino-1,3-dihydro-1-methyl-7-nitro-5-phenyl-2H-1,4-benzodiazepin-2-one Following General Procedure 8-B and using 3-(benzyloxycarbonyl)-amino-2,3-dihydro-1-methyl-7-nitro-5-phenyl-1H-1,4-benzodiazepin-2-one, the title intermediate was prepared as a yellow foam which was used immediately in Step F.

Step F—Preparation of 3-[N-(tert-Butylcarbamate)-L-alaninyl]-amino-2,3-dihydro-1-methyl-7-nitro-5-phenyl-1H-1,4-benzodiazepin-2-one Following General Procedure D using N-Boc-L-alanine and 3-amino-1,3-dihydro-1-methyl-7-nitro-5-phenyl-2H-1,4-benzodiazepin-2-one, the title intermediate was prepared as a yellow solid.

$C_{24}H_{27}N_5O_6$ (MW=481.56); mass spectroscopy found (M+H) 482.3. Anal. calcd for $C_{24}H_{27}N_5O_6$: C, 59.88; H, 5.61; N, 14.55. Found: C, 60.22; H, 5.75; N, 13.91.

Step G—Preparation of 3-(L-Alaninyl)-amino-2,3-dihydro-1-methyl-7-nitro-5-phenyl-1H-1,4-benzodiazepin-2-one Following General Procedure 8-C using 3-[N'-(tert-butylcarbamate)-L-alaninyl]-amino-2,3-dihydro-1-methyl-7-nitro-5-phenyl-1H-1,4-benzodiazepin-2-one, the title intermediate was prepared as a yellow foam. The crude material was used immediately.

Example 8-I

Synthesis of 3-(L-Alaninyl)amino-2,3-dihydro-1-methyl-5-(2-fluorophenyl)-1H-1,4-benzodiazepin-2-one Step A—Preparation of 3-Amino-1,3-dihydro-1-methyl-5-(2-fluorophenyl)-2H-1,4-benzodiazepin-2-one A flask was charged with 3-(benzyloxycarbonyl)-amino-7-bromo-2,3-dihydro-1-methyl-5-(2-fluorophenyl)-1H-1,4-benzodiazepin-2-one (1 eq.; Example 8-D, Step A) and 10% palladium on carbon. Methanol was added, and the flask was placed under a balloon of H$_2$. The reaction was stirred for 21 hours. The mixture was filtered through celite washing with methanol. The filtrate was concentrated to a white solid.

$C_{16}H_{14}FN_3O$ (MW=283.33); mass spectroscopy found (M+H) 284.1.

Step B—Preparation of 3-[N'-(tert-Butylcarbamate)-L-alaninyl]-amino-1,3-dihydro-1-methyl-5-(2-fluorophenyl)-2H-1,4-benzodiazepin-2-one Following General Procedure D using N-Boc-L-alanine and 3-amino-1,3-dihydro-1-methyl-5-(2-fluorophenyl)-2H-1,4-benzodiazepin-2-one, the title intermediate was prepared as a white solid.

$C_{24}H_{27}FN_4O_4$ (MW=454.50); mass spectroscopy found (M+H) 455.4. Anal. calcd for $C_{24}H_{27}FN_4O_4$: C, 63.44; H, 5.95; N, 12.33. Found: C, 63.64; H, 6.08; N, 12.16.

Step C—Preparation of 3-(L-Alaninyl)-amino-7-bromo-1,3-dihydro-1-methyl-5-(2-fluorophenyl)-2H-1,4-benzodiazepin-2-one Following General Procedure 8-C using 3-[N'-(tert-butylcarbamate)-L-alaninyl]-amino-1,3-dihydro-1-methyl-5-(2-fluorophenyl)-2H-1,4-benzodiazepin-2-one, the title intermediate was prepared as a white foam. The crude material was used immediately.

Example 8-J

Synthesis of 3-(L-Alaninyl)-amino-2,3-dihydro-1-methyl-5-(3-fluorophenyl)-1H-1,4-benzodiazepin-2-one Step A—Preparation of 2-Amino-3'-fluorobenzophenone A solution of 3-bromofluorobenzene (1 eq.) in THF was cooled to −78° C. under nitrogen and treated with tert-butyllithium (2.05 eq., 1.6 M solution in pentane) at a rate of 40 ml/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over Na$_2$SO$_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3. $^1$H NMR (300 MHz, CDCl$_3$) d 7.44–7.19 (6H, m), 6.74 (1H, d, J=8.0 Hz), 6.61 (1H, dd, J=0.94, 7.9 Hz), 6.10 (2H, bs).

Step B—Preparation of 2-[N-(a-Isopropylthio)-N-(benzyloxycarbonyl)-glycinyl]-amino-3-fluorobenzophenone A solution of a-(isopropylthio)-N-(benzyloxycarbonyl) glycine (1 eq; prepared according to Zoller, V.; Ben-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-3'-fluorobenzophenone (0.9 eq.) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was purified via preparative LC2000 eluting with a gradient of 15620% ethyl acetate/hexanes giving an off-white foam.

$C_{26}H_{25}N_2O_4S$ (MW=480.60); mass spectroscopy found (M+$NH_4^+$) 498.3. $^1$H NMR (300 MHz, $CDCl_3$) d 11.39 (1H, s), 8.59 (1H, d, J=6.0 Hz), 7.63–7.55 (2H, m), 7.48–7.27 (9H, m), 7.14 (1H, dt, J=1.2, 8.4 Hz), 5.94 (1H, d, J=7.2 Hz), 5.58 (1H, d, J=8.7 Hz), 5.17 (2H, ABq, J=14.7 Hz), 3.25 (1H, sep, J=6.6 Hz), 1.44 (3H, d, J=6.0 Hz), 1.28 (3H, d, J=6.6 Hz).

Step C—Preparation of 2-[N-(α-Amino)-N'-(benzyloxycarbonyl)-glycinyl]-amino-3-fluorobenzophenone Ammonia gas was bubbled into a solution 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D—Preparation of 3-(Benzyloxycarbonyl)-amino-2,3-dihydro-5-(3-fluorophenyl)-1H-1,4-benzodiazepin-2-one 2-[N-(α-Amino)-N'-(benzyloxycarbonyl)-glycinyl]-amino-3'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 263% isopropyl alcohol/methylene chloride.

$C_{23}H_{18}FN_3O_3$ (MW=403.44); mass spectroscopy found (M+H) 404.4. Anal. calcd for $C_{23}H_{18}FN_3O_3C0.5H_2O$: C, 66.98; H, 4.64; N, 10.18. Found: C, 67.20; H, 4.64; N, 9.77.

Step E—Preparation of 3-(Benzyloxycarbonyl)-amino-2,3-dihydro-1-methyl-5-(3-fluorophenyl)-1H-1,4-benzodiazepin-2-one Following General Procedure 8-A and using 3-(benzyloxycarbonyl)-amino-2,3-dihydro-5-(3-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.3. Anal. calcd for $C_{24}H_{20}FN_3O_3$: C, 69.06; H, 4.83; N, 10.07. Found: C, 69.33; H, 4.95; N, 9.82.

Step F—Preparation of 3-Amino-1,3-dihydro-1-methyl-5-(3-fluorophenyl)-2H-1,4-benzodiazepin-2-one Following General Procedure 8-B and using 3-(benzyloxycarbonyl)-amino-2,3-dihydro-1-methyl-5-(3-fluorophenyl)-1H-1,4-benzodiazepin-2-one, the title intermediate was prepared as a yellow foam which was used immediately in Step G.

Step G—Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.3. Anal. calcd for $C_{24}H_{27}FN_4O_4$: C, 63.42; H, 5.99; N, 12.33. Found: C, 63.34; H, 6.01; N, 12.08.

Step H—Preparation of 3-(L-Alaninyl)-amino-2,3-dihydro-1-methyl-5-(3-fluorophenyl)-1H-1,4-benzodiazepin-2-one Following General Procedure 8-C using 3-[N'-(tert-butylcarbamate)-L-alaninyl]-amino-2,3-dihydro-1-methyl-5-(3-fluorophenyl)-1H-1,4-benzodiazepin-2-one, the title intermediate was prepared as a yellow foam. The crude material was used immediately.

Example 8-K

Synthesis of 3-(L-Alaninyl)amino-2,3-dihydro-1-methyl-5-(4-fluorophenyl)-1H-1,4-benzodiazepin-2-one Step A—Preparation of 2-Amino-4-fluorobenzophenone A solution of 4-bromofluorobenzene (1 eq.) in THF was cooled to −78° C. under nitrogen and treated with tert-butyllithium (2.05 eq., 1.6 M solution in pentane) at a rate of 40 ml/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over $Na_2SO_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3. Anal. calcd for $C_{13}H_{10}FNO$: C, 72.55; H, 4.68; N, 6.51. Found: C, 72.80; H, 4.51; N, 6.74.

Step B—Preparation of 2-[N-(α-Isopropylthio)-N'-(benzyloxycarbonyl)-glycinyl]-amino-4-fluorobenzophenone A solution of α-(isopropylthio)-N-(benzyloxycarbonyl) glycine (1 eq; prepared according to Zoller, V.; Ben-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-4'-fluorobenzophenone (0.9 eq.) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO4$, filtered, and concentrated. The residue was purified via preparative LC2000 eluting with a gradient of 15→20% ethyl acetate/hexanes giving an off-white foam.

$C_{26}H_{25}N_2O_4S$ (MW=480.60); mass spectroscopy found (M+$NH_4^+$) 498.2. $^1$H NMR (300 MHz, $CDCl_3$) d 11.28 (1H, s), 8.56 (1H, d, J=8.4 Hz), 7.78–7.73 (2H, m), 7.61–7.53 (2H, m), 7.36–7.32 (5H, m), 7.20–7.14 (3H, m), 5.98 (1H, d, J=7.5 Hz), 5.57 (1H, d, J=7.8 Hz), 5.16 (2H, ABq, J=14.7 Hz), 3.25 (1H, sep, J=6.0 Hz), 1.43 (3H, d, J=6.3 Hz), 1.27 (3H, d, J=6.6 Hz).

Step C—Preparation of 2-[N-(α-Amino)-N'-(benzyloxycarbonyl)-glycinyl]-amino-4'-fluorobenzophenone Ammonia gas was bubbled into a solution 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D—Preparation of 3-(Benzyloxycarbonyl)amino-2,3-dihydro-5-(4-fluorophenyl)-1H-1,4-benzodiazepin-2-one 2-[N-(α-Amino)-N'-(benzyloxycarbonyl)-glycinyl]-amino-4'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 263% isopropyl alcohol/methylene chloride.

$C_{23}H_{18}FN_3O_3$ (MW=403.44); mass spectroscopy found (M+H) 404.4. Anal. calcd for $C_{23}H_{18}FN_3O_3 \cdot 1.25H_2O$: C, 64.85; H, 4.85. Found: C, 64.80; H, 4.55.

Step E—Preparation of 3-(Benzyloxycarbonyl)-amino-2,3-dihydro-1-methyl-5-(4-fluorophenyl)-1H-1,4-benzodiazepin-2-one Following General Procedure 8-A and using 3-(benzyloxycarbonyl)-amino-2,3-dihydro-5-(4-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.2. Anal. calcd for $C_{24}H_{20}FN_3O_3$: C, 69.06; H, 4.83; N, 10.07. Found: C, 69.35; H, 4.93; N, 9.97.

Step F—Preparation of 3-Amino-1,3-dihydro-1-methyl-5-(4-fluorophenyl)-2H-1,4-benzodiazepin-2-one Following General Procedure 8-B and using 3-(benzyloxycarbonyl)-amino-2,3-dihydro-1-methyl-5-(4-fluorophenyl)-1H-1,4-benzodiazepin-2-one, the title intermediate was prepared as a yellow foam which was used immediately in Step G.

Step G—Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.4. Anal. calcd for $C_{24}H_{27}FN_4O_4 \cdot 1.5H_2O$: C, 59.86; H, 6.28; N, 11.64. Found: C, 60.04; H, 5.62; N, 11.27.

Step H—Preparation of 3-(L-Alaninyl)-amino-2,3-dihydro-1-methyl-5-(4-fluorophenyl)-1H-1,4-benzodiazepin-2-one Following General Procedure 8-C using 3-[N'-(tert-butylcarbamate)-L-alaninyl]-amino-2,3-dihydro-1-methyl-5-(4-fluorophenyl)-1H-1,4-benzodiazepin-2-one, the title intermediate was prepared as a yellow foam. The crude material was used immediately.

Example 8-L

Synthesis of 3-(N'-L-Alaninyl)amino2,3-dihydro-1-isobutyl-5-phenyl-1H-1,4-benzodiazepin-2-one Step A: 1,3-Dihydro-5-phenyl-2H-1,4-benzodiazepin-2-one (prepared according to the procedure of M. G. Bock et al., *J. Org. Chem.* 1987, 52, 3232–3239) was alkylated with isobutyl iodide using General Procedure 8-G to afford 1,3-dihydro-1-isobutyl-5-phenyl-2H-1,4-benzodiazepin-2-one.

Step B: Following General Procedures 8-D and 8-F and using the product from Step A, 3-amino-1,3-dihydro-1-isobutyl-5-phenyl-2H-1,4-benzodiazepin-2-one was prepared.

Step C: The product from Step B and N-Boc-L-alanine (Sigma) were coupled using General Procedure D, followed by removal of the Boc group using General Procedure 8-J, to afford 3-(N'-L-alaninyl)amino-1,3-dihydro-1-isobutyl-5-phenyl-2H-1,4-benzodiazepin-2-one.

By substituting isopropyl iodide, n-propyl iodide, cyclopropylmethyl iodide and ethyl iodide for isobutyl iodide in Step A above, the following additional intermediates were prepared:

3-(N'-L-alaninyl)amino-1,3-dihydro-1-isopropyl-5-phenyl-2H-1,4-benzodiazepin-2-one 3-(N'-L-alaninyl)amino-1,3-dihydro-1-propyl-5-phenyl-2H-1,4-benzodiazepin-2-one 3-(N'-L-alaninyl)amino-1,3-dihydro-1-cyclopropylmethyl-5-phenyl-2H-1,4-benzodiazepin-2-one 3-(N'-L-alaninyl)amino-1,3-dihydro-1-ethyl-5-phenyl-2H-1,4-benzodiazepin-2-one.

Example 8-M

Synthesis of 3-(N'-L-Alaninyl)amino-1-methyl-5-phenyl-1,3,4,5-tetrahydro-2H-1,5-benzodiazepin-2-one Step A: 1,3,4,5-Tetrahydro-5-phenyl-2H-1,5-benzodiazepin-2-one (CAS No. 32900-17-7) was methylated using General Procedure 8-I to afford 1-methyl-5-phenyl-1,3,4,5-tetrahydro-2H-1,5-benzodiazepin-2-one.

Step B: Following General Procedures 8-E and 8-F and using the product from Step A, 3-amino-1-methyl-5-phenyl-1,3,4,5-tetrahydro-2H-1,5-benzodiazepin-2-one was prepared.

Step C: The product from Step B and N-Boc-L-alanine (Sigma) were coupled using General Procedure D, followed by removal of the Boc group using General Procedure 8-N, to afford 3-(N'-L-alaninyl)amino-1-methyl-5-phenyl-1,3,4,5-tetrahydro-2H-1,5-benzodiazepin-2-one.

Example 8-N

Synthesis of 3-(N'-L-Alaninyl)amino-2,4-dioxo-1-methyl-5-phenyl-2,3,4,5-tetrahydro-1H-1,5-benzodiazepine 3-Amino-2,4-dioxo-1-methyl-5-phenyl-2,3,4,5-tetrahydro-1H-1,5-benzodiazepine (CAS No. 131604-75-6) was coupled with N-Boc-L-alanine (Sigma) using General Procedure D, followed by removal of the Boc group using General Procedure 8-N, to afford the title compound.

Example 8-O

Synthesis of 3-((R)-Hydrazinopropionyl)amino-2,3-dihydro-1-methyl-5-phenyl-1H-1,4-benzodiazepin-2-one 3-Amino-2,3-dihydro-1-methyl-5-phenyl-1H-1,4-benzodiazepin-2-one was coupled to (R)-N,N'-di-BOC-2- hydrazinopropionic acid (Example N) using General Procedure D. Removal of the BOC group using General Procedure 5-B afforded the title compound.

Example 8-P

Synthesis of 3-Amino-2,4-dioxo-1,5-bis-(1-methylethyl)-2,3,4,5-tetrahydro-1H-1,5-benzodiazepine Step A:—Synthesis of 2,4-Dioxo-2,3,4,5-tetrahydro-1H-1,5-benzodiazepine 2,4-Dioxo-2,3,4,5-tetrahydro-1H-1,5-benzodiazepine (CAS No. 49799-48-6) was prepared from 1,2-phenylenediamine (Aldrich) and malonic acid (Aldrich) using the procedure of Claremon, D. A.; et al, PCT Application: WO 96-US8400960603.

Step B:—Synthesis of 2,4-Dioxo-1,5-bis-(1-methylethyl)-2,3,4,5-tetrahydro-1H-1,5-benzodiazepine 2,4-Dioxo-1,5-bis-(1-methylethyl)-2,3,4,5-tetrahydro-1H-1,5-benzodiazepine (CAS No. 113021-84-4) was prepared following General Procedure 8-M using the product from Step A and 2-iodopropane (Aldrich). Purification was by flash chromatography eluting with EtOAc/hexanes (3:7 gradient to 1:1), then recrystalization from EtOAc/hexanes.

Step C:—Synthesis of 3-Azido-2,4-dioxo-1,5-bis-(1-methylethyl)-2,3,4,5-tetrahydro-1H-1,5-benzodiazepine Following General Procedure 8-K using the product from Step B, 3-azido-2,4-dioxo-1,5-bis-(1-methylethyl)-2,3,4,5-tetrahydro-1H-1,5-benzodiazepine (CAS No. 186490-50-6) was prepared as a white solid. The product was purified by flash chromatography eluting with hexanes/EtOAc (4:1) to provide a separable 23:1 mixture of pseudo-axial/pseudo-equatorial azides. The pure pseudo-axial azide was used in the next step.

Step D:—Synthesis of 3-Amino-2,4-dioxo-1,5-bis-(1-methylethyl)-2,3,4,5-tetrahydro-1H-1,5-benzodiazepine Following General Procedure 8-L using the product from Step C, 3-amino-2,4-dioxo-1,5-bis-(1-methylethyl)-2,3,4,5-tetrahydro-1H-1,5-benzodiazepine (CAS No. 186490-51-7) was prepared as a white solid. Purification was by flash chromatography eluting with $CH_2Cl_2$/MeOH (98:2 gradient to 95:5). The isolated pseudo-axial amine atropisomer was completely converted to the pseudo-equatorial amine atropisomer by heating in toluene to 100–105 EC for 15 minutes, and the pseudo-equatorial amine atropisomer was used in the next step. The isomers were distinguished by $^1$H-NMR in $CDCl_3$. Selected $^1$H-NMR ($CDCl_3$): Pseudo-axial amine 4.40 (s, 1H); Pseudo-equatorial amine 3.96 (s, 1H).

Example 8-Q

Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Step A:—Synthesis of N-(t-Butoxycarbonyl)-R-2-thienylglycine N-(t-Butoxycarbonyl)-R-2-thienylglycine (CAS No. 74462-03-1) was prepared from L-a-(2-thienyl)glycine (Sigma) by the procedure described in Bodansky, M. et al; *The Practice of Peptide Synthesis*; Springer Verlag; 1994, p. 17.

Step B:—Synthesis of 3-[N'-(t-Butoxycarbonyl)-R-2-thienylglycinyl]-amino-2,4-dioxo-1,5-bis-(1-methylethyl)-2,3,4,5-tetrahydro-1H-1,5-benzodiazepine Following General Procedure J above using the product from Example 8-P and the product from Step A above, 3-[N'-(t-butoxycarbonyl)-R-2-thienylglycinyl]-amino-2,4-dioxo-1,5-bis-(1-methylethyl)-2,3,4,5-tetrahydro-1H-1,5-benzodiazepine was prepared as a white foam. Purification was by flash chromatography eluting with $CH_2Cl_2$/EtOAc (9:1 gradient to 5:1).

Step C:—Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Following General Procedure 8-N above using the product from Step B, the title compound was prepared as a white solid.

Example 8-R

Synthesis of 3-(L-Alaninyl)-amino-2,4-dioxo-1,5-bis-methyl-2,3,4,5-tetrahydro-1H-1,5-benzodiazepine Hydrochloride Step A:—Synthesis of 2,4-Dioxo-1,5-bis-methyl-2,3,4,5-tetrahydro-1H-1,5-benzodiazepine 2,4-Dioxo-1,5-bis-methyl-2,3,4,5-tetrahydro-1H-1,5-benzodiazepine (CAS No. 23954-54-3) was prepared following General Procedure 8-M using the product from Example 8-P, Step A and iodomethane (Aldrich). The white solid product precipitated during partial concentration of the reaction after work-up, and was isolated by filtration.

Step B:—Synthesis of 3-Azido-2,4-dioxo-1,5-bis-methyl-2,3,4,5-tetrahydro-1H-1,5-benzodiazepine For this substrate, General Procedure 8-K was modified in the following manner. Initially the product from Step A was suspended (not a solution) in THF at –78° C., and following addition of the $KN(TMS)_2$ solution, this suspension was allowed to warm to –35° C. over a period of 12 minutes, during which the suspension became a solution, and was re-cooled to –78° C.; then treated as described in the General Procedure. 3-Azido-2,4-dioxo-1,5-bis-methyl-2,3,4,5-tetrahydro-1H-1,5-benzodiazepine was purified by flash chromatography eluting with $CHCl_3$/EtOAc (7:1), then trituration from hot $CHCl_3$ with hexanes and cooled to –23° C. The product was isolated as a white solid.

Step C:—Synthesis of 3-Amino-2,4-dioxo-1,5-bis-methyl-2,3,4,5-tetrahydro-1H-1,5-benzodiazepine Following General Procedure 8-L using the product from Step B, 3-amino-2,4-dioxo-1,5-bis-methyl-2,3,4,5-tetrahydro-1H-1,5-benzodiazepine was prepared as a white solid. The crude product was used without further purification.

Step D:—Synthesis of 3-[N'-(t-Butoxycarbonyl)-L-alaninyl]-amino-2,4-dioxo-1,5-bis-methyl-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-methyl-2,3,4,5-tetrahydro-1H-1,5-benzodiazepine was prepared as a white foam. Purification was by flash chromatography eluting with $CH_2Cl_2$/EtOAc (2:1 gradient to 1:1).

Step E:—Synthesis of 3-(L-alaninyl)-amino-2,4-dioxo-1,5-bis-methyl-2,3,4,5-tetrahydro-1H-1,5-benzodiazepine Hydrochloride Following General Procedure 8-N above using the product from Step D, the title compound was prepared as an off-white amorphous solid.

Example 8-S

Synthesis of 3-(L-Alaninyl)amino-2,4-dioxo-1,5-bis-(2-methylpropyl)-2,3,4,5-tetrahydro-1H-1,5-benzodiazepine Hydrochloride Step A:—Synthesis of 2,4-Dioxo-1,5-bis-(2-methylpropyl)-2,3,4,5-tetrahydro-1H-1,5-benzodiazepine 2,4-Dioxo-1,5-bis-(2-methylpropyl)-2,3,4,5-tetrahydro-1H-1,5-benzodiazepine was prepared following General Procedure 8-M using the product from Example 8-P, Step A and 1-iodo-2-methylpropane (Aldrich). Purification was by flash chromatography eluting with EtOAc/hexanes (3:7 gradient to 1:1), then recrystalization from EtOAc/hexanes.

Step B:—Synthesis of 3-Azido-2,4-dioxo-1,5-bis-(2-methylpropyl)-2,3,4,5-tetrahydro-1H-1,5-benzodiazepine Following General Procedure 8-K (a precipitate formed during the addition of the KN(TMS)$_2$, but dissolved upon addition of the trisyl azide) using the product from Step A, 3-azido-2,4-dioxo-1,5-bis-(2-methylpropyl)-2,3,4,5-tetrahydro-1H-1,5-benzodiazepine was prepared as a white solid. The product was purified by flash chromatography eluting with hexanes/EtOAc (4:1) and a second flash chromatography eluting with CH$_2$Cl$_2$/hexanes/EtOAc (10:10:1 gradient to 8:6:1).

Step C:—Synthesis of 3-Amino-2,4-dioxo-1,5-bis-(2-methylpropyl)-2,3,4,5-tetrahydro-1H-1,5-benzodiazepine Following General Procedure 8-L using the product from Step B, 3-amino-2,4-dioxo-1,5-bis-(2-methylpropyl)-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH).

Step D:—Synthesis of 3-[N'-(t-Butoxycarbonyl)-L-alaninyl]-amino-2,4-dioxo-1,5-bis-(2-methylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2-methylpropyl)-2,-tetrahydro-1H-1,5-benzodiazepine was prepared as a white foam. Purification was by flash chromatography eluting with CH$_2$Cl$_2$/EtOAc (3:1 gradient to 3:2).

Step E:—Synthesis of 3-(L-Alaninyl)-amino-2,4-dioxo-1,5-bis-(2-methylpropyl)-2,3,4,5-tetrahydro-1H-1,5-benzodiazepine Hydrochloride Following General Procedure 8-N above using the product from Step D, the title compound was prepared as an amorphous white solid.

Example 8-T

Synthesis of 3-(S-Phenylglycinyl)amino-2,4-dioxo-1,5-bis-(2-methylpropyl)-2,3,4,5-tetrahydro-1H-1,5-benzodiazepine Hydrochloride Step A:—Synthesis of 3-[N'-(t-Butoxycarbonyl)-S-phenylglycinyl]-amino-2,4-dioxo-1,5-bis-(2-methylpropyl)-2,3,4,5-tetrahydro-1H-1,5-benzodiazepine Following General Procedure J above using the product from Example 8-S, Step C and the Boc-L-phenylglycine (Novabiochem, CAS No. 2900-27-8), 3-[N'-(t-butoxycarbonyl)-S-phenylglycinyl]-amino-2,4-dioxo-1,5-bis-(2-methylpropyl)-2,3,4,5-tetrahydro-1H-1,5-benzodiazepine was prepared as a white foam. Purification was by flash chromatography eluting with CH$_2$Cl$_2$/EtOAc (9:1 gradient to 5:1).

Step B:—Synthesis of 3-(S-Phenylglycinyl)-amino-2,4-dioxo-1,5-bis-(2-methylpropyl)-2,3,4,5-tetrahydro-1H-1,5-benzodiazepine Hydrochloride Following General Procedure 8-N above using the product from Step A, 3-(S-phenylglycinyl)-amino-2,4-dioxo-1,5-bis-(2-methylpropyl)-2,3,4,5-tetrahydro-1H-1,5-benzodiazepine hydrochloride was prepared as an off-white solid.

Example 8-U

Synthesis of 3-(L-Alaninyl)amino-2,4-dioxo-1,5-bis-(cyclopropylmethyl)-2,3,4,5-tetrahydro-1H-1,5-benzodiazepine Hydrochloride Step A:—Synthesis of 2,4-Dioxo-1,5-bis-(cyclopropylmethyl)-2,3,4,5-tetrahydro-1H-1,5-benzodiazepine 2,4-Dioxo-1,5-bis-(cyclopropylmethyl)-2,3,4,5-tetrahydro-1H-1,5-benzodiazepine was prepared following General Procedure 8-M using the product from Example 8-P, Step A, and (bromomethyl)cyclopropane (Lancaster). Purification was by flash chromatography eluting with EtOAc/hexanes (3:7 gradient to straight EtOAc), then recrystalization from EtOAc/hexanes.

Step B:—Synthesis of 3-Azido-2,4-dioxo-1,5-bis-(cyclopropylmethyl)-2,3,4,5-tetrahydro-1H-1,5-benzodiazepine For this substrate General Procedure 8-K was modified in the following manner. Initially the product from Step A was suspended (not a solution) in THF at −78° C., and following addition of the KN(TMS)$_2$ solution, this suspension was allowed to warm to −30° C., during which the suspension became a solution, and was re-cooled to −78° C. Upon re-cooling to −78° C. a precipitate began to form, therefore the reaction flask containing the mixture was partially raised above the cooling bath until the internal temperature rose to −50° C.; then the trisyl azide solution was added. The cooling bath was removed and the mixture allowed to warm to −20° C. whereupon the mixture had become a nearly homogenous solution, and the AcOH was added. Then, treated as described in the general procedure. 3-Azido-2,4-dioxo-1,5-bis-(cyclopropylmethyl)-2,3,4,5-tetrahydro-1H-1,5-benzodiazepine was purified by trituration with hot to room temperature EtOAc, followed by recrystalization from hot to −23° C. CHCl$_3$/EtOAc/EtOH (5:5:1) and isolated as a white solid.

Step C:—Synthesis of 3-Amino-2,4-dioxo-1,5-bis-(cyclopropylmethyl)-2,3,4,5-tetrahydro-1H-1,5-benzodiazepine Following General Procedure 8-L using the product from Step B, 3-amino-2,4-dioxo-1,5-bis-(cyclopropylmethyl)-2,3,4,5-tetrahydro-1H-1,5-benzodiazepine was prepared as a white solid. Purification was by flash chromatography eluting with CH$_2$Cl$_2$/MeOH (98:2 gradient to 95:5, with 5% NH$_3$ in the MeOH) followed by recrystalization from warm CH$_2$Cl$_2$/hexanes (1:1) to −23° C.

Step D:—Synthesis of 3-[N'-(t-Butoxycarbonyl)-L-alaninyl]-amino-2,4-dioxo-1,5-bis-(cyclopropylmethyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(cyclopropylmethyl)-2,3,4,5-tetrahydro-1H-1,5-benzodiazepine was prepared as a white foam. Purification was by flash chromatography eluting with CH$_2$Cl$_2$/EtOAc (3:1 gradient to 2:1).

Step E:—Synthesis of 3-(L-Alaninyl)-amino-2,4-dioxo-1,5-bis-(cyclopropylmethyl)-2,3,4,5-tetrahydro-1H-1,5-benzodiazepine Hydrochloride Following General Procedure 8-N above using the product from Step D, the title compound was prepared as an off-white solid.

Example 8-V

Synthesis of 3-(L-Alaninyl)-amino-2,4-dioxo-1,5-bis-(2,2-dimethylpropyl)-2,3,4,5-tetrahydro-1H-1,5-benzodiazepine Hydrochloride Step A:—Synthesis of 2,4-Dioxo-1,5-bis-(2,2-dimethylpropyl)-2,3,4,5-tetrahydro-1H-1,5-benzodiazepine To a stirred suspension of the product from Example 8-P, Step A (1.0 eq., 17.08 g) in DMSO (500 mL) at room temperature was added neopentyl iodide (43.01 g, 2.24 eq., Aldrich) and $Cs_2CO_3$ (72.65 g, 2.3 eq., Aldrich). The resulting mixture was heated to 75° C. for 30 minutes, then additional $Cs_2CO_3$ (31.59 g, 1.0 eq.) was added and the mixture rapidly stirred at 75° C. for 6 hours. The mixture was allowed to cool and $H_2O$ (500 mL) and EtOAc (1000 mL) were added. The phases were partitioned and the organic phase washed with $H_2O$ (1×500 mL), 1 M aq. HCl (2×500 mL), and brine (1×500 mL). Then, the organic phase was dried over $MgSO_4$, filtered, concentrated, and purified by flash chromatography eluting with hexanes/EtOAc (3:2 gradient to 2:3) to provide 2,4-dioxo-1,5-bis-(2,2-dimethylpropyl)-2,3,4,5-tetrahydro-1H-1,5-benzodiazepine as a white solid.

Step B:—Synthesis of 3-Azido-2,4-dioxo-1,5-bis-(2,2-dimethylpropyl)-2,3,4,5-tetrahydro-1H-1,5-benzodiazepine Following General Procedure 8-K using the product from Step A, 3-azido-2,4-dioxo-1,5-bis-(2,2-dimethylpropyl)-2,3,4,5-tetrahydro-1H-1,5-benzodiazepine was prepared as a white solid. The product was purified by flash chromatography eluting with hexanes/$CH_2Cl_2$/EtOAc (10:5:1 gradient to 5:5:1) to provide a separable 13:1 mixture of pseudo-axial/pseudo-equatorial azides. The pure pseudo-axial azide was used in the next step. Selected $^1$H-NMR ($CDCl_3$): Pseudo-axial azide 5.12 (s, 1H); Pseudo-equatorial azide 4.03 (s, 1H).

Step C:—Synthesis of 3-Amino-2,4-dioxo-1,5-bis-(2,2-dimethylpropyl)-2,3,4,5-tetrahydro-1H-1,5-benzodiazepine Following General Procedure 8-L using the product from Step B, 3-amino-2,4-dioxo-1,5-bis-(2,2-dimethylpropyl)-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH). The isolated white solid product was identified as a ~4:1 mixture of pseudo-axial and pseudo-equatorial amines atropisomers by $^1$H-NMR. The mixture was heated in toluene to 100 EC for 20 minutes, then re-concentrated to provide the pure pseudo-equatorial amine atropisomer, as a white solid, and this was for the next step. Selected $^1$H-NMR ($CDCl_3$): Pseudo-axial amine 4.59 (s, 1H); Pseudo-equatorial amine 4.03 (s, 1H).

Step D:—Synthesis of 3-[N'-(t-Butoxycarbonyl)-L-alaninyl]-amino-2,4-dioxo-1,5-bis-(2,2-dimethylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2,2-dimethylpropyl)-2,3,4,5-tetrahydro-1H-1,5-benzodiazepine was prepared as a white foam. Purification was by flash chromatography eluting with $CH_2Cl_2$/EtOAc (4:1 gradient to 5:2).

Step E:—Synthesis of 3-(L-Alaninyl)-amino-2,4-dioxo-1,5-bis-(2,2-dimethylpropyl)-2,3,4,5-tetrahydro-1H-1,5-benzodiazepine Hydrochloride Following General Procedure 8-N above using the product from Step D, the title compound was prepared as an off-white solid.

Example 8-W

Synthesis of 3-(L-Alaninyl)amino-2,4-dioxo-1,5-bis-phenyl-2,3,4,5-tetrahydro-1H-1,5-benzodiazepine Hydrochloride Step A:—Synthesis of 2,4-Dioxo-1,5-bis-phenyl-2,3,4,5-tetrahydro-1H-1,5-benzodiazepine This procedure is a modification of the procedure described in Chan, D. M. T. *Tetrahedron Lett.* 1996, 37, 9013–9016. A mixture of the product from Example 8-P, Step A (1.0 eq., 7.50 g), $Ph_3Bi$ (2.2 eq., 41.26 g, Aldrich); $Cu(OAc)_2$ (2.0 eq., 15.48 g, Aldrich), $Et_3N$ (2.0 eq., 8.62 g) in $CH_2Cl_2$ (100 mL) was stirred under $N_2$ at room temperature for 6 days (monitoring by TLC). The solids were removed by filtration through a plug of Celite rinsing with $CH_2Cl_2$/MeOH (3×75 mL). The filtrate was concentrated, dissolved in hot $CH_2Cl_2$/MeOH (9:1) and filtered through a large plug of silica gel eluting with $CH_2Cl_2$/MeOH (9:1, 2L). The filtrate was concentrated and the residue purified by flash chromatography eluting with straight $CH_2Cl_2$ gradient to $CH_2Cl_2$/MeOH (9:1). 2,4-Dioxo-1,5-bis-phenyl-2,3,4,5-tetrahydro-1H-1,5-benzodiazepine crystallized during concentration of the fractions containing the product, and was isolated by filtration as a white solid.

Step B:—Synthesis of 3-Azido-2,4-dioxo-1,5-bis-phenyl-2,3,4,5-tetrahydro-1H-1,5-benzodiazepine For this substrate, General Procedure 8-K was modified in the following manner. Initially the product from Step A was suspended (not a solution) in THF at –70° C., and following addition of the $KN(TMS)_2$ solution, this suspension was allowed to warm to –20° C. over a period of 10 minutes, during which the suspension became a solution, and was re-cooled to –70° C.; then treated as described in the general procedure. The title compound was purified by trituration with hot $CHCl_3$/hexanes (1:1) to yield 3-azido-2,4-dioxo-1,5-bis-phenyl-2,3,4,5-tetrahydro-1H-1,5-benzodiazepine as a white solid.

Step C:—Synthesis of 3-Amino-2,4-dioxo-1,5-bis-phenyl-2,3,4,5-tetrahydro-1H-1,5-benzodiazepine Following General Procedure 8-L using the product from Step B, 3-amino-2,4-dioxo-1,5-bis-phenyl-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH).

Step D:—Synthesis of 3-[N'-(t-Butoxycarbonyl)-L-alaninyl]-amino-2,4-dioxo-1,5-bis-phenyl-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-phenyl-2,3,4,5-tetrahydro-1H-1,5-benzodiazepine was prepared as a white foam. Purification was by flash chromatography eluting with $CH_2Cl_2$/EtOAc (4:1 gradient to 3:1).

Step E:—Synthesis of 3-(L-Alaninyl)-amino-2,4-dioxo-1,5-bis-phenyl-2,3,4,5-tetrahydro-1H-1,5-benzodiazepine Hydrochloride Following General Procedure 8-N above using the product from Step D, the title compound was prepared as a white amorphous solid.

Example 8-X

Synthesis of 3-Amino-2,3-dihydro-1-methyl-5-phenyl-1H-1,4-benzodiazepin-2-one

Following the method of R. G. Sherrill et al., *J. Org. Chem.*, 1995, 60, 730–734 and using glacial acetic acid and HBr gas, the title compound was prepared.

Example 8-Y

Synthesis of 3-(L-Valinyl)-amino-2,3-dihydro-1-methyl-5-phenyl-1H-1,4-benzodiazepin-2-one Step A—Synthesis of 3-[N'-(tert-Butylcarbamate)-L-valinyl]-amino-2,3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2.2.1]heptane-1-methanesulfonate (Example 8-B, Step A) was free based by partitioning between methylene chloride and 1M potassium carbonate. The free amine was then coupled with N-Boc-valine following General Procedure D to give the title compound.

$C_{26}H_{32}N_4O_4$ (MW 464.62); mass spectroscopy 464.3. Anal. Calcd for $C_{26}H_{32}N_4O_4$: C, 67.22; H, 6.94; N, 12.06. Found: C, 67.29; H, 6.79; N, 11.20.

Step B—Synthesis of 3-(L-valinyl)-amino-2,3-dihydro-1-methyl-5-phenyl-1H-1,4-benzodiazepin-2-one Following General Procedure 8-C and using 3-[N'-(tert-butylcarbamate)-L-alaninyl]-amino-2,3-dihydro-1-methyl-5-phenyl-1H-1,4-benzodiazepine-2-one, the title compound was prepared as a white foam.

$C_{21}H_{23}N_4O_2$ (MW 363.48); mass spectroscopy (M+H) 364.2.

Example 8-Z

Synthesis of 3-(L-tert-Leucinyl)-amino-2,3-dihydro-1-methyl-5-phenyl-1H-1,4-benzodiazepin-2-one Step A—Synthesis of 3-[N'-(tert-Butylcarbamate)-L-tert-leucinyl]-amino-2,3-dihydro-1-methyl-5-phenyl-1H-1,4-benzodiazepin-2-one (S)-3-amino-1,3-dihydro-1-methyl-5-phenyl-2H-1,4-benzodiazepin-2-one, (1S)-7,7-dimethyl-2-oxobicyclo[2.2.1]heptane-1-methanesulfonate (Example 8-B, Step A) was free based by partitioning between methylene chloride and 1M potassium carbonate. The free amine was then coupled with N-Boc-tert-leucine following General Procedure D to give the title compound.

$C_{27}H_{35}N_4O_4$ (MW 479.66); mass spectroscopy 479.

Step B—Synthesis of 3-(L-tert-Leucinyl)-amino-2,3-dihydro-1-methyl-5-phenyl-1H-1,4-benzodiazepin-2-one Following General Procedure 8-C and using 3-[N'-(tert-butylcarbamate)-L-tert-leucinyl)-amino-2,3-dihydro-1-methyl-5-phenyl-1H-1,4-benzodiazepine-2-one, the title compound was prepared as a white foam.

Anal. Calcd for $C_{22}H_{25}N_4O_2 \cdot 0.5H_2O$: C, 68.19; H, 7.02; N, 14.40. Found: C, 68.24; H, 7.00; N, 14.00.

Example 8-AA

Synthesis of 3-(L-Alaninyl)-amino-2,3-dihydro-1,5-dimethyl-1H-1,4-benzodiazepine 2,3-Dihydro-1,5-dimethyl-1H-1,4-benzodiazepine was prepared following General Procedures 8-I (using methyl iodide), 8-D and 8-F. Coupling of this intermediate with Boc-L-alanine (Novo) using General Procedure D, followed by deprotection using General Procedure 5-B afforded the title compound which was used without further purification.

Example 8-AB

Synthesis of 3-(L-3-Thienylglycinyl)amino-2,4-dioxo-1,5-bis-(2,2-dimethylpropyl)-2,3,4,5-tetrahydro-1H-1,5-benzodiazepine Step A:—Synthesis of N-(t-Butoxycarbonyl)-L-3-thienylglycine N-(t-Butoxycarbonyl)-L-3-thienylglycine was prepared from L-a-(3-thienyl)glycine (Sigma) by the procedure described in Bodansky, M. et al; *The Practice of Peptide Synthesis*; Springer Verlag; 1994, p. 17.

Step B:—Synthesis of 3-[N'-(t-Butoxycarbonyl)-L-3-thienylglycinyl]-amino-2,4-dioxo-1,5-bis-(2,2-dimethylpropyl)-2,3,4,5-tetrahydro-1H-1,5-benzodiazepine Following General Procedure D above using the product from Example 8-V, Step C and the product from Step A above, 3-[N'-(t-butoxycarbonyl)-L-3-thienylglycinyl]-amino-2,4-dioxo-1,5-bis-(2,2-dimethylpropyl)-2,3,4,5-tetrahydro-1H-1,5-benzodiazepine was prepared.

Step C:—Synthesis of 3-(L-3-Thienylglycinyl)amino-2,4-dioxo-1,5-bis-(2,2-dimethylpropyl)-2,3,4,5-tetrahydro-1H-1,5-benzodiazepine Following General Procedure 8-N above using the product from Step B, the title compound was prepared.

Using the following combinatorial procedures, the following additional intermediates and examples were prepared.

General Procedure C-A

To a 4 mL vial containing 60–100 mg (0.06–0.1 mmol) of polymer bound 1-(1-pyrrolidinyl propyl)-3-ethyl carbodiimide was added 2 m-L of a 0.015 mM stock solution of starting material 1 in DMF/chloroform and 1 mL of a 0.0148 mM stock solution of starting material 2 in chloroform. The resulting slurry were shaken for 48 h and filtered. The filtered resin was washed with chloroform and the filtrate was concentrated to dryness under vacuum. All product structures and purities were confirmed by HPLC using UV detection and IEX MS. Samples were submitted for testing with out any further purification.

General Procedure C-B

To a 4 mL vial was added 840 µL of 0.05 mM stock solution of starting material 1 in DMF/chloroform, 100 µL of a 0.21 mM stock solution of starting material 2 in chloroform and 100 µL of a 0.63 mM stock solution of 1-(3-dimethylaminopropyl)-3-ethyl carbodiimide in chloroform. After allowing to stand undisturbed for 48 h, the reaction mixture was concentrated and the residue redissolved in 2 mL of a 10% methanol/methylene chloride solution. This solution was then filtered through a prewashed (methanol) 500 mg SCX column (Varian Sample Preparation; Harbor City, Calif.) using an additional 8 mL of the same solvent. The filtrate was concentrated under reduced pressure and the residue was dissolved in 20% methanol/methylene chloride and passed through a plug of silica gel (100 mg, Varian Sample Preparation). The collected filtrate was concentrated under reduced pressure and the crude products were submitted for testing without further purification. Product structure and purity were confirmed by HPLC and IEX MS.

General Procedure C-C

To a 4 mL vial was added 540 µL of 0.05 mM stock solution of starting material 1 in DMF/chloroform, 100 µL of a 0.44 mM stock solution of starting material 2 in chloroform and 100 µL of a 0.38 mM stock solution of 1-(3-dimethylaminopropyl)-3-ethyl carbodiimide in chloroform. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under reduced pressure and the residue was dissolved in 20% methanol/methylene chloride and passed through a plug of silica gel (100 mg, Varian Sample Preparation). The collected filtrate was concentrated under reduced pressure and the crude products were submitted for testing without further purification. Product structure and purity were confirmed by HPLC and IEX MS.

General Procedure C-D

To a 4 mL vial was added 540 µL of 0.05 mM stock solution of starting material 1 in DMF/chloroform, 100 µL of a 0.44 mM stock solution of starting material 2 in chloroform, 100 µL of a 0.38 mM stock solution of 1-(3-dimethylaminopropyl)-3-ethyl carbodiimide in chloroform and 100 µL of a 0.38 mM stock solution of PP-HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under reduced pressure and the residue was dissolved in 20% methanol/methylene chloride and passed through a plug of silica gel (100 mg, Varian Sample Preparation). The collected filtrate was concentrated under reduced pressure and the crude products were submitted for testing without further purification. Product structure and purity were confirmed by HPLC and IEX MS.

General Procedure C-E

To a 4 mL vial was added 870 µL of 0.05 mM stock solution of starting material 1 in DMF/chloroform, 1000 µL of a 0.05 mM stock solution of starting material 2 in chloroform, 1000 µL of a 0.05 mM stock solution of 1-(3-dimethylaminopropyl)-3-ethyl carbodiimide in chloroform and 100 µL of a 0.48 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under a stream of nitrogen to approximately ⅓ its original volume and then passed over a plug (200 mg) of AG 1–8×anion exchange resin (BioRad; Hercules, Calif.; Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

General Procedure C-F

Starting material 1 (9.1 µL, 0.109 mmol) was added neat to a mixture of starting material 2 (22.5 mg, 0.054 mmol) and piperidinylmethyl polystyrene (45 mg, 3.6 mmol/g (Fluka)) in 1 mL of methylene. The mixture was shaken for 80 h at ambient temperatures and then treated with methylisocyanate polystyrene (100 mg, 1.0 mmol/g (Novabiochem)) for 24 h with shaking. The reaction mixture was filtered and the resin washed with methylene chloride. The crude product was loaded onto a 500 mg SCX ion exchange column (Varian Sample Preparation), washed 3× with 3 mL of methanol and then eluted with 4 mL of 2 M ammonia methanol. Further purification of the final product was achieved using semi-preparative HPLC (0–100% acetonitrile (0.08% TFA)/water (0.1% TFA); 25 mL/min.; 20×50 ODS-A column) to give 17 mg of the final product as an off white foam.

NMR data was as follows:

$^1$H NMR (300 MHz, CDCl$_3$) 1.45–1.65 (m, 3H), 1.70–2.00 (m, 4H), 2.55–2.80 (m, 4H), 3.25 (s, 2H), 3.50 (s, 3H), 4.65–4.80 (m, 1H), 5.45–5.55 (m, 1H), 7.20–7.80 (m, 11H).

General Procedure C-G

To a 4 mL vial containing 0.03 mmol of starting material 2 was added 100 µL of 0.25 mM stock solution of starting material 1 in chloroform, 100 µL of a 0.3 mM stock solution of 1-(3-dimethylaminopropyl)-3-ethyl carbodiimide in chloroform and 100 µL of a 0.3 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under a stream of nitrogen to approximately ⅓ its original volume and then passed over a plug (200 mg) of AG 1–8×anion exchange resin (BioRad; Hercules, Calif.; Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

General Procedure C-H

The intermediates shown in Table C-1 (i.e., Starting material 2) were synthesized in parallel in using the following procedure:

Step A: To a solution of 3-(tert-butoxycarbonyl)amino-2,3-dihydro-5-phenyl-1H-1,4-benzodiazepin-2-one (CA No. 125:33692: 100 mg, 0.28 mmol) in 1 mL of anhydrous DMF was added 600 µL of a solution of 0.5 M potassium bis(trimethylsilyl)amide (0.30 mmol) in toluene. Neat alkyl halide (0.56 mmol; as indicated in Table C-1) was added immediately in one portion and the reaction mixture was left undisturbed overnight. When an alkyl chloride was used, 1 equivalent of sodium iodide was added to the reaction mixture. After concentration under reduced pressure, the crude reaction residue was partitioned between methylene chloride (2 mL) and aqueous saturated bicarbonate (2 mL) and then passed through a 5 g Extralut QE cartridge (EM Science; Gibbstown, N.J.) using 10 mL of methylene chloride. The resulting filtrate was concentrated under reduced pressure and the crude product was further purified using automated semi-preparative HPLC (YMC 20×50 mm Silica column; gradient elution; 0–5% (5.5 min.), 5–20% (3.5 min.), 20–100% (2 min.), 100% (4 min.) ethyl acetate/methylene chloride, flow rate of 25 mL/min.). Product provided the expected M+1 peak by IEX MS and were carried on without further purification and characterization.

Step B: The product obtained from Step A was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3× with 2 mL portions of methanol and the product was eluted from the column using 6 mL of 2.0 M solution of ammonia/methanol. After concentration under reduced pressure, the product were characterized by IEX MS and carried on without further purification.

Step C: To the crude product obtained from Step B (1.05 equiv.) was added sequentially a 0.3 mM stock solution of HOBt H$_2$O (1.05 equiv.) in DMF, a 0.3 mM stock solution of N-t-BOC-L-alanine (1.0 equiv.) in THF and 0.3 mM stock solution of 1-(3-dimethylaminopropyl)-3-ethyl carbodiimide (1.05 equiv.) in THF. After standing undisturbed for 24 h, the reaction mixture was concentrated and the residue redissolved in 2 mL of a 10% methanol/methylene chloride solution. This solution was then filtered through a pre-washed (methanol) 1 g SCX (Varian Sample Preparation) column using an additional 8 mL of the same solvent. For Example C-V a 1 g Si column (Varian Sample Preparation) was used). The filtrate was concentrated under a stream of nitrogen to approximately ⅓ its original volume and then passed over a plug (500 mg) of AG 1–8×anion exchange resin (BioRad; Hercules, Calif.; Columns were pre-washed with 1N NaOH, water and methanol) using an additional 10 mL of methanol. The resulting filtrate was concentrated under reduced pressure and the crude product was carried on without further purification after characterization by IEX MS.

Step D: The crude product obtained from Step C was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3× with 2 mL portions of methanol and the product were eluted from the column using 6 mL of 2.0 M solution of ammonia/methanol. After concentration under reduced pressure, the product were characterized by IEX MS and carried on without further purification.

General Procedure C-I

To a 4 mL vial containing 0.03 mmol of starting material 2 (from General Procedure C-H) was added 100 µL of 0.25 mM stock solution of starting material 1 in chloroform, 100 µL of a 0.3 mM stock solution of 1-(3-dimethylaminopropyl)-3-ethyl carbodiimide in chloroform and 100 µL of a 0.3 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg Si column using an additional 8 mL of the same solvent. The filtrate was concentrated under a stream of nitrogen to approximately ⅓ its original volume and then passed over a plug (200 mg) of AG 1–8×anion exchange resin (Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

General Procedure C-J

A vial was charged with a CHCl$_3$ solution of Starting material 1 (71 mmol), a DMF solution of HOBt monohydrate (71 µmol), a CHCl$_3$ solution of diisopropylcarbodiimide (71 µmol), and a CHCl$_3$ solution of starting material 2 (60/mol). The vial was capped and the solution allowed to stand at room temperature for two days. The reaction mixture was loaded onto a cation exchange column, washed with MeOH and eluted with 2 N NH$_3$/MeOH. The eluents were concentrated and dried to give the desired product as determined by MS (IS) and HPLC.

General Procedure C-K

To a 4 mL vial was added 870 µL of 0.05 mM stock solution of starting material 1 in DMF/chloroform, 1000 µL of a 0.05 mM stock solution of starting material 2 in chloroform, 1000 µL of a 0.05 mM stock solution of 1-(3-dimethylaminopropyl)-3-ethyl carbodiimide in chloroform and 100 µL of a 0.48 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under a stream of nitrogen to approximately ⅓ its original volume and then passed over a plug (200 mg) of AG 1–8×anion exchange resin (BioRad; Hercules, Calif.; Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

General Procedure C-L

The following amino acids were employed in this procedure: L-alanine (Aldrich), L-valine (Aldrich), L-norvaline (Aldrich), L-methione (Aldrich), L-phenylalanine (Aldrich), L-(+)--phenylglycine (Aldrich), L--(2-thienyl)glycine (Sigma), L--(3-thienyl)glycine (Sigma), L-cyclohexylglycine hydrochloride (Senn Chemical AG), O-tert-butyl-L-serine (Sigma), O-tert-butyl-L-threonine (Bachem) and O-tert-butyl-L-tyrosine (Bachem).

The amino acid (60 µmoles), 305 mg (150 µmoles) of N,O-bistrimethylsilylacetamide and 1.5 mL of DMF were introduced into separate fritted screw capped vials. The mixtures were heated mildly and upon cooling 132 mg (15 µmoles) of p-nitrophenylcarbonate Wang resin (actual load of 1.14 mmole/g) (Novabiochem) was added to the individual vials. In addition, 73 mg (60 mmoles) of dimethylaminopyridine was introduced into vials containing L-cyclohexylglycine hydrochloride. The vials were shaken at room temperature for 48 hours. Each reaction mixture was filtered through the internal frit and the resulting resin was washed with (9×1.0 mL) of DMF, (9×1.0 mL) of methanol and (6×1.0 mL) of diethyl ether. Each reaction vial containing the resin bound amino acid was then dried in a vacuum oven at 30° C.

General Procedure C-M

Into each fritted screw capped vial containing a resin bound amino acid (from General Procedure C-L) was introduced 81 mg (60 μmoles) of 1-hydroxybenzotriazole hydrate (HOBT H$_2$O), 115 mg (60 μmoles) of 1-(3-dimethylaminopropyl)-3-ethyl-carbodiimide hydrochloride (EDC HCl), and 2 mL of THF. A 3-amino-2,4-dioxo-1,5-bis-(alkyl)-2,3,4,5-tetrahydro-1H-1,5-benzodiazepin (30 μmoles) selected from 3-amino-2,4-dioxo-1,5-bis(2-methylpropyl)-2,3,4,5-tetrahydro-1H-1,5-benzodiazepin (Example 8S, Step C), 3-amino-2,4-dioxo-1,5-bis(methyl)-2,3,4,5-tetrahydro-1H-1,5-benzodiazepin (Example 8-R, Step C) and 3-amino-2,4-dioxo-1,5-bis(cyclopropylmethyl)-2,3,4,5-tetrahydro-1H-1,5-benzodiazepin (Example 8-U, Step C) was added to the vials. Each vial was then capped and shaken at room temperature for 4 days. Each reaction mixture was filtered through the internal frit and the resulting resin was washed with (3×2.0 mL) of DMF, (3×2.0 mL) of a 10% solution of acetic acid in methanol, (3×2.0 mL) of a 10% solution of acetic acid in THF, and (3×2.0 mL) of a 10% solution of acetic acid in dichloromethane.

General Procedure C-N

Each resin from General Procedure C-M was suspended in 2.0 mL of trifluoroacetic acid for 30 minutes. Each reaction was filtered through the internal frit into a 10 mL vial and the resin was washed with (3×1.0 mL) of methanol. The filtrate was concentrated under a flow of nitrogen at 30° C. The concentrated residue was dissolved in 1.5 mL of methanol and partitioned into 3 portions. Each portion was subjected to affinity chromatography on a pretreated SCX column (pretreatment consisted of flushing with 2 mL of a 10% solution of acetic acid in methanol followed by 2 mL of methanol). Once loaded, all columns were flushed with 5 mL of methanol, discarding each wash. Each compound was liberated from the column with 5 mL of a 1 N solution of ammonia in a 1/1 solution of methanol and chloroform. Each solution was transferred to a tarred vial followed by concentration under a stream of nitrogen, followed by final concentration under vacuum.

General Procedure C-O

To each vial containing a specific amino acid benzodiazepine (from General Procedure C-N) is added 1 mL of a 0.4 M solution of 1-(3-dimethylaminopropyl)-3-ethyl-carbodiimide (EDC) and 0.9 equivalents of a carboxylic acid. The vials are capped and shaken for 4 days. The reaction mixture is then concentrated under a continuous flow of nitrogen. The residue is subjected to affinity chromatography on a pretreated SCX column (pretreatment includes flushing with 2 mL of a 10% solution of acetic acid in methanol followed by 2 mL of methanol). Once loaded, all columns are eluted with 5 mL of methanol. Each solution is transferred to a tared vial followed by concentration under a stream of nitrogen with final concentration under vacuum.

General Procedure C-P

A solution of the carboxylic acid (0.75 mL, 0.05 M in DCM) is reacted with L-alaninyl-5-amino-7-methyl-5,7-dihydro-6H-dibenz[b,d]azepin-6-one (0.75 mL, 0.06 M in DCM) (from Example 7-I), PP-HOBT (0.3 mL, 0.15 M in DMF, this reagent is used only with a substituted carboxylic acids), and EDC (0.3 mL, 0.15 M). The reaction is mixed for 18 hours, then purified on a Varian SCX column (500 mg column prewashed with MeOH (3×2.5 mL) and 20% MeOH:DCM (3×2.5 mL)) eluting with 2.5 mL of 20% MeOH:DCM.

General Procedure C-Q

Step A: FMOC-Gly Wang resin (20 g, 10.8 mmole, Novabiochem A16415) was reacted with a 30% solution of piperidine in N-methylpyrrolidinone (NMP) for 30 minutes. The solution was drained and the resin washed with NMP (5×200 mL). Benzophenone imine (19.5 g, 108 mmole) in NMP (150 mL) was added to the resin followed by glacial acetic acid (5.6 g, 94 mmole) and the reaction was mixed overnight at room temperature. Reagents were drained and the resin washed with NMP (5×150 mL) followed by DCM (5×150 mL). The resin was dried under vacuum to afford (benzophenone imine)-Gly Wang resin with a theoretical loading of 0.56 mmole per gram.

Step B: A suspension of the resin from Step A in NMP (9 mL) was reacted with an alkyl bromide (5.6 mL of 1 M solution in NMP) selected from 1-bromo-2-ethylbutane, 1-bromo-3-methylbutane, cyclopropylmethyl bromide, 1-bromo-2-cyclohexylethane, 1-bromo-4-fluorobutane, and 1-bromo-2-methylbutane; and BEMP (5.6 mL of 1 M solution in NMP) and Bu$_4$NI (5.6 mL of 1 M solution in NMP) for 20 hours at room temperature. Reagents were drained and the resin washed with NMP (3×15 mL). To a mixture of the resin in THF (7 mL) was added hydroxylamine hydrochloride (2 mL of a 1.6 M solution in water) and the reaction was mixed for 20 hours at room temperature. Reagents were drained and the resin washed sequentially with THF (2×5 mL), 0.5 M solution of diisopropylethylamine in THF (5 mL), THF (5 mL), and NMP (3×5 mL).

Step C: The resin from Step B was divided into 12 equal reactions using an isopicnic solution in NMP:CH$_2$Cl$_2$. To each reaction was added sequentially a carboxylic acid (0.75 mL of a 0.45 M solution in NMP), HOBT (0.75 mL of a 0.45 M solution in NMP) and DIC (0.75 mL of a 0.45 M solution in NMP). The reaction was mixed for 18 hours at room temperature. Reagents were drained and the resin washed with NMP (5×0.5 mL), and DCM (5×0.5 mL). The resin was mixed with TFA:H$_2$O (95:5, 0.5 mL) for 4 hours. The filtrate was collected, resin washed with TFA:H$_2$O (95:5, 0.5 mL) and the filtrates combined. Solvents were evaporated to yield the N-acyl amino acid.

General Procedure C-R

Various acylated amino acids (approximately 0.02 mmole) (from General Procedure C-Q) in separate vials were reacted with 5-amino-7-methyl-5,7-dihydro-6H-dibenz[bd]azepin-6-one (0.1 mL, 0.3 M in DCM) (Example 7-A), PP-HOBT (0.2 mL, 0.15 M in DMF), and EDC-HCl (0.4 mL, 0.08 M in DCM). Reactions were mixed for 18 hours at room temperature. Reactions were diluted with 0.5 mL MeOH, loaded onto a Varian SCX column (500 mg, Varian Sample Preparations, pre-washed with MeOH (2.5 mL) and 10% MeOH:CHCl (2.5 mL)), and eluted with 10% MeOH:CHCl$_3$ (2.5 mL). Solvents were evaporated from the products and the crude products purified by semi-prep reverse phase chromatography (gradient 0 to 100%, 0.1% TFA in H$_2$O to 0.08% TFA in CH$_3$CN). The correct molecular ion was detected for each product by ionspray mass spec and analytical reverse phase chromatography (gradient 0 to 100%, 0.01% TFA in H$_2$O to 0.08% TFA in CH$_3$CN) showed the products to be greater than 90% pure.

General Procedure C-S

Step A: Each amino acid (150 μmol) was weighed into an 8-mL capacity vial and dissolved in 1.5 mL of 10% DMF in dichloromethane (DCM). To each vial was added 0.8 mL (175 μmol) of a solution of 5-amino-7-methyl-5,7-dihydro-6H-dibenz[b,d]azepin-6-one hydrochloride (481 mg, 1.75 mmol) (from Example 7-A) and 670 mg (1.75 mmol) of PP-HOBT (from Example C-AF) dissolved in 7.5 mL DMF. This was followed by the addition to each vial of 2 mL (approximately 200 μmol) of a solution of EDC hydrochloride in DCM (383 mg, 2.0 mmol in 20 mL DCM). After rocking the vials at room temperature for 14 hours, approximately 100–125 mg of polystyrene-piperidine resin (approximately 3.6 mmol/g, 350 μmol, 2.33 eq.) was added to each vial and rocking continued for 15 minutes. Methanol (2.5 mL) was added to each vial and the material put on a 1 g SCX column (Varian) pre-equilibrated with 5 mL of MeOH and 5 mL of 10% MeOH/chloroform. After pushing the liquid through the column with nitrogen, the column was washed with 5 mL of 10% MeOH/chloroform. The combined eluents (collected in 25 mL roundbottom flasks) were evaporated at reduced pressure with a warm water bath at 30–35° C. and then further evaporated in a vacuum oven at 40–45° C. When the net weight of the residues was below 100 mg, 5 mL of dioxane and, if necessary, 1 mL of MeOH was added to redissolve the residue and solvent was again removed on the rotary evaporator and in the vacuum oven. After drying in the vacuum oven overnight, an HPLC was taken of each product. HPLC show primarily the desired product and with about 15% deblocked product (i.e., product with the BOC group removed).

Step B: To each round bottom flask was added 5 mL of 4 N HCl in dioxane. After sitting at room temperature for 2–3 hours, an HPLC was taken and was solvent removed on the rotary evaporator (bath temp 30–35° C.) and in the vacuum oven overnight (at approximately 40° C.). The HPLC of the t-butyl threonine adduct showed incomplete removal of the t-butyl group. An additional 5 mL of 4 N HCl in dioxane was added and the reaction (at room temperature) monitored by HPLC at 4 hours and approximately 20 hours. Complete removal of the t-butyl group was observed after 20 hours. All products were pure by HPLC with only a single peak or resolved diastereomeric peaks observed except for some trace impurities in the methione case. Yields varied from 80 to 100%. Each round bottom contained approximately 150 μmoles of the amino acid linked to 5-amino-7-methyl-5,7-dihydro-6H-dibenz[b,d]azepin-6-one.

Step C: A stock solution of 567 mg (1.48 mmol) PP-HOBT in 8.5 mL DMF (approximately 0.175 M PP-HOBT in DMF) was prepared and 0.81 g (0.86 mL, 150 μmol) of this PP-HOBT solution was added to each of the nine round-bottom vessels containing the products from Step B. Clear solutions were obtained for all, except where the linked amino acid was α amino isobutyric acid. In this case, an additional 0.86 mL of DMF was added but still the mixture remained heterogeneous. The contents of each of the nine round bottoms "n" (where n=1 to 9) were divided into four equal portions (approximately 37 μmols each) and placed in vials. Stock solutions (0.1 M) of the carboxylic acids were then made up in 10% DMF/DCM. The appropriate stock solution (0.3 mL, 30 μmol) was then added to each of the vials. A 0.1 M stock solution (20 mL) of EDC hydrochloride in DMF was prepared. This stock solution (0.4 mL, 40 μmol) was then added to each of the vials which were then capped and put on a rotator for 12 hours. Normal SCX workup and evaporation of solvent afforded products as white solids or clear to light caramel resins. Each of these products was taken up in methanol/chloroform and divided into three tared vials, plus a vial for MS and HPLC characterization. After evaporation of solvent, the final weights in each vial were determined. Product identity was verified by ionspray mass spec and purity assessed by reverse phase HPLC.

Example C-AF

Preparation of PP-HOBT

To a stirred solution of 7.68 g (30 mmol) sulfonyl chloride in 120 mL of dichloromethane was added dropwise, over a 10 min period, 5.04 g (30 mmol) of 4-piperidino-piperidine (Aldrich, 90%) and 3.6 g (36 mmol) of triethylamine in 30 mL of dichloromethane. A mildly exothermic reaction ensued. After stirring 2 hours at room temperature, the orange solution was diluted with 100 mL of dichloromethane and washed with 10% sodium bicarbonate solution (2×100 mL) and brine (1×100 mL). After drying over sodium sulfate, the solvent was removed at reduced pressure to afford 10.7 g of crude product as a light tan solid ($R_f$=0.5, Silica, 10% MeOH/chloroform).

To this crude material was added 200 mL of 95% EtOH/ 5% MeOH followed by 60 mL of hydrazine hydrate. The mixture was refluxed for 3 hours. During the first 0.5 hour, the initially orange solution turned deep red-orange before turning orange again. After refluxing for 3 hours, most of the solvent, water and hydrazine was removed at reduced pressure. To the residue was added 50 mL of EtOH and solvent removed at reduced pressure. This was repeated 2 or more times to give a tan solid which was further dried in the vacuum oven to a constant weight of 13.5 g. To the flask containing this solid was added 250 mL of water. Almost all of the solid went into solution, then a fine light yellow precipitate formed. After stirring cooled in an ice bath for two hours, the solid was collected by vacuum filtration through a sintered glass filter, and rinsed with about 20 mL of cold water. Drying in the vacuum oven at 40° C. overnight afforded 7.3 g (63% yield) of the title compound (PP-HOBT) as an off-white crunchy powder, mp 195–200° C. (dec).

Example C-AA

Synthesis of (S)-3-(L-Phenylglycinyl)amino-2,3-dihydro-1-methyl-5-phenyl-1H-1,4-benzodiazepin-2-one Step A: Synthesis of (S)-3-(N'-(tert-Butoxycarbonyl)-L-phenylglycinyl)amino-2,3-dihydro-1-methyl-5-phenyl-1H-1,4-benzodiazepin-2-one To a solution of triethyl amine (519 μL, 3.8 mmol) and (S)-3-amino-5-phenyl-2-oxo-1,4-benzodiazepine (1.0 g, 3.8 mmol) (prepared according to the procedure of M. G. Bock et al., *J. Org. Chem.* 1987, 52, 3232–3239) in 100 mL of anhydrous methylene chloride at –20° C. was added N-Boc-L-phenylglycine fluoride (Carpino et al, *J. Org. Chem.* 1991, 56, 2611–2614) in one portion. The reaction mixture was stirred for 15 min. and quenched with saturated aqueous bicarbonate (10 mL). The layers were separated, the organic layer washed sequentially with saturated aqueous bicarbonate, water and brine and then dried over sodium sulfate. Purification of the crude product using silica gel chromatography (10–50% ethyl acetate/hexane) gave 1.3 g (69%) of a hydroscopic white foam.

NMR data was as follows:

$^1$H NMR (300 MHz, CDCl$_3$): d=1.35 (br s, 9H), 3.41 (s, 3H), 5.30–5.45 (m, 2H), 5.75–5.95 (m, 1H), 7.15–7.75 (m, 15H). IR (CDCl$_3$): 1709.7, 1676.6, 1489, 1166.3 cm$^{-1}$. IEX MS (M+1): 498.0.

Step B: Synthesis of (S)-3-(L-Phenylglycinyl)amino-2,3-dihydro-1-methyl-5-phenyl-1H-1,4-benzodiazepin-2-one (S)-3-(N'-(tert-Butoxycarbonyl)-L-phenylglycinyl)amino-2,3-dihydro-1-methyl-5-phenyl-1H-1,4-benzodiazepin-2-one (1.27 g, 2.55 mmol) was added to 50 mL of a stirring solution of 15% TFA in methylene chloride in one portion. After stirring 1 h, the reaction mixture was concentrated under reduced pressure and the residue dissolved in 100 mL of methylene chloride. This solution was washed twice with saturated sodium bicarbonate, once with brine and then dried over sodium sulfate. Purification of the crude product using silica gel column chromatography (5–10% methanol/methylene chloride) gave 743 mg (73%) of a very light green foam.

NMR data was as follows:

$^1$H NMR (CDCl$_3$): d=2.05 (br s, 1H), 3.45 (s, 3H), 5.51 (d, J=8.39 Hz, 1H), 7.15–7.70 (m, 14H), 8.60 (d, J=830 Hz, 1H). IR (CDCl$_3$): 1673.3, 1601.1, 1506.1 cm$^{-1}$. IEX MS (M+1): 399.2.

Example C-AB

Synthesis of 3-(L-Alaninyl)amino-2,3-dihydro-1-(2-oxo-2-phenylethyl)-5-phenyl-1H-1,4-benzodiazepin-2-one Step A: Synthesis of 3-(Benzoxycarbonyl)amino-2,3-dihydro-1-(2-oxo-2-phenylethyl)-5-phenyl-1H-1,4-benzodiazepin-2-one To a solution of 3-(Benzoxycarbonyl)amino-5-phenyl-1H-1,4-benzodiazepin-2-one (Bock, M. G. et al, *Tetrahedron Lett.* 1987, 28, 939; 4.0 g, 10.4 mmol) in 40 mL of anhydrous DMF at 0° C. was added potassium tert-butoxide (1.51 g, 13.5 mmol) in one portion. The reaction mixture was stirred 20 min. and α-broinoacetophenone (Lancaster; Windham, N.H.; 2.9 g, 14.6 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–5% ethyl acetate/methylene chloride) gave 4.2 g (81%) of an off white foam.

NMR data was as follows:

$^1$H NMR (300 MHz, CDCl$_3$): d=5.16 (s, 2H), 5.34 (s, 2H), 5.50 (d, J=8.33 Hz, 1H), 6.70 (d, J=8.28 Hz, 1H), 7.20–7.70 (m, 12H), 7.91 (d, J=7.54 Hz, 2H). IR (CHCl$_3$): 1706.04, 1685.3, 1505.9, 1489.1, 1450.3, 1244.7 cm$^{-1}$. IEX MS (M+1): 504.3.

Step B: Synthesis of 3-Amino-2,3-dihydro-1-(2-oxo-2-phenylethyl)-5-phenyl-1H-1,4-benzodiazepin-2-one A solution of 3-(Benzoxycarbonyl)amino-2,3-dihydro-1-(2-oxo-2-phenylethyl)-5-phenyl-1H-1,4-benzodiazepin-2-one (3.7 g, 7.36 mmol) in 100 mL of anhydrous methylene chloride was cooled to 0° C. under nitrogen. A stream of anhydrous HBr gas was then bubbled through this solution for 1 h. The bubbler was removed and the reaction was warmed to room temperature under nitrogen. After stirring 1 h the reaction was concentrated under vacuum and the residue was redissolved in 20 mL of methylene chloride. The crude HBr salt of the product was precipitated from solution using 300 mL of anhydrous ether and collected by filtration as a light yellow solid. After washing with ether, the solid was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 2.27 g of the product was obtained as an orange foam which was carried on without further purification.

NMR data was as follows:

$^1$H NMR (300 MHz, CDCl$_3$): d=2.60 (br s, 2H), 4.72 (s, 1H), 5.34 (s, 2H), 7.10–7.70 (m, 12H), 7.91 (d, J=7.60 Hz, 2H). IEX MS (M+1): 370.2.

Step C: Synthesis of 3-(N'-(tert-Butoxycarbonyl)-L-alaninyl)amino-2,3-dihydro-1-(2-oxo-2-phenylethyl)-5-phenyl-1H-1,4-benzodiazepin-2-one To a solution of HOBt-H$_2$O (697 mg, 5.16 mmol), N,N-diisopropylethylamine (900 μL, 5.16 mmol) and N-t-BOC-L-alanine (975 mg, 5.16 mmol) in 20 mL of anhydrous THF at 0° C. was added 1-(3-dimethylaminopropyl)-3-ethyl carbodiimide hydrochloride (EDCI; 986 mg, 5.16 mmol) in one portion. After stirring 5 min., a solution of 3-amino-2,3-dihydro-1-(2-oxo-2-phenylethyl)-5-phenyl-1H-1,4-benzodiazepin-2-one (2.0 g, 5.43 mmol) in 20 mL of anhydrous THF was added via syringe and the reaction mixture was warmed to room temperature and stirred overnight. The reaction mixture was diluted with 200 mL methylene chloride, extracted sequentially with 10% citric acid, saturated sodium bicarbonate, water and brine and then dried over sodium sulfate. Purification of the crude product using silica gel chromatography (10%–30% ethyl acetate/methylene chloride) gave 2.59 g (93%) of a white foam.

NMR data was as follows:

$^1$H NMR (300 MHz, CDCl$_3$): d=1.30–1.60 (m, 12H), 4.35 (br s, 1H), 5.00–5.50 (m, 3H), 5.65–5.70 (m, 1H), 7.15–7.65 (m, 12H), 7.70–7.80 (m, 1H), 7.85–7.95 (m, 1H). IR (CHCl$_3$): 1705.8, 1678.8, 1488.7, 1450.2, 1230.4, 1164.4 cm$^1$. IEX MS (M+1): 541.2.

Step D: Synthesis of 3-(L-Alaninyl)amino-2,3-dihydro-1-(2-oxo-2-phenylethyl)-5-phenyl-1H-1,4-benzodiazepin-2-one 3-(N'-(tert-Butoxycarbonyl)-L-alaninyl)amino-2,3-dihydro-1-(2-oxo-2-phenylethyl)-5-phenyl-1H-1,4-benzodiazepin-2-one (2.5 g, 4.63 mmol) was added to 100 mL of a stirring solution of 15% TFA/methylene chloride in one portion. After stirring 2 h, the reaction mixture was concentrated under reduced pressure and the residue was dissolved in 150 mL of methylene chloride. This solution was washed twice with saturated sodium bicarbonate, once with brine and then dried over sodium sulfate. Purification of the crude product using silica gel column chromatography (1–10% methanol/methylene chloride) gave 1.91 g (94%) of the title compound as a white foam.

NMR data was as follows:

$^1$H NMR (300 MHz, CDCl$_3$): d=1.30–1.50 (m, 3H), 1.80–2.20 (br s, 2H), 3.55–3.75 (m, 1H), 5.20–5.45 (m, 2H), 5.67 (t, J=7.48 Hz, 1H), 7.20–7.65 (m, 12H), 7.90 (d, J=7.7 Hz, 2H), 8.80 (dd, J$_1$=25.09 Hz, J$_2$=8.33 Hz, 1H). EX MS (M+1): 441.2.

Example C-AC

Synthesis of 3-(L-Alaninyl)amino-2,3-dihydro-1-(4,4,4trifluorobutyl)-5-phenyl-1H-1,4-benzodiazepin-2-one Step A: Synthesis of 3-(Benzoxycarbonyl)amino-2,3-dihydro-1-(4,4,4-trifluorobutyl)-5-phenyl-1H-1,4-benzodiazepin-2-one To a solution of 3-(benzoxycarbonyl)amino-2,3-dihydro-5-phenyl-1H-1,4-benzodiazepin-2-one (3.7 g, 9.61 mmol) in 40 mL of anhydrous DMF at 0° C. was added potassium tert-butoxide (1.6 g, 14.4 mmol) in one portion. The reaction mixture was stirred 20 min. and 4,4,4-trifluoro-1-bromobutane (Lancaster; Windham, N.H.; 2.6 g, 13.4 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–3% ethyl acetate/methylene chloride) gave 1.52 g (32%) of an off white foam.

NMR data was as follows:

$^1$H NMR (300 MHz, CDCl$_3$): d=1.50–2.10 (m, 4H), 3.70–3.90 (m, 1H), 4.35–4.55 (m, 1H), 5.15 (s, 2H), 5.33 (d, J=8.47 Hz, 1H), 6.67 (d, J=8.40 Hz, 1H), 7.2–7.70 (m, 14H). IR (CHCl$_3$): 1720.4, 1683.0, 1604.8, 1505.5, 1451.1, 1323.9, 1254.5, 1148.4 cm$^{-1}$. IEX MS (M+1): 496.3.

Step B: Synthesis of 3-Amino-2,3-dihydro-1-(4,4,4-trifluorobutyl)-5-phenyl-1H-1,4-benzodiazepin-2-one A solution of 3-(benzoxycarbonyl)amino-2,3-dihydro-1-(4,4,4-trifluorobutyl)-5-phenyl-1H-1,4-benzodiazepin-2-one (1.42 g, 2.87 mmol) in 50 mL of anhydrous methylene chloride was cooled to 0° C. under nitrogen. A stream of anhydrous HBr gas was slowly bubbled through the solution for 1 h. The bubbler was removed and the reaction was warmed to room temperature under nitrogen. After stirring for 1 h, the reaction was concentrated under vacuum and the residue was redissolved in 10 mL of methylene chloride. The crude HBr salt of the product was precipitated from solution using 90 mL of anhydrous ether and collected by filtration. After washing with ether, the HBr salt was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 1.06 g (100%) of the product was obtained as a white foam which was carried on without further purification.

NMR data was as follows:

$^1$H NMR (300 MHz, CDCl$_3$): d=1.60–2.10 (m, 4H), 2.76 (br s, 2H), 3.75–3.85 (m, 1H), 4.40–4.60 (m, 2H), 7.20–7.70 (m, 9H). IEX MS (M+1): 362.1.

Step C: Synthesis of 3-(N'-(tert-Butoxycarbonyl)-L-alaninyl)amino-2,3-dihydro-1-(4,4,4-trifluorobutyl)-5-phenyl-1H-1,4-benzodiazepin-2-one To a solution of HOBt-H$_2$O (373 mg, 2.76 mmol), N,N-diisopropylethylamine (481 µL, 2.76 mmol) and N-t-BOC-L-alanine (522 mg, 2.76 mmol) in 10 mL of anhydrous THF at 0° C. was added 1-(3-dimethylaminopropyl)-3-ethyl carbodiimide hydrochloride (EDCI; 527 mg, 2.76 mmol) in one portion. After stirring 5 min., a solution of 3-amino-2,3-dihydro-1-(4,4,4-trifluorobutyl)-5-phenyl-1H-1,4-benzodiazepin-2-one (1.05 g, 2.91 mmol) in 10 mL of anhydrous THF was added via syringe and the reaction mixture was warmed to room temperature and stirred overnight. The reaction mixture was diluted with 100 mL methylene chloride, extracted sequentially with 10% citric acid, saturated sodium bicarbonate, water and brine and then dried over sodium sulfate. Purification of the crude product using silica gel chromatography (10%–30% ethyl acetate/methylene chloride) gave 1.28 g (83%) of a white foam.

NMR data was as follows:

$^1$H NMR (300 MHz, CDCl$_3$): d=1.40–2.10 (m, 16H), 3.70–3.85 (m, 1H), 4.30–4.55 (m, 2H), 5.10 (br s, 1H), 5.45–5.55 (m, 1H), 7.25–7.80 (m, 10H). IR (CDCl$_3$): 1676.6, 1605.2, 1488.6, 1450.9, 1393.2, 1338.7, 1324.9, 1253.8, 1150.4 cm$^{-1}$. IEX MS (M+1): 533.1.

Step D: Synthesis of 3-(L-Alaninyl)amino-2,3-dihydro-1-(4,4,4-trifluorobutyl)-5-phenyl-1H-1,4-benzodiazepin-2-one 3-(N'-(tert-Butoxycarbonyl)-L-alaninyl)amino-2,3-dihydro-1-(4,4,4-trifluorobutyl)-5-phenyl-1H-1,4-benzodiazepin-2-one (1.21 g, 2.27 mmol) was added to 50 mL of a stirring solution of 15% TFA/methylene chloride in one portion. After stirring 2 h, the reaction mixture was concentrated under reduced pressure and the residue was dissolved in 100 mL of methylene chloride. This solution was washed twice with saturated sodium bicarbonate, once with brine and then dried over sodium sulfate. Purification of the crude product using silica gel column chromatography (1–5% methanol/methylene chloride) gave 670 mg (68%) of a light pink foam.

NMR data was as follows:

$^1$H NMR (300 MHz, CDCl$_3$): d=1.43 (t, J=7.0 Hz, 3H), 1.60–2.20 (m, 7H), 3.60–3.85 (m, 2H), 4.35–4.55 (m, 1H), 5.51 (dd, J$_1$=8.36 Hz, J$_2$=2.48 Hz, 1H), 7.20–7.70 (m, 9H), 8.80 (dd, J$_1$=27.73 Hz, J$_2$=8.34 Hz, 1H). IEX MS (M+1): 433.2.

Example C-AD

Synthesis of 3-(N'-(Chloroacetyl)-L-alaninyl)amino-2,3-dihydro-1-methyl-5-phenyl-1H-1,4-benzodiazepin-2-one A solution of 3-(L-alaninyl)amino-2,3-dihydro-1-methyl-5-phenyl-1H-1,4-benzodiazepin-2-one (20.0 mg, 0.0595 mmol), a-chloroacetyl chloride (5.9 µL, 0.0744 mmol) and piperidinylmethyl polystyrene (59.5 mg, 3.6 mmol/g (Fluka)) in 1 mL of methylene chloride were shaken for 20 min. Aminomethyl polystyrene (58 mg, 3.0 mmol/g (Advanced Chemtech)) was then added and the reaction mixture was shaken for an additional 15 min. and filtered. Removal of the solvent under reduced pressure provided 23.9 mg (98%) of the crude product which was used without further purification.

NMR data was as follows:

$^1$H NMR (300 MHz, CDCl$_3$): d=1.40–1.60 (m, 3H), 3.40–3.6 (m, 3H), 4.1 (s, 2H), 4.60–4.80 (m, 1H), 5.45–5.50 (m, 1H), 7.20–7.90 (m, 11H).

Example C-AE

Synthesis of 3-[(L-Alaninyl)amino]-2,3-dihydro-1-methyl-5-(2-pyridyl)-1H-1,4-benzodiazepin-2-one Step A: Synthesis of 3-Amino-2,3-dihydro-1-methyl-5-(2-pyridyl)-1H-1,4-benzodiazepin-2-one The title compound was synthesized as described in *Synth. Commun.*, 26(4), 721–727 (1996).

Step B: Synthesis of 3-[(N-tert-Butoxycarbonyl-L-alaninyl)amino]-2,3-dihydro-1-methyl-5-(2-pyridyl)-1H-1,4-benzodiazepin-2-one A solution of L-Boc-alanine (1.74 g, 9.20 mmol), HOBt monohydrate (1.24 g, 9.20 mmol), diisopropylethylamime (1.6 mL, 9.20 mmol) and $CHCl_2$ (30 mL) was purged with nitrogen and cooled in an ice bath. To the cold solution was added 1-(3-dimethylaminopropyl)-3-ethylcarbodiimide hydrochloride (1.76 g, 9.20 mmol) followed by a solution of 3-amino-2,3-dihydro-1-methyl-5-(2-pyridyl)-1H-1,4-benzodiazepin-2-one (2.45 g, 9.20 mmol) dissolved in $CH_2Cl_2$ (15 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a tan foam. The title compound was crystallized from $CH_2Cl_2$/EtOAc to give 3.47 g (86% yield) of white crystals, mp. 228–229° C.

Anal. Calcd for $C_{23}H_{27}N_5O_4$: C, 63.14; H, 6.22; N, 16.01. Found: C, 63.25; H, 6.15; N, 15.95. MS (FD$^+$) 437 m/z.

Step C: Synthesis of 3-[(L-Alaninyl)amino]-2,3-dihydro-1-methyl-5-(2-pyridyl)-1H-1,4-benzodiazepin-2-one A solution of 3-[(N-tert-butoxycarbonyl-L-alaninyl) amino]-2,3-dihydro-1-methyl-5-(2-pyridyl)-1H-1,4-benzodiazepin-2-one (3.42 g, 7.82 mmol) in $CH_2Cl_2$ (90 mL) was cooled in an ice bath and treated with TFA (13.2 mL, 172 mmol). The cold bath was removed and the solution stirred at room temperature for four hours. The reaction mixture was washed with 1 M aq. $K_2CO_3$ and the aqueous back-extracted with $CH_2Cl_2$. The combined extracts were washed with $H_2O$, dried ($MgSO_4$) and concentrated to obtain 1.75 g (66% yield) of the title compound as an off-white foam. MS (IS$^+$) 338 (m/e).

$^1$H NMR (CDCl$_3$): d=8.76–8.86 (1H, m), 8.63 (1H, m), 8.17 (1H, m), 7.82 (2H, m), 7.60 (1H, m), 7.41 (3H, m), 5.60 (1H, m), 3.63 (1H, m), 3.49 (3H, s), 1.66 (2H, broad), 1.45 (3H, m).

Example C-AF

Synthesis of 3-[(L-Alaninyl)amino]-2,3-dihydro-1-(2-N,N-diethylaminoethyl)-5-(2-pyridyl)-1H-1,4-benzodiazepin-2-one Step A: Synthesis of 3-Amino-2,3-dihydro-1-(2-N,N-diethylaminoethyl)-5-(2-pyridyl)-1H-1,4-benzodiazepin-2-one The title compound was synthesized as described in *Synth. Commun.*, 26(4), 721–727 (1996).

Step B: Synthesis of 3-[(N-tert-Butoxycarbonyl-L-alaninyl)amino]-2,3-dihydro-1-(2-N,N-diethylaminoethyl)-5-(2-pyridyl)-1H-1,4-benzodiazepin-2-one A solution of L-Boc-alanine (1.80 g, 9.50 mmol), HOBt monohydrate (1.28 g, 9.50 mmol), diisopropylethylamime (1.65 mL, 9.50 mmol) and $CH_2Cl_2$ (40 mL) was purged with nitrogen and cooled in an ice bath. To the cold solution was added 1-(3-dimethylaminopropyl)-3-ethylcarbodiimide hydrochloride (1.82 g, 9.50 mmol) followed by a solution of 3-amino-2,3-dihydro-1-(2-N,N-diethylaminoethyl)-5-(2-pyridyl)-1H-1,4-benzodiazepin-2-one (3.34 g, 9.50 mmol) dissolved in $CH_2Cl_2$ (25 mL). The cold bath was removed and the solution stirred overnight at room temperature. The reaction mixture was extracted with $H_2O$, 5% aq. $NaHCO_3$, and brine. The remaining $CH_2Cl_2$ solution was dried ($MgSO_4$) and concentrated to a tan foam. The title compound was isolated via column chromatography (2% MeOH/$CH_2Cl_2$ to 10% MeOH/$CH_2Cl_2$) to give 3.53 g (71% yield) of yellow foam.

MS (FD$^+$) 522 (m/z).

$^1$H NMR (CDCl$_3$): d=8.62 (1H, d), 8.11 (1H, m), 7.80 (2H, m), 7.59 (2H, m), 7.32–7.45 (2H, m), 5.54 (1H, m), 5.02–5.18 (1H, m), 4.38 (1H, m), 4.20 (1H, m), 3.83 (1H, m), 2.62 (2H, t), 2.44 (4H, m), 1.40–1.56 (12H, m), 0.88 (6H, m).

Step C: Synthesis of 3-[(L-Alaninyl)amino]-2,3-dihydro-1-(2-N,N-diethylaminoethyl)-5-(2-pyridyl)-1H-1,4-benzodiazepin-2-one The title compound was synthesized using the procedure described in Example C-AE, Step C. A solution of 3-[(N-tert-butoxycarbonyl-L-alaninyl)amino]-2,3-dihydro-1-(2-N,N-diethylaminoethyl)-5-(2-pyridyl)-1H-1,4-benzodiazepin-2-one (3.52 g, 6.73 mmol) was treated with TFA (11.4 mL, 148 mmol) to give 2.61 g (92% yield) the title compound as a light yellow foam.

MS (IS$^+$) 423 (m/e).

$^1$H NMR (CDCl$_3$): d=8.78–8.93 (1H, m), 8.62 (1H,d), 8.11 (1H, m), 7.80 (2H, m), 7.58 (2H, m), 7.39 (2H, m), 5.58 (1H, m), 4.22 (1H, m), 3.88 (1H, m), 3.61 (1H, m), 2.67 (2H, t), 2.49 (4H, m), 1.73 (2H, broad), 1.42 (3H, m), 0.91 (6H, m).

Example C-AG

Synthesis of 3-[(L-Alaninyl)amino]-2,3-dihydro-1-(3,3-dimethyl-2-oxobutyl)-5-(2-pyridyl)-1H-1,4-benzodiazepin-2-one Step A: Synthesis of 3-Amino-2,3-dihydro-1-(3,3-dimethyl-2-oxobutyl)-5-(2-pyridyl)-1H-1,4-benzodiazepin-2-one The title compound was synthesized as described in *Synth. Commun.*, 26(4), 721–727 (1996).

Step B: Synthesis of 3-[(N-tert-Butoxycarbonyl-L-alaninyl)amino]-2,3-dihydro-1-(3,3-dimethyl-2-oxobutyl)-5-(2-pyridyl)-1H-1,4-benzodiazepin-2-one A solution of L-Boc-alanine (1.57 g, 8.33 mmol), HOBt monohydrate (1.13 g, 8.33 mmol), diisopropylethylamime (1.45 mL, 8.33 mmol) and $CH_2Cl_2$ (40 mL) was purged with nitrogen and cooled in an ice bath. To the cold solution was added 1-(3-dimethylaminopropyl)-3-ethylcarbodiimide hydrochloride (1.60 g, 8.33 mmol) followed by a solution of 3-amino-2,3-dihydro-1-(3,3-dimethyl-2-oxobutyl)-5-(2-pyridyl)-1H-1,4-benzodiazepin-2-one (2.92 g, 8.33 mmol) dissolved in $CH_2Cl_2$ (25 mL). The cold bath was removed and the solution stirred overnight at room temperature. The reaction mixture was extracted with $H_2O$, 0.1 N aq. citric acid, 5% aq. NaHCO, and brine. The remaining $CH_2Cl_2$ solution was dried ($MgSO_4$) and concentrated to a yellow foam. The title compound was isolated via column chromatography (20% EtOAc/hexanes to 60% EtOAc/hexanes) to give 4.19 g (96% yield) of light yellow foam.

MS (FD$^+$) 521 (m/z).

$^1$H NMR (CDCl$_3$): d=8.65 (1H, t), 8.17 (1H, t), 7.90 (1H, t), 7.71–7.85 (1H, m), 7.54 (1H, m), 7.44 (1H, t), 7.37 (1H, d), 7.24–7.32 (1H, m), 7.14 (1H, m), 5.67 (1H, dd), 5.18 (1H, broad), 4.93–5.07 (1H, m), 4.50–4.64 (1H, m), 4.38 (1H, broad), 1.42–1.51 (12H, m), 1.26 (9H, d).

Step C: Synthesis of 3-[(L-Alaninyl)amino]-2,3-dihydro-1-(3,3-dimethyl-2-oxobutyl)-5-(2-pyridyl)-1H-1,4-benzodiazepin-2-one The title compound was synthesized using the procedure described in Example C-AE, Step C. A solution of 3-[(N- tert-butoxycarbonyl-L-alaninyl)amino]-2,3-dihydro-1-(3,3-dimethyl-2-oxobutyl)-5-(2-pyridyl)-1H-1,4-benzodiazepin-2-one (4.18 g, 8.01 mmol) was treated with TFA (13.6 mL, 176 mmol) to give 3.14 g (93% yield) the title compound as an off-white foam.

MS (IS$^+$) 422 (m/e).

$^1$H NMR (CDCl$_3$) d=8.85–8.99 (1H, m), 8.68 (1H, d), 8.20 (1H, t), 7.87 (1H, t), 7.58 (1H, t), 7.42 (2H, m), 7.30 (1H, t), 7.17 (1H, d), 5.72 (1H, m), 5.08 (1H, d), 4.60 (1H, d), 3.66 (1H, m), 1.47 (3H, m), 1.28 (9H, m).

Example C-AH

Synthesis of 3-[(L-Alaninyl)amino]-2,3-dihydro-1-methyl-5-(2-thiazyl)-1H-1,4-benzodiazepin-2-one Step A: Synthesis of 3-Amino-2,3-dihydro-1-methyl-5-(2-thiazyl)-1H-1,4-benzodiazepin-2-one The title compound was synthesized in a manner similar to the procedure described in *Synth. Commun.*, 26(4), 721–727 (1996), starting with 2-(2-aminobenzoyl)thiazole (prepared as described in Tetrahedron, 51(3), 773–786, (1995)).

MS (IS$^+$) 273 (m/e).

$^1$H NMR (CDCl$_3$): d=7.83–7.94 (2H, m), 7.61 (1H, t), 7.50 (1H, d), 7.34 (2H, m), 4.60 (1H, s), 3.46 (3H, s), 1.97 (2H, broad).

Step B: Synthesis of 3-[(N-tert-Butoxycarbonyl-L-alaninyl)amino]-2,3-dihydro-1-methyl-5-(2-thiazyl)-1H-1,4-benzodiazepin-2-one A solution of L-Boc-alanine (1.85 g, 9.77 mmol), HOBt monohydrate (1.32 g, 9.77 mmol), diisopropylethylamime (1.70 mL, 9.77 mmol) and CH$_2$Cl$_2$ (30 mL) was purged with nitrogen and cooled in an ice bath. To the cold solution was added 1-(3-dimethylaminopropyl)-3-ethylcarbodiimide hydrochloride (1.87 g, 9.77 mmol) followed by a solution of 3-amino-2,3-dihydro-1-methyl-5-(2-thiazyl)-1H-1,4-benzodiazepin-2-one (2.66 g, 9.77 mmol) dissolved in CH$_2$Cl$_2$ (20 mL). The cold bath was removed and the solution stirred overnight at room temperature. The reaction mixture was extracted with H$_2$O, 0.1 N aq. citric acid, 5% aq. NaHCO$_3$, and brine. The remaining CH$_2$Cl$_2$ solution was dried (MgSO$_4$) and concentrated to a light yellow foam. The title compound was crystallized from EtOAc/hexane to give 3.22 g (74% yield) of white crystals, mp. 196–197° C.

Anal. Calcd for C$_{21}$H$_{25}$N$_5$O$_4$S: C, 56.87; H, 5.68; N, 15.79. Found: C, 56.74; H, 5.75; N, 15.55. MS (IS$^+$) 444 m/e.

Step C: Synthesis of 3-[(L-Alaninyl)amino]-2,3-dihydro-1-methyl-5-(2-thiazyl)-1H-1,4-benzodiazepin-2-one The title compound was synthesized using the procedure described in Example C-AE, Step C.

Example C-AI

Synthesis of 3-[(L-Alaninyl)amino]-2,3-dihydro-1-methyl-5-(thiophen-2-yl)-1H-1,4-benzodiazepin-2-one Step A: Synthesis of 3-Amino-2,3-dihydro-1-methyl-5-(2-thiophen-2-yl)-1H-1,4-benzodiazepin-2-one The title compound was synthesized in a manner similar to the procedure described in *Synth. Commun.*, 26(4), 721–727 (1996), starting with 2-(2-aminobenzoyl)thiophene (prepared as described in *Collect. Czech. Chem. Commun.*, 34(2), 468–478, (1969)).

MS (IS$^+$) 272 (m/e).

$^1$H NMR (CDCl$_3$): d=7.68 (1H, d), 7.60 (1H, t), 7.48 (1H, m), 7.35 (2H, d), 7.28 (1H, m), 7.15 (1H, d), 7.05 (1H, d), 4.50 (1H, broad), 3.45 (3H, s), 2.26 (2H, broad).

Step B: Synthesis of 3-[(N-tert-Butoxycarbonyl-L-alaninyl)amino]-2,3-dihydro-1-methyl-5-(2-thiophenyl)-1H-1,4-benzodiazepin-2-one The title compound was synthesized in a manner similar to the procedure described in Example C-AH, Step B.

MS (IS$^+$) 443 (m/e).

$^1$H NMR (CDCl$_3$): d=7.69 (1H, d), 7.61 (2H, m), 7.48 (1H, d), 7.27–7.42 (2H, m), 7.18 (1H, m), 7.05 (1H, m), 5.51 (1H, d), 5.13 (1H, broad), 4.36 (1H, broad), 3.44 (3H, s), 1.38–1.57 (12H, m).

Step C: Synthesis of 3-[(L-Alaninyl)amino]-2,3-dihydro-1-methyl-5-(2-thiophenyl)-1H-1,4-benzodiazepin-2-one The title compound was synthesized in a manner similar to the procedure described in Example C-AE, Step C.

MS (IS$^+$) 343 (m/e).

$^1$H NMR (CDCl$_3$): d=8.55 (1H, d), 7.68 (1H, d), 7.59 (1H, m), 7.48 (1H, d), 7.36 (1H, d), 7.31 (1H, d), 7.16 (1H, m), 7.04 (1H, t), 5.54 (1H, d), 3.58 (1H, m), 3.45 (3H, s), 1.41 (3H, d).

Additionally, the following procedures provide various carboxylic acid esters which can be hydrolyzed using General Procedures AC or BD below to afford the corresponding carboxylic acids. Coupling of the resulting carboxylic acids to the amines employed above using the General Procedures set forth above provides for additional compounds within the scope of this invention.

General Procedure AA

Reductive Amination

To a solution of the arylamine in ethanol in a hydrogenation flask was added 1 equivalent of the 2-oxocarboxylic acid ester (e.g., pyruvate ester), followed by 10% palladium on carbon (25 weight percent based on the arylamine). The reaction was hydrogenated at 20 psi H$_2$ on a Parr shaker until complete reaction was indicated by tlc (30 minutes to 16 hours). The reaction mixture was then filtered through a pad of Celite 545 (available from Aldrich Chemical Company, Inc.) and stripped free of solvent on a rotary evaporator. The crude product residue was then further purified via chromatography.

General Procedure AB

First Transesterification Technique

A solution of 1–5 equivalents of the desired alcohol was added to 1 equivalent of sodium hydride in toluene. After off-gassing had ceased, the compound to be transesterified, dissolved in toluene, was added. After 0.5 hours, the reaction was either heated to 40° C. and placed under house vacuum (20 mmHg), or nitrogen was bubbled through the solution while it was heated at 90° C. The reaction was followed by tlc, and when the reaction was complete the solution was cooled and quenched with water or 1M HCl, and in smaller scale reactions diluted with ethyl acetate. The organic phase was extracted with saturated aqueous NaHCO$_3$, then washed with saturated aqueous NaCl and dried over MgSO$_4$. The solution was stripped free of solvent on a rotary evaporator, and the crude product residue was then further purified by chromatography. Alternatively, the reaction mixture was worked-up by evaporation of the solvents and direct chromatography of the crude mixture.

This procedure is particularly useful in the case of costly and/or high boiling alcohols.

General Procedure AC

Second Transesterification Technique

The compound to be transesterified was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous NaHCO$_3$ was added. The organic phase was washed with saturated aqueous NaCl and dried over MgSO$_4$. The solution was stripped free of solvent on a rotary evaporator, and the crude product residue was then further purified by chromatography.

General Procedure AD

Third Transesterification Technique

The compound to be transesterified was placed in a large excess of the desired alcohol. A catalytic amount of dry NaH was added, and the reaction was followed by tic until the presence of starting material was no longer detected. The reaction was quenched with a few milliliters of 1N HCl, and after a few minutes of stirring saturated aqueous NaHCO$_3$ was added. The volume of the reaction mixture was reduced on a rotary evaporator until the excess alcohol was removed and then the remaining residue was taken up in ethyl acetate and additional water was added. The organic phase was washed with saturated aqueous NaCl and dried over MgSO$_4$. The solution was stripped free of solvent on a rotary evaporator, and the crude product residue was then further purified by chromatography.

This procedure is particularly employed in the case of low boiling, inexpensive alcohols, miscible with water.

General Procedure AE

O-Alkylation Technique

To a carboxylic acid compound (prepared, for example, by reductive amination via General Procedure AA to provide for the N-aryl amino acid ester, followed by hydrolysis via Procedure AF) in DMF was added 1.5 equivalents K$_2$CO$_3$, followed by 1 equivalent of alkylating agent (e.g., tert-butyl bromoacetate). The reaction was stirred at room temperature for 2 hours, then was quenched with water and extracted into ethyl acetate. The organic phase was washed with saturated aqueous NaHCO$_3$, water, and saturated aqueous NaCl, and was then dried over MgSO$_4$. The solution was stripped free of solvent on a rotary evaporator to yield the crude product.

General Procedure AF

Ester Hydrolysis to Free Acid

To a carboxylic ester compound (prepared, for example, by reductive amination via General Procedure AA to provide for the N-aryl amino acid ester) in a 1:1 mixture of CH$_3$OH/H$_2$O was added 2–5 equivalents of K$_2$CO$_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over MgSO$_4$. The solution was stripped free of solvent on a rotary evaporator to yield the crude product.

General Procedure AG

N-Heteroarylation of Alanine

A solution of 1.1 equivalents of L-alanine and 2 equivalents NaOH in DMSO was stirred at room temperature for 1 hour, then 1 equivalent of 2-chlorobenzothiazole was added. The mixture was heated to 100° C. for 4 hours, then cooled to room temperature and poured onto ice. The pH of the resulting aqueous solution was adjusted to ~2, and the precipitated solid was removed by filtration. This solid was then dissolved in 1N NaOH and the resulting solution was filtered through a pad of Celite 545. The pH of the filtrate was adjusted to ~2, and the white precipitate was removed by filtration and washed with water to yield the crude product.

General Procedure AH

EDC Coupling

To a 1:1 mixture of the desired acid and alcohol in CH$_2$Cl$_2$ at 0° C. was added 1.5 equivalents triethylamine, followed by 2.0 equivalents hydroxybenzotriazole monohydrate, then 1.25 equivalents of ethyl-3-(3-dimethylamino)-propyl carbodiimide.HCl (EDC). The reaction was stirred overnight at room temperature, then transferred to a separatory funnel and washed with water, saturated aqueous NaHCO$_3$, 1N HCl, and saturated aqueous NaCl, and was then dried over MgSO$_4$. The solution was stripped free of solvent on a rotary evaporator to yield the crude product.

General Procedure AI

Oxime or Amine Coupling Technique

The trichlorophenyl ester (1 eq) of a carboxylic acid was stirred in DMF or THF. The oxime or amine (1.2 eq) was added and the mixture was stirred at ambient temperature for 14 hours. In cases where the hydrochloride salt form of an amine was used, a suitable base such as N,N-diisopropylethylamine (1.2 eq) was also added. The resulting mixture was concentrated under reduced pressure to yield a crude product which was used without purification or was purified by silica gel chromatography and/or crystallization.

General Procedure AJ

Alkylation Technique

The amine (1 eq), the α-bromo ester (1.1 eq) and a suitable base (such as triethylamine) (2 eq) were stirred in chloroform. The resulting solution was heated at reflux for 4–12 hours. After cooling, the mixture was diluted with chloroform and washed with water. The organic portion was dried (sodium sulfate) and concentrated under reduced pressure. The crude product was purified by silica gel chromatography.

General Procedure AK

Oxime or Alcohol Coupling Technique

The carboxylic acid (1 eq) was stirred in a suitable solvent (such as THF, dioxane or DMF). An alcohol or oxime (1–5 eq) was added. EDC hydrochloride (1.2 eq) and hydroxybenzotriazole hydrate (1 eq) were added. A suitable base (such as 4-methylmorpholine or triethylamine) (0–1 eq) was added. A catalytic amount (0.1 eq) of 4-dimethylaminopyridine was added. The mixture was stirred at ambient temperature and under a dry atmosphere of nitrogen. After 20 hours, the mixture was concentrated under reduced pressure. The resulting concentrate was partitioned between ethyl acetate and water. The organic portion was separated and washed with aqueous sodium bicarbonate and brine. The organic portion was dried (sodium sulfate) and concentrated under reduced pressure. The crude product was used without purification or was purified by silica gel chromatography and/or crystallization.

General Procedure AL

EDC Coupling

The carboxylic acid was dissolved in methylene chloride. The amino acid (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride (EDC) was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product. Pure products were obtained by flash chromatography in an appropriate solvent.

General Procedure AM

Triflate Displacement

To a 0° C. solution of iso-butyl R-(+)-lactate in $CH_2Cl_2$ was added 1.1 equivalents of trifluoromethanesulfonic anhydride. After stirring at room temperature for 20 min, 1.1 equivalents of 2,6-lutidine was added and stirring was continued for 10 min. This solution was then transferred to a flask containing 1 equivalent of the arylamine and 1 equivalent N,N-diisopropylethylamine in $CH_2Cl_2$ or $CH_3NO_2$ at 0° C. The reaction was held overnight at room temperature and then stripped free of solvent on a rotary evaporator. The residue was dissolved in ethyl acetate, washed with 5% citric acid, followed by saturated aqueous NaCl, dried over magnesium sulfate or sodium sulfate and then the solution was stripped free of solvent on a rotary evaporator to yield the crude product, which was then purified by chromatography.

General Procedure AN

BOC Removal

The BOC-protected compound was added to a 1:1 mixture of $CH_2Cl_2$ and trifluoroacetic acid, and was stirred until tlc indicated complete conversion, typically 2h. The solution was then stripped to dryness and the residue was taken up in ethyl acetate and extracted with dilute HCl. The acid reaction was neutralized and extracted with ethyl acetate. The organic phase was washed with saturated aqueous NaCl and dried over $MgSO_4$. The solution was stripped free of solvent on a rotary evaporator to yield the product.

General Procedure AO

Synthesis of Pyruvate Esters

To a mixture of pyruvic acid (8.8 g, 0.1 mol) (Aldrich) in 100 mL of benzene was added iso-butanol (14.82 g, 0.2 mol) and a catalytic amount of p-toluenesulfonic acid. The mixture was then refluxed using a Dean Stark apparatus. After 4 hours, the reaction appeared to be complete with the isolation of 1.8 g (0.1 mol) of water. The benzene and iso-butanol were removed on a rotary evaporator. The residue (14 g, 0.1 mol), which was primarily the pyruvate iso-butyl ester by nmr [$^1$H-Nmr ($CDCl_3$): =4.0 (d, 2H), 2.5 (s, 3H), 2.0 (m, 1H), 1.0 (d, 6H)], was used without further purification. By substituting other alcohols in place of iso-butanol (e.g., ethanol, isopropanol, n-butanol, benzyl alcohol and the like), other esters of pyruvic acid can be prepared in a similar manner.

General Procedure AP

Aromatic Nucleophilic Substitution of Fluorobenzenes

A mixture of 1.82 g (10 mmol) of D,L-alanine iso-butyl ester hydrochloride, the fluorobenzene (10 mmol) and 3 g of anhydrous potassium carbonate in 10 mL of DMSO was stirred at 120° C. for 2–5 hours. The reaction mixture was then cooled to room temperature and diluted with 100 mL of ethyl acetate. The ethyl acetate extract was washed with water (3×), dried over $MgSO_4$ and evaporated to dryness to afford the crude product, which was further purified by column chromatography.

General Procedure AQ

Fourth Transesterification Technique

The ester to be transesterified was dissolved in a large excess of the alcohol and 0.3 equivalents of titanium(IV) isopropoxide (Aldrich) was added. The reaction was followed by tlc until complete and then the volatiles were removed at reduced pressure. The resulting crude material was then chromatographed to obtain the desired product.

General Procedure AR

Synthesis on N-BOC Anilines

To a solution of the aniline in THF was added dropwise 1 equivalent of di-tert-butyl dicarbonate (Aldrich) in THF and then 1.5 equivalents of 10N aqueous sodium hydroxide at 0° C. After stirring at room temperature for 16 hours, or heating at 80° C. for 3 hours, if needed, the reaction mixture was diluted with ether and washed with $NaHCO_3$, brine, dried over sodium sulfate and potassium carbonate, concentrated at reduced pressure and chromatographed to afford the N-BOC aniline.

General Procedure AS

Oxime Ester Formation

The trichlorophenyl ester (1 eq.) was stirred in DMF or THF. The oxime (1.2 eq.) was added and the mixture was stirred at ambient temperature for 1 to 4 hours. The resulting mixture was concentrated under reduced pressure and the residue was purified by silica gel chromatography and/or crystallization.

Example AA

Synthesis of D,L-Alanine iso-Butyl Ester Hydrochloride

A mixture of 35.64 g (0.4 mol) of D,L-alanine (Aldrich), 44 mL (0.6 mol) of thionyl chloride (Aldrich) and 200 mL of iso-butanol was refluxed for 1.5 hours. The volatiles were removed at reduced pressure at 90° C. under reduced pressure to give the title compound as an oil, which was used without further purification.

NMR data was as follows:

$^1$H-NMR (CDCl$_3$): d=8.72 (br s, 3H), 4.27 (q, J=7.4 Hz, 1H), 3.95 (m, 2H), 1.96 (s, 1H), 1.73 (d, J=7.2 Hz, 3H), 0.92 (d, J=6.7 Hz, 6H). $^{13}$C-nmr (CDCl$_3$): d=170.0, 72.2, 49.2, 27.5, 18.9, 16.1.

General Procedure BA

Coupling of Acid Halides With H$_2$NCH(R$^2$)C(O)XR$^3$

To a stirred solution of (D,L)-alanine iso-butyl ester hydrochloride (from Example BB below) (4.6 mmol) in 5 mL of pyridine is added 4.6 mmol of an acid chloride. Following precipitation of the pyridinium hydrochloride, the mixture is stirred for 3.5 h, diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

General Procedure BB

Coupling of R$^1$C(X')(X")C(O)OH With H$_2$NCH(R$^2$)C(O)XR$^3$

A solution of the acid (3.3 mmol) and CDI in 20 mL THF was stirred for 2 h. L-alanine iso-butyl ester hydrochloride (from Example BB below) (3.6 mmol) was added, followed by 1.5 mL (10.8 mmol) of triethylamine. The reaction mixture was stirred overnight. The reaction mixture was diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

General Procedure BC

Esterification of R$^1$C(X')(X")C(O)NHCH(R$^2$)C(O)OH With HOR$^3$

CDI is added to a stirred solution of an N-acyl amino acid, and the mixture is stirred for about 1.5 h. An alcohol is added the mixture, followed by addition of an equivalent of NaH. Bubbling should occur immediately to evolve the generated hydrogen gas. The reaction mixture is stirred overnight, diluted with diethyl ether, washed with 10% HCl three times, brine once, 20% potassium carbonate once and brine once. The solution is then dried over magnesium sulfate, filtered, and evaporated at reduced pressure to yield the product.

General Procedure BD

Ester Hydrolysis to the Free Acid

Ester hydrolysis to the free acid was conducted by conventional methods. Below are two examples of such conventional de-esterification methods.

To the ester in a 1:1 mixture of CH$_3$OH/H$_2$O was added 2–5 equivalents of K$_2$CO$_3$. The mixture was heated to about 50° C. for about 0.5 to 1.5 hours until tlc showed complete reaction. The reaction was cooled to room temperature and the methanol was removed at reduced pressure. The pH of the remaining aqueous solution was adjusted to about 2, and ethyl acetate was added to extract the product. The organic phase was then washed with saturated aqueous NaCl and dried over MgSO$_4$. The solution was stripped free of solvent at reduced pressure to yield the product.

The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was diluted with EtOAc, the layers were separated and the aqueous layer acidified to pH 2. The aqueous layer was back extracted with EtOAc, the combined organics were dried over Na$_2$SO$_4$ and the solvent was removed under reduced pressure after filtration. The residue was purified by conventional methods (e.g., recrystallization).

The following exemplifies this later example. The methyl ester of 3-NO$_2$ phenylacetyl alanine 9.27 g (0.0348 mols) was dissolved in 60 mL dioxane and 15 mL of H$_2$O and adding LiOH (3.06 g, 0.0731 mol) that has been dissolved in 15 mL of H$_2$O. After stirring for 4 hours, the dioxane was removed under reduced pressure and the residue diluted with EtOAc, the layers were separated and the aqueous layer acidified to pH 2. The aqueous layer was back extracted with EtOAc (4×100 mL), the combined organics were dried over Na$_2$SO$_4$ and the solvent was removed under reduced pressure after filtration. The residue was recrystallized from EtOAc/isooctane giving 7.5 g (85%) of 3-nitrophenylacetyl alanine. C$_{11}$H$_{12}$N$_2$O$_5$ requires C=52.38, H=4.80, and N=11.11. Analysis found C=52.54, H=4.85, and N=11.08. [ ]$_{23}$=−29.9 @ 589 nm.

General Procedure BE

Low Temperature BOP Coupling of Acid and Alcohol

A solution of methylene chloride containing the carboxylic acid (100 M%) and N-methyl morpholine (150 M%) was cooled to −20° C. under nitrogen. BOP (105 M%) was added in one portion and the reaction mixture was maintained at −20° C. for 15 minutes. The corresponding alcohol (120 M%) was added and the reaction mixture was allowed to warm to room temperature and stirred for 12 hours. The reaction mixture was then poured into water and extracted with ethyl acetate (3×). The combined ethyl acetate portions were backwashed with saturated aqueous citric acid (2×), saturated aqueous sodium bicarbonate (2×), brine (1×), dried over anhydrous magnesium sulfate or sodium sulfate and the solvent removed under reduced pressure to yield the crude product.

General Procedure BF

EDC Coupling of Acid and Amine

The acid derivative was dissolved in methylene chloride. The amine (1 eq.), N-methylmorpholine (5 eq.), and hydroxybenzotriazole monohydrate (1.2 eq.) were added in sequence. The reaction was cooled to about 0° C. and then 1.2 eq. of 1-(3-dimethylaminopropyl)-3-ethylcarbodiimide hydrochloride was added. The solution was allowed to stir overnight and come to room temperature under N$_2$ pressure. The reaction mixture was worked up by washing the solution with saturated, aqueous Na$_2$CO$_3$, 0.1M citric acid, and brine before drying with $Na_2SO_4$ and removal of solvents to yield crude product. Pure products were obtained by flash chromatography in an appropriate solvent.

General Procedure BG

EDC Coupling of Acid and Amine A round bottom flask was charged with carboxylic acid (1.0 eq.), hydroxybenzotriazole hydrate (1.1 eq.) and amine (1.0 eq.) in THF under nitrogen atmosphere. An appropriate amount (1.1 eq. for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in EtOAc (or similar solvent)/water. The organic layer was washed with saturated aqueous sodium bicarbonate solution, 1N HCl, brine and dried over anhydrous sodium sulfate. In some cases, the isolated product was analytically pure at this stage while, in other cases, purification via chromatography and/or recrystallization was required prior to biological evaluation.

General Procedure BH

Coupling of $R^1C(X')(X'')C(O)Cl$ with $H_2NCH(R^2)C(O)XR^3$

An excess of oxalyl chloride in dichloromethane was added to the acid derivative together with one drop of DMF. The resulting mixture was stirred for about 2 hours or until bubbling ceases. The solvent was then removed under reduced pressure and rediluted with dry methylene chloride. To the resulting solution was added about 1.1 eq. of the appropriate amino acid ester and triethylamine (1.1 eq. in methylene chloride). The system was stirred at room temperature for 2 hours and then the solvent was removed under reduced pressure. The residue was dissolved in ethyl acetate, washed with 1N HCl followed by 1N NaOH. The organic layer was dried over anhydrous sodium sulfate, filtered and the solvent removed under reduced pressure to provide for the desired product.

General Procedure BI

P-EPC coupling

P-EPC coupling employs an amino acid ester and a substituted acetic acid compound. The acetic acid derivative is well known in the art and is typically commercially available. The amino acid ester is prepared by conventional methods from the known and typically commercially available N-BOC amino acid as described in General Procedure BJ below.

Specifically, the appropriate amino ester free base (0.0346 mmols) and substituted phenylacetic acid (0.069 mmols) were dissolved in 2.0 mL $CHCl_3$ (EtOH free), treated with 150 mg of P-EPC (0.87 meq./g) and the reaction was mixed for 4 days at 23 C. The reaction was filtered through a plug of cotton, rinsed with 2.0 mL of $CHCl_3$ and the filtrate evaporated under a stream of nitrogen. The purity of each sample was determined by $^1H$ NMR and ranged from 50% to >95%. Between 8.0 and 15.0 mg of final product was obtained from each reaction and was tested without additional purification.

General Procedure BJ

Synthesis of Amino Acid Esters From the Corresponding N-BOC Amino Acid

A. Esterification of the Acid.

The N-BOC amino acid was dissolved in dioxane and treated with an excess of alcohol (~1.5 eq.) and catalytic DMAP (100 mg) at 0° C. Stirring was continued until reaction completion whereupon the product was recovered by conventional methods.

B. Removal of N-BOC Group.

The N-BOC protected amino acid was dissolved in methylene chloride (0.05M) and treated with 10 eq. of TFA at room temperature under a nitrogen atmosphere. The reaction was monitored by tlc until starting material was consumed usually within 1–5 hours. An additional 10 eq. of TFA was added to the reaction if the starting material was still present after 5 hours. The reaction was carefully neutralized with $Na_2CO_3$, separated, the organic layer washed with brine and dried over anhydrous $Na_2SO_4$. The crude amine was then used without purification.

Specific exemplification of these procedures are as follows:

1. Racemic (+/−)-N-BOC-α-amino butyric acid (Aldrich) (9.29 g, 0.0457 mol) was dissolved in 100 mL of dioxane and treated with iso-butyl alcohol (6.26 mL, 0.0686 mol), EDC (8.72 g, 0.0457) and catalytic DMAP (100 mg) at 0° C. After stirring for 17 hours, the organics were evaporated at reduced pressure, the residue diluted with EtOAc washed with $NaHCO_3$, brine and dried over $Na_2SO_4$. Evaporation yields 8.42 g (71%) of an oil. $C_{13}H_{25}NO_4$ requires: C=60.21, H=9.72, and N=5.40. Anal found: C=59.91, H=9.89, and N=5.67.

The above N-BOC amino acid ester (8.00 g, 0.032 mol) was deprotected as above giving 3.12 g (61%) of the free base as a colorless oil which solidifies upon standing.

2. L-N-BOC-alanine (Aldrich) (8.97 g, 0.047 mol) was dissolved in 100 mL of $CH_2Cl_2$, iso-butyl alcohol (21.9 mL, 0.238 mol) and treated with DMAP (100 mg) and EDC (10.0 g, 0.52 mol) at O C. The mixture was stirred for 17 hours, diluted with $H_2O$, washed with 1.0 N HCl, $NaHCO_3$, then brine and the organics were dried over $Na_2SO_4$. Filtration and evaporation yields 11.8 g (quantitative) of L-N-BOC alanine iso-butyl ester which is contaminated with a small amount of solvent. A sample was vacuum dried for analytical analysis. $C_{12}H_{23}NO_4$ requires: C=58.79, H=9.38, and N=5.71. Anal found: C=58.73, H=9.55, and N=5.96.

The above N-BOC amino acid ester (11.8 g, 0.0481 mol) was deprotected as above. The free base was converted to the corresponding HCl salt using saturated HCl (g)/EtOAc to give L-N-alanine iso-butyl ester hydrochloride. Obtained 4.2 g (48%) of a colorless solid. Anal. Calc. for $C_7H_{15}NO_2 \cdot HCl$: C=46.28, H=8.88, and N=7.71. Found: C=46.01, H=8.85, and N=7.68.

General Procedure BK

Methyl Ester Formation From Amino Acids

The amino acid (amino acid or amino acid hydrochloride) is suspended in methanol and chilled to 0° C. HCl gas is bubbled through this solution for 5 minutes. The reaction is allowed to warm to room temperature then stirred for 4 hours. The solvents are then removed at reduced pressure to afford the desired amino acid methyl ester hydrochloride. This product is usually used without further purification.

Example BA

Synthesis of Free and Polymer Bound PEPC
N-Ethyl-N'-3-(1-pyrrolidinyl)1propylurea To a solution of 27.7 g (0.39 mol) ethyl isocyanate in 250 mL chloroform was added 50 g (0.39 mol) 3-(1-pyrrolidinyl) propylamine dropwise with cooling. Once the addition was complete, the cooling bath was removed and the reaction mixture stirred at room temperature for 4 hours. The reaction mixture was then concentrated under reduced pressure to give 74.5 g (96.4%) of the desired urea as a clear oil.
1-(3-(1-pyrrolidinyl)propyl)-3-ethylcarbodiimide (P-EPC)

To a solution of 31.0 g (0.156 mol) N-ethyl-N'-3-(1-pyrrolidinyl)propyl-urea in 500 mL dichloromethane was added 62.6 g (0.62 mol) triethylamine and the solution was cooled to 0° C. To this solution were then added 59.17 g (0.31 mol) 4-toluenesulfonyl chloride in 400 mL dichloromethane dropwise at such a rate as to maintain the reaction at 0–5° C. After the addition was complete, the reaction mixture was warmed to room temperature and then heated to reflux for 4 hours. After cooling to room temperature, the reaction mixture was washed with saturated aqueous potassium carbonate (3×150 mL). The aqueous phases were combined and extracted with dichloromethane. All organic phases were combined and concentrated under reduced pressure. The resultant orange slurry was suspended in 250 mL diethyl ether and the solution decanted off from the solid. The slurry/decantation process was repeated 3 more times. The ether solutions were combined and concentrated under reduced pressure to give 18.9 g (67%) of the desired product as a crude orange oil. A portion of the oil was distilled under vacuum to give a colorless oil distilling at 78–82° C. (0.4 mm Hg).
Preparation of a Polymer Supported Form of 1-(3-(1-Pyrrolidinyl)propyl)-3-ethylcarbodiimide (P-EPC)

A suspension of 8.75 g (48.3 mmol) 1-(3-(1-pyrrolidinyl)propyl)-3-ethylcarbodiimide and 24.17 g (24.17 mmol) Merrifield's resin (2% cross-linked, 200–400 mesh, chloromethylated styrene/divinylbenzene copolymer, 1 meq. Cl/g) in dimethylformamide was heated at 100° C. for 2 days. The reaction was cooled and filtered and the resulting resin washed sequentially with 1 L DMF, 1 L THF and 1 L diethyl ether. The remaining resin was then dried under vacuum for 18 hours.

Example BB

Preparation of Alanine iso-Butyl Ester Hydrochloride

A mixture of 35.64 g (0.4 mol) of (D,L)-alanine (Aldrich) (or L-alanine (Aldrich)); 44 mL (0.6 mol) of thionyl chloride (Aldrich) and 200 mL of isobutanol was refluxed for 1.5 hours and the volatiles were removed completely on a rotavapor of 90° C. under reduced pressure to give (D,L)-alanine iso-butyl ester hydrochloride (or L-alanine iso-butyl ester hydrochloride), which was pure enough to be used for further transformations.

III. PREPARATION OF FINAL COMPOUNDS

Example 1-1

Preparation of (S)-3-[(N'-(2-Thiophenecarboxyl)-L-alaninyl)]amino-2,3-dihydro-1-methyl-5-phenyl-1H-1,4-benzodiazepin-2-one Following General Procedure C-B above using 2-thiophenecarboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 447 (M+H).

Example 1-2

Preparation of (S)-3-[(N'-(2-Furoyl)-L-alaninyl)] amino-2,3-dihydro-1-methyl-5-phenyl-1H-1,4-benzodiazepin-2-one Following General Procedure C-B above using 2-furoic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 431 (M+H).

Example 1-3

Preparation of (S)-3-[(N'-(Cyclobutanecarboxyl)-L-alaninyl)]amino-2,3-dihydro-1-methyl-5-phenyl-1H-1,4-benzodiazepin-2-one Following General Procedure C-B above using cyclobutanecarboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 419 (M+H).

Example 1-4

Preparation of (S)-3-[(N'-(1-Phenyl-1-cyclopropanecarboxyl)-L-alaninyl)]amino-2,3-dihydro-1-methyl-5-phenyl-1H-1,4-benzodiazepin-2-one Following General Procedure C-B above using 1-phenyl-1-cyclopropanecarboxylic acid and (S)-3-[(L-alaninyl)] amino-2,3-dihydro-1-methyl-5-phenyl-1H-1,4-benzodiazepin-2-one, as described in Example 8-B above, the title compound was prepared. The molecular weight as determined by mass spectrometry (FD) was: 481 (M+H).

Example 1-5

Preparation of (S)-3-[(N'-(Cyclohexanecarboxyl)-L-alaninyl)]amino-2,3-dihydro-1-methyl-5-phenyl-1H-1,4-benzodiazepin-2-one Following General Procedure C-B above using cyclohexanecarboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 447 (M+H).

Example 1-6

Preparation of (S)-3-[(N'-(2-Benzofurancarboxyl)-L-alaninyl)]amino-2,3-dihydro-1-methyl-5-phenyl-1H-1,4-benzodiazepin-2-one Following General Procedure C-B above using 2-benzofurancarboxylic acid and (S)-3-[(L-alaninyl))amino-2,3-dihydro-1-methyl-5-phenyl-1H-1,4-benzodiazepin-2-one, as described in Example 8-B above, the title compound was prepared. The molecular weight as determined by mass spectrometry (FD) was: 481 (M+H).

Example 1-7

Preparation of (S)-3-[(N'-(5-Chlorobenzofuran-2-carboxyl)-L-alaninyl)]amino-2,3-dihydro-1-methyl-5-phenyl-1H-1,4-benzodiazepin-2-one Following General Procedure C-B above using 5-chlorobenzofuran-2-carboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 515 (M+H).

Example 1-8

Preparation of (S)-3-[(N'-(5,5-Dimethyl-butyrolactone-yl)-L-alaninyl)]amino-2,3-dihydro-1-methyl-5-phenyl-1H-1,4-benzodiazepin-2-one Following General Procedure C-B above using terebic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 477 (M+H).

Example 1-9

Preparation of (S)-3-[(N'-(3-Furoyl)-L-alaninyl)]amino-2,3-dihydro-1-methyl-5-phenyl-1H-1,4-benzodiazepin-2-one Following General Procedure D above using 3-furoic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 523 (M+H).

Example 1-10

Preparation of (S)-3-[(N'-(4-(Methylsulfonyl)benzoyl)-L-alaninyl)]amino-2,3-dihydro-1-methyl-5-phenyl-1H-1,4-benzodiazepin-2-one Following one or more of the general procedures outlined above, using 4-(methylsulfonyl)benzoic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 519 (M+H).

Example 1-11

Preparation of (S)-3-[(N'-(trans-2-Phenyl-1-cyclopropanecarboxyl)-L-alaninyl)]amino-2,3-dihydro-1-methyl-5-phenyl-1H-1,4-benzodiazepin-2-one Following General Procedure D above using trans-2-phenyl-1-cyclopropanecarboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 481 (M+H).

Example 1-12

Preparation of (S)-3-[(N'-(5-Methylsulfonyl)thiophene-2-carboxyl)-L-alaninyl)]amino-2,3-dihydro-1-methyl-5-phenyl-1H-1,4-benzodiazepin-2-one Following one or more of the general procedures outlined above, using (5-methylsulfonyl)thiophene-2-carboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 525 (M+H).

Example 1-13

Preparation of (S)-3-[(N'-(1,8-Dimethyl-6-Hydroxy-bicyclo(2.2.2)octane-2-carboxyl)-L-alaninyl)]amino-2,3-dihydro-1-methyl-5-phenyl-1H-1,4-benzodiazepin-2-one Following General Procedure D above using 1,8-dimethyl-6-hydroxy-bicyclo(2.2.2)octane-2-carboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 489 (M+H).

Example 1-14

Preparation of (S)-3-[(N'-(1,4-Benzodioxan-2-carboxyl)-L-alaninyl)]amino-2,3-dihydro-1-methyl-5-phenyl-1H-1,4-benzodiazepin-2-one Following General Procedure D above using 1,4-benzodioxan-2-carboxylic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 499 (M+H).

Example 1-15

Preparation of (S)-3-[(N'-(Tetrahydro-3-furoyl)-L-alaninyl)]amino-2,3-dihydro-1-methyl-5-phenyl-1H-1,4-benzodiazepin-2-one Following General Procedure D above using tetrahydro-3-furoic acid and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 435 (M+H).

Example 1-16

Preparation of (S)-3-[(N'-(3-Cyclohexenecarboxyl)-L-phenylglycinyl)]amino-2,3-dihydro-1-methyl-5-phenyl-1H-1,4-benzodiazepin-2-one Following General Procedure D above using 3-cyclohexenecarboxylic acid and (S)-3-[(L-phenylglycinyl)]amino-2,3-dihydro-1-methyl-5-phenyl-1H-1,4-benzodiazepin-2-one, the title compound was prepared. The molecular weight as determined by mass spectrometry (FD) was: 507 (M+H).

Example 1-17

Preparation of (S)-3-(N'-(Cyclopropanecarboxyl)-L-phenylglycinyl)]amino-2,3-dihydro-1-methyl-5-phenyl-1H-1,4-benzodiazepin-2-one Following General Procedure D above using cyclopropanecarboxylic acid and (S)-3-[(L-phenylglycinyl)]amino-2,3-dihydro-1-methyl-5-phenyl-1H-1,4-benzodiazepin-2-one, the title compound was prepared. The molecular weight as determined by mass spectrometry (FD) was: 467 (M+H).

Example 1-18

Preparation of (S)-3-[(N'-(3,5-Difluorobenzoyl)-L-phenylglycinyl)]amino-2,3-dihydro-1-methyl-5-phenyl-1H-1,4-benzodiazepin-2-one Following General Procedure D above using 3,5-difluorobenzoic acid and (S)-3-[(L-phenylglycinyl)]amino-2,3-dihydro-1-methyl-5-phenyl-1H-1,4-benzodiazepin-2-one, the title compound was prepared. The molecular weight as determined by mass spectrometry (FD) was: 539 (M+H).

Example 1-19

Preparation of 3-[(N'-(L-2-Pyrrolidinone-5-yl)-L-alaninyl)]amino]-2,3-dihydro-1-methyl-5-(2-pyridyl)-1H-1,4-benzodiazepin-2-one Following General Procedure C-J above using L-pyroglutamic acid and 3-[(L-alaninyl)]amino]-2,3-dihydro-1-methyl-5-(2-pyridyl)-1H-1,4-benzodiazepin-2-one, as described in Example C-AE, the title compound was prepared. The molecular weight as determined by mass spectrometry (FD) was: 448 (M+H).

Example 1-21

Preparation of 3-[(N'-(1-Phenyl-1-cyclopropanecarboxyl)-L-alaninyl)]amino]-2,3-dihydro-1-methyl-5-(2-pyridyl)-1H-1,4-benzodiazepin-2-one Following General Procedure C-J above using 1-phenyl-1-cyclopropanecarboxylic acid and 3-[(L-alaninyl)]amino]-2,3-dihydro-1-methyl-5-(2-pyridyl)-1H-1,4-benzodiazepin-2-one, as described in Example C-AE, the title compound was prepared. The molecular weight as determined by mass spectrometry (FD) was: 482 (M+H).

Example 1-22

Preparation of 3-[(N'-(1-Phenyl-1-cyclopropanecarboxyl)-L-alaninyl)]amino]-2,3-dihydro-1-(3,3-dimethyl-2-oxobutyl)-5-(2-pyridyl)-1H-1,4-benzodiazepin-2-one Following General Procedure C-J above using 1-phenyl-1-cyclopropanecarboxylic acid and 3-[(L-alaninyl)]amino]-2,3-dihydro-1-(3,3-dimethyl-2-oxobutyl)-5-(2-pyridyl)-1H-1,4-benzodiazepin-2-one, as described in Example C-AG, the title compound was prepared. The molecular weight as determined by mass spectrometry (FD) was: 566 (M+H).

Example 1-23

Preparation of 3-[(N'-(3,5-Difluorobenzoyl)-L-alaninyl)]amino]-2,3-dihydro-1-(3,3-dimethyl-2-oxobutyl)-5-(2-pyridyl)-1H-1,4-benzodiazepin-2-one Following General Procedure C-J above using 3,5-difluorobenzoic acid and 3-[(L-alaninyl)]amino]-2,3-dihydro-1-(3,3-dimethyl-2-oxobutyl)-5-(2-pyridyl)-1H-1,4-benzodiazepin-2-one, as described in Example C-AG, the title compound was prepared. The molecular weight as determined by mass spectrometry (FD) was: 561 (M+H).

Example 1-24

Preparation of 3-[(N'-(L-2-Pyrrolidinone-5-yl)-L-alaninyl)]amino]-2,3-dihydro-1-(3,3-dimethyl-2-oxobutyl)-5-(2-pyridyl)-1H-1,4-benzodiazepin-2-one Following General Procedure C-J above using L-pyroglutamic acid and 3-[(L-alaninyl)]amino]-2,3-dihydro-1-(3,3-dimethyl-2-oxobutyl)-5-(2-pyridyl)-1H-1,4-benzodiazepin-2-one, as described in Example C-AG, the title compound was prepared. The molecular weight as determined by mass spectrometry (FD) was: 533 (M+H).

Example 1-26

Preparation of 3-[(N'-(1-Phenyl-1-cyclopropanecarboxyl)-L-alaninyl)]amino]-2,3-dihydro-1-(2-N,N-diethylaminoethyl)-5-(2-pyridyl)-1H-1,4-benzodiazepin-2-one Following General Procedure C-J above using 1-phenyl-1-cyclopropanecarboxylic acid and 3-[(L-alaninyl)]amino]-2,3-dihydro-1-(2-N,N-diethylaminoethyl)-5-(2-pyridyl)-1H-1,4-benzodiazepin-2-one, as described in Example C-AF, the title compound was prepared. The molecular weight as determined by mass spectrometry (FD) was: 567 (M+H).

Example 1-27

Preparation of 3-[(N'-(4-Methylbenzoyl)-D-phenylglycinyl)]amino-2,3-dihydro-1-methyl-5-phenyl-1H-1,4-benzodiazepin-2-one Following one or more of the general procedures outlined above, using 4-methylbenzoic acid and 3-[(D-phenylglycinyl)]amino-2,3-dihydro-1-methyl-5-phenyl-1H-1,4-benzodiazepin-2-one, the title compound was prepared. The molecular weight as determined by mass spectrometry (FD) was: 517 (M+H).

Example 1-28

Preparation of 3-[(N'-(4-Methylbenzoyl)-L-alaninyl)]amino-2,3-dihydro-1-methyl-5-phenyl-1H-1,4-benzodiazepin-2-one Following one or more of the general procedures outlined above, using 4-methylbenzoylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 455 (M+H).

Example 1-30

Preparation of 3-[(N'-(2-Naphthoyl)-L-alaninyl)]amino-2,3-dihydro-1-methyl-5-phenyl-1H-1,4-benzodiazepin-2-one Following General Procedure C-A above using 2-naphthoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 491 (M+H).

Example 1-31

Preparation of 3-[(N'-(1-Naphthoyl)-L-alaninyl)]amino-2,3-dihydro-1-methyl-5-phenyl-1H-1,4-benzodiazepin-2-one Following General Procedure C-A above using 1-naphthoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: (M+H).

Example 1-32

Preparation of 3-[(N'-(5-Chloro-2-thiophenecarboxyl)-L-alaninyl)]amino-2,3-dihydro-1-methyl-5-phenyl-1H-1,4-benzodiazepin-2-one Following General Procedure C-A above using 5-chloro-2-thiophenecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 481 (M+H).

Example 1-33

Preparation of 3-[(N'-(4-Cyanobenzoyl)-L-alaninyl)] amino-2,3-dihydro-1-methyl-5-phenyl-1H-1,4-benzodiazepin-2-one Following General Procedure C-A above using 4-cyanobenzoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 466 (M+H).

Example 1-34

Preparation of 3-[(N'-(Tetrahydro-2-furoyl)-L-alaninyl)]amino-2,3-dihydro-1-methyl-5-phenyl-1H-1,4-benzodiazepin-2-one Following General Procedure C-A above using tetrahydro-2-furoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 466 (M+H).

Example 1-35

Preparation of 3-[(N'-(3,5-Difluorobenzoyl)-L-alaninyl)]amino-2,3-dihydro-1-methyl-5-phenyl-1H-1,4-benzodiazepin-2-one Following General Procedure C-A above using 3,5-difluorobenzoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 477 (M+H).

Example 1-36

Preparation of 3-[(N'-(3-Cyclohexenecarboxyl)-L-alaninyl)]amino-2,3-dihydro-1-methyl-5-phenyl-1H-1,4-benzodiazepin-2-one Following General Procedure C-A above using 3-cyclohexenecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 445 (M+H).

Example 1-37

Preparation of 3-[(N'-(1,2,3,4-Tetrahydro-2-naphthoyl)-L-alaninyl)]amino-2,3-dihydro-1-methyl-5-phenyl-1H-1,4-benzodiazepin-2-one Following General Procedure C-A above using 1,2,3,4-tetrahydro-2-naphthoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 495 (M+H).

Example 1-38

Preparation of 3-[(N'-(Cyclopentanecarboxyl)-L-alaninyl)]amino-2,3-dihydro-1-methyl-5-phenyl-1H-1,4-benzodiazepin-2-one Following General Procedure C-A above using cyclopentanecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 433 (M+H).

Example 1-39

Preparation of (S)-3-[(N'-(4-(Trifluoromethyl) cyclohexane Carboxyl)-L-alaninyl)]amino-2,3-dihydro-1-methyl-5-phenyl-1H-1,4-benzodiazepin-2-one Following General Procedure D above using trifluoromethyl)cyclohexane carboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 515 (M+H).

Example 1-40

Preparation of (S)-3-[(N'-(Bicyclo[2.2.1]heptane-2-carboxyl)-L-alaninyl)]amino-2,3-dihydro-1-methyl-5-phenyl-1H-1,4-benzodiazepin-2-one Following General Procedure D above using (bicyclo [2.2.1]heptane-2-carboxylic acid and 3-[(L-alaninyl)] amino-2,3-dihydro-1-methyl-5-phenyl-1H-1,4-benzodiazepin-2-one, as described in Example 8-B above, the title compound was prepared. The molecular weight as determined by mass spectrometry (FD) was: 459 (M+H).

Example 1-41

Preparation of (S)-3-[(N'-(Bicyclo(2.2.1)hept-5-ene-2-carboxyl)-L-alaninyl)]amino-2,3-dihydro-1-methyl-5-phenyl-1H-1,4-benzodiazepin-2-one Following General Procedure D above using bicyclo (2.2.1)hept-5-ene-2-carboxylic acid and 3-[(L-alaninyl)] amino-2,3-dihydro-1-methyl-5-phenyl-1H-1,4-benzodiazepin-2-one, as described in Example 8-B above, the title compound was prepared. The molecular weight as determined by mass spectrometry (FD) was: 457 (M+H).

Example 1-42

Preparation of (S)-3-[(N'-(2,2-Dichlorocyclopropane Carboxyl)-L-alaninyl)]amino-2,3-dihydro-1-methyl-5-phenyl-1H-1,4-benzodiazepin-2-one Following General Procedure D above using 2,2-dichlorocyclopropane carboxylic acid and 3-[(L-alaninyl)] amino-2,3-dihydro-1-methyl-5-phenyl-1H-1,4-benzodiazepin-2-one, as described in Example 8-B above, the title compound was prepared. The molecular weight as determined by mass spectrometry (FD) was: 473 (M+H).

Example 1-43

Preparation of (S)-3-[(N'-(Cycloheptanecarboxyl)-L-alaninyl)]amino-2,3-dihydro-1-methyl-5-phenyl-1H-1,4-benzodiazepin-2-one Following General Procedure D above using cycloheptanecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 461 (M+H).

Example 1-44

Preparation of (S)-3-[(N'-(1-(2,4-Dichlorophenyl)cyclopropanecarboxyl)-L-alaninyl)]amino-2,3-dihydro-1-methyl-5-phenyl-1H-1,4-benzodiazepin-2-one Following General Procedure D above using 2,4-dichlorophenyl)cyclopropanecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: (M+H).

Example 1-45

Preparation of (S)-3-[(N'-(2-Methylcyclopropanecarboxyl)-L-alaninyl)]amino-2,3-dihydro-1-methyl-5-phenyl-1H-1,4-benzodiazepin-2-one Following General Procedure D above using 2-methylcyclopropanecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 419 (M+H).

Example 1-46

Preparation of (S)-3-[(N'-(1-(4-Chlorophenyl)-1-cyclobutanecarboxyl)-L-alaninyl)]amino-2,3-dihydro-1-methyl-5-phenyl-1H-1,4-benzodiazepin-2-one Following General Procedure D above using 4-chlorophenyl)-1-cyclobutanecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 529 (M+H).

Example 1-47

Preparation of (S)-3-[(N'-(2-Biphenylcarboxyl)-L-alaninyl)]amino-2,3-dihydro-1-methyl-5-phenyl-1H-1,4-benzodiazepin-2-one Following General Procedure D above using 2-biphenylcarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 517 (M+H).

Example 1-48

Preparation of (S)-3-[(N'-(1,2-Dihydro-1-oxo-2-phenyl-4-isoquinolinecarboxyl)-L-alaninyl)]amino-2,3-dihydro-1-methyl-5-phenyl-1H-1,4-benzodiazepin-2-one Following General Procedure D above using 1,2-dihydro-1-oxo-2-phenyl-4-isoquinolinecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 584 (M+H).

Example 1-49

Preparation of (S)-3-[(N'-(Bicyclo (3.3.1)non-6-ene-3-Carboxyl)-L-alaninyl)]amino-2,3-dihydro-1-methyl-5-phenyl-1H-1,4-benzodiazepin-2-one Following General Procedure D above using bicyclo (3.3.1)non-7-ene-3-carboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 485 (M+H).

Example 1-50

Preparation of (S)-3-[(N'-(Cyclopropanecarboxyl)-L-alaninyl)]amino-2,3-dihydro-1-methyl-5-phenyl-1H-1,4-benzodiazepin-2-one Following General Procedure D above using cyclopropanecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 405 (M+H).

Example 1-51

Preparation of (S)-3-[(N'-(Tetrahydro-2-furoyl)-L-alaninyl)]amino-2,3-dihydro-1-methyl-5-phenyl-1H-1,4-benzodiazepin-2-one Following General Procedure D above using tetrahydro-2-furoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 435 (M+H).

Example 1-52

Preparation of (S)-3-[(N'-(3,5-Difluorobenzoyl)-L-alaninyl)]amino-2,3-dihydro-1-methyl-5-phenyl-1H-1,4-benzodiazepin-2-one Following General Procedure D above using 3,5-difluorobenzoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 477 (M+H).

Example 1-53

Preparation of (S)-3-[(N'-(3-Cyclohexenecarboxyl)-L-alaninyl)]amino-2,3-dihydro-1-methyl-5-phenyl-1H-1,4-benzodiazepin-2-one Following General Procedure D above using 3-cyclohexenecarboxylic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 445 (M+H).

Example 1-54

Preparation of (S)-3-[(N'-(1,2,3,4-Tetrahydro-2-naphthoyl)-L-alaninyl)]amino-2,3-dihydro-1-methyl-5-phenyl-1H-1,4-benzodiazepin-2-one Following General Procedure D above using 1,2,3,4-tetrahydro-2-naphthoic acid and (S)-3-(-L-alaninyl)amino- 2,3-dihydro-1-methyl-5-phenyl-1H-1,4-benzodiazepin-2-one, as described in Example 8-B above, the title compound was prepared. The molecular weight as determined by mass spectrometry (FD) was: 495 (M+H).

Example 1-55

Preparation of (S)-3-[(N'-(Cyclopentanecarboxyl)-L-alaninyl)]amino-2,3-dihydro-1-methyl-5-phenyl-1H-1,4-benzodiazepin-2-one Following General Procedure D above using cyclopentanecarboxylic acid and 3-[(L-alaninyl)]amino-2,3-dihydro-1-methyl-5-phenyl-11H-1,4-benzodiazepin-2-one, as described in Example 8-B above, the title compound was prepared. The molecular weight as determined by mass spectrometry (FD) was: 433 (M+H).

Example 1-56

Preparation of 5-{N'-(Tetrahydro-3-furoyl)-L-alaninyl}-amino-7-methyl-5,7-dihydro-6H-dibenz[b,d]azepin-6-one Following General Procedure C-P above using tetrahydro-3-furoic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 408 (M+H).

Example 1-57

Preparation of 5-{N'-(Cyclopropane Carboxyl)-L-alaninyl}-amino-7-methyl-5,7-dihydro-6H-dibenz[b,d]azepin-6-one Following General Procedure C-P above using cyclopropane carboxylic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 378 (M+H).

Example 1-59

Preparation of 5-{N'-(Bicyclo[2.2.1]heptane-2-carboxyl)-L-alaninyl}-amino-7-methyl-5,7-dihydro-6H-dibenz[b,d]azepin-6-one Following General Procedure C-P above using bicyclo[2.2.1]heptane-2-carboxylic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 432 (M+H).

Example 1-60

Preparation of 5-{N'-(Tetrahydro-2-furoyl)-L-alaninyl}-amino-7-methyl-5,7-dihydro-6H-dibenz[b,d]azepin-6-one Following General Procedure C-P above using tetrahydro-2-furoic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 408 (M+H).

Example 1-61

Preparation of 5-{N'-(Cyclopentanecarboxyl)-L-alaninyl}-amino-7-methyl-5,7-dihydro-6H-dibenz[b,d]azepin-6-one Following General Procedure C-P above using cyclopentanecarboxylic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 406 (M+H).

Example 1-62

Preparation of 5-{N'-(2-Thiophenecarboxyl)-L-alaninyl}-amino-7-methyl-5,7-dihydro-6H-dibenz[b,d]azepin-6-one Following General Procedure C-P above using 2-thiophenecarboxylic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 420 (M+H).

Example 2-1

Preparation of (S)-3-[(N'-(2,3-Diphenylpropionyl)-L-alaninyl)]amino-2,3-dihydro-1-methyl-5-phenyl-1H-1,4-benzodiazepin-2-one Following General Procedure C-B above using 2,3-diphenylpropionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 545 (M+H).

Example 2-2

Preparation of (S)-3-[(N'-(2-Phenoxypropionyl)-L-alaninyl)]amino-2,3-dihydro-1-methyl-5-phenyl-1H-1,4-benzodiazepin-2-one Following General Procedure C-B above using 2-phenoxypropionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 485 (M+H).

Example 2-4

Preparation of (S)-3-[(N'-(2-Isopropyl-2-phenylacetyl)-L-alaninyl)]amino-2,3-dihydro-1-methyl-5-phenyl-1H-1,4-benzodiazepin-2-one Following General Procedure C-B above using 2-isopropyl-2-phenylacetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 497 (M+H).

Example 2-5

Preparation of (S)-3-[(N'-(2-Ethylhexanoyl)-L-alaninyl)]amino-2,3-dihydro-1-methyl-5-phenyl-1H-1,4-benzodiazepin-2-one Following General Procedure C-B above using 2-ethylhexanoic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 463 (M+H).

Example 2-6

Preparation of (S)-3-[(N'-(2-Methylbutyryl)-L-alaninyl)]amino-2,3-dihydro-1-methyl-5-phenyl-1H-1,4-benzodiazepin-2-one Following General Procedure C-B above using 2-methylbutyric acid and 3-[(L-alaninyl)]amino-2,3- dihydro-1-methyl-5-phenyl-1H-1,4-benzodiazepin-2-one, as described in Example 8-B above, the title compound was prepared. The molecular weight as determined by mass spectrometry (FD) was: 421 (M+H).

Example 2-7

Preparation of (S)-3-[(N'-(2-Methyl-4,4,4-trifluorobutyryl)-L-alaninyl)]amino-2,3-dihydro-1-methyl-5-phenyl-1H-1,4-benzodiazepin-2-one Following General Procedure C-B above using 2-methyl-4,4,4-trifluorobutyric acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 475 (M+H).

Example 2-8

Preparation of (S)-3-[(N'-(Diphenylacetyl)-L-phenylglycinyl)]amino-2,3-dihydro-1-methyl-5-phenyl-1H-1,4-benzodiazepin-2-one Following General Procedure D above using diphenylacetic acid and 3-[(L-phenylglycinyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 593 (M+H).

Example 2-9

Preparation of (S)-3-[(N'-(4-Chloro-α-methylphenylacetyl)-L-alaninyl)]amino-2,3-dihydro-1-methyl-5-phenyl-1H-1,4-benzodiazepin-2-one Following General Procedure D above using 4-chloro-α-methylphenylacetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 503 (M+H).

Example 2-10

Preparation of (S)-3-[(N'-(4-Chloro-α,α-dimethylphenylacetyl)-L-alaninyl)]amino-2,3-dihydro-1-methyl-5-phenyl-1H-1,4-benzodiazepin-2-one Following General Procedure D above using 4-chloro-α,α-dimethylphenylacetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 517 (M+H).

Example 2-11

Preparation of (S)-3-[(N'-((S)-(+)-2-Hydroxy-2-phenylpropionyl)-L-alaninyl)]amino-2,3-dihydro-1-methyl-5-phenyl-1H-1,4-benzodiazepin-2-one Following General Procedure D above using (S)-(+)-2-hydroxy-2-phenylpropionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 485 (M+H).

Example 2-12

Preparation of (S)-3-[(N'-(α-Hydroxy-diphenylacetyl)-L-alaninyl)]amino-2,3-dihydro-1-methyl-5-(2-pyridyl)-1H-1,4-benzodiazepin-2-one Following one or more of the general procedures outlined above, using α-hydroxy-diphenylacetic acid and (S)-3-(L-alaninyl)amino-2,3-dihydro-1-methyl-5-(2-pyridyl)-1H-1,4-benzodiazepin-2-one, as described in Example C-AE, the title compound was prepared. The molecular weight as determined by mass spectrometry (FD) was: 548 (M+H).

Example 2-17

Preparation of (S)-3-[(N'-(α-Hydroxy-diphenylacetyl)-L-alaninyl)]amino-2,3-dihydro-1-2-(diethylamino)ethyl-5-(2-pyridyl)-1H-1,4-benzodiazepin-2-one Following one or more of the general procedures outlined above, using α-hydroxy-diphenylacetic acid and (S)-3-(L-alaninyl)amino-2,3-dihydro-1-2-(diethylamino)ethyl-5-(2-pyridyl)-1H-1,4-benzodiazepin-2-one, the title compound was prepared. The molecular weight as determined by mass spectrometry (FD) was: 633 (M+H).

Example 2-18

Preparation of 3-[N'-(3,5-Difluorophenyl-α-hydroxy-α-methylacetyl)-L-alaninyl]-amino-2,3-dihydro-1-methyl-5-(2-fluorophenyl)-1H-1,4-Benzodiazepin-2-one A. Preparation of 3,5-Difluorophenyl-α-hydroxy-α-methylacetic Acid The compound was prepared according to the general procedure of Stiller et al., *J. Med. Chem.*, 15:1029 (1972). A solution of alpha-keto-3,5-difluorophenylacetic acid (prepared according to Middleton et al., *J. Org Chem.*, 45:2883 (1980)) in diethyl ether was cooled to 0° C. Methylmagnesium chloride (4.7 eq., 3.0 M solution in THF) was added dropwise via syringe pump at a rate of 10 ml/min so that the internal temperature did not exceed 5.5° C. The cooling bath was removed and stirring continued at ambient for 1.5 hours. After approximately 30 minutes, the clumps of solid dissolved. The mixture was poured onto ice and acidified with 1N HCl. The aqueous layer was extracted thrice with ethyl acetate. The combined organics were washed with 5% $NaHSO_3$, water and brine. The organic layer was dried over sodium sulfate, filtered, and concentrated to a yellowish solid. The solid was recrystallized from dichloromethane, giving a white crystalline solid having a melting point of 102.5–103.2 C. $C_9H_8F_2O_3$ (MW 202.17); mass spectroscopy found (M–H) 201.2. Anal calcd for $C_9H_8F_2O_3$: C, 53.47, H, 3.99. Found: C, 53.76; H, 3.82.

B. Preparation of the Title Compound

Following General Procedure D above using 3,5-difluorophenyl-α-hydroxy-α-methylacetic acid and 3-(L-alaninyl)-amino-2,3-dihydro-1-methyl-5-(2-fluorophenyl)-1H-1,4-Benzodiazepin-2-one (Example 8-b), the title compound was prepared. $^1H$ NMR ($CDCl_3$, 300 MHz) δ=1.43 (3H, d, J=7.1 Hz), 1.79 (3H, s), 3.47 (3H, s), 4.15 (1H, s), 4.58 (1H, p, J=7.3 Hz), 5.45 (1H, d, J=8.0 Hz), 6.70 (1H, m), 7.14–7.27 (3H, m), 7.32–7.47 (6H, m), 7.55–7.63 (3H, m), 7.78 (1H, d, J=7.8 Hz). HRMS calc for $C_{28}H_{27}N_4O_4F_2$ 521.2000 ($MH^+$), Found: 521.2.

Example 2-19

Preparation of 3-[N'-(3,5-Difluorophenyl-α-hydroxy-α-methylacetyl)-L-alaninyl]-amino-2,3-dihydro-1-methyl-5-(2-fluorophenyl)-1H-1,4-Benzodiazepin-2-one Following General Procedure D above using 3,5-difluorophenyl-α-hydroxy-α-methylacetic acid (described above in Example 2-18) and 3-(L-alaninyl)-amino-2,3-dihydro-1-methyl-5-(2-fluorophenyl)-1H-1,4-Benzodiazepin-2-one (Example 8-b), the title compound was prepared.

$^1$H NMR (CDCl$_3$, 300 MHz) δ=1.48 (3H, d, J=7.0 Hz), 1.78 (3H, s), 3.45 (3H, s), 3.86 (1H, s), 4.62 (1H, p, J=7.1 Hz), 5.42 (1H, d, J=7.6 Hz), 6.69 (1H, m), 7.13–7.59 (12H, m), 7.67 (1H, d, J=7.6 Hz). HRMS calc for C28H27N4O4F2 521.2000 (MH$^+$), Found: 521.2.

Example 2-20

Preparation of 3-[(N'-(Diphenylacetyl)-L-alaninyl)]amino-2,3-dihydro-1-methyl-5-phenyl-1H-1,4-benzodiazepin-2-one Following General Procedure C-A above using diphenylacetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 531 (M+H).

Example 2-21

Preparation of 3-[(N'-(Acetyl)-L-alaninyl)]amino-2,3-dihydro-1-methyl-5-phenyl-1H-1,4-benzodiazepin-2-one Following General Procedure C-A above using acetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 379 (M+H).

Example 2-22

Preparation of (S)-3-[(N'-(2-Methylvaleryl)-L-alaninyl)]amino-2,3-dihydro-1-methyl-5-phenyl-1H-1,4-benzodiazepin-2-one Following General Procedure D above using 2-methylvaleric acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 435 (M+H).

Example 2-23

Preparation of (S)-3-[(N'-(α-(Hydroxymethyl)phenylacetyl)-L-alaninyl)]amino-2,3-dihydro-1-methyl-5-phenyl-1H-1,4-benzodiazepin-2-one Following General Procedure D above using α-(hydroxymethyl)phenylacetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 485 (M+H).

Example 2-24

Preparation of (S)-3-[(N'-(2-Ethylbutyryl)-L-alaninyl)]amino-2,3-dihydro-1-methyl-5-phenyl-1H-1,4-benzodiazepin-2-one Following General Procedure D above using 2-ethylbutyric acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 435 (M+H).

Example 2-25

Preparation of (S)-3-[(N'-(Pivalyl)-L-alaninyl)]amino-2,3-dihydro-1-methyl-5-phenyl-1H-1,4-benzodiazepin-2-one Following General Procedure D above using pivalic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 421 (M+H).

Example 2-26

Preparation of (S)-3-[(N'-(Diphenylacetyl)-L-alaninyl)]amino-2,3-dihydro-1-methyl-5-phenyl-1H-1,4-benzodiazepin-2-one Following General Procedure D above using diphenylacetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 531 (M+H).

Example 2-27

Preparation of (S)-3-[(N'-(Acetyl)-L-phenylglycinyl)]amino-2,3-dihydro-1-methyl-5-phenyl-1H-1,4-benzodiazepin-2-one Following General Procedure D above using acetic acid and 3-[(L-phenylglycinyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 441 (M+H).

Example 2-28

Preparation of 3-[N'-(2-Thioacetyl-3-methyl-butanoyl)-L-alaninyl]-amino-2,3-dihydro-1-methyl-5-phenyl-1H-1,4-benzodiazepin-2-one Following General Procedure D above using 2-thioacetyl-3-methyl butanoic acid (Coric et al., *J. Med. Chem.* 39, 1210 (1996)) and 3-(L-alaninyl)-amino-2,3-dihydro-1-methyl-5-phenyl-1H-1,4-benzodiazepin-2-one, as described in Example 8-B, the title compound was prepared.

$^1$H NMR (CDCl$_3$, 300 MHz) δ 1.01 (6H, d, J=6.8 Hz), 1.04 (3H, d, J=7.2 Hz), 1.07 (3H, d, J=6.8 Hz), 1.45 (3H, d, J=6.8 Hz), 1.49 (3H, d, J=7.2 Hz), 2.35 (2H, m), 2.38 (3H, s), 2.40 (3H, s), 3.45 (3H, s), 3.46 (3H, s), 3.84 (1H, d, J=7.9 Hz), 3.85 (1H, d, J=7.9 Hz), 4.63 (2H, m), 5.47 (1H, d, J=7.9 Hz), 5.48 (1H, d, J=7.9 Hz), 6.73 (1H, d, J=8.4 Hz), 6.80 (1H, d, J=7.5 Hz), 7.20–7.62 (20H, m). MS calcd for C26H31N4O4S 495.21 (MH$^+$), found 495.2.

Example 2-29

Preparation of 3-[N'-(2-Mercapto-3-methyl-butanoyl)-L-alaninyl]-amino-2,3-dihydro-methyl-5-phenyl-1H-1,4-benzodiazepin-2-one A solution of 3-[N'-(2-thioacetyl-3-methyl-butanoyl)-L-alaninyl]-amino-2,3-dihydro-1-methyl-5-phenyl-1H-1,4- benzodiazepin-2-one as prepared in Example 2-28 in degassed methanol was treated with degassed 1N NaOH (3 equiv.). After stirring at ambient temperature for 3 hours, the reaction was acidified to pH 1 by adding 1N HCl. The solution was concentrated in vacuo; the residue was partitioned between ethyl acetate and brine. The organic phase was dried over sodium sulfate, filtered, and concentrated to afford the title compound.

$^1$H NMR (CDCl$_3$, 300 MHz) δ 0.99 (3H, d, J=6.0 Hz), 1.01 (3H, d, J=6.8 Hz), 1.05 (3H, d, J=6.4 Hz), 1.06 (3H, d, J=6.8 Hz), 1.51 (6H, d, J=6.8 Hz), 1.90 (1H, d, J=8.8 Hz), 1.91 (1H, d, J=8.8 Hz), 2.31 (2H, o, J=6.8 Hz), 3.17 (1H, dd, J=9.2 Hz), 3.22 (1H, dd, H=6.4, 8.8 Hz), 3.48 (6H, s), 4.67 (2H, p, J=6.8 Hz), 5.48 (1H, d, J=7.6 Hz), 5.49 (1H, d, J=7.6 Hz), 7.04 (1H, d, J=7.2 Hz), 7.09 (1H, d, J=7.2 Hz), 7.23–7.27 (2H, m), 7.34–7.40 (8H, m), 7.45–7.49 (2H, m), 7.58–7.64 (8H, m). MS calcd for C24H29N4O3S 453.20 (MH$^+$), found 453.1.

Example 2-30

Preparation of 5-{N'-(2-Phenylpropionyl)-L-alaninyl}-amino-7-methyl-5,7-dihydro-6H-dibenz[b,d]azepin-6-one Following General Procedure C-P above using 2-phenylpropionic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 442 (M+H).

Example 2-31

Preparation of 5-{N'-(2-Methylhexanoyl)-L-alaninyl}-amino-7-methyl-5,7-dihydro-6H-dibenz[b,d]azepin-6-one Following General Procedure C-P above using 2-methylhexanoic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 422 (M+H).

Example 2-32

Preparation of 5-{N'-(Diphenylacetyl)-L-alaninyl}-amino-7-methyl-5,7-dihydro-6H-dibenz[b,d]azepin-6-one Following General Procedure C-P above using diphenylacetic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 504 (M+H).

Example 2-33

Preparation of 5-{N'-((S)-(+)-2-Hydroxy-2-phenylpropionyl)-L-alaninyl}-amino-7-methyl-5,7-dihydro-6H-dibenz[b,d]azepin-6-one Following one or more of the general procedures outlined above, using (S)-(+)-2-hydroxy-2-phenylpropionic acid and 5-(L-alaninyl)-amino-7-methyl-5,7-dihydro-6H-dibenz[b,d] azepin-6-one, as described in Example 7-B, the title compound was prepared. The molecular weight as determined by mass spectrometry (FD) was: 458 (M+H).

Example 2-34

Preparation of 5-{N'-((R)-(−)-2-Hydroxy-2-phenylpropionyl)-L-alaninyl}-amino-7-methyl-5,7-dihydro-6H-dibenz[b,d]azepin-6-one Following one or more of the general procedures outlined above, using (R)-(−)-2-hydroxy-2-phenylpropionic acid and 5-(L-alaninyl)-amino-7-methyl-5,7-dihydro-6H-dibenz[b,d] azepin-6-one, as described in Example 7-B, the title compound was prepared. The molecular weight as determined by mass spectrometry (FD) was: 458 (M+H).

Example 2-35

Preparation of 5-{N'-(2-Hydroxy-2-methylpropionyl)-L-alaninyl}-amino-7-methyl-5,7-dihydro-6H-dibenz[b,d]azepin-6-one Following General procedure D above using 2-methyllactic acid (Aldrich) and 5-(L-alaninyl)-amino-7-methyl-5,7-dihydro-6H-dibenz[b,d]azepin-6-one, as described in Example 7-B, the title compound was prepared. The product was purified by flash chromatography CHCl$_3$/MeOH (98:2) to yield the title compound.

C22H$_{25}$N3O4 (MW=395.457); mass spectroscopy (MH$^+$) 396. Anal. Calcd for C22H$_{25}$N3O4; C, 66.06; H, 6.25; N, 10.50. Found: C, 65.91; H, 6.30; N, 10.52.

Example 2-36

Preparation of 5-{N'-(2-Hydroxy-2-methylbutanoyl)-L-alaninyl}-amino-7-methyl-5,7-dihydro-6H-dibenz[b,d]azepin-6one Following General Procedure D above using 5-(S)-[L-alaninyl]-amino-7-methyl-5,7-dihydro-6H-dibenz[b,d] azepin-6-one, as described in Example 7-B, and 2-hydroxy-2-methylbutyric acid (Aldrich) the title compound was prepared. The product was purified by flash chromatography (CHCl$_3$/MeOH (98:2) yielding the title compound.

C23H27N3O4 (MW=409–483); mass spectroscopy (MH$^+$) 410. Anal. Calcd for C23H27N3O4; C, 67.46; H, 6.65; N, 10.26. Found: C, 67.63; H, 6.64; N, 10.31.

Example 2-37

Preparation of 5-(S)-[N'-(2-Thioacetyl-3-methyl-butanoyl)-L-alaninyl]-amino-7-methyl-5,7-dihydro-6H-dibenz[b,d]azepin-6one Following General Procedure D, using 2-thioacetyl-3-methylbutanoic acid and 5-(L-alaninyl)-amino-7-methyl-5,7-dihydro-6H-dibenz[b,d]azepin-6-one, as described in Example 7-B, the title compound was prepared.

$^1$H NMR (CDCl$_3$, 300 MHz) δ 0.86–0.96 (12H, m), 1.25 (3H, d, J=7.2 Hz), 2.05 (2H, m), 2.33 (3H, s), 2.35 (3H, s), 3.25 (6H, s), 4.02 (2H, m), 4.56 (2H, m), 5.09 (1H, d, J=7.9 Hz), 5.12 (1H, d, H=7.9 Hz), 7.39–7.70 (16H, m), 8.48 (1H, d, J=7.2 Hz), 8.53 (1H, d, J=7.5 Hz), 8.56 (2H, d, J=8.3 Hz). MS calcd for C$_{25}$H$_{30}$N$_3$O$_4$S 468.20 (MH$^+$), found 468.2.

Example 2-38

Preparation of 5-{N'-(Acetyl)-L-alaninyl}-amino-7-methyl-5,7-dihydro-6H-dibenz[b,d]azepin-6-one Following General Procedure C-P using acetic acid and 5-(L-alaninyl)-amino-7-methyl-5,7-dihydro-6H-dibenz[b,d] azepin-6-one, as described in Example 7-B, the title com-

Example 2-39

Preparation of 5-(S)-[N'-(2-Mercapto-3-methylbutanoyl)-L-alaninyl]-amino-7-methyl-5,7-dihydro-6H-dibenz[b,d]azepin-6-one A solution of 5-(S)-[N'-(2-thioacetyl-3-methyl-butanoyl)-L-alaninyl]-amino-7-methyl-5,7-dihydro-6H-dibenz[b,d]azepin-6-one (Example 2-37) in degassed methanol was treated with degassed 1N NaOH (3 equiv.). After stirring at ambient temperature for 3 hours, the reaction was acidified to pH 1 by adding 1N HCl. The solution was concentrated in vacuo; the residue was partitioned between ethyl acetate and brine. The organic phase was dried over sodium sulfate, filtered, and concentrated to afford the title compound.

$^1$H NMR (CDCl$_3$, 400 MHz) δ 0.98 (6H, d, J=6.8 Hz), 1.03 (6H, d, J=6.8 Hz), 1.45 (3H, d, J=7.6 Hz), 1.46 (3H, d, J=6.8 Hz), 1.88 (1H, d, J=8.8 Hz), 1.89 (1H, d, J=8.8 Hz), 2.29 (2H, m), 3.15 (1H, dd, J=6.4, 8.8 Hz), 3.18 (1H, dd, J=6.4, 8.8 Hz), 3.36 (6H, s), 4.71 (2H, m), 5.27 (2H, d, J=6.8 Hz), 6.95 (1H, d, J=7.2 Hz), 7.02 (1H, d, J=7.2 Hz), 7.30–7.67 (18H, m). MS calcd for C23H28N3O3S 426.18 (MH$^+$), found 426.1.

Example 3-1

Preparation of (S)-3-[(N'-(trans-Cinnamyl)-L-alaninyl)]amino-2,3-dihydro-1-methyl-5-phenyl-1H-1,4-benzodiazepin-2-one Following General Procedure D above using trans-cinnamic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 467 (M+H).

Example 3-2

Preparation of 3-[(N'-(trans-Cinnamyl)-L-alaninyl)]amino]-2,3-dihydro-1-methyl-5-(2-pyridyl)-1H-1,4-benzodiazepin-2-one Following General Procedure C-J above using trans-cinnamic acid and 3-[(N'-(trans-cinnamyl)-L-alaninyl)]amino]-2,3-dihydro-1-methyl-5-(2-pyridyl)-1H-1,4-benzodiazepin-2-one, as described in Example C-AE, the title compound was prepared. The molecular weight as determined by mass spectrometry (FD) was: 468 (M+H).

Example 3-5

Preparation of 5-{N'-(trans-Cinnamyl)-L-alaninyl}-amino-7-methyl-5,7-dihydro-6H-dibenz[b,d]azepin-6-one Following General Procedure C-P above using trans-cinnamic acid and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 440 (M+H).

Example 4-1

Preparation of (S)-3-[(N'-(2-Phenoxybutyryl)-L-alaninyl)]amino-2,3-dihydro-1-methyl-5-phenyl-1H-1,4-benzodiazepin-2-one Following General Procedure C-B above using 2-phenoxybutyric acid and 3-[(L-alaninyl)]amino-2,3dihydro-1-methyl-5-phenyl-1H-1,4-benzodiazepin-2-one, as described in Example 8-B above, the title compound was prepared. The molecular weight as determined by mass spectrometry (FD) was: 499 (M+H).

Example 4-2

Preparation of (S)-3-[(N'-((R,S)-(–)-α-Methoxyphenylacetyl)-L-alaninyl)]amino-2,3-dihydro-1-methyl-5-phenyl-1H-1,4-benzodiazepin-2-one Following General Procedure C-B above using (R,S)-(–)-α-methoxyphenylacetic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 485 (M+H).

Example 4-3

Preparation of (S)-3-[(N'-(2-(4-Chlorophenoxy)-2-methylpropionyl)-L-alaninyl)]amino-2,3-dihydro-1-methyl-5-phenyl-1H-1,4-benzodiazepin-2-one Following General Procedure C-B above using 2-(4-chlorophenoxy)-2-methylpropionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 533 (M+H).

Example 4-4

Preparation of (S)-3-[(N'-((R,S)-2-Phenoxypropionyl)-L-alaninyl)]amino-2,3-dihydro-1-methyl-5-phenyl-1H-1,4-benzodiazepin-2-one Following General Procedure C-B above using (R,S)-2-phenoxypropionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 485 (M+H).

Example 4-5

Preparation of 3-[N'-(3,5-Difluorophenyl-α-methoxyacetyl)-L-alaninyl]-amino-2,3-dihydro-1-methyl-5-phenyl-1H-1,4-Benzodiazepin-2-one A. Preparation of 3,5-Difluorophenyl-α-methoxyacetic Acid The title compound was prepared according to the general procedure in Reeve, et al, $_{J.A.C.S.}$, 83 :2755 (1961). A solution of 3,5-difluorobenzaldehyde (Aldrich) and bromoform (1.2 eq.) In methanol was cooled to –5° C. and treated dropwise with methanolic KOH. The reaction temperature was held below 6 C during the addition. The mixture was slowly warmed to room temperature and stirred overnight. The suspension was diluted with water and 50% saturated aqueous brine. The mixture was extracted with ether, and the aqueous layer was acidified to a pH around 3.5 and extracted with ether. The latter organic phase was dried over sodium sulfate, filtered and concentrated. The crude acid was purified via flash chromatography eluting with 1:4:95 acetic acid/methanol/methylene chloride to give a white solid. $^1$H NMR (300 MHz, CDCl$_3$) δ 11.36 (1H, bs), 7.05 (1H, m), 6.81 (2H, tt, J=2.4, 8.8 Hz), 4.77 (1H, s), 3.47 (3H, s)/C9H8F2O3 (MW=202.17); mass spectroscopy—202.

B. Following General Procedure D above using 3,5-difluorophenyl-α-methoxyacetic acid and 3-[(L-alaninyl)]amino-2,3-dihydro-1-methyl-5-phenyl-1H-1,4-benzodiazepin-2-one, as described in Example 8-B above, the title compound was prepared. Anal. Calcd for $C_{28}H_{28}F_2N_4O_4$; C, 64.61; H, 5.03; N, 10.76. Found: C, 64.36; H, 5.23; N, 10.53. MS calcd for $C_{28}H_{28}F_2N_4O_4$ 520.5, found 520.0.

Example 4-6

Preparation of 3-[N'-(3,5-Difluorophenyl-α-methoxyacetyl)-L-alaninyl]-amino-2,3-dihydro-1-methyl-5-phenyl-1H-1,4-benzodiazepin-2-one Following General Procedure D above using 3,5-difluorophenyl-α-methoxyacetic acid (as described in Example 4-5) and 3-[(L-alaninyl)]amino-2,3-dihydro-1-methyl-5-phenyl-1H-1,4-benzodiazepin-2-one, as described in Example 8-B above, the title compound was prepared. Anal. Calcd for $C_{28}H_{28}F_2N_4O_4$; C, 64.61; H, 5.03; N, 10.76. Found: C, 64.85; H, 5.18; N, 10.76. MS calcd for $C_{28}H_{28}F_2N_4O_4$ 520.5, found 519.9.

Example 4-7

Preparation of 3-[(N'-(2-(4-Hydroxyphenoxy)propionyl)-L-alaninyl)]amino-2,3-dihydro-1-methyl-5-phenyl-1H-1,4-benzodiazepin-2-one Following General Procedure D above using 2-(4-hydroxyphenoxy)propionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 501 (M+H).

Example 4-8

Preparation of (S)-3-[(N'-(2-(4-Trifluorophenyoxy)propionyl)-L-alaninyl)]amino-2,3-dihydro-1-methyl-5-phenyl-1H-1,4-benzodiazepin-2-one Following one or more of the general procedures outlined above, using 2-(4-trifluorophenyoxy)propionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 469 (M+H).

Example 4-9

Preparation of (S)-3-[(N'-(2-(4-Biphenylyloxy)propionyl)-L-alaninyl)]amino-2,3-dihydro-1-methyl-5-phenyl-1H-1,4-benzodiazepin-2-one Following General Procedure D above using 2-(4-biphenylyloxy)propionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 561 (M+H).

Example 4-15

Preparation of 3-[(N'-(α-Methoxyphenylacetyl)-L-alaninyl)]amino]-2,3-dihydro-1-(2-N,N-diethylaminoethyl)-5-(2-pyridyl)-1H-1,4-benzodiazepin-2-one Following General Procedure C-J above using α-methoxyphenylacetic acid and 3-(L-alaninyl)amino]-2,3-dihydro-1-(2-N,N-diethylaminoethyl)-5-(2-pyridyl)-1H-1,4-benzodiazepin-2-one, as described in Example C-AF, the title compound was prepared. The molecular weight as determined by mass spectrometry (FD) was: 571 (M+H).

Example 4-16

Preparation of (S)-3-[(N'-(2-(4-Cyanophenoxy)-2-methylpropionyl)-L-alaninyl)]amino-2,3-dihydro-1-methyl-5-phenyl-1H-1,4-benzodiazepin-2-one Following General Procedure D above using 2-(4-cyanophenoxy)-2-methylpropionic acid and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 524 (M+H).

General Procedure 5-A1 for Urea Preparation

In a round bottom flask was added an amine (1.0 eq.) in THF or $CH_2Cl_2$ followed by an isocyanate (1.0 eq.). The reaction mixture was allowed to stir 2–20 hours at room temperature under an atmosphere of nitrogen. The mixture was diluted with EtOAc or $CH_2Cl_2$ and washed with saturated $NaHCO_3$ (1×5mL), $H_2O$ (1×5 mL), and brine and dried over $MgSO_4$. The drying agent was removed by filtration and the filtrate was concentrated in vacuo. The residue was either purified by trituration or silica gel flash chromatography.

General Procedure (5-B1)—Urea Preparation 5-(S)-(L-alaninyl)-amino-7-methyl-5,7-dihydro-6H-dibenz[b,d]azepin-6-one hydrochloride (1.0 eq) methylene chloride ($CH_2Cl_2$), triethylamine (1.5 eq), and a suitable isocyanate (4 eq) are combined in a brown glass vial and placed on an orbital shaker for 5–48 hours. At this time aminomethylated polystyrene resin (Aldrich) (6 eq) is added and the mixture is shaken for an additional 5–24 hours. The reaction mixture is then filtered, the flask washed with an additional 15 mL CH2Cl2, and the filtrate removed in vacuo. The remaining solid is then purified by passing through a small silica gel plug with ethyl acetate (EtOAc). The solvent is removed in vacuo to yield the product as a white solid. The product is then analyzed by reverse phase HPLC (Waters C18 mBondapak 3.9×300mm column, eluent: 30% CH3CN in 0.1% aqueous triflouroacetic acid, UV detection: 233 nm). Ionspray-MS is also used to analyze the products.

General Procedure (5-C1)—Urea Preparation

A solution of 5-(S)-[L-alaninyl]-amino-7-methyl-5,7-dihydro-6H-dibenz[b,d]azepin-6-one hydrochloride (Example 7B) (1.0 eq) in dichloromethane is stirred at 0° C. with aqueous saturated sodium bicarbonate solution. After 15 minutes, the stirring is stopped and the layers allowed to separate. A phosgene solution (20% in toluene, Aldrich, 2.0 eq) is added to the organic layer, and stirring is resumed. After 15 additional minutes of stirring at 0° C., the layers are separated, and the organic layer is washed with aqueous saturated sodium bicarbonate solution, dried over anhydrous sodium sulfate and the solvents removed in vacuo to yield a colorless oil. This oil is diluted with dichloromethane, and transferred to a brown glass vial. A suitable amine (4 eq) is added, and the vial is placed on an orbital shaker, and shaken for 3–28 hours. At this time, aminomethylated polystyrene resin (6 eq, Aldrich) is added, and shaking continued for 4–28 hours. The reaction mixture is filtered through a sintered glass funnel, the solvents removed in vacuo to yield the product as a white solid. The product is characterized by reverse phase HPLC (Waters 3.9×300 mBondapak column, eluent: 30% acetonitrile in 0.1% aqueous triflouroacetic acid buffer, monitored by UV detection @ 233 nm) and IEX-MS.

General Procedure (5-D1)—Urea Preparation

A solution of 5-(S)-[L-alaninyl]-amino-7-methyl-5,7-dihydro-6H-dibenz[b,d]azepin-6-one hydrochloride (Example 7B) (1.0 eq) in dichloromethane is stirred at 0° C. with aqueous saturated sodium bicarbonate solution. After 15 minutes, the stirring is stopped and the layers allowed to separate. A phosgene solution (20% in toluene, Aldrich, 2.0 eq) is added to the organic layer, and stirring is resumed. After 15 additional minutes of stirring at 0° C., the layers are separated, and the organic layer is washed with aqueous saturated sodium bicarbonate solution, dried over anhydrous sodium sulfate and the solvents removed in vacuo to yield a colorless oil. This oil is diluted with dichloromethane, and a suitable amine is added (1.5–4 eq). The reaction mixture is stirred for 17 hours, at which time the reaction mixture is washed with 0.1N HCl. The organic layer is dried over anhydrous sodium sulfate, and the solvents removed in vacuo. Purification by chromatography provides the product as a white solid.

Example 5-1

Preparation of (S)-3-[(N'-((trans-2-Phenylcyclopropyl)ureylenyl)-L-alaninyl)]amino-2,3-dihydro-1-methyl-5-phenyl-1H-1,4-benzodiazepin-2-one Following General Procedure (5-A1) using trans-2-phenylcyclopropyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 495 (M+H).

Example 5-2

Preparation of (S)-3-[(N'-((3,4-Dichlorophenyl)aminocarbonyl)-L-alaninyl]amino-2,3-dihydro-1-methyl-5-phenyl-1H-1,4-benzodiazepin-2-one Following General Procedure (5-A1) using 3,4-dichlorophenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 523 (M+H).

Example 5-3

Preparation of (S)-3-[(N'-((2-Propenyl)aminocarbonyl)-]amino-2,3-dihydro-1-methyl-5-phenyl-1H-1,4-benzodiazepin-2-one Following General Procedure (5-A1) using 2-propenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: (M+H).

Example 5-4

Preparation of (S)-3-[(N'-((R)-(–)-1-(1-Naphthyl)ethyl)aminocarbonyl)-L-alaninyl]amino-2,3-dihydro-1-methyl-5-phenyl-1H-1,4-benzodiazepin-2-one Following General Procedure (5-A1) using (R)-(–)-1-(1-naphthyl)ethyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 533 (M+H).

Example 5-5

Preparation of (S)-3-[(N'-((2,6-Diisopropylphenyl)aminocarbonyl)-L-alaninyl-]amino-2,3-dihydro-1-methyl-5-phenyl-1H-1,4-benzodiazepin-2-one Following General Procedure (5-A1) using 2,6-diisopropylphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 539 (M+H).

Example 5-6

Preparation of (S)-3-[(N'-((3-[(Trifluoromethyl)phenyl)aminocarbonyl)-L-alaninyl)]amino-2,3-dihydro-1-methyl-5-phenyl-1H-1,4-benzodiazepin-2-one Following General Procedure (5-A1) using 3-[(trifluoromethyl)phenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 523 (M+H).

Example 5-7

Preparation of (S)-3-[(N'-((Phenyl)aminocarbonyl)-L-alaninyl)]amino-2,3-dihydro-1-methyl-5-phenyl-1H-1,4-benzodiazepin-2-one Following General Procedure (5-A1) using phenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 455 (M+H).

Example 5-8

Preparation of (S)-3-[(N'-((4-Ethoxycarbonylphenyl)aminocarbonyl)-L-alaninyl)]amino-2,3-dihydro-1-methyl-5-phenyl-1H-1,4-benzodiazepin-2-one Following General Procedure (5-A1) using 4-ethoxycarbonylphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 527 (M+H).

Example 5-9

Preparation of (S)-3-[(N'-((2-Bromophenyl)aminocarbonyl)-L-alaninyl)]amino-2,3-dihydro-1-methyl-5-phenyl-1H-1,4-benzodiazepin-2-one Following General Procedure (5-A1) using 2-bromophenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 534 (M+H).

Example 5-10

Preparation of (S)-3-[(N'-((o-Tolyl)aminocarbonyl)-L-alaninyl)]amino-2,3-dihydro-1-methyl-5-phenyl-1H-1,4-benzodiazepin-2-one Following General Procedure (5-A1) using o-tolyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 469 (M+H).

Example 5-11

Preparation of (S)-3-[(N'-((2-Ethyl-6-methylphenyl)aminocarbonyl)-L-alaninyl)]amino-2,3-dihydro-1-methyl-5-phenyl-1H-1,4-benzodiazepin-2-one Following General Procedure (5-A1) using 2-ethyl-6-methylphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 497 (M+H).

Example 5-12

Preparation of (S)-3-[(N'-((2-Fluorophenyl)aminocarbonyl)-L-alaninyl)]amino-2,3-dihydro-1-methyl-5-phenyl-1H-1,4-benzodiazepin-2-one Following General Procedure (5-A1) using 2-fluorophenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 473 (M+H).

Example 5-13

Preparation of (S)-3-[(N'-((2,4-Difluorophenyl)aminocarbonyl)-L-alaninyl)]amino-2,3-dihydro-1-methyl-5-phenyl-1H-1,4-benzodiazepin-2-one Following General Procedure (5-A1) using 2,4-difluorophenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 491 (M+H).

Example 5-14

Preparation of (S)-3-[(N'-((2-Ethoxyphenyl)aminocarbonyl)-L-alaninyl)]amino-2,3-dihydro-1-methyl-5-phenyl-1H-1,4-benzodiazepin-2-one Following General Procedure (5-A1) using 2-ethoxyphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 499 (M+H).

Example 5-15

Preparation of (S)-3-[(N'-((3-Acetylphenyl)aminocarbonyl)-L-alaninyl-2,3-dihydro-1-methyl-5-phenyl-1H-1,4-benzodiazepin-2-one Following General Procedure (5-A1) using 3-acetylphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 497 (M+H).

Example 5-16

Preparation of (S)-3-[(N'-((3-[(Cyano)phenyl)aminocarbonyl)-L-alaninyl)]amino-2,3-dihydro-1-methyl-5-phenyl-1H-1,4-benzodiazepin-2-one Following General Procedure (5-A1) using 3-[(cyano)phenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 501 (M+H).

Example 5-18

Preparation of (S)-3-[(N'-((Phenethyl)aminocarbonyl)-L-alaninyl)]amino-2,3-dihydro-1-methyl-5-phenyl-1H-1,4-benzodiazepin-2-one Following General Procedure (5-A1) using phenethyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 483 (M+H).

Example 5-19

Preparation of (S)-3-[(N'-((4-n-Butylphenyl)aminocarbonyl)-L-alaninyl)]amino-2,3-dihydro-1-methyl-5-phenyl-1H-1,4-benzodiazepin-2-one Following General Procedure (5-A1) using 4-n-butylphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 511 (M+H).

Example 5-20

Preparation of (S)-3-[(N'-((Octyl)aminocarbonyl)-L-alaninyl)]amino-2,3-dihydro-1-methyl-5-phenyl-1H-1,4-benzodiazepin-2-one Following General Procedure (5-A1) using octyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 491 (M+H).

Example 5-21

Preparation of (S)-3-[(N'-((4-Biphenyl)aminocarbonyl)-L-alaninyl)]amino-2,3-dihydro-1-methyl-5-phenyl-1H-1,4-benzodiazepin-2-one Following General Procedure (5-A1) using 4-biphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 531 (M+H).

Example 5-22

Preparation of (S)-3-[(N'-((4-Isopropylphenyl)aminocarbonyl)-L-alaninyl)]amino-2,3-dihydro-1-methyl-5-phenyl-1H-1,4-benzodiazepin-2-one Following General Procedure (5-A1) using 4-isopropylphenyl isocyanate and (S)-3-[(L-alaninyl)]

amino-2,3-dihydro-1-methyl-5-phenyl-1H-1,4-benzodiazepin-2-one, as described in Example 8-B above, the title compound was prepared. The molecular weight as determined by mass spectrometry (FD) was: 497 (M+H).

Example 5-23

Preparation of (S)-3-[(N'-((Hexyl)aminocarbonyl)-L-alaninyl)]amino-2,3-dihydro-1-methyl-5-phenyl-1H-1,4-benzodiazepin-2-one Following General Procedure (5-A1) using hexyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 463 (M+H).

Example 5-24

Preparation of (S)-3-[(N'-((2-Isopropylphenyl)aminocarbonyl)-L-alaninyl)]amino-2,3-dihydro-1-methyl-5-phenyl-1H-1,4-benzodiazepin-2-one Following General Procedure (5-A1) using 2-isopropylphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 513 (M+H).

Example 5-25

Preparation of (S)-3-[(N'-((2,6-Difluorophenyl)aminocarbonyl)-L-alaninyl]amino-2,3-dihydro-1-methyl-5-phenyl-1H-1,4-benzodiazepin-2-one Following General Procedure (5-A1) using 2,6-difluorophenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 491 (M+H).

Example 5-26

Preparation of (S)-3-[(N'-((Octadecyl)aminocarbonyl)-L-alaninyl)]amino-2,3-dihydro-1-methyl-5-phenyl-1H-1,4-benzodiazepin-2-one Following General Procedure (5-A1) using octadecyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 631 (M+H).

Example 5-27

(S)-3-[(N'-((4-(Trifuoromethoxy)phenyl)aminocarbonyl)-L-alaninyl)]amino-2,3-dihydro-1-methyl-5-phenyl-1H-1,4-benzodiazepin-2-one Following General Procedure (5-A1) using trifluoromethoxy)phenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 539 (M+H).

Example 5-28

Preparation of (S)-3-[(N'-((2,4-Dichlorophenyl)aminocarbonyl)-L-alaninyl)]amino-2,3-dihydro-1-methyl-5-phenyl-1H-1,4-benzodiazepin-2-one Following General Procedure (5-A1) using 2,4-dichlorophenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 524 (M+H).

Example 5-29

Preparation of (S)-3-[(N'-((3-Ethoxycarbonylphenyl)aminocarbonyl)-L-alaninyl)]amino-2,3-dihydro-1-methyl-5-phenyl-1H-1,4-benzodiazepin-2-one Following General Procedure (5-A1) using ethoxycarbonylphenyl isocyanate and (S)-3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 527 (M+H).

Example 5-30

Preparation of (S)-3-[(N'-((4-Chlorophenyl)aminocarbonyl)-L-alaninyl)]amino-2,3-dihydro-1-methyl-5-phenyl-1H-1,4-benzodiazepin-2-one Following General Procedure (5-A1) using 4-chlorophenyl isocyanate and (S)-3-[(N'-((4-Chlorophenyl)aminocarbonyl)-L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 489 (M+H).

Example 5-31

Preparation of (S)-3-[(N'-((4-Butoxyphenyl)aminocarbonyl)-L-alaninyl)]amino-2,3-dihydro-1-methyl-5-phenyl-1H-1,4-benzodiazepin-2-one Following General Procedure (5-A1) using 4-butoxyphenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 547 (M+H).

Example 5-32

Preparation of (S)-3-[(N'-((4-Phenoxyphenyl)aminocarbonyl)-L-alaninyl)]amino-2,3-dihydro-1-methyl-5-phenyl-1H-1,4-benzodiazepin-2-one Following General Procedure (5-A1) using 4-phenoxyphenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 527 (M+H).

Example 5-33

Preparation of (S)-3-[(N'-((1-Naphthyl)aminocarbonyl)-L-alaninyl)]amino-2,3-dihydro-1-methyl-5-phenyl-1H-1,4-benzodiazepin-2-one Following General Procedure (5-A1) using naphthyl isocyanate and (S)-3-(L-alaninyl)amino-2,3-dihydro-1-methyl-5-phenyl-1H-1,4-benzodiazepin-2-one, as described in Example 8-B above, the title compound was prepared. The molecular weight as determined by mass spectrometry (FD) was: 505 (M+H).

Example 5-34

Preparation of (S)-3-[(N'-((2-Biphenyl)aminocarbonyl)-L-alaninyl)]amino-2,3-dihydro-1-methyl-5-phenyl-1H-1,4-benzodiazepin-2-one Following General Procedure (5-A1) using (2-phenyl)phenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 531 (M+H).

Example 5-35

Preparation of (S)-3-[(N'-((2-(Methylthio)phenyl)aminocarbonyl)-L-alaninyl)]amino-2,3-dihydro-1-methyl-5-phenyl-1H-1,4-benzodiazepin-2-one Following General Procedure (5-A1) using 2-(methylthio)phenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 501 (M+H).

Example 5-36

Preparation of (S)-3-[(N'-((2-Ethylphenyl)aminocarbonyl)-L-alaninyl)]amino-2,3-dihydro-1-methyl-5-phenyl-1H-1,4-benzodiazepin-2-one Following General Procedure (5-A1) using 2-ethylphenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 483 (M+H).

Example 5-37

Preparation of (S)-3-[(N'-((3-Methoxyphenyl)aminocarbonyl)-L-alaninyl)]amino-2,3-dihydro-1-methyl-5-phenyl-1H-1,4-benzodiazepin-2-one Following General Procedure (5-A1) using 3-methoxyphenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 485 (M+H).

Example 5-38

Preparation of (S)-3-[(N'-((3,4,5-Trimethoxyphenyl)aminocarbonyl)-L-alaninyl)]amino-2,3-dihydro-1-methyl-5-phenyl-1H-1,4-benzodiazepin-2-one Following General Procedure (5-A1) using 3,4,5-trimethoxyphenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 545 (M+H).

Example 5-39

Preparation of (S)-3-[(N'-((2,4,6-Trimethylphenyl)aminocarbonyl)-L-alaninyl)]amino-2,3-dihydro-1-methyl-5-phenyl-1H-1,4-benzodiazepin-2-one Following General Procedure (5-A1) using 2,4,6-trimethylphenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: 497 (M+H).

Example 5-40

Preparation of, (S)-3-[(N'-((2-Methyl-6-t-butylphenyl)aminocarbonyl)-L-alaninyl)]amino-2,3-dihydro-1-methyl-5-phenyl-1H-1,4-benzodiazepin-2-one Following General Procedure (5-A1) using 2-methyl-6-t-butylphenyl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: (M+H).

Example 5-41

Preparation of (S)-3-[(N'-((2-(2-Thiophene-yl)ethyl)aminocarbonyl)-L-alaninyl)amino-2,3-dihydro-1-methyl-5-phenyl-1H-1,4-benzodiazepin-2-one Following General Procedure (5-A1) using 2-thiophene-yl isocyanate and 3-[(L-alaninyl)]amino-2,3-dihydro-1-methyl-5-phenyl-1H-1,4-benzodiazepin-2-one, as described in Example 8-B above, the title compound was prepared. The molecular weight as determined by mass spectrometry (FD) was: (M+H).

Example 5-43

Preparation of 5-(S)-(N'-((2-(Thiophen-2-yl)ethylaminocarbonyl)-L-alaninyl)amino-7-methyl-5,7-dihydro-6H-dibenz[b,d]azepin-6-one Following General Procedure (5-A1) using 2-(thien-2-yl)ethyl isocyanate and 5-(S)-(N'-L-alaninyl)-amino-7-methyl-5,7-dihydro-6H-dibenz[b,d]azepin-6-one, as described in Example 7-B, the title compound was prepared as a white solid. The reaction was monitored by tlc ($R_f$=0.35 in 10% MeOH/CH$_2$Cl$_2$) and the product was purified by silica gel chromatography using gradient elution of MeOH/CH$_2$Cl$_2$ (1:99–2:98).

NMR data was as follows:

$^1$H-nmr (CDCl$_3$): delta=7.86 (d, J=7.0 Hz, 1H), 7.51–7.24 (m, 10H), 7.06 (d, J=6.0 Hz, 1H), 6.87–6.84 (m, 1H), 6.72–6.71 (m, 1H), 5.20 (d, J=6.5 Hz, 1H), 4.554.53 (m, 1H), 3.27 (s, 3H), 3.20–3.05 (m, 2H), 2.75–2.70 (m, 2H), 1.25 (d, J=7.0 Hz, 3H). C$_{25}$H$_{26}$N$_4$O$_3$S (MW=462.57); mass spectroscopy (MH$^+$) 463.6. Anal Calcd for C$_{25}$H$_{26}$N$_4$O$_3$S, C, 64.91; H, 5.67; N, 12.1 1; Found: C, 65.12; H, 5.71; N, 12.10.

Example 5-44

Preparation of 5-(S)-(N'-((Phenethylaminocarbonyl)-L-alaninyl)-amino-7-methyl-5,7-dihydro-6H-dibenz[b,d]azepin-6-one Following General Procedure (5-A1) using phenethyl isocyanate and 5-(S)-(N'-L-alaninyl)-amino-7-methyl-5,7-dihydro-6H-dibenz[b,d]azepin-6-one, the title compound was prepared as a white solid. The reaction was monitored by tlc ($R_f$=0.53 in 10% MeOH/CH$_2$Cl$_2$) and the product was purified by silica gel chromatography using gradient elution of MeOH/CH$_2$Cl$_2$ (1:99–3:97).

NMR data was as follows:

$^1$H-nmr (CDCl$_3$): δ=7.78 (d, J=6.6 Hz, 1H), 7.54–7.12 (m, 15H), 5.23 (d, J=6.7 Hz, 1H), 4.58–4.53 (m, 1H), 3.32–3.27 (m, 5H), 2.64 (t, J=7.4 Hz, 2H), 1.33 (d, J=7.0 Hz, 3H). Optical Rotation: [α]$_{20}$=−80.3 @ 589 nm (c=1, MeOH); C$_{27}$H$_{28}$N$_4$O$_3$ (MW=456.5); mass spectroscopy (MH$^+$) 457.5; Anal Calcd for C$_{27}$H$_{28}$N$_4$O$_3$; C, 71.03; H, 6.18; N, 12.27; Found: C, 70.90; H, 6.38; N, 12.00.

Example 5-45

Preparation of 5-(S)-(N'-((Butylaminocarbonyl)-L-alaninyl)-amino-7-methyl-5,7-dihydro-6H-dibenz[b,d]azepin-6-one Following General Procedure (5-A1) using butyl isocyanate and 5-(S)-(N'-L-alaninyl)-amino-7-methyl-5,7-dihydro-6H-dibenz[b,d]azepin-6-one, as described in Example 7-B, the title compound was prepared as a white solid. The reaction was monitored by tlc (R$_f$=0.49 in 10% MeOH/CH$_2$Cl$_2$) and the product was purified by silica gel chromatography using gradient elution of MeOH/CH$_2$Cl$_2$ (1:99–3:97).

NMR data was as follows:

$^1$H-nmr (CDCl$_3$): delta=7.74–7.33 (m, 11H), 5.24 (d, J=6.7 Hz, 1H), 4.57–4.53 (m, 1H), 3.35 (s, 3H), 3.08–2.85 (m, 2H), 1.39–1.25 (m, 7H), 0.88 (t, J=7.0 Hz, 3H). Optical Rotation: [α]$_{20}$=−97.1 @ 589 nm (c=1, MeOH); C$_{23}$H$_{28}$N$_4$O$_3$ (MW=408.5); mass spectroscopy (MH$^+$) 409.4; Anal Calcd for C$_{23}$H$_{28}$N$_4$O$_3$; C, 67.63; H, 6.91; N, 13.72; Found: C, 67.46; H, 6.93; N, 13.64.

Example 5-46

Preparation of 5-(S)-(N'-((Benzylaminocarbonyl)-L-alaninyl)-amino-7-methyl-5,7-dihydro-6H-dibenz[b,d]azepin-6-one Following General Procedure (5-A1) using benzyl isocyanate and 5-(S)-(N'-L-alaninyl)-amino-7-methyl-5,7-dihydro-6H-dibenz[b,d]azepin-6-one, as described in Example 7-B, the title compound was prepared as a white solid. The reaction was monitored by tlc (R$_f$=0.63 in 10% MeOH/CH$_2$Cl$_2$) and the product was purified by trituration from EtOAc and Hex.

NMR data was as follows:

$^1$H-nmr (CDCl$_3$): δ=7.86 (d, J=6.7 Hz, 1H), 7.46–7.09 (m, 15H), 5.21 (d, J=6.7 Hz, 1H), 4.59–4.40 (m, 1H), 4.38–4.00 (m, 2H), 3.27 (s, 3H), 1.29 (d, J=7.1 Hz, 3H). C$_{26}$H$_{26}$N$_4$O$_3$ (MW=442.52); mass spectroscopy (MH$^+$) 443.3. Anal Calcd for C$_{26}$H$_{26}$N$_4$O$_3$; C, 70.57; H, 5.92; N, 12.66; Found: C, 70.36; H, 6.05; N, 12.47.

Example 5-47

Preparation of 5-(S)-(N'-((Ethylaminocarbonyl)-L-alaninyl)-amino-7-methyl-5,7-dihydro-6H-dibenz[b,d]azepin-6-one Following General Procedure (5-A1) using ethyl isocyanate and 5-(S)-(N'-L-alaninyl)-amino-7-methyl-5,7-dihydro-6H-dibenz[b,d]azepin-6-one, as described in Example 7-B, the title compound was prepared as a white solid. The reaction was monitored by tlc (R$_f$=0.35 in 10% MeOH/CH$_2$Cl$_2$) and the product was purified by silica gel chromatography using gradient elution of MeOH/CH$_2$Cl$_2$ (1:99–4:96).

NMR data was as follows:

$^1$H-nmr (CDCl$_3$): δ=7.84 (d, J=6.8 Hz, 1H), 7.56–7.30 (m, 10H), 5.23 (d, J=6.7 Hz, 1H), 4.60–4.53 (m, 1H), 3.33 (s, 3H), 3.00–2.87 (m, 2H), 1.30 (d, 7.0Hz, 3H), 0.85 (t, J=7.1 Hz, 3H). C$_{21}$H$_{24}$N$_4$O$_3$ (MW 380.45); mass spectroscopy (MH$^+$) 381.3. Anal Calcd for C$_{21}$H$_{24}$N$_4$O$_3$; C, 66.30; H, 6.36; N, 14.73; Found: C, 66.14; H, 6.58; N, 14.49.

Example 5-48

Preparation of 5-(R/S)-(N'-(2-Hydroxy-2-phenylaminocarbonyl)-L-alaninyl)-amino-7-methyl-5,7-dihydro-6H-dibenz[b,d]azepin-6-one Following General Procedure (5-D1) above using 5-(R/S)-[L-alaninyl]-amino-7-methyl-5,7-dihydro-6H-dibenz[b,d]azepin-6-one hydrochloride (Example 7B) and 2-(R/S)-amino-1-phenylethanol (Sigma) the title compound was prepared. The final product was purified by flash chromatography (5% CH3OH in 2:1 CH2Cl2:EtAc) to give a mixture of diastereomers.

C27H28N4O4 (MW=472.54), mass spectroscopy (MH+) 473. Anal. Calcd for C27H28N4O4, C, 68.63, H, 5.97, N, 11.86. Found C, 68.14, H, 5.98, N, 11.50.

Example 5-49

Preparation of 5-(S)-(N'-((Hexylaminocarbonyl)-L-alaninyl)-amino-7-methyl-5,7-dihydro-6H-dibenz[b,d]azepin-6-one Following General Procedure (5-B1) above using 5-(S)-(L-alaninyl)-amino-7-methyl-5,7-dihydro-6H-dibenz[b,d]azepin-6-one hydrochloride (Example 7B) and hexyl isocyanate (Aldrich) the title compound was prepared.

C25H32N4O3 (MW=436.56); mass spectroscopy (MH+) 437. Retention time; 11.0 minutes.

Example 5-50

Preparation of 5-(S)-(N'-((Cyclohexylaminocarbonyl)-L-alaninyl)amino-7-methyl-5,7-dihydro-6H-dibenz[b,d]azepin-6-one Following General Procedure (5-B1) above using 5-(S)-(L-alaninyl)-amino-7-methyl-5,7-dihydro-6H-dibenz[b,d]azepin-6-one hydrochloride (Example 7B) and cyclohexyl isocyanate (Aldrich) the title compound was prepared.

C25H30N4O3 (MW=434.54); mass spectroscopy (MH+) 435. Retention time; 8.2 minutes.

Example 5-51

Preparation of 5-(S)-(N'-((Isopropylaminocarbonyl)-L-alaninyl)-amino-7-methyl-5,7-dihydro-6H-dibenz[b,d]azepin-6-one Following General Procedure (5-B1) above using 5-(S)-(L-alaninyl)-amino-7-methyl-5,7-dihydro-6H-dibenz[b,d]azepin-6-one hydrochloride (Example 7B) and isopropyl isocyanate (Aldrich) the title compound was prepared.

C22H26N4O3 (MW=394.48); mass spectroscopy (MH+) 395. Retention time; 5.3 minutes.

Example 5-52

Preparation of 5-(S)-(N'-((tert-Butylaminocarbonyl)-L-alaninyl)-amino-7-methyl-5,7-dihydro-6H-dibenz[b,d]azepin-6-one Following General Procedure (5-B1) above using 5-(S)-(L-alaninyl)-amino-7-methyl-5,7-dihydro-6H-dibenz[b,d]

azepin-6-one hydrochloride (Example 7B) and tert-butyl isocyanate (Aldrich) the title compound was prepared.

C23H28N4O3 (MW=408.50); mass spectroscopy (MH+) (409). Retention time; 6.9 minutes.

Example 5-53

Preparation of 5-(S)-(N'-((1-Adamantylaminocarbonyl]-L-alaninyl)-amino-7-methyl-5,7-dihydro-6H-dibenz[b,d]azepin-6-one Following General Procedure (5-B1) above using 5-(S)-(L-alaninyl)-amino-7-methyl-5,7-dihydro-6H-dibenz[b,d]azepin-6-one hydrochloride (Example 7B) and 1-adamantyl isocyanate (Aldrich) the title compound was prepared.

C29H34N4O3 (MW=486.62); mass spectroscopy (MH+) 487. Retention time; 20.3 minutes.

Example 5-54

Preparation of 5-(S)-(N'-((2-Methylpropylaminocarbonyl)-L-alaninyl)-amino-7-methyl-5,7-dihydro-6H-dibenz[b,d]azepin-6-one Following General Procedure (5-C1) above using 5-(S)-[L-alaninyl]-amino-7-methyl-5,7-dihydro-6H-dibenz[b,d]azepin-6-one hydrochloride (Example 7B) and isobutylamine (Aldrich) the title compound was prepared.

C23H28N4O3 (MW=408.50); mass spectroscopy (MH+) 409. HPLC retention time: 6.592 minutes.

Example 5-55

Preparation of 5-(S)-(N'-(R/S)-3-Hydroxy-3-phenylethylaminocarbonyl)-L-alaninyl)-amino-7-methyl-5,7-dihydro-6H-dibenz[b,d]azepin-6-one Following General Procedure (5-C1) above using 5-(S)-[L-alaninyl]-amino-7-methyl-5,7-dihydro-6H-dibenz[b,d]azepin-6-one hydrochloride (Example 7B) and 2-(R/S)-amino-1-phenylethanol (Sigma) the title compound was prepared.

C27H28N4O4 (MW=472.55); mass spectroscopy (MH+) 473. HPLC retention time: 5.707 minutes.

Example 5-56

Preparation of 5-(S)-(N'-((3-Methybutylaminocarbonyl)-L-alaninyl)-amino-7-methyl-5,7-dihydro-6H-dibenz[b,d]azepin-6-one Following General Procedure (5-C1) above using 5-(S)-[L-alaninyl)-amino-7-methyl-5,7-dihydro-6H-dibenz[b,d]azepin-6-one hydrochloride (Example 7B) and isoamylamine (Aldrich) the title compound was prepared.

C24H30N4O3 (MW=422.53); mass spectroscopy (MH+) 423. HPLC retention time: 8.575 minutes.

Example 5-57

Preparation of 5-(S)-((N'-(S)-1-Hydroxymethyl-3-methylbutylaminocarbonyl)-L-alaninyl)-amino-7-methyl-5,7-dihydro-6H-dibenz[b,d]azepin-6-one Following General Procedure (5-D1) above using 5-(S)-[L-alaninyl]-amino-7-methyl-5,7-dihydro-6H-dibenz[b,d]azepin-6-one hydrochloride (Example 7B) and (S)-leucinol (Aldrich) the title compound was prepared.

C25H32N4O4 (MW 452.56); mass spectroscopy (MH+) 453. Anal. Calcd for C25H32N4O4; C, 66.35, H, 7.13, N, 12.38. Found: C, 66.02, H, 7.03, N, 11.84.

Example 5-58

Preparation of 5-(S)-((N'-(1S)-(2S)-1-Hydroxymethyl-2-methylbutylaminocarbonyl)-L-alaninyl)-amino-7-methyl-5,7-dihydro-6H-dibenz[b, d]azepin-6-one Following General Procedure (5-D1) above using 5-(S)-[L-alaninyl]-amino-7-methyl-5,7-dihydro-6H-dibenz[b,d]azepin-6-one hydrochloride (Example 7B) and (L)-isoleucinol (Aldrich) the title compound was prepared.

C25H32N4O4 (MW=452.56); mass spectroscopy (MH+) 453. Anal. Calcd for C25H32N4O4; C, 66.35, H, 7.13, N 12.38. Found: C, 66.31, H, 6.93, N, 12.21.

Example 5-59

Preparation of 5-(S)-(N'-(3-Chloropropylaminocarbonyl)-L-alaninyl)-amino-7-methyl-5,7-dihydro-6H-dibenz[b,d]azepin-6-one Following General Procedure (5-B1) above using 5-(S)-(L-alaninyl)-amino-7-methyl-5,7-dihydro-6H-dibenz[b,d]azepin-6-one hydrochloride (Example 7B) and 3-chloropropyl isocyanate (Aldrich) the title compound was prepared.

$C22H_{25}ClN4O3$ (MW 428.92); mass spectroscopy (MH+) 429. Retention time; 6.0 minutes.

Example 5-60

Preparation of 5-(S)-(N'-Octylaminocarbonyl)-L-alaninyl)-amino-7-methyl-5,7-dihydro-6H-dibenz[b, d]azepin-6-one Following General Procedure (5-B1) above using 5-(S)-(L-alaninyl)-amino-7-methyl-5,7-dihydro-6H-dibenz[b,d]azepin-6-one hydrochloride (Example 7B) and octyl isocyanate (Aldrich) the title compound was prepared.

C27H36N4O3 (MW=464.61); mass spectroscopy (MH+) 465. Retention time; 29.7 minutes.

Example 5-61

Preparation of 5-(S)-(N'-1,1,3,3-Tetramethylbutylaminocarbonyl)-L-alaninyl)-amino-7-methyl-5,7-dihydro-6H-dibenz[b,d]azepin-6-one Following General Procedure (5-B1) above using 5-(S)-(L-alaninyl)-amino-7-methyl-5,7-dihydro-6H-dibenz[b,d]azepin-6-one hydrochloride (Example 7B) and 1,1,3,3-tetramethylbutyl isocyanate (Aldrich) the title compound was prepared.

C27H36N4O3 (MW=464.61); mass spectroscopy (MH+) 465. Retention time; 20.3 minutes.

Example 5-62

Preparation of 5-(S)-(N'-(R/S)-1-Methylbutylaminocarbonyl)-L-alaninyl)-amino-7-methyl-5,7-dihydro-6H-dibenz[b,d]azepin-6-one Following General Procedure (5-C1) above using 5-(S)-[L-alaninyl]-amino-7-methyl-5,7-dihydro-6H-dibenz[b,d]azepin-6-one hydrochloride (Example 7B) and 1-(R/S)-methylbutylamine (Aldrich) the title compound was prepared.

C24H30N4O3 (MW=422.53); mass spectroscopy (MH+) 423. HPLC retention time: 8.0 minutes.

Example 5-63

Preparation of 5-(S)-((N'-(R/S)-1-Hydroxymethylbutylaminocarbonyl)-L-alaninyl)-amino-7-methyl-5,7-dihydro-6H-dibenz[b,d]azepin-6-one Following General Procedure (5-C1) above using 5-(S)-[L-alaninyl]-amino-7-methyl-5,7-dihydro-6H-dibenz[b,d]azepin-6-one hydrochloride (Example 7B) and 2-(R/S)-amino-1-pentanol (Aldrich) the title compound was prepared.

C24H30N4O4 (MW=438.53); mass spectroscopy (MH+) 439. HPLC retention time: 4.6 minutes.

Example 5-64

Preparation of 5-(S)-((N'-(R/S)-1,3-Dimethylbutylaminocarbonyl)-L-alaninyl)-amino-7-methyl-5,7-dihydro-6H-dibenz[b,d]azepin-6-one Following General Procedure (5-C1) above using 5-(S)-[L-alaninyl]-amino-7-methyl-5,7-dihydro-6H-dibenz[b,d]azepin-6-one hydrochloride (Example 7B) and (R/S)-1,3-dimethylbutylamine (Aldrich) the title compound was prepared.

C25H32N4O3 (MW=436.56); mass spectroscopy (MH+) 437. HPLC retention time: 10.6 minutes.

Example 5-65

Preparation of 5-(S)-((N'-(R)-1-Hydroxymethyl-3-metylbutylaminocarbonyl)-L-alaninyl)-amino-7-methyl-5,7-dihydro-6H-dibenz[b,d]azepin-6-one Following General Procedure (5-C1) above using 5-(S)-[L-alaninyl]-amino-7-methyl-5,7-dihydro-6H-dibenz[b,d]azepin-6-one hydrochloride (Example 7B) and (R)-Leucinol (Aldrich) the title compound was prepared.

C25H32N4O4 (MW=452.56); mass spectroscopy (MH+) 453. HPLC retention time: 5.0 minutes.

Example 5-66

Preparation of 5-(S)-((N'-(R/S)-2-Methylbutylaminocarbonyl)-L-alaninyl)-amino-7-methyl-5,7-dihydro-6H-dibenz[b,d]azepin-6-one Following General Procedure (5-C1) above using 5-(S)-[L-alaninyl]-amino-7-methyl-5,7-dihydro-6H-dibenz[b,d]azepin-6-one hydrochloride (Example 7B) and 2-(R/S)-methylbutylamine (Aldrich) the title compound was prepared.

C24H30N4O3 (MW=422.53); mass spectroscopy (MH+) 423. HPLC retention time: 8.1 minutes.

Example 5-67

Preparation of 5-(S)-(N'-Morpholinoaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and morpholine (Aldrich) the title compound was prepared.

C23H26N4O4 (MW=422.48); mass spectroscopy (MH+) 423. Retention time; 4.5 minutes.

Example 5-68

Preparation of 5-(S)-(N'-(2-(2-Hydroxyethoxy)-ethylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and 2-(2-aminoethoxy)ethanol (Aldrich) the title compound was prepared.

C23H28N4O5 (MW=440.50); mass spectroscopy (MH+) 441. Retention time; 3.8 minutes.

Example 5-69

Preparation of 5-(S)-(N -Piperidinylaminocarbonyl)-L-alaninyl)-amino-7-methyl-5,7-dihydro-6H-dibenz[b,d]azepin-6one Following General Procedure (5-C1) above using 5-(S)-(L-alaninyl)-amino-7-methyl-5,7-dihydro-6H-dibenz[b,d]azepin-6-one hydrochloride (Example 7B), piperidine (Aldrich), and diisopropylethylamine (Aldrich) (1.5 eq) the title compound was prepared.

C24H28N4O3 (MW=420.51); mass spectroscopy (MH+) 421. Retention time; 6.9 minutes.

Example 5-70

Preparation of 5-(S)-(N'-(N''-methyl-N''-Butylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and N-methyl-butylamine (Aldrich) the title compound was prepared.

C24H30N4O3 (MW 422.53); mass spectroscopy (MH+) 423. Retention time; 8.8 minutes.

Example 5-71

Preparation of 5-(S)-(N'-(1-(R/S)-Hydroxymethylcyclopentylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and 1-aminocyclopentane methanol (Aldrich) the title compound was prepared.

C25H30N4O4 (MW=450.54); mass spectroscopy (MH+) 451. Retention time; 5.3 minutes.

Example 5-72

Preparation of 5-(S)-(N'-(4-Hydroxybutylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and 4-aminobutanol (Aldrich) the title compound was prepared.

C23H28N4O4 (MW=424.50); mass spectroscopy (MH+) 425. Retention time; 3.9 minutes.

Example 5-73

Preparation of 5-(S)-(N'-(1-(R/S)-Hydroxymethyl-2-methylpropylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]

azepin-6-one hydrochloride (Example 7B) and 2-amino-3-methylbutanol (Aldrich) the title compound was prepared.

C24H30N4O4 (MW=438.53); mass spectroscopy (MH+) 439. Retention time; 4.7 minutes.

Example 5-74

Preparation of 5-(S)-(N'-(2-(R/S)-Hydroxycyclohexylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B), 2-aminocyclohexanol (Janssen), and diisopropylethylamine (Aldrich) (1.5 eq) the title compound was prepared.

C25H30N4O4 (MW=450.54); mass spectroscopy (MH+) 451. Retention time; 4.9 minutes.

Example 5-75

Preparation of 5-(S)-(N'-(Isopropyl-hydroxyaminocarbonyl)-L-alaninyl)-amino-7-methyl-5,7-dihydro-6H-dibenz[b,d]azepin-6-one Following General Procedure (5-D1) above using 5-(R/S)-[L-alaninyl]-amino-7-methyl-5,7-dihydro-6H-dibenz[b,d]azepin-6-one hydrochloride (Example 7B) and N-isopropylhydroxylamine hydrochloride (Aldrich), in the presence of diisopropylethylamine (Aldrich) the title compound was prepared. The final product was purified by flash chromatography (ethyl acetate) to give a mixture of diastereomers.

C22H26N4O4 (MW=410.471), mass spectroscopy (MH+) 411. 1H NMR (CD3OD, 400 MHz, d) 7.64–7.36 (m, 8H), 5.17 (s, 1H), 4.48–4.38 (m, 1H), 4.354.25 (m, 1H), 3.29 (s, 3H), 1.40 (d, J=7.3 Hz, 3H), 1.12–1.09 (m, 6H).

Example 5-76

Preparation of 5-(S)-(N'-(Benzyl-hydroxyaminocarbonyl)-L-alaninyl)-amino-7-methyl-5,7-dihydro-6H-dibenz[b,d]azepin-6-one Following General Procedure (5-D1) above using 5-(R/S)-[L-alaninyl]-amino-7-methyl-5,7-dihydro-6H-dibenz[b,d]azepin-6-one hydrochloride (Example 7B) and N-benzylhydroxylamine hydrochloride (Aldrich), in the presence of diisopropylethylamine (Aldrich) the title compound was prepared. The final product was purified by flash chromatography (ethyl acetate) to yield a mixture of diastereomers.

C26H26N4O4 (MW=458.52), mass spectroscopy (MH+) 459. 1H NMR (CD3OD, 400 MHz, d) 7.65–7.12 (m, 13H), 5.19 (s, 1H), 4.70–4.58 (m, 2H), 4.51–4.44 (m, 1H), 3.32 (s, 3H), 1.44–1.41 (m, 3H).

Example 5-77

Preparation of 5-(S)-(N'-(Thiomorpholinylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and thiomorpholine (Aldrich) the title compound was prepared.

C23H26N4O3S (MW=438.55); mass spectroscopy (MH+) 439. Retention time; 5.9 minutes.

Example 5-78

Preparation of 5-(S)-(N'-(2(R/S)-Hydroxybutylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and 2-(R/S)-hydroxybutylamine (Transworld) the title compound was prepared.

C23H28N4O4 (MW=424.50); mass spectroscopy (MH+) 425. Retention time; 4.2 minutes.

Example 5-79

Preparation of 5-(S)-(N'-2,2,2-Trifluoroethylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and 2,2,2-triflouroethylamine (Aldrich) the title compound was prepared.

C21H21F3N4O3 (MW=434.42); mass spectroscopy (MH+) 435. Retention time; 6.0 minutes.

Example 5-80

Preparation of 5-(S)-(N'-(4R/S)-Cyclohexylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and 4-aminocyclohexanol (Fluka) the title compound was prepared.

C25H30N4O4 (MW=450.54); mass spectroscopy (MH+) 451. Retention time; 4.0 minutes.

Example 5-81

Preparation of 5-(S)-(N'-(1R)-Hydroxymethyl-3-methylthiopropylaminocarbonyl)-L-alaninyl)-amino-7-methyl-5,7-dihydro-6H-dibenz[b,d]azepin-6-one Following General Procedure (5-C1) above using 5-(S)-(L-alaninyl)-amino-7-methyl-5,7-dihydro-6H-dibenz[b,d]azepin-6-one hydrochloride (Example 7B) and L-methioninol (Lancaster) the title compound was prepared.

C24H30N4O4S (MW=470.60); mass spectroscopy (MH+) 471. Retention time; 4.6 minutes.

Example 6-1

Preparation of 5-{N'-(Benzenesulfonyl)-L-alaninyl}-amino-7-methyl-5,7-dihydro-6H-dibenz[b,d]azepin-6-one To 5-(L-alaninyl)amino-7-methyl-5,7-dihydro-6H-dibenz[b,d]azepin-6-one hydrochloride (Example 7B) (0.1500 g, 0.434 mmol) in THF (4 ml) were added pyridine (0.088ml, 1.09 mmol) and benzenesulfonyl chloride (Aldrich) (0.061 ml, 0.477 mmol), stirred at RT for 2 days. The reaction mixture was evaporated to dryness. Water and CH$_2$Cl$_2$ were added. CH$_2$Cl$_2$ layer was dried over MgSO$_4$. Evaporation and flash chromatography (silica, 5–6% MeOH/CH$_2$Cl$_2$) gave a residue, which was crystallized in CHCl$_3$/hexane and washed with Et$_2$O to give the title compound (0.027 g, 14%) as a white solid.

C24H$_{23}$N3O4S (MW=449.529); mass spectroscopy (MH$^+$) 448. Anal. Calcd for C24H$_{23}$N3O4S: C, 64.13; H, 5.16; N, 9.35; Found: C, 63.99; H, 5.05; N, 9.24.

Example 6-2

Preparation of 5-{N'-(3-Fluorobenzenesulfonyl)-L-alaninyl}-amino-7-methyl-5,7-dihydro-6H-dibenz[b,d]azepin-6-one To 5-(L-alaninyl)-amino-7-methyl-5,7-dihydro-6H-dibenz[b,d]azepin-6-one hydrochloride (Example 7B) (0.1500 g, 0.434 mmol) in THF (4 ml) was added pyridine (0.088ml, 1.09 mmol) and 3-fluorobenzenesulfonyl chloride (Fluorochem Limited) (0.0928 ml, 0.477 mmol), stirred at RT overnight. The reaction mixture was evaporated to dryness. Water was added, filtered. The solid was purified with flash chromatography (silica, 6% MeOH/CH$_2$Cl$_2$, crystallized with CH$_2$Cl$_2$/hexane and washed with Et$_2$O/hexane (1:1, v/v) to give the title compound (0.0580 g, 29%) as a white solid.

C24H22FN3O4S (MW=467.519); mass spectroscopy (MH$^+$) 468. Anal. Calcd for C24H22FN3O4S: C, 61.66; H, 4.74; N, 8.99; Found: C, 61.76; H, 4.93; N, 8.76.

Example 6-3

Preparation of 5-{N'-(benzylsulfonyl)-L-alaninyl}-amino-7-methyl-5,7-dihydro-6H-dibenz[b,d]azepin-6one To 5-(L-alaninyl)-amino-7-methyl-5,7-dihydro-6H-dibenz[b,d]azepin-6-one (Example 7B) (0.2050 g, 0.66 mmol) in DMF (5 ml) was added benzylsulfonyl chloride (Aldrich) (0.0632 g, 0.33 mmol), stirred at RT for 3.5 days. The reaction mixture was evaporated to dryness. Water was added, extracted with CH$_2$Cl$_2$, washed with brine, dried over MgSO$_4$. Evaporation and flash chromatography (silica, 5% MeOH /CH$_2$Cl$_2$), gave a residue, which was washed with Et$_2$O /hexane (1:2, v/v) to give the title compound (0.0531 g, 35%) as a light yellow solid.

C25H$_{25}$N3O4S (MW=463.555); mass spectroscopy (MH$^+$) 464. Anal. Calcd for C25H$_{25}$N3O4S: C, 64.78; H, 5.44; N, 9.06; Found: C, 64.83; H, 5.17; N, 8.86.

Example 6-4

Preparation of 5-{N'-(Butylsulfonyl)-L-alaninyl}-amino-7-methyl-5,7-dihydro-6H-dibenz[b,d]azepin-6one To 5-(L-alaninyl)-amino-7-methyl-5,7-dihydro-6H-dibenz[b,d]azepin-6-one (Example 7B) (0.1500 g, 0.0485 mmol) in DMF (4 ml) were added pyridine (0.059 ml, 0.728 mmol) and 1-butanesulfonyl chloride (Aldrich) (0.063 ml, 0.485 mmol), stirred at RT overnight. The reaction mixture was evaporated to dryness. Water was added, extracted with EtOAc, washed with brine, dried over MgSO$_4$. Evaporation and flash chromatography (silica, 5% MeOH/CH$_2$Cl$_2$), gave the title compound (0.0714 g, 34%) as a yellow solid.

C22H27N3O4S (MW=429.538); mass spectroscopy (MH$^+$) 430. Anal. Calcd for C22H27N3O4S: C, 61.52; H, 6.34; N, 9.78; Found: C, 61.78; H, 6.40; N, 9.51.

Example 6-5

Preparation of 5-{N'-(Octylsulfonyl)-L-alaninyl}-amino-7-methyl-5,7-dihydro-6H-dibenz[b,d]azepin-6-one To 5-(L-alaninyl)-amino-7-methyl-5,7-dihydro-6H-dibenz[b,d]azepin-6-one (Example 7B) (0.1500 g, 0.0485 mmol) in DMF (4 ml) were added pyridine (0.059 ml, 0.728 mmol) and 1-octanesulfonyl chloride (Aldrich) (0.095 ml, 0.485 mmol), stirred at RT overnight. The reaction mixture was evaporated to dryness. Water was added, extracted with EtOAc, washed with brine, dried over MgSO$_4$. Evaporation and flash chromatography (silica, 5% MeOH/CH$_2$Cl$_2$), gave the title compound (0.0805 g, 34%) as a yellow solid.

C26H35N3O4S (MW=485.646); mass spectroscopy (MH$^+$) 486. Anal. Calcd for C26H35N3O4S : C, 64.30; H, 7.26; N, 8.65; Found: C, 64.14; H, 7.13; N, 8,48.

Example 7-1

Preparation of 5-(S)-(N'-(3,5-Difluorophenyl-α-aminoacetyl)-L-valinyl]-amino-7-methyl-5,7-dihydro-6H-dibenz[b,d]azepin-6-one Following General Procedure D above using N-boc-3,5-difluorophenylglycine and 5-(S)-(L-valinyl)-amino-7-methyl-5,7-dihydro-6H-dibenz[b,d]azepin-6-one hydrochloride (Example 7B), the protected intermediate was prepared as a colorless oil. The Boc-group was removed using 5.0 M HCl in dioxane and the resulting free-base purified by flash chromatography using 98:2 CHCl$_3$/MeOH yielding the title compound.

NMR data was as follows:

$^1$H-nmr (CDCl$_3$): delta=7.78 (d, 1H), 7.53–7.25 (m, 8H), 6.86 (m, 2H), 6.71 (m, 2H), 5.22 (d, 1H), 4.76 (s, 1H), 4.43 (m, 1H), 3.34 (s, 3H), 2.08 (m, 1H), 0.91 (m, 6H). C$_{28}$H$_{28}$F$_2$N$_4$O$_3$ (MW=506); mass spectroscopy (MH$^+$) 506.9; Anal Calcd for C$_{28}$H$_{28}$F$_2$N$_4$O$_3$; C, 66.39; H, 5.57, N, 11.06; Found: C, 66.33; H, 5.67; N, 10.89.

Example 7-2

Preparation of 5-(S)-(N'-(3,5-Difluorophenyl-α-aminoacetyl)-L-tert-leucinyl-amino-7-methyl-5,7-dihydro-6H-dibenz[b,d]azepin-6-one Following General Procedure D above using N-boc-3,5-difluorophenylglycine and 5-(S)-(L-tert-leucinyl)-amino-7-methyl-5,7-dihydro-6H-dibenz[b,d]azepin-6-one hydrochloride, the protected intermediate was prepared as a colorless oil. The Boc-group was removed using 5.0 M HCl in dioxane and the resulting free-base purified by flash chromatography using 98:2 CHCl$_3$/MeOH yielding the title compound.

C$_{29}$H$_{30}$F$_2$N$_3$O$_4$ (MW=520.57); mass spectroscopy (MH$^+$) 521; Anal Calcd for C$_{29}$H$_{30}$F$_2$N$_3$O$_4$; C, 66.91; H, 5.81, N, 10.76; Found: C, 66.66; H, 5.70; N, 10.55.

Example 7-3

Preparation of 5-(S)-(N'-(Valinyl)-L-alaninyl-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d] azepin-6-one hydrochloride (Example 7B) and L-Boc-Valine (Aldrich), the protected intermediate was prepared. This was purified by flash chromatography using CHCl$_3$/

MeOH (99: 1). The Boc-group was removed using 5.0 M HCl in dioxane and the resulting free-base purified by flash chromatography CHCl3/MeOH (95:5) yielding the title compound.

C23H28N4O3 (MW=408.499); mass spectroscopy (MH$^+$) 409. Anal. Calcd for C23H28N4O3; C, 67.63; H, 6.91; N, 13.72. Found: C, 67.48; H, 7.01; N, 13.70.

Example 7-4

Preparation of 5-(S)-(N'-(Phenylglycinyl)-L-alaninyl-amino-7-methyl-5,7-dihydro-6H-dibenz[b,d]azepin-6-one Following General Procedure F above using 5-(S)-[L-alaninyl]-amino-7-methyl-5,7-dihydro-6H-dibenz[b,d]azepin-6-one hydrochloride (Example 7B) and the acid fluoride of L-Boc-phenylglycine (Carpino, et. al., *J. Org. Chem.*, (1991), 56, 2611–2614), the protected intermediate was prepared. This was purified by flash chromatography using CHCl$_3$/MeOH (99:1). The Boc-group was removed using 5.0 M HCl in dioxane and the resulting hydrochloride purified by flash chromatography CHCl$_3$/MeOH (99:1) yielding the title compound.

C26H26N4O3 (MW=442.516); mass spectroscopy (MH+) 443. Anal. Calcd for C26H26N4O3.HCl; C, 65.79; H, 5.68; N, 11.69. Found: C, 65.69; H, 5.63; N, 11.42.

Example 7-5 AND 7-6

Preparation of 5-(S)-(N'-(R and S)-3,5-Difluorophenyl-α-aminoacetyl)-L-alaninyl-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d]azepin-6-one hydrochloride (Example 7B) and D/L-Boc-3,5-difluorophenylglycine, the protected intermediate was prepared. The Boc-group was removed using 5.0 M HCl in dioxane and the resulting free-base diastereomers were purified by flash chromatography CHCl$_3$/MeOH (98:2) yielding the title compounds.

Isomer A: C26H24F2N4O3 (MW=478.497); mass spectroscopy (MH+) 479. Anal. Calcd for C26H24F2N4O3. 0.6681 mol H2O; C, 63.66; H, 5.20; N, 11.42. Found: C, 63.65; H, 5.35; N, 11.56.

Isomer B: C26H24F2N4O3 (MW=478.497); mass spectroscopy (MH+) 479. Anal. Calcd for C26H24F2N4O3. 0.5146 mol H2O; C, 64.02; H, 5.17N, 11.49. Found: C, 64.04; H, 5.01; N, 11.30.

Example 7-8

Preparation of 5-(S)-(N'-(D-Valinyl)-L-alaninyl-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d]azepin-6-one hydrochloride (Example 7B) and D-Boc-Valine (Aldrich), the protected intermediate was prepared. This was purified by flash chromatography using CHCl$_3$/MeOH (99:1). The Boc-group was removed using 5.0 M HCl in dioxane and the resulting free-base purified by flash chromatography CHCl$_3$/MeOH (95:5) yielding the title compound.

C23H28N4O3 (MW=408.499); mass spectroscopy (MH+) 409. Anal. Calcd for C23H28N4O3; C, 67.63; H, 6.91; N, 13.72. Found: C, 68.18; H, 6.88; N, 13.79.

Example 7-9

Preparation of 5-(S)-(N'-(D-Phenylglycinyl)-L-alaninyl-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d]azepin-6-one hydrochloride (Example 7-B) and D-boc-phenylglycine (Aldrich), the protected intermediate was prepared. The Boc-group was removed using 5.0 M HCl in dioxane and the resulting free-base purified by flash chromatography CHCl$_3$/MeOH (95:5) yielding the title compound.

C26H26N4O3 (MW=442.516); mass spectroscopy (MH+) 443. Anal. Calcd for C26H26N4O3; C, 70.57; H, 5.92; N, 12.66. Found: C, 70.39; H, 5.93; N, 12.43.

Example 7-10

Preparation of 5-(S)-(N'-(3,5-Difluorophenyl-α-aminoacetyl)-L-alaninyl-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d]azepin-6-one hydrochloride (Example 7-B) and N-boc-3,5-difluorophenylglycine, the protected intermediate was prepared. The Boc-group was removed using 5.0 M HCl in dioxane and the resulting free-base purified by flash chromatography yielding the title compound. The molecular weight as determined by mass spectrometry (FD) was: (M+H).

Example 7-11

Synthesis of 5-(S)-[N'-(L-Trifluoromethylphenylglycinyl)-L-alaninyl]-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d]azepin-6-one hydrochloride (Example 7B) and (S)-2-Phenyl-N-(trifluoroacetyl)glycine (Aldrich), the title compound was prepared. The product was purified by flash chromatography using CHCl3/MeOH (99:1).

C28H25F3N4O4 (MW=538.524); mass spectroscopy (MH+) 539. Anal. Calcd for C28H25F3N4O4; C, 62.45; H, 4.68; N, 10.40. Found: C, 62.33; H, 4.78; N, 10.16.

Example 7-12

Synthesis of 5-(S)-[N'-(L-N-Methyl-valinyl)-L-alaninyl]-amino-7-methyl-5,7-dihydro-6H-dibenz[b,d]azepin-6one Following General Procedure D above using 5-(S)-[L-alaninyl]-amino-7-methyl-5,7-dihydro-6H-dibenz[b,d]azepin-6-one hydrochloride (Example 7B) and L-N-Methyl-Boc-Valine (Aldrich), the protected intermediate was prepared. This was purified by flash chromatography using CHCl3/MeOH (98:2). The Boc-group was removed using 5.0 M HCl in dioxane and the resulting free-base purified by flash chromatography CHCl3/MeOH (98:2) yielding the title compound.

C24H30N4O3 (MW=422.526); mass spectroscopy (MH$^+$) 423. Anal. Calcd for C24H30N4O3. 0.6269 mol H2O; C, 66.44; H, 7.26; N, 12.91. Found: C, 66.50; H, 7.47; N, 12.70.

Example 7-13

Synthesis of 5-(S)-[N'-(Hexafluorovalinyl)-L-alaninyl]-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d] azepin-6-one hydrochloride (Example 7B) and Boc-Hexafluorovaline (Aldrich), the protected intermediate was prepared. This was purified by flash chromatography using CHCl3/MeOH (98:2). The Boc-group was removed using 5.0 M HCl in dioxane and the resulting free-base purified by flash chromatography CHCl3/MeOH (97:3) yielding the title compound.

$C_{23}H_{22}F_6N_4O_3$ (MW=516.44); mass spectroscopy (MH+) 517. Anal. Calcd for $C_{23}H_{22}F_6N_4O_3$; C, 51.68 H, 4.49; N, 10.47. Found: C, 51.46; H, 4.22; N, 9.94.

Example 7-15

Preparation of 5-(S)-(N'-(L-Valinyl)-L-alaninyl-)] amino-2,3-dihydro-1-methyl-5-phenyl-1H-1,4-benzodiazepin-2-one Following General Procedure D above using N-boc-L-valine and 5-(S)-(L-alaninyl)-amino-2,3-dihydro-1-methyl-5-phenyl-1H-1,4-benzodiazepin-2-one hydrochloride (Example 8-B), the protected intermediate was prepared. The Boc-group was removed using 5.0 M HCl in dioxane and the resulting free-base purified by flash chromatography yielding the title compound. Anal. Calc'd for $C_{24}H_{29}N_5O_3$:C, 66.19, H, 6.71; N, 16.08. Found: C: 66.50; H, 6.68; N, 15.87. MS Found (M+H) 436.

Example 7-17

Preparation of 5-(S)-(N"-(S)-Phenylglycinyl)-N'-L-alaninyl]amino-1-methyl-5-phenyl-1,3,4,5-tetrahydro-2H-1,5-benzodiazepin-2-one Step A—Preparation of 3-[(N'''-t-Butoxycarbonyl)-N"-(S)-phenylglycinyl)-N'-L-alaninyl]amino-1-methyl-5-phenyl-1,3,4,5-tetrahydro-2H-1,5-benzodiazepin-2-one To a solution of 3-[(N'-L-alaninyl]amino-1-methyl-5-phenyl-1,3,4,5-tetrahydro-2H-1,5-benzodiazepin-2-one (Example 8M) (300 mg, 0.89 mmol) in THF (30 mL) was added L-Boc-phenylglycine (246 mg, 0.98 mmol, NovaBioChem) and 2-ethoxy-1-ethoxycarbonyl-1,2-dihydroquinoline (242 mg, 0.98 mmol, Aldrich). The resulting mixture was stirred at ambient temperature under nitrogen overnight. The mixture was diluted with EtOAc (500 mL) and washed with water (1×100 mL) and brine (1×100 mL). The organic layer was dried over $Na_2SO_4$, filtered, and concentrated. The residue was purified by HPLC eluting with hexanes/EtOAc (1:1) to yield the title intermediate (230 mg).

Step B—Synthesis of 5-(S)-(N"-(S)-Phenylglycinyl)-N'-L-alaninyl]amino-1-methyl-5-phenyl-1,3,4,5-tetrahydro-2H-1,5-benzodiazepin-2-one Through a solution of the product from step A (230 mg, 0.40 mmol) in 1,4-dioxane (50 mL) was passed a stream of HCl gas for 10 minutes. The resulting solution was capped and stirred overnight at ambient temperature, then concentrated. The residue was dissolved in water (100 mL) and washed with $Et_2O$ (1×100 mL). Then, the aqueous layer was basified to pH 9 with 1 M aq. NaOH, and the product extracted into EtOAc (100 mL). The EtOAc extract was dried over $Na_2SO_4$, filtered, and concentrated. The residue was purified by HPLC eluting with $CH_2Cl_2$/MeOH (95:5) to yield the title compound (114 mg) as a white solid.

$C_{27}H_{29}N_5O_3$ (MW=471.56) mass spectroscopy (MH+) 472.3, (MH−) 470.3; HRMS. Calcd. for $C_{27}H_{30}N_5O_3$: 472.2348. Found: 472.2352.

Example 7-18

Preparation of 5-(S)-[(N"-L-Valinyl)-N'-L-alaninyl] amino-1-methyl-5-phenyl-1,3,4,5-tetrahydro-2H-1,5-benzodiazepin-2-one Step A—Synthesis of 3-[(N'''-t-Butoxycarbonyl)-N'-(S)-valinyl)-N'-L-alaninyl]amino-1-methyl-5-phenyl-1,3,4,5-tetrahydro-2H-1,5-benzodiazepin-2-one To a solution of 3-[(N'-L-alaninyl]amino-1-methyl-5-phenyl-1,3,4,5-tetrahydro-2H-1,5-benzodiazepin-2-one (Example 8M) (300 mg, 0.89 mmol) in THF (30 mL) was added L-Boc-valine (212 mg, 0.98 mmol, NovaBioChem) and 2-ethoxy-1-ethoxycarbonyl-1,2-dihydroquinoline (242 mg, 0.98 mmol, Aldrich). The resulting mixture was stirred at ambient temperature under nitrogen overnight. The mixture was diluted with EtOAc (500 mL) and washed with water (1×100 mL) and brine (1×100 mL). The organic layer was dried over $Na_2SO_4$, filtered, and concentrated. The residue was purified by HPLC eluting with hexanes/EtOAc (1:1) to yield the title intermediate (240 mg).

Step B—Synthesis of 5-(S)-(N'-L-Alaninyl-N"-L-valinyl] amino-1-methyl-5-phenyl-1,3,4,5-tetrahydro-2H-1,5-benzodiazepin-2-one Through a solution of the product from step A (240 mg, 0.44 mmol) in 1,4-dioxane (50 mL) was passed a stream of HCl gas for 10 minutes. The resulting solution was capped and stirred overnight at ambient temperature, then concentrated. The residue was dissolved in water (100 mL) and washed with $Et_2O$ (1×100 mL). Then, the aqueous layer was basified to pH 9 with 1 M aq. NaOH, and the product extracted into EtOAc (100 mL). The EtOAc extract was dried over $Na_2SO_4$, filtered, and concentrated. The residue was purified by HPLC eluting with $CH_2Cl_2$/MeOH (95:5) to yield the title compound (180 mg) as a white solid.

$C_{24}H_{31}N_5O_3$ (MW 437.54) mass spectroscopy (MH+) 438.2, (MH−) 436.5; HRMS. Calcd. for $C_{24}H_{31}N_5O_3$: 438.2505. Found: 438.2502.

Examples 7-19 AND 7-20

Preparation of 3-(N"-(3,5-Difluorophenylglycinyl)-N'-L-alaninyl]amino-2,4-dioxo-1-methyl-5-phenyl-2,3,4,5-tetrahydro-2H-1,5-benzodiazepine Hydrochloride Step A—Preparation of 3-[((N'''-t-butoxycarbonyl)-N"-(3,5-difluorophenylglycinyl)-N'-L-alaninyl]amino-2,4-dioxo-1-methyl-5-phenyl-2,3,4,5-tetrahydro-2H-1,5-benzodiazepine Hydrochloride To a solution of 3-(N'-L-alaninyl)-amino-2,4-dioxo-1-methyl-5-phenyl-2,3,4,5-tetrahydro-2H-1,5-benzodiazepine (Example 8-N) (500 mg, 1.28 mmol) in THF (15 mL) was added N-t-boc-D,L-3,5-difluorophenylglycine (404 mg, 1.41 mmol), 1-(3-dimethylaminopropyl)-3-ethyl-carbodiimide hydrochloride (270 mg, 1.41 mmol), 1-hydroxybenzotriazole hydrate (190 mg, 1.41 mmol), followed by N,N-diisopropylethylamine (490 µL, 2.82 mmol).

The resulting mixture was stirred at ambient temperature under nitrogen overnight. The mixture was diluted with EtOAc (200 mL) and washed with water (1×200 mL). The organic layer was dried over $Na_2SO_4$, filtered, and concentrated. The residue was purified by HPLC eluting with hexanes/EtOAc (1:1) to yield the title intermediate as two separated diastereomers (labeled isomer 1 as the less polar intermediate (280 mg), and isomer 2 as the more polar intermediate (316 mg)).

Data for isomer 1:
$C_{32}H_{33}N_5O_6F_2$ (MW 621.64) mass spectroscopy (MH$^+$) 622.5, (MH$^-$) 620.7; Anal. Calcd. for $C_{32}H_{33}N_5O_6F_2$: C, 61.83; H, 5.35; N, 11.27. Found: C, 61.58; H, 5.23; N, 10.97.

Data for isomer 2:
$C_{32}H_{33}N_5O_6F_2$ (MW 621.64) mass spectroscopy (MH$^+$) 622.5, (MH$^-$) 620.7; Anal. Calcd. for $C_{32}H_{33}N_5O_6F_2$: C, 61.83; H, 5.35; N, 11.27. Found: C, 61.95; H, 5.24; N, 10.98.

Step B—Preparation of 3-[(N"-(3,5-Difluorophenylglycinyl)-N'-L-alaninyl]amino-2,4dioxo-1-methyl-5-phenyl-2,3,4,5-tetrahydro-2H-1,5-benzodiazepine Hydrochloride Through a solution of isomer 1 from step A (250 mg, 0.40 mmol) in 1,4-dioxane (80 mL) was passed a stream of HCl gas for 5 minutes. The resulting solution was capped and stirred overnight at ambient temperature, then concentrated. The title compound was isolated (161 mg) as a white solid by trituration with hexanes/EtOAc.

Data for the title compound from isomer 1:
$C_{27}H_{25}N_5O_4F_2$ HCl (FW 557.98) mass spectroscopy (MH$^+$, —HCl) 523.4, (MH$^-$, —HCl) 520.3; HRMS. Calcd. for $C_{27}H_{26}N_5O_4F_2$: 522.1953. Found: 522.1949. Optical rotation: $[\ ]^{20}_D$=73.02 (c 0.5, MeOH); m.p. 218–219 C.

Isomer 2 (280 mg, 0.45 mmol) was processed in the same manner as isomer 1, except using 90 mL of 1,4-dioxane. Yielding 200 mg of the title compound as a white solid.

Data for the title compound from isomer 2:
$C_{27}H_{25}N_5O_4F_2$ HCl (FW 557.98) mass spectroscopy (MH$^+$, —HCl) 523.4, (MH$^-$, —HCl) 520.3; HRMS. Calcd. for $C_{27}H_{26}N_5O_4F_2$: 522.1953. Found: 522.1959. Optical rotation: $[\ ]^{20}_D$=134.28 (c 0.5, MeOH). m.p. at 184 C the white solid became a foam.

Example 7-21

Preparation of 5-(S)-[N'-(2-Amino-3,3,3-trifluoromethylbutyryl)-L-alaninyl]-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d]azepin-6-one hydrochloride (Example 7B) and D/L-Boc4,4,4-trifluorovaline (Oakwood), the protected intermediate was prepared. This was purified by flash chromatography using $CHCl_3$/MeOH (99:1). The Boc-group was removed using 5.0 M HCl in dioxane and the resulting free-base purified by flash chromatography $CHCl_3$/MeOH (98:2) yielding the title compounds.

Isomer 1:
$C_{23}H_{25}F_3N_4O_3$ (MW=462.47); mass spectroscopy (MH+) 463. Anal. Calcd for $C_{23}H_{25}F_3N_4O_3$.0.95 mol $H_2O$; C, 57.59; H, 5.65; N, 11.62. Found: C, 57.64; H, 5.77; N, 11.52.

Isomer 2:
$C_{23}H_{25}F_3N_4O_3$ (MW=462.47); mass spectroscopy (MH+) 463. Anal. Calcd for $C_{23}H_{25}F_3N_4O_3$.0.91 mol $H_2O$; C, 57.67; H, 5.65; N, 11.70. Found: C, 57.69; H, 5.65; N, 11.40.

Example 7-22

Preparation of 5-(S)-[N'-(2-Amino -5,5,5-trifluoropentanyl)-L-alaninyl]-amino-7-methyl-5,7-dihydro-6H-dibenz[b,d]azepin-6one Following General Procedure D above using 5-(S)-[L-alaninyl]-amino-1-methyl-5,7-dihydro-6H-dibenz[b,d]azepin-6-one hydrochloride (Example 7B) and D/L-Boc-5,5,5-trifluoronorvaline (Oakwood), the protected intermediate was prepared. This was purified by flash chromatography using $CHCl_3$/MeOH (9:1). The Boc-group was removed using 5.0 M HCl in dioxane and the resulting free-base purified by flash chromatography $CHCl_3$/MeOH (95:5) yielding the title compounds.

Isomer 1:
$C_{23}H_{25}F_3N_4O_3$ (MW=462.47); mass spectroscopy (MH+) 463. Anal. Calcd for $C_{23}H_{25}F_3N_4O_3$.0.4295 mol $H_2O$; C, 58.75; H, 5.54; N, 11.91. Found: C, 58.81H, 5.38; N, 11.53.

Isomer 2:
$C_{23}H_{25}F_3N_4O_3$ (MW=462.47); mass spectroscopy (MH+) 463. Anal. Calcd for $C_{23}H_{25}F_3N_4O_3$.0.2318 mol $H_2O$; C, 59.19; H, 5.50; N, 12.00. Found: C, 59.27; H, 5.55; N, 11.67.

Example 7-23

Preparation of 5-(S)-[N'-(2-Amino-4,4,4trifluorobutyryl)-L-alaninyl]-amino-7-methyl-5,7-dihydro-6H-dibenz[b,d]azepin-6-one Following General Procedure D above using 5-(S)-[L-alaninyl]-amino-7-methyl-5,7-dihydro-6H-dibenz[b,d]azepin-6-one hydrochloride (Example 7B) and D/L-(2-N-Boc-amino)-4,4,4-trifluorobutyric acid (Oakwood), the protected intermediate was prepared. The Boc-group was removed using 5.0 M HCl in dioxane and the resulting free-base purified by flash chromatography $CHCl_3$/MeOH (95.5) yielding the title compounds.

Isomer 1:
$C_{22}H_{23}F_3N_4O_3$ (MW=448.443); mass spectroscopy (MH+) 449. Anal. Calcd for $C_{22}H_{23}F_3N_4O_3$. 0.7377 mol $H_2O$; C, 57.23; H, 5.34; N, 12.13. Found: C, 57.27; H, 5.13; N, 11.82.

Isomer 2:
$C_{22}H_{23}F_3N_4O_3$ (MW=448.443); mass spectroscopy (MH+) 449. Anal. Calcd for $C_{22}H_{23}F_3N_4O_3$. 0.6657 mol $H_2O$; C, 57.39; H, 5.32; N, 12.17. Found: C, 57.42; H, 5.19; N, 11.95.

Example 7-24

Preparation of 1-(S)-[N -(2-Amino-3,3,3-trifluorobutyryl)-L-alaninyl]-amino-3-methyl-4,5,6,7-tetrahydro-2H-3-benzazepin-2-one Following General Procedure D above using 1-(S)-[L-alaninyl]-amino-3-methyl-4,5,6,7-tetrahydro-2H-3-benzazepin-2-one hydrochloride (Example 7-30, below) and D/L-N-Boc-4,4,4-trifluorovaline (Oakwood), the protected intermediate was prepared. This was purified by flash chromatography using $CHCl_3$/MeOH (99:1). The Boc-group was removed using 5.0 M HCl in dioxane and the resulting free-base purified by flash chromatography $CHCl_3$/MeOH (95:5) yielding the title compounds.

Isomer 1(single diastereomer):
$C_{19}H_{25}F_3N_4O_3$ (MW=414.426); mass spectroscopy (MH+) 415; Anal. Calcd for $C_{19}H_{25}F_3N_4O_3$; C, 55.07; H, 6.08; N, 13.52. Found: C, 55.18; H, 6.11; N, 13.49.

Isomer 2(single diastereomer):
$C_{19}H_{25}F_3N_4O_3$ (MW=414.426); mass spectroscopy (MH+) 415; Anal. Calcd for $C_{19}H_{25}F_3N_4O_3$; C, 55.07; H, 6.08; N, 13.52. Found: C, 54.82; H, 6.06; N, 13.35.

Isomer 3(mixture of two diastereomers):

$C_{19}H_{25}F_3N_4O_3$ (MW=414.426); mass spectroscopy (MH+) 415; Anal. Calcd for C,9H$_{21}$F$_3$N$_4$O$_3$; 0.255 mol H$_2$O C, 54.46; H, 6.14; N, 13.37. Found: C, 54.54; H, 6.14; N, 13.05.

Example 7-25

Preparation of 1-(S)-[N'-(2-Amino-5,5,5-trifluoropentanoyl)-L-alaninyl]-amino-3-methyl-4,5,6,7-tetrahydro-2H-3-benzazepin-2-one Following General Procedure D above using 1-(S)-[L-alaninyl]-amino-3-methyl-4,5,6,7-tetrahydro-2H-3-benzazepin-2-one hydrochloride (Example 7-30, below) and D/L-N-Boc-5,5,5-trifluoronorvaline (Oakwood), the protected intermediate was prepared. The Boc-group was removed using 5.0 M HCl in dioxane and the resulting free-base purified by flash chromatography CHCl$_3$/MeOH (95:5) yielding the title compounds.

Isomer 1(single diastereomer):

$C_{19}H_{25}F_3N_4O_3$ (MW 414.1967); High resolution MS (MH+) 415.1957; 400 MHZ $^1$H NMR (CDCl$_3$) d=6.17 ppm (d, 1H), 4.61 (m, 1H), 3.01 (s, 3H), 1.49 (d, 3H).

Isomer 2(single diastereomer):

$C_{19}H_{25}F_3N_4O_3$ (MW=414.1967); High resolution MS (MH+) 415.1946; 400 MHZ $^1$H NMR (CDCl$_3$) d=6.18 ppm (d, 1H), 4.64 (m, 1H), 3.01 (s, 3H), 1.48 (d, 3H).

Example 7-26

Preparation of 1-(S)-[N'-(2-Amino-4,4,4-trifluorobutyryl)-L-alaninyl]-amino-3-methyl-4,5,6,7-tetrahydro-2H-3-benzazepin-2-one Following General Procedure D above using 1-(S)-[L-alaninyl]-amino-3-methyl-4,5,6,7-tetrahydro-2H-3-benzazepin-2-one hydrochloride (Example 7-30, below) and 2-(N-Boc-amino)-4,4,4-trifluorobutyric acid (Oakwood), the protected intermediate was prepared. The Boc-group was removed using 5.0 M HCl in dioxane and the resulting free-base purified by flash chromatography CHCl$_3$/MeOH (97.3) yielding the title compounds.

Isomer 1(single diastereomer):

$C_{18}H_{23}F_3N_4O_3$ (MW=400.399); mass spectroscopy (MH+) 401; Anal. Calcd for $C_{18}H_{23}F_3N_4O_3$; C, 53.99; H, 5.79N, 13.99 Found: C, 54.08; H, 5.90; N, 13.70.

Isomer 2 (single diastereomer):

$C_{18}H_{23}F_3N_4O_3$ (MW 400.399); high resolution MS (MH+) 401.1800; 400 MHZ $^1$H NMR (CDCl$_3$) d=6.18 ppm (d, 1H), 4.61 (m, 1H), 3.01 (s, 3H), 2.22 (m, 2H), 1.48 (d, 3H).

Example 7-27

Preparation of 1-(S)-N'-(2-Aminobutyryl)-L-alaninyl]-amino-3-methyl-4,5,6,7-tetrahydro-2H-3-benzazepin-2-one Following General Procedure D above using 1-(S)-[L-alaninyl]-amino-3-methyl-4,5,6,7-tetrahydro-2H-3-benzazepin-2-one hydrochloride (Example 7-30, below) and 2-(L-N-Boc-amino)butyric acid (Aldrich), the protected intermediate was prepared. The Boc-group was removed using 5.0 M HCl in dioxane and the resulting free-base purified by chromatography CHCl$_3$/MeOH (95:5) yielding the title compound.

$C_{18}H_{26}N_4O_3$ (MW=346.428); mass spectroscopy (MH+) 347; Anal. Calcd for $C_{18}H_{26}N_4O_3$; C, 62.41; H, 7.56; N, 16.17 Found: C, 62.46; H, 7.73; N, 15.98.

Example 7-28

Preparation of 1-(S)-[N'-(Hexafluorovalinyl)-L-alaninyl]-amino-3-methyl-4,5,6,7-tetrahydro-2H-3-benzazepin-2-one Following General Procedure D above using 1-(S)-[L-alaninyl]-amino-3-methyl-4,5,6,7-tetrahydro-2H-3-benzazepin-2-one hydrochloride (Example 7-30, below) and N-Boc-hexafluorovaline (Aldrich), the protected intermediate was prepared. The Boc-group was removed using 5.0 M HCl in dioxane and the resulting free-base purified by chromatography CHCl$_3$/MeOH (95:5) yielding the title compound as a mixture of diastereomers.

$C_{19}H_{22}F_6N_4O_3$ (MW=468.396); mass spectroscopy (MH+) 469; Anal. Calcd for $C_{19}H_{22}F_6N_4O_3$; C, 48.72; H, 4.73; N, 11.96 Found: C, 48.56; H, 4.73; N, 11.83.

Example 7-29

Preparation of 1-(S)-[N'-(L-2-Aminobutyryl)-L-alaninyl]-amino-3-(2-methylpropyl)-4,5,6,7-tetrahydro-2H-3-benzazepin-2-one Following General Procedure D above using 1-(S)-[L-alaninyl]-amino-3-(2-methylpropyl)-4,5,6,7-tetrahydro-2H-3-benzazepin-2-one hydrochloride (Example 7-31, below) and L-2-(N-Boc)-aminobutyric acid (Aldrich), the protected intermediate was prepared. The Boc-group was removed using 5.0 M HCl in dioxane and the resulting free-base purified by chromatography CHCl$_3$/MeOH (95:5) yielding the title compound as a mixture of diastereomers.

$C_{21}H_{32}N_4O_3$ (MW 388.509); mass spectroscopy (MH+) 389; Anal. Calcd for $C_{21}H_{32}N_4O_3$; C, 64.92; H, 8.30; N, 14.42 Found: C, 64.62; H, 8.12; N, 14.29.

Example 7-30

Preparation of 1-(S)-[L-Alaninyl]-amino-3-methyl-4,5,6,7-tetrahydro-2H-3-benzazepin-2-one Hydrochloride Step A: Synthesis of 1-Hydroxyimino-3-methyl-4,5,6,7-tetrahydro-2H-3-benzazepin-2-one Following the procedure described for Example 7-A (Step B) and using 3-methyl-4,5,6,7-tetrahydro-2H-3-benzazepin-2-one (CS# 73644-95-8), 1-hydroxyimino-3-methyl-4,5,6,7-tetrahydro-2H-3-benzazepin-2-one was prepared.

$C_{11}H_{12}N_2O_2$(MW=204.1); mass spectroscopy (MH+) 205.

Step B: Synthesis of (R/S)-1-Amino-3-methyl-4,5,6,7-tetrahydro-2H-3-benzazepin-2-one.

The compound isolated above was reduced following General Procedure 7-A (Step C), (R/S)-1-amino-3-methyl-4,5,6,7-tetrahydro-2H-3-benzazepin-2-one was prepared.

$C_{11}H_{14}N_2O$ (MW=190.1); mass spectroscopy (MH+) 191.

Step C: Resolution of (S)-1-Amino-3-methyl-4,5,6,7-tetrahydro-2H-3-benzazepin-2-one.

The amine isolated above was resolved as described in General Procedure 7-C using Di-p-Toluoyl-L-tartaric acid (Aldrich, CAS# 32634-66-5). Enantiomeric excess (ee) was determined by Capillary Electrophoresis using a Beckman Place MDQ and 5% sulfated α-cyclodrextrin, 20 mM (Et$_3$N) (NH$_4$)PO$_4$ (pH=2.5) on a 50 m capillary @ 15 kVolts and the detector set at 20° C.m (200 nM). The desired enantiomer had a migration time of 7.4 minutes relative to the undesired enantiomer (migration time=6.83 minutes).

[a]=−72 (c=1, MeOH) as tartarate salt. ee=97%.

Step D: Synthesis of 1-(S)-[N-t-Boc-L-alaninyl]-amino-3-methyl-4,5,6,7-tetrahydro-2H-3-benzazepin-2-one.

Using the amine isolated above and following the procedure described in Example 7-B (Step A) the title compound was isolated.

$C_{19}H_{27}N_3O_4$ (MW=362.19); mass spectroscopy (MH+) 362; Anal. Calcd for $Cl_{19}H_{27}N_3O_4$; C, 63.14; H, 7.53; N, 11.62 Found: C, 63.01H, 7.44; N, 11.59. [a]=+16.22 (c=1, $CH_2Cl_2$)

Step E: Synthesis of 1-(S)-[L-Alaninyl]-amino-3-methyl-4,5,6,7-tetrahydro-2H-3-benzazepin-2-one hydrochloride.

The compound isolated above was treated as described in Example 7-B (Step B).

$C_{14}H_{19}N_3O_2$ HCl (MW=297.78); mass spec (MH+, free base) 262; Anal. Calcd for $C_{14}H_{19}N_3O_2$ HCl; C, 56.47; H, 6.77; N, 14.11; Found: C, 56.27; H, 6.56; N, 13.63. [a]=+38.99 (c=0.5, MeOH).

Example 7-31

Preparation of 1-(S)-[L-Alaninyl]-amino-3-(2-methylpropyl)-4,5,6,7-tetrahydro-2H-3-benzazepin-2-one Hydrochloride Step A: Synthesis of 3-(2-Methylpropen-2-yl)-4,5,6,7-tetrahydro-2H-3-benzazepin-2-one.

A solution of 4,5,6,7-tetrahydro-2H-3-benzazepin-2-one (61 g, 0.379 mol) in DMF was cooled to 0° C. and treated with a solution of LiHMDS (1.0 M, 398 ml, 0.391 mols) over 30 minutes. Methallyl bromide (42 ml, 0.041 mols) was added neat and the reaction allowed to stir for 2 hours at 0° C. under nitrogen atmosphere. Most of the solvent was removed under reduced pressure, the residue diluted into $CH_2Cl_2$ and washed with two portions of 1.0 N HCl. The organics were washed 0.2 M LiCl, dried over $Na_2SO_4$ and chromatographed over $SiO_2$ using 9:1 $CHCl_3$/MeOH. The appropriate fractions were pooled, evaporated to an oil which was recrystallized from hexanes/EtOAc yielding 17 g of a tan solid.

$C_{14}H_{17}NO$ (MW=215); mass spectroscopy (MH+) 216. 400 MHZ $^1$H NMR (CDCl$_3$) d=7.18–7.05 ppm (m, 4H), 4.88 (s, 1H), 4.79 (s, 1H), 3.98 (s, 2H), 3.93 (s, 2H), 4.67 (m, 2H), 3.09 (m, 2H), 1.66 (s, 3H). Anal. Calcd for $C_{14}H_{17}NO$; C, 78.10; H, 7.97; N, 6.51 Found: C, 78.40; H, 8.08; N, 6.54.

Step B. Synthesis of 3-(2-Methylpropyl)-4,5,6,7-tetrahydro-2H-3-benzazepin-2-one.

The compound isolated above was hydrogenated over 10% Pd/C at 35 psi in a Parr shaker for 2h at room temperature. The catalyst was filtered and the titled compound isolated as a yellow oil.

$C_{14}H_{19}NO$ (MW=217); mass spectroscopy (MH+) 218; Anal. Calcd for $C_{14}H_{19}NO$; C, 77.38; H, 8.81; N, 6.45; Found: C, 77.04; H, 8.81; N, 6.43.

Step C: Synthesis of 1-Hydroxyimino-3-(2-methylpropyl)-4,5,6,7-tetrahydro-2H-3-benzazepin-2-one.

Following the procedure described for Example 7-A (Step B) and using 3-(2-methylpropyl)-4,5,6,7-tetrahydro-2H-3-benzazepin-2-one, 1-hydroxyimino-3-methyl-4,5,6,7-tetrahydro-2H-3-benzazepin-2-one was prepared.

$C_{14}H_{18}N_2O_2$ (MW=246.3); mass spectroscopy (MH+) 247.

Step D: Synthesis of (R/S)-1-Amino-3-(2-methylpropyl)-4,5,6,7-tetrahydro-2H-3-benzazepin-2-one.

The compound isolated above was reduced following General Procedure 7-A (Step C), (R/S)-1-amino-3-(2-methylpropyl)-4,5,6,7-tetrahydro-2H-3-benzazepin-2-one was prepared.

$C_{14}H_{20}N_2O$ (MW=232.14); mass spectroscopy (MH+) 233.

Step E: Resolution of (S)-1-amino-3-(2-methylpropyl)-4,5,6,7-tetrahydro-2H-3-benzazepin-2-one.

The amine isolated above was resolved as described in General Procedure 7-C using Di-p-Toluoyl-L-tartaric acid (Aldrich, CAS# 32634-66-5). Enantiomeric excess (ee) was determined by Capillary Electrophoresis using a Beckman Place MDQ and 5% sulfated a-cyclodrextrin, 20 mM ($Et_3N$) ($NH_4$)$PO_4$ (pH=2.5) on a 50 m capillary @ 15 kVolts and the detector set at 20° C.m (200 nM). The desired enantiomer had a migration time of 6.95 minutes relative to the undesired enantiomer (migration time=6.51 minutes).

[a]=−78 (c=1, MeOH) as tartarate salt. ee=99%.

Step F: Synthesis of 1-(S)-[N-t-boc-L-Alaninyl]-amino-3-(2-methylpropyl)-4,5,6,7-tetrahydro-2H-3-benzazepin-2-one.

Using the amine isolated above and following the procedure described in Example 7-B (Step A) the title compound was isolated.

$C_{22}H_{33}N_3O_4$ (MW=403.52); mass spectroscopy (MH+) 404; Anal. Calcd for $C_{22}H_{33}N_3O_4$; C, 65.48; H, 8.24; N, 10.41; Found: C, 65.40; H, 7.99; N, 10.66. [a]=−9.7 (c=0.5, MeOH).

Step G: Synthesis of 1-(S)-[L-Alaninyl]-amino-3-(2-methylpropyl)-4,5,6,7-tetrahydro-2H-3-benzazepin-2-one Hydrochloride.

The compound isolated above was treated as described in Example 7-B (Step B).

$C_{17}H_{25}N_3O_2$ HCl (MW=339.864); mass spec (MH+, free base) 304; [a]=+29.5 (c=1, MeOH).

Example 7-32

Synthesis of 5-[N'-(S)-2-(4-Methylpentyl)amino-3-methylbutyryl-L-alaninyl]-amino-7-methyl-5,7-dihydro-6H-dibenz[b,d]azepin-6-one Step A: Synthesis of 5-[N'-(S)-2-tert-boc-Amino-3-methylbutyryl-L-alaninyl]-amino-7-methyl-5,7-dihydro-6H-dibenz[b,d]azepin-6-one Following General Procedure D using N-tert-Boc-L-valine and (S)- and (R)-5-(L-alaninyl)-amino-7-methyl-5,7-dihydro-6H-dibenz[b,d]azepin-6-one (Example 3-B), the title compound was prepared.

$C_{28}H_{36}N_4O_5$ (MW=508.615); mass spectroscopy (MH$^+$) 509.

Step B: Synthesis of 5-[N'-(S)-2-Amino-3-methylbutyryl-L-alaninyl]-amino-7-methyl-5,7-dihydro-6H-dibenz[b,d]azepin-6-one Following General Procedure 4-N using the compound made above, the title compound was prepared after passing through an SCX column [5% MeOH(7N $NH_3$)/$CH_2Cl_2$].

$C_{23}H_{28}N_4O_3$ (MW=408.499); mass spectroscopy (MH$^+$) 409.

Step C: Synthesis of 5-[N'-(S)-2-(4-Methylpentyl)amino-3-methylbutyryl-L-alaninyl]-amino-7-methyl-5,7-dihydro-6H-dibenz[b,d]azepin-6-one To a solution of the compound made above (2.00 eq.) in MeOH was added a few drops of HCl-MeOH, 4-methyl-1-pentanal (1.00 eq.) (made by following the procedure described in Tetrahedron Letter, No.31, 1975, pp2647, incorporated herein by reference) and molecular sieves. $NaBH_3CN$ (0.67 eq.) was added. The pH of the reaction mixture was maintained at 5–6 by adding HCl-MeOH. The reaction mixture was stirred at RT overnight. The reaction mixture was basified, extracted with EtOAc, dried over $Na_2SO_4$. Concentration and flash chromatography [silica gel, 5% MeOH (7 N $NH_3$)/$CH_2Cl_2$] gave the title compound.

$C_{29}H_{40}N_4O_3$ (MW=492.660); mass spectroscopy (MH$^+$) 493. Anal. Calcd for $C_{29}H_{40}N_4O_3$: C, 70.70; H, 8.18; N, 11.37; Found: C, 70.92; H, 8.21; N, 11.41.

Example 8-1

Preparation of 3-[N'-3,5-Difluorophenyl-α-azidoacetyl)-L-alaninyl]-3-amino-2,3-dihydro-1-methyl-5-phenyl-1H-1,4-benzodiazepine Following general procedure D using 3,5-difluorophenyl-α-azidoacetic acid and 3-(L-alaninyl)-3-amino-2,3-dihydro-1-methyl-5-phenyl-1H-1,4-benzodiazepine, as described in Example 8-B above, the title compound was prepared. The molecular weight as determined by mass spectrometry (FD) was: (M+H).

Examples 9-1 and 9-2

Preparation of 3-(S)-[2-((1H)-Isoquinoline-3,4-dihydro-3-oxo)-2-methyl-acetyl]-amino-2,3-dihydro-1-methyl-5-phenyl-1H-1,4-benzodiazepin-2-one Step A—Preparation of 2-((1H)-Isoquinoline-3,4-dihydro-3-oxo)-2-methyl-acetic Acid Ethyl Ester Through a solution of 3-isochromanone (1.00 g, 6.75 mmol, Aldrich) in absolute EtOH (100 mL) was passed a stream of HBr gas for 10 minutes, during which time the temperature rose to 40° C. Alanine ethyl ester hydrochloride (1.036 g, 6.75 mmol, Aldrich) was then added and the reaction mixture heated to reflux for 2 hours. The mixture was allowed to cool, then concentrated. The residue was dissolved in absolute EtOH (100 ml), and $K_2CO_3$ (3.66 g, 27 mmol) was added and the mixture heated to reflux for 18 hours. The mixture was allowed to cool, then concentrated. The residue was dissolved in EtOAc (200 mL) and washed with water (1×100 mL). The organic phase was dried over $Na_2SO_4$, filtered, and concentrated. The residue was purified by HPLC, eluting with hexanes/EtOAc (1:1) to yield the title intermediate (204 mg).

$C_{14}H_{17}N_1O_3$ (MW 247.30) mass spectroscopy (MH$^+$) 248.2, (MH$^-$) 246.4; Anal. Calcd. for $C_{14}H_{17}N_1O_3$: C, 68.02; H, 6.88; N, 5.67. Found: C, 68.12; H, 6.88; N, 5.40.

Step B—Preparation of 2-((1H)-Isoquinoline-3,4-dihydro-3-oxo)-2-methyl-acetic Acid To the intermediate from step A (170 mg, 9.688 mmol) in 1,4-dioxane (3 mL) and water (1 mL) was added LiOH (57.7 mg, 1.38 mmol) and the resulting mixture was stirred at ambient temperature for 2.5 hours. The mixture was diluted into EtOAc (100 mL) and carboxylate extracted into water (100 mL). The aqueous extract was acidified with 0.1 M aq. HCl and the product extracted into EtOAc. The EtOAc extract was dried over $Na_2SO_4$, filtered, and concentrated to give the title intermediate as a white solid (150 mg).

$C_{12}H_{13}N_1O_3$ (MW 219.24) mass spectroscopy (MH$^+$) 220.2, (MH$^-$) 218.4; Anal. Calcd. for $C_{12}H_{13}N_1O_3$: C, 65.75; H, 5.94; N, 6.39. Found: C, 66.22; H, 6.01; N, 6.03.

Step C—Preparation of 3-(S)-[2-((1H)-Isoquinoline-3,4-dihydro-3-oxo)-2-methyl-acetyl]-amino-2,3-dihydro-1-methyl-5-phenyl-1H-1,4-benzodiazepin-2-one To the intermediate from step B (112 mg, 0.511 mmol) in THF (5 mL) was added 3-(S)-(amino-2,3-dihydro-1-methyl-5-phenyl-1H-1,4-benzodiazepin-2-one (136 mg, 0.511 mmol), 1-(3-dimethylaminopropyl)-3-ethyl-carbodiimide hydrochloride (98 mg, 0.511 mmol), 1-hydroxybenzotriazole hydrate (70 mg, 0.511 mmol), and N,N-diisopropylethylamine (88 µL, 0.511 mmol). The resulting mixture was stirred overnight at ambient temperature, then diluted into EtOAc (100 mL) and washed with 10% aqueous citric acid (1×50 mL), brine (1×50 mL), and 1M aqueous $K_2CO_3$ (1×50 mL). The organic layer was dried over $Na_2SO_4$, filtered, concentrated, and the residue purified by HPLC eluting with hexanes/EtOAc (1:1 gradient to 1:3) to provide the two separated isomers.

Isomer 1 (60 mg): $C_{28}H_{26}N_4O_3$ (MW 466.54) mass spectroscopy 466.05; Anal. Calcd. for $C_{28}H_{26}N_4O_3$: C, 72.10; H, 5.58; N, 12.02. Found: C, 71.99; H, 5.80; N, 11.73. Optical rotation: $[\ ]^{20}_D$=18.52 (c 0.5, MeOH); m.p. 125–126 C.

Isomer 2 (76 mg): $C_{28}H_{26}N_4O_3$ (MW 466.54) mass spectroscopy 466.02; Anal. Calcd. for $C_{28}H_{26}N_4O_3$: C, 72.10; H, 5.58; N, 12.02. Found: C, 72.38; H, 5.50; N, 11.72. Optical rotation: $[\ ]^{20}_D$=−137.9 (c 0.5, MeOH); m.p. 209–210 C.

Example 10-1

Preparation of 3-[N'-3,5-Difluorophenyl-acetamido)-L-alaninyl]-3-amino-2,3-dihydrol-methyl-5-phenyl-1H-1,4benzodiazepine Following general procedure D, using difluorophenylacetamido and 3-(L-alaninyl)-3-amino-2,3-dihydrol-methyl-5-phenyl-1H-1,4-benzodiazepine, as described in Example 8-B above, the title compound was prepared. The molecular weight as determined by mass spectrometry (FD) was: (M+H).

Example 10-2

Preparation of 5-{N'-(N-Acetyl-N-phenylglycinyl)-L-alaninyl}-amino-7-methyl-5,7-dihydro-6H-dibenz[b,d]azepin-6-one Following one or more of the general procedures outlined above, using acetyl-N-phenylglycine and 5-(L-alaninyl)-amino-7-methyl-5,7-dihydro-6H-dibenz[b,d]azepin-6-one, as described in Example 7-B, the title compound was prepared. The molecular weight as determined by mass spectrometry (FD) was: 485 (M+H).

Additionally, each of the carboxylic acids described above (or the carboxylic acids prepared by hydrolysis of the above carboxylic acid esters) could be coupled with an appropriate α-amino lactam to provide for compounds of the formulas:

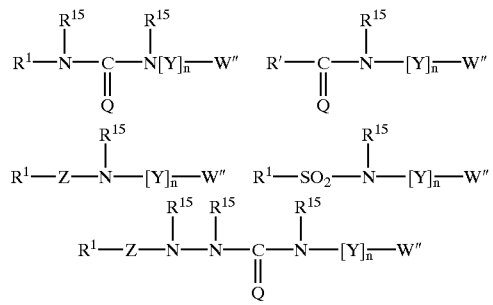

where $R^1$—(NR$^5$)$_2$)$_1$—C(X)—NR$^5$—Y, $R^1$—Z—NR$^5$—Y, —R$_1$—SO$_2$—NR$^5$—Y, R$_1$—Z—NR$^5$—NR$^5$—C(O)—NR$^5$—Y and

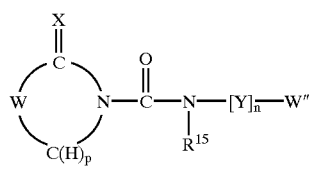
are the residues of the associated carboxylic acids (i.e., $R^1$, $R^2$, $R^5$, X, X', X", Z, l and n are defined above), Y=—$CHR^2$—C(O)—, and W" is selected from the following structures:
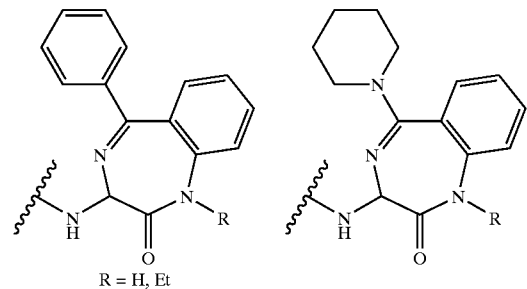
R = H, Et
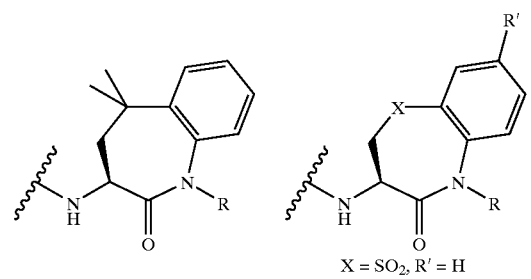
X = $SO_2$, R' = H
X = O, R' = F
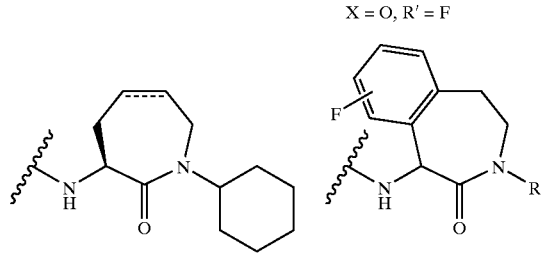
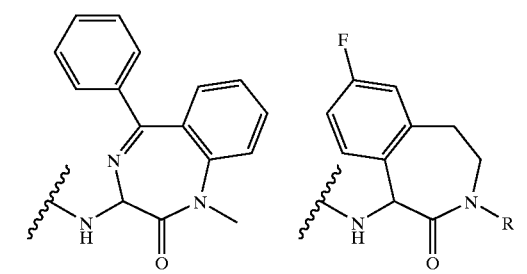
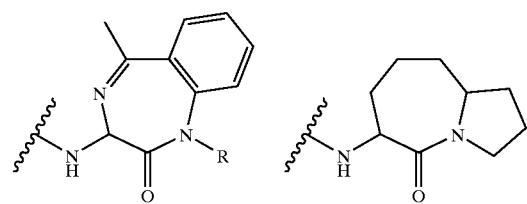
-continued
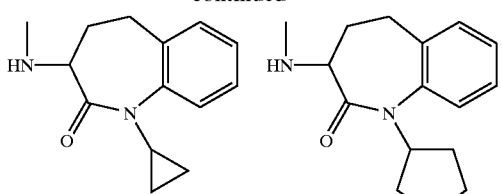
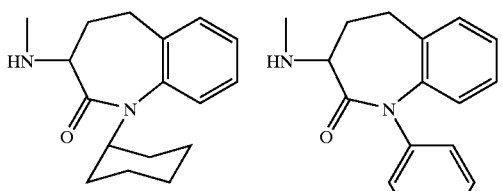
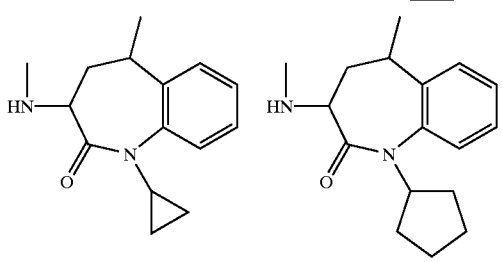
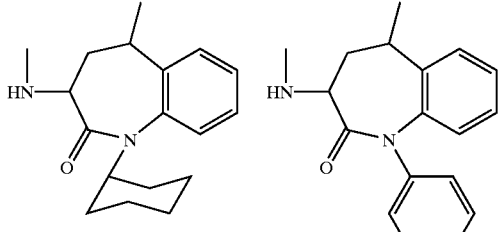
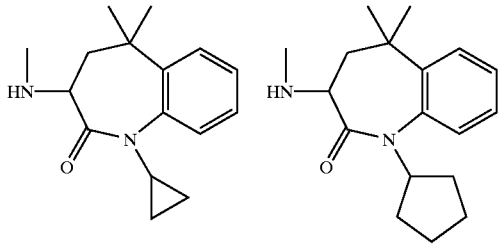
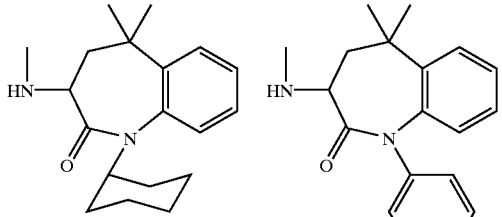
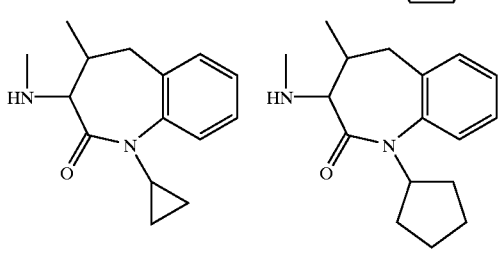

209
-continued
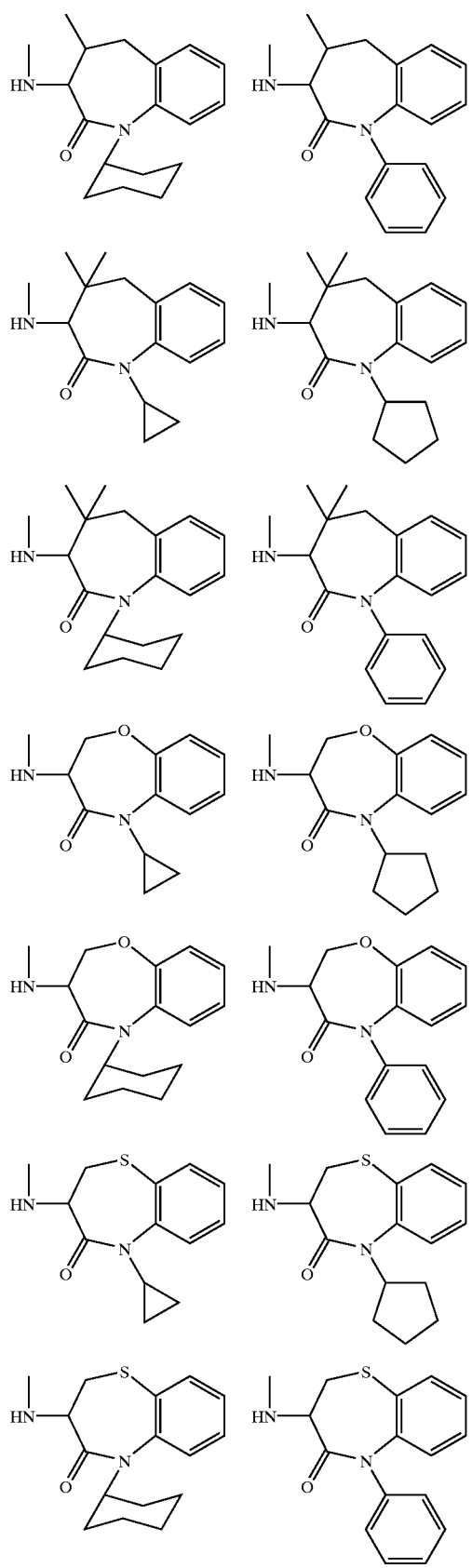
210
-continued
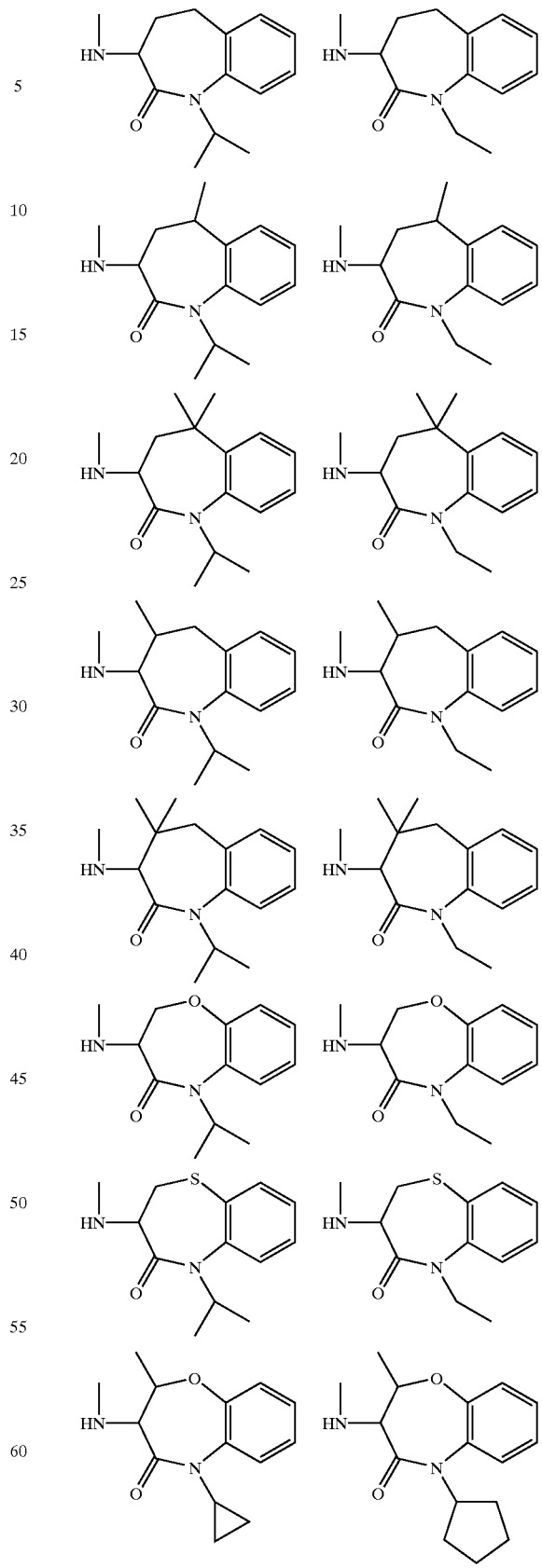

211
-continued
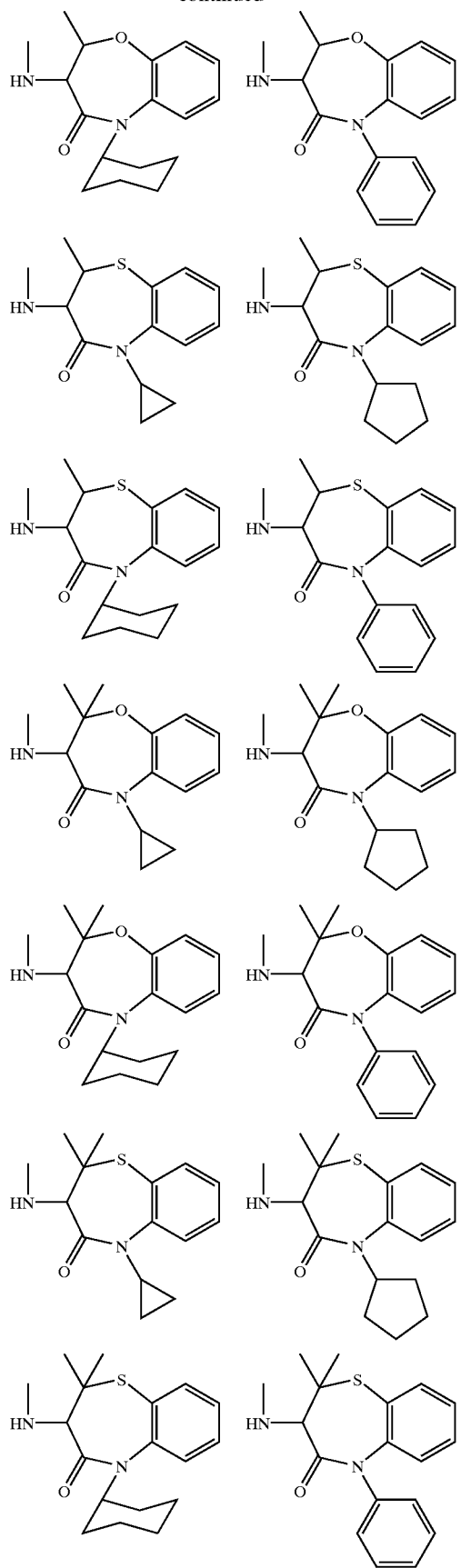
212
-continued
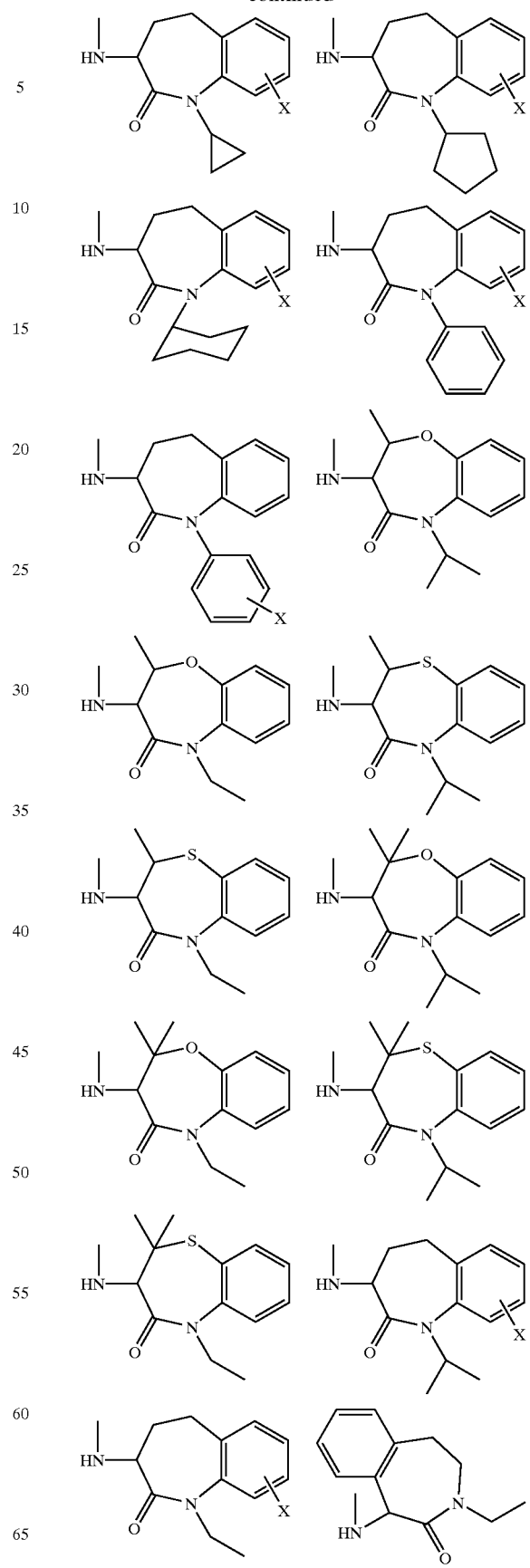

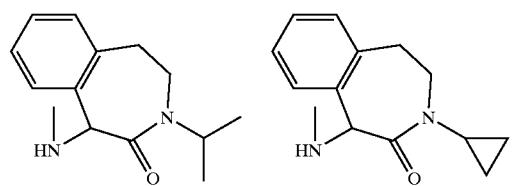
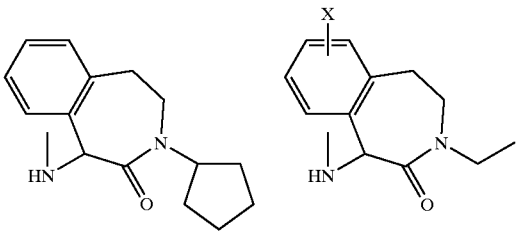
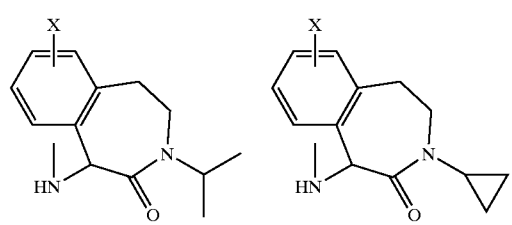
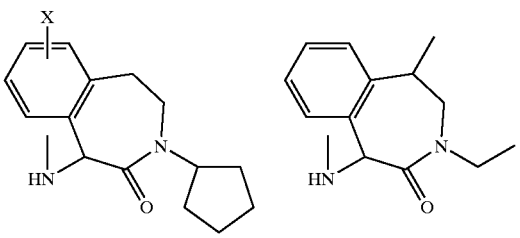
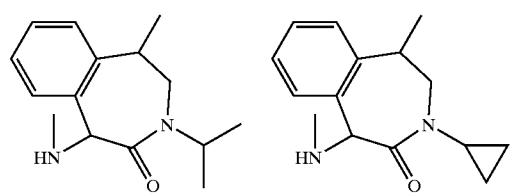
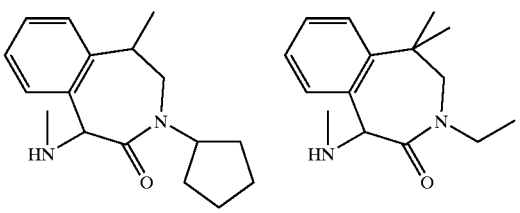
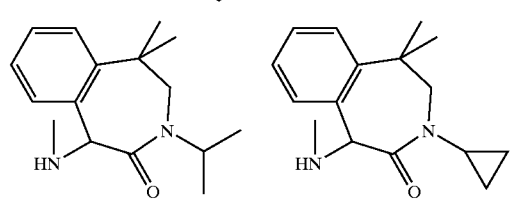
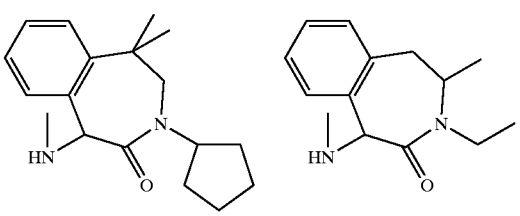
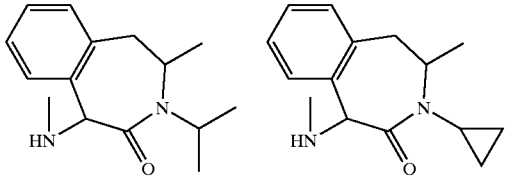
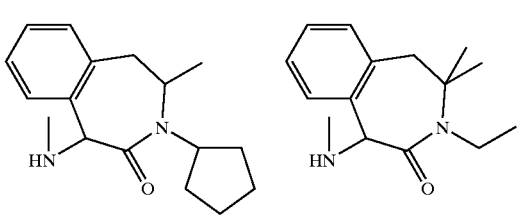
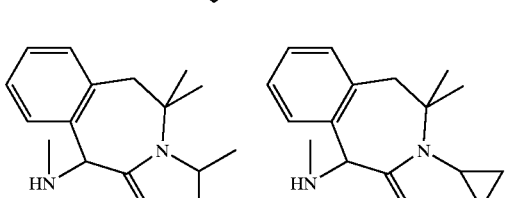
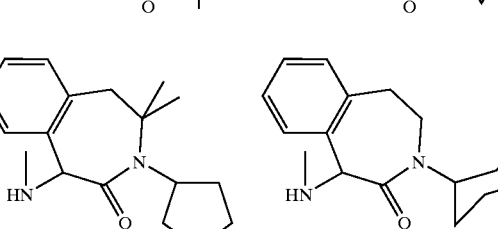
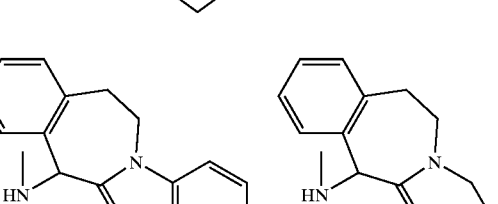
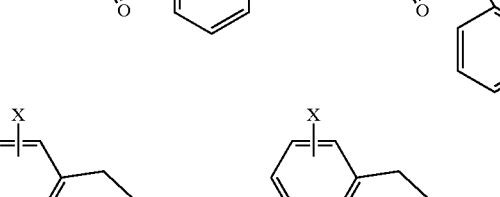
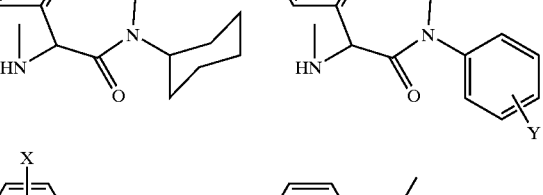
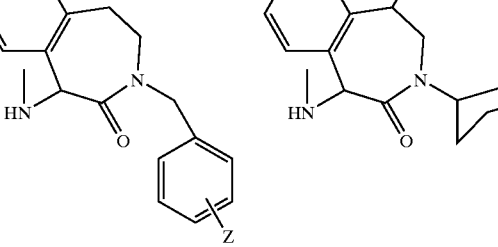

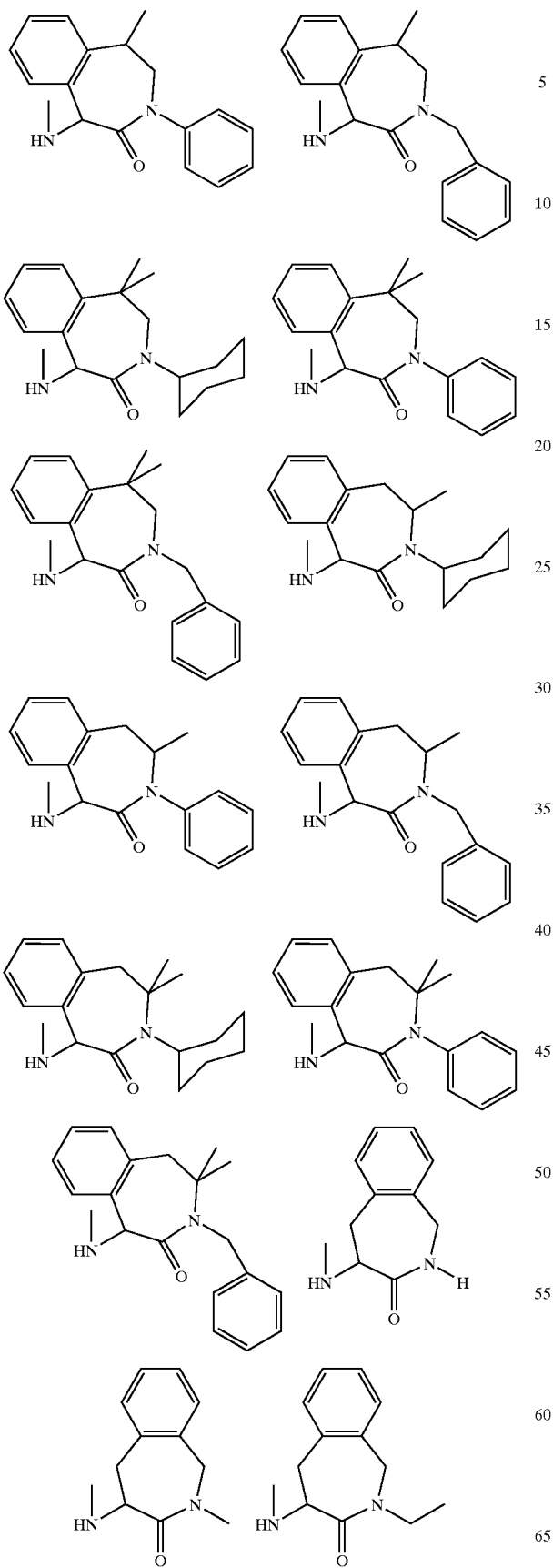
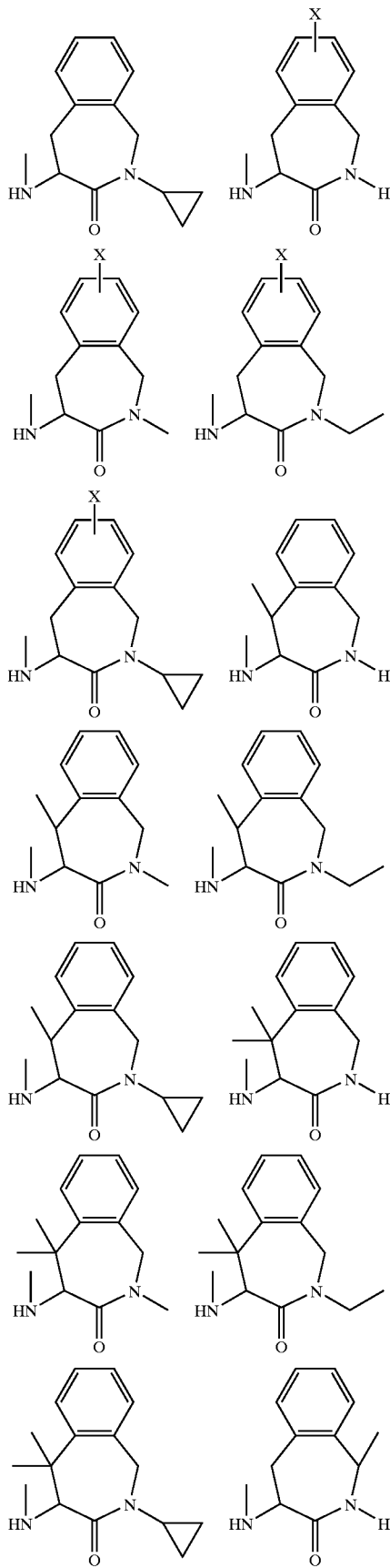

217
-continued
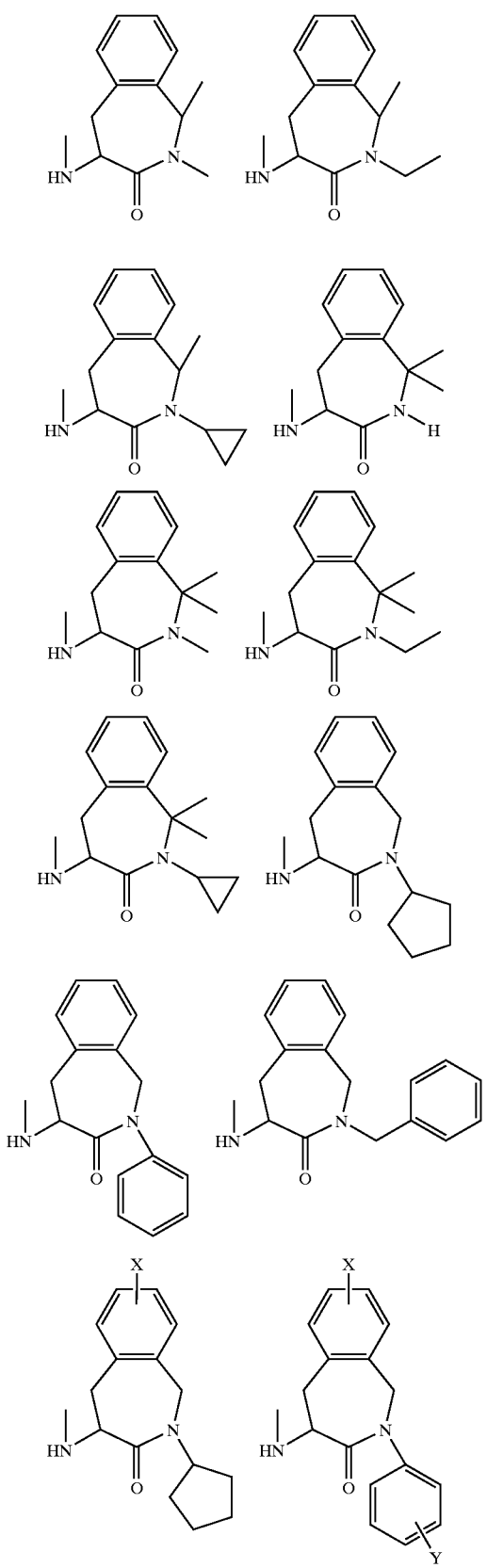
218
-continued
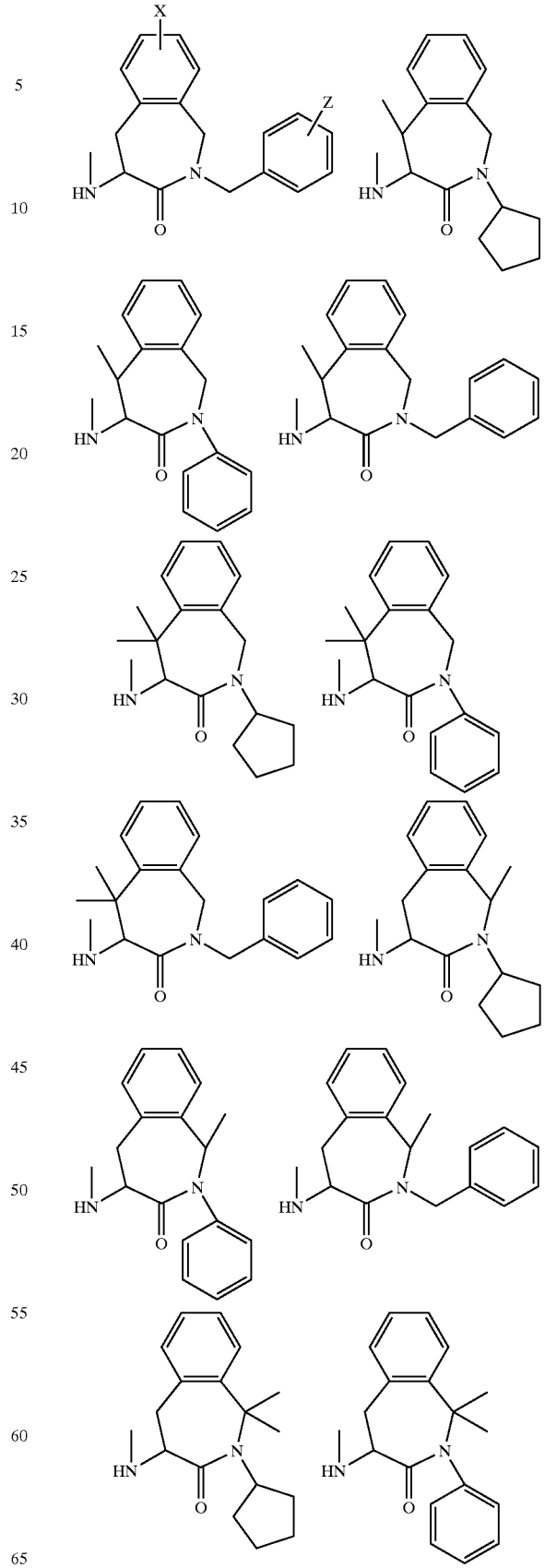

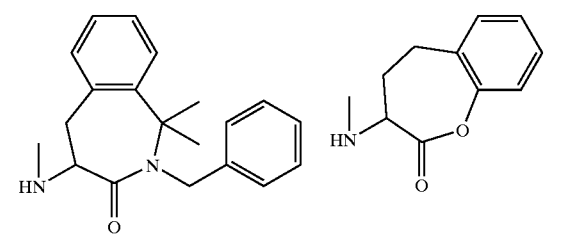
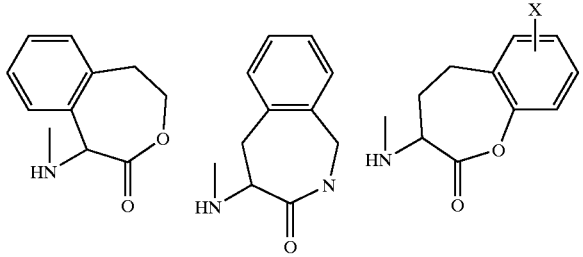
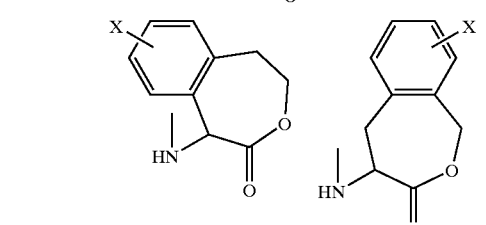
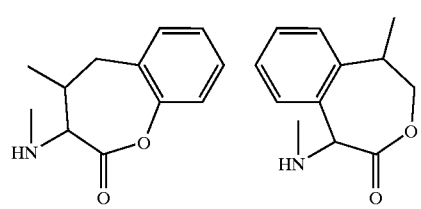
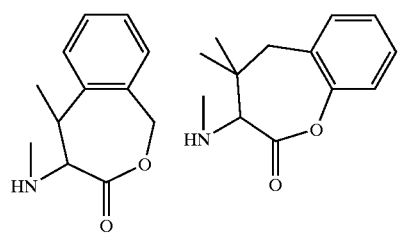
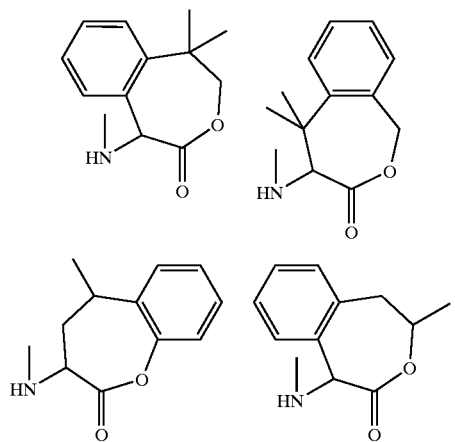
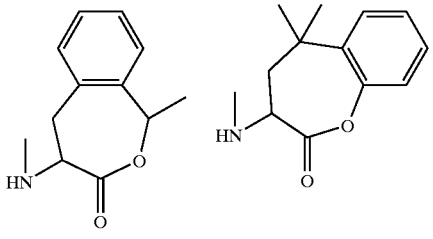
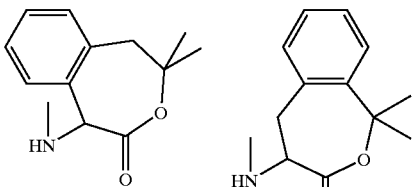
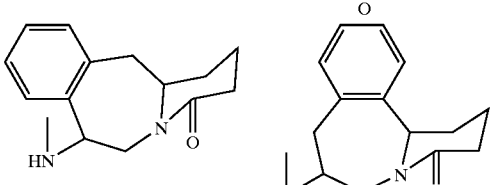
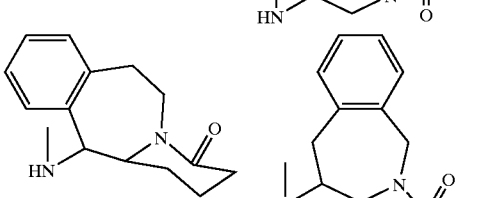
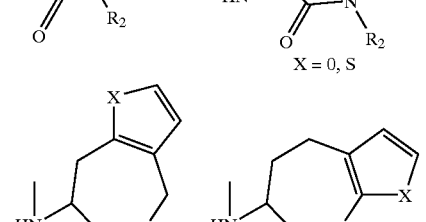
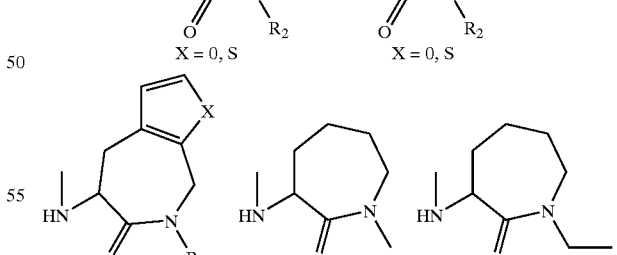
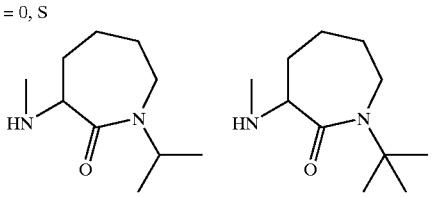

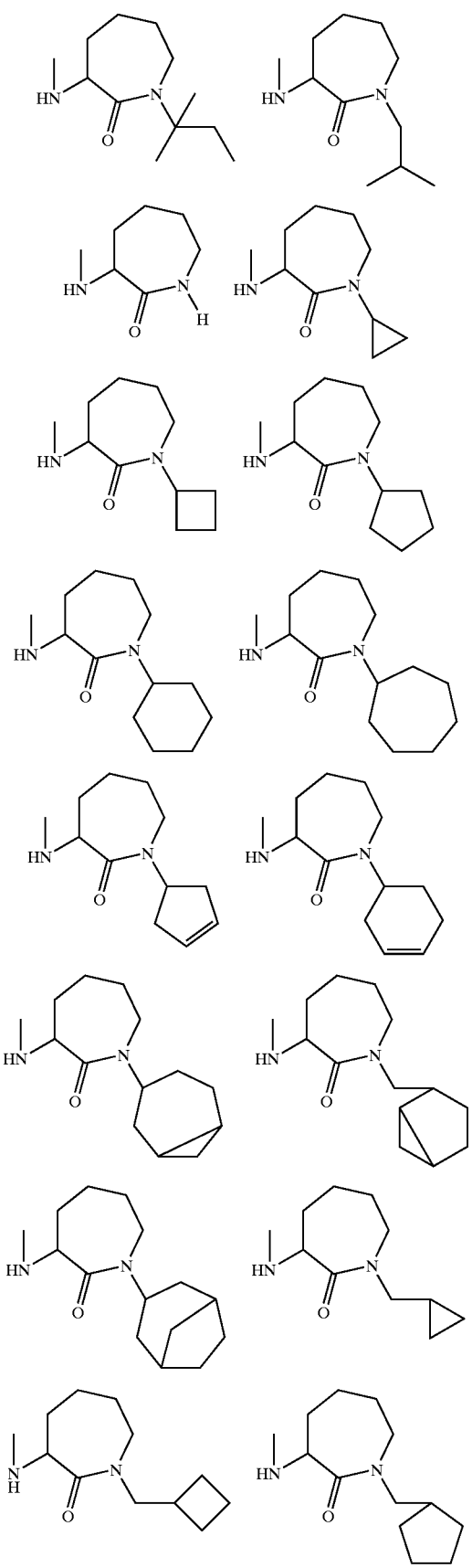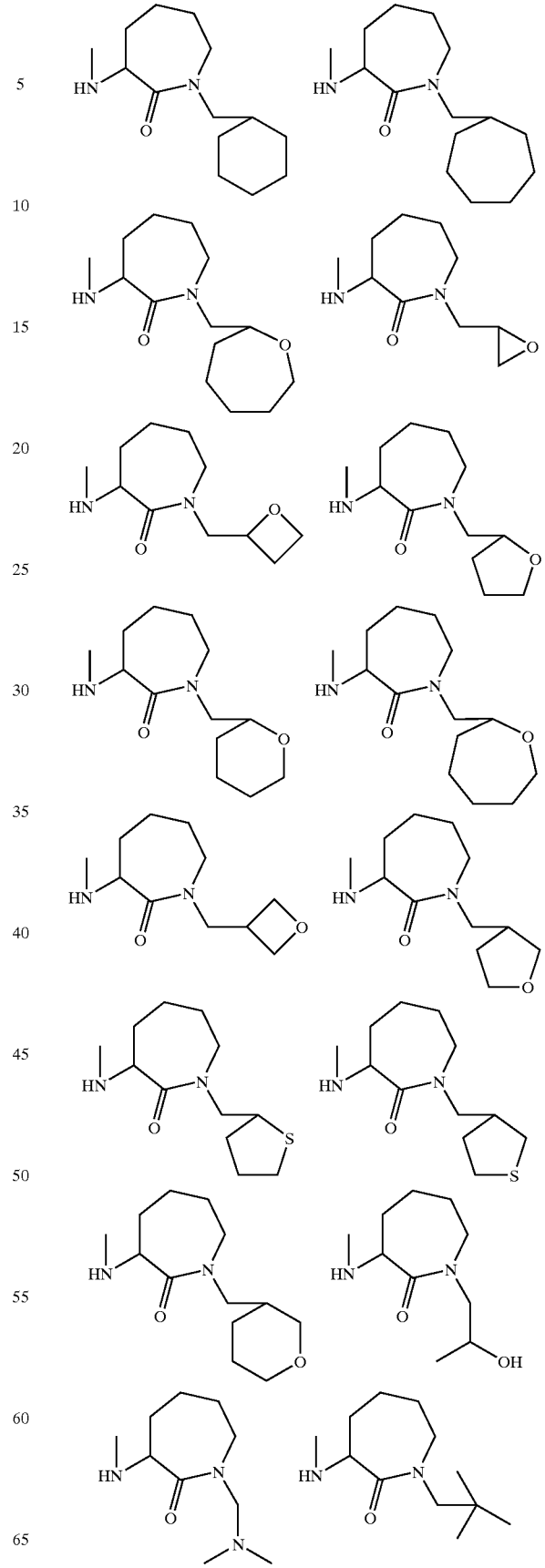

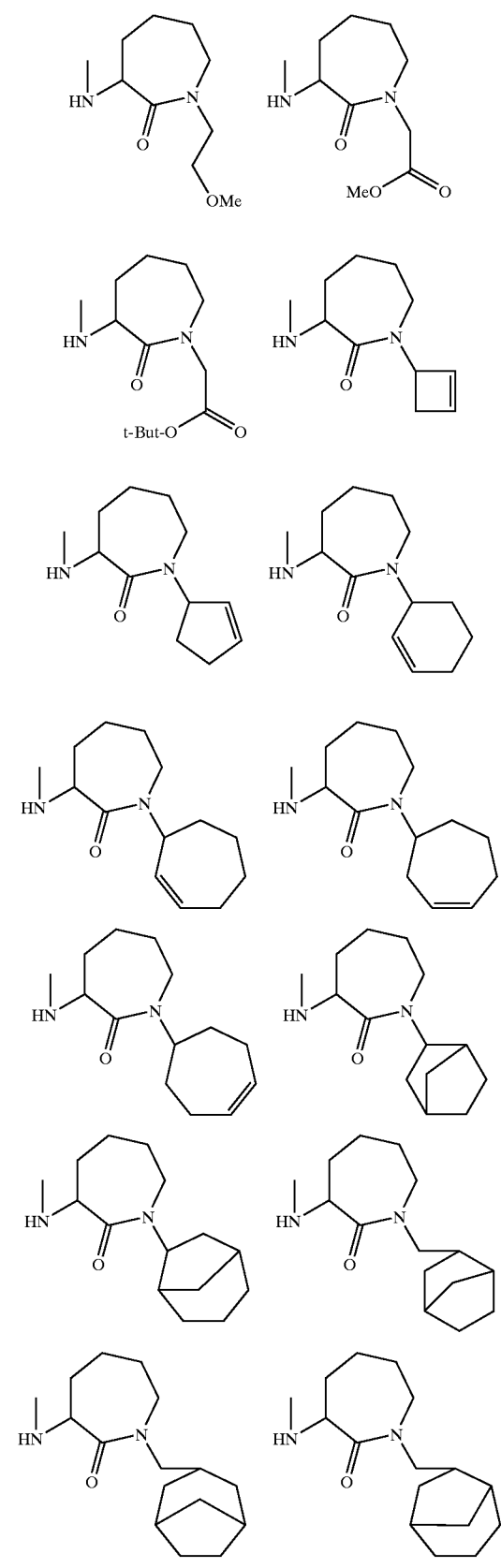
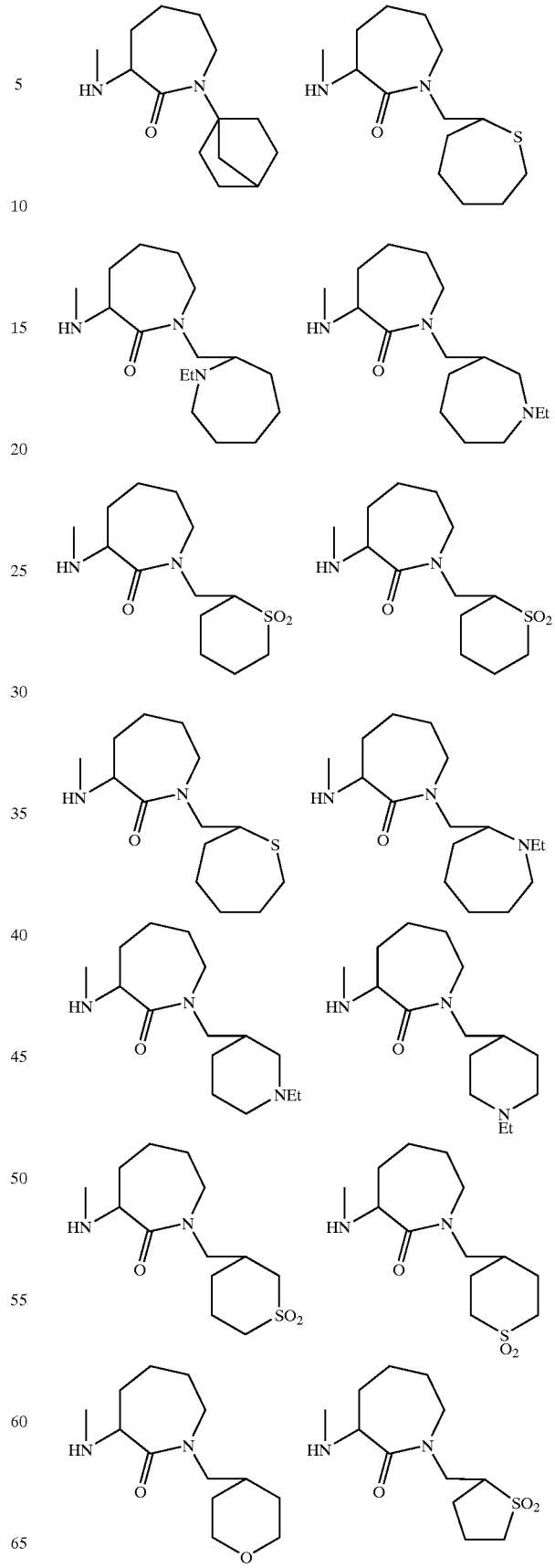

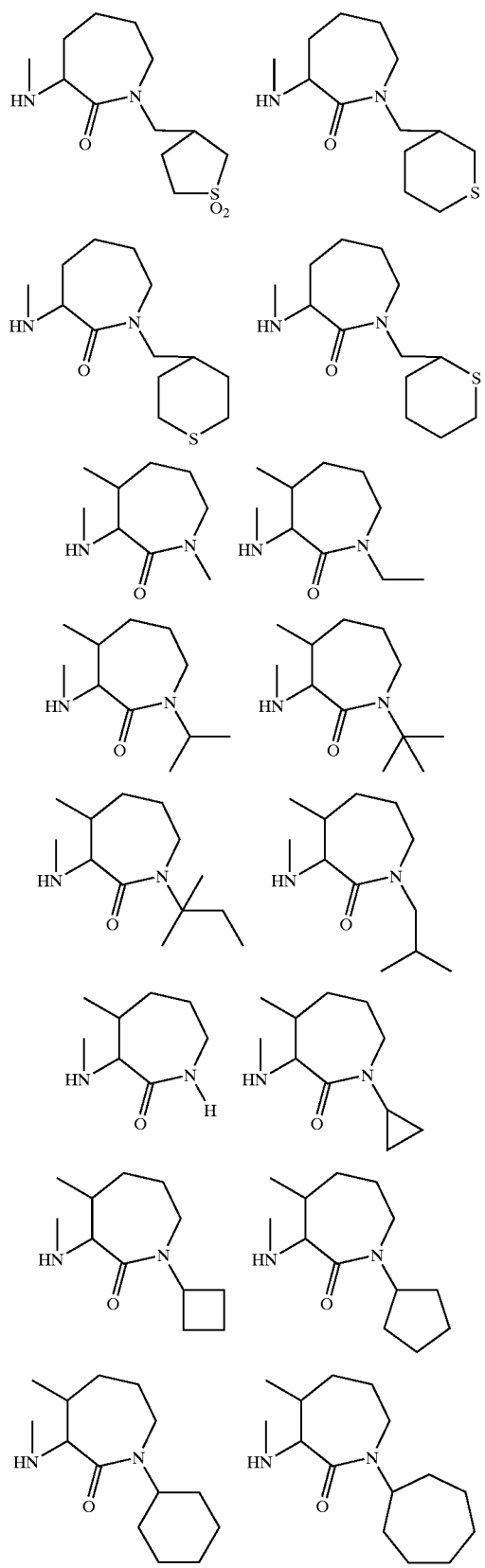
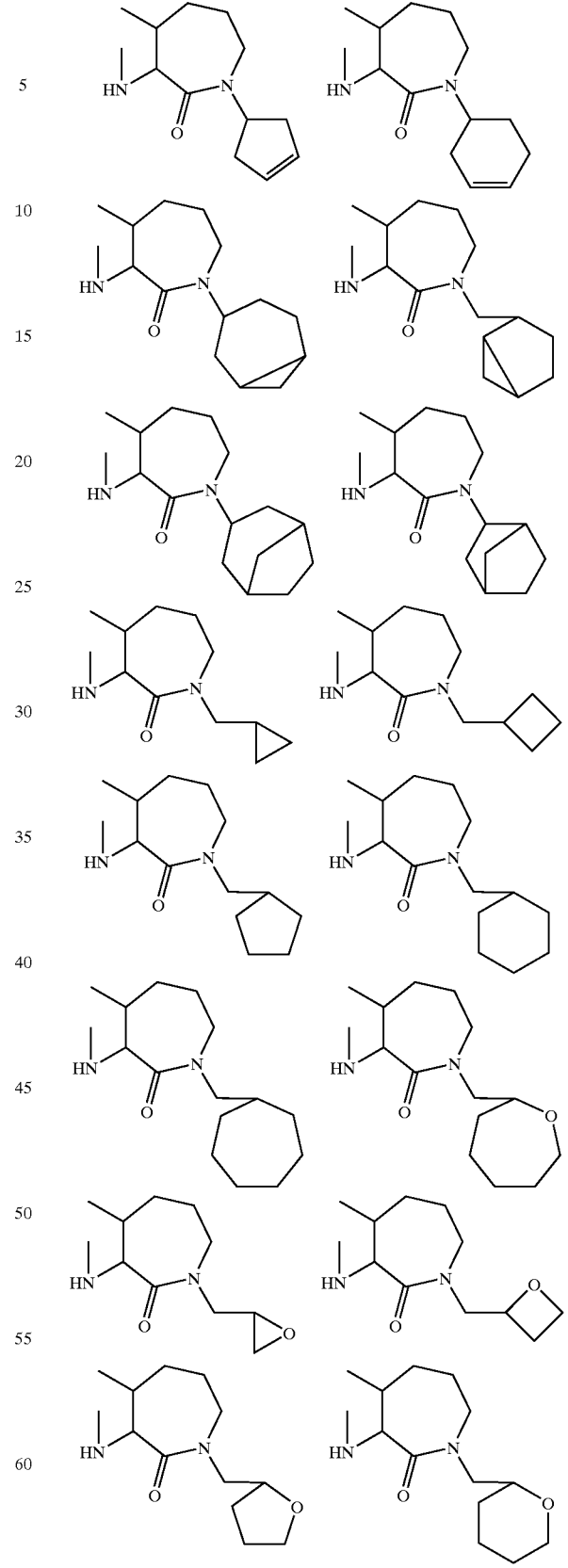

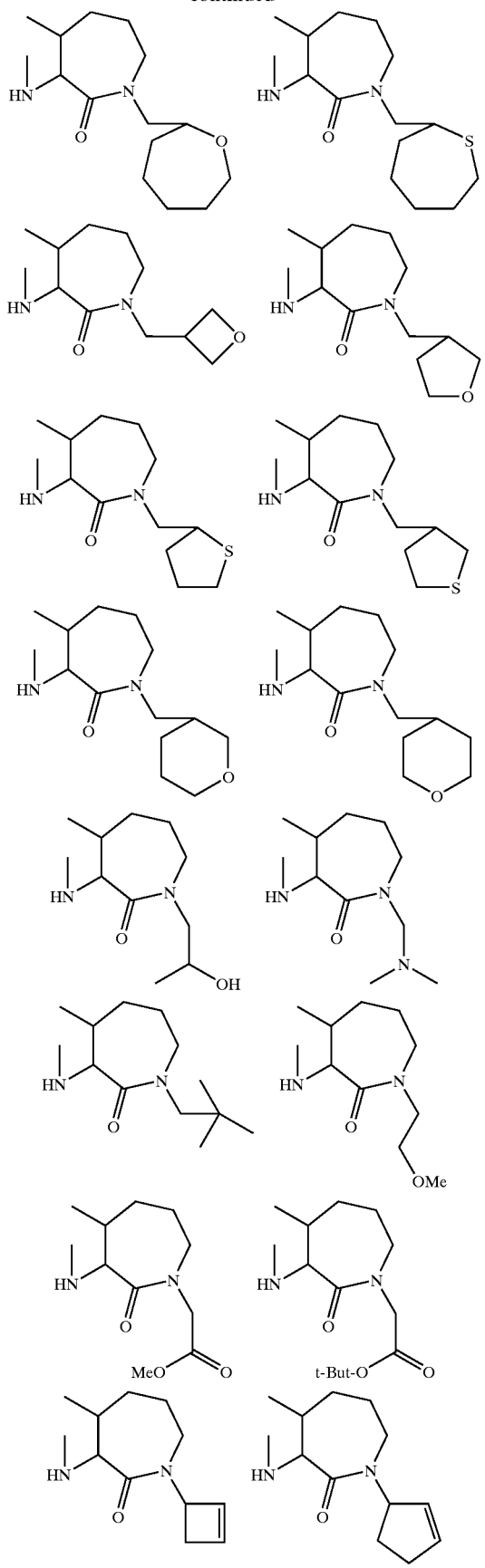
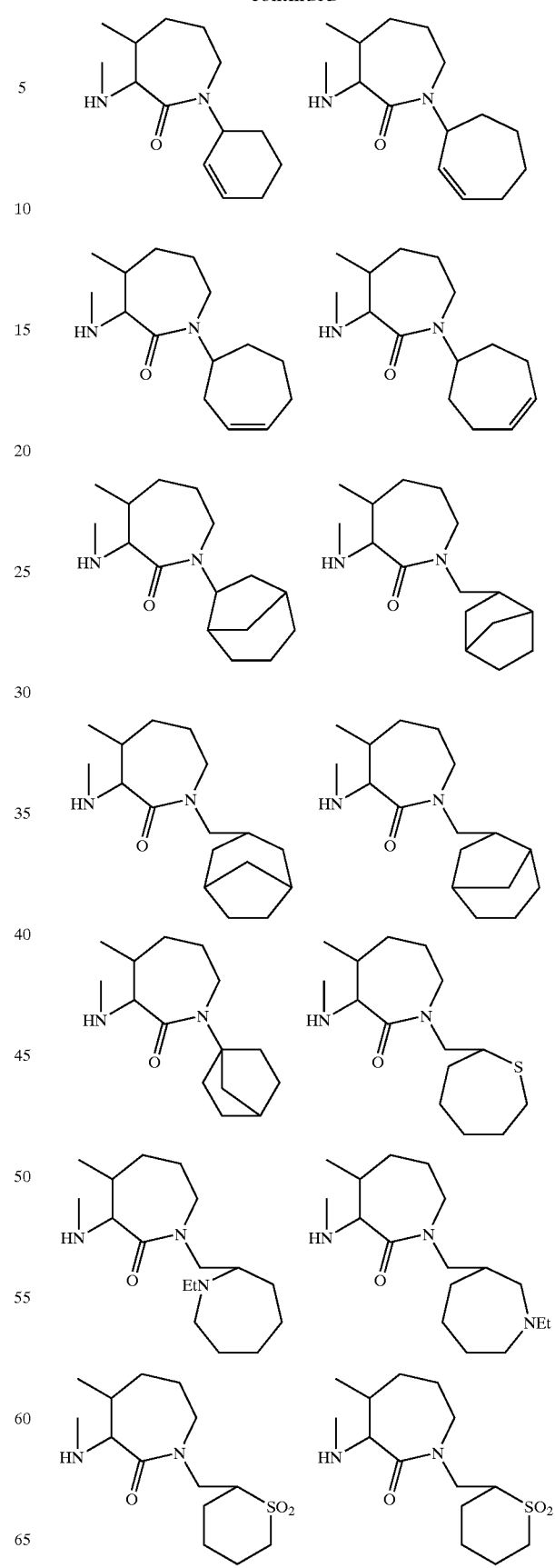

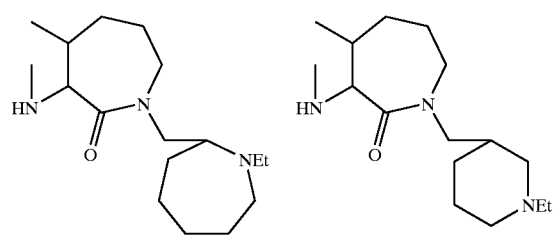
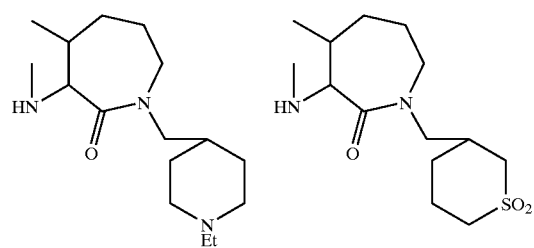
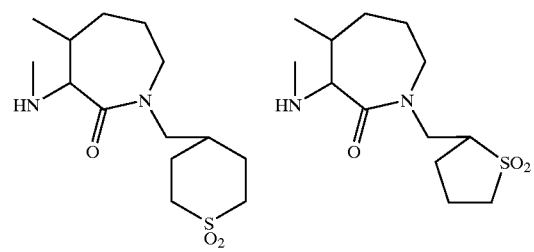
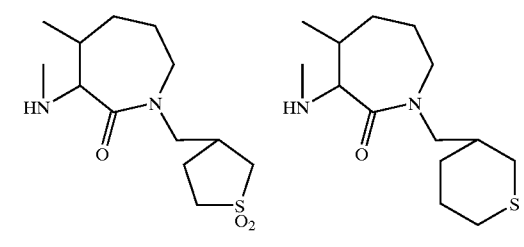
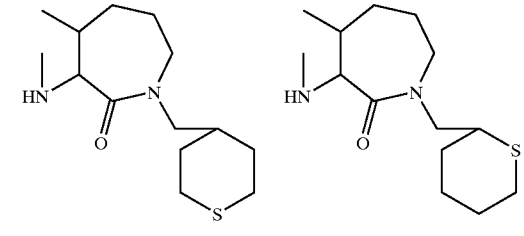
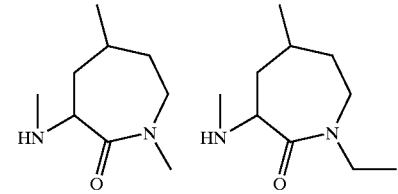
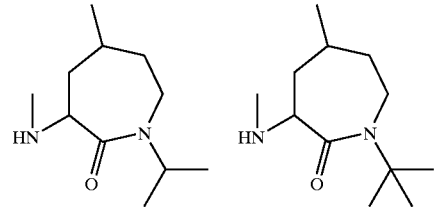
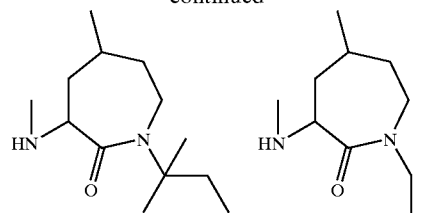
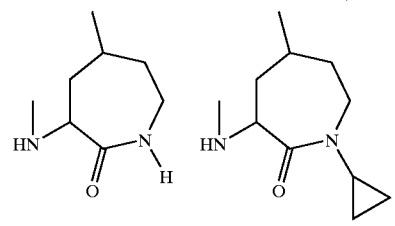
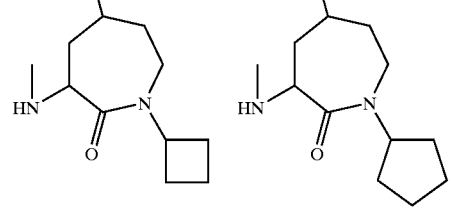
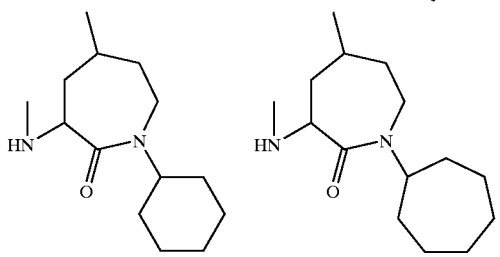
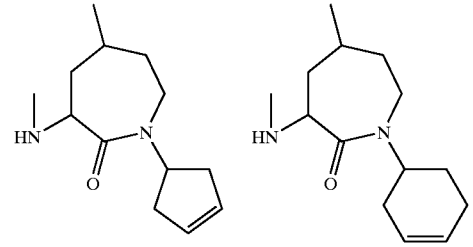
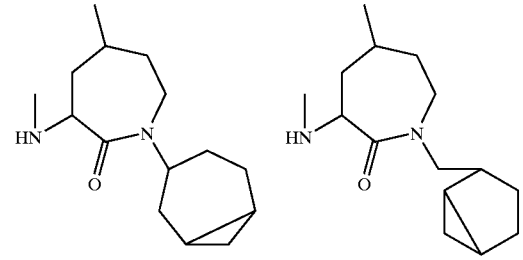
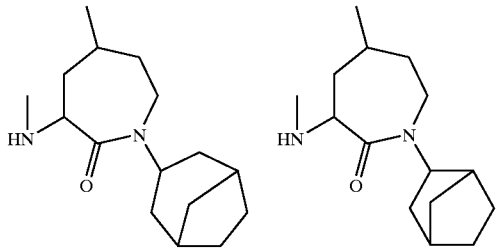

231
-continued
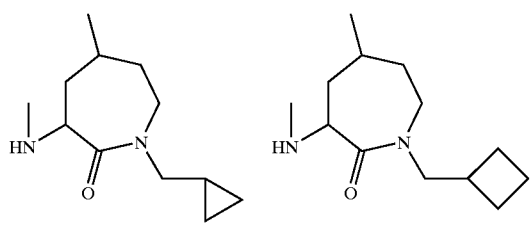
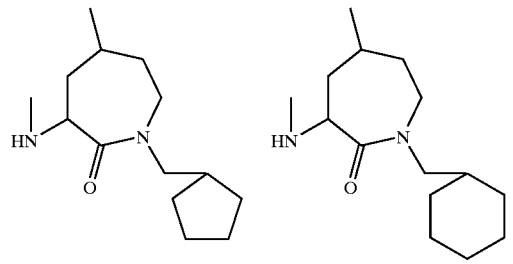
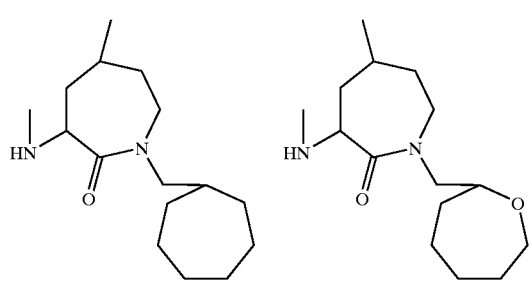
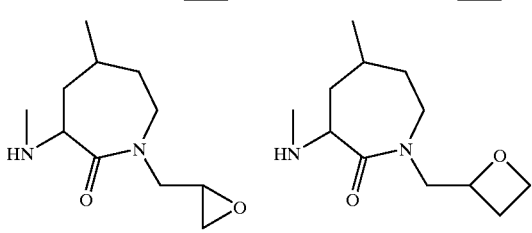
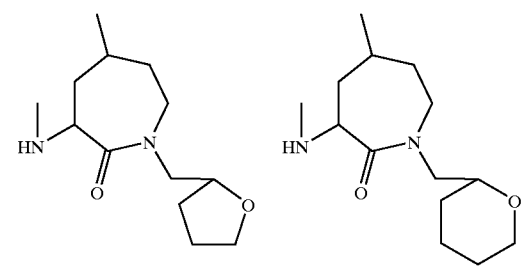
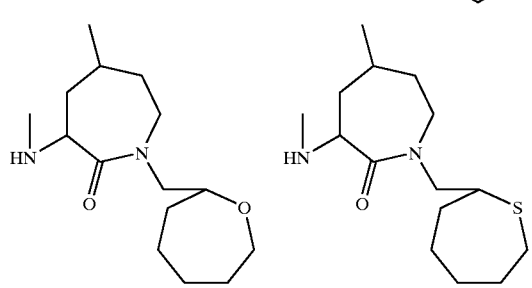
232
-continued
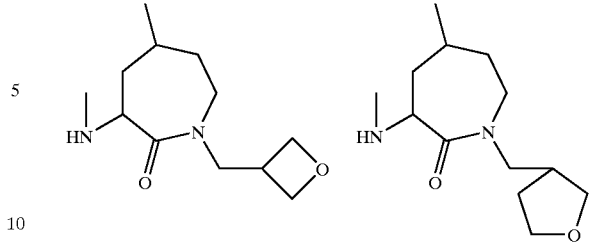
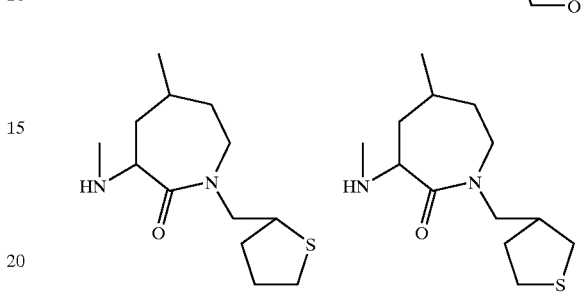
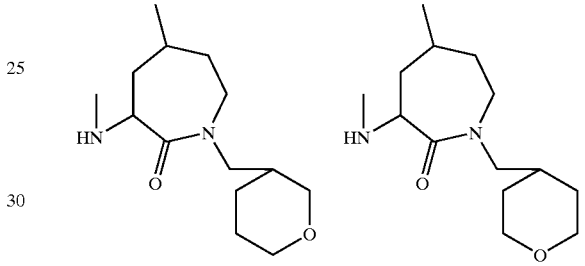
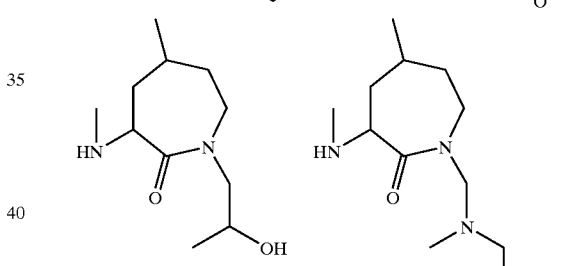
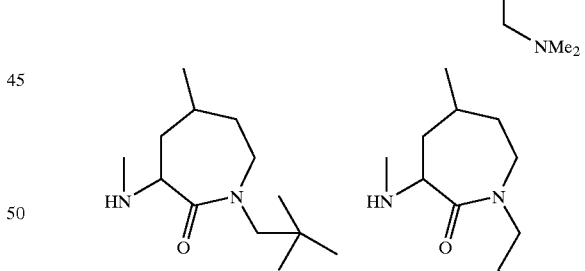
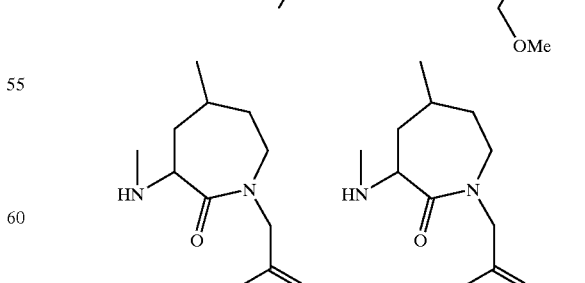

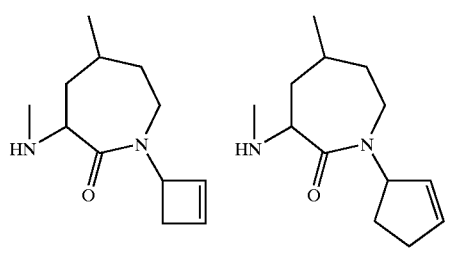
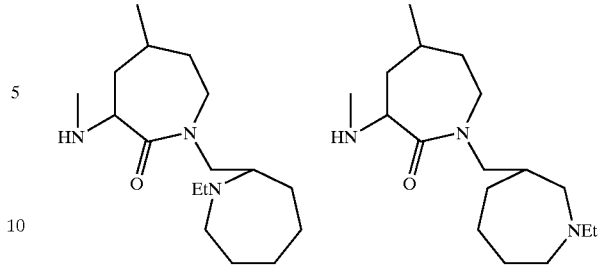
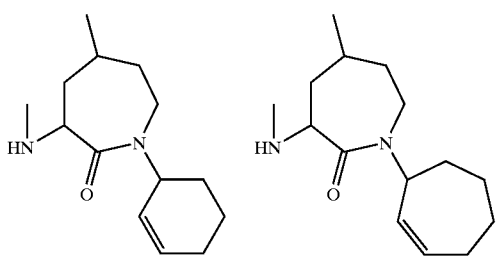
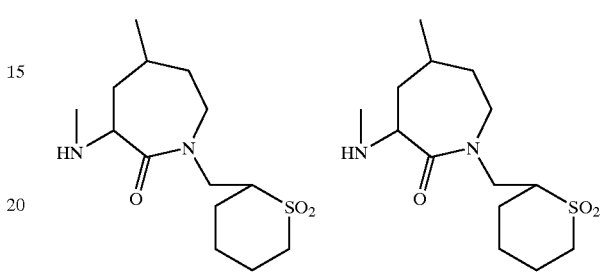
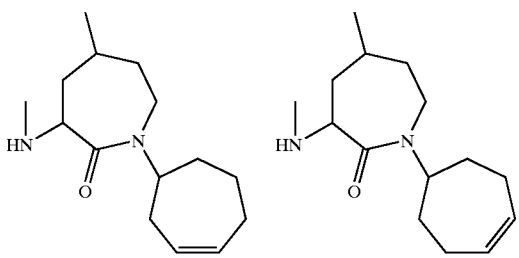
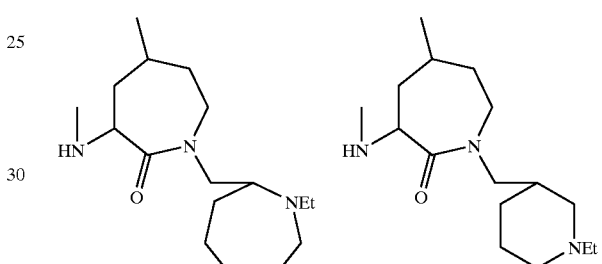
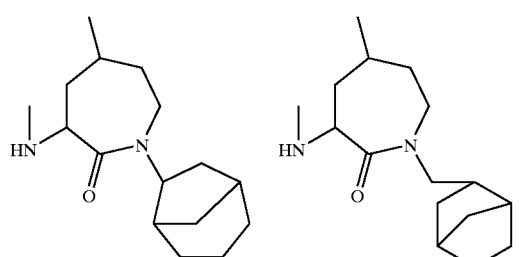
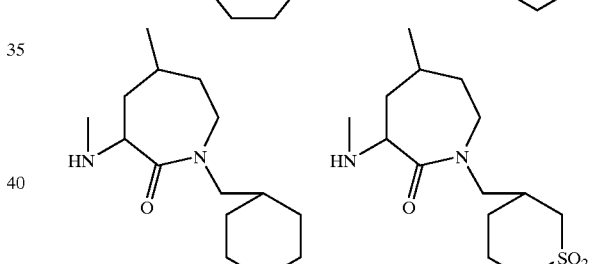
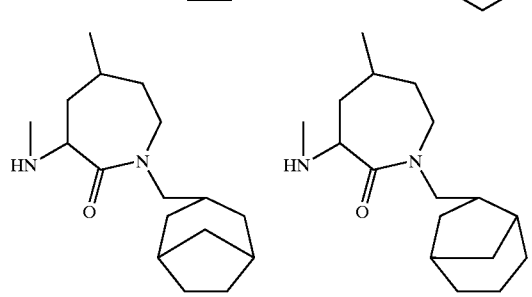
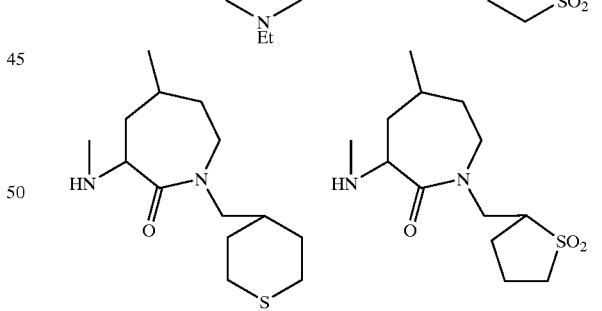
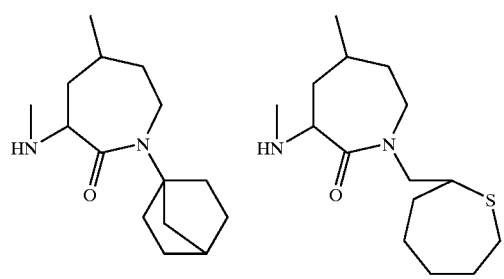
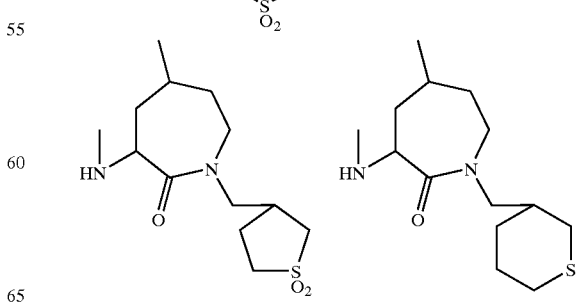

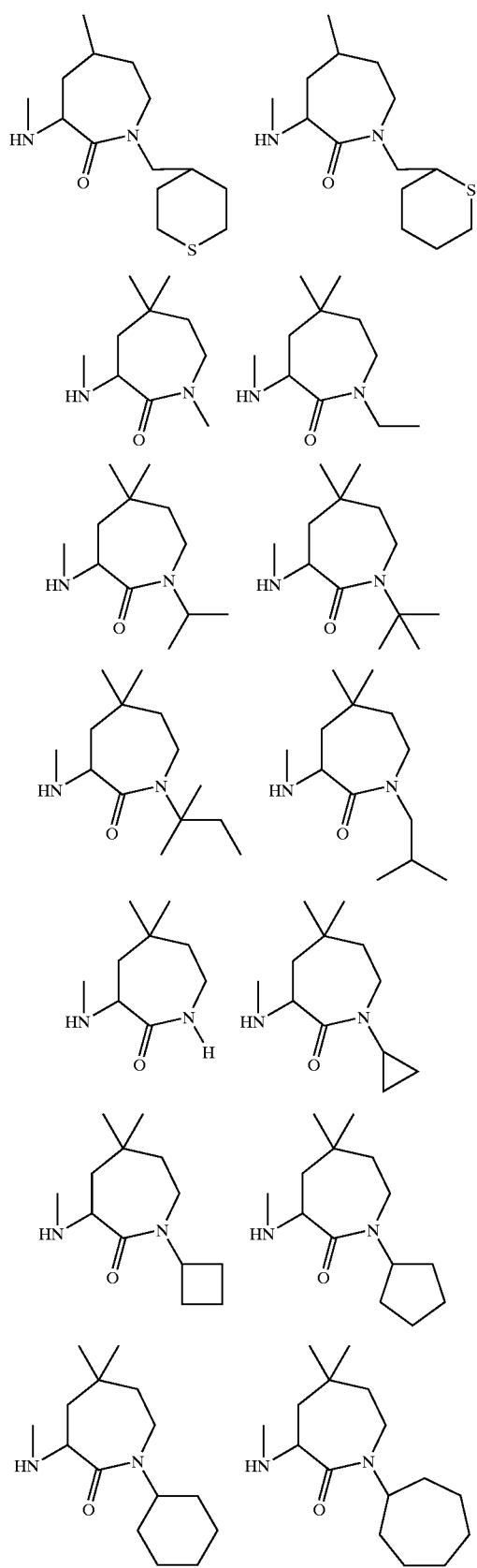
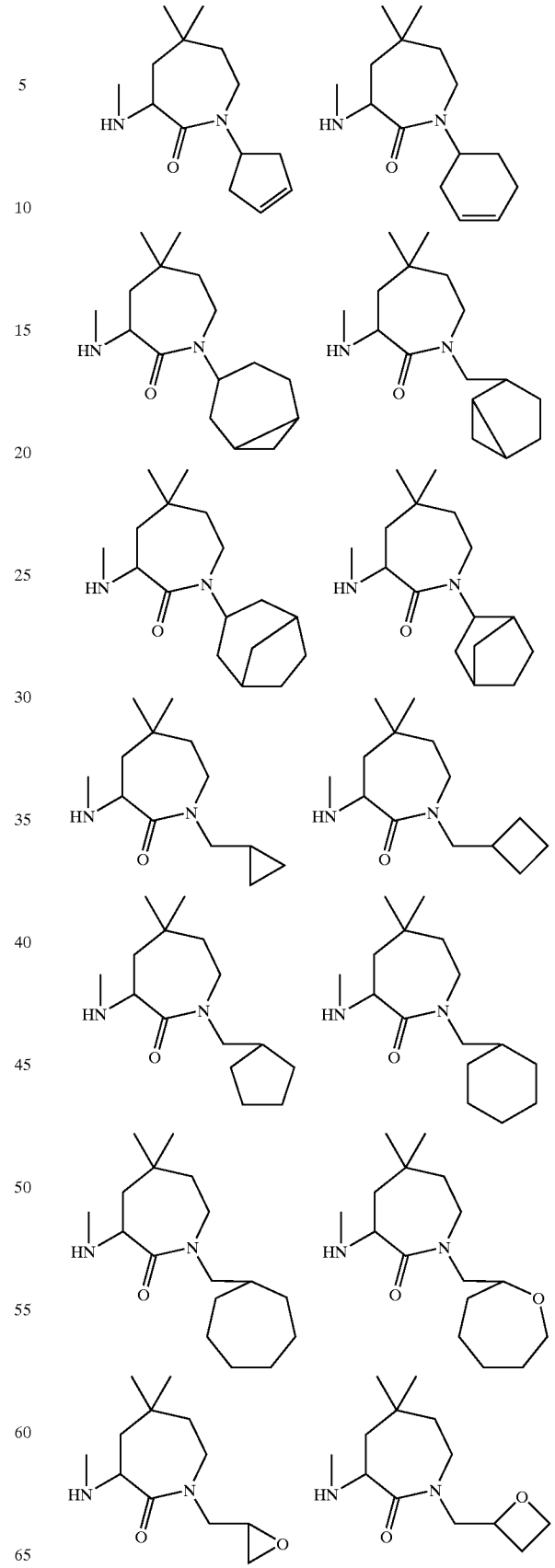

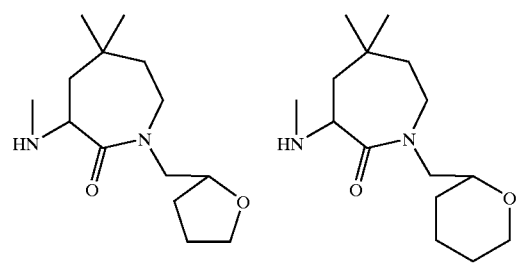
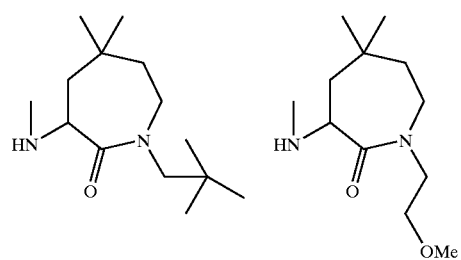
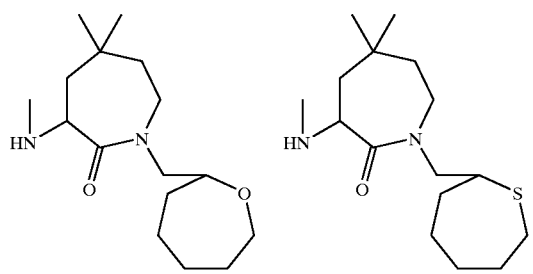
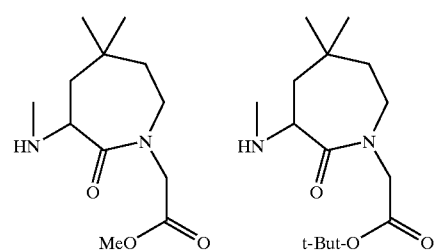
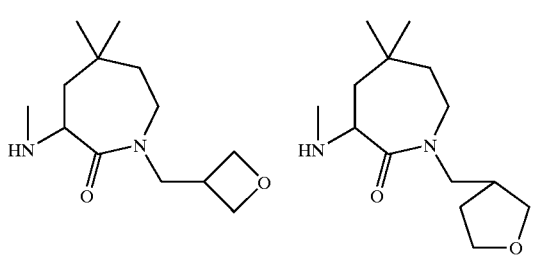
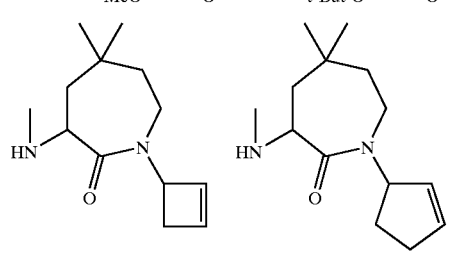
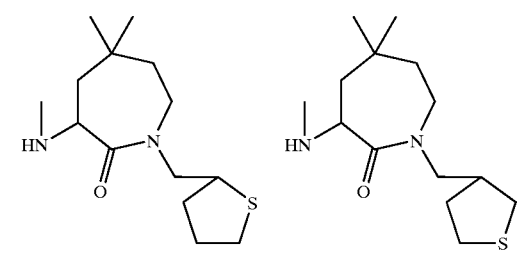
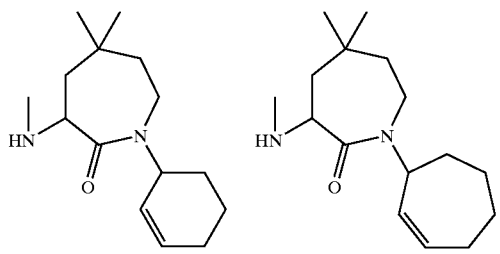
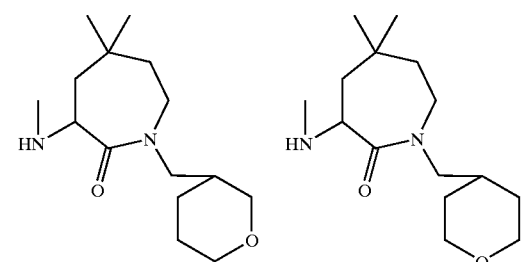
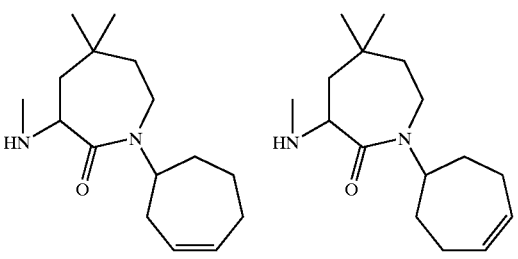
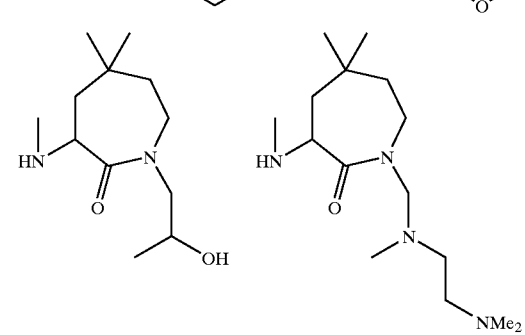
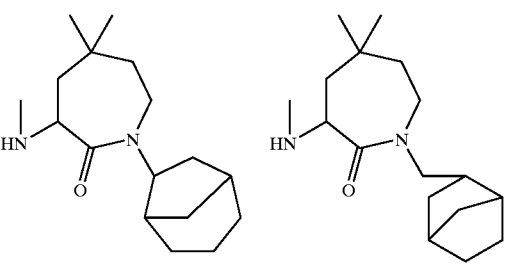

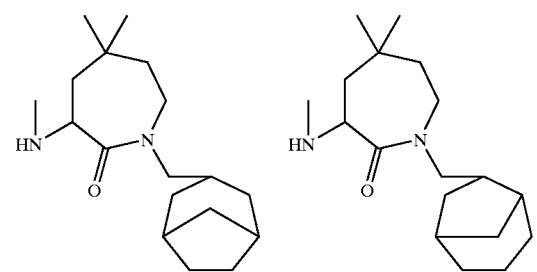
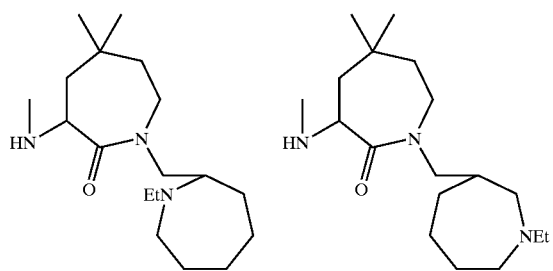
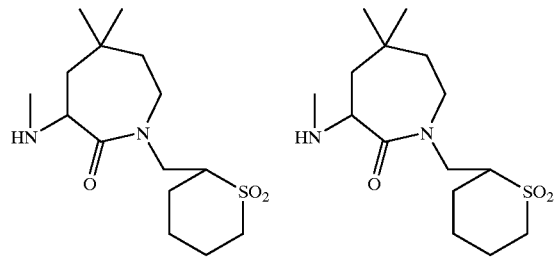
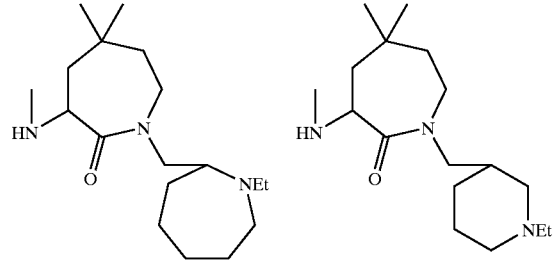
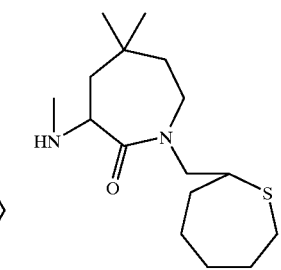
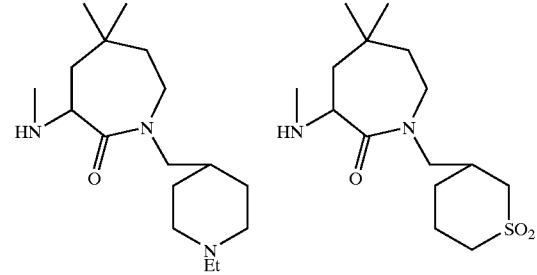
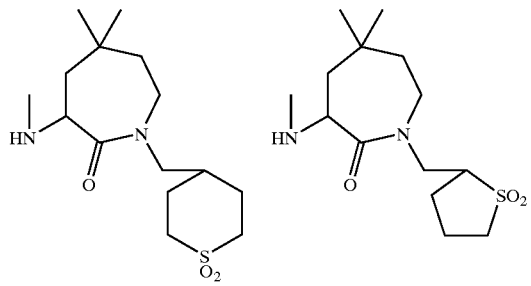
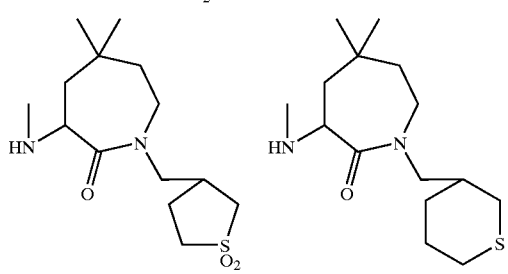
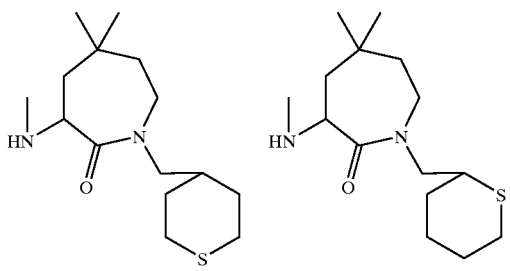
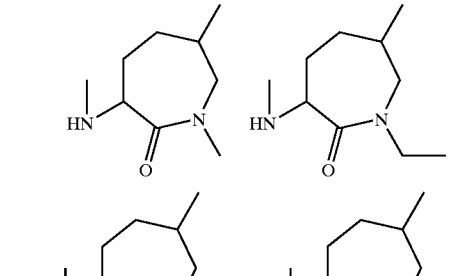
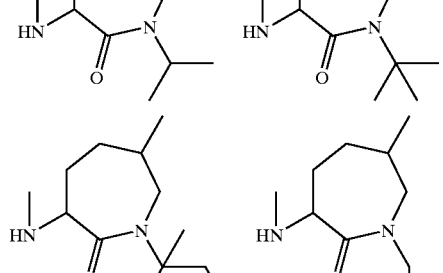
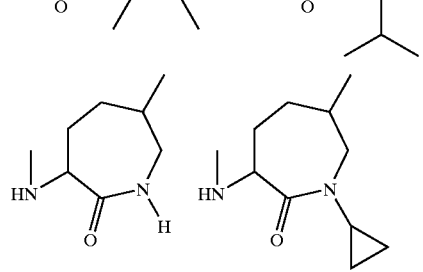

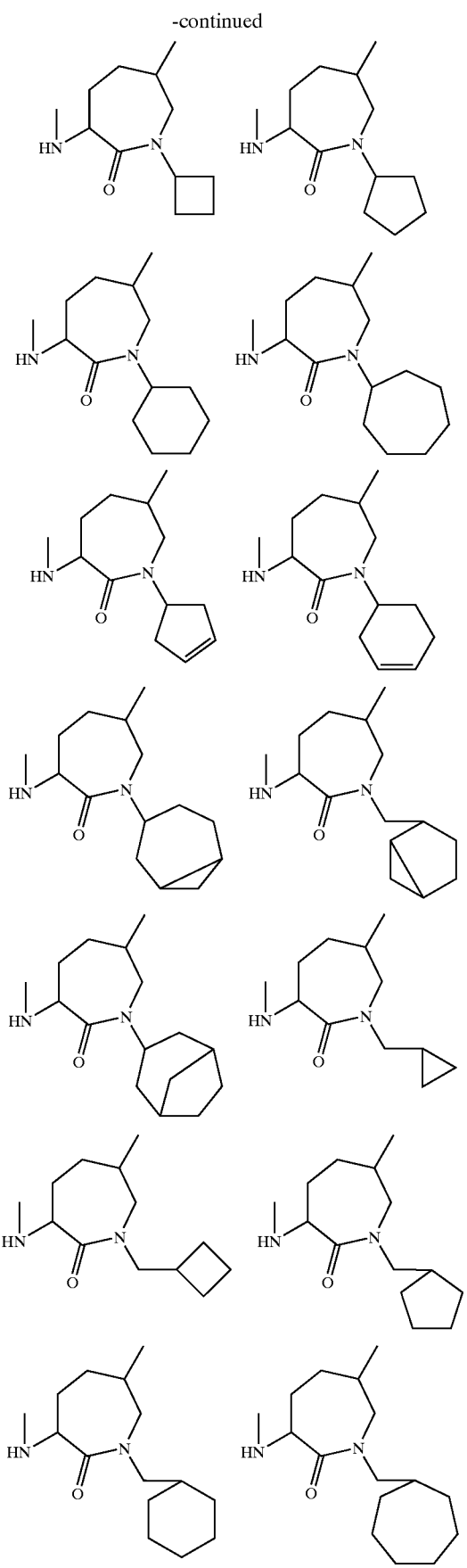
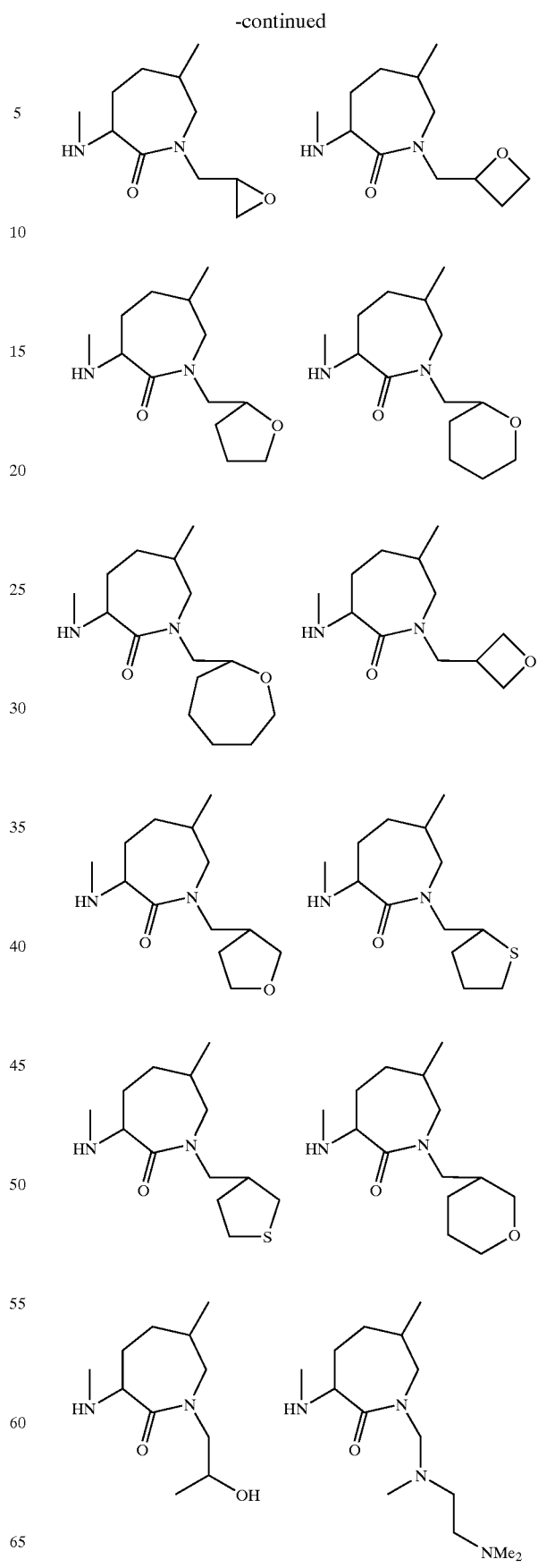

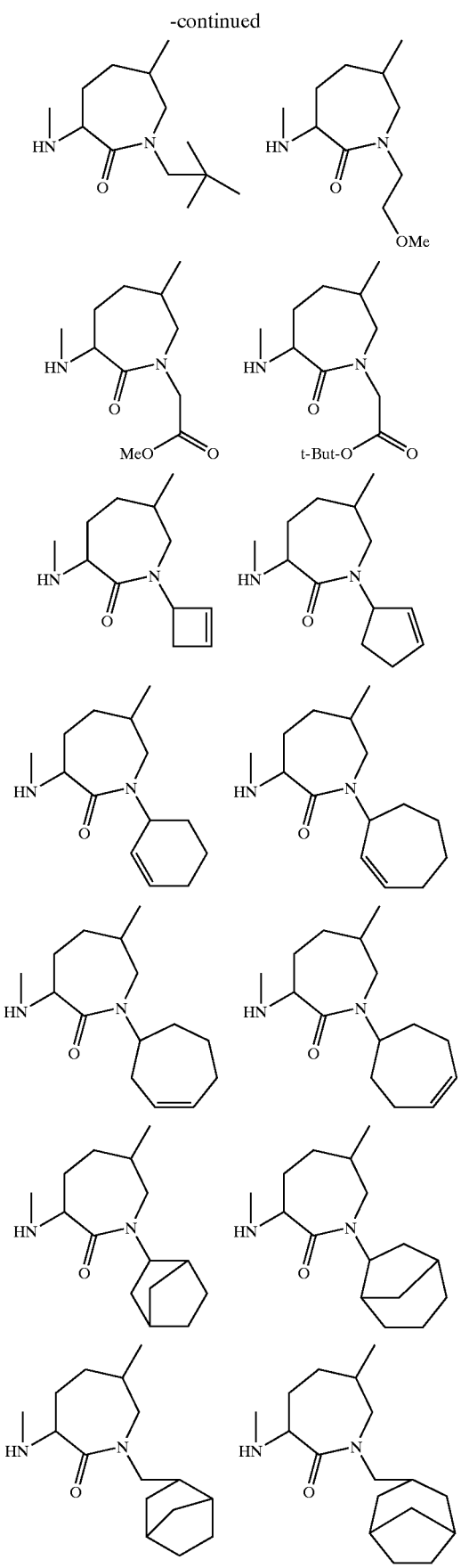
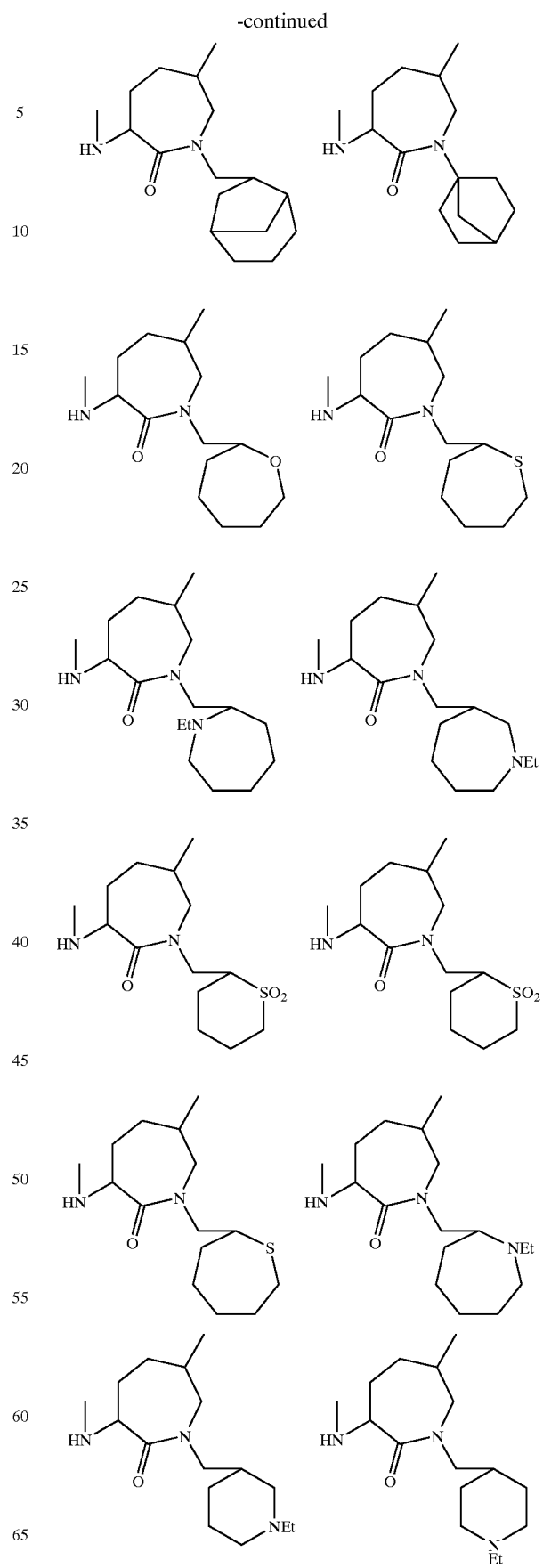

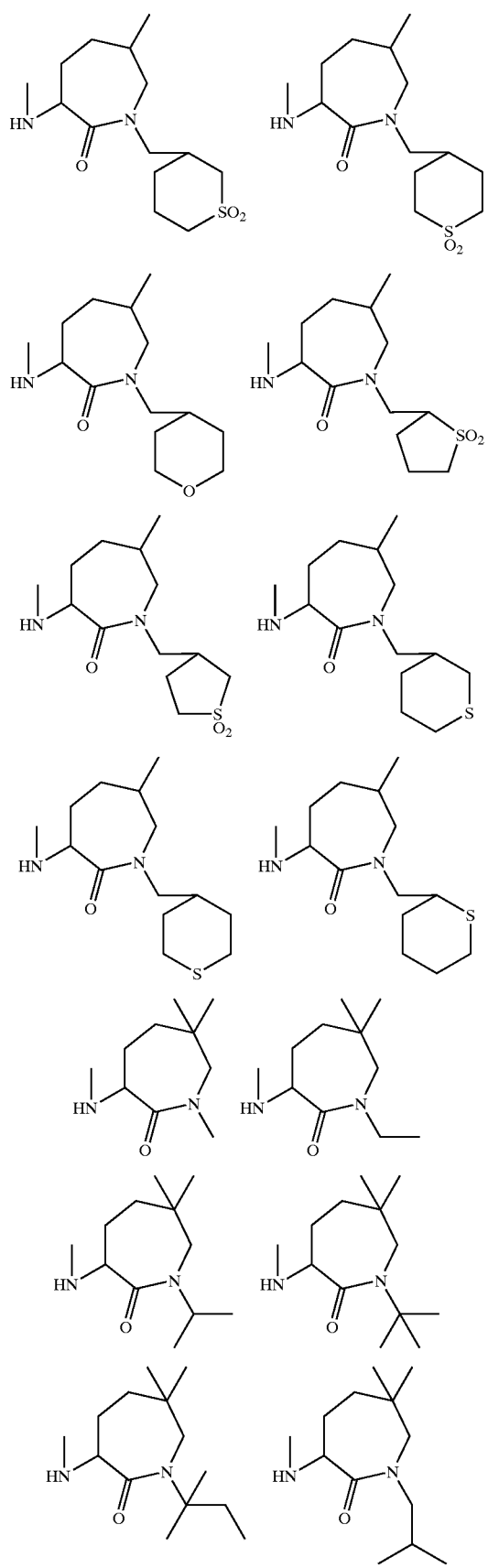
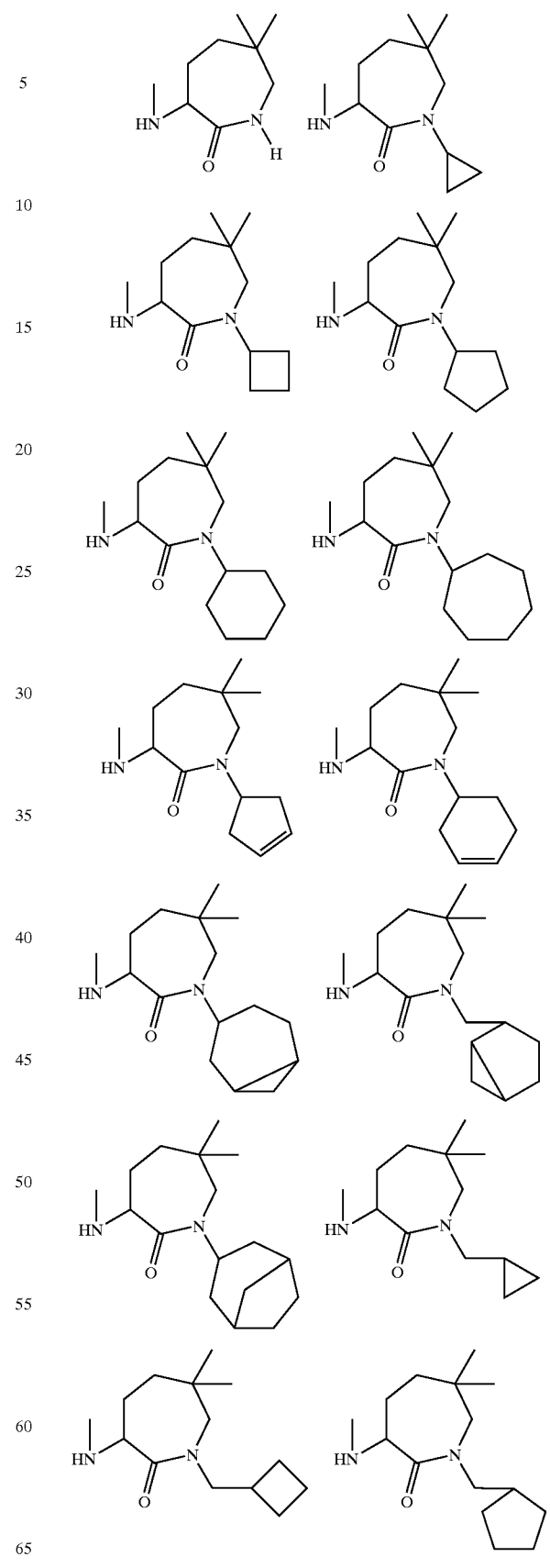

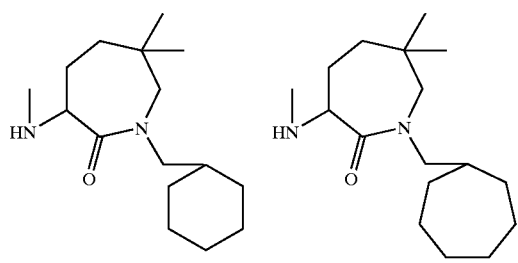
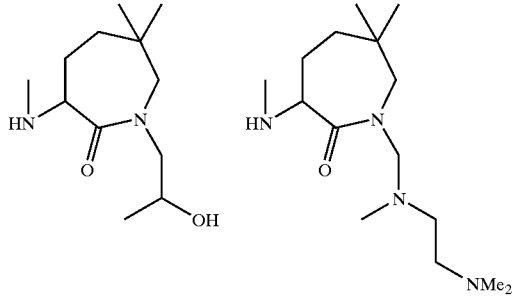
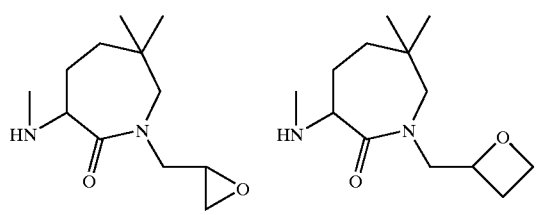
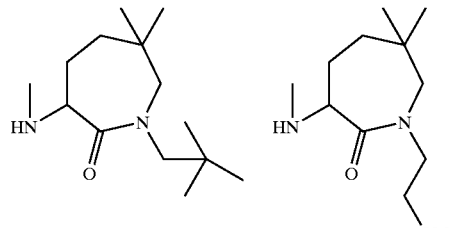
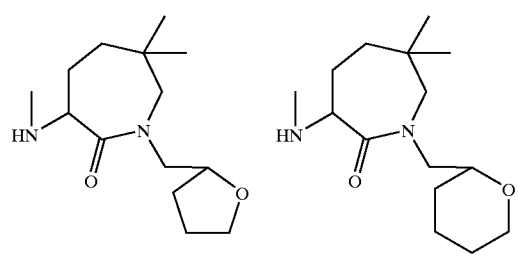
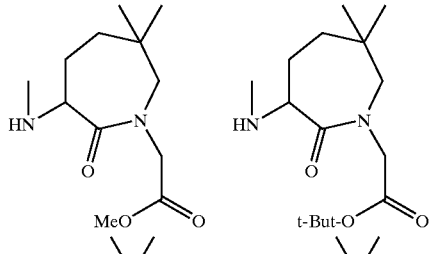
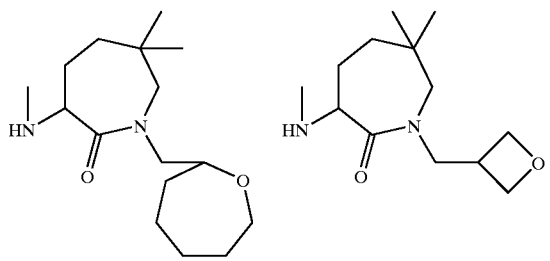
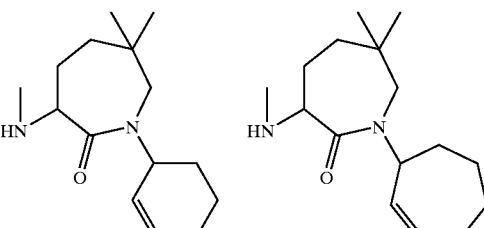
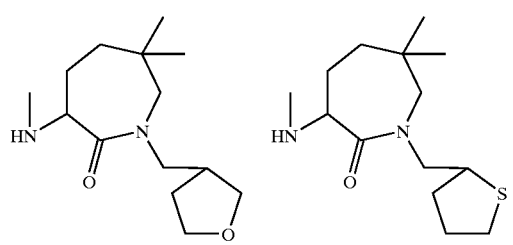
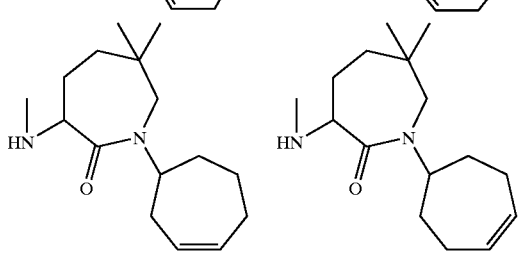
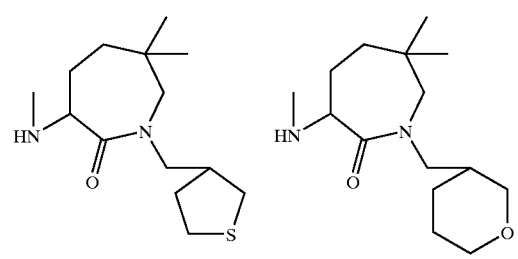
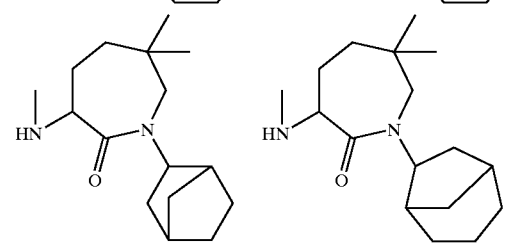

249
-continued
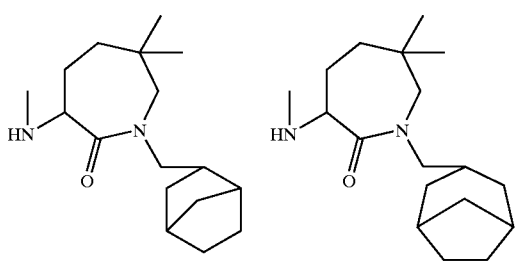
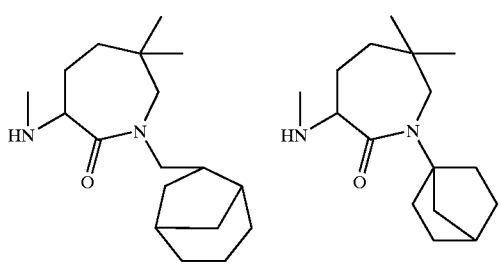
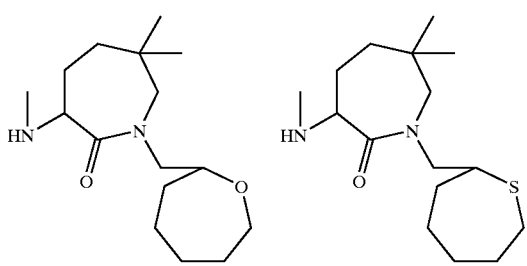
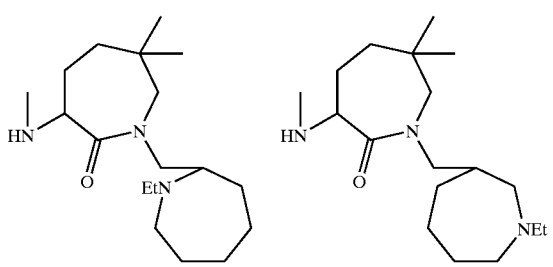
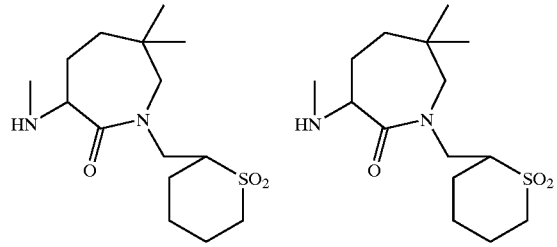
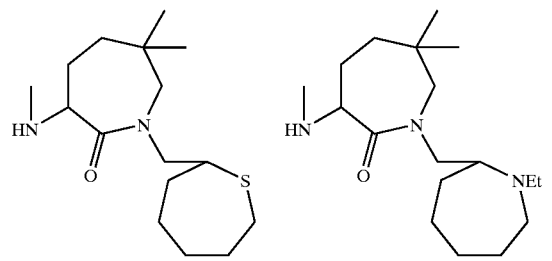
250
-continued
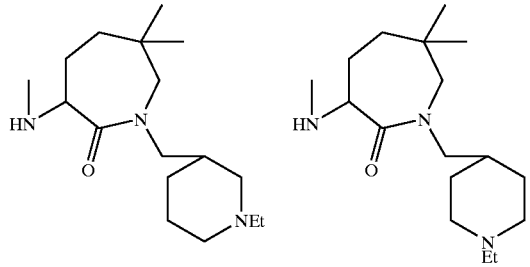
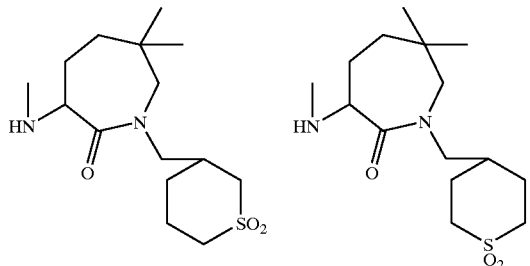
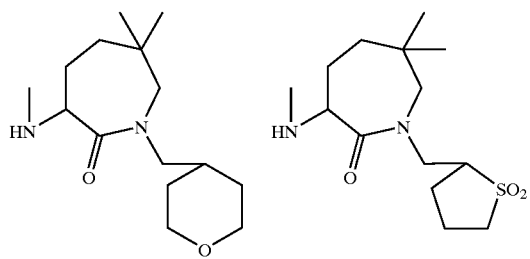
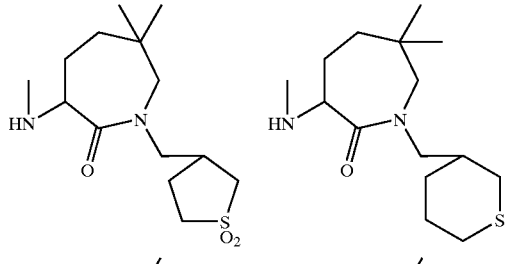
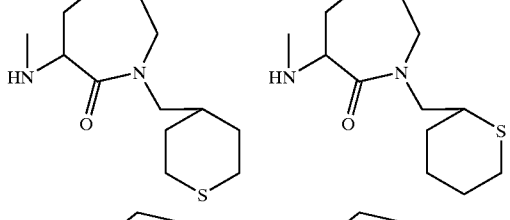
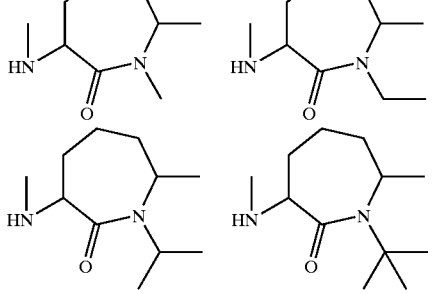

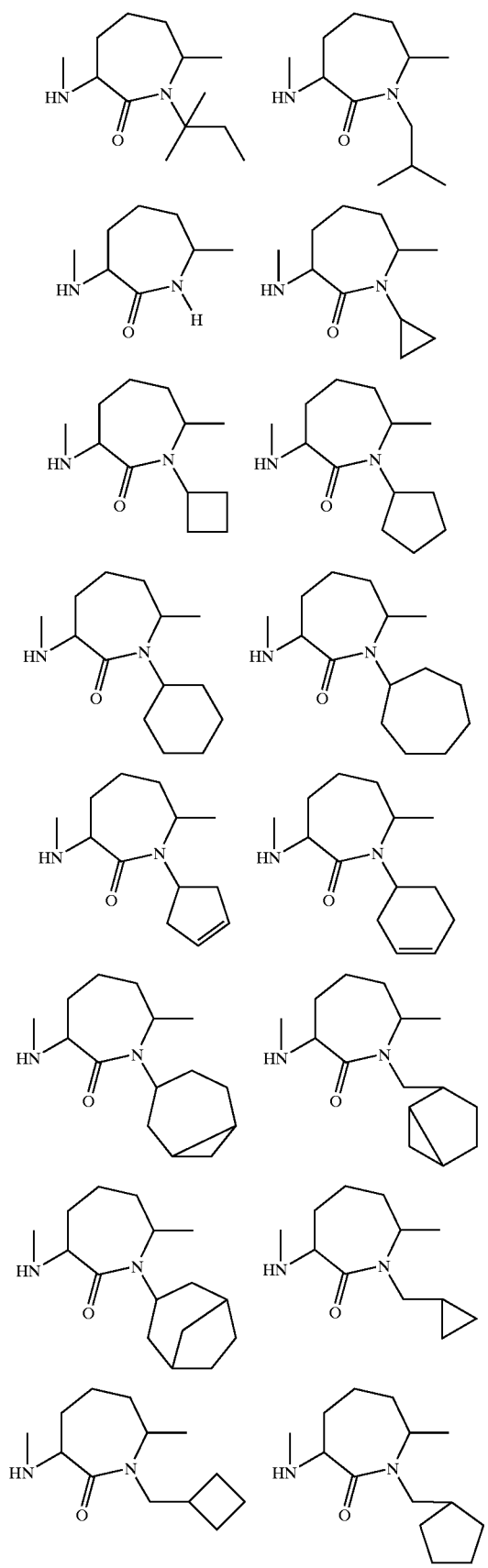
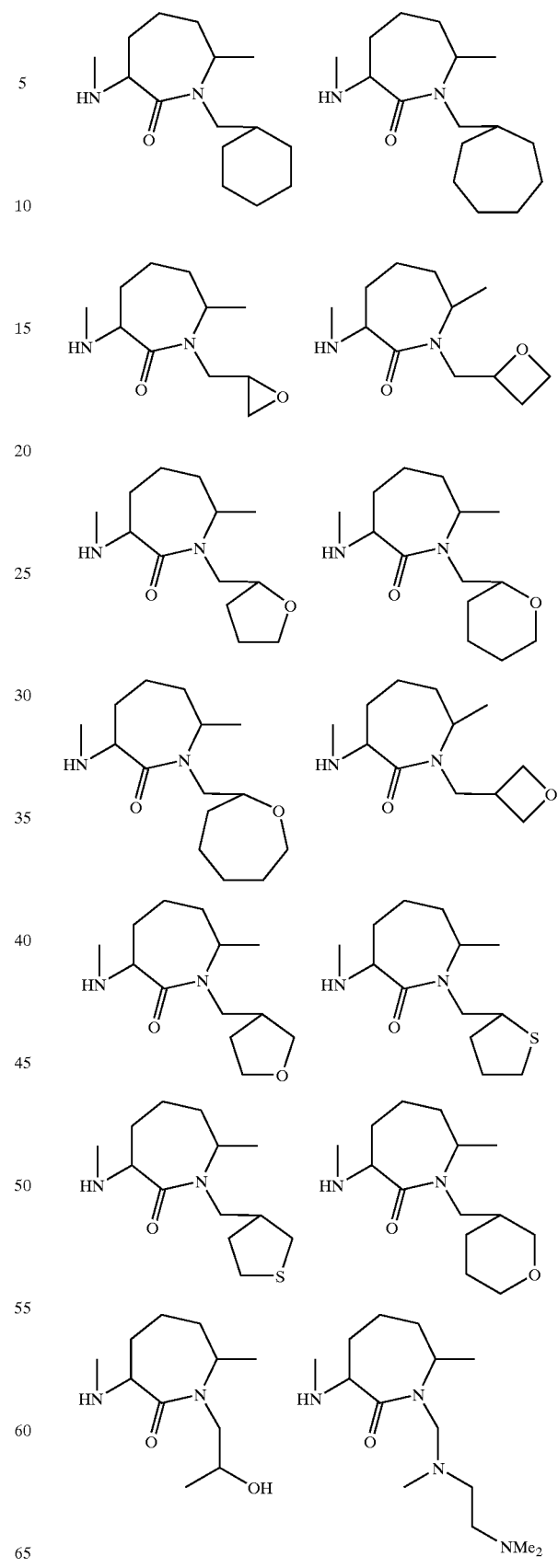

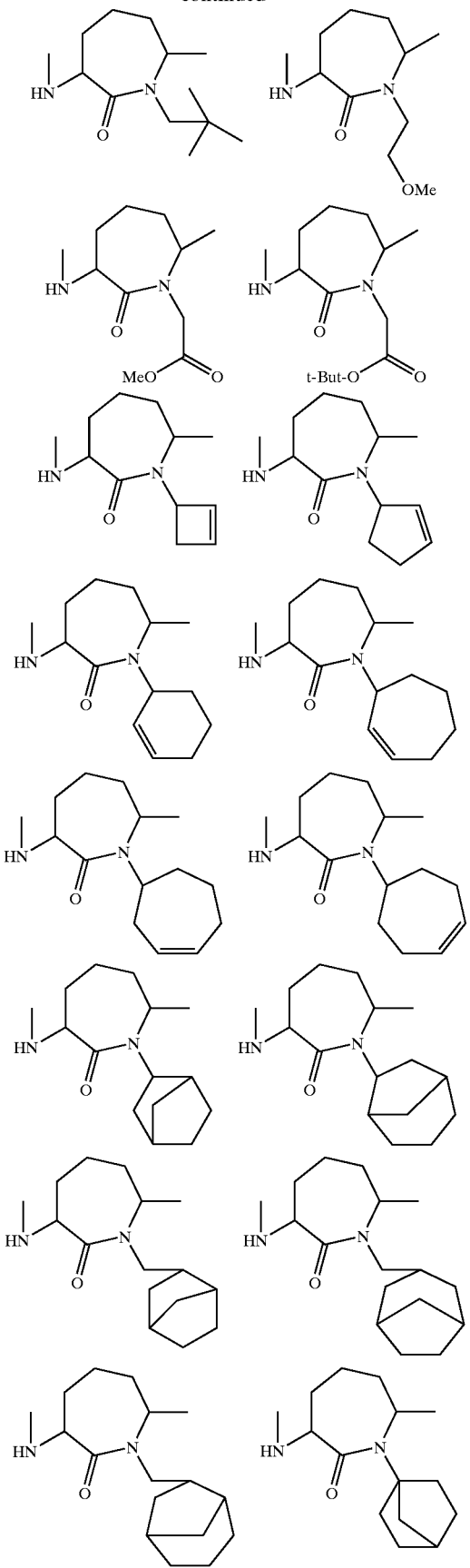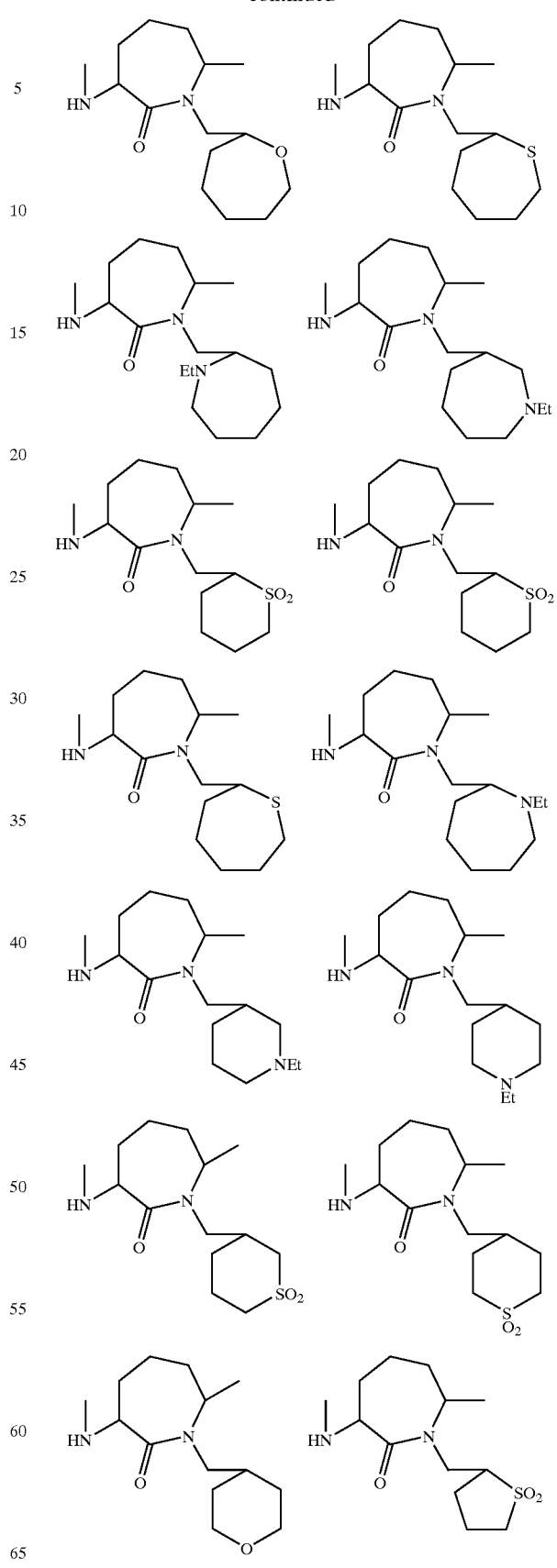

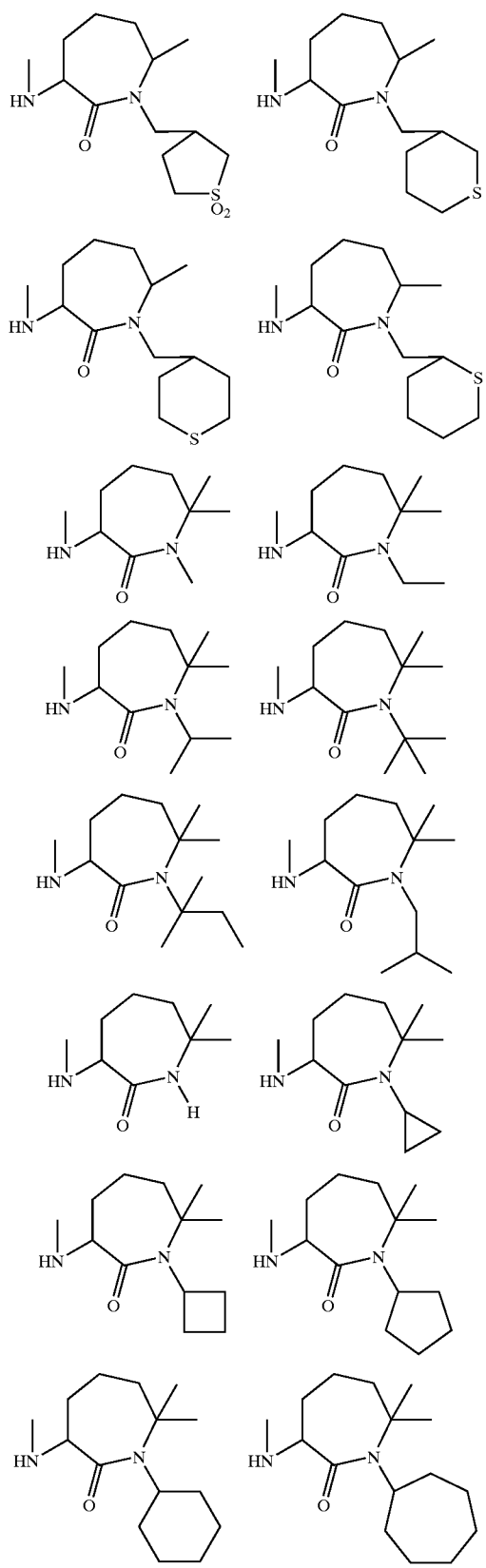
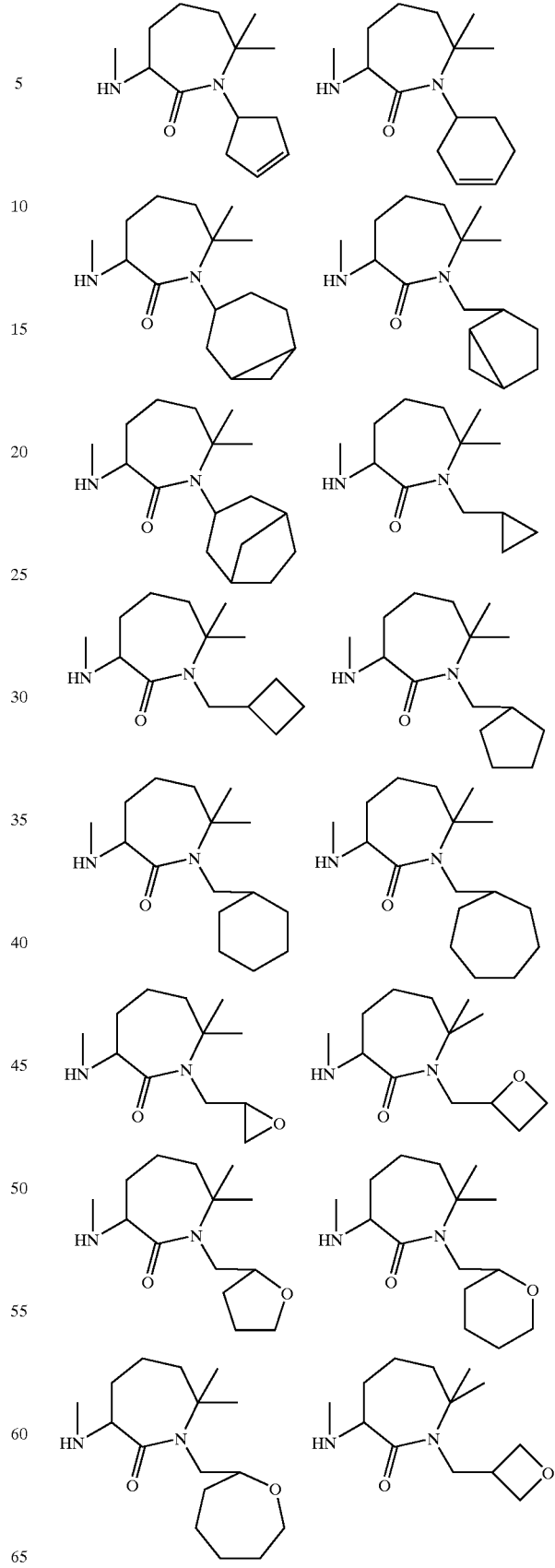

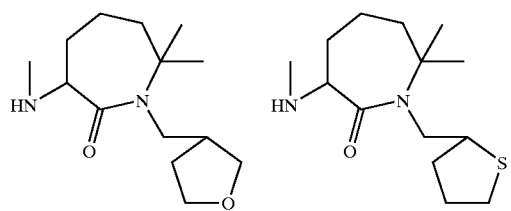
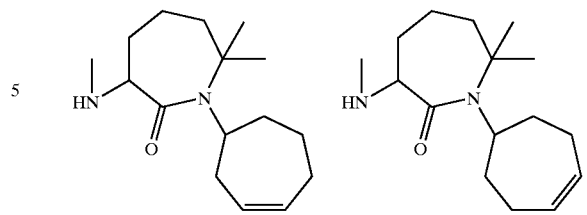
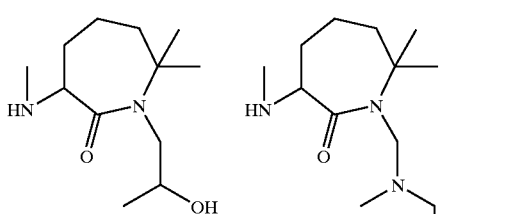
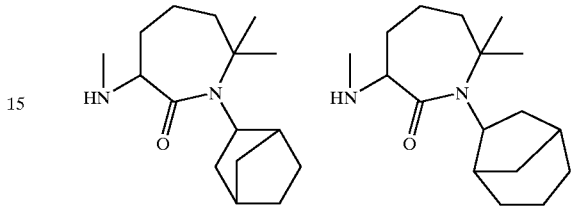
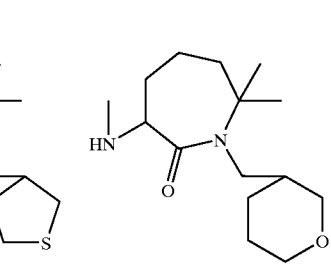
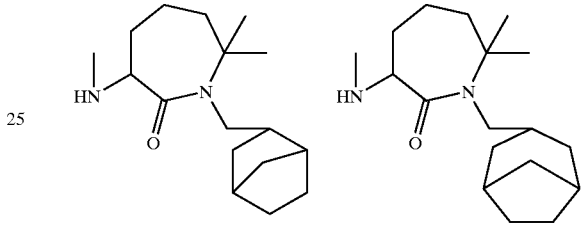
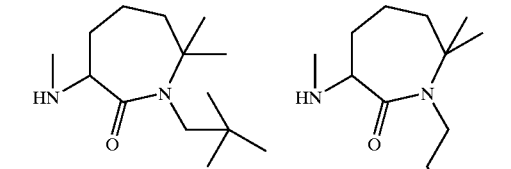
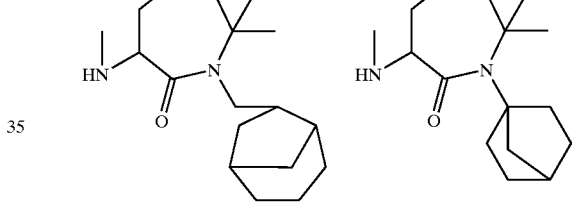
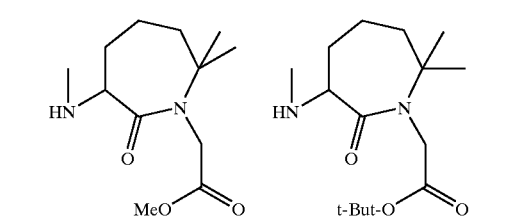
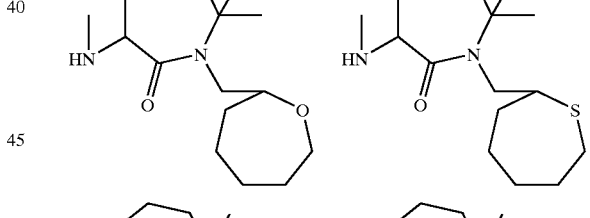
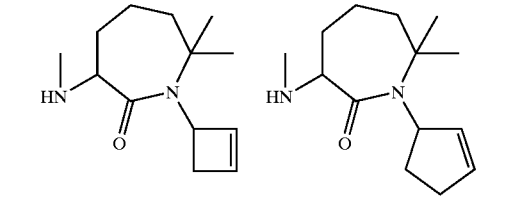
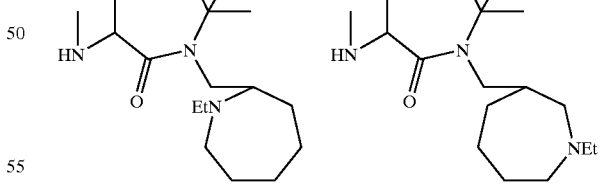
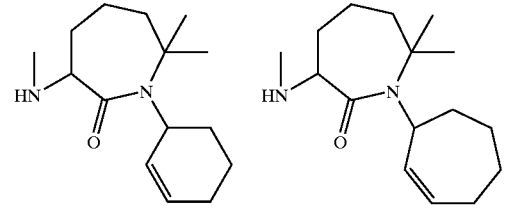
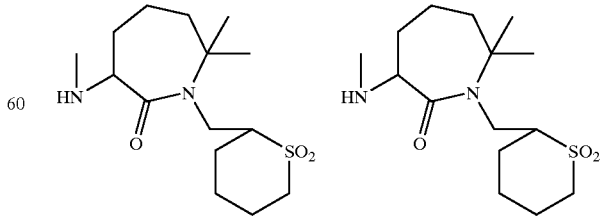

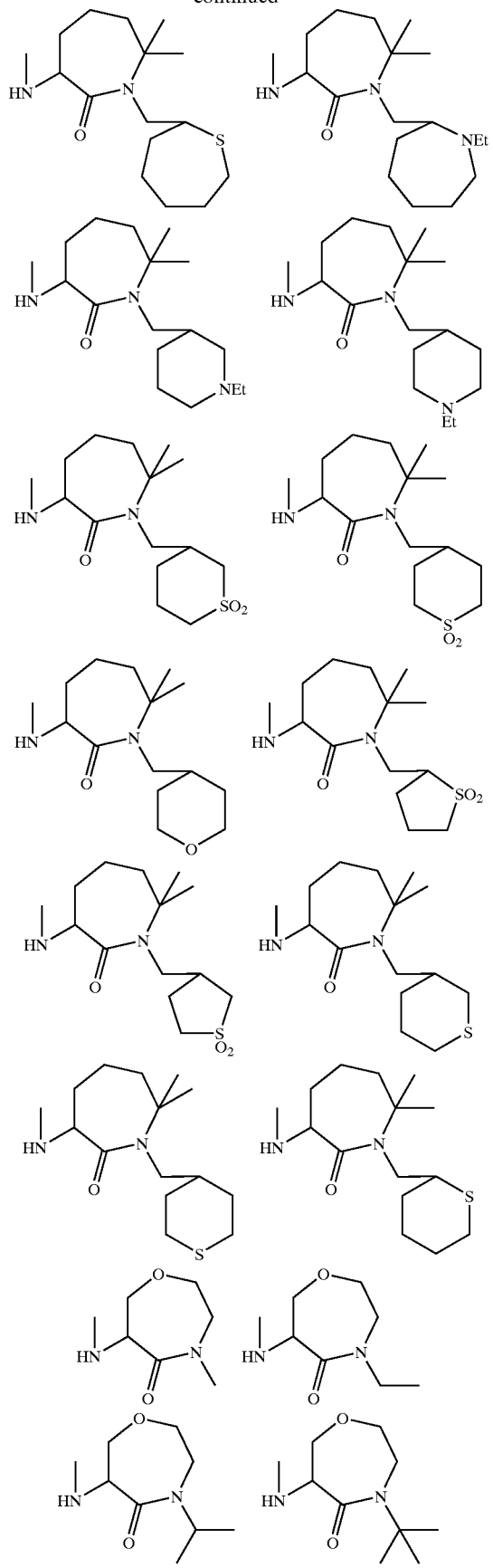
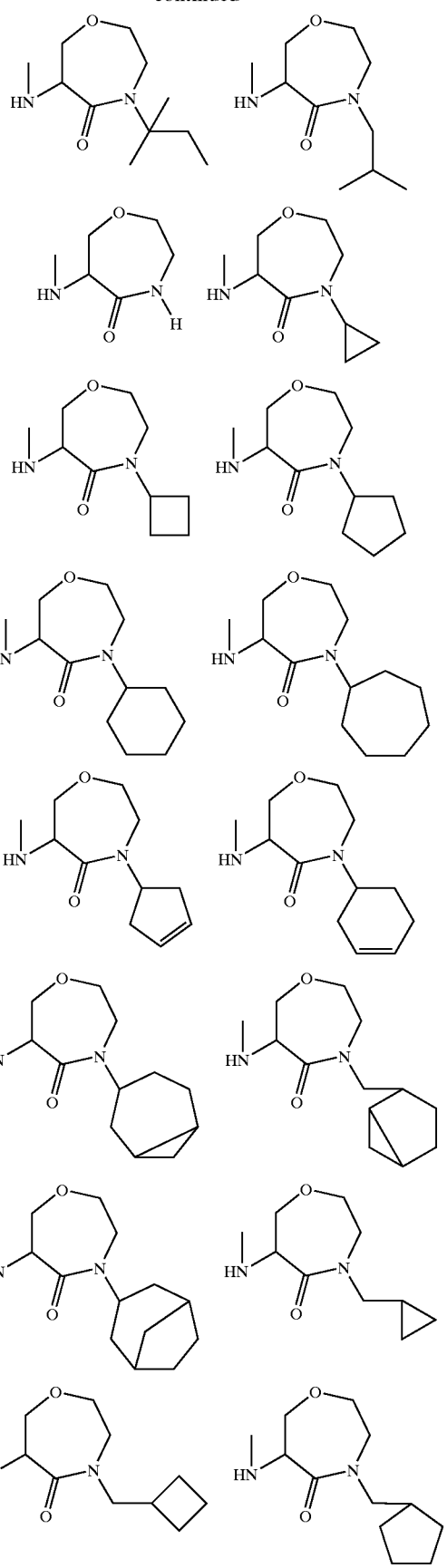

-continued
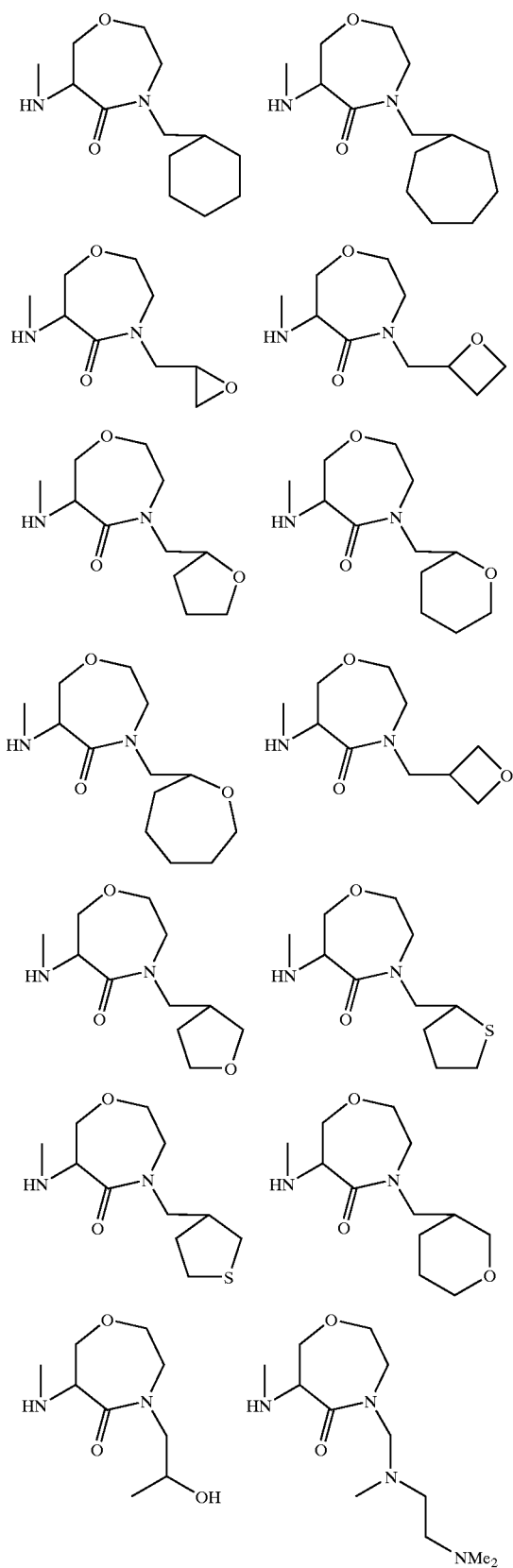
-continued
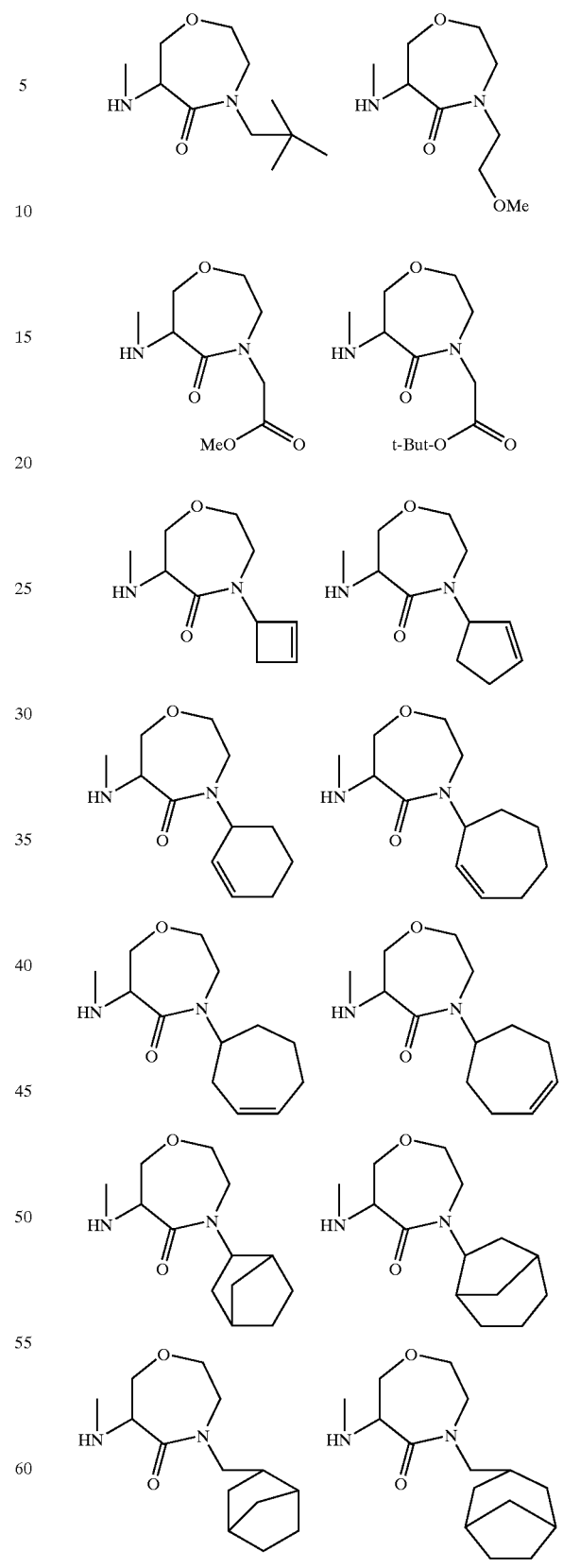

263
-continued
264
-continued
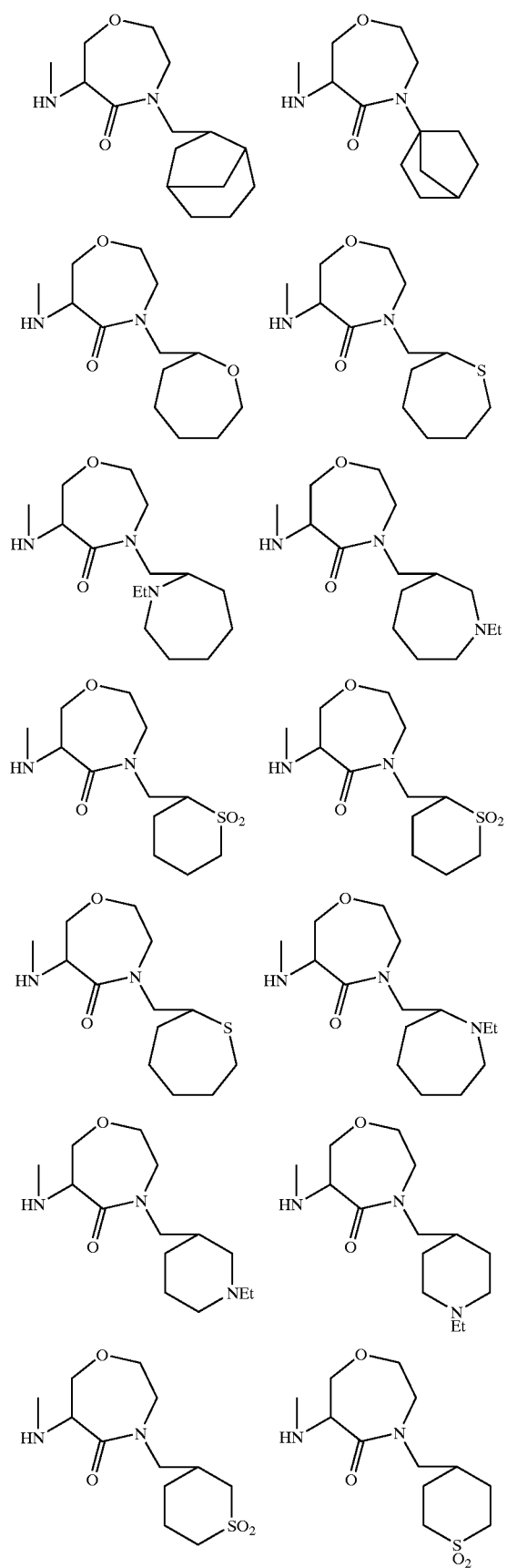
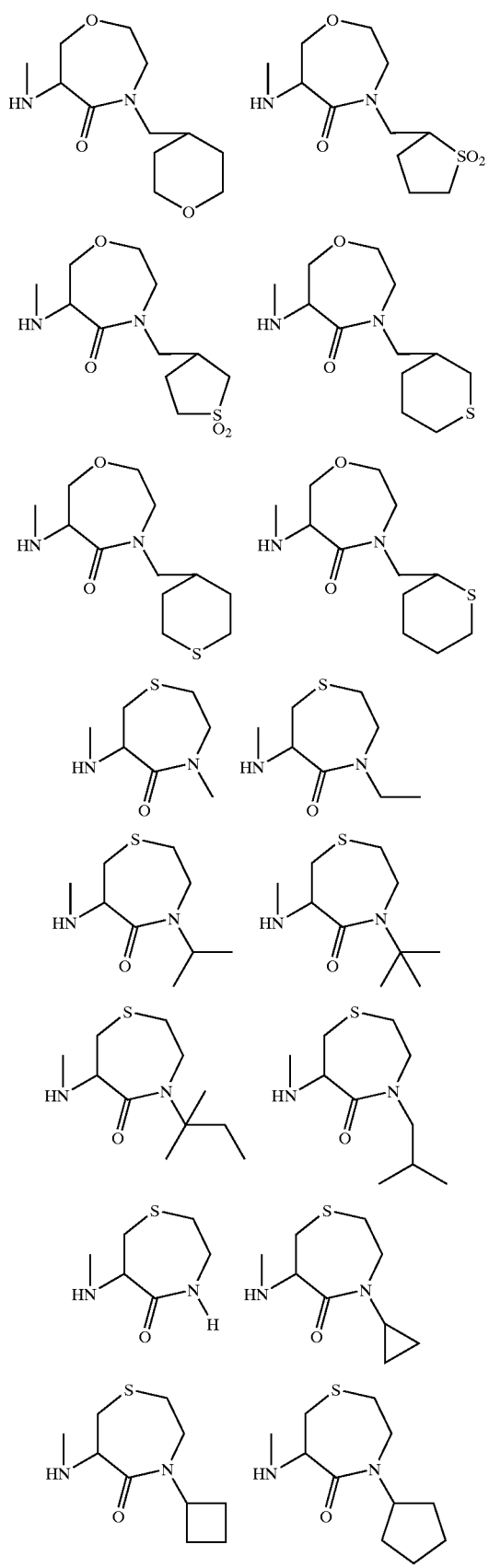

265
-continued
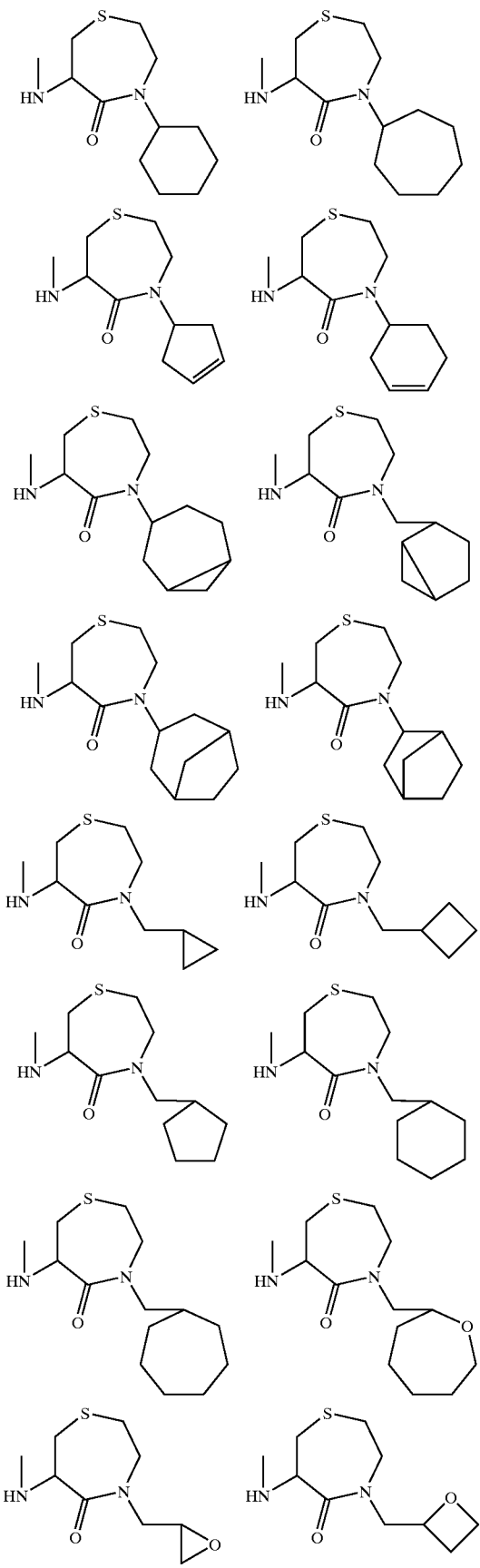
266
-continued
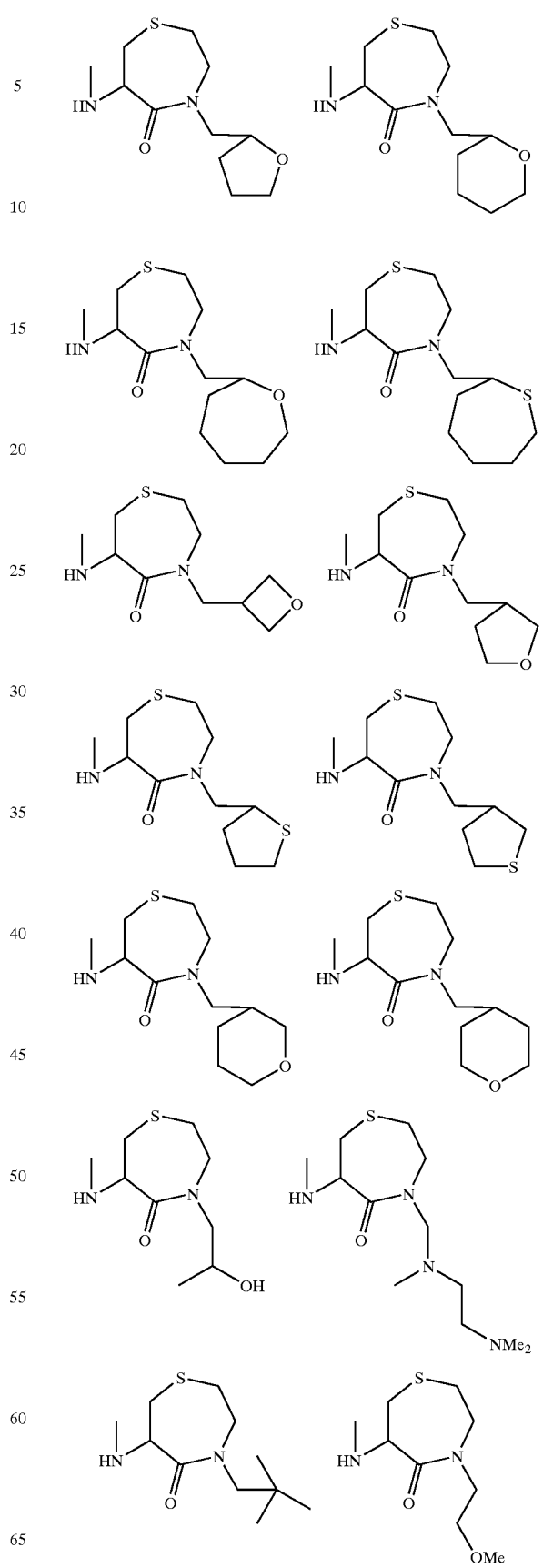

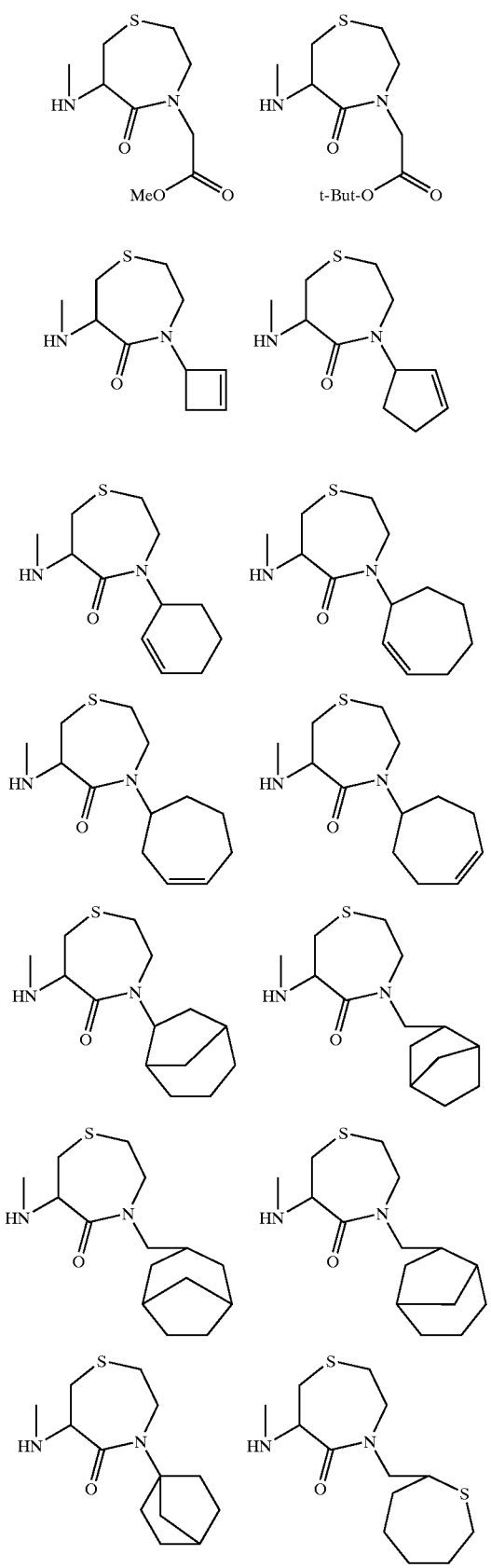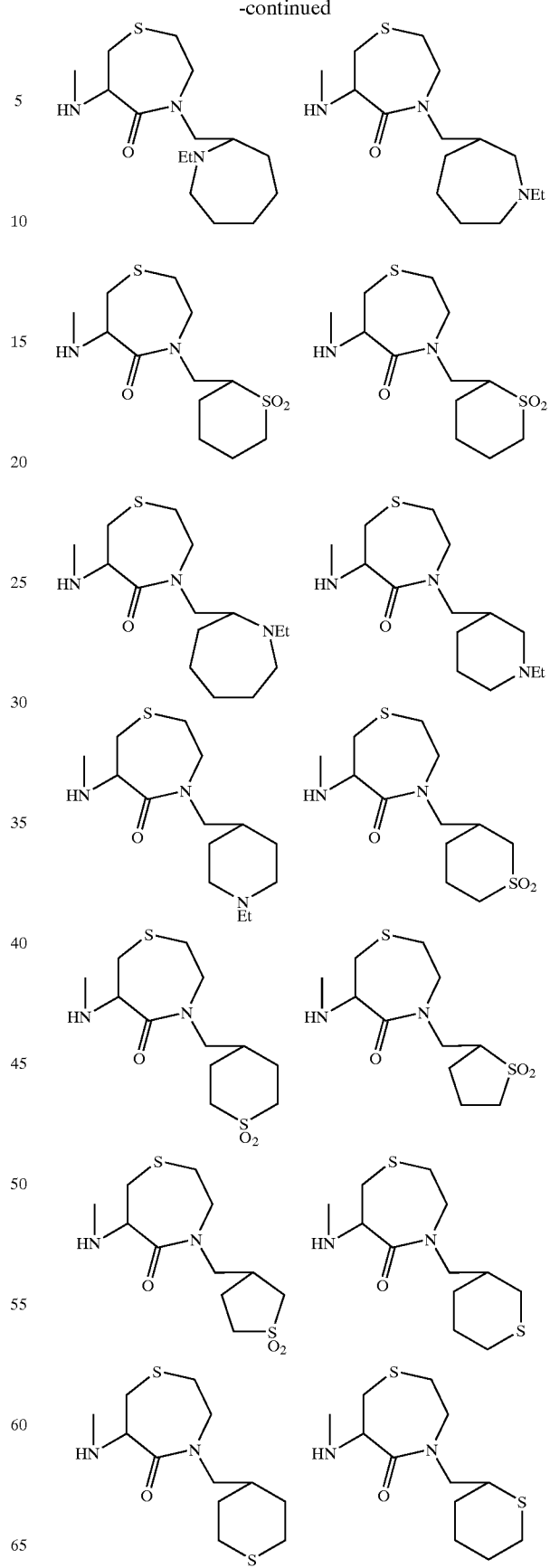

269
-continued
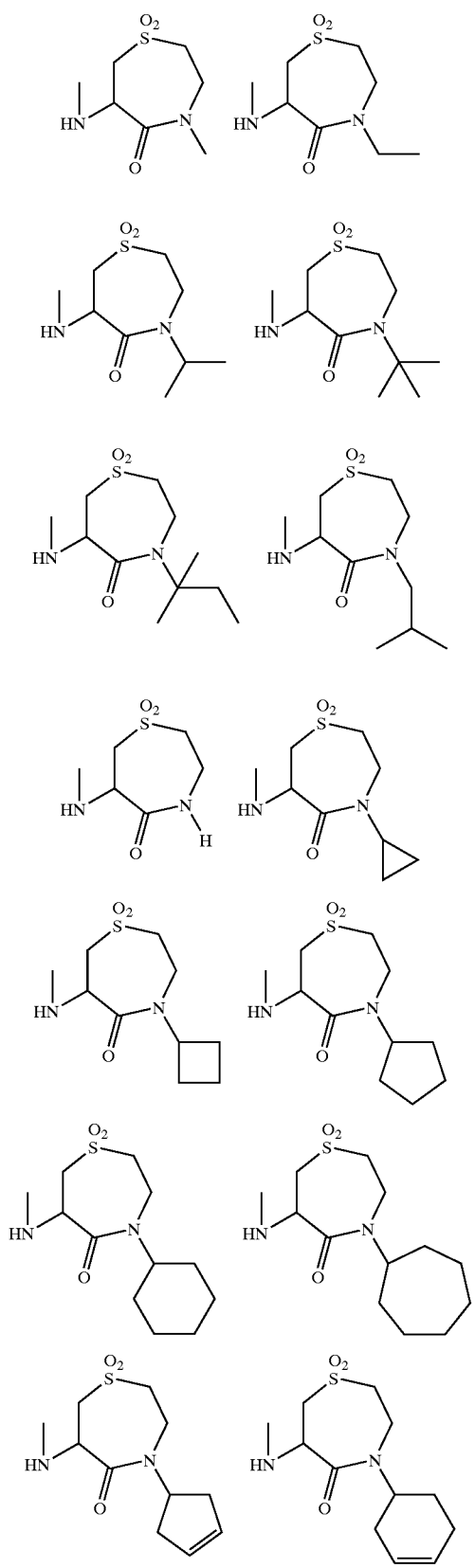
270
-continued
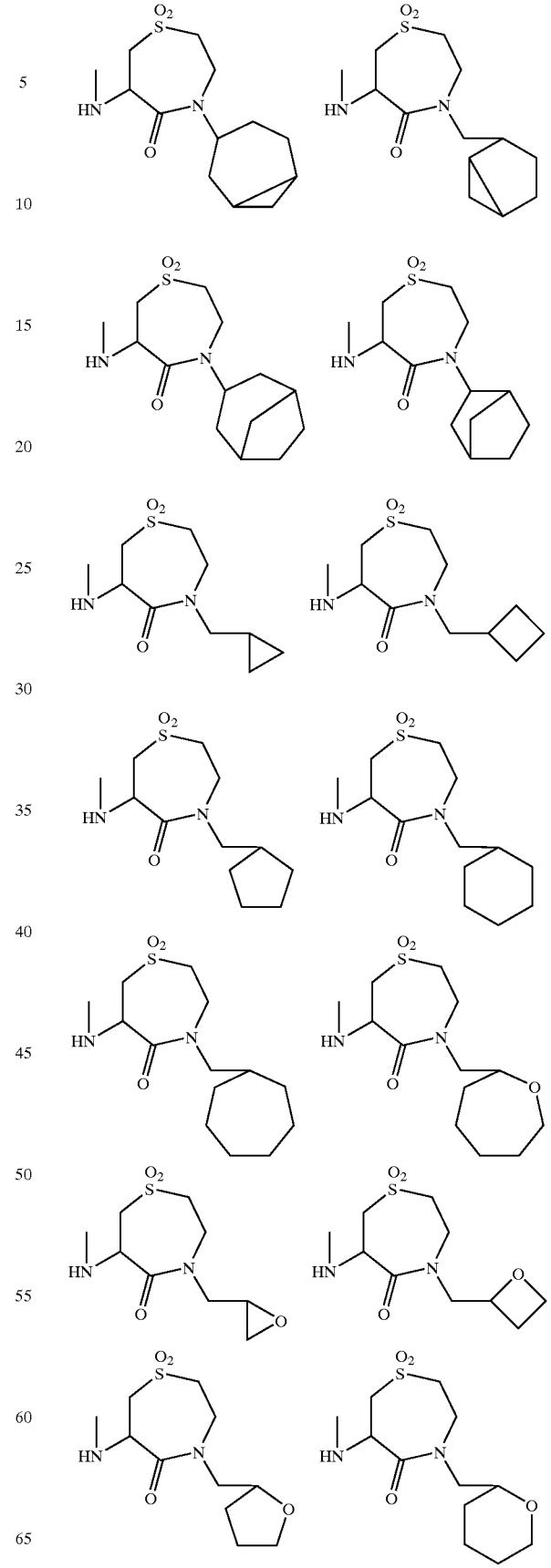

271
-continued
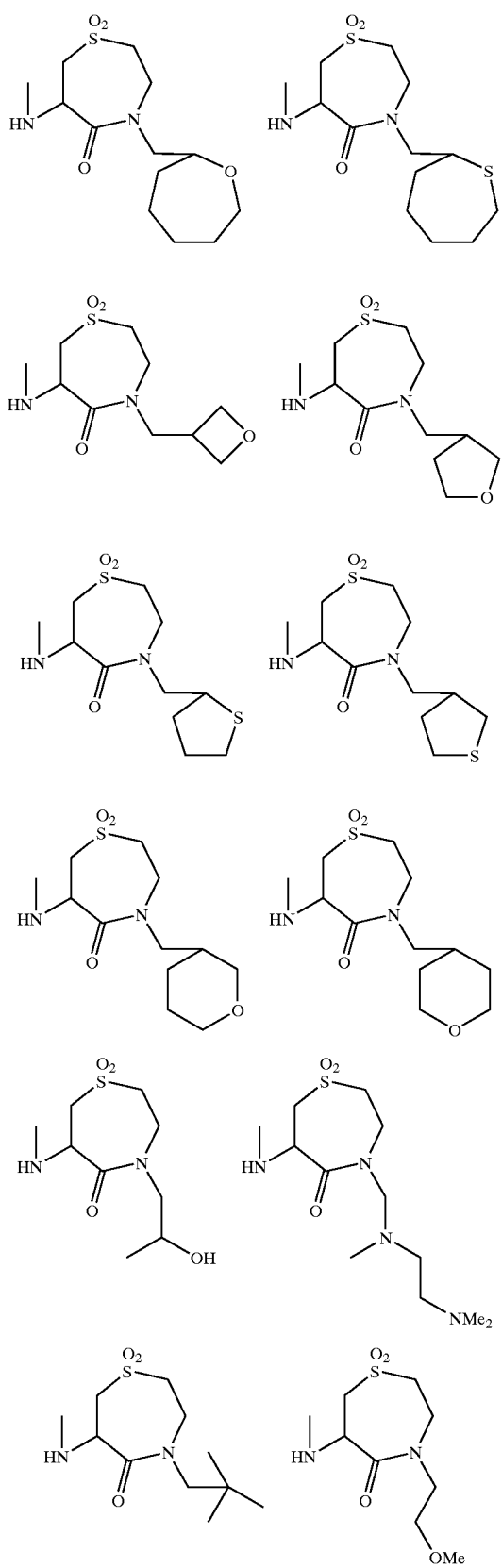
272
-continued
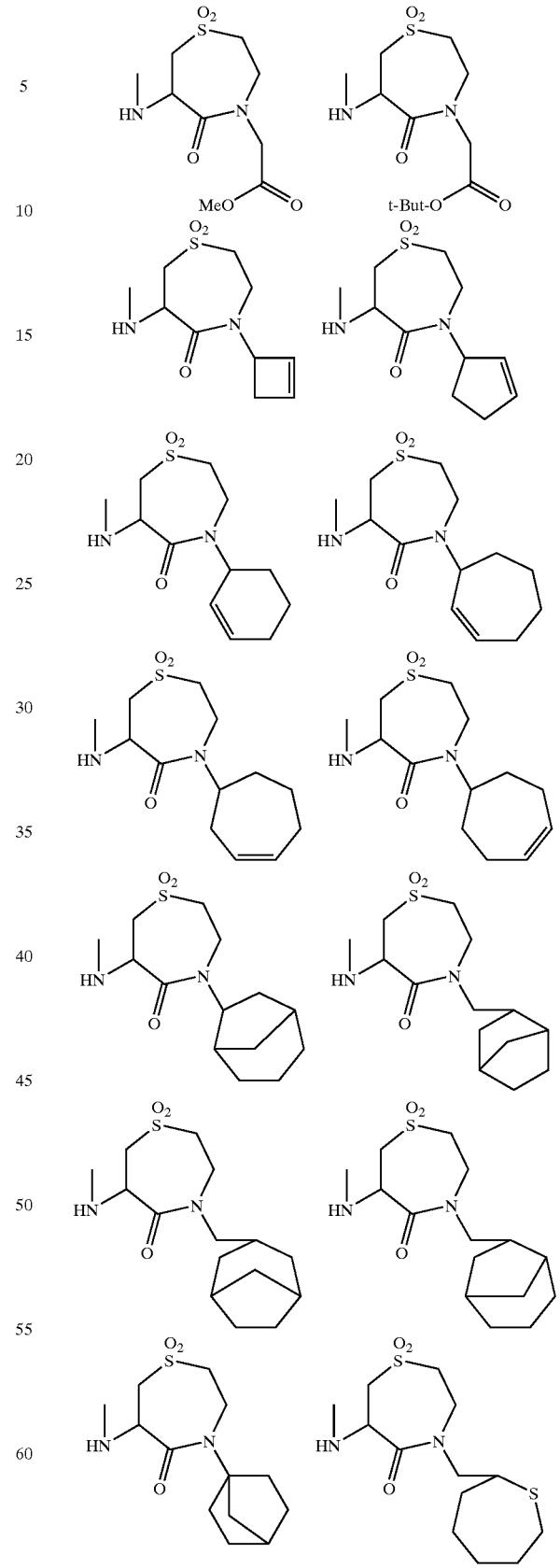

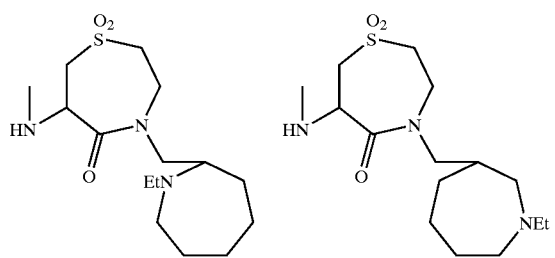
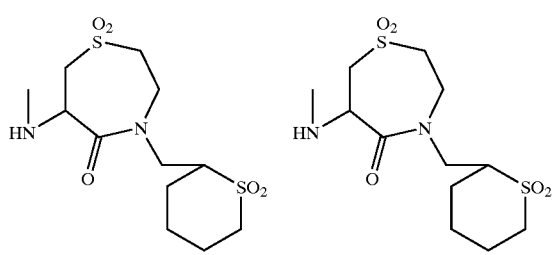
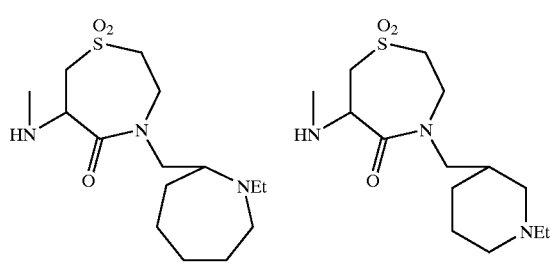
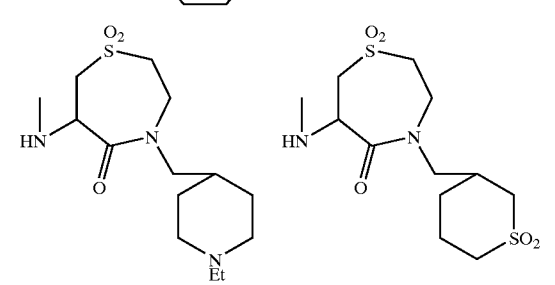
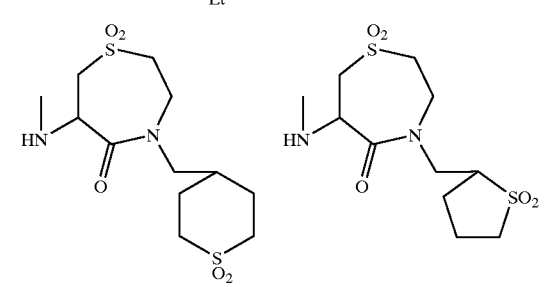
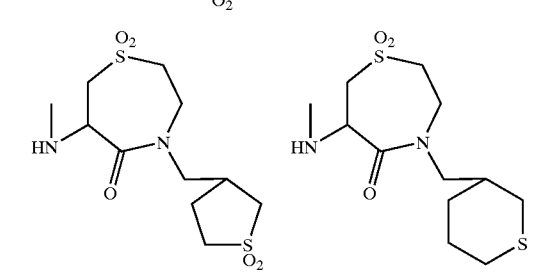
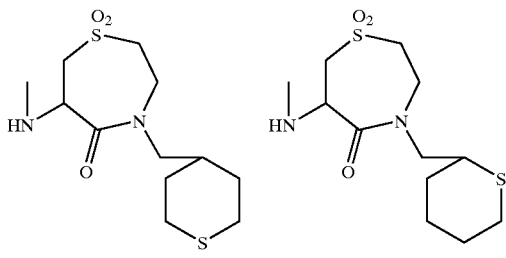
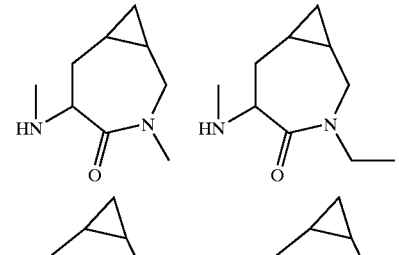
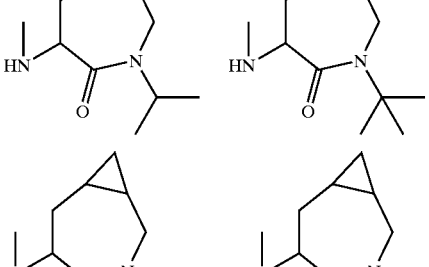
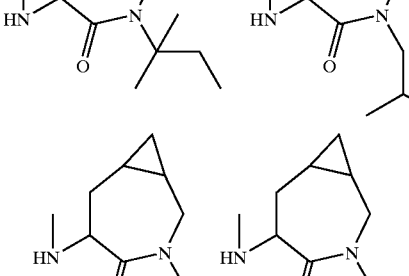
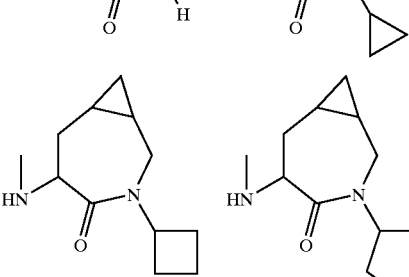
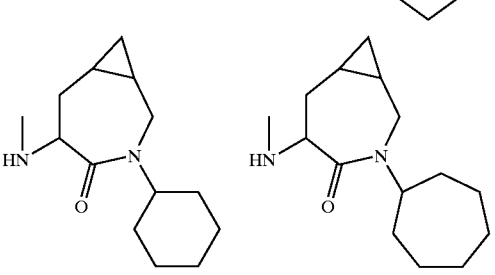

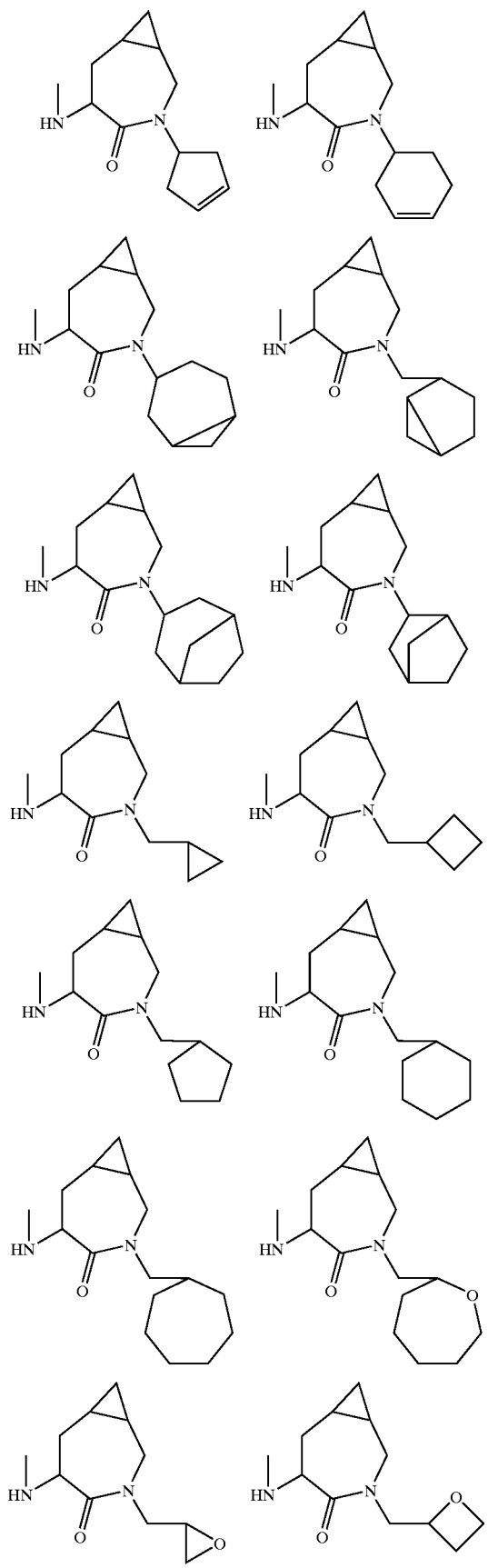
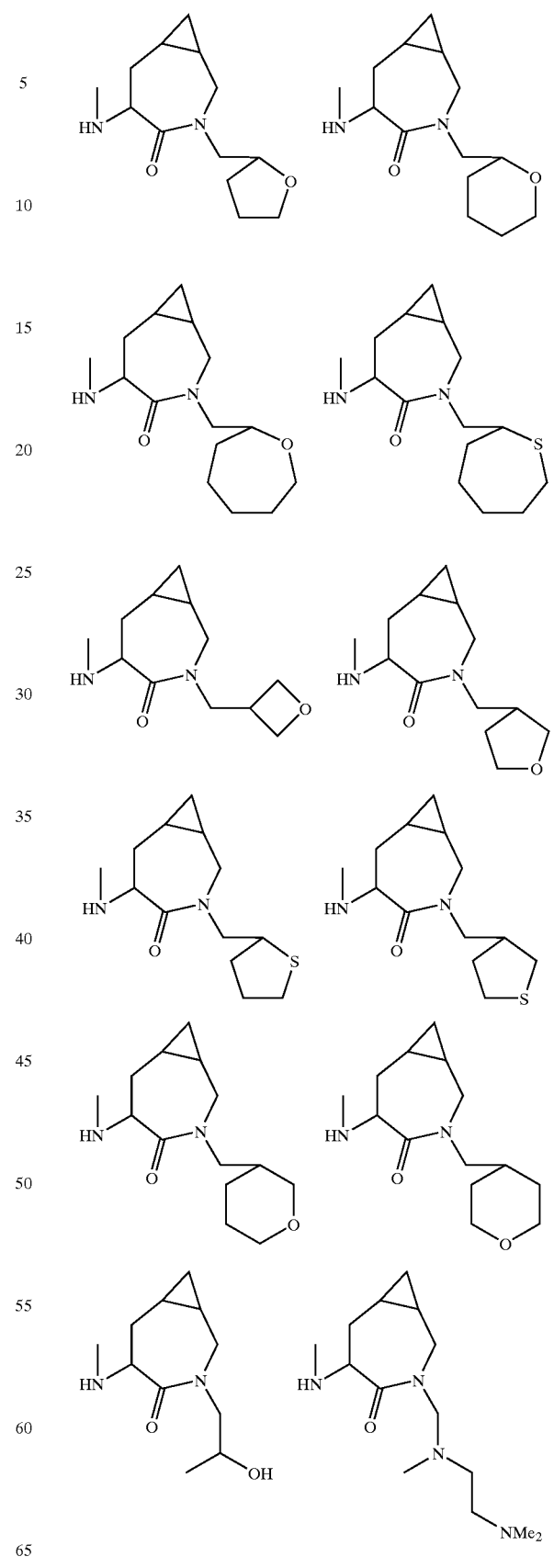

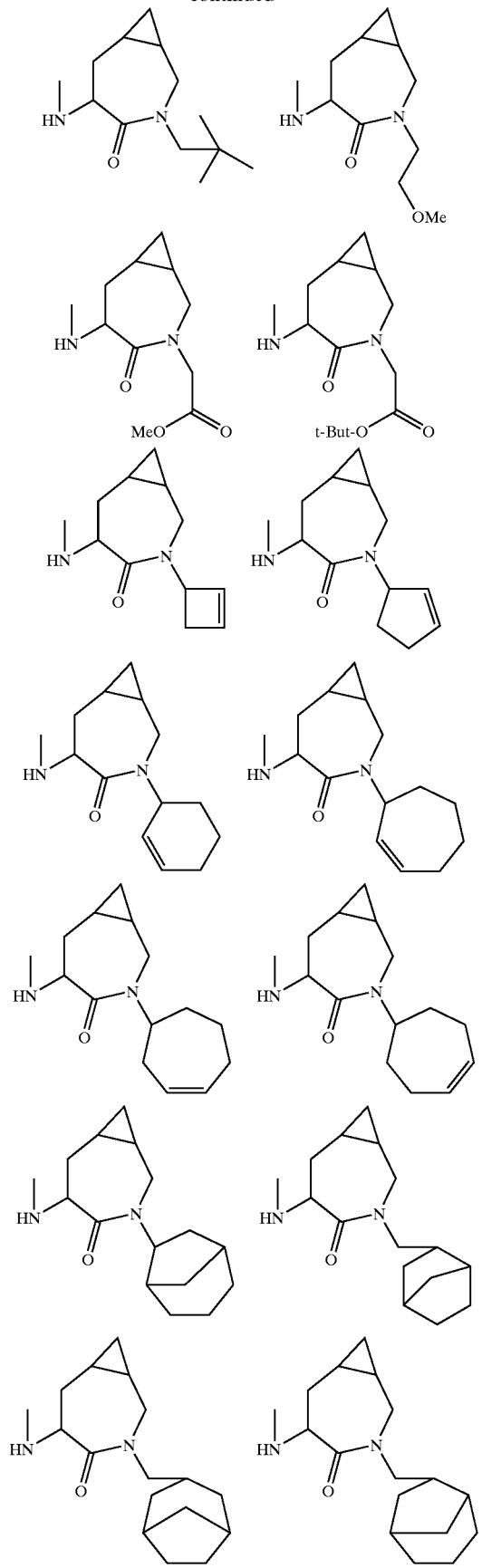
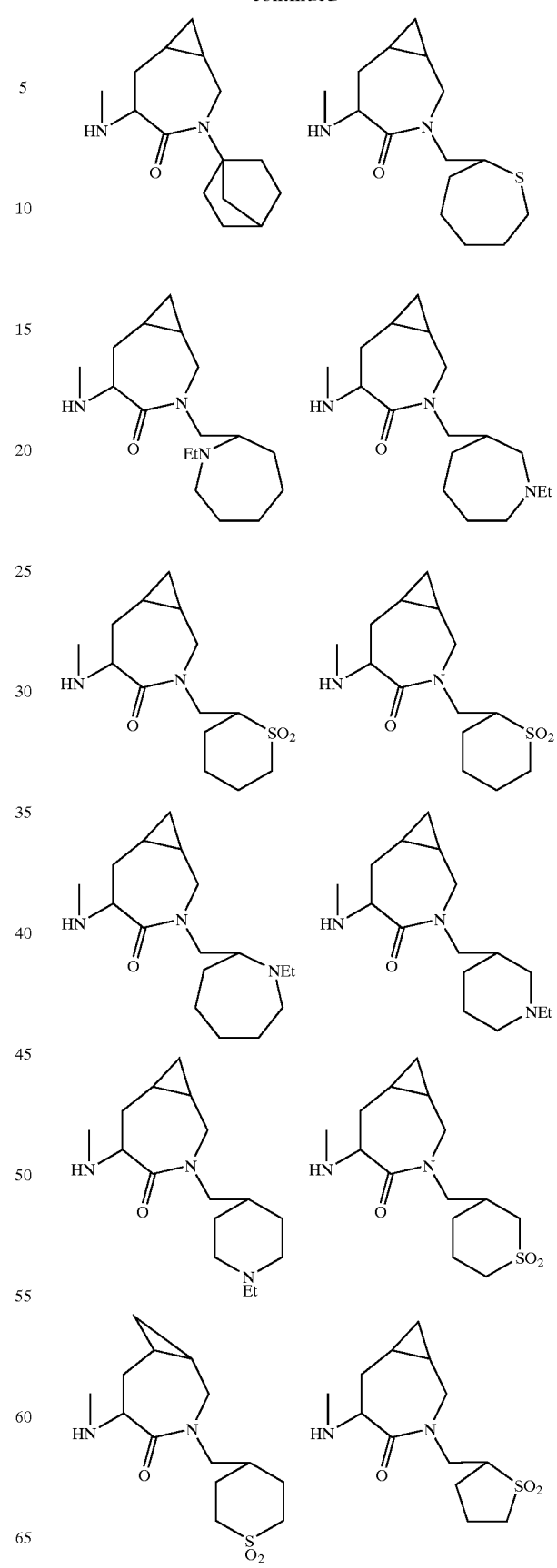

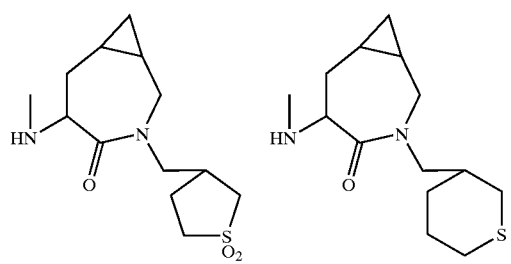
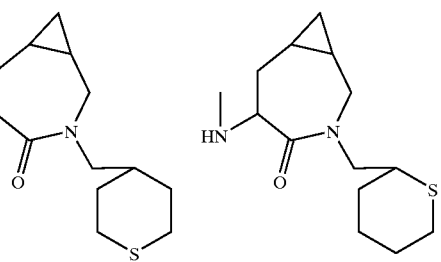
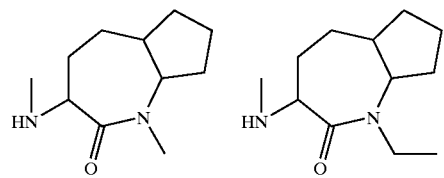
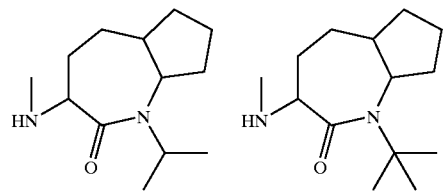
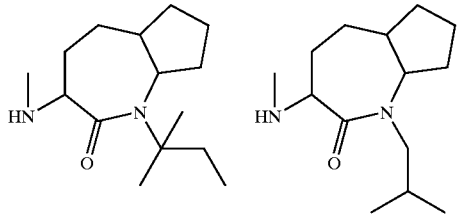
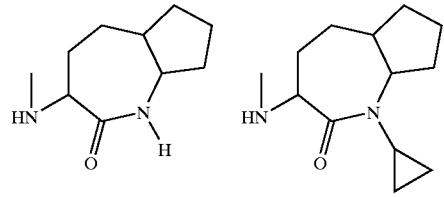
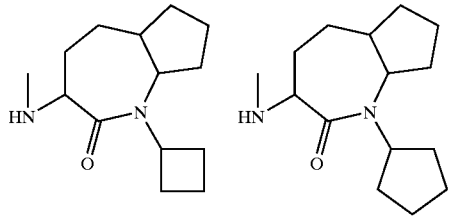
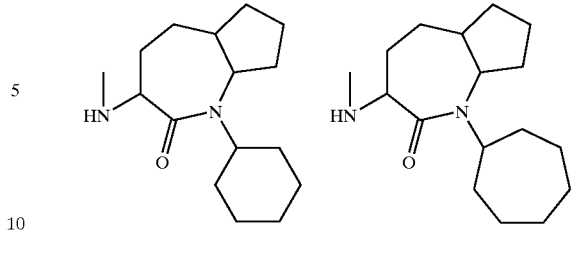
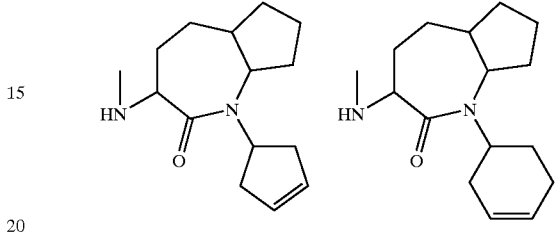
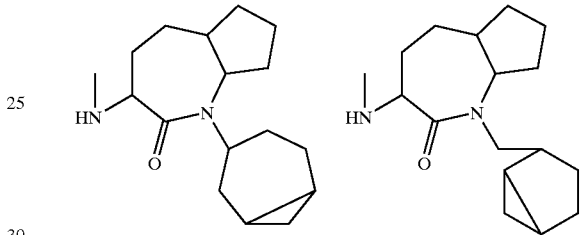
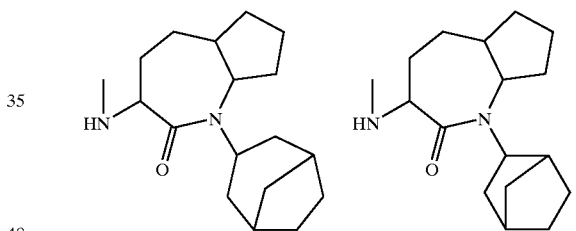
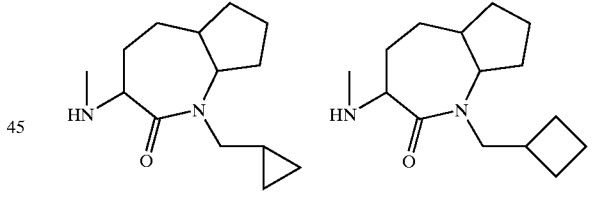
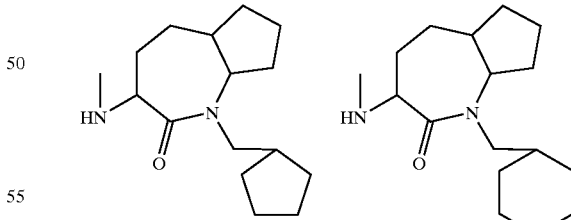
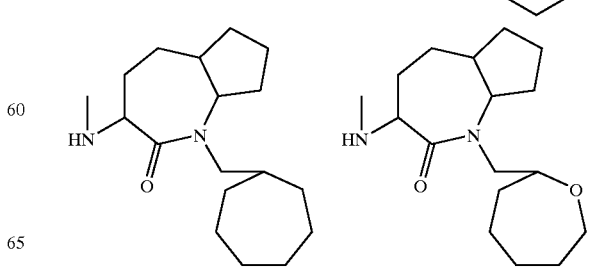

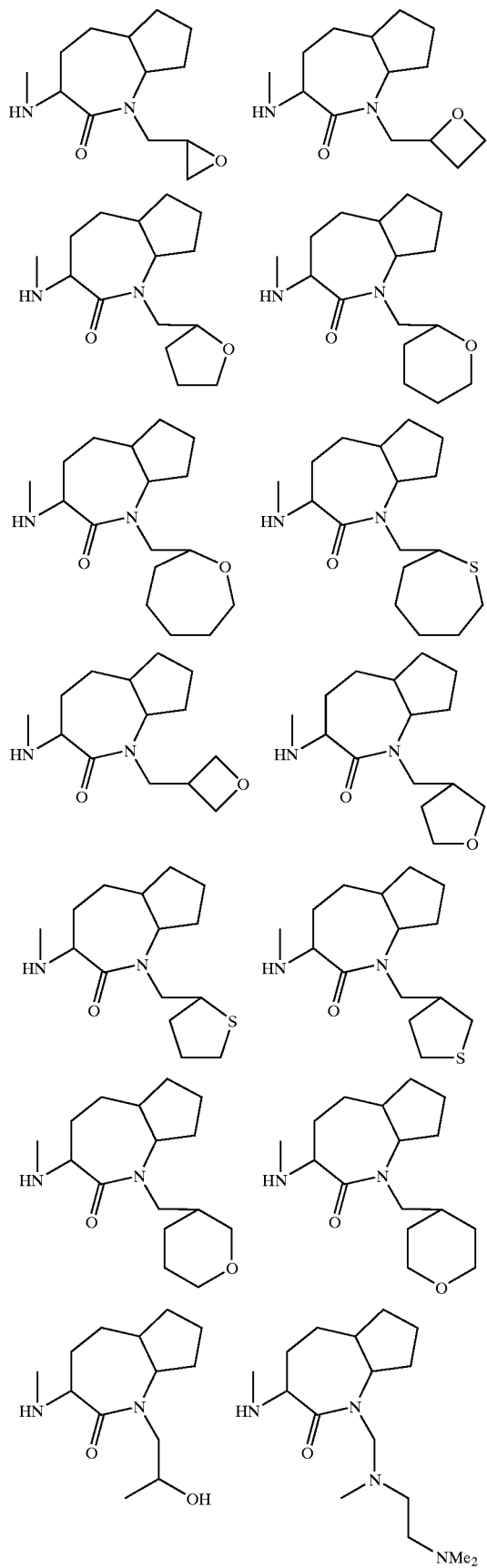
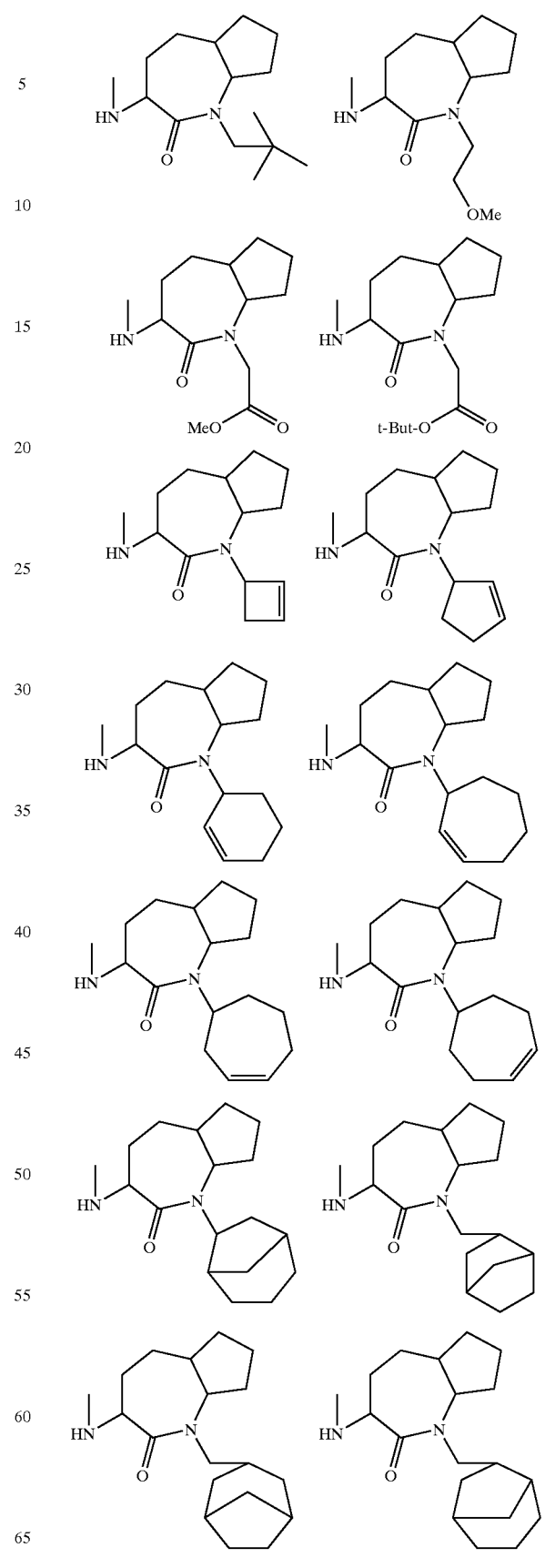

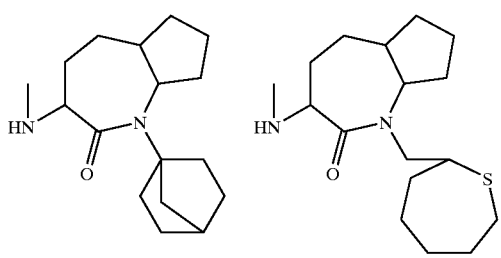
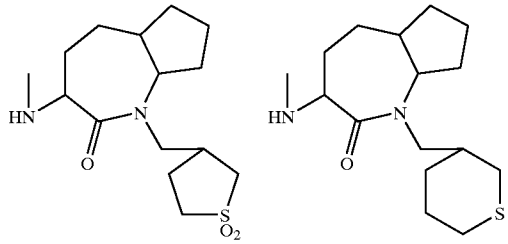
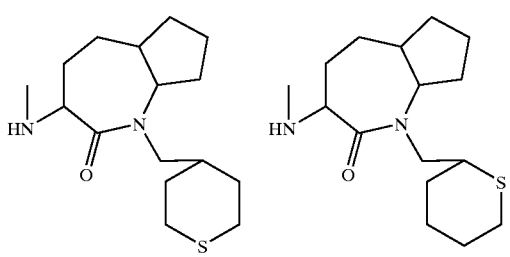
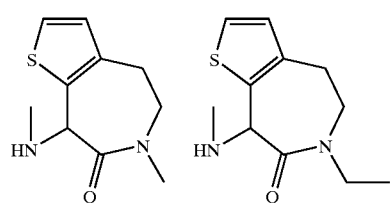
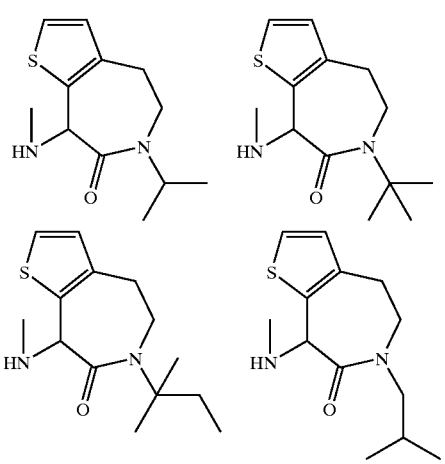
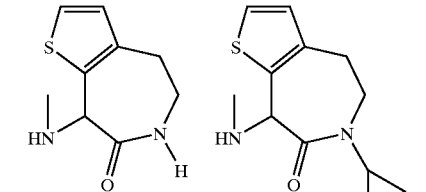
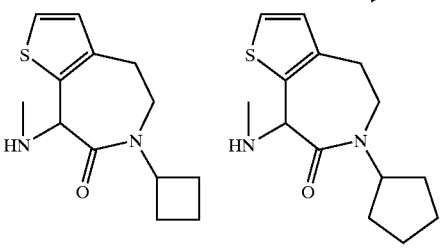

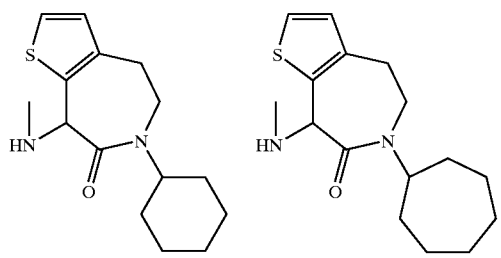
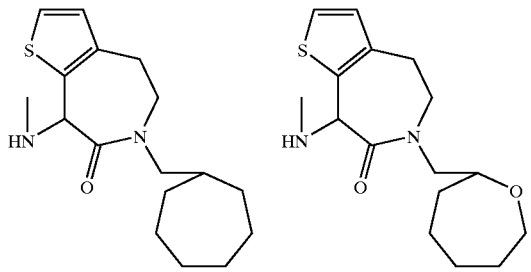
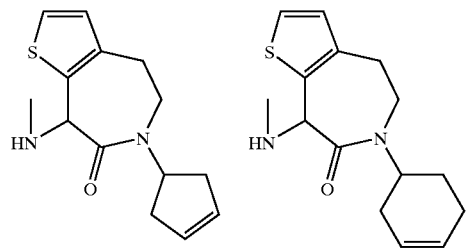
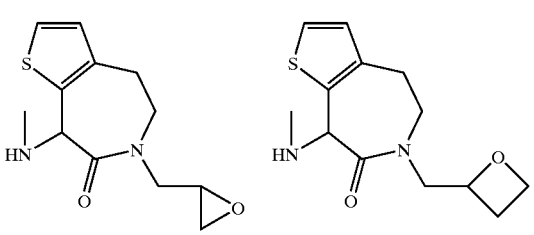
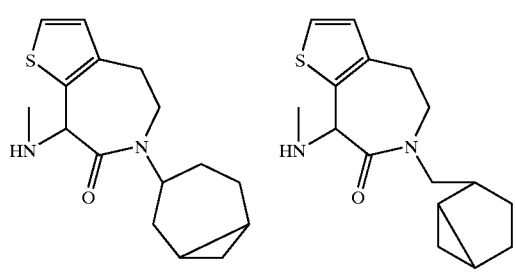
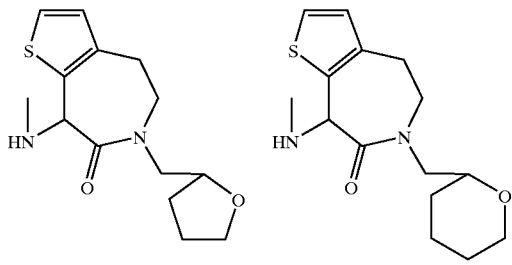
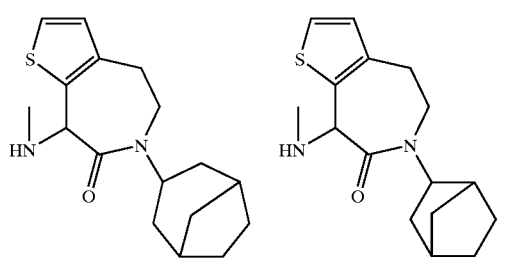
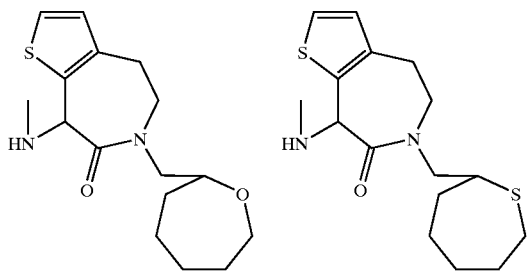
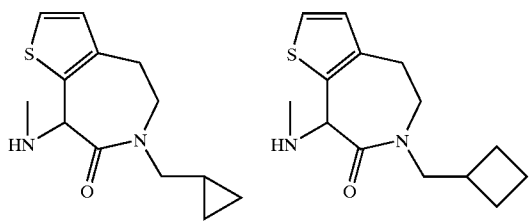
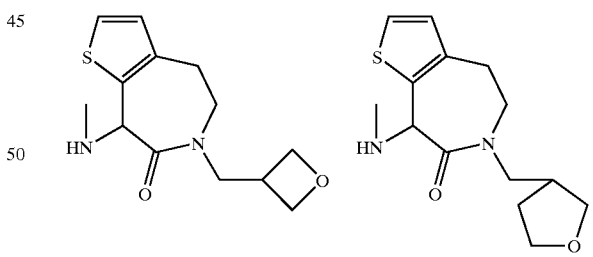
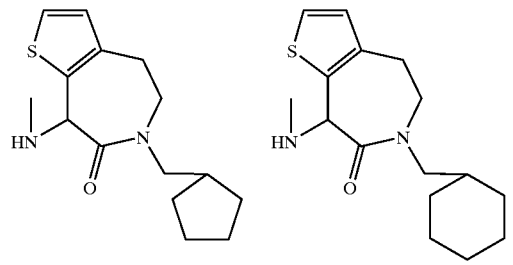
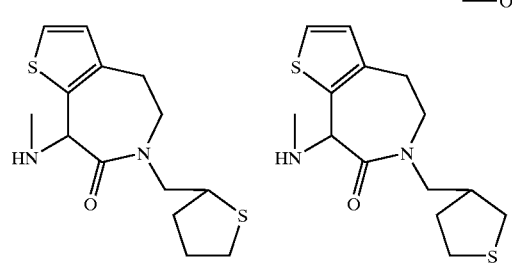

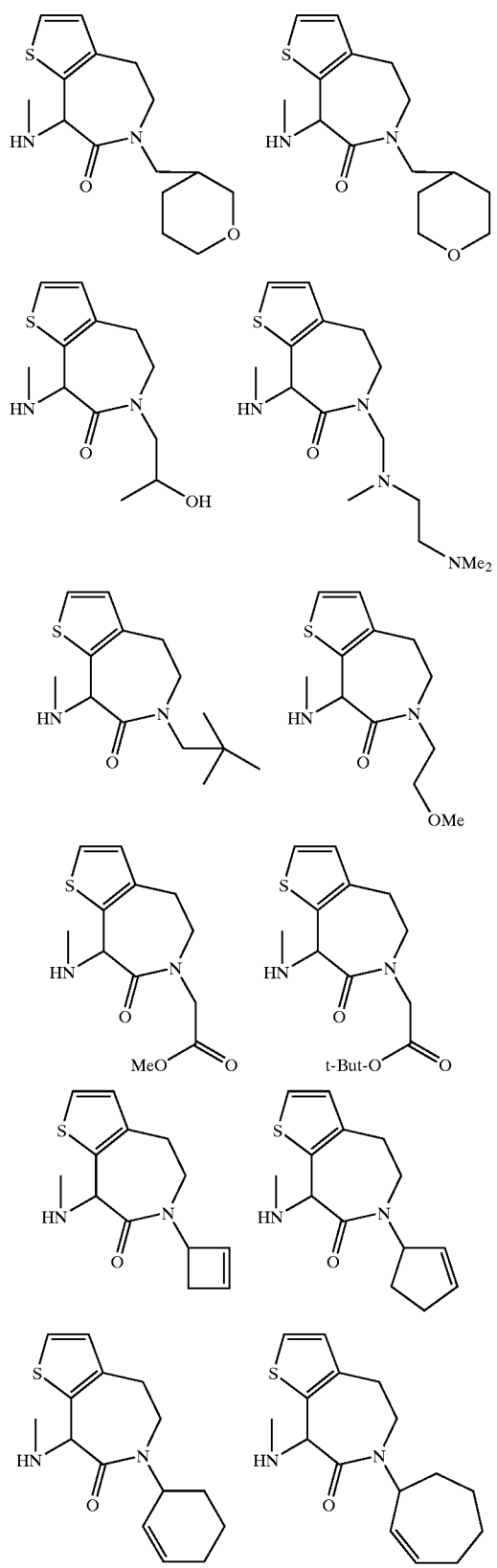
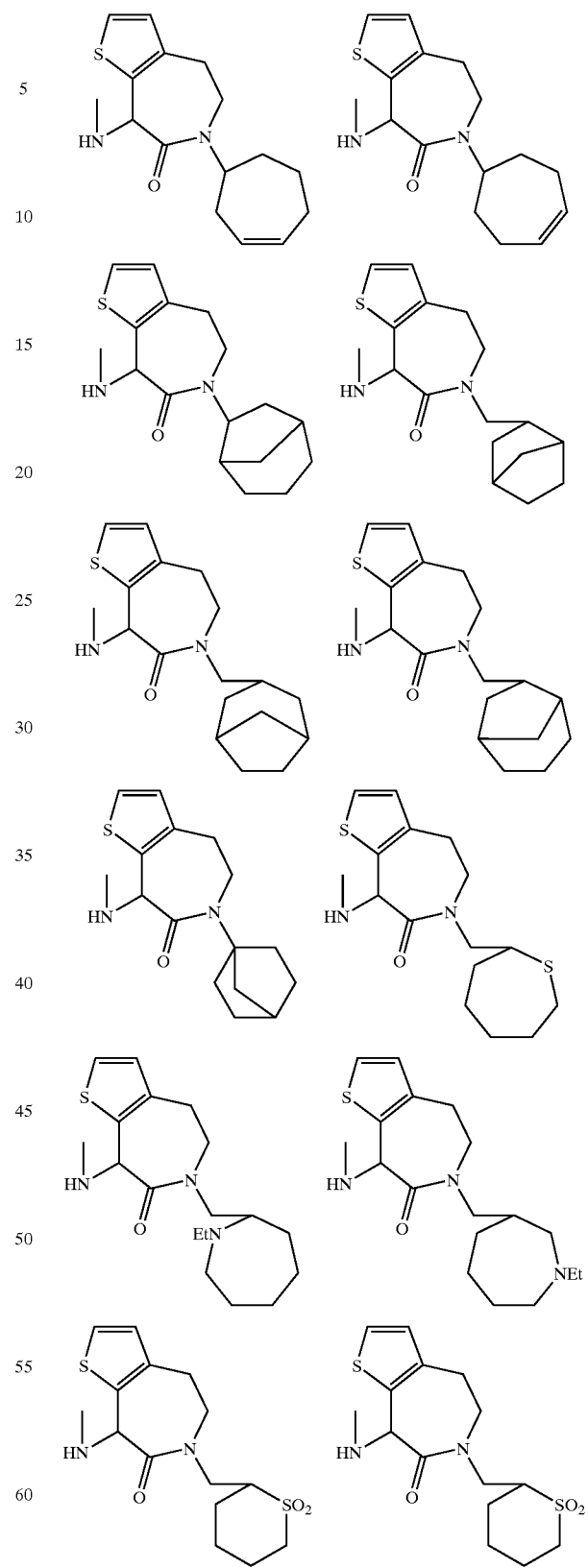

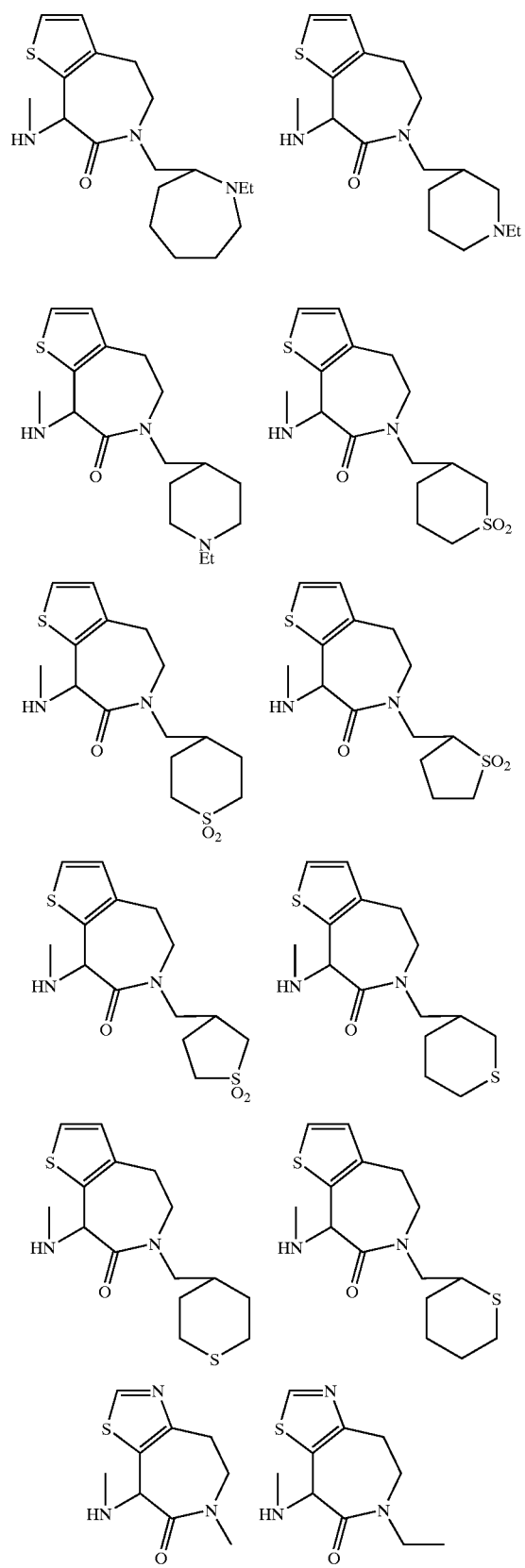
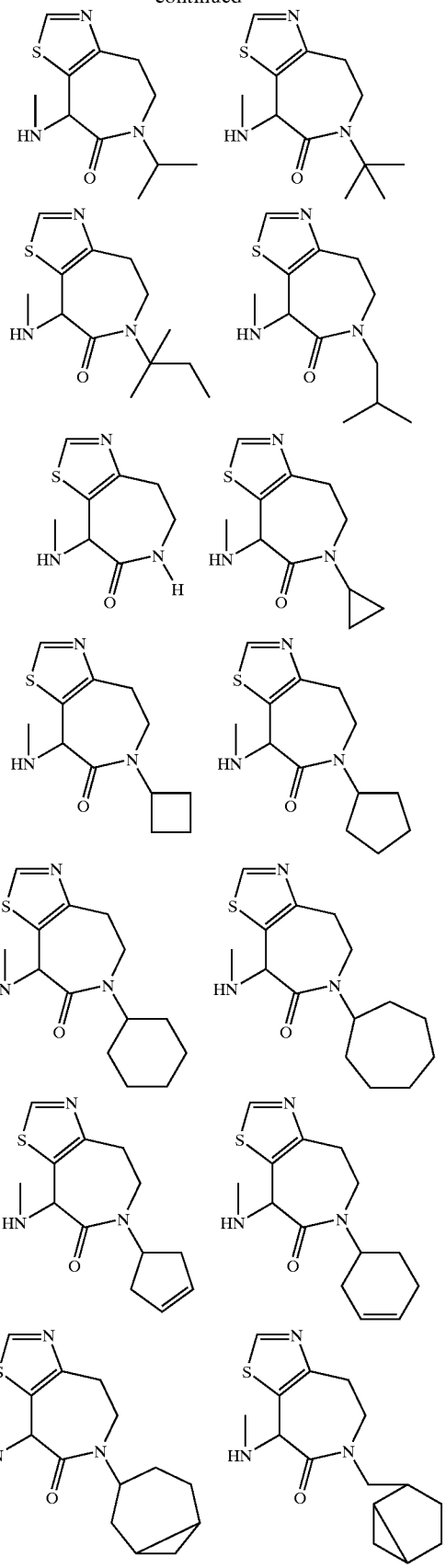

291
-continued
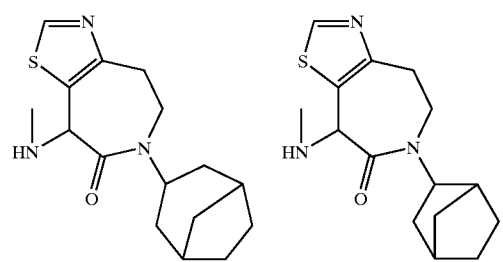
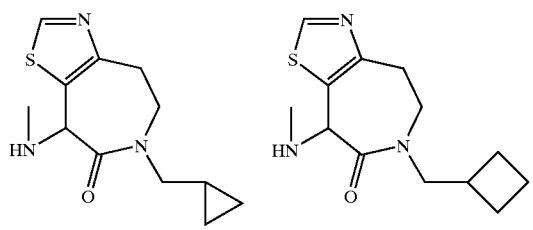
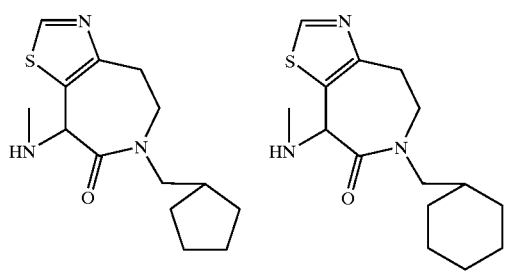
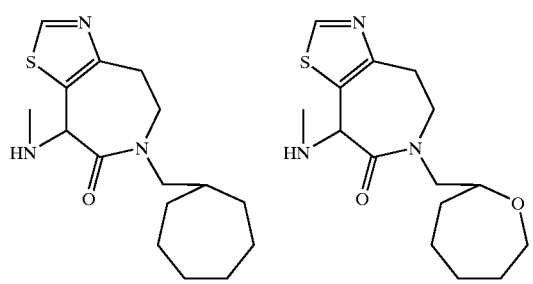
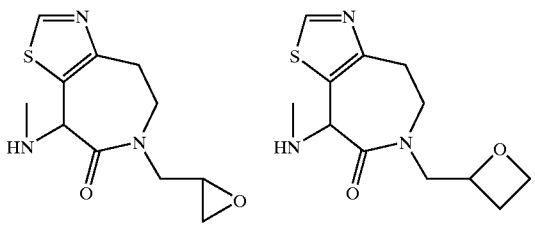
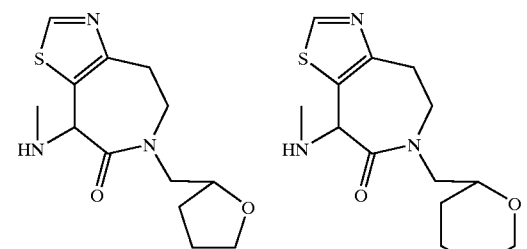
292
-continued
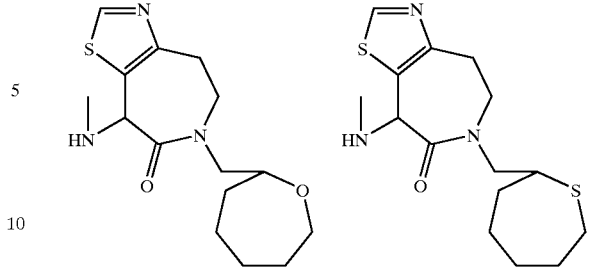
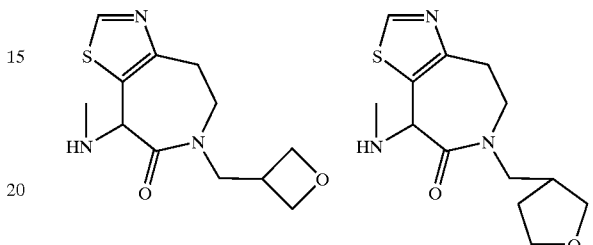
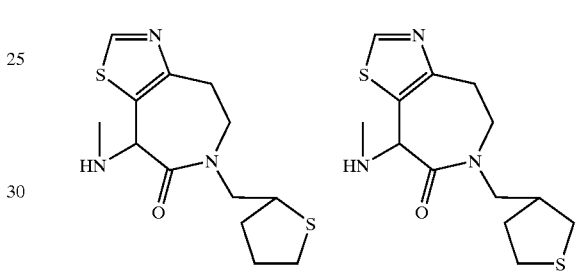
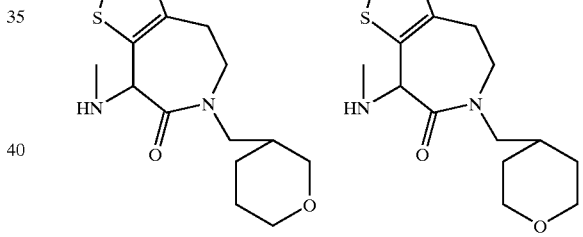
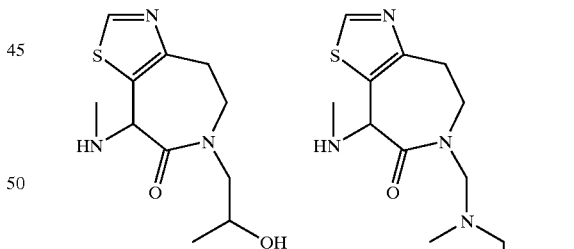
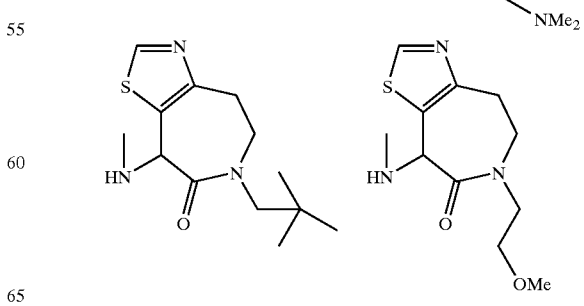

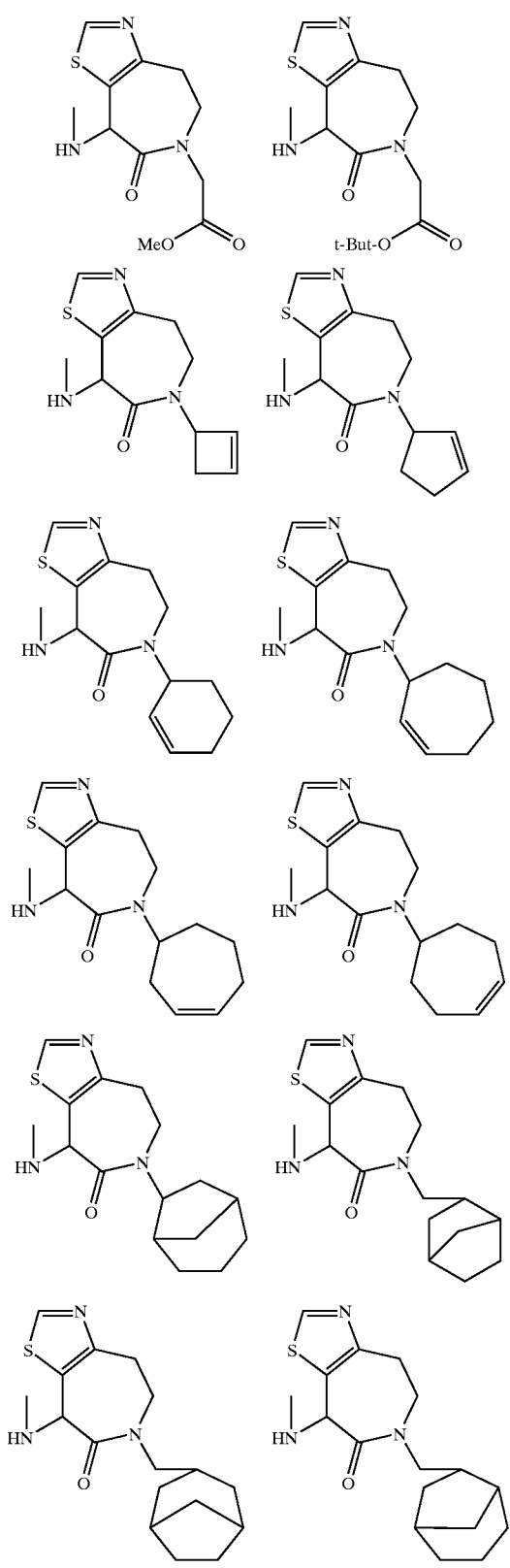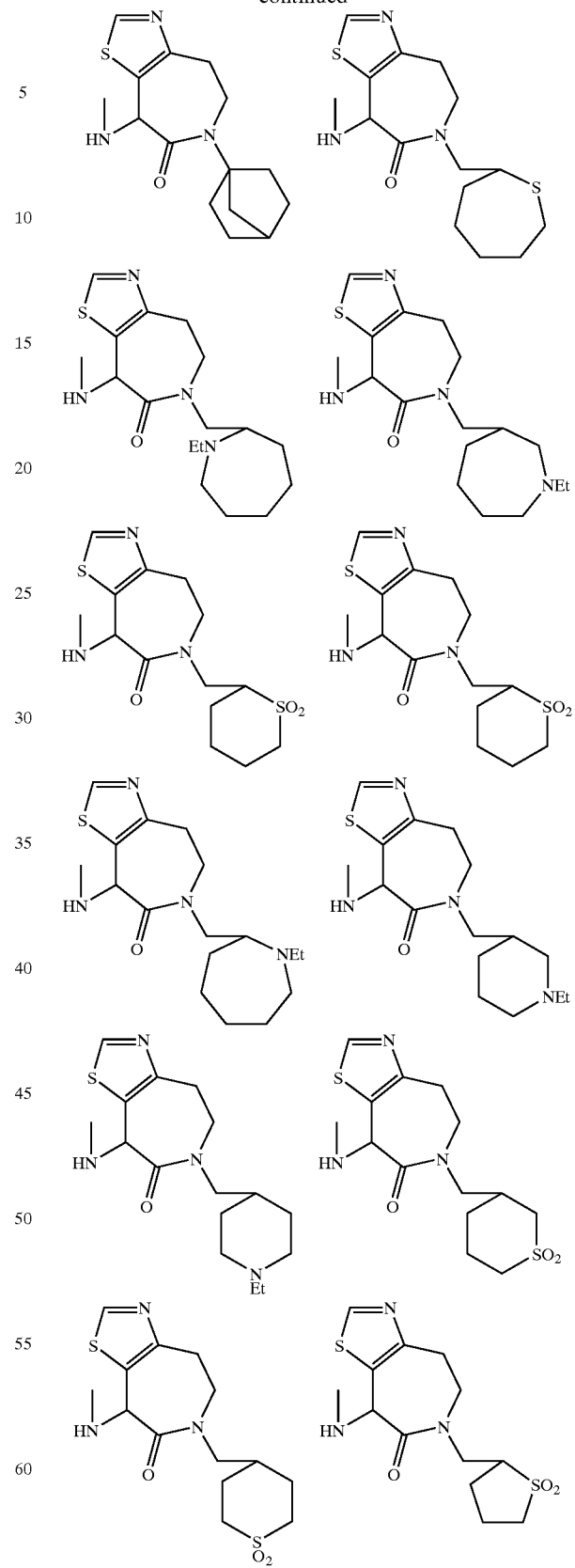

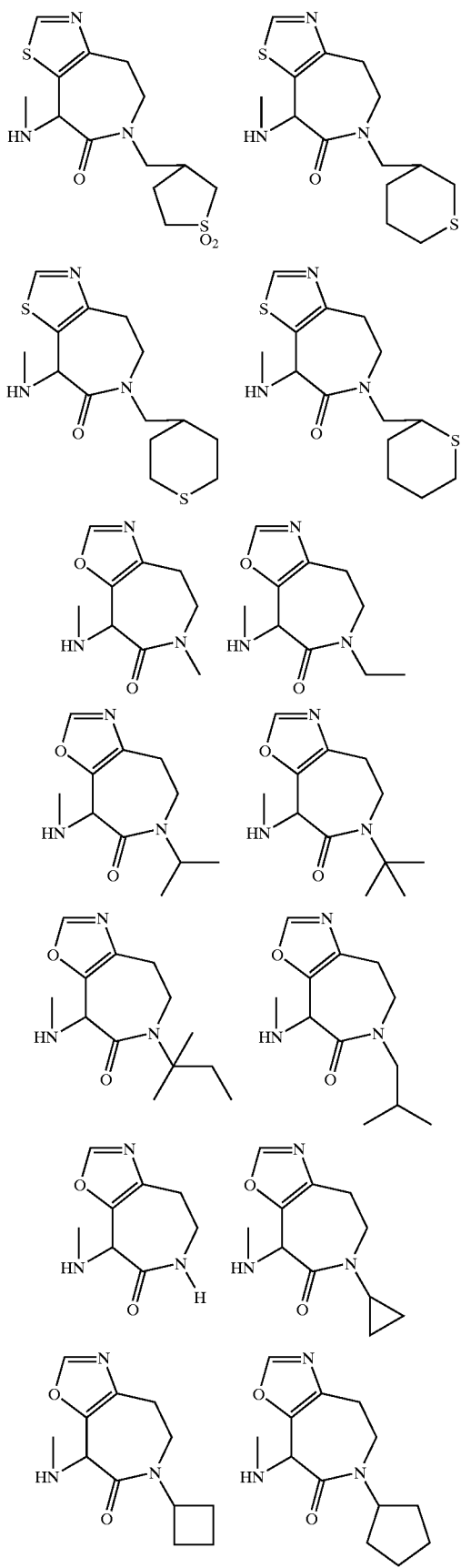
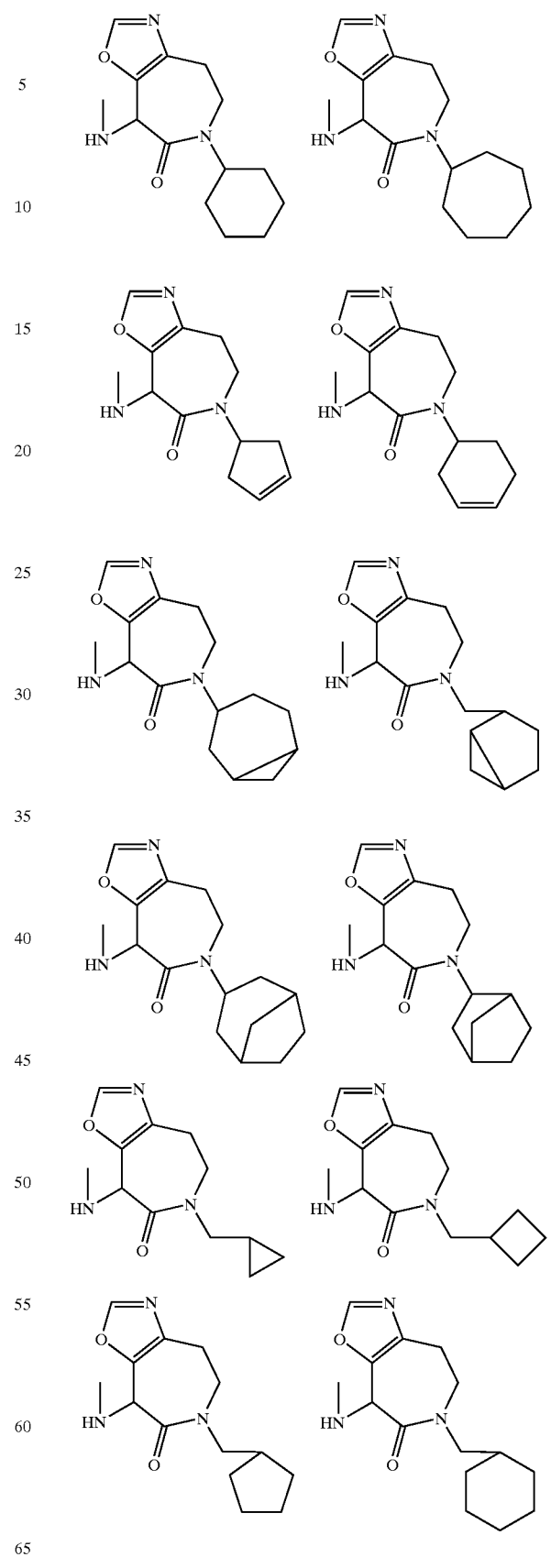

297
-continued
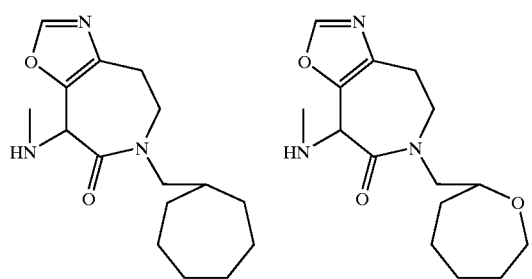
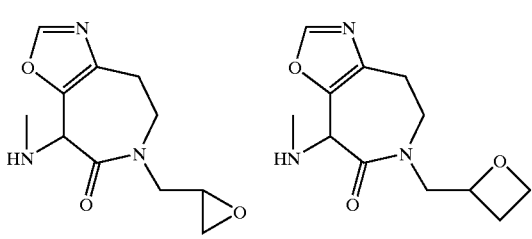
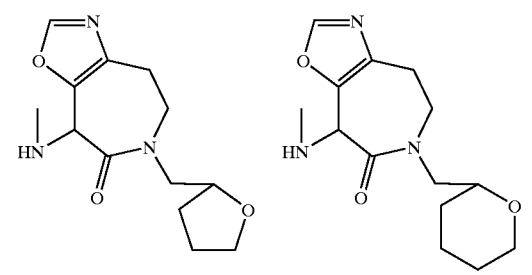
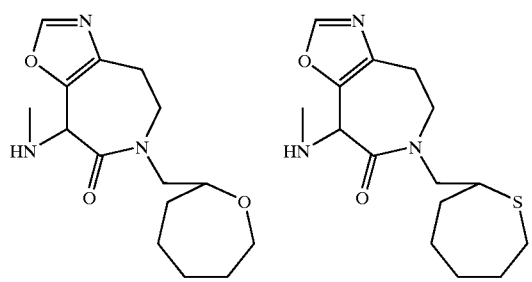
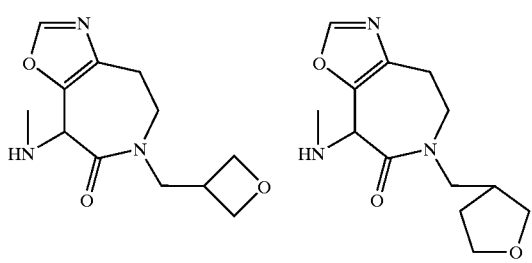
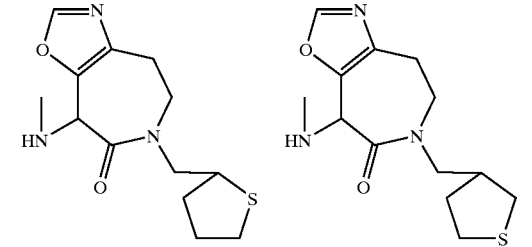
298
-continued
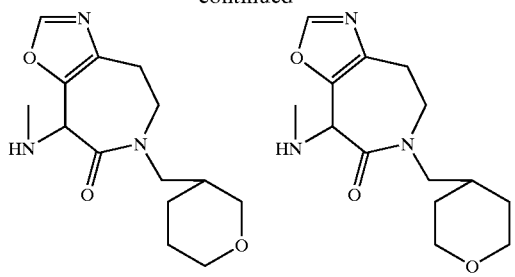
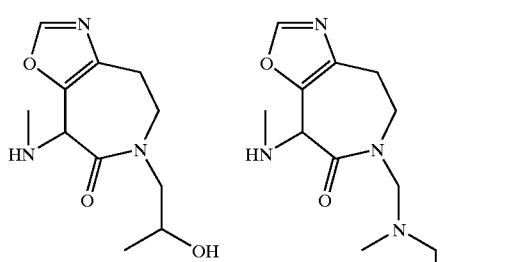
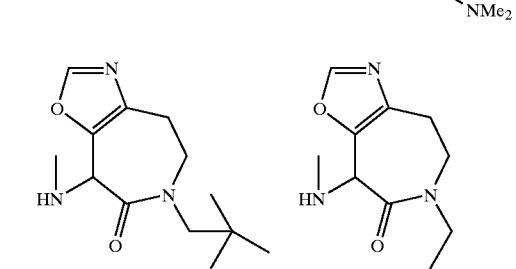
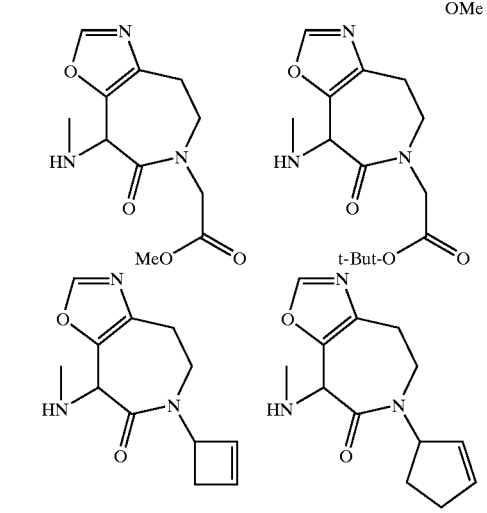
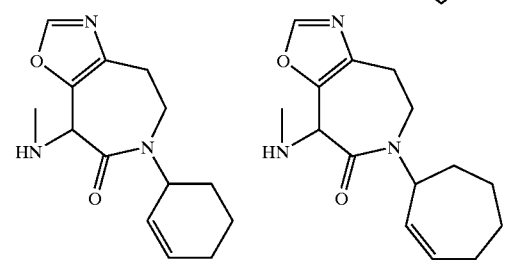

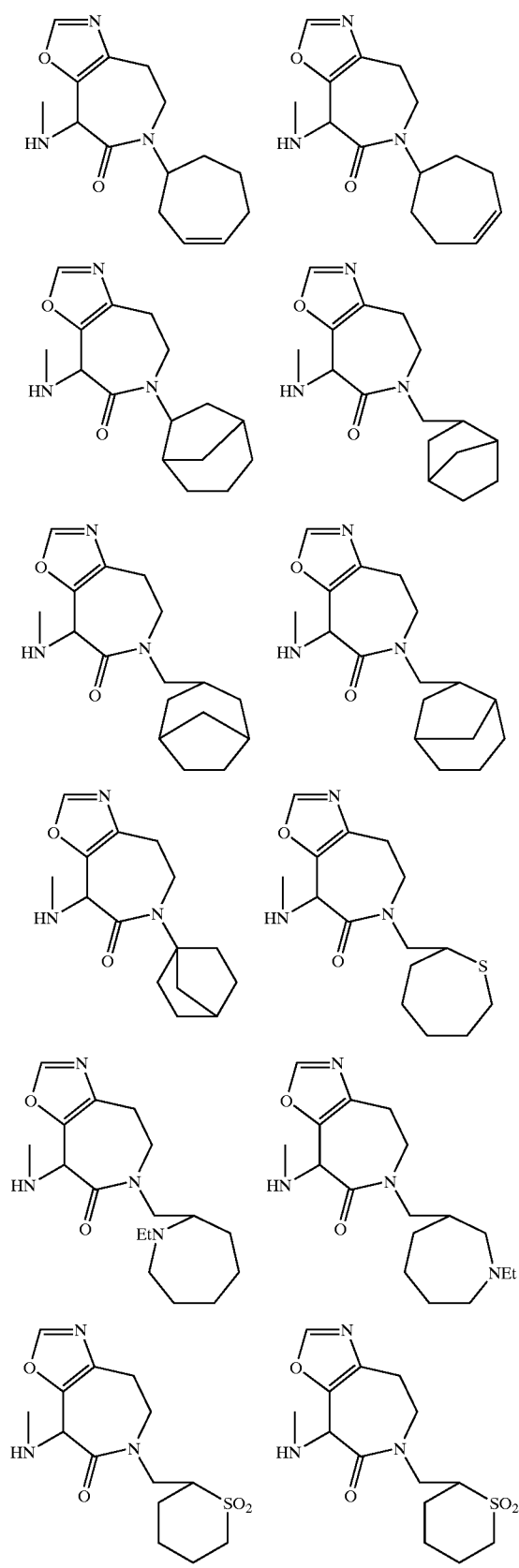
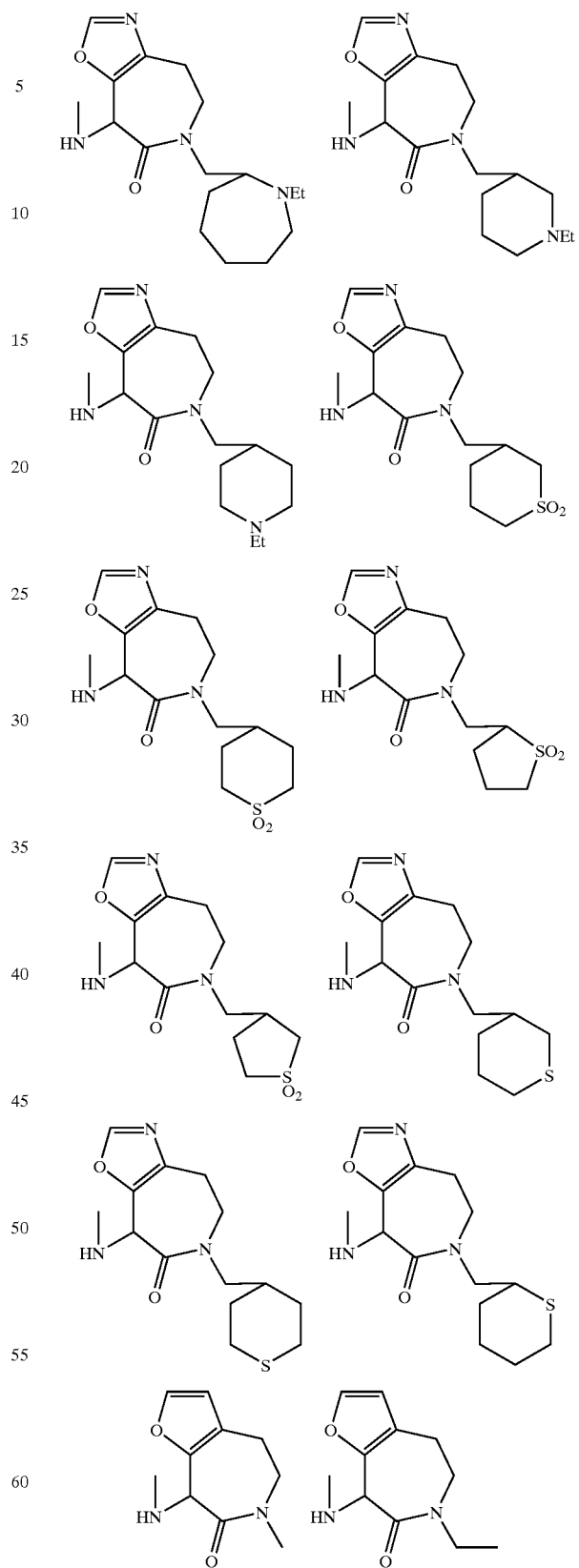

301
-continued
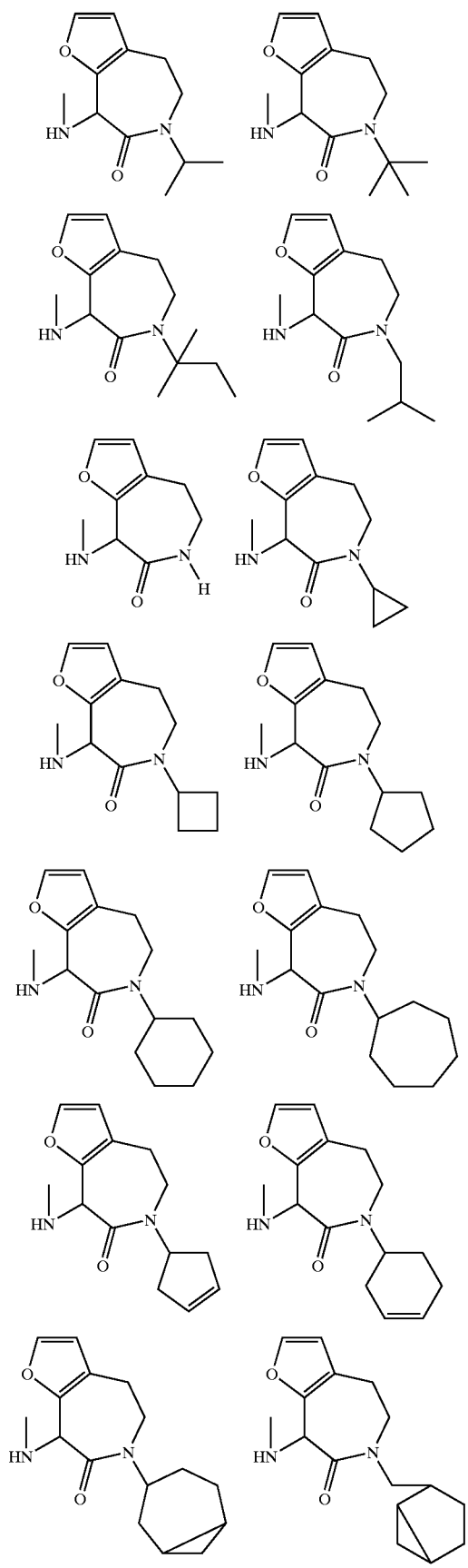
302
-continued
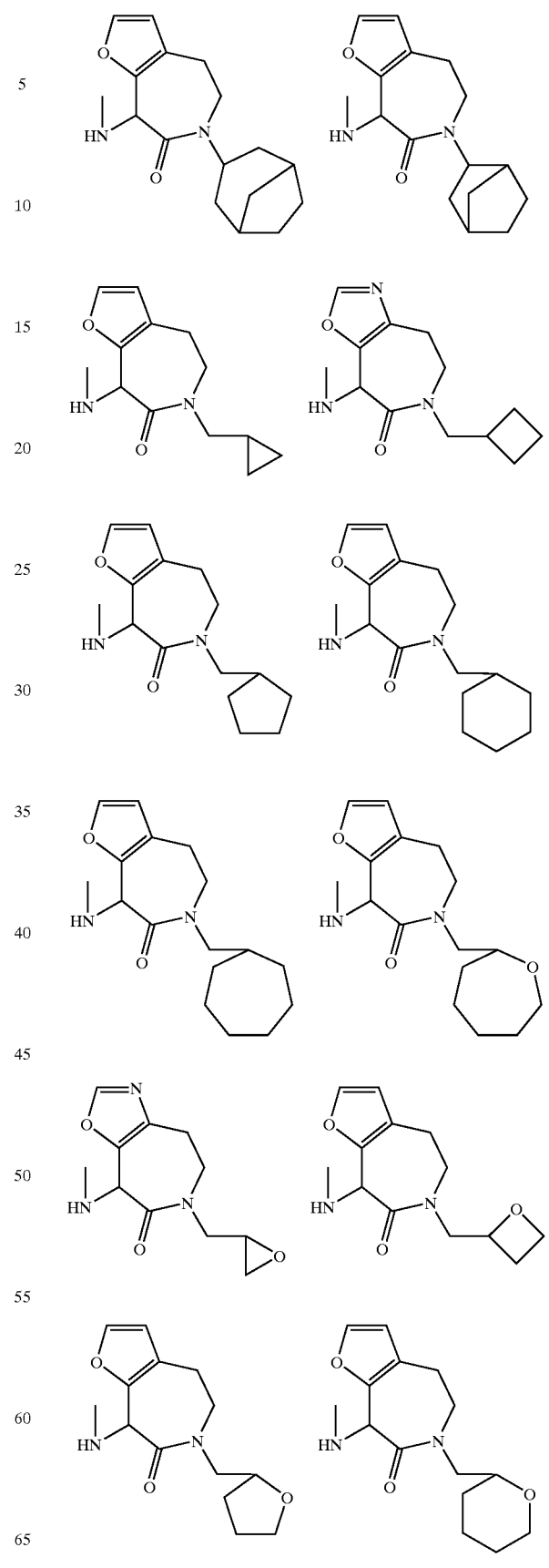

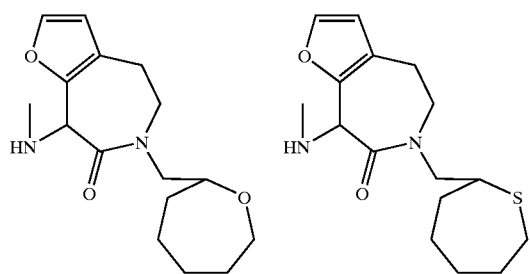
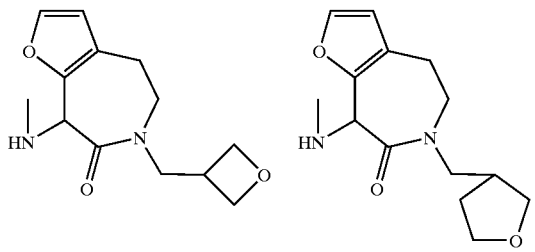
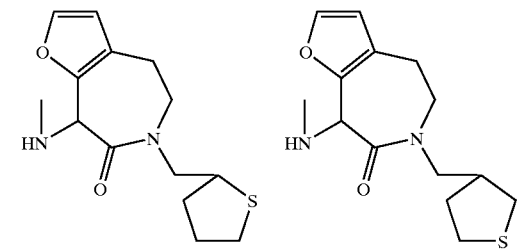
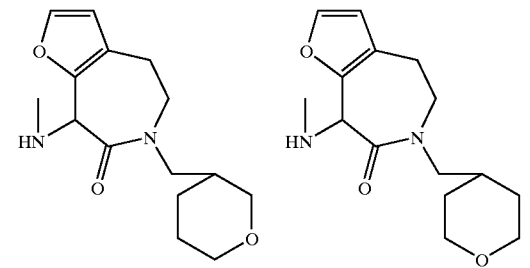
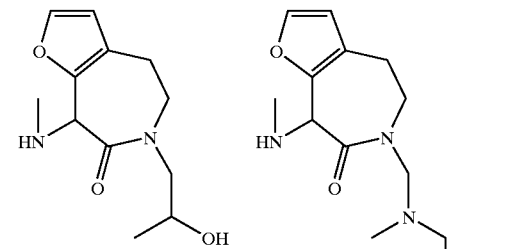
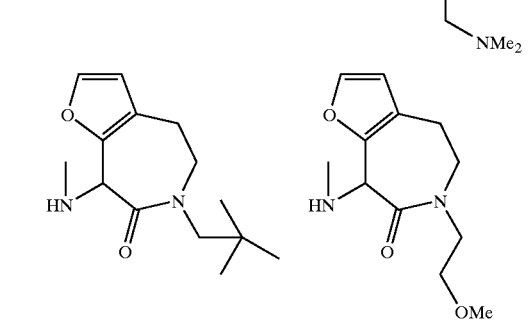
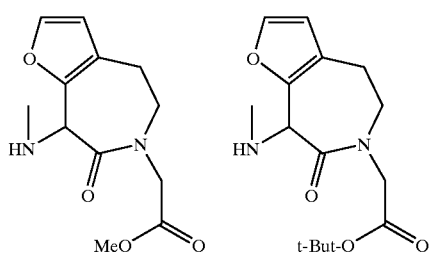
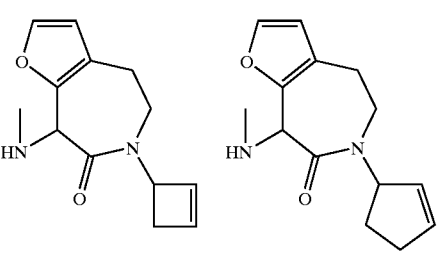
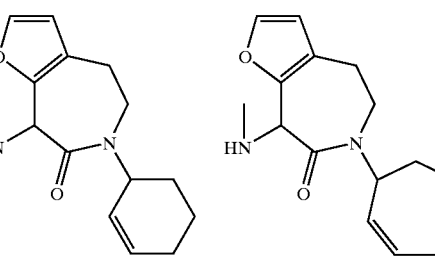
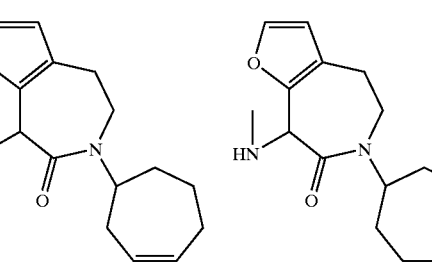
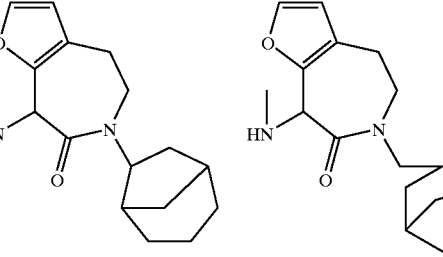
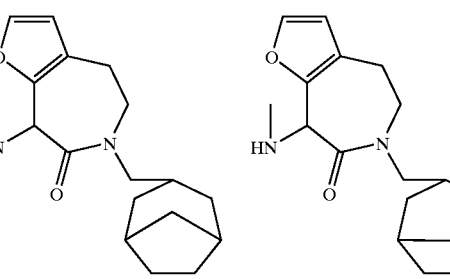

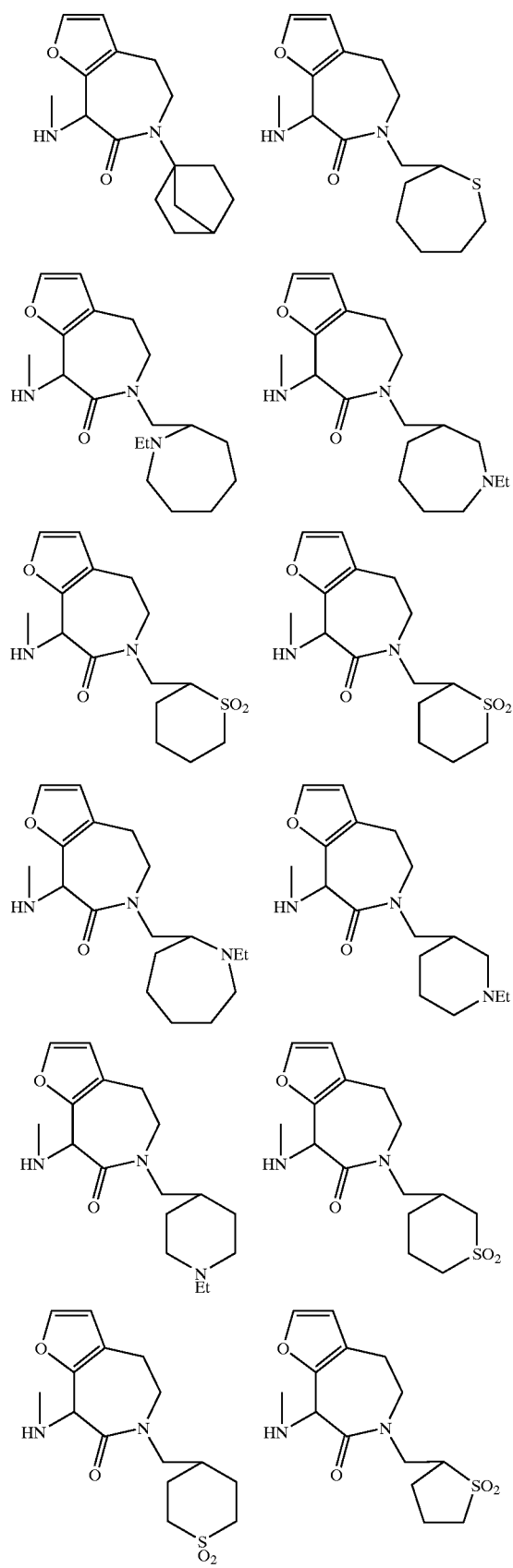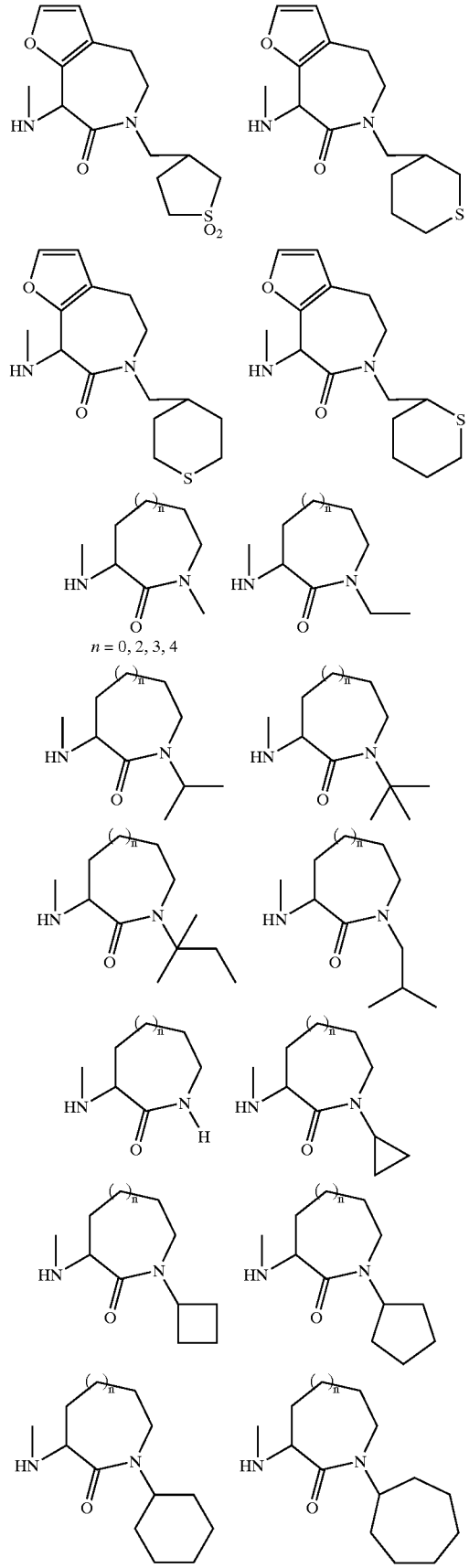

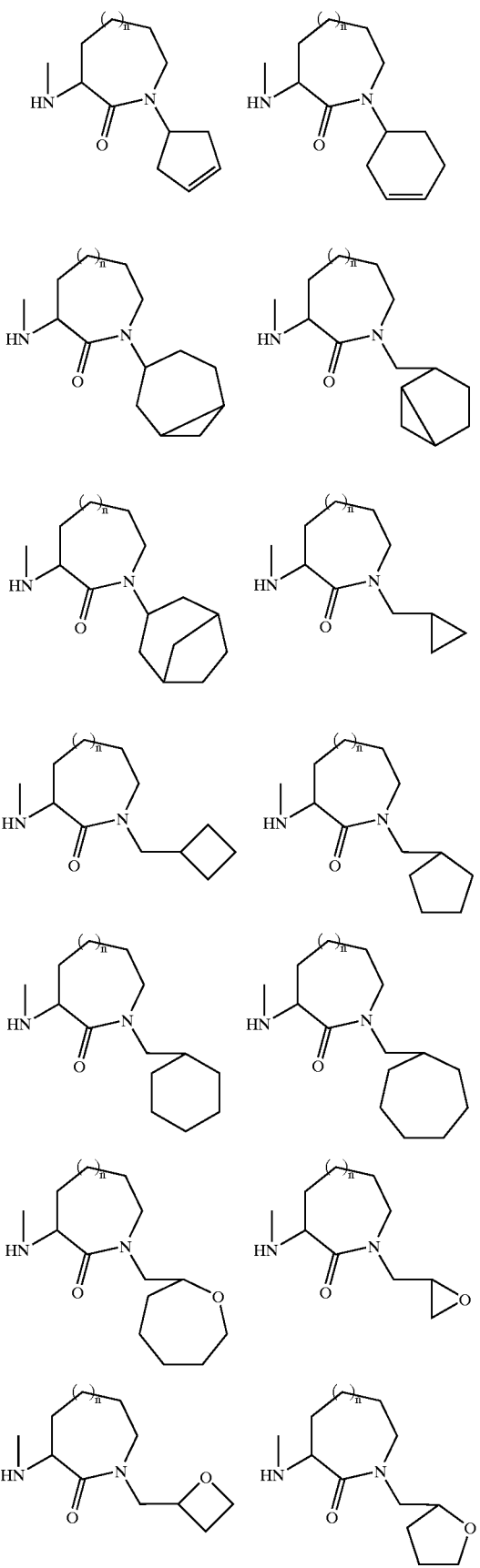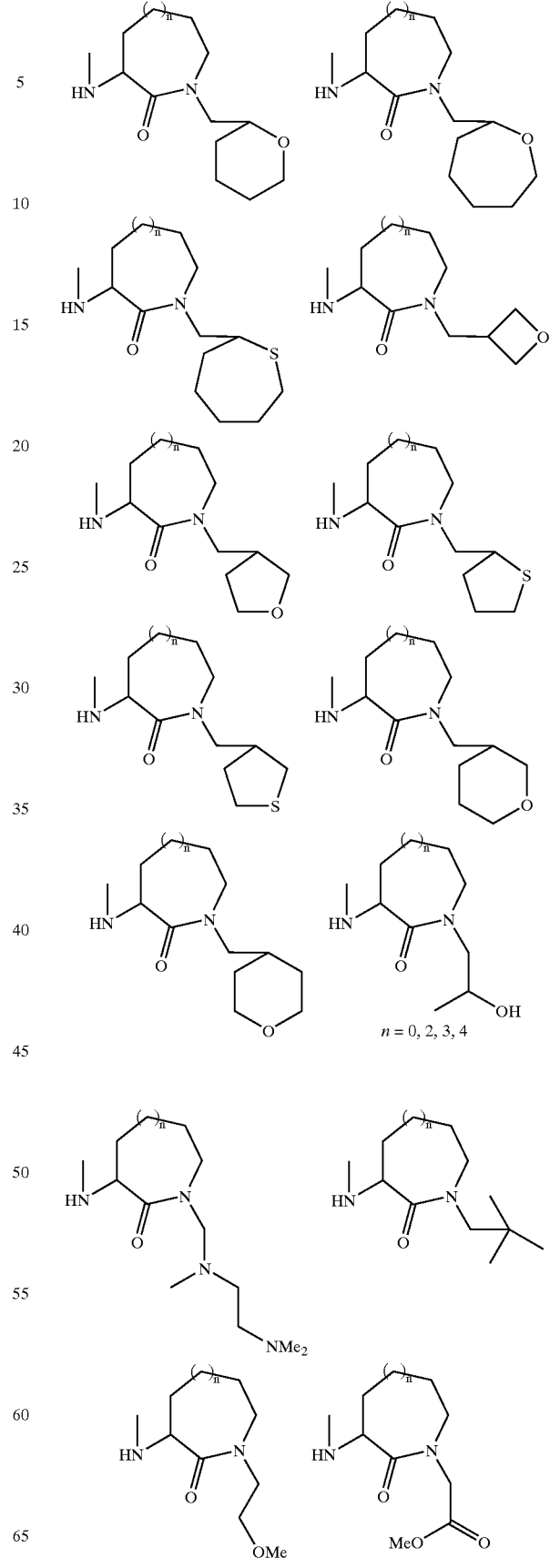
n = 0, 2, 3, 4

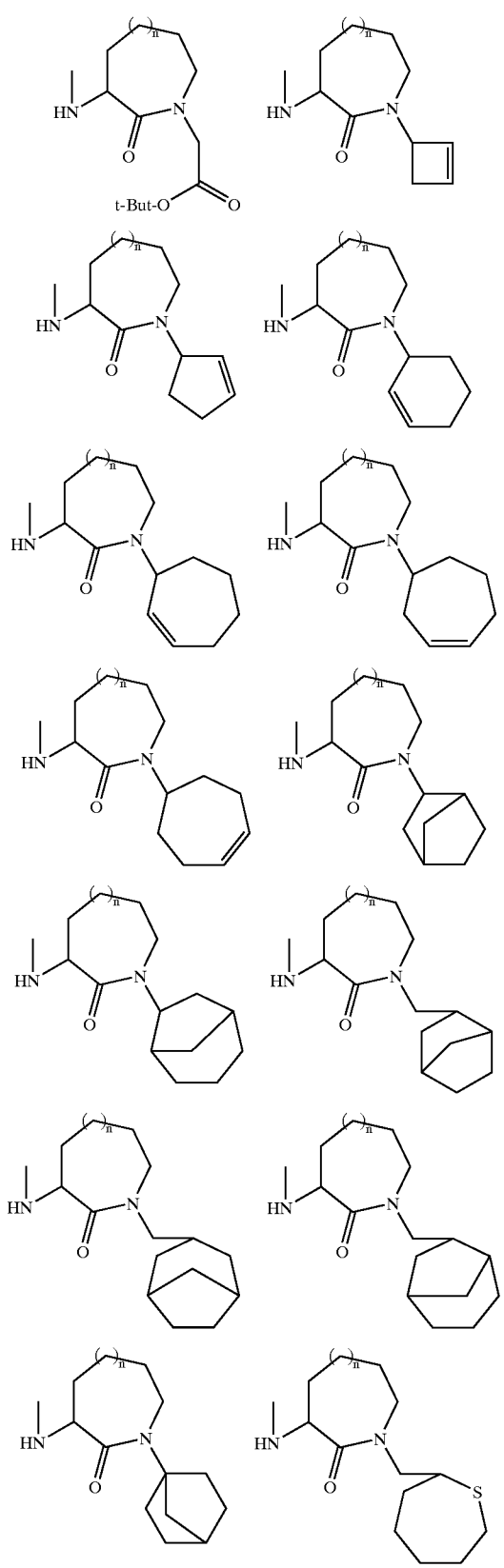
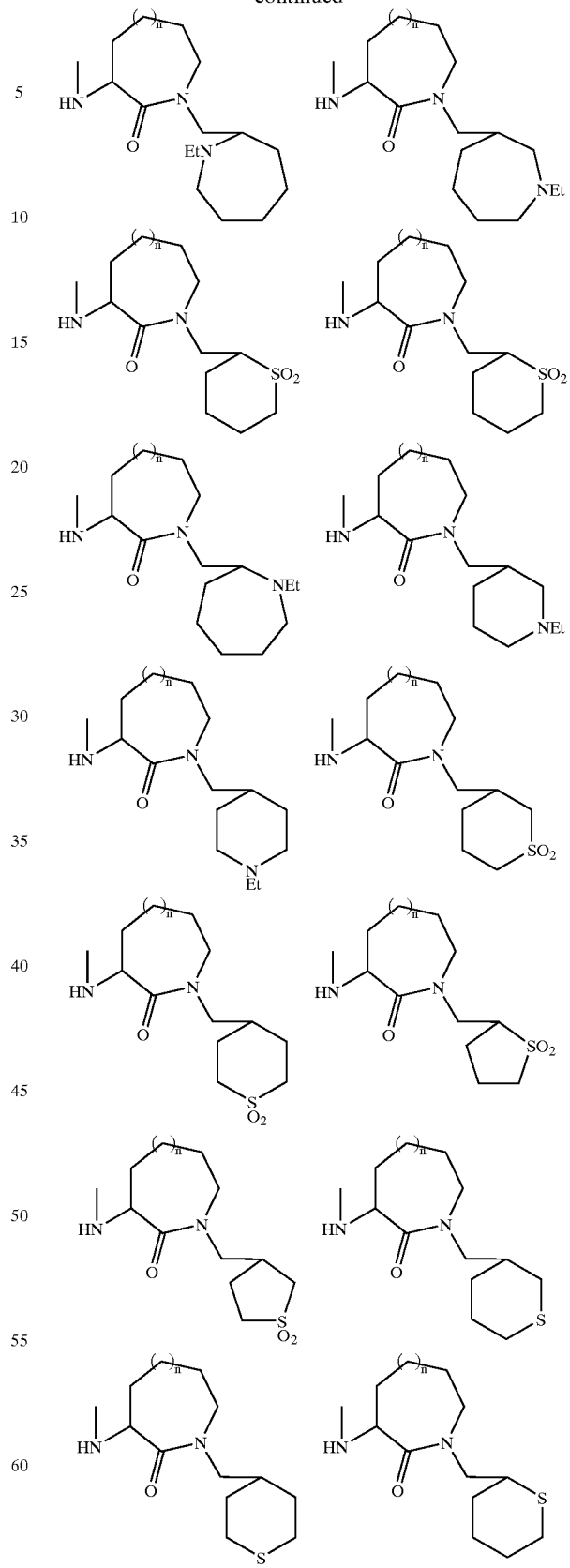

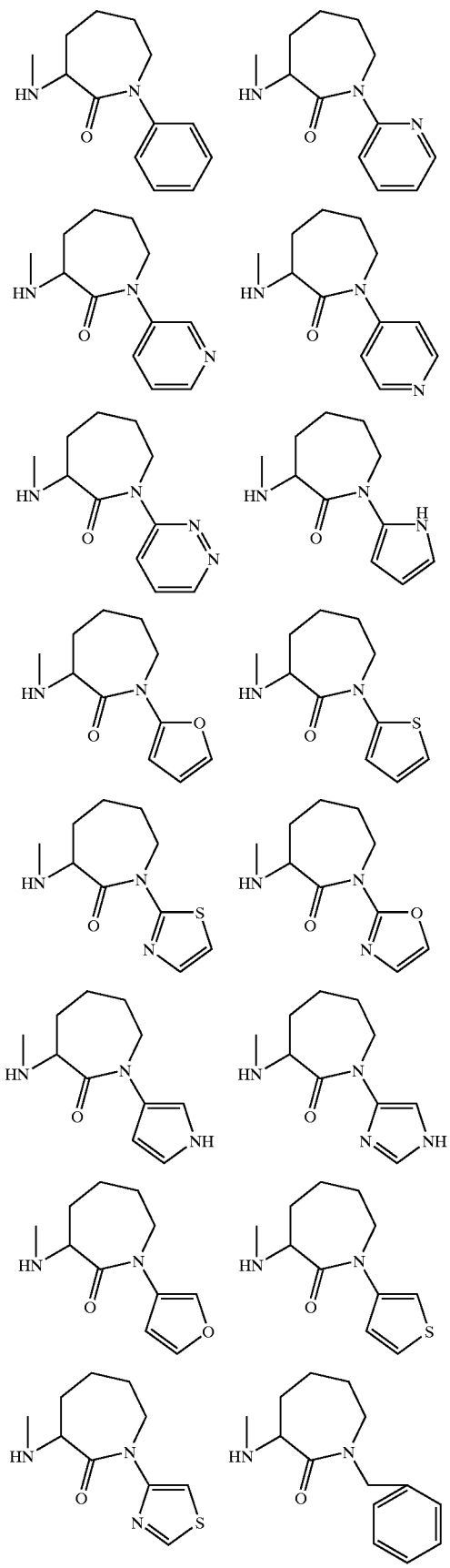
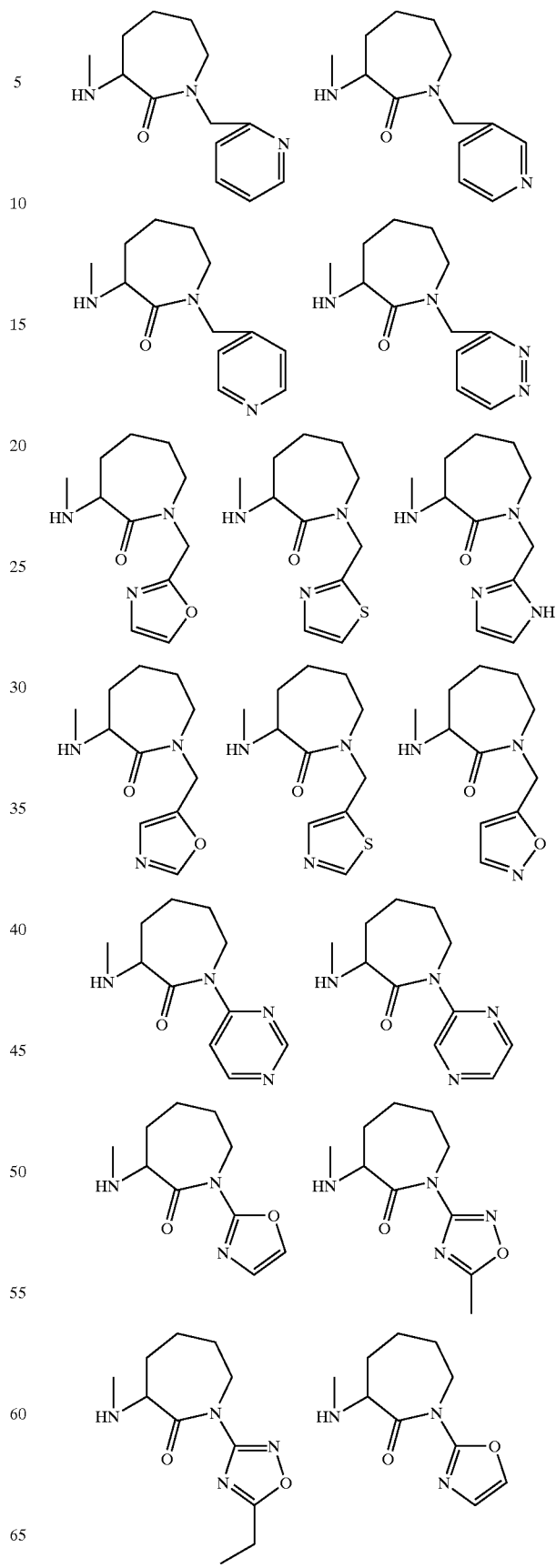

313
-continued
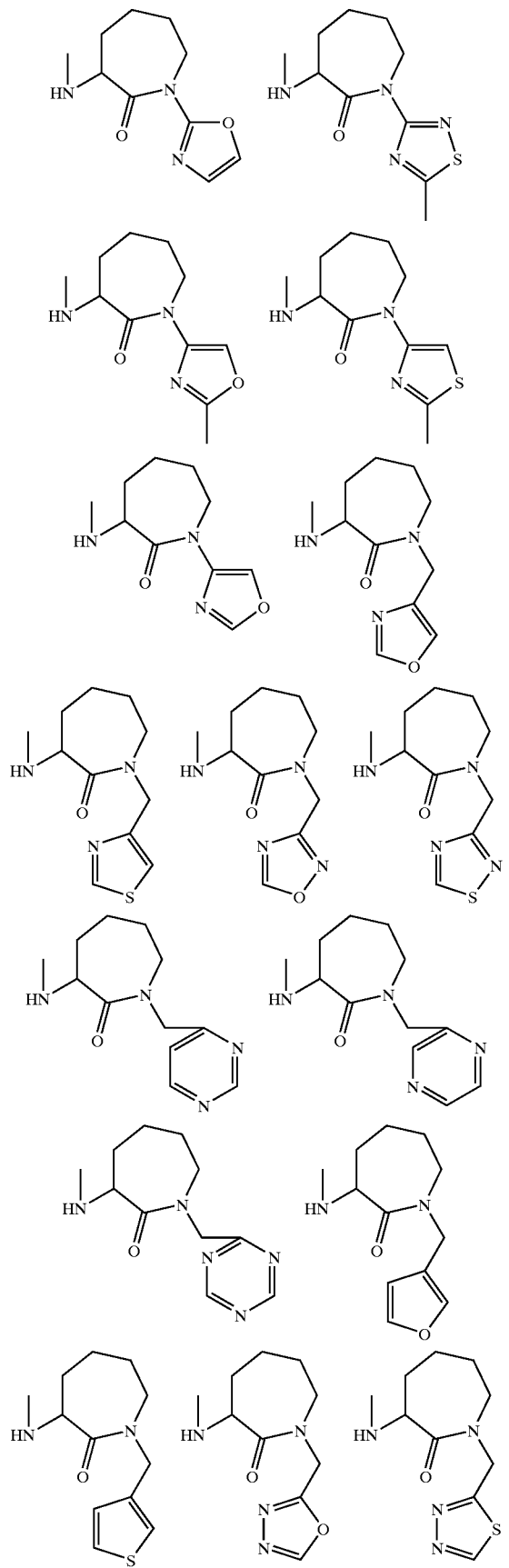
314
-continued
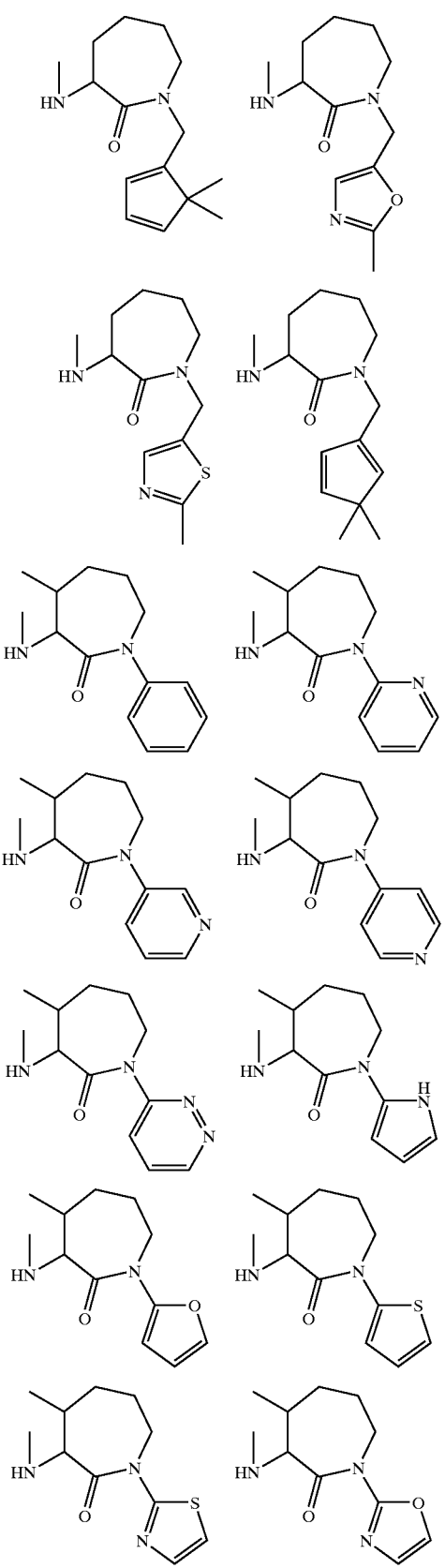

315
-continued
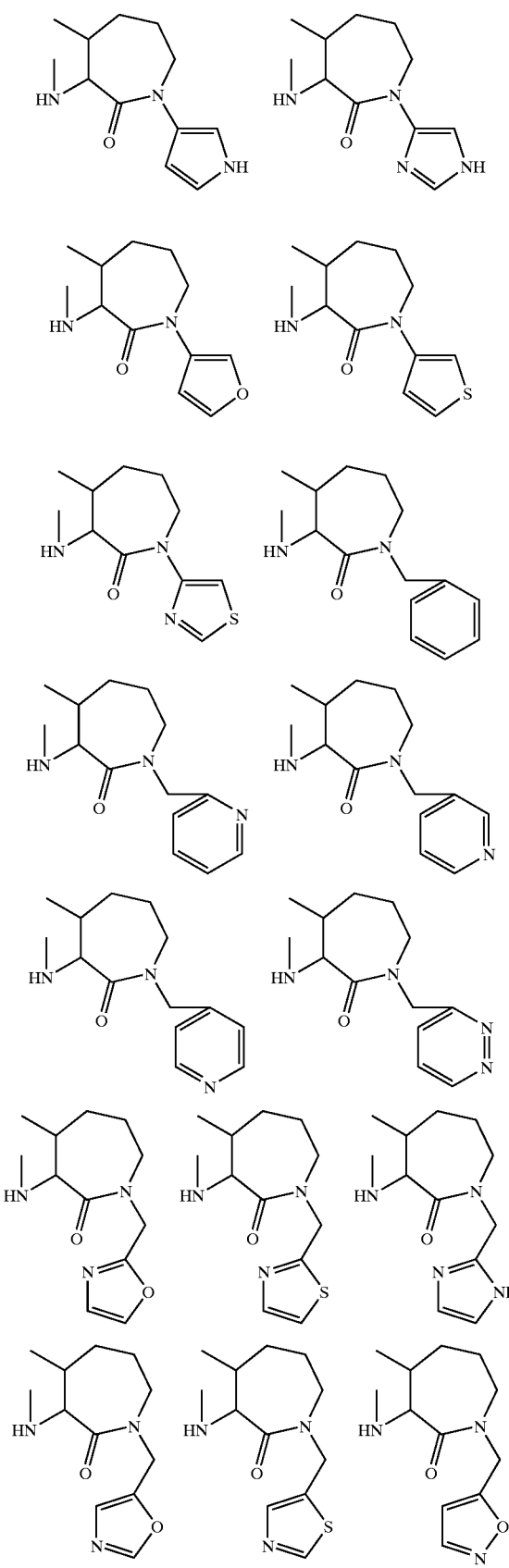
316
-continued
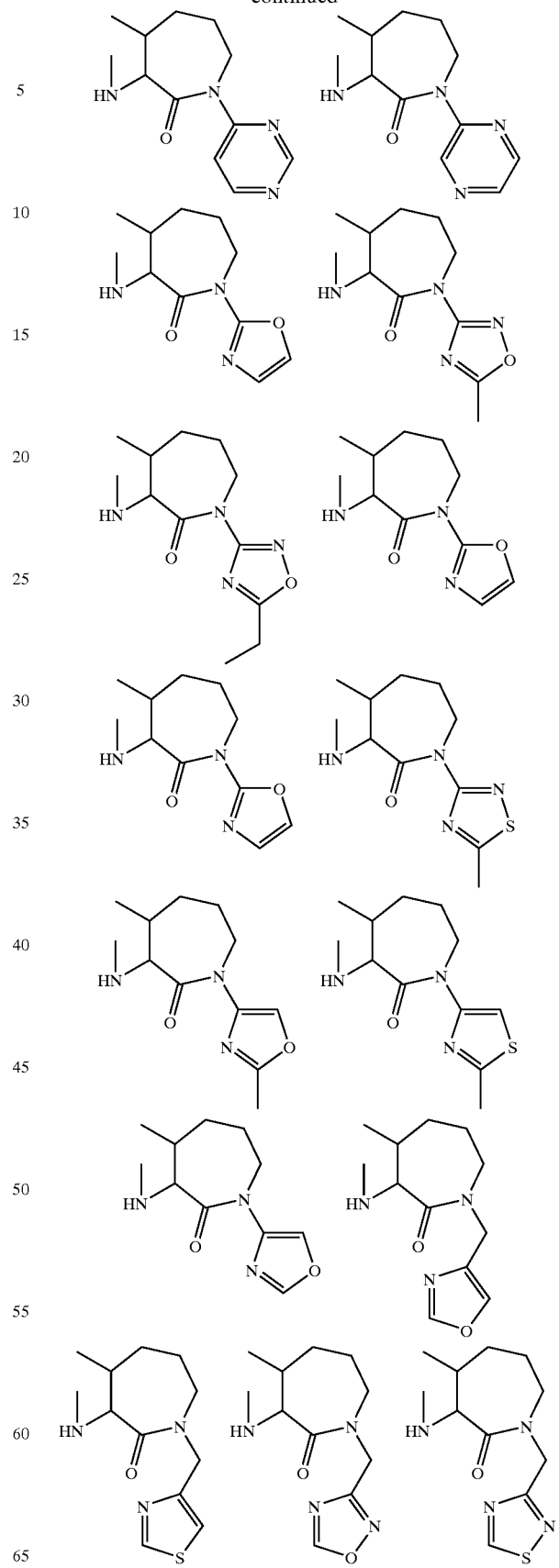

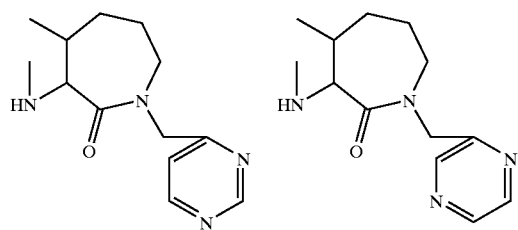
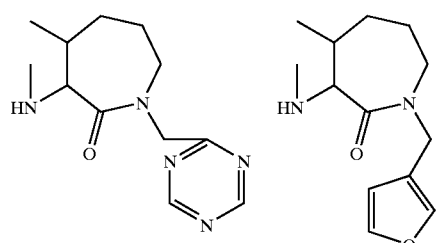
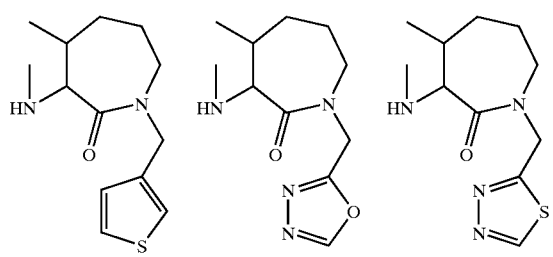
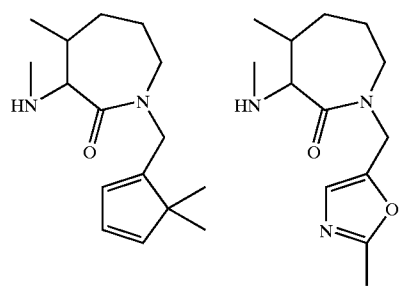
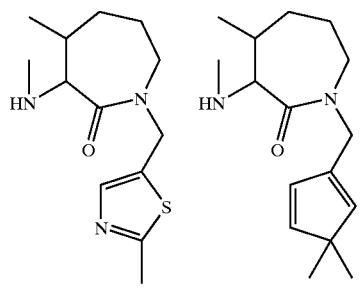
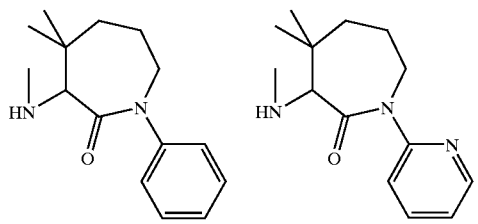
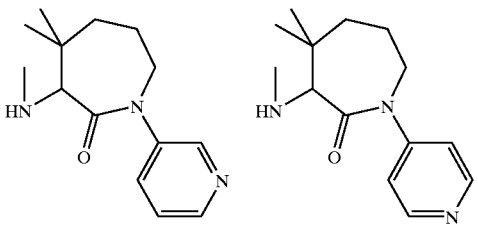
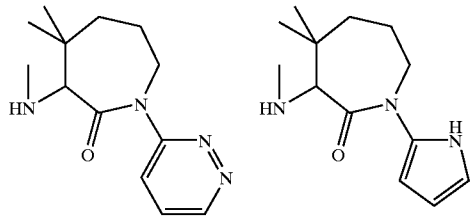
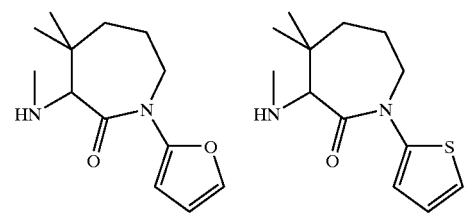
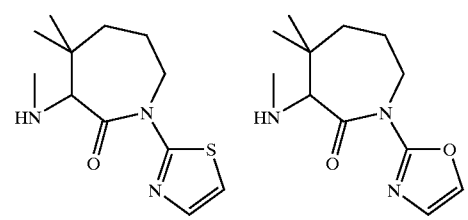
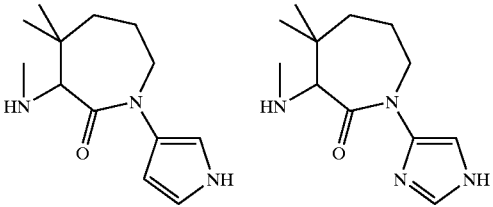
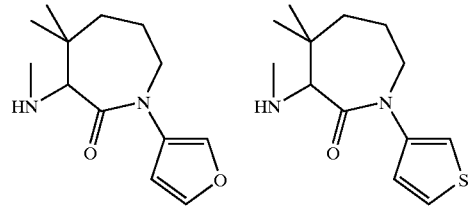
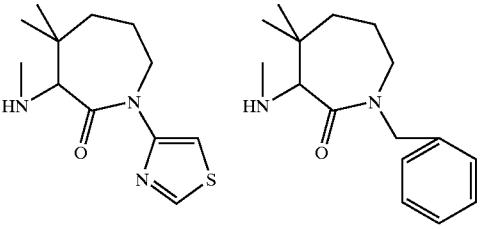

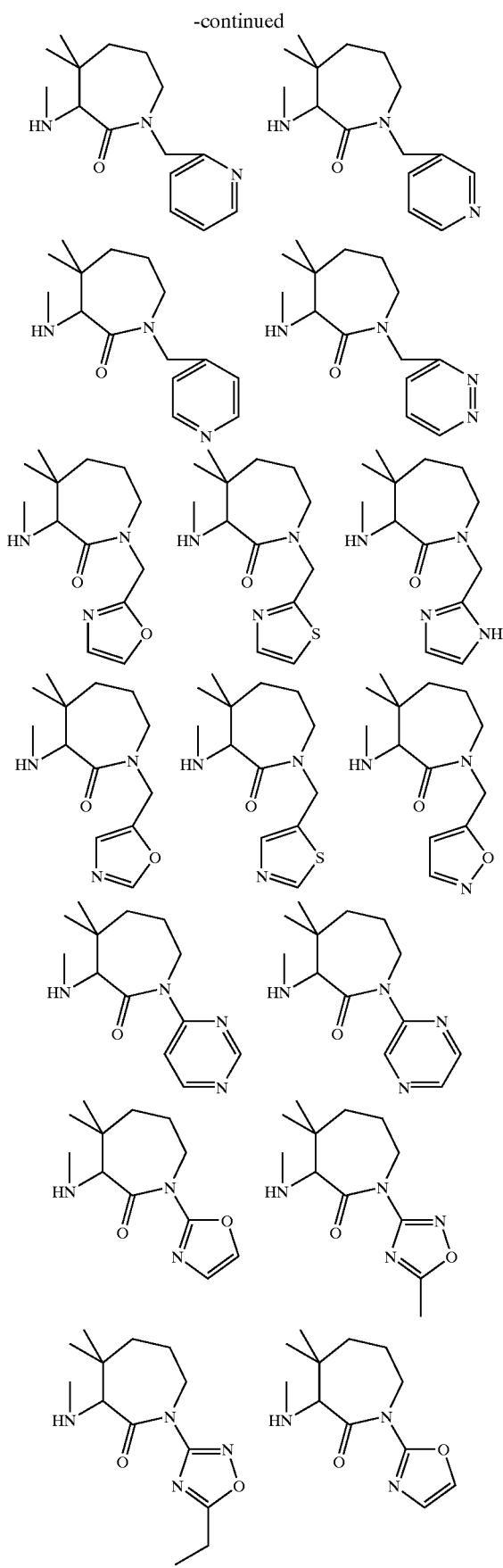
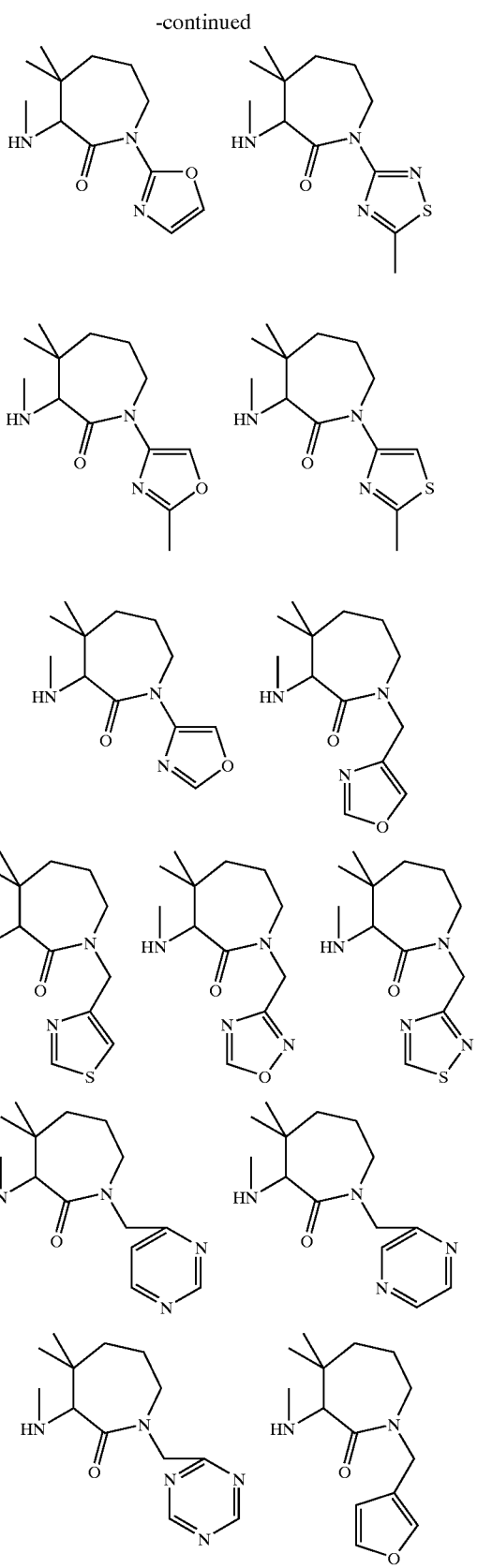

321
-continued
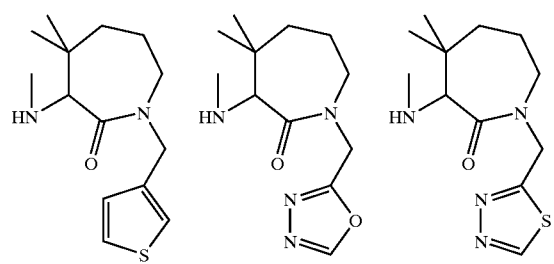
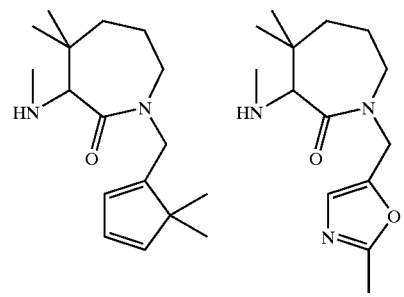
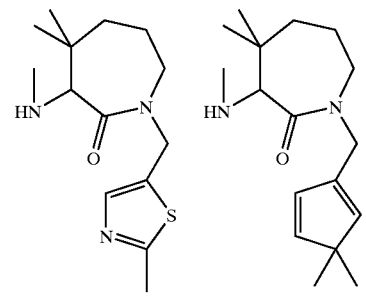
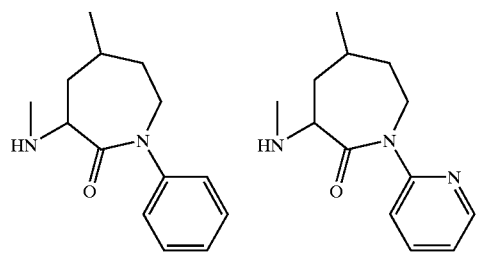
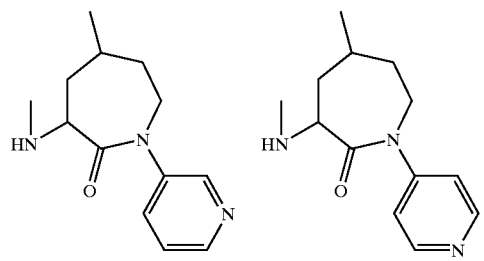
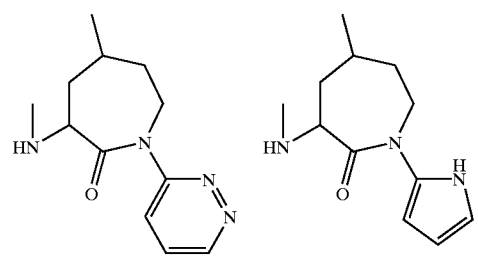
322
-continued
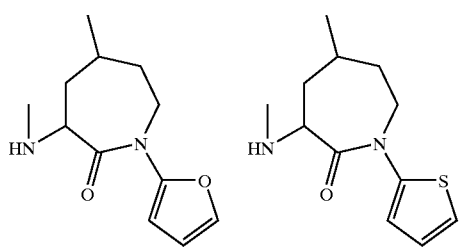
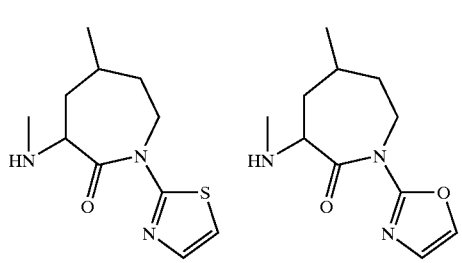
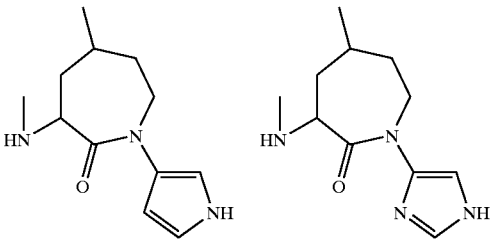
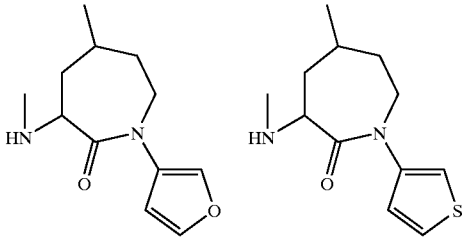
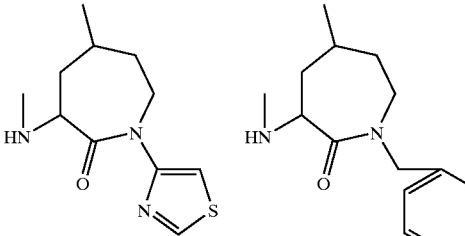
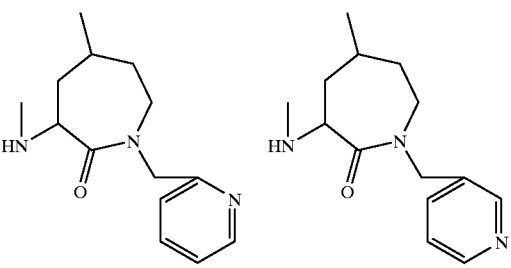

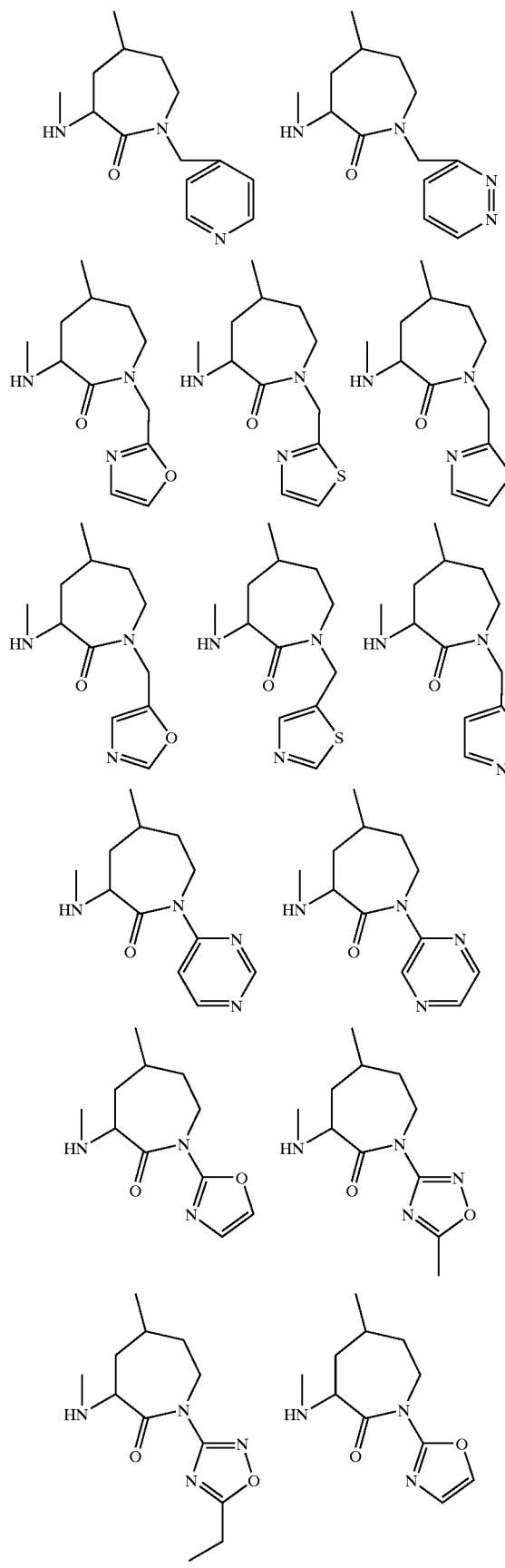
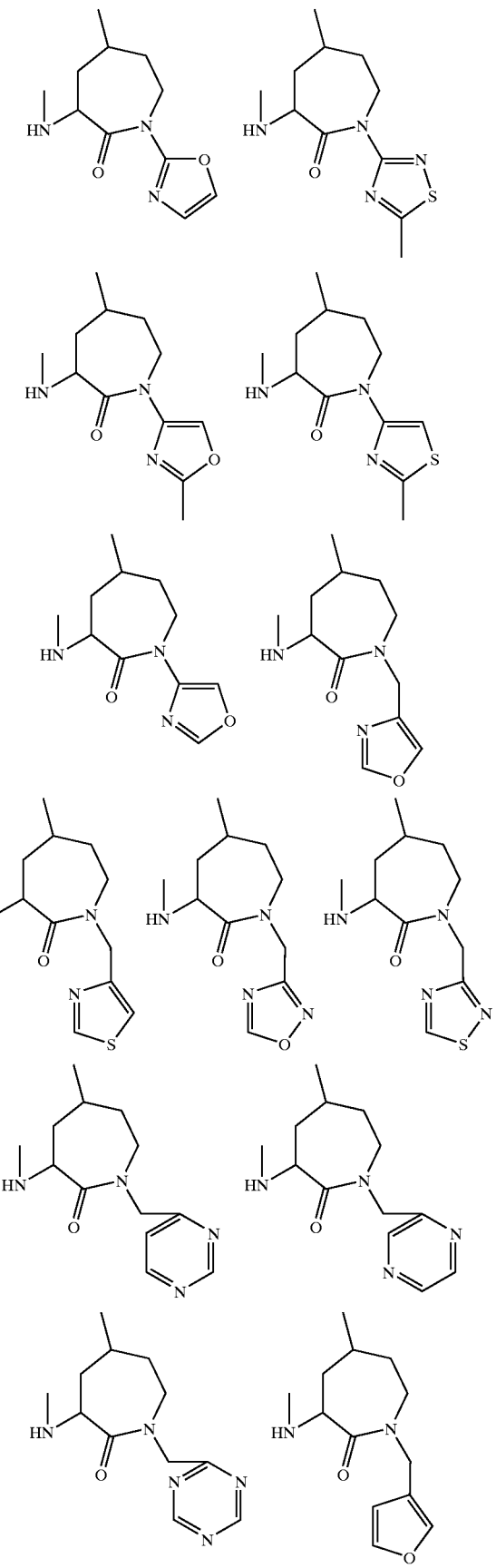

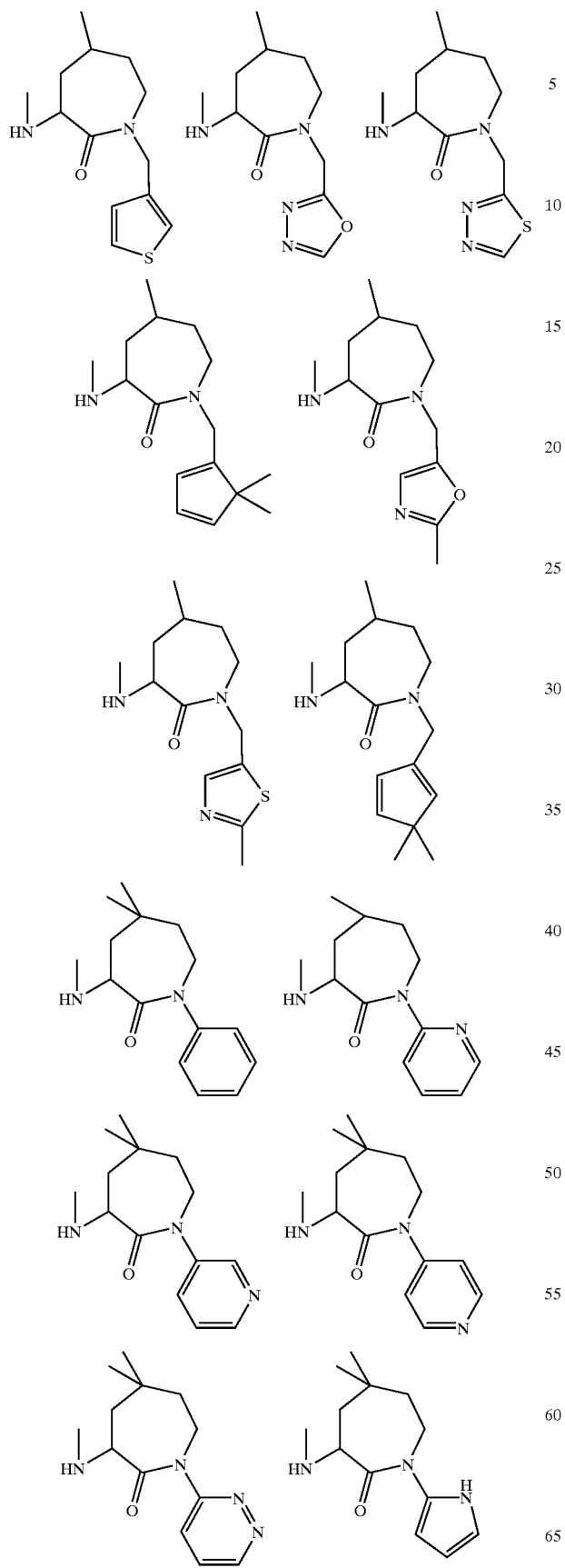
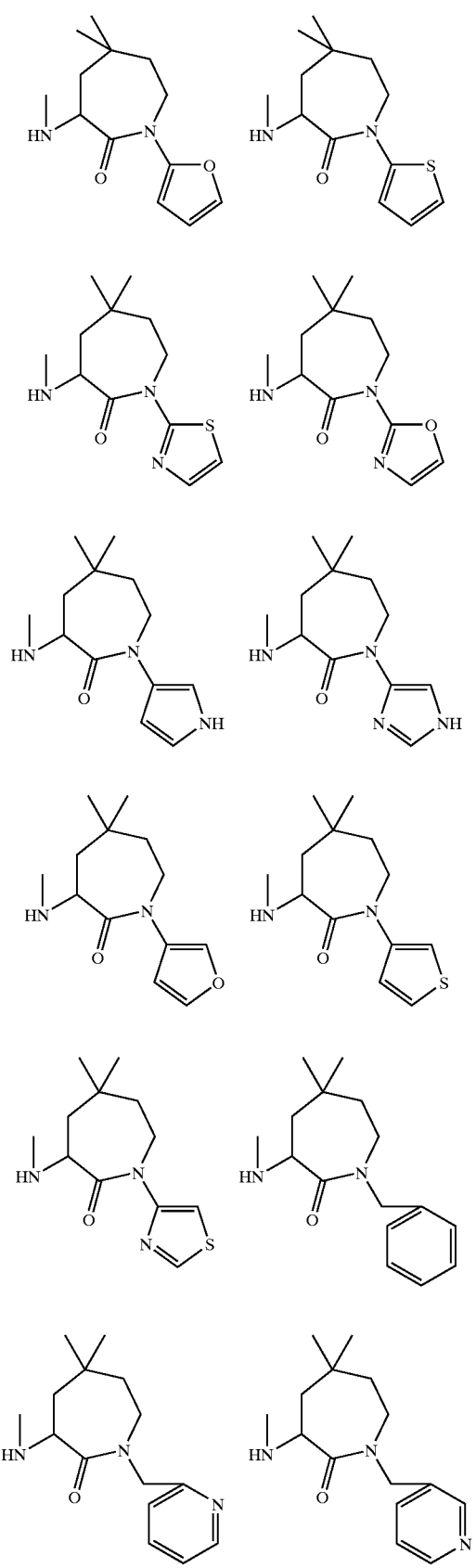

327
-continued
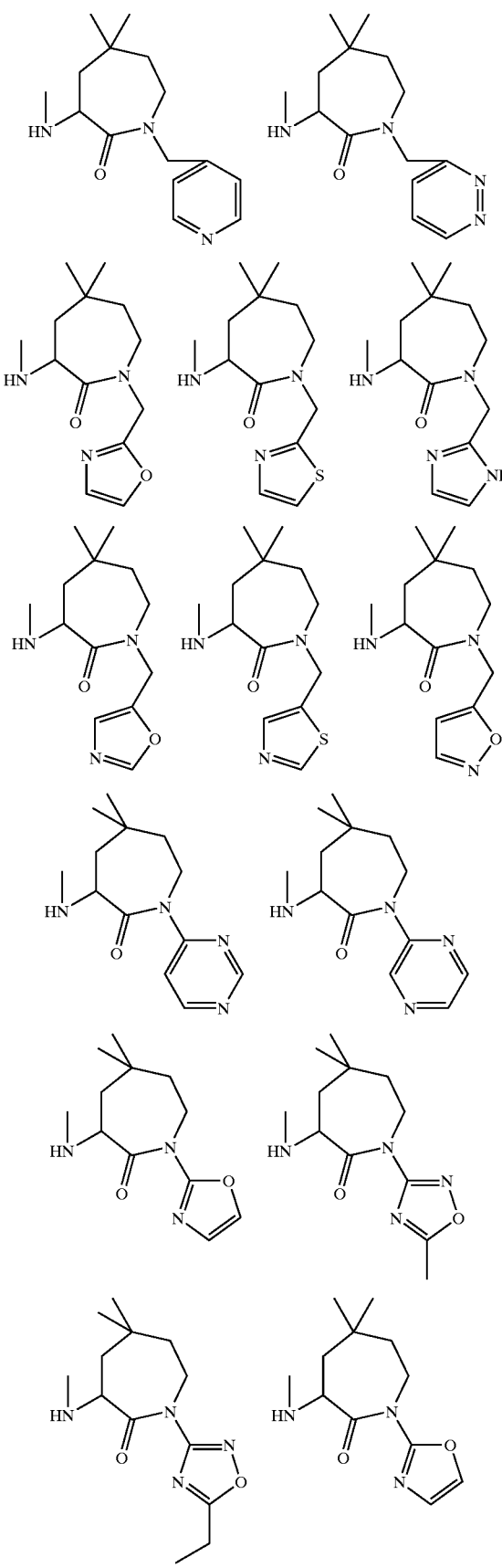
328
-continued
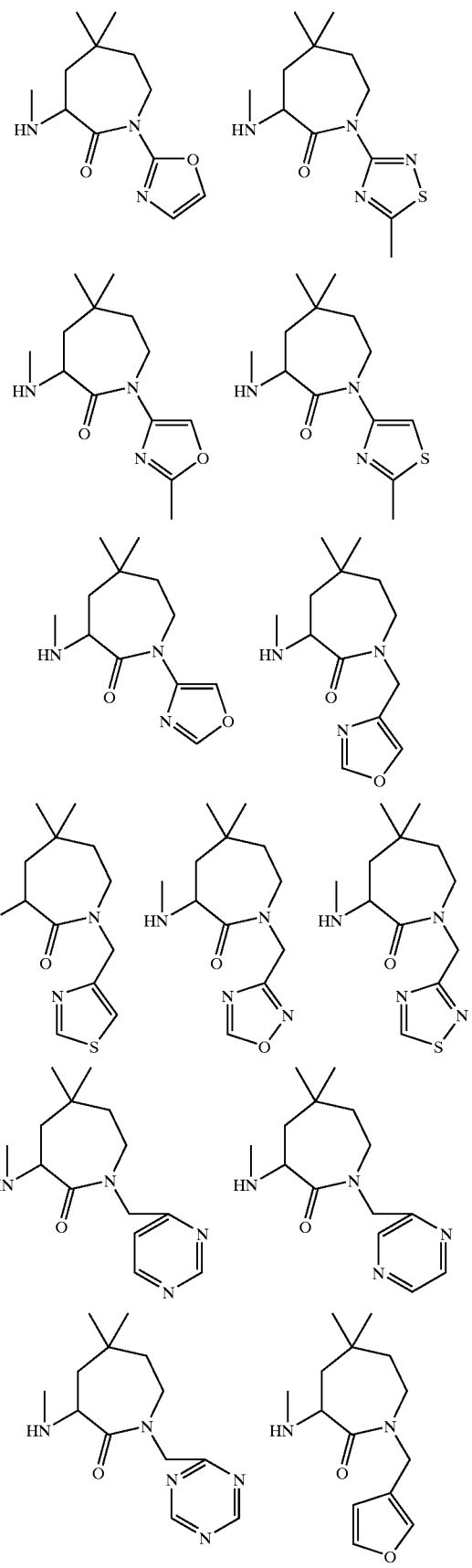

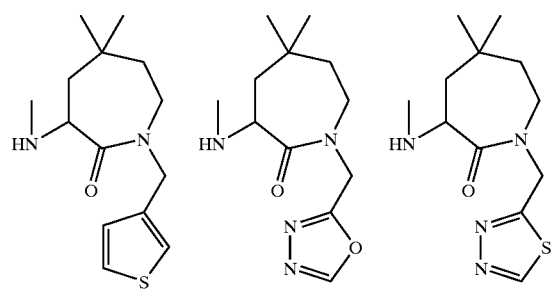
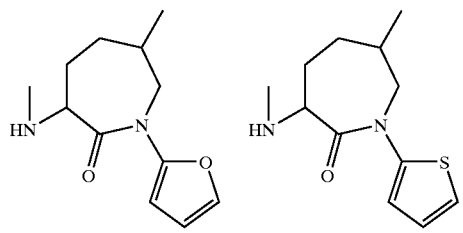
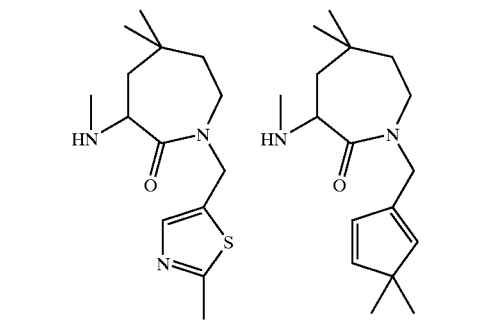
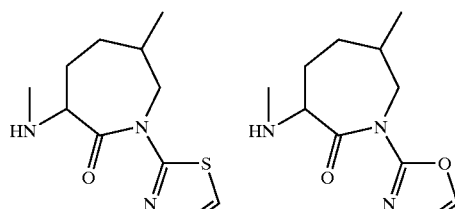
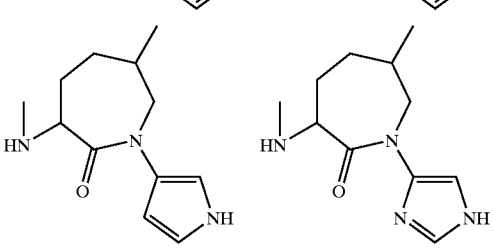
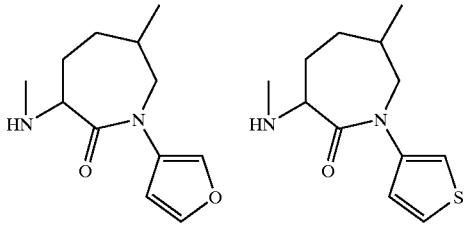
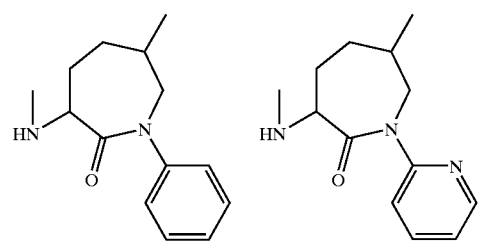
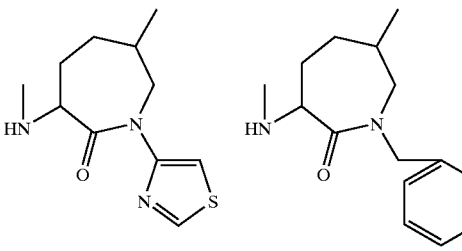
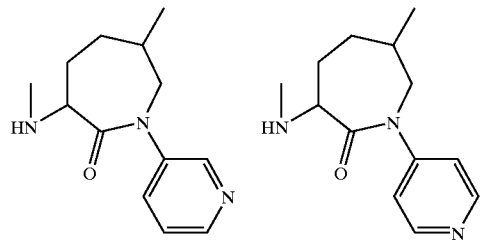
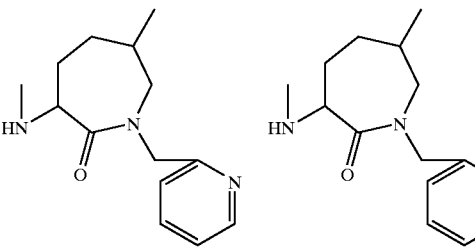
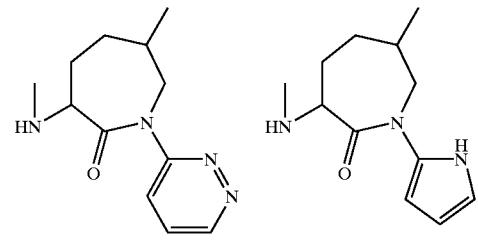
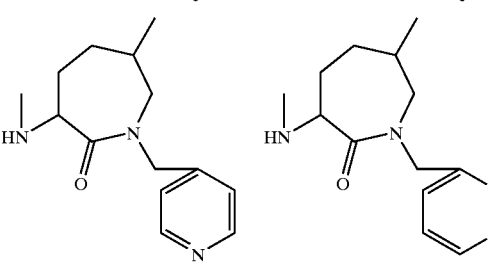

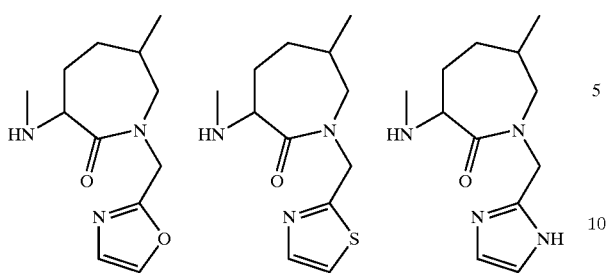
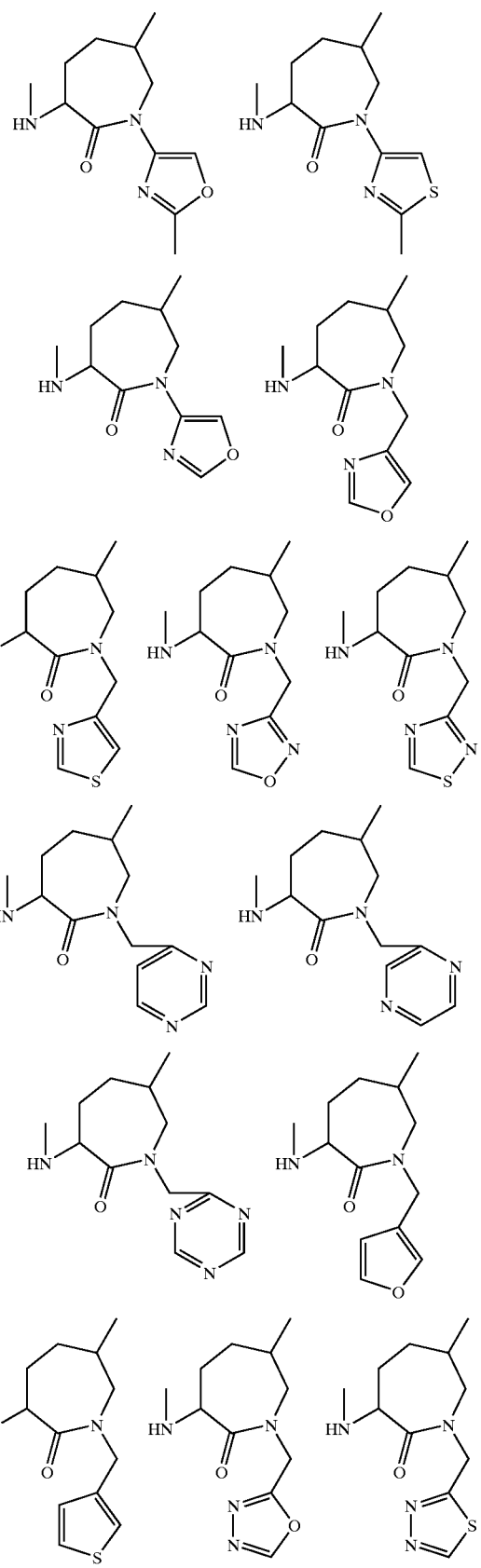

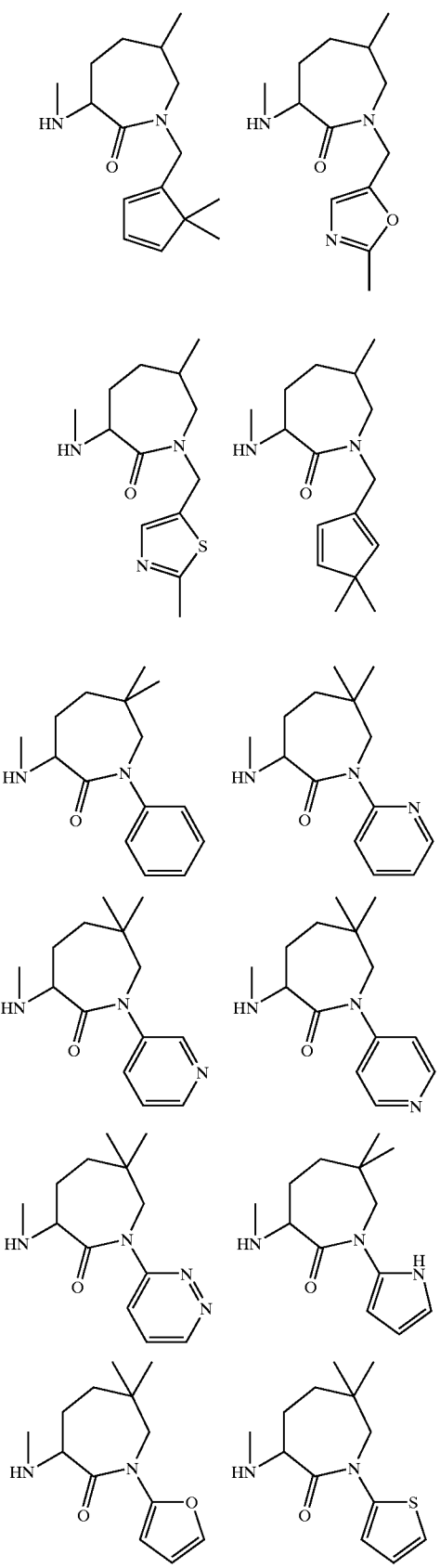
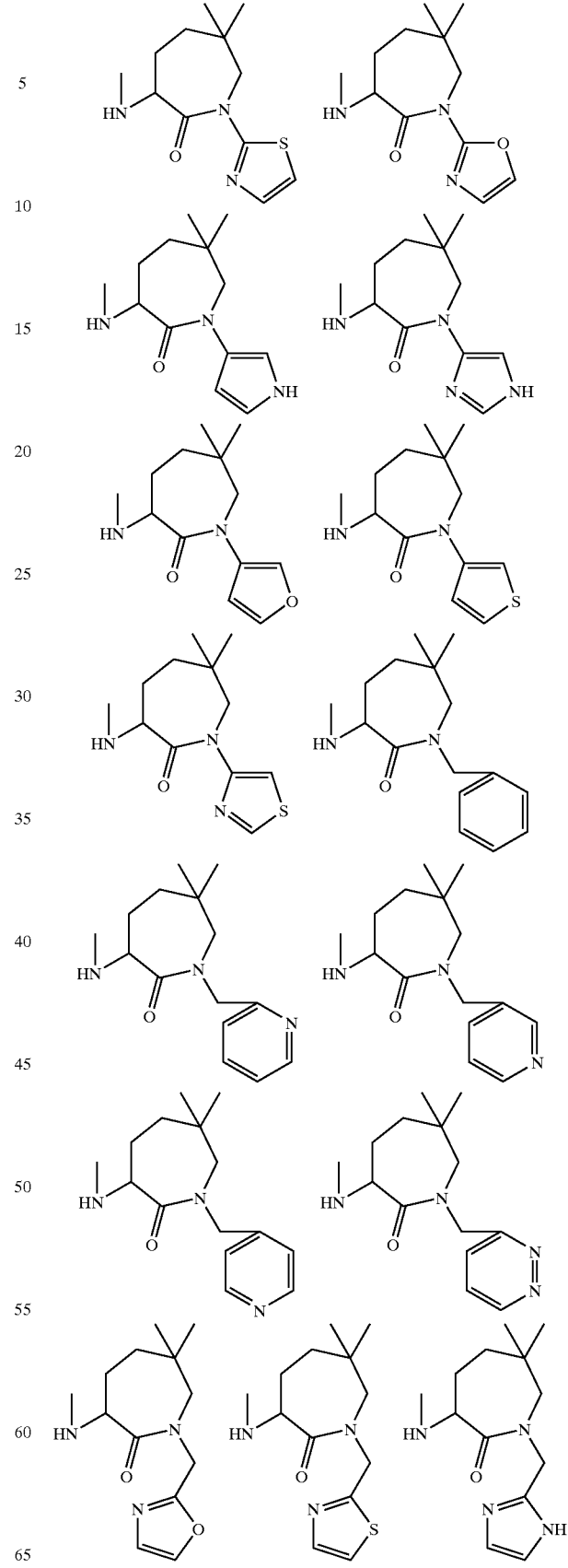

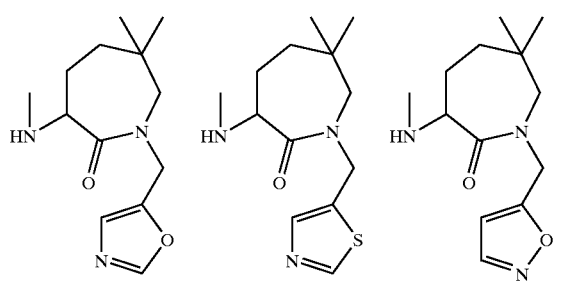
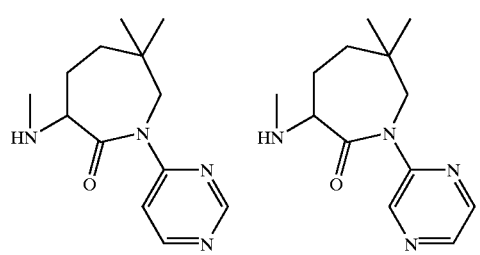
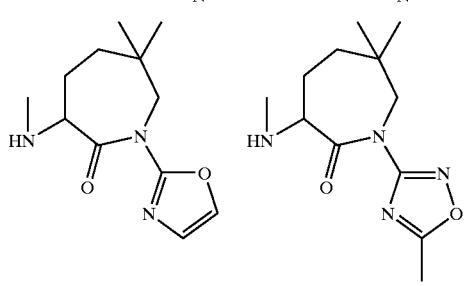
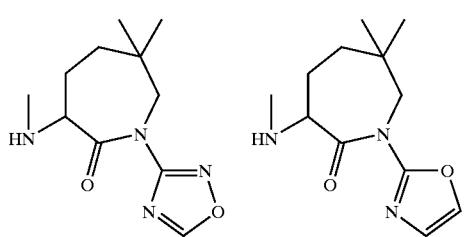
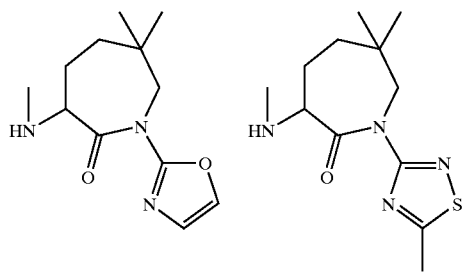
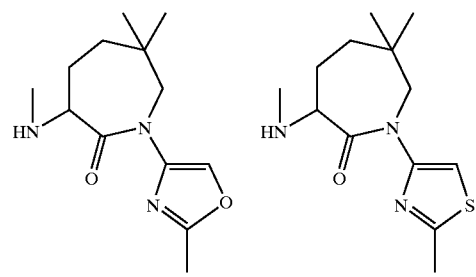
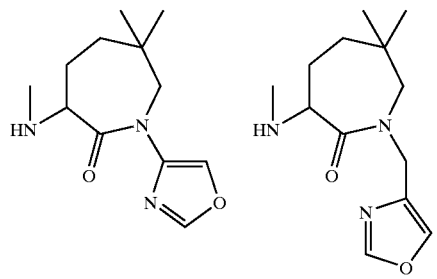
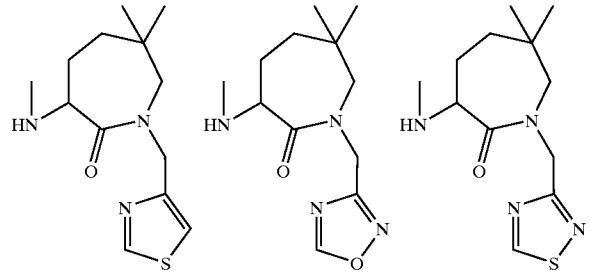
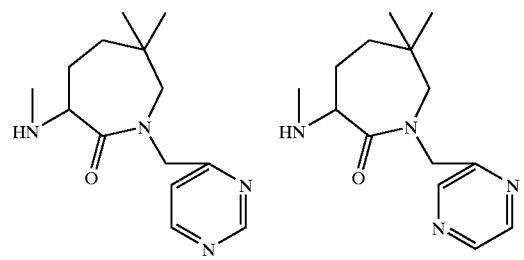
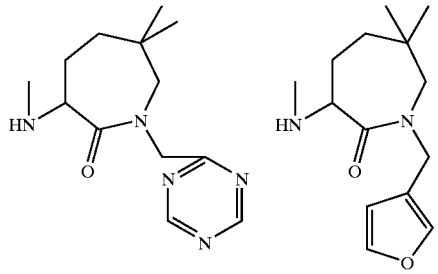
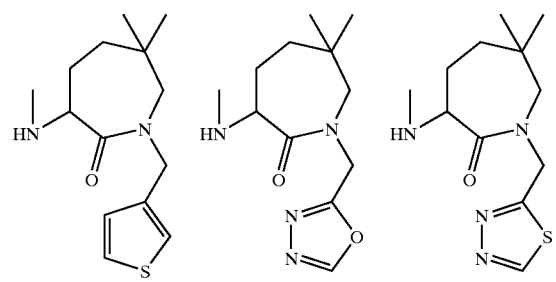
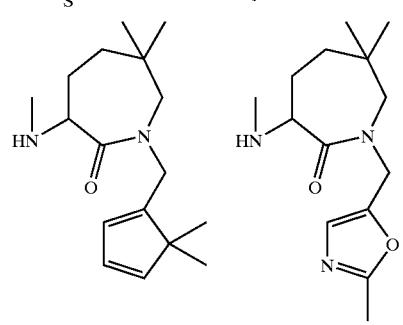

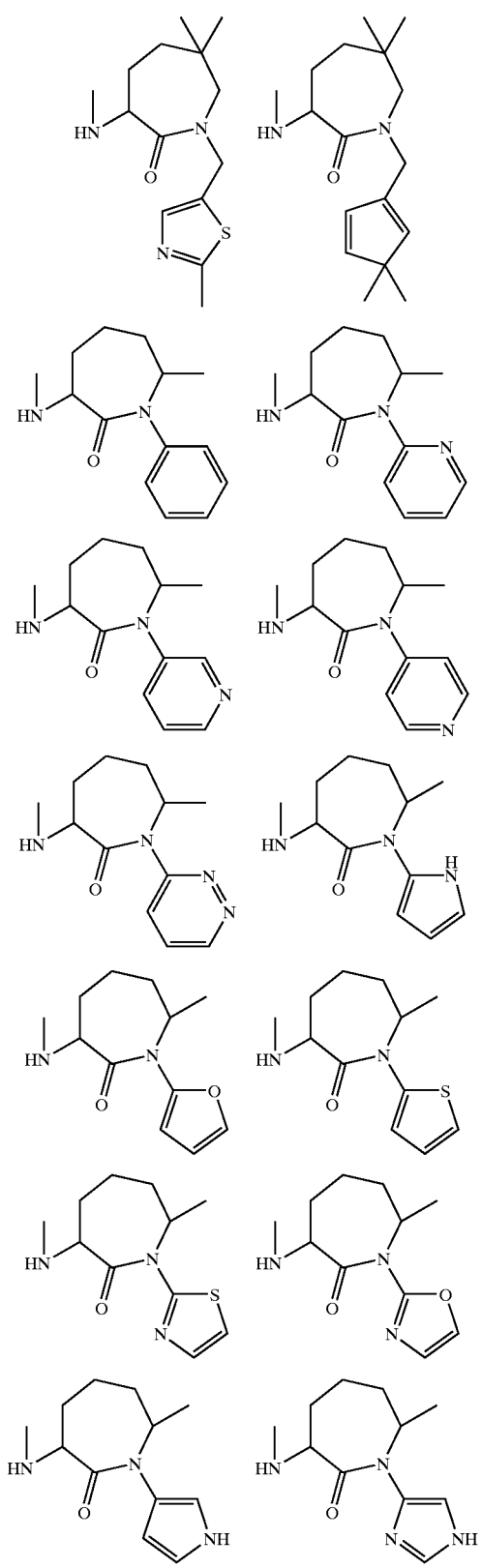
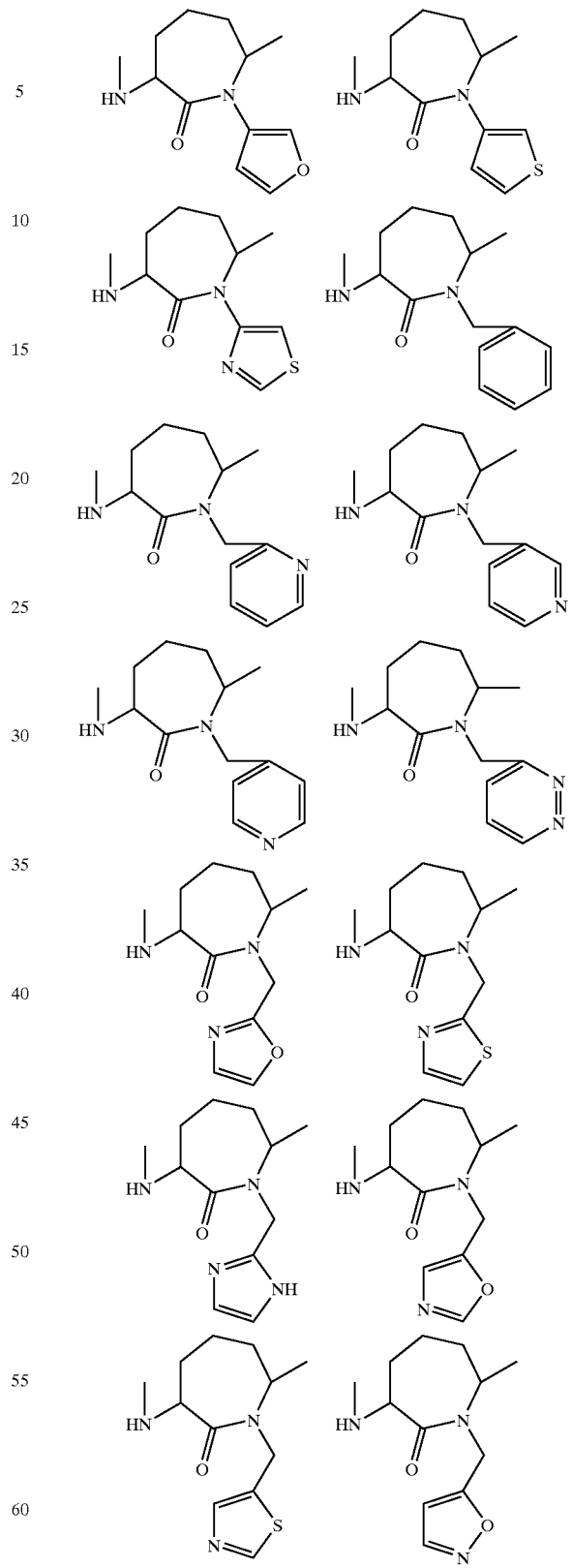

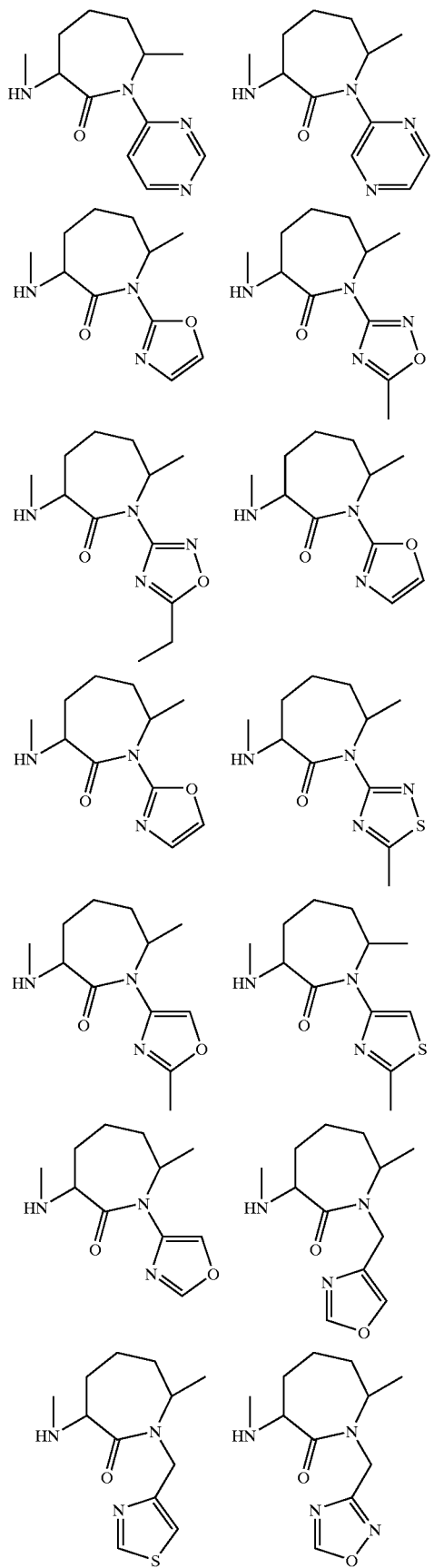
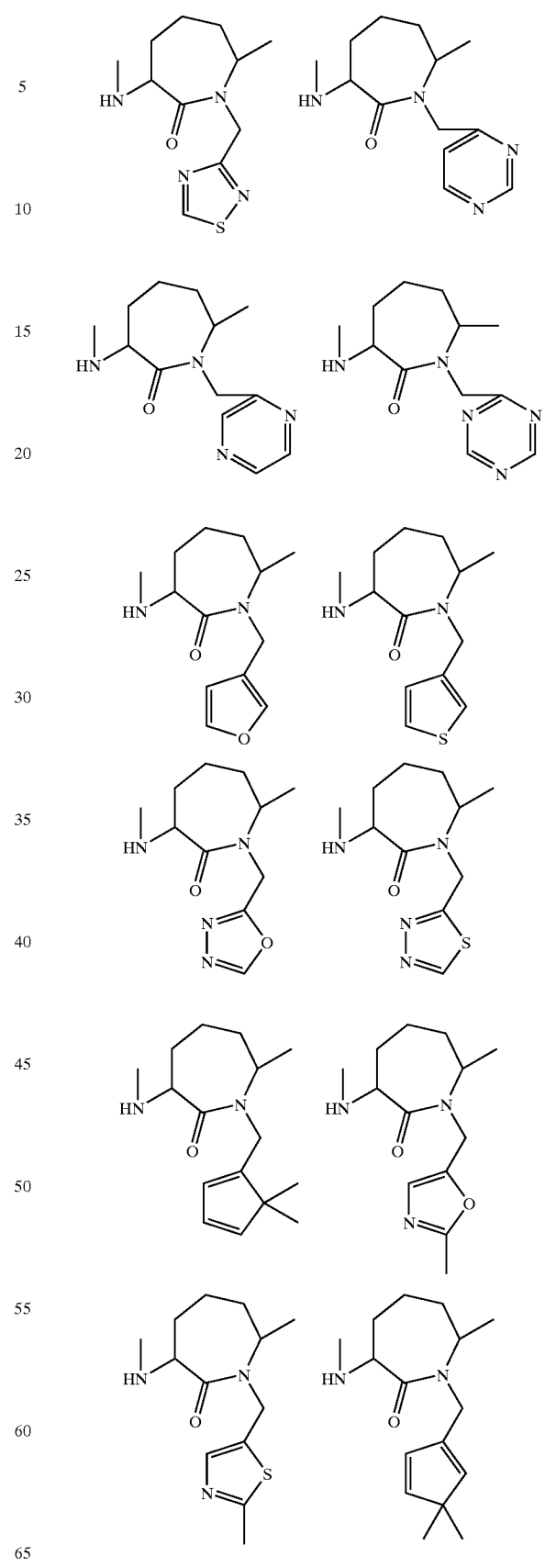

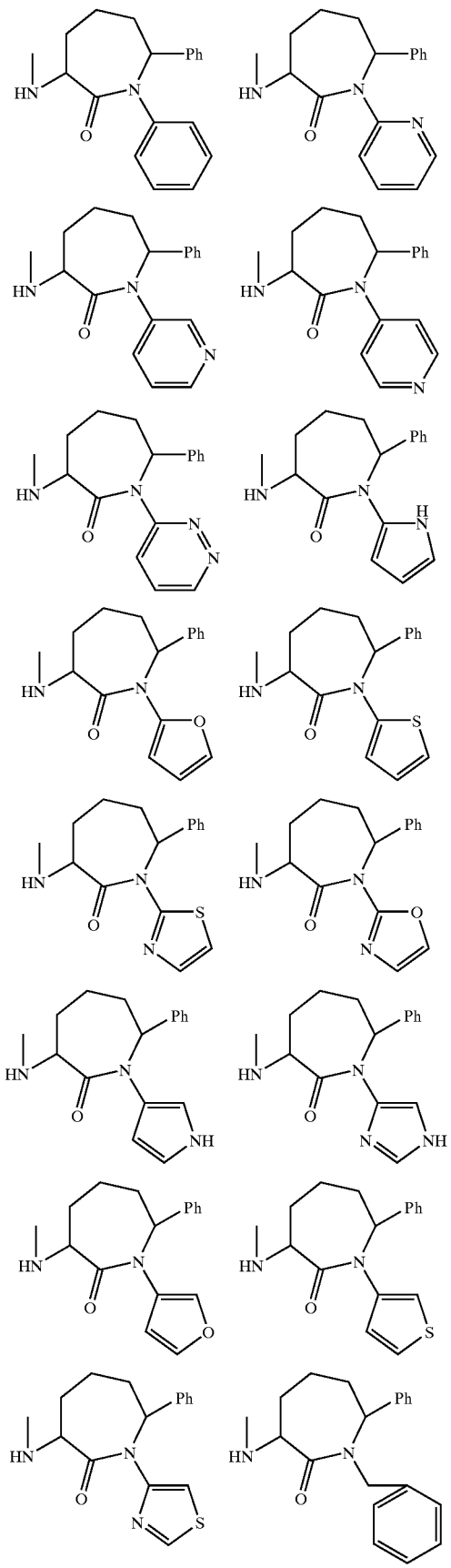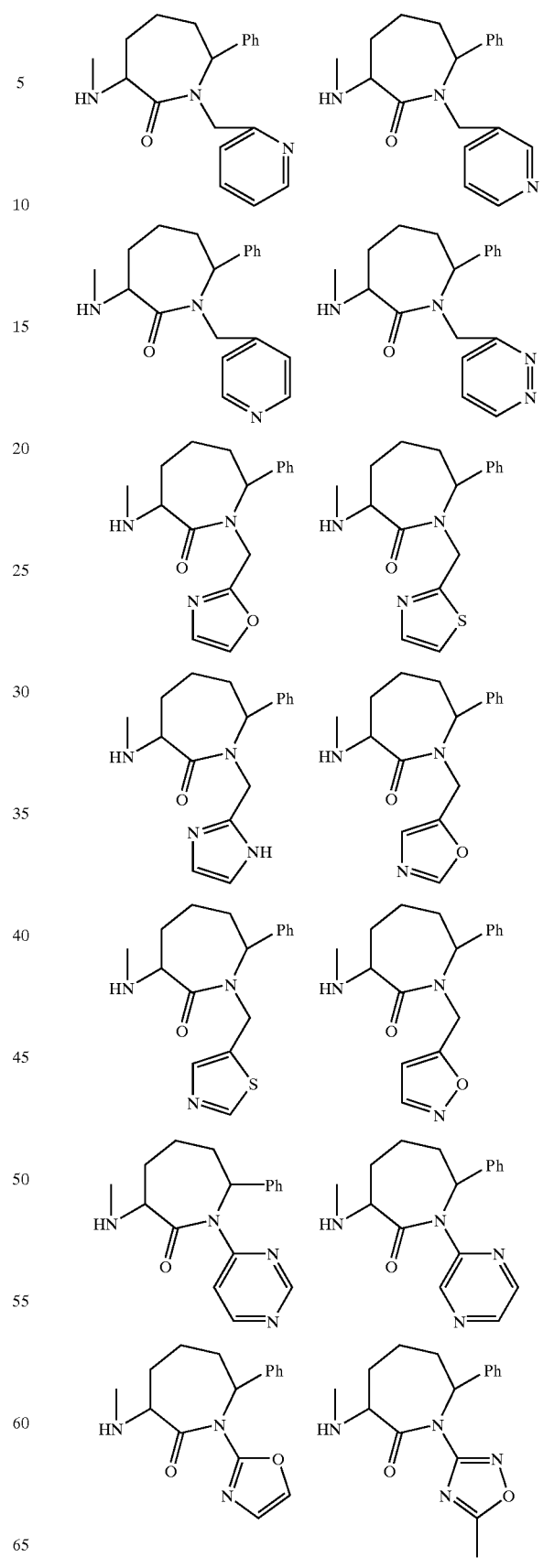

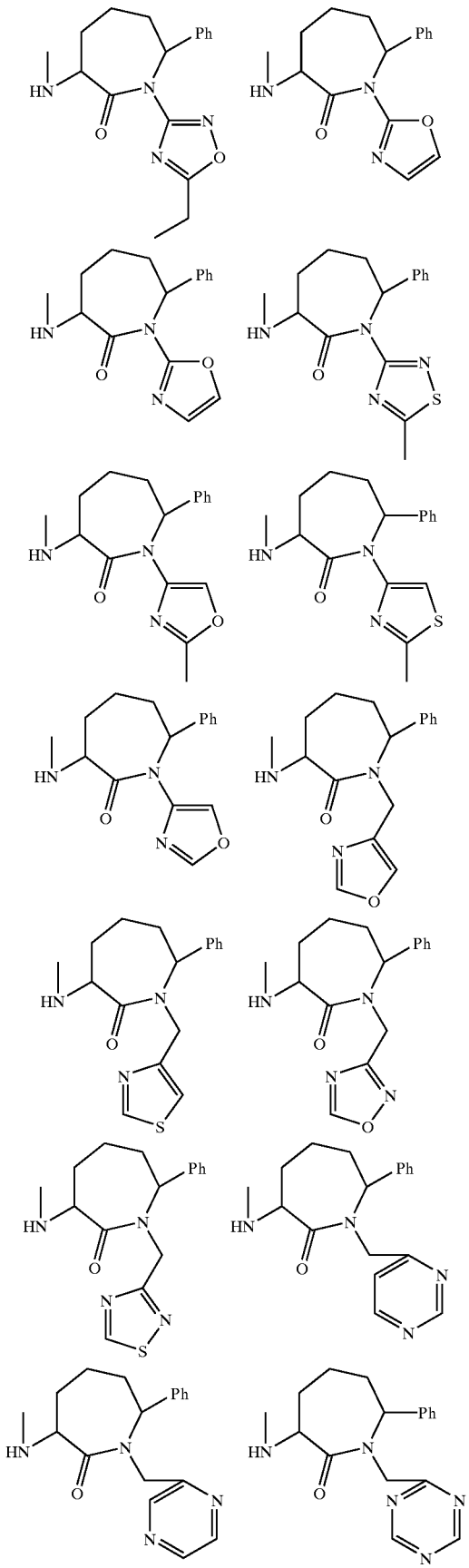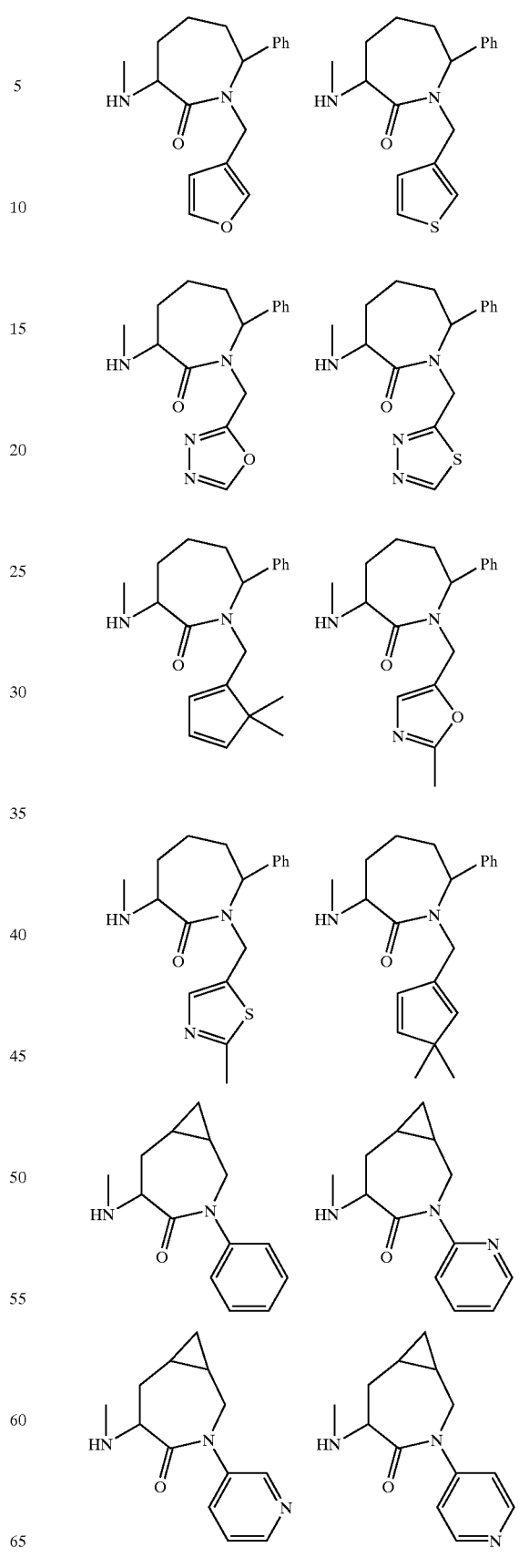

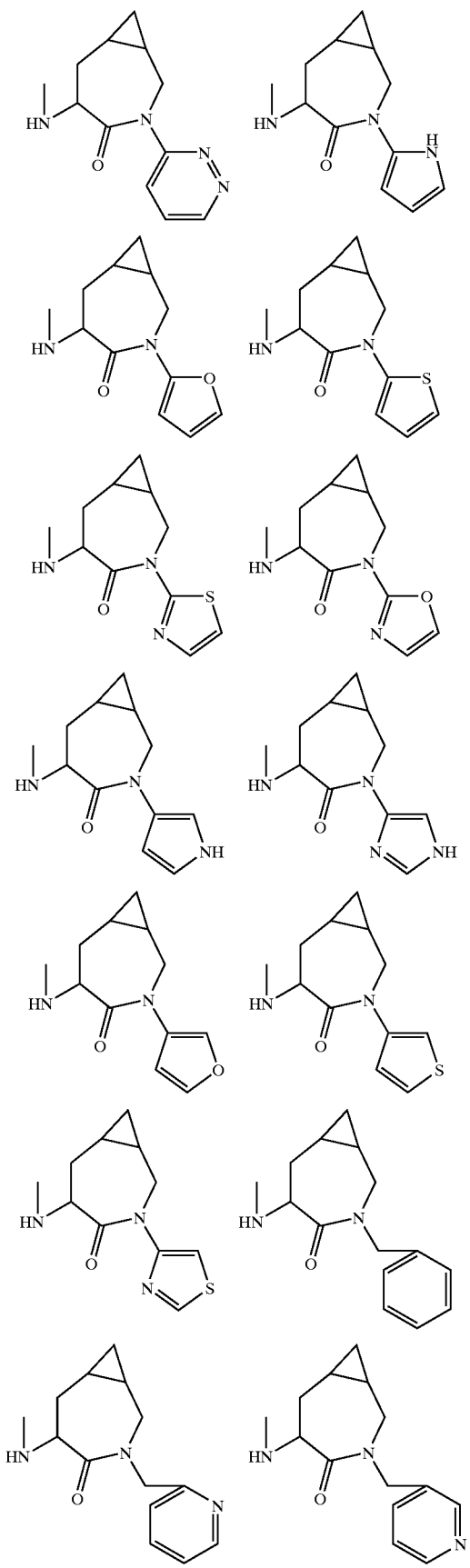
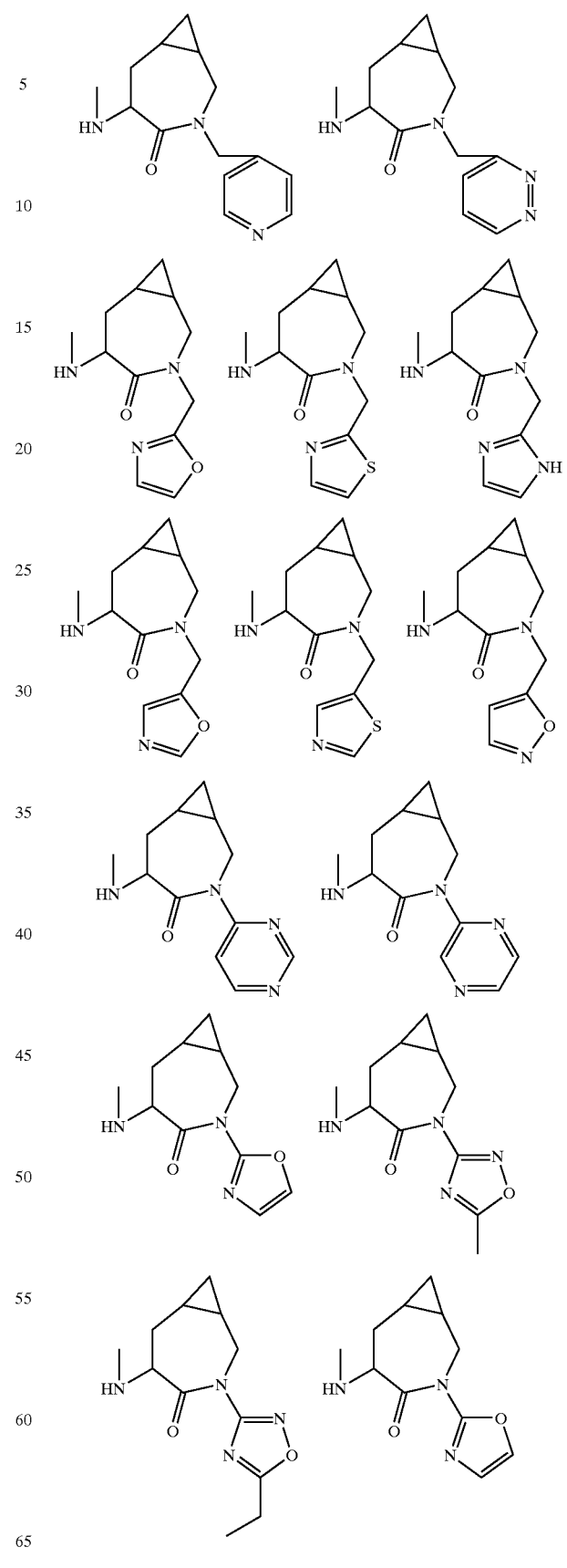

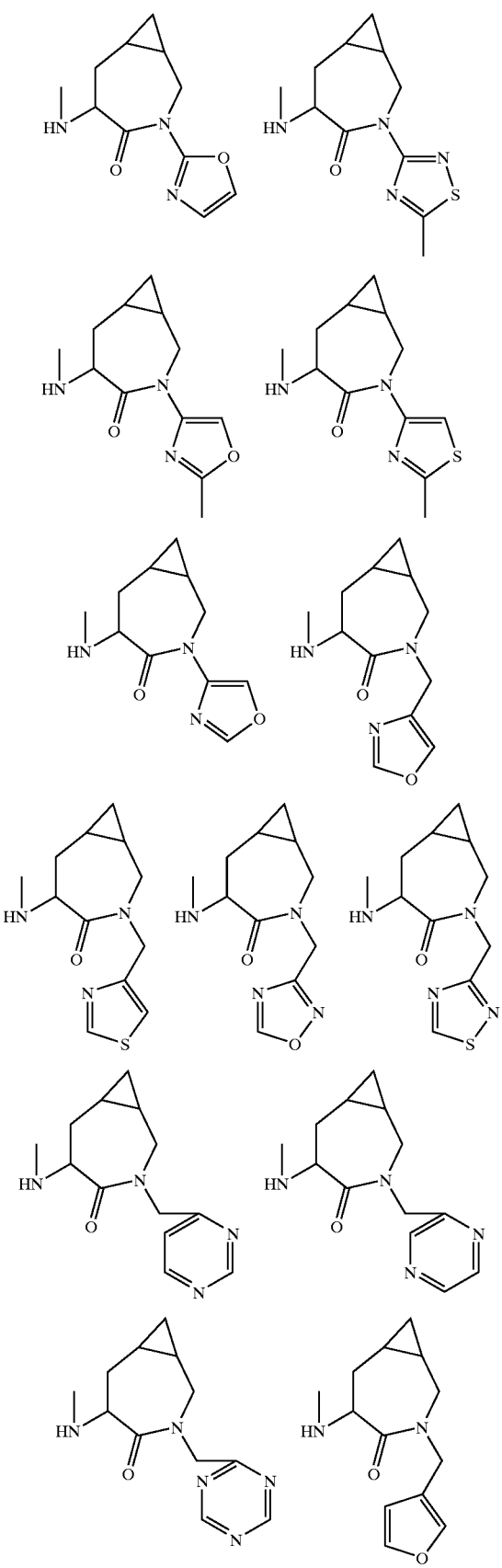
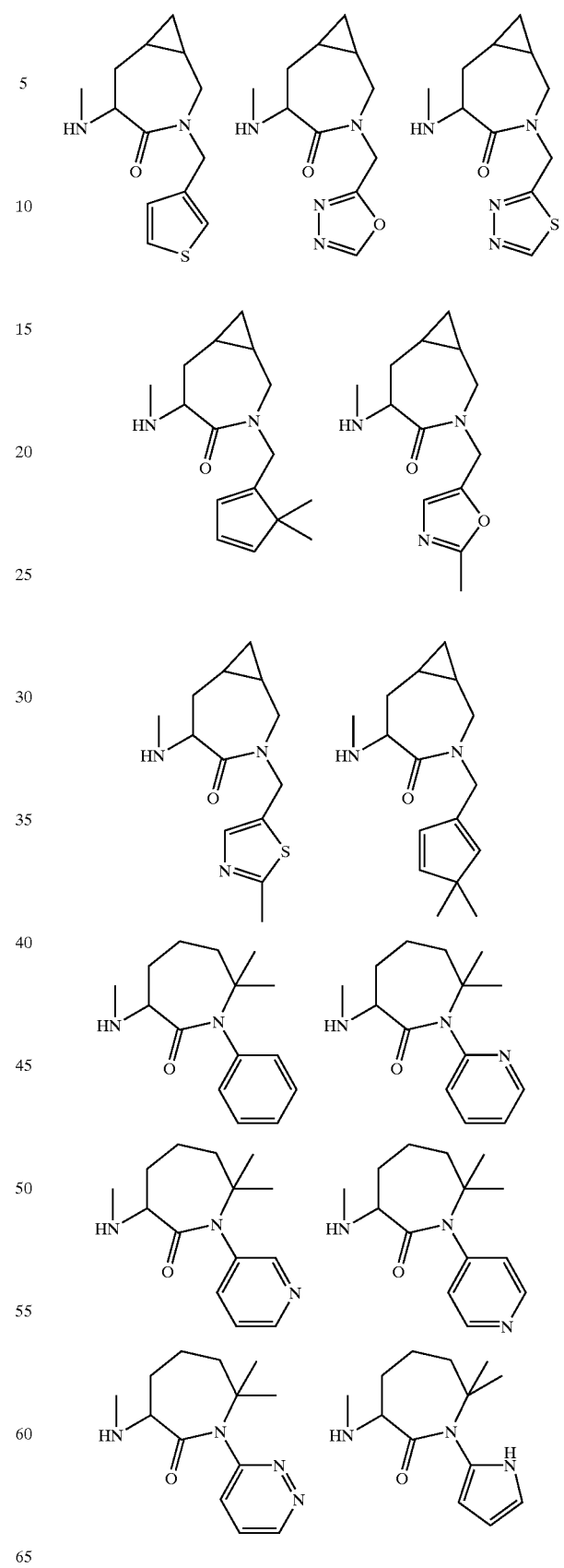

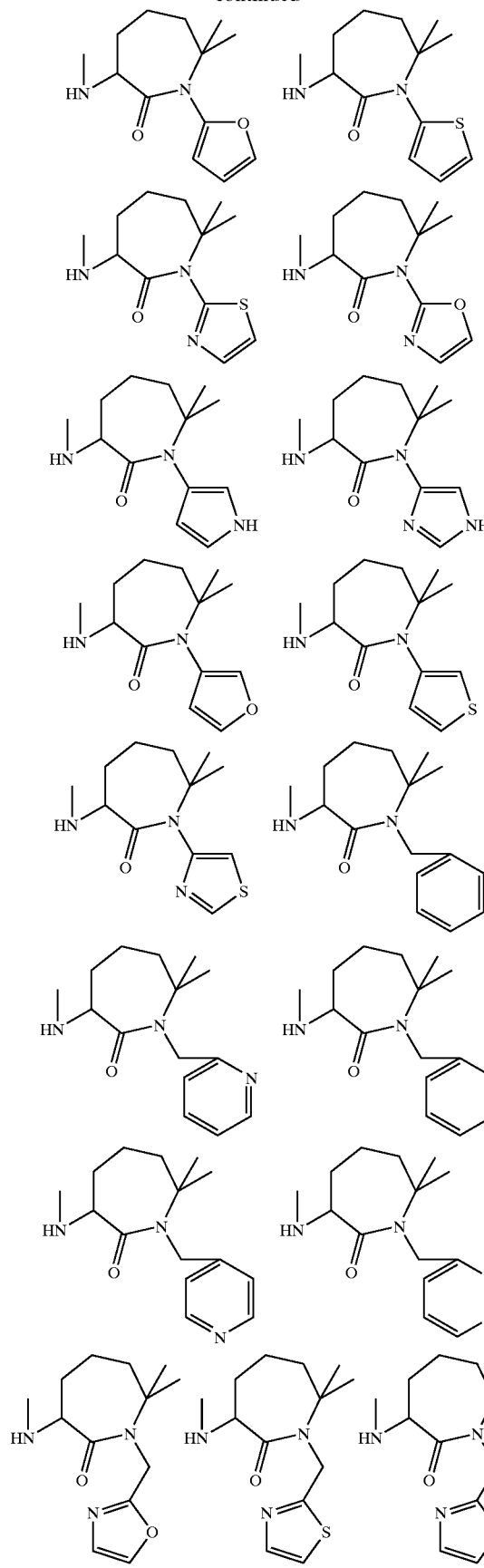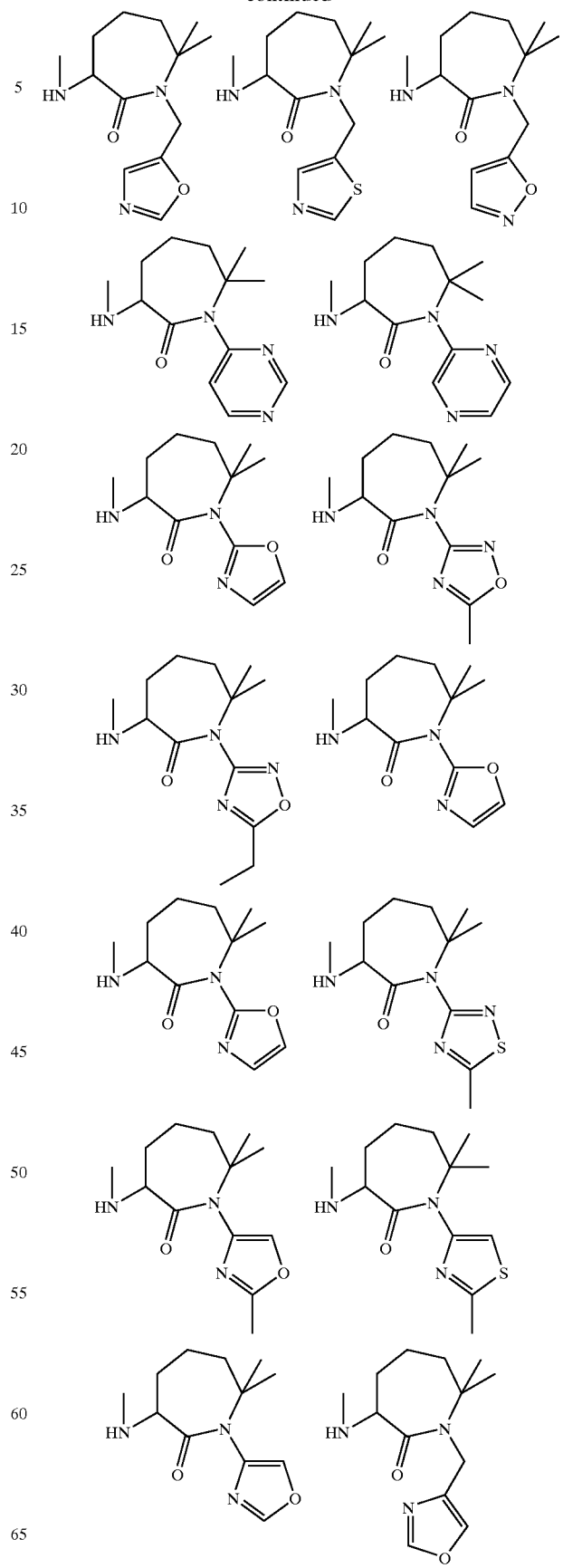

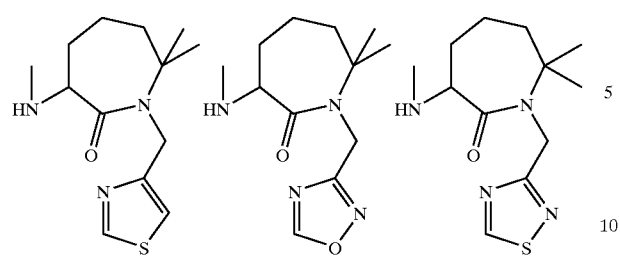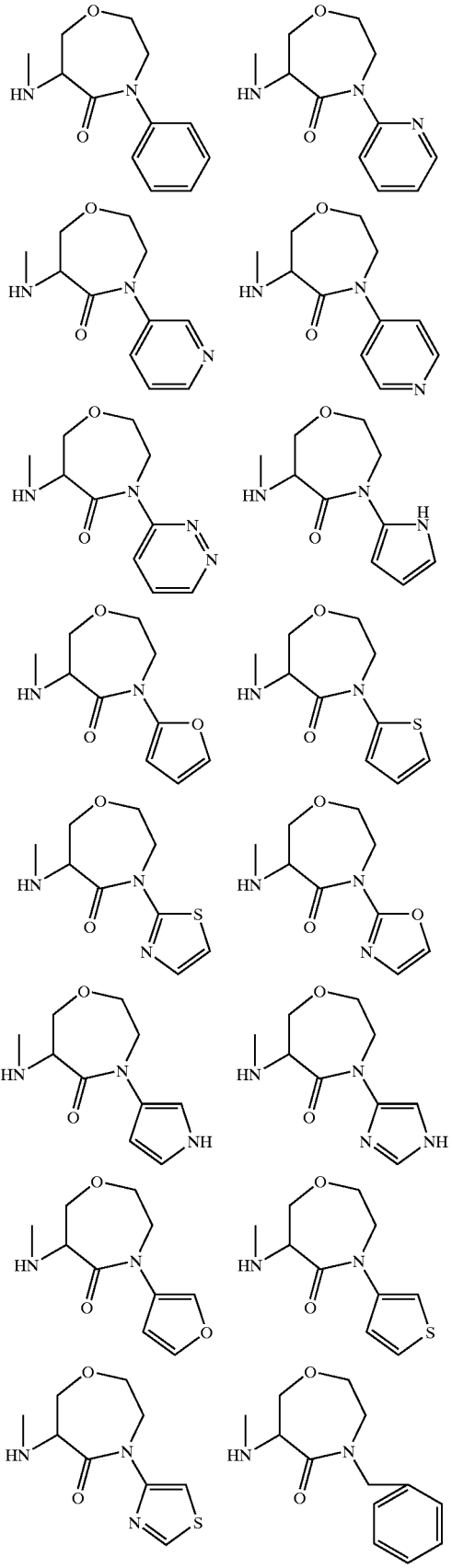

353
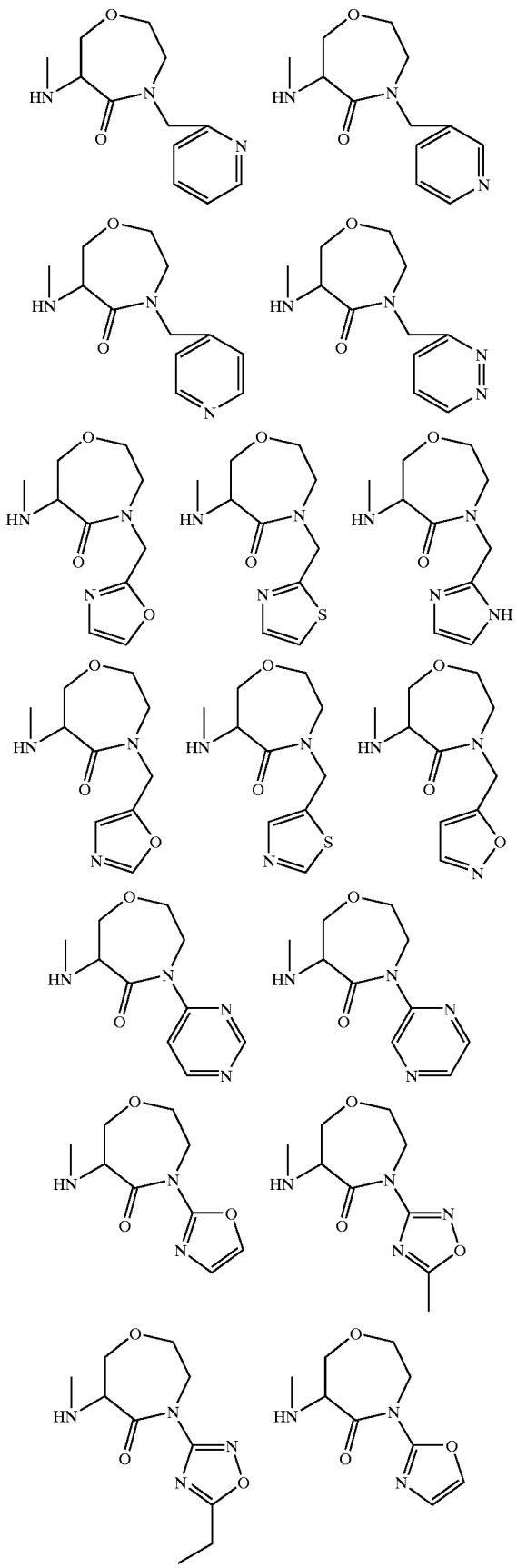
354
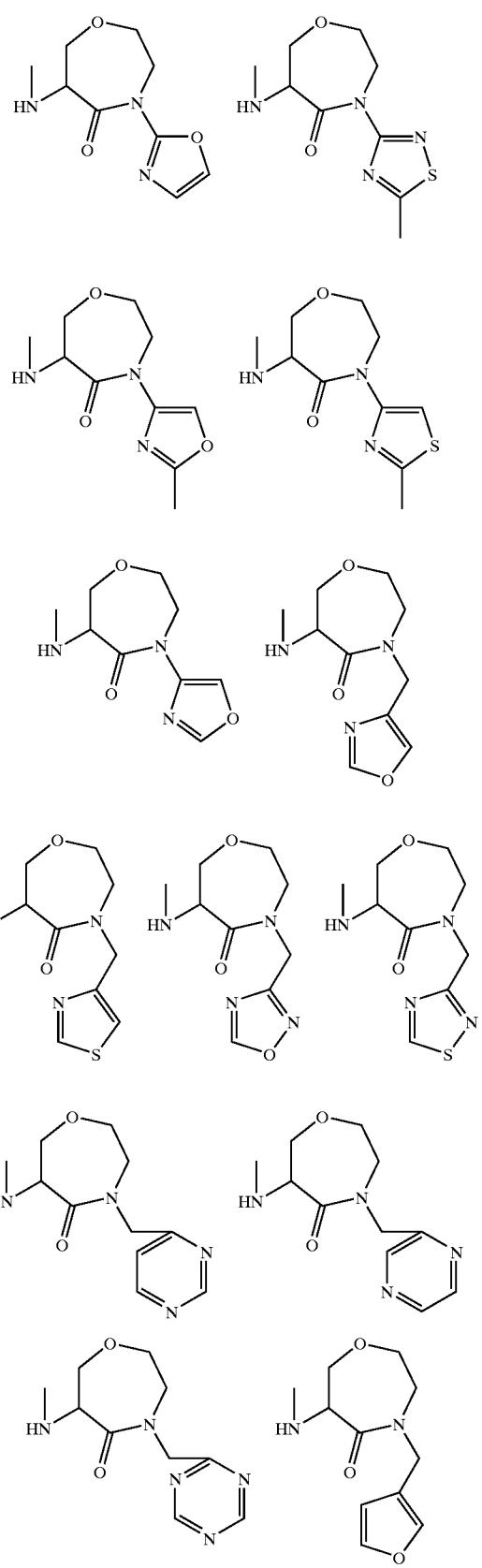

-continued
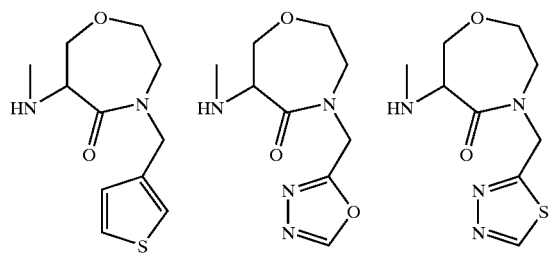
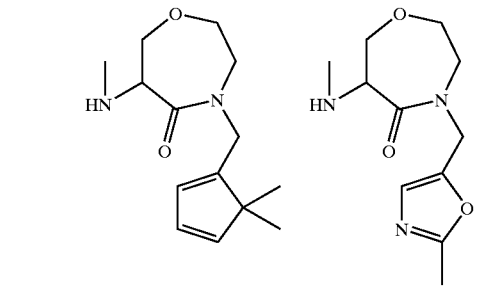
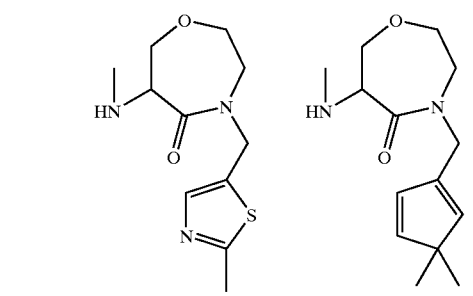
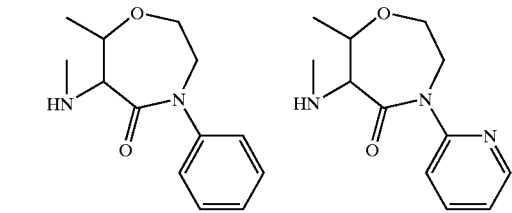
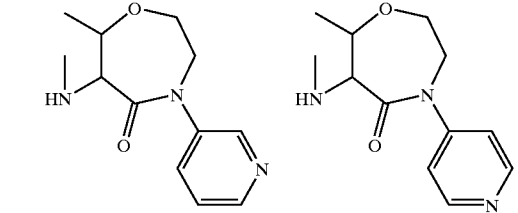
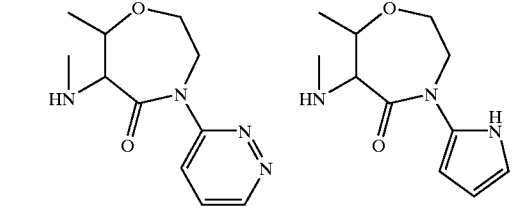
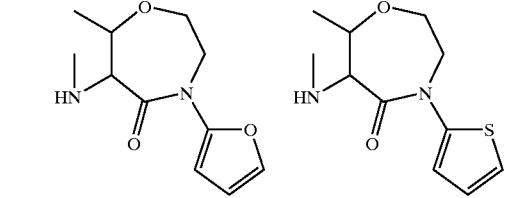
-continued
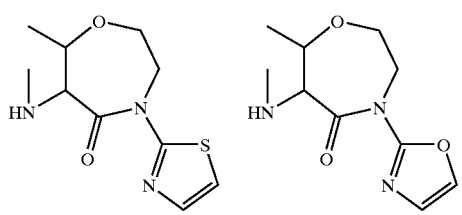
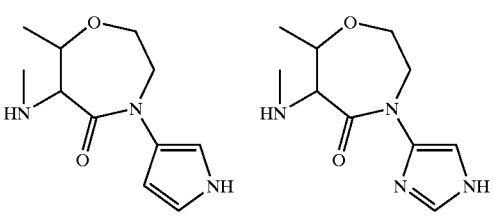
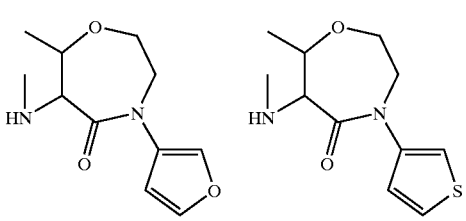
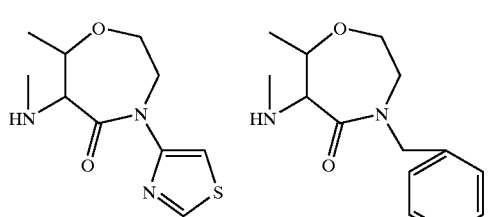
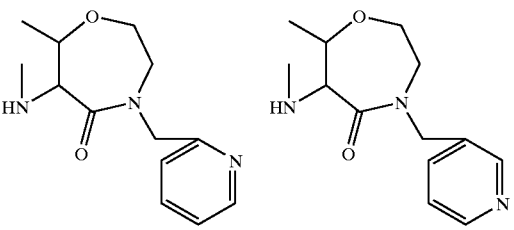
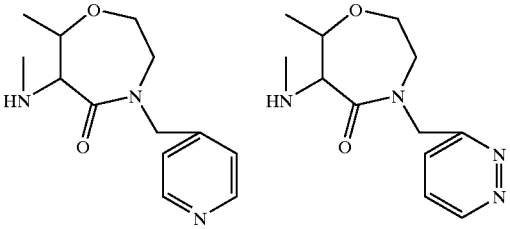
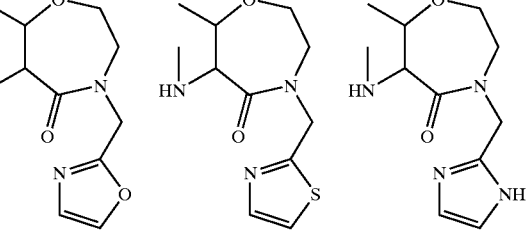

357 -continued

358 -continued

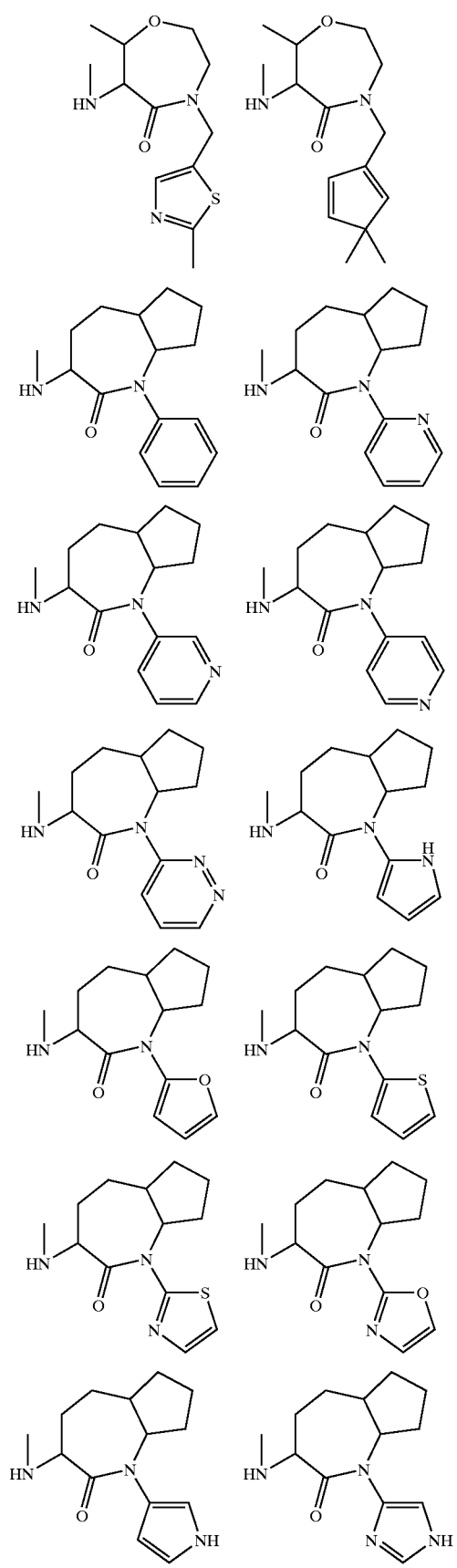
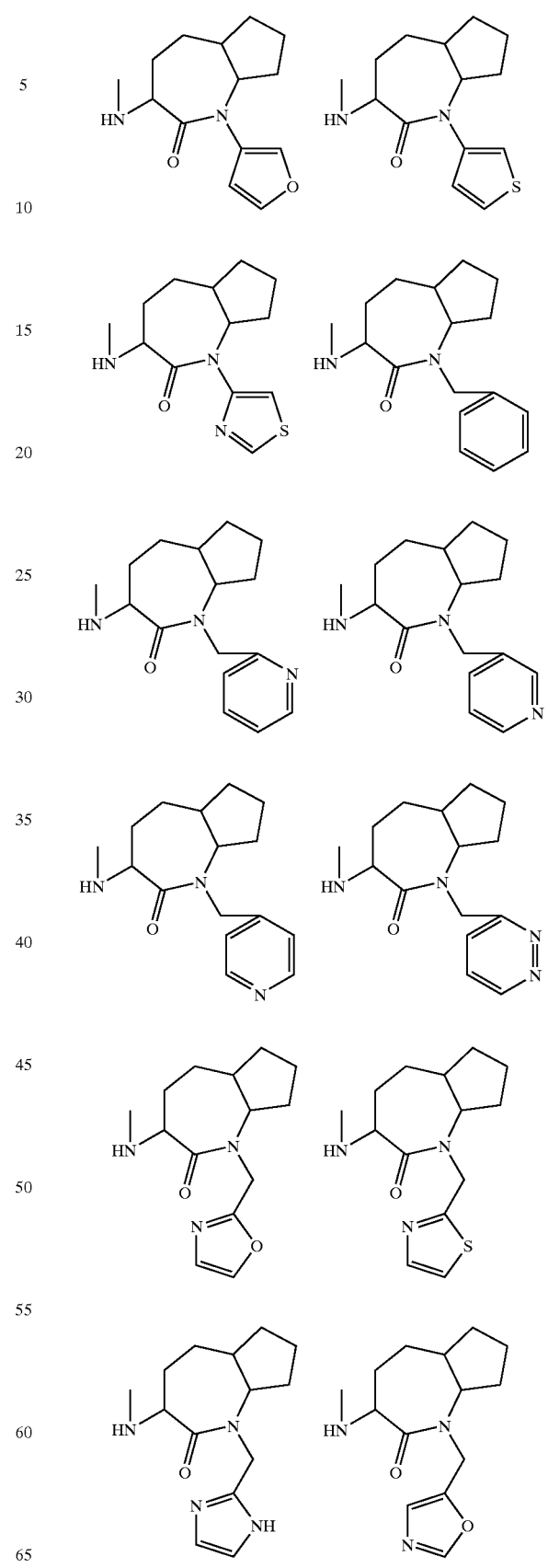

361
-continued
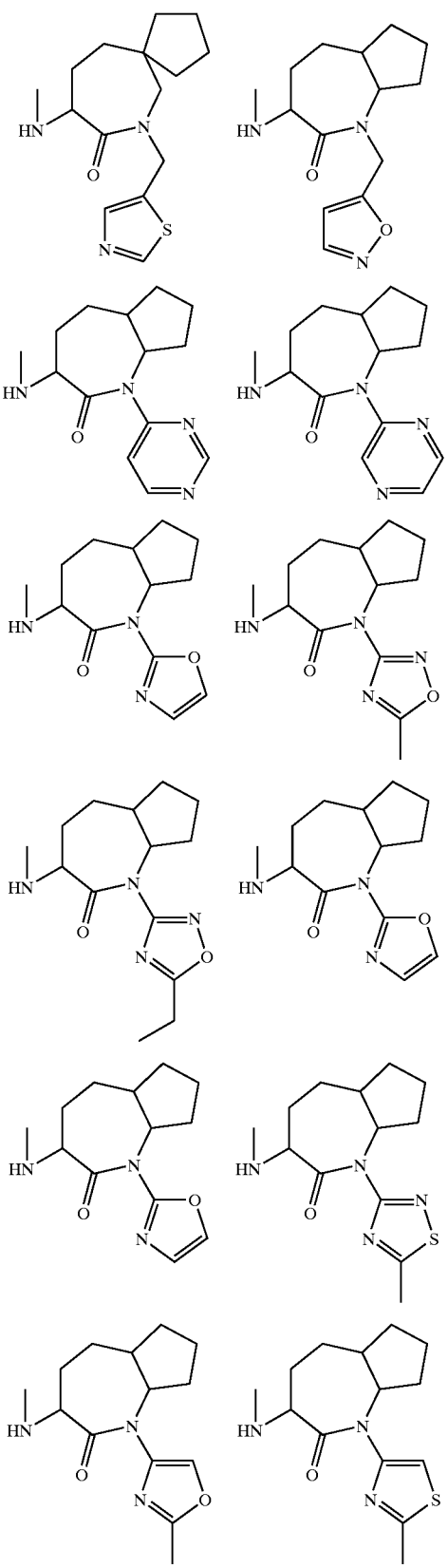
362
-continued
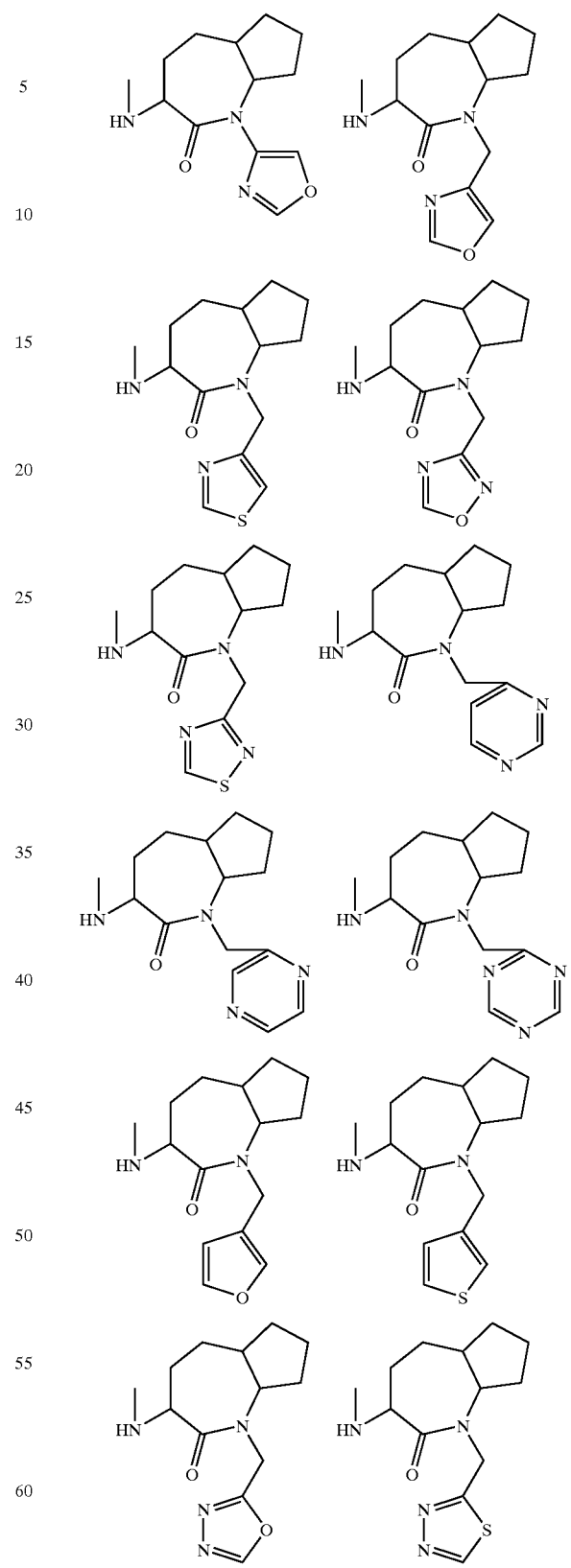

363
-continued
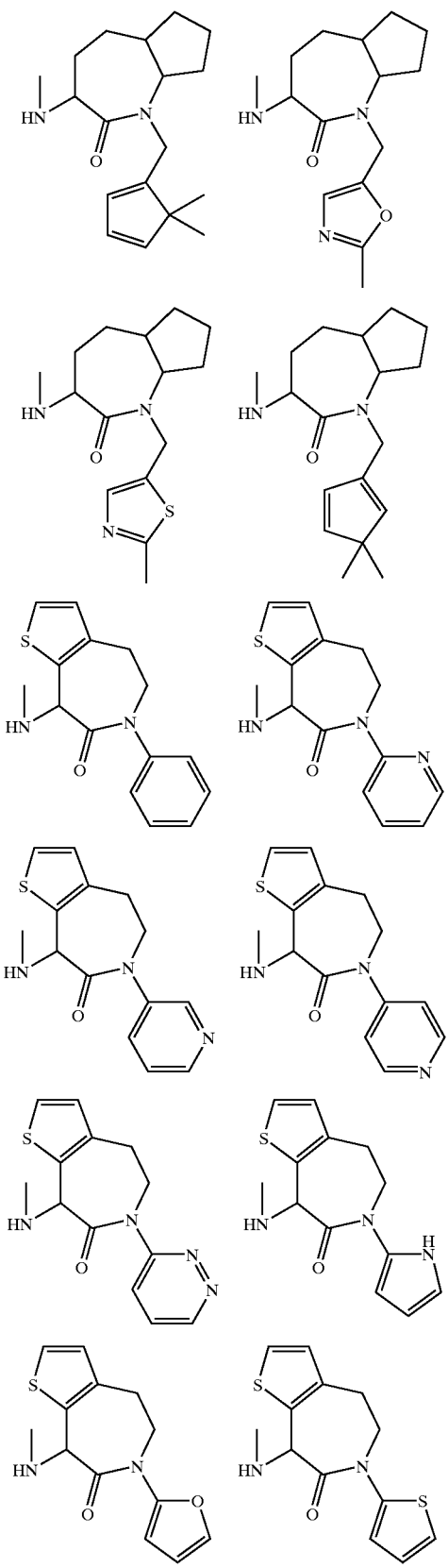
364
-continued
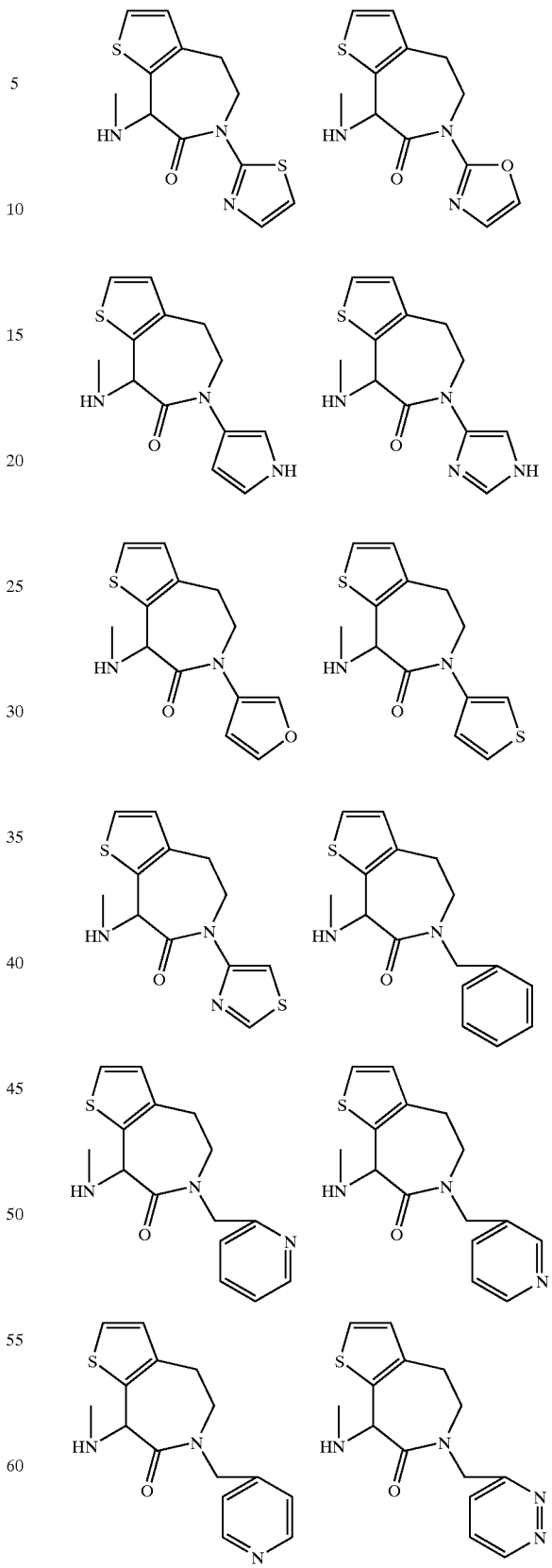

365
-continued

366
-continued

367
-continued
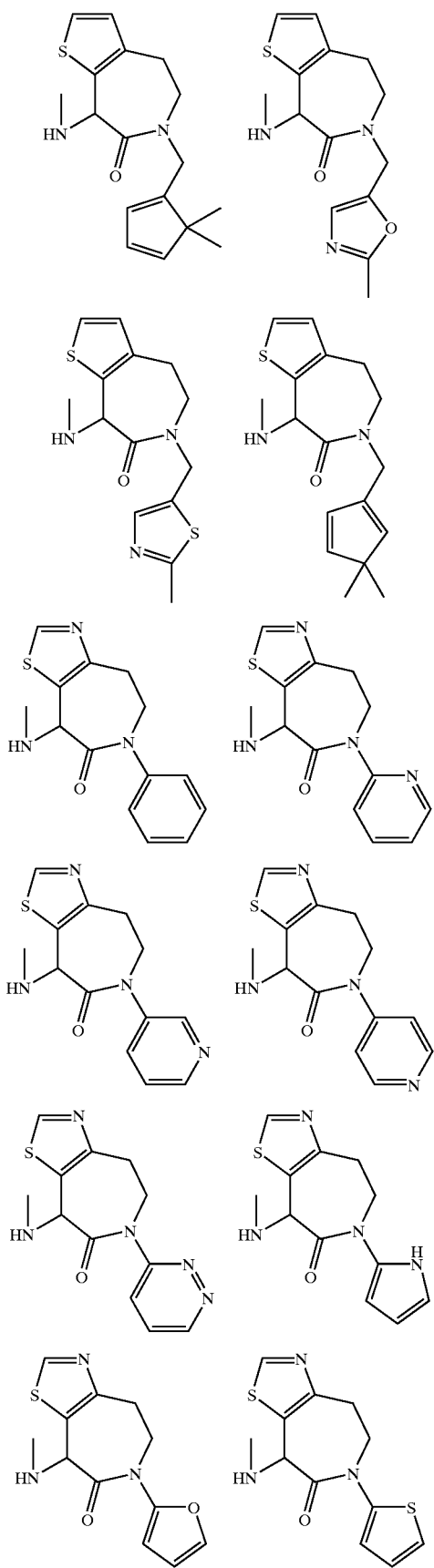
368
-continued
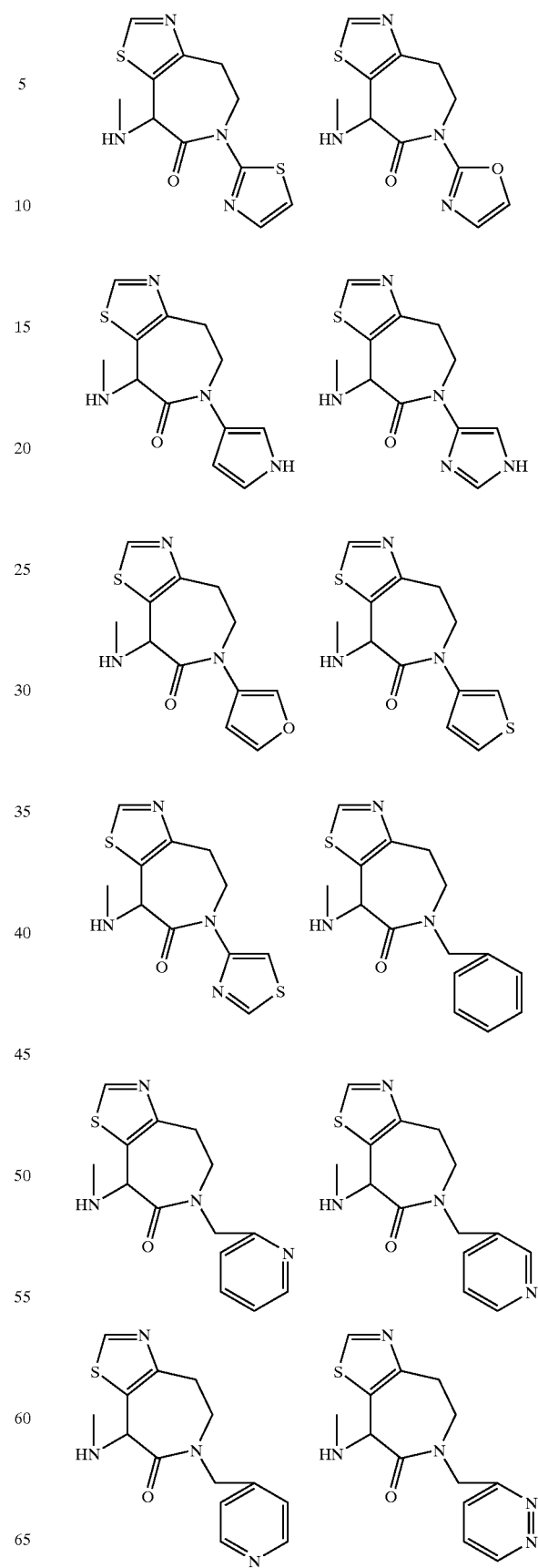

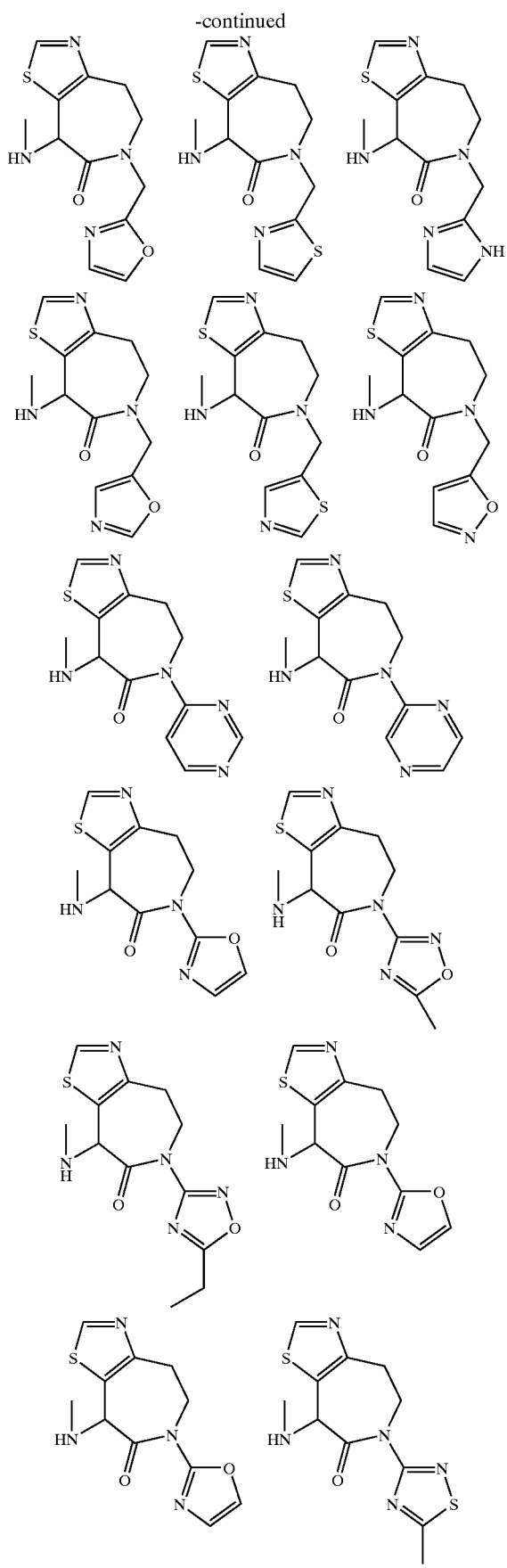
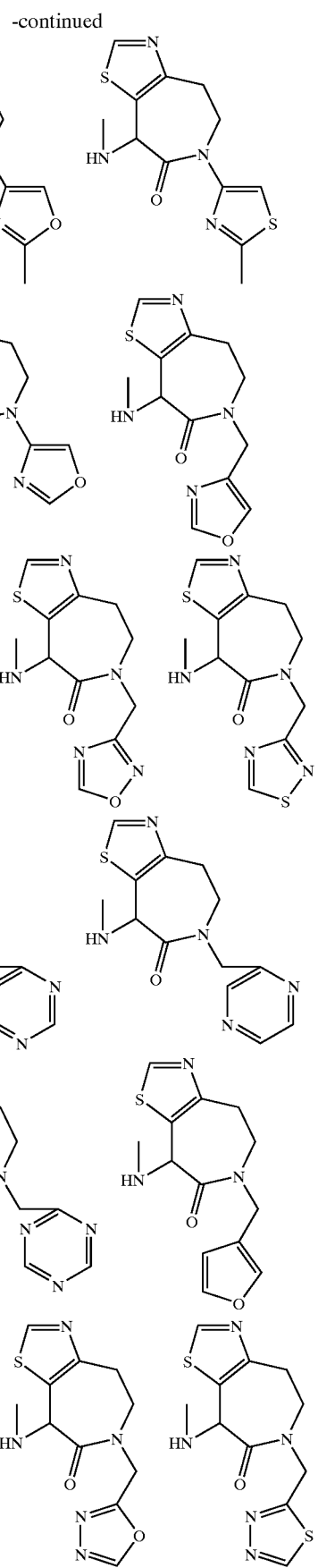

371
-continued
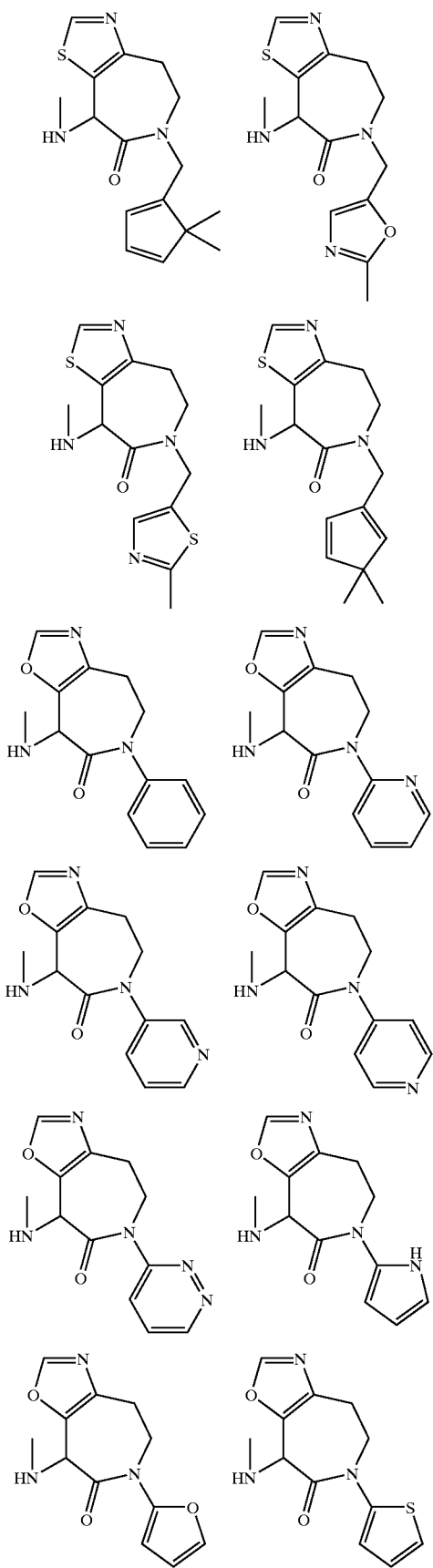
372
-continued
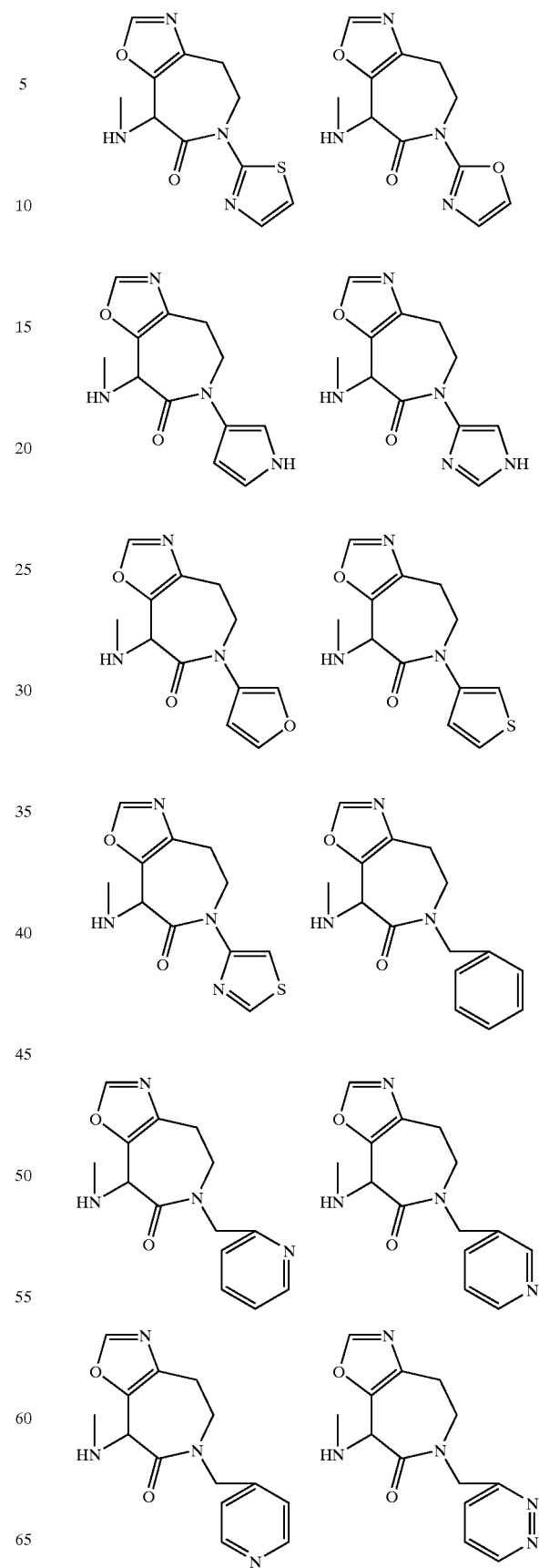

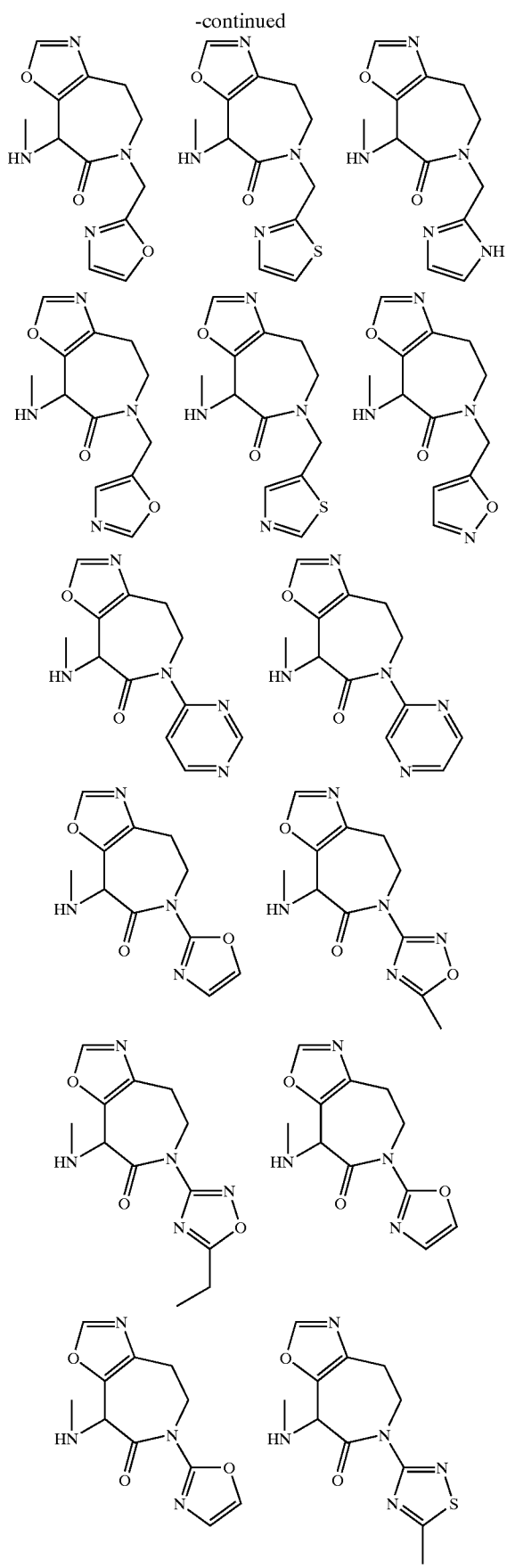
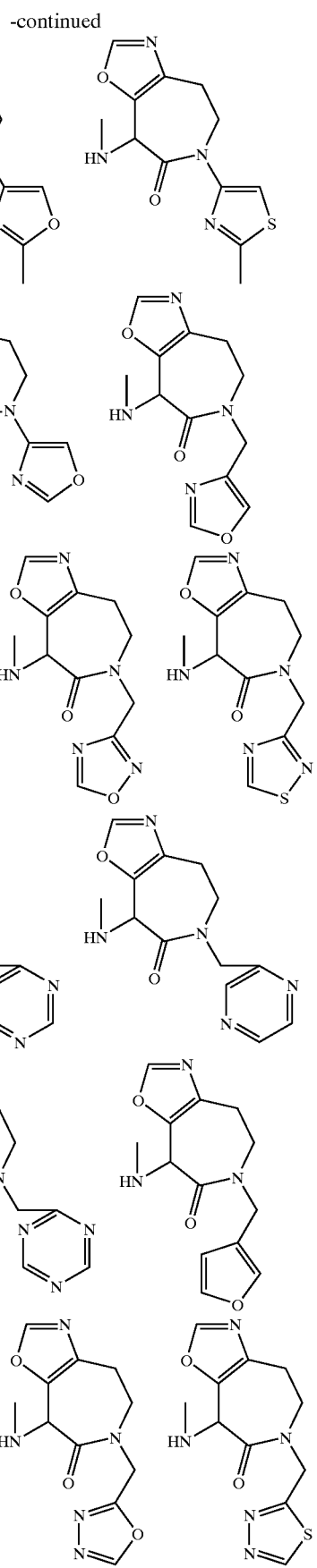

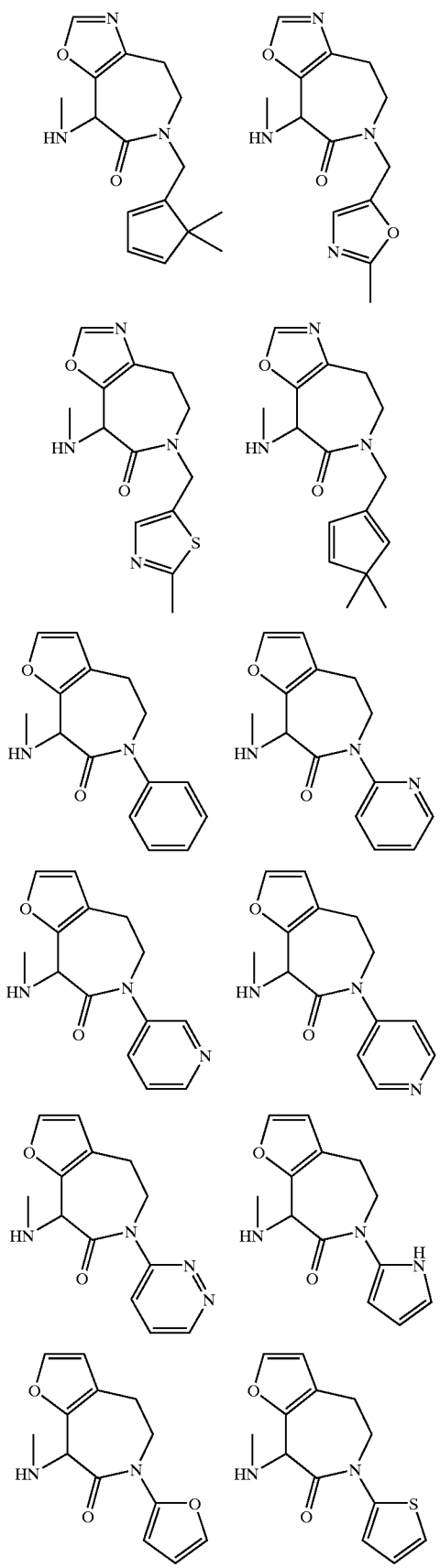
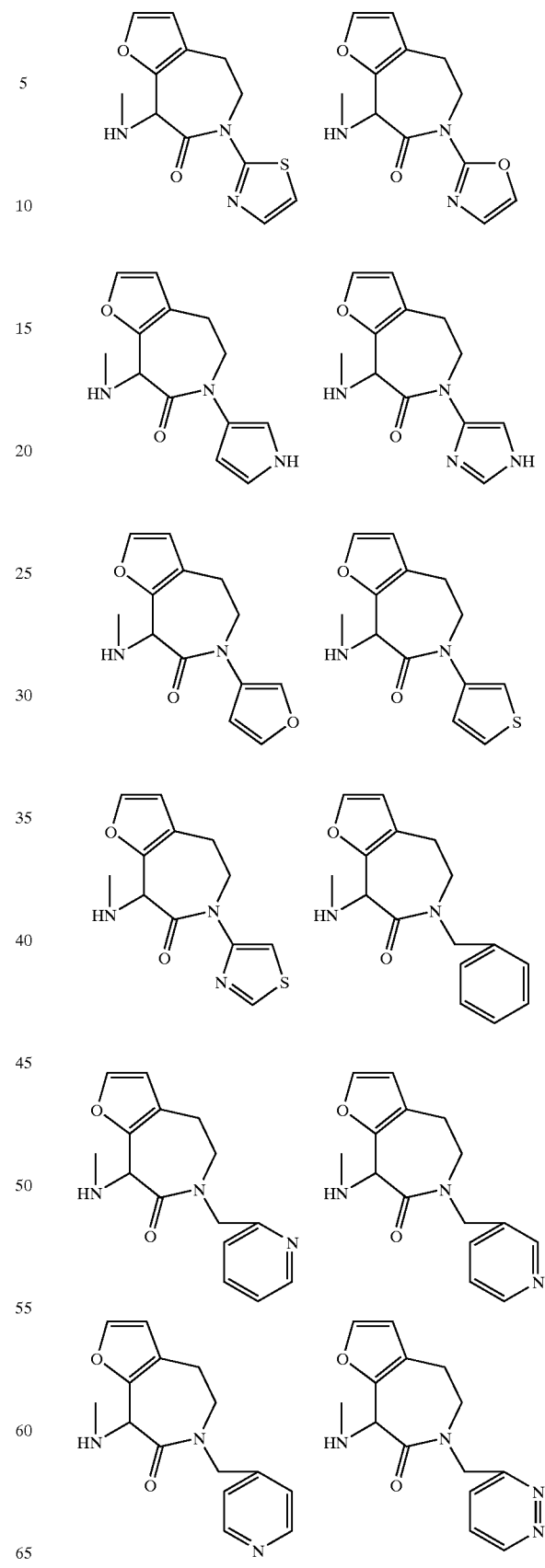

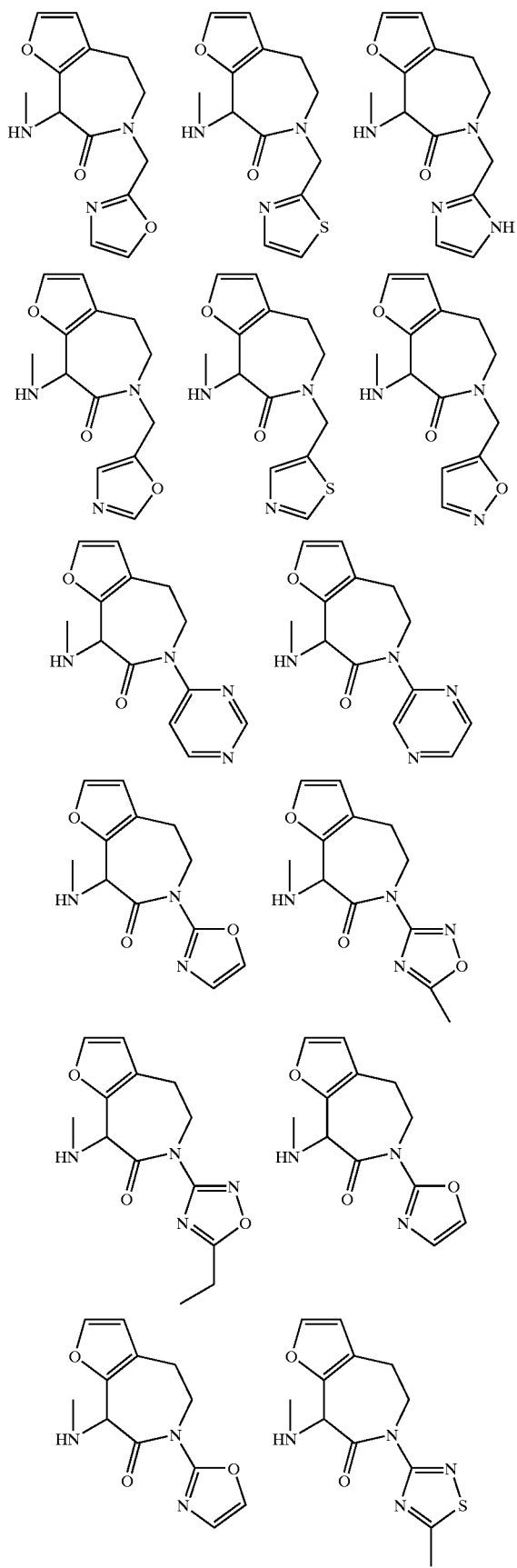
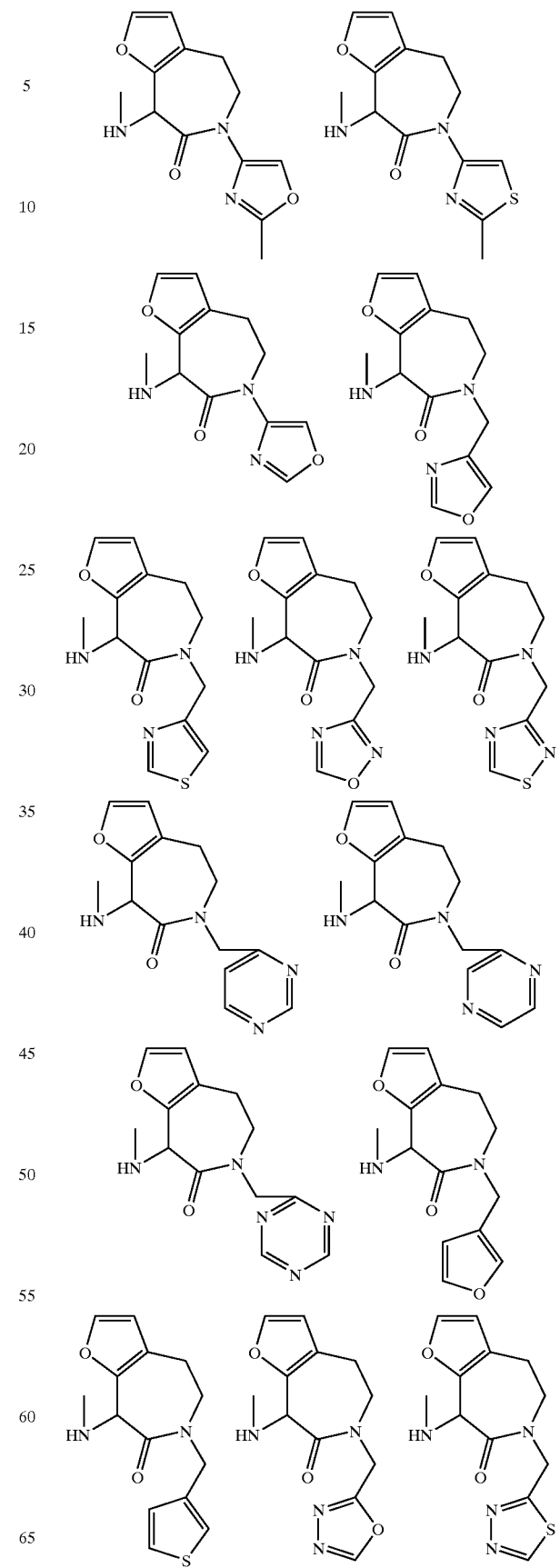

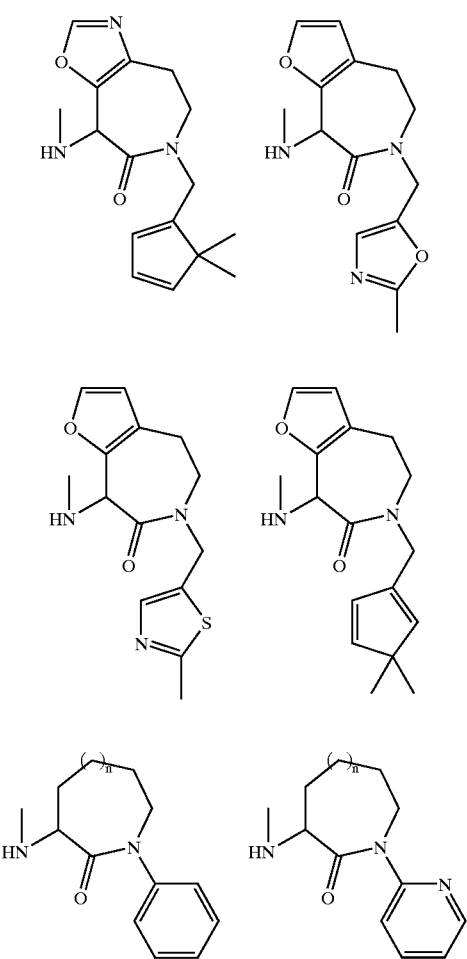
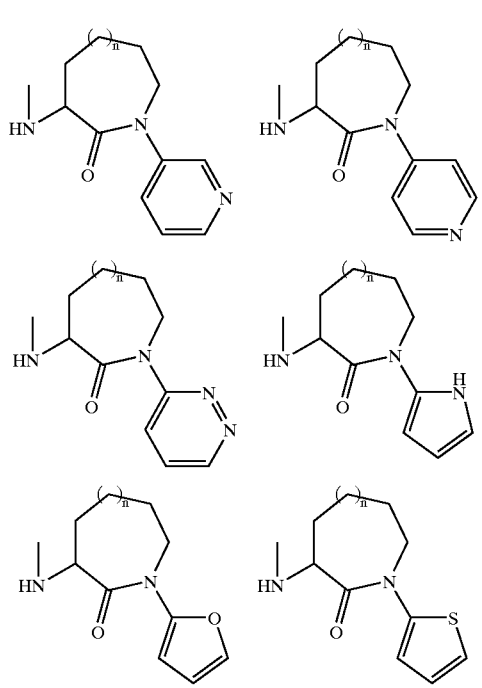
n = 0, 2, 3, 4
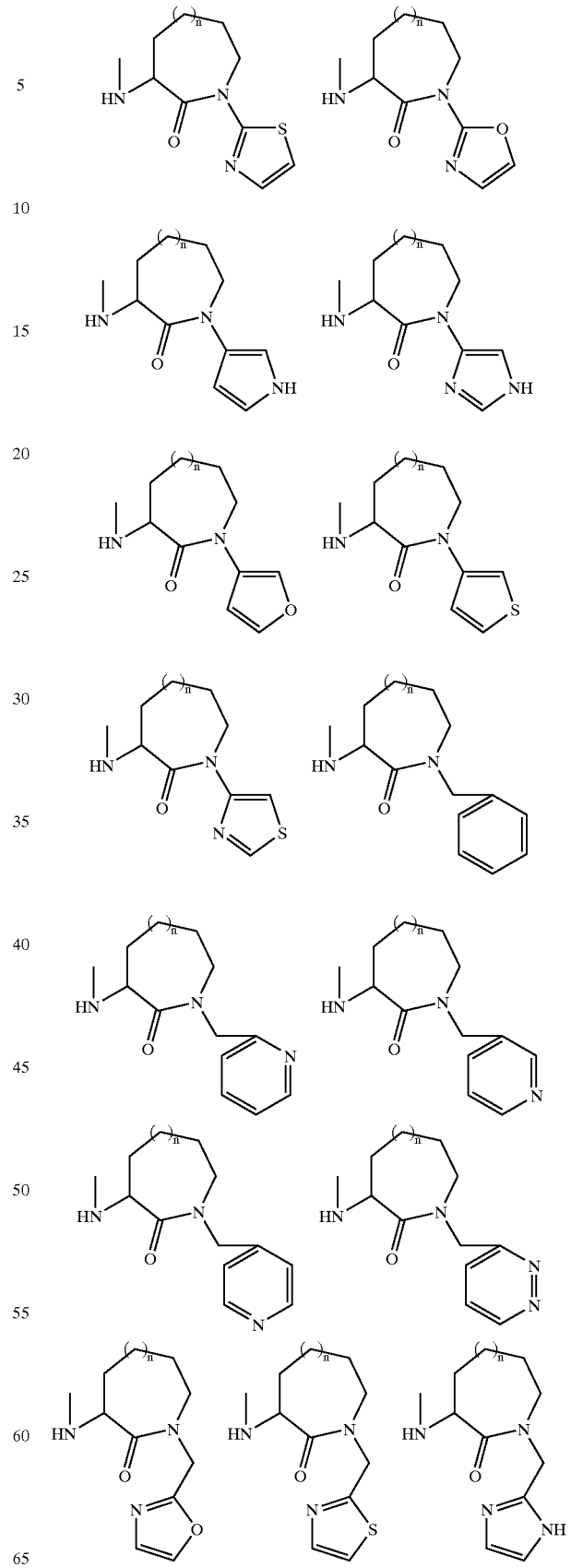

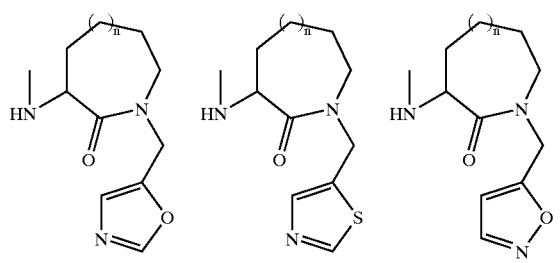
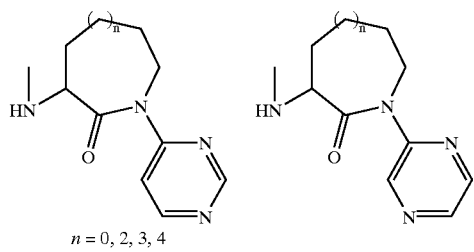
n = 0, 2, 3, 4
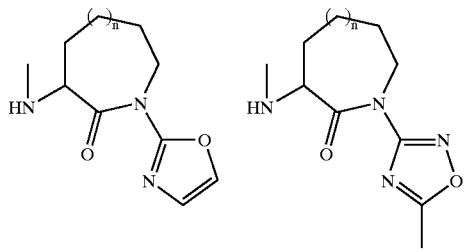
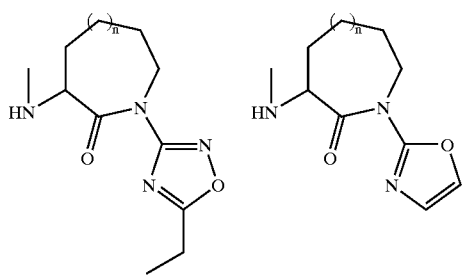
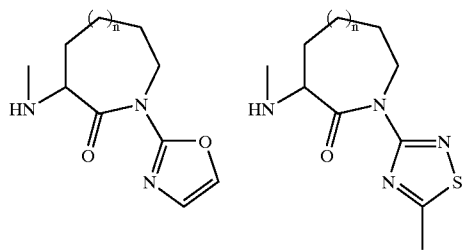
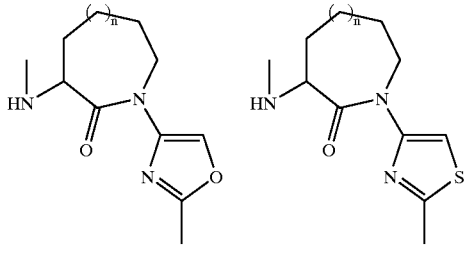
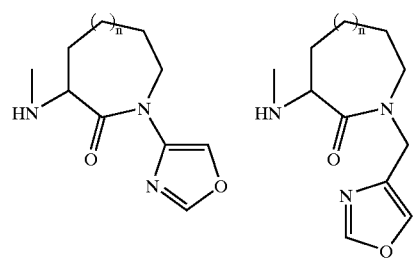
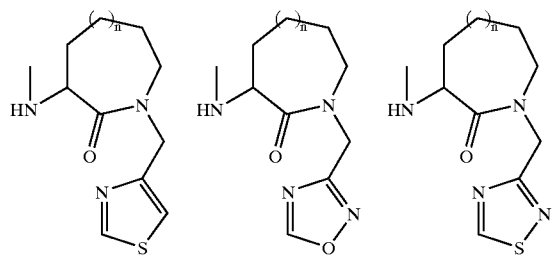
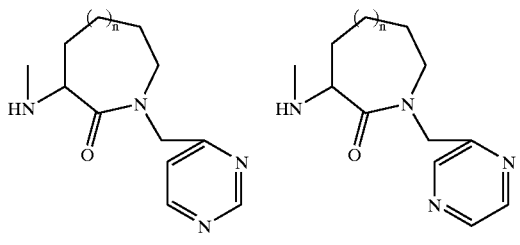
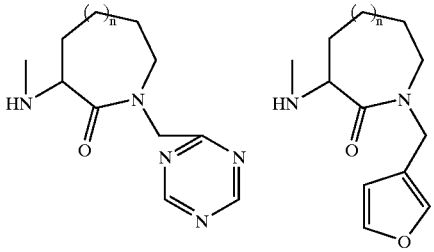
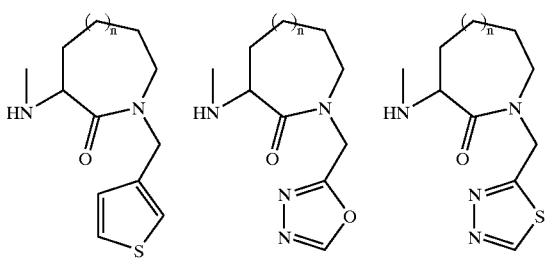
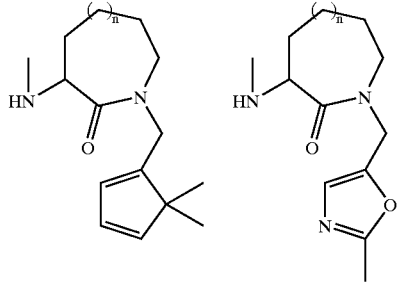

-continued

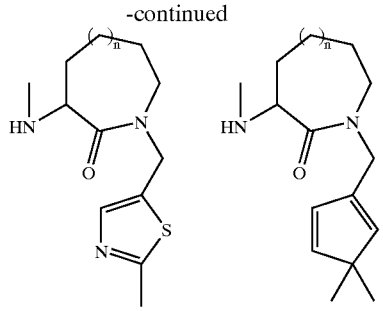

Example Bio-1

Cellular Screen for the Detection of Inhibitors of β-amyloid Production

Numerous compounds described above were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation $LYS_{651}$, $Met_{652}$ to $Asn_{651}$, $LeU_{652}$ (APP751 numbering) in the manner described in International Patent Application Publication No. 94/10569[8] and Citron et al.[12]. This mutation is commonly called the Swedish mutation and the cells, designated as "293 751 SWE", were plated in Corning 96-well plates at $2-4\times10^4$ cells per well in Dulbecco's minimal essential media (Sigma, St. Louis, Mo.) plus 10% fetal bovine serum. Cell number is important in order to achieve β-amyloid ELISA results within the linear range of the assay (around 0.2 to 2.5 ng per mL).

Following overnight incubation at 37° C. in an incubator equilibrated with 10% carbon dioxide, media were removed and replaced with 200 microliters of a compound described above (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media were again removed and replaced with fresh drug-containing media as above and cells were incubated for an additional two hours. After treatment, plates were centrifuged in a Beckman GPR at 1200 rpm for five minutes at room temperature to pellet cellular debris from the conditioned media. From each well, 100 αL of conditioned media or appropriate dilutions thereof were transferred into an ELISA plate pre-coated with antibody 266 [P. Seubert, Nature (1992) 359:325–327] against amino acids 13–28 of β-amyloid peptide as described in International Patent Application Publication No. 94/10569[8] and stored at 4° C. overnight. An ELISA assay employing labelled antibody 3D6 [P. Seubert, Nature (1992) 359:325–327] against amino acids 1–5 of β-amyloid peptide was run the next day to measure the amount of β-amyloid peptide produced.

Cytotoxic effects of the compounds were measured by a modification of the method of Hansen, et al.[13] To the cells remaining in the tissue culture plate was added 25 microliters of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562nm}$ and the $OD_{650nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compounds were assayed for β-amyloid peptide production inhibition activity in cells using this assay. The results of this assay demonstrate that the compounds described herein inhibit β-amyloid peptide production by at least 30% as compared to control.

Example Bio-2

In Vivo Suppression of β-amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) Nature 373:523–527]. Depending upon which compound is being tested, the compound is usually formulated at between 1 and 10 mg/mL. Because of the low solubility factors of the compounds, they may be formulated with various vehicles, such as corn oil (Safeway, South San Francisco, Calif.); 10% ethanol in corn oil; 2-hydroxypropyl-β-cyclodextrin (Research Biochemicals International, Natick Mass.); and carboxy-ethyl-cellulose (Sigma Chemical Co., St. Louis Mo.).

The mice are dosed subcutaneously with a 26 gauge needle and 3) hours later the animals are euthanized via $CO_2$ narcosis and blood is taken by cardiac puncture using a 1 cc 25G 5/8" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid peptide.

The brain homogenates are diluted 1:10 with ice-cold casein buffer [0.25% casein, phosphate buffered saline (PBS), 0.05% sodium azide, 20 micrograms/ml aprotinin, 5 mM EDTA, pH 8.0, 10 micrograms/ml leupeptin], thereby reducing the final concentration of guanidine to 0.5 M, before centrifugation at 16,000×g for 20 minutes at 4° C. Samples are further diluted, if necessary, to achieve an optimal range for the ELISA measurements by the addition of casein buffer with 0.5 M guanidine hydrochloride added. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) includes two monoclonal antibodies (mAb) to β-amyloid. The capture antibody, 266 [P. Seubert, Nature (1992) 359:325–327], is specific to amino acids 13–28 of β-amyloid. The antibody 3D6 [Johnson-Wood et al., PNAS USA (1997) 94:1550–1555], which is specific to amino acids 1–5 of β-amyloid, is biotinylated and serves as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of about 50 pg/ml (11 pM) and shows no crossreactivity to the endogenous murine β-amyloid peptide at concentrations up to 1 ng/ml.

The configuration of the sandwich ELISA quantitating the level of β-amyloid (aa 1–42) employs the mAb 21F12 [Johnson-Wood et al., PNAS USA (1997) 94:1550–1555] (which recognizes amino acids 33–42 of β-amyloid) as the capture antibody. Biotinylated 3D6 is also the reporter antibody in this assay which has a lower limit of sensitivity of around 125 pg/ml (28 pM).

The 266 and 21F12 capture mAbs are coated at 10 micrograms/ml into 96 well immunoassay plates (Costar, Cambidge CIA) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed 3 or more times with wash buffer between each step of the assay. The biotinylated 3D6, diluted to 0.5 micrograms/ml in casein incubation buffer (0.25% casein, PBS, 0.05% Tween 20, pH 7.4) is incubated in the well for I hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Mass.), is added and allowed to react for 15 minutes, after which the enzymatic reaction is stopped with addition of 2 N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium phosphate-$H_2O$ (monobasic), 2.16 gm/l sodium phosphate-$7H_2O$ (dibasic), 0.5 gm/l thimerosal, 8.5 gm/l sodium chloride, 0.5 ml Triton X405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

Formulations other than those described above can also be used for oral delivery and intravenous delivery to a mammal. For oral delivery, the compound can be mixed with either 100% corn oil or, alternatively, in a solution containing 80% corn oil, 19.5% oleic acid and 0.5% labrafil. The compound can be mixed with the above solutions in concentrations ranging from 1 mg/mL to 10 mg/mL. The compound in solution is preferably administered orally to the mammal at a dose volume of 5 mL/kg of body weight. For IV delivery, the compound is preferably mixed with a solution of 3% ethanol, 3% solutol HS-15 and 94% saline. The compound is preferably mixed with the above solution in concentrations ranging from 0.25 mg/mL to 5 mg/mL. The compound in solution is preferably administered by IV to the mammal at a dose volume of 2 mL/kg of body weight.

From the foregoing description, various modifications and changes in the composition and method will occur to those skilled in the art. All such modifications coming within the scope of the appended claims are intended to be included therein.

What is claimed is:

1. A method for inhibiting β-amyloid peptide release and/or its synthesis in a cell which method comprises administering to such a cell an amount of a compound or a mixture of compounds effective in inhibiting the cellular release and/or synthesis of β-amyloid peptide wherein said compounds are represented by the following formula:

Formula IA

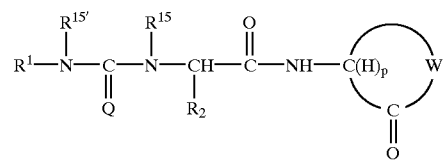

wherein $R^1$ is selected from the group consisting of alkyl, alkenyl, alkynyl, cycloalkyl, cycloalkenyl, substituted alkyl, substituted alkenyl, substituted alkynyl, substituted cycloalkyl, substituted cycloalkenyl, optionally substituted aryl, optionally substituted heteroaryl and optionally substituted heterocyclic;

Q is S or O;

$R^{15}$ is selected from the group consisting of hydrogen, alkyl, substituted alkyl, optionally substituted aryl, optionally substituted heterocyclic and optionally substituted heteroaryl;

$R^{15'}$ is selected from the group consisting of hydrogen, hydroxyl, alkyl, substituted alkyl, optionally substituted aryl, optionally substituted heterocyclic and optionally substituted heteroaryl;

$R^2$ is independently selected from the group consisting of alkyl, substituted alkyl, alkenyl, substituted alkenyl, alkynyl, substituted alkynyl, cycloalkyl, optionally substituted aryl, optionally substituted heteroaryl and optionally substituted heterocyclic;

and the moiety:

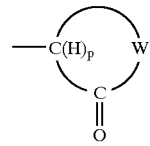

is selected from the group having the formulas:

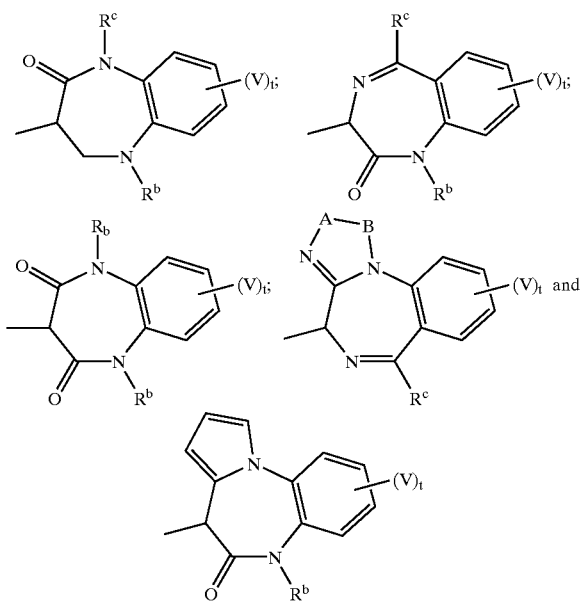

wherein A—B is selected from the group consisting of alkylene, alkenylene, substituted alkylene, substituted alkenylene, and —N=CH—; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, optionally substituted alkaryl, optionally substituted aryl, optionally substituted aryloxy, carboxyl, carboxylalkyl, cyano, halo, nitro, optionally substituted heteroaryl, thioalkoxy, substituted thioalkoxy, and trihalomethyl; $R^b$ is selected from the group consisting of alkyl, substituted alkyl, alkenyl, substituted alkenyl, alkynyl, substituted alkynyl, acyl, optionally substituted aryl, optionally substituted heteroaryl, and optionally substituted heterocyclic; $R^c$ is selected from the group consisting of alkyl, substituted alkyl, alkenyl, substituted alkenyl, optionally substituted aryl, optionally substituted heteroaryl, optionally substituted heterocyclic, cycloalkyl, and substituted cycloalkyl; and t is an integer from 0 to 4;
and the pharmaceutically salts thereof;
with the following provisos:
when $R^1$ is trans-cinnamyl, $R^2$ is methyl, and $R^{15}$ is hydrogen, then W, together with >CH and >C=O, does not form a 2,3-dihydro-1-(3,3-dimethyl-2-oxobutyl)-5-(2-pyridyl)-1H-1,4-benzodiazepin-2-one
when $R^1$ is trans-cinnamyl, $R^2$ is methyl, and $R^{15}$ is hydrogen, then W, together with >CH and >C=O, does not form a 2,3dihydro-1-(2-N,N-diethylaminoethyl)-5-(2-pyridyl)-1H-1,4-benzodiazepin-2-one and
when $R^1$—N($R^{15'}$)C(Q) is (2,5-dimethoxyphenyl) aminocarbonyl and $R^2$ is methyl, then W, together with >CH and >C=O, does not form a 2,3-dihydro-1-methyl-5-phenyl-1H-1,4-benzodiazepin-2-one.

2. A method for treating a human patient with AD in order to inhibit further deterioration in the condition of that patient which method comprises administering to said patient a pharmaceutical composition comprising a pharmaceutically inert carrier and an effective amount of a compound or a mixture of compounds of the following formula:

Formula IA

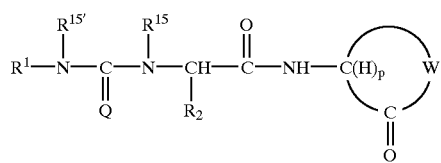

wherein $R^1$ is selected from the group consisting of alkyl, alkenyl, alkynyl, cycloalkyl, cycloalkenyl, substituted alkyl, substituted alkenyl, substituted alkynyl, substituted cycloalkyl, substituted cycloalkenyl, optionally substituted aryl, optionally substituted heteroaryl and optionally substituted heterocyclic;

Q is S or O;

$R^{15}$ is selected from the group consisting of hydrogen, alkyl, substituted alkyl, optionally substituted aryl, optionally substituted heterocyclic and optionally substituted heteroaryl, $R^{15'}$ is selected from the group consisting of hydrogen, hydroxyl, alkyl, substituted alkyl, optionally substituted aryl, optionally substituted heterocyclic and optionally substituted lactam and wherein said optionally substituted lactam heteroaryl, $R^2$ is independently selected from the group consisting of alkyl substituted alkyl, alkenyl, substituted alkenyl, alkynyl, substituted alkynyl, cycloalkyl,m optionally substituted aryl, optionally substituted heteroaryl and optionally substituted heterocyclic; and the moiety:

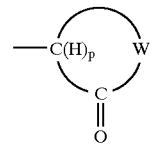

is selected from the group having the formulas:

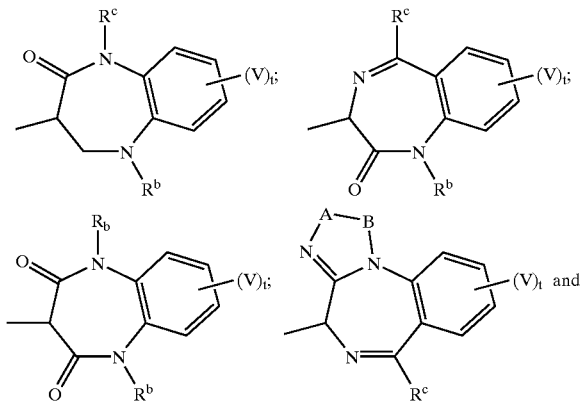

-continued

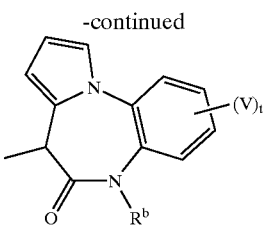

wherein A—B is selected from the group consisting of alkylene, alkenylene, substituted alkylene, substituted alkenylene, and —N=CH—; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, optionally substituted alkaryl, optionally substituted aryl, optionally substituted aryloxy, carboxyl, carboxylalkyl, cyano, halo, nitro, optionally substituted heteroaryl, thioalkoxy, substituted thioalkoxy, and trihalomethyl; $R^b$ is selected from the group consisting of alkyl, substituted alkyl, alkenyl, substituted alkenyl, alkynyl, substituted alkynyl, acyl, optionally substituted aryl, optionally substituted heteroaryl, and optionally substituted heterocyclic; $R^c$ is selected from the group consisting of alkyl, substituted alkyl, alkenyl, substituted alkenyl, optionally substituted aryl, optionally substituted heteroaryl, optionally substituted heterocyclic, cycloalkyl, and substituted cycloalkyl; and t is an integer from 0 to 4;
and the pharmaceutically salts thereof;
with the following provisos:
when $R^1$ is trans-cinnamyl, $R^2$ is methyl, and $R^{15}$ is hydrogen, then W, together with >CH and >C=O, does not form a 2,3-dihydro-1-(3,3-dimethyl-2-oxobutyl)-5-(2-pyridyl)-1H-1,4-benzodiazepin-2-one
when $R^1$ is trans-cinnamyl, $R^2$ is methyl, and $R^{15}$ is hydrogen, then W, together with >CH and >C=O, does not form a 2,3dihydro-1-(2-N,N-diethylaminoethyl)-5-(2-pyridyl)-1H-1,4-benzodiazepin-2-one and
when $R^1$—$N(R^{15'})C(Q)$ is (2,5-dimethoxyphenyl) aminocarbonyl and $R^2$ is methyl, then W, together with >CH and >C=O, does not form a 2,3-dihydro-1-methyl-5-phenyl-1H-1,4-benzodiazepin-2-one.

3. A method according to claims 1 or 2 wherein $R^1$ is aryl or optionally substituted heteroaryl.

4. A method according to claim 3 wherein $R^1$ is selected from the group consisting of
(a) alkyl
(b) phenyl,
(c) a substituted phenyl group of the formula:

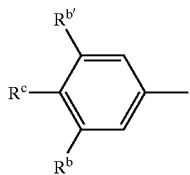

wherein $R^c$ is selected from the group consisting of acyl, alkyl, alkoxy, alkylalkoxy, azido, substituted amino, cyano, halo, hydrogen, nitro, trihalomethyl, thioalkoxy, and wherein $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur
$R^b$ and $R^{b'}$ are independently selected from the group consisting of hydrogen, halo, nitro, cyano, trihalomethyl, alkoxy, and thioalkoxy with the proviso that when $R^c$ is hydrogen, then $R^b$ and $R^{b'}$ are either both hydrogen or both substituents other than hydrogen,
(d) 2-naphthyl,
(e) 2-naphthyl substituted at the 4,5,6,7 and/or 8 positions with 1 to 5 substituents selected from the group consisting alkyl, alkoxy, halo, cyano, nitro, trihalomethyl, thioalkoxy, aryl, and heteroaryl,
(f) heteroaryl, and
(g) substituted heteroaryl containing 1 to 3 substituents selected from the group consisting of alkyl, alkoxy, aryl, aryloxy, cyano, halo, nitro, heteroaryl, thioalkoxy, thioaryloxy provided that said substituents are not ortho to the heteroaryl attachment to the —NH group.

5. The method according to claim 3 wherein $R^1$ is selected from the group consisting of mono-, di- and tri-substituted phenyl groups.

6. The method according to claim 5 wherein $R^1$ is a disubstituted phenyl selected from the group consisting of 3,5-dichlorophenyl, 3,5-difluorophenyl, 3,5-di (trifluoromethyl)-phenyl, 3,4-dichlorophenyl, 3,4-difluorophenyl, 3-(trifluoromethyl)-4-chlorophenyl, 3-chloro-4-cyanophenyl, 3-chloro-4-iodophenyl, and 3,4-methylenedioxyphenyl.

7. The method according to claim 5 wherein $R^1$ is a monosubstituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)phenyl, and 4-(1-ethoxy) ethylphenyl.

8. The method according to claim 5 wherein $R^1$ is a trisubstituted phenyl selected from the group consisting of 3,4,5-trifluorophenyl and 3,4,5-trichlorophenyl.

9. The method according to claim 3 wherein $R^1$ is selected from the group consisting of 2-naphthyl, quinolin-3-yl, 2-methylquinolin-6-yl, benzothiazol-6-yl, 5-indolyl, and phenyl.

10. A method according to claims 1 or 2 wherein $R^1$ is selected from the group consisting of phenyl, 1-naphthyl, 2-naphthyl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenyoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di(trifluoromethyl) phenyl, 3,5-dimethoxyphenyl, 2,4-dichlorophenyl, 2,4-difluorophenyl, 2,6-difluorophenyl, 3,4,5-trifluorophenyl, 3,4,5-trimethoxyphenyl, 3,4,5-tri(trifluoromethyl)phenyl, 2,4,6-trifluorophenyl, 2,4,6-trimethylphenyl, 2,4,6-tri(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5,6-pentafluorophenyl, 2,5-dimethylphenyl, 4-phenylphenyl, 2-fluoro-3-trifluoromethylphenyl, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyrid-2-yl, pyrid-3-ly, pyrid-4-yl, fluoropyridyls, chlorpryidyls, thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetrazol-5-yl, allyl, 2-(cyclohexyl)ethyl, (CH$_3$)$_2$CH=CHCH$_2$CH$_2$CH(CH$_3$)—, C(O)CH$_2$—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl)methyl, (2-methoxyphenyl)methyl, (3-methoxyphenyl)methyl, (3-hydroxyphenyl)methyl, (4-hydroxyphenyl)methyl, (4-methoxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH$_3$OC(O)CH$_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH$_3$CH=CH—, CH$_3$CH$_2$CH=CH—, (4-chlorophenyl)C(O)CH$_2$—, (4-fluorophenyl)C(O)CH$_2$—, (4-methoxyphenyl)C(O)CH$_2$—, 4-(fluorophenyl)-NHC(O)CH$_2$—, 1-phenyl-n-butyl, (phenyl)$_2$CHNHC(O)CH$_2$CH$_2$—, (CH$_3$)$_2$NC(O)CH$_2$—, (phenyl)$_2$CHNHC(O)CH$_2$CH$_2$—, methylcarbonylmethyl, (2,4-dimethylphenyl)C(O)CH$_2$—, 4-methoxyphenyl-C(O)CH$_2$—, phenyl-C(O)CH$_2$—, CH$_3$C(O)N(phenyl)—, ethenyl, methylthiomethyl, (CH$_3$)$_3$CNHC(O)CH$_2$—, 4-fluorophenyl-C(O)CH$_2$—, diphenylmethyl, phenoxymethyl, 3,4-methylenedioxyphenyl-CH$_2$—, benzo[b]thiophen-3-yl, (CH$_3$)$_3$COC(O)NHCH$_2$—, trans-styryl, H$_2$NC(O)CH$_2$CH$_2$—, 2-trifluoromethylphenyl-C(O)CH$_2$, C(O)NHCH(phenyl)CH$_2$—, mesityl, CH$_3$CH(=NHOH)CH$_2$—, 4-CH$_3$-phenyl-NHC(O)CH$_2$CH$_2$—, C(O)CH(phenyl)CH$_2$—, (CH$_3$)$_2$CHC(O)NHCH(phenyl)—, CH$_3$CH$_2$OCH$_2$—, CH$_3$OC(O)CH(CH$_3$)(CH$_2$)$_3$—, 2,2,2-trifluoroethyl, 1-(trifluoromethyl)ethyl, 2-CH$_3$-benzofuran-3-yl, 2-(2,4-dichlorophenoxy)ethyl, SO$_2$CH$_2$—, 3-cyclohexyl-n-propyl, CF$_3$CH$_2$CH$_2$CH$_2$— and N-pyrrolidinyl.

11. A method according to claims 1 or 2 where each R$^2$ is independently selected from the group consisting of alkyl, substituted alkyl, alkenyl, cycloalkyl, optionally substituted aryl, optionally substituted heteroaryl and optionally substituted heterocyclic.

12. The method according to claim 11 wherein R$^2$ is selected from the group consisting of methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$-C(O)O-t-butyl, —CH$_2$-C(CH$_3$)$_3$, —CH$_2$CH(CH$_2$CH$_3$)$_2$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl, pyridyl, —CH$_2$-naphthyl, —CH$_2$—(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl, and thien-3-yl.

13. The method of claims 1 or 2 wherein the —C(H)$_p$WC(O) moiety is selected from the group having the formulas:

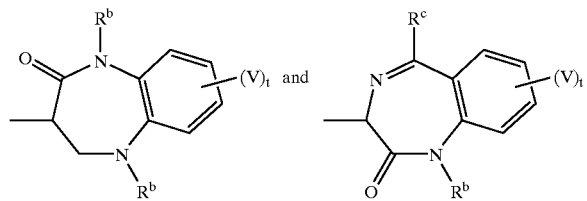

wherein R$^b$, R$^c$, V and t are as defined in claims 1 or 2, respectively.

14. A pharmaceutical composition comprising a pharmaceutically inert carrier and a pharmaceutically effective amount of a compound of formula IA:

Formula IA

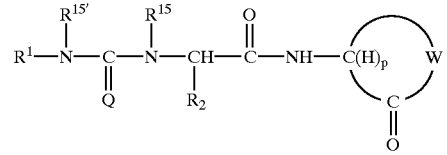

wherein
R$^1$ is selected from the group consisting of:
  A) alkyl of from 1 to 20 carbon atoms;
  B) alkenyl of from 2 to 10 carbon atoms and 1–2 sites of alkenyl unsaturation;
  C) alkynyl of from 2 to 10 carbon atoms and from 1–2 sites of alkynyl unsaturation;
  D) cycloalkyl of from 3 to 12 carbon atoms;
  E) cycloalkenyl of from 4 to 12 carbon atoms;
  F) substituted alkyl of from 1 to 10 carbon atoms, having from 1 to 3 substituents selected from:
    1) alkoxy having the formula alkyl-O— wherein alkyl is as defined in A herein;

2) substituted alkoxy of the formula substituted alkyl-O— wherein substituted alkyl is as defined in F herein;
3) cycloalkyl as defined in D herein;
4) substituted cycloalkyl as defined in I herein;
5) cycloalkenyl as defined in E herein;
6) substituted cycloalkenyl as defined in J herein;
7) acyl having a formula selected from the group consisting of alkyl-C(O)—, substituted alkyl-C(O)—, cycloalkyl-C(O)—, substituted cycloalkyl-C(O)—, optionally substituted aryl-C(O)—, optionally substituted heteroaryl-C(O)— and optionally substituted heterocyclic-C(O)— wherein alkyl is defined in A herein; wherein substituted alkyl is defined in F herein; wherein cycloalkyl is defined in D herein; wherein substituted cycloalkyl is defined in I herein; wherein optionally substituted aryl is defined in F25 herein; wherein optionally substituted heteroaryl is defined in F27 herein; and wherein optionally substituted heterocyclic is defined in F29 herein;
8) acylamino having the formula —C(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
9) acyloxy having a formula selected from the group consisting of alkyl-C(O)O—, substituted alkyl-C(O)O—, cycloalkyl-C(O)O—, optionally substituted aryl-C(O)O—, optionally substituted hetaryl-C(O)O— and optionally substituted heterocyclic-C(O)O— wherein alkyl is defined in A herein; wherein substituted alkyl is defined in F herein; wherein cycloalkyl is defined in D herein; wherein optionally substituted aryl is defined in F25 herein; wherein optionally substituted heteroaryl is defined in F27 herein; and wherein optionally substituted heterocyclic is defined in F29 herein;
10) amino;
11) substituted amino having the formula —N(R)$_2$ wherein each R is independently selected from the group consisting of:
  a) hydrogen;
  b) alkyl as defined in A herein;
  c) substituted alkyl as defined in F herein;
  d) alkenyl as defined in B herein;
  e) substituted alkenyl as defined in G herein;
  f) alkynyl as defined in C herein;
  g) substituted alkynyl as defined in H herein;
  h) optionally substituted aryl as defined in F25 herein;
  i) cycloalkyl as defined in D herein;
  j) substituted cycloalkyl as defined in I herein;
  k) optionally substituted heteroaryl as defined in F27 herein; and
  l) optionally substituted heterocyclic as defined in F29 herein;
    wherein both R groups may be joined together to form a heterocyclic group as defined in F29 herein; and
12) aminoacyl having the formula —NRC(O)R wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein heteroaryl is defined in F27 herein; and wherein optionally substituted heterocyclic is defined in F29 herein;
13) aminoacyloxy having the formula —NRC(O)OR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
14) oxyacylamino having the formula —OC(O)NRR wherein each R is independently hydrogen, alkyl, substituted alkyl, optionally substituted aryl, optionally substituted heteroaryl,
15) or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
15) cyano;
16) halogen selected from fluoro, chloro, bromo and iodo;
17) hydroxyl;
18) keto;
19) thioketo;
20) carboxyl;
21) optionally substituted carboxyalkyl having the formula —C(O)O-alkyl and —C(O)O-substituted alkyl wherein alkyl is as defined in A and substituted alkyl is as defined in F;
22) thiol;
23) thioalkoxy having the formula —S-alkyl, wherein alkyl is defined in A herein;
24) substituted thioalkoxy having the formula —S-substituted alkyl, wherein substituted alkyl is defined in F herein;
25) optionally substituted aryl having 6 to 14 carbon atoms and optionally substituted with 1 to 5 substituents selected from:
  a) acyloxy;
  b) hydroxy;
  c) acyl as defined in F7 herein;
  d) alkyl as defined in A herein;
  e) alkoxy as defined in F1 herein;
  f) alkenyl as defined in B herein;
  g) alkynyl as defined in C herein;
  h) substituted alkyl as defined in F herein;
  i) substituted alkoxy as defined in F2 herein;
  j) substituted alkenyl as defined in G herein;
  k) substituted alkynyl as defined in H herein;
  l) amino;
  m) substituted amino as defined in F11 herein;
  n) aminoacyl as defined in F12 herein;
  o) acylamino as defined in F8 herein;
  p) optionally substituted alkaryl of the formula -alkylene-aryl where alkylene has from 1 to 10 carbon atoms and is optionally substituted with from 1 to 3 substituents selected from the group consisting of:
1) alkoxy as defined in F1 herein;
2) substituted alkoxy as defined in F2 herein;
3) acyl as defined in F7 herein;
4) acylamino as defined in F8 herein;
5) acyloxy as defined in F9 herein;
6) amino;
7) substituted amino as defined in F11 herein;
8) aminoacyl as defined in F12 herein;
9) aminoacyloxy as defined in F13 herein;
10) oxyacylamino as defined in F14 herein;
11) cyano;
12) halogen selected from fluoro, chloro, bromo and iodo;
13) hydroxyl;
14) keto;
15) thioketo;
16) carboxyl;
17) optionally substituted carboxyalkyl as defined in F21;
18) thiol;
19) thioalkoxy as defined in F23 herein;
20) substituted thioalkoxy as defined in F24 herein;
21) optionally substituted aryl as defined in F25 herein;
22) optionally substituted heteroaryl as defined in F27 herein;
23) optionally substituted saturated or unsaturated heterocyclic as defined in F29 herein;
24) heterocyclooxy as defined in G24 herein;
25) nitro;
26) mono- and di-alkylamino as defined in F41 herein;
27) mono- and di-(substituted alkyl) amino as defined in F42 herein;
28) mono- and di-arylamino as defined in F43 herein;
29) mono- and di-heteroarylamino as defined in F44 herein;
30) mono- and di-heterocyclic amino as defined in F45 herein; and
31) unsymmetric di-substituted amines as defined in F46 herein;
q) optionally substituted aryl as defined in F25 herein;
r) optionally substituted aryloxy as defined in F26 herein;
s) azido;
t) carboxyl;
u) optionally substituted carboxylalkyl as defined in F21 herein;
v) cyano;
w) halo as defined in F16 herein;
x) nitro;
y) optionally substituted heteroaryl as defined in F27 herein;
z) optionally substituted heteroaryloxy as defined in F28 herein
aa) optionally substituted heterocyclic as defined in F29 herein;
bb) optionally substituted heterocyclooxy as defined in G24 herein;
cc) aminoacyloxy as defined in F13 herein;
dd) oxyacylamino as defined in F14 herein;
ee) thioalkoxy as defined in F23 herein;
ff) substituted thioalkoxy as defined in F24 herein;
gg) optionally substituted thioaryloxy having the formula aryl-S— wherein aryl is optionally substituted as defined in F25 herein;
hh) optionally substituted thioheteroaryloxy having the formula heteroaryl-S— wherein heteroaryl is optionally substituted as defined in F27 herein;
ii) —SO-alkyl wherein alkyl is as defined in A herein;
jj) —SO-substituted alkyl wherein substituted alkyl is as defined in F herein;
kk) —SO-optionally substituted aryl wherein optionally substituted aryl is as defined in F25 herein;
ll) —SO-optionally substituted heteroaryl wherein optionally substituted heteroaryl is as defined in F27 herein;
mm) —SO$_2$-alkyl wherein alkyl is as defined in A herein;
nn) —SO$_2$-substituted alkyl wherein substituted alkyl is as defined in F herein;
oo) —SO$_2$-optionally substituted aryl wherein optionally substituted aryl is as defined in F25 herein;
pp) —SO$_2$-optionally substituted heteroaryl wherein optionally substituted heteroaryl is as defined in F27 herein; and
qq) trihalomethyl wherein halo is as defined in F16 herein;
26) optionally substituted aryloxy having the formula aryl-O— wherein aryl is optionally substituted aryl as defined in F25 herein;
27) optionally substituted heteroaryl having 1 to 15 ring carbon atoms and 1 to 4 ring heteroatoms selected from oxygen, nitrogen and sulfur and optionally substituted with 1 to 5 substituents selected from the group of substituents as defined in F25 herein
28) optionally substituted heteroaryloxy having the formula —O-heteroaryl wherein heteroaryl is optionally substituted heteroaryl as defined in F27 herein;
29) optionally substituted saturated or unsaturated heterocyclic having from 1 to 15 ring carbon atoms and from 1 to 4 ring heteroatoms selected from nitrogen, sulfur and oxygen and optionally substituted with 1 to 5 substituents selected from the group of substituents consisting of alkyl as defined in A herein; substituted alkyl as defined in F herein; alkoxy as defined in F1 herein; substituted alkoxy as defined in F2 herein; aryl as defined in F25 herein; aryloxy, halo as defined in F16 herein; nitro, heteroaryl as defined in F27 herein; thiol, thioalkoxy as defined in F23 herein; substituted thioalkoxy as defined in F24 herein; thioaryloxy wherein aryloxy is as defined in F26 herein; and trihalomethyl wherein halo is as defined in F16 herein;
30) hydroxyamino;
31) alkoxyamino wherein alkoxy is as defined in F1;
32) nitro;
33) —SO-alkyl wherein alkyl is as defined in A herein;
34) —SO-substituted alkyl wherein substituted alkyl is as defined in F herein;
35) —SO-optionally substituted aryl wherein aryl is optionally substituted as defined in F25 herein;
36) —SO-optionally substituted heteroaryl wherein optionally substituted heteroaryl is as defined in F27 herein;
37) —SO$_2$-alkyl wherein alkyl is as defined in A herein;

38) —SO₂-substituted alkyl wherein substituted alkyl is as defined in F herein;
39) —SO₂-optionally substituted aryl wherein optionally substituted aryl is as defined in F25 herein;
40) —SO₂-optionally substituted heteroaryl wherein optionally substituted heteroaryl is as defined in F27 herein;
41) mono- and di-alkylamino wherein alkyl is as defined in A herein;
42) mono- and di-(substituted alkyl) amino wherein substituted alkyl is as defined in F herein;
43) mono- and di-arylamino wherein aryl is as defined in F25 herein;
44) mono- and di-heteroarylamino wherein heteroaryl is as defined in F27 herein;
45) mono- and di-heterocyclic amino wherein heterocyclic is as defined in F29 herein; and
46) unsymmetric di-substituted amines having different substituents selected from alkyl, substituted alkyl, optionally substituted aryl, optionally substituted heteroaryl and optionally substituted heterocyclic, wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;

G) substituted alkenyl having 2 to 10 carbon atoms and having of from 1 to 3 substituents selected from the group consisting of:
1) alkoxy having the formula alkyl-O— wherein alkyl is as defined in A herein;
2) substituted alkoxy of the formula substituted alkyl-O— wherein substituted alkyl is as defined in F herein;
3) acyl as defined in F7 herein;
4) acylamino as defined in F8 herein;
5) acyloxy as defined in F9 herein;
6) amino;
7) substituted amino as defined in F11 herein;
8) aminoacyl as defined in F12 herein;
9) aminoacyloxy as defined in F13 herein;
10) oxyacylamino as defined in F14 herein;
11) cyano;
12) halogen selected from fluoro, cholo, bromo and iodo;
13) hydroxyl;
14) keto;
15) thioketo;
16) carboxyl;
17) optionally substituted carboxyalkyl having the formula —C(O)O-alkyl and —C(O)O-substituted alkyl wherein alkyl is as defined in A and substituted alkyl is as defined in F;
18) thiol;
19) thioalkoxy as defined in F23 herein;
20) substituted thioalkoxy as defined in F24 herein;
21) optionally substituted aryl as defined in F25 herein;
22) optionally substituted heteroaryl as defined in F27 herein;
23) optionally substituted saturated or unsaturated heterocyclic as defined in F29 herein;
24) optionally substituted heterocyclooxy having the formula —O-heterocyclic wherein heterocyclic is as defined in F29 herein;
25) nitro;
26) —SO-alkyl wherein alkyl is as defined in A herein;
27) —SO-substituted alkyl wherein substituted alkyl is as defined in F herein;
28) —SO-aryl wherein optionally substituted aryl is optionally substituted as defined in F25 herein;
29) —SO-optionally substituted heteroaryl wherein optionally substituted heteroaryl is as defined in F27 herein;
30) —SO₂-alkyl wherein alkyl is as defined in A herein;
31) —SO₂-substituted alkyl wherein substituted alkyl is as defined in F herein;
32) —SO₂-optionally substituted aryl wherein optionally substituted aryl is as defined in F25 herein; and
33) —SO₂-optionally substituted heteroaryl wherein optionally substituted heteroaryl is as defined in F27 herein;
34) mono- and di-alkylamino as defined in F41 herein;
35) mono- and di-(substituted alkyl) amino as defined in F42 herein;
36) mono- and di-arylamino as defined in F43 herein;
37) mono- and di-heteroarylamino as defined in F44 herein;
38) mono- and di-heterocyclic amino as defined in F29 herein; and
39) unsymmetric di-substituted amines having different substituents selected from alkyl, substituted alkyl, optionally substituted aryl, optionally substituted heteroaryl and optionally substituted heterocyclic;

H) substituted alkynyl having 2 to 10 carbon atoms having 1–2 sites of alkynyl unsaturation and having 1 to 3 substituents selected from the group consisting of:
1) alkoxy as defined in F1 herein;
2) substituted alkoxy as defined in F2 herein;
3) acyl as defined in F7 herein;
4) acylamino as defined in F8 herein;
5) acyloxy as defined in F9 herein;
6) amino;
7) substituted amino as defined in F11 herein;
8) aminoacyl as defined in F12 herein;
9) aminoacyloxy as defined in F13 herein;
10) oxyacylamino as defined in F14 herein,
11) cyano;
12) halogen as defined in F16 herein;
13) hydroxyl;
14) keto;
15) thioketo;
16) carboxyl;
17) carboxylalkyl as defined in F21 herein;
18) thiol;
19) thioalkoxy as defined in F23 herein;
20) substituted thioalkoxy as defined in F24 herein;
21) aryl as defined in F25 herein;
22) heteroaryl as defined in F27 herein;
23) heterocyclic as defined in F29 herein;
24) heterocyclooxy as defined in G24 herein;
25) nitro;
26) —SO-alkyl as defined in F33 herein;
27) —SO-substituted alkyl as defined in F34 herein;
28) —SO-aryl as defined in F35 herein;
29) —SO-heteroaryl as defined in F36 herein;
30) —SO₂-alkyl as defined in F37 herein;
31) —SO₂-substituted alkyl as defined in F38 herein;
32) —SO₂-aryl as defined in F39 herein;
33) —SO₂-heteroaryl as defined in F40 herein;
34) mono- and di-alkylamino as defined in F41 herein;
35) mono- and di-(substituted alkyl) amino as defined in F42 herein;
36) mono- and di-arylamino as defined in F43 herein;

37) mono- and di-heteroarylamino as defined in F44 herein;
38) mono- and di-heterocyclic amino as defined in F42 herein; and
39) unsymmetric di-substituted amines as defined in F29 herein;
I) substituted cycloalkyl having 3 to 12 carbon atoms and having from 1 to 5 substituents selected from the group of substituents consisting of:
1) hydroxy;
2) acyl as defined in F7 herein;
3) acyloxy as defined in F9 herein;
4) alkyl as defined in A herein;
5) substituted alkyl as defined in F herein;
6) alkoxy as defined in F1 herein;
7) substituted alkoxy as defined in F2 herein;
8) alkenyl as defined in B herein;
9) substituted alkenyl as defined in G herein;
10) alkynyl as defined in C herein;
11) substituted alkynyl as defined in H herein,
12) amino;
13) substituted amino as defined in F11 herein;
14) aminoacyl as defined in F12 herein;
15) alkaryl as defined in F25(p) herein;
16) aryl as defined in F29 herein;
17) aryloxy as defined in F26 herein;
18) carboxyl;
19) carboxylalkyl as defined in F21 herein;
20) cyano;
21) halo as defined in F16 herein;
22) nitro;
23) heteroaryl as defined in F27 herein;
24) thioalkoxy as defined in F23 herein;
25) substituted thioalkoxy as defined in F24 herein; and
26) trihalomethyl;
J) substituted cycloalkenyl as defined in E herein having from 1 to 5 substituents selected from the group of consisting of:
1) hydroxy;
2) acyl as defined in F7 herein;
3) acyloxy as defined in F9 herein;
4) alkyl as defined in A herein;
5) substituted alkyl as defined in F herein;
6) alkoxy as defined in F1 herein;
7) substituted alkoxy as defined in F2 herein;
8) alkenyl as defined in B herein;
9) substituted alkenyl as defined in G herein;
10) alkynyl as defined in C herein;
11) substituted alkynyl as defined in H herein;
12) amino;
13) substituted amino as defined in F11 herein;
14) aminoacyl as defined in F12 herein;
15) alkaryl as defined in F25(p) herein;
16) aryl as defined in F29 herein;
17) aryloxy as defined in F26 herein;
18) carboxyl;
19) carboxylalkyl as defined in F21 herein;
20) cyano;
21) halo as defined in F16 herein;
22) nitro;
23) heteroaryl as defined in F27 herein;
24) thioalkoxy as defined in F23 herein;
25) substituted thioalkoxy as defined in F24 herein; and
26) trihalomethyl;
K) optionally substituted aryl as defined in F25 herein;
L) optionally substituted heteroaryl as defined in F27 herein; and
M) optionally substituted heterocyclic as defined in F29 herein;

$R^2$ is independently selected from the group consisting of:
O) alkyl as defined in A herein;
P) substituted alkyl as defined in F herein;
Q) alkenyl of from 2 to 10 carbon atoms and 1–2 sites of alkenyl unsaturation;
R) substituted alkenyl as defined in G herein;
S) alkynyl of from 2 to 10 carbon atoms and from 1–2 sites of alkynyl unsaturation;
T) substituted alkynyl as defined in H herein;
U) cycloalkyl of from 3 to 12 carbon atoms;
V) optionally substituted aryl as defined in F25 herein;
W) optionally substituted heteroaryl as defined in F27 herein; and
X) optionally substituted heterocyclic as defined in F29 herein;

Q is S and O;
wherein $R^{15}$ is independently selected from the group consisting of:
Y) hydrogen;
Z) alkyl as defined in A herein;
AA) substituted alkyl as defined in F herein;
AB) optionally substituted aryl as defined in F25 herein;
AC) optionally substituted heterocyclic as defined in F29 herein;
AD) optionally substituted heteroaryl as defined in F27 herein;

wherein $R^{15'}$ is independently selected from the group consisting of:
AE) hydrogen;
AF) hydroxyl;
AG) alkyl as defined in A herein;
AH) substituted alkyl as defined in F herein;
AI) optionally substituted aryl as defined in F25 herein;
AJ) optionally substituted heterocyclic as defined in F29 herein;
AK) optionally substituted heteroaryl as defined in F27 herein;
and the moiety:

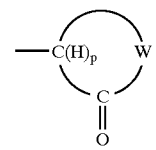

is selected from the group having the formulas:

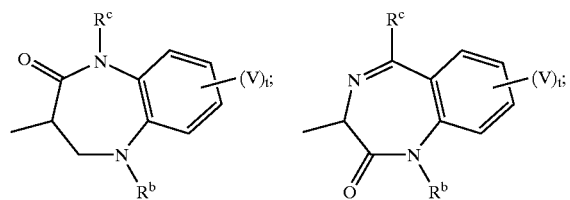

-continued

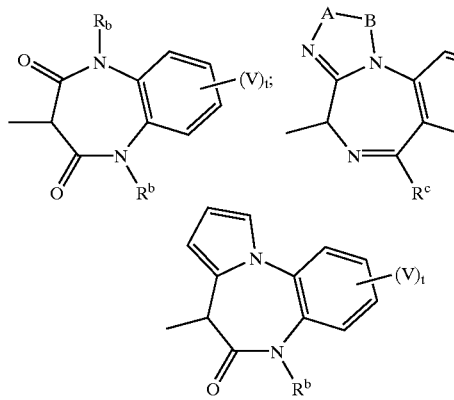

is selected from the group having the formulas:

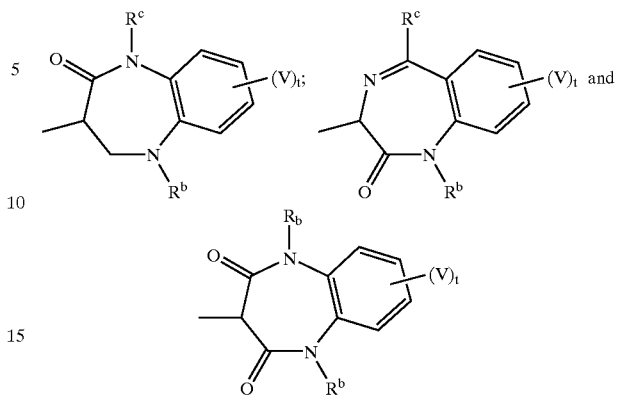

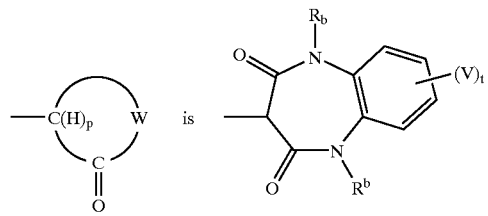

wherein A—B is selected from the group consisting of alkylene, alkenylene, substituted alkylene, substituted alkenylene, and —N═CH—; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, optionally substituted alkaryl, optionally substituted aryl, optionally substituted aryloxy, carboxyl, carboxylalkyl, cyano, halo, nitro, optionally substituted heteroaryl, thioalkoxy, substituted thioalkoxy, and trihalomethyl; $R^b$ is selected from the group consisting of hydrogen, alkyl, substituted alkyl, alkenyl, substituted alkenyl, alkynyl, substituted alkynyl, acyl, optionally substituted aryl, optionally substituted heteroaryl, and optionally substituted heterocyclic; $R^c$ is selected from the group consisting of alkyl, substituted alkyl, alkenyl, substituted alkenyl, optionally substituted aryl, optionally substituted heteroaryl, optionally substituted heterocyclic, thioalkoxy, substituted amino, cycloalkyl, and substituted cycloalkyl; and t is an integer from 0 to 4;

or pharmaceutically salts thereof;

with the following provisos:

when $R^1$ is trans-cinnamyl, $R^2$ is methyl, and $R^{15}$ is hydrogen, then W, together with >CH and >C═O, does not form a 2,3-dihydro-1-(3,3-dimethyl-2-oxobutyl)-5-(2-pyridyl)-1H-1,4-benzodiazepin-2-one when $R^1$ is trans-cinnamyl, $R^2$ is methyl, and $R^{15}$ is hydrogen, then W, together with >CH and >C═O, does not form a 2,3-dihydro-1-(2-N,N-diethylaminoethyl)-5-(2-pyridyl)-1H-1,4-benzodiazepin-2-one when $R^1$-N($R^{15'}$)C(Q) is (2,5-dimethoxyphenyl) aminocarbonyl and $R^2$ is methyl, then W, together with >CH and >C═O, does not form a 2,3-dihydro-1-methyl-5-phenyl-1H-1,4-benzodiazepin-2-one and when Q is S, $R^{15}$ and $R^{15'}$ are hydrogen, and the moiety:

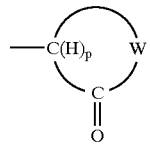

then $R^1$ is not phenyl.

15. The pharmaceutical composition according to claim 4, wherein the moiety:

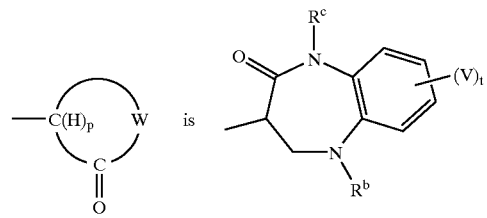

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

$R^b$ is selected from the group consisting of alkyl, substituted alkyl as defined in F, alkenyl, substituted alkenyl as defined in G, alkynyl, acyl, optionally substituted aryl as defined in F25, optionally substituted heteroaryl as defined in F27, and optionally substituted heterocyclic as defined in F29;

or pharmaceutically acceptable salts thereof.

16. The pharmaceutical composition according to claim 14, wherein the moiety:

wherein $R^b$ is selected from the group consisting of alkyl, substituted alkyl as defined in F, alkenyl, substituted alkenyl as defined in G, alkynyl, acyl, optionally substituted aryl as defined in F25, optionally substituted heteroaryl as defined in F27, and optionally substituted heterocyclic as defined in F29;

R<sup>c</sup> is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

or pharmaceutically acceptable salts thereof.

17. The pharmaceutical composition according to claim 14, wherein the moiety:

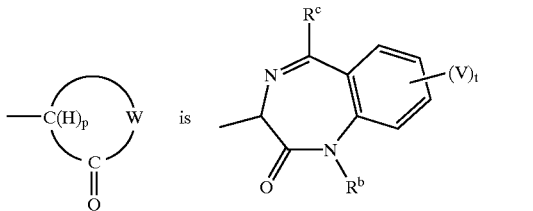

wherein R<sup>b</sup> is selected from the group consisting of alkyl, substituted alkyl as defined in F, alkenyl, substituted alkenyl as defined in G, alkynyl, acyl, optionally substituted aryl as defined in F25, optionally substituted heteroaryl as defined in F27, and optionally substituted heterocyclic as defined in F29;

R<sup>c</sup> is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

18. The pharmaceutical composition according to claim 14, wherein the moiety:

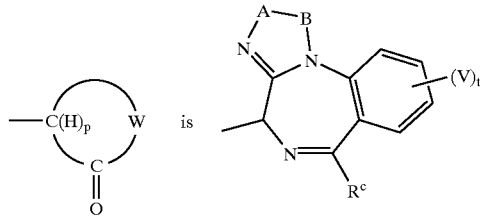

wherein A—B is selected from the group consisting of alkylene, alkenylene, substituted alkylene, substituted alkenylene and —N=CH—;

R<sup>c</sup> is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

19. The pharmaceutical composition according to claim 14, wherein the moiety:

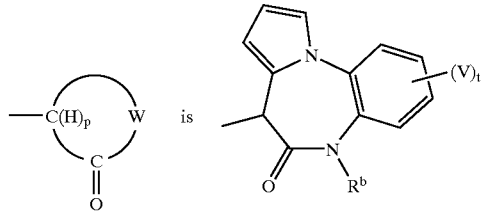

R<sup>c</sup> is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

20. The pharmaceutical composition according to claim 19, wherein $R^1$ is selected from the group consisting of:

(a) alkyl;

(b) phenyl;

(c) a substituted phenyl group of the formula:

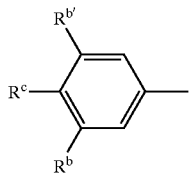

wherein $R^c$ is selected fron the group consisting of acyl, alkyl, alkoxy, alkylalkoxy, azido, cyano, subsstituted amino, halo, hydrogen, nitro, trihalomethyl, thioalkoxy, and wherein $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur, $R^b$ and $R^{b'}$ are independently selected from the group consisting of hydrogen, halo, nitro, cyano, trihalomethyl, alkoxy, and thioalkoxy with the proviso that when $R^c$ is hydrogen, the $R^b$ and $R^{b'}$ are either both hydrogen or both substituents other than hydrogen, (d) 2-naphthyl, (e) 2-naphthyl substituted at the 4,5,6,7 and/or 8 positions with 1 to 5 substituents selected from the group consisting of alkyl, alkoxy, halo, cyano, nitro, trihalomethyl, thioalkoxy, aryl, and heteroaryl, (f) heteroaryl, and (g) substituted heteroaryl containing 1 to 3 substituents selected from the group consisting of alkyl, alkoxy, aryl, aryloxy, cyano, halo, nitro, heteroaryl, thioalkoxy, thioaryloxy provided that said substituents are not othro to the heteroaryl attachment to the —NH group.

21. The pharmaceutical composition according to claim 14, wherein $R^1$ is selected from the group consisting of mono-, di-, and tri-substituted phenyl groups.

22. The pharmaceutical composition according to claim 21, wherein $R^1$ is a monosubstituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)-phenyl, and 4-(1-ethoxy)ethylphenyl.

23. The pharmaceutical composition according to claim 21, wherein $R^1$ is a disubstituted phenyl selected from the group consisting of 3,5-dichlorophenyl, 3,5-difluorophenyl, 3,5-di(trifluoromethyl)-phenyl, 3,4-dichlorophenyl, 3,4-difluorophenyl, 3-(trifluoromethyl)-4-chlorophenyl, 3-chloro-4-cyanophenyl, 3-chloro-4-iodophenyl, and 3,4-methylenedioxyphenyl.

24. The pharmaceutical composition according to claim 21, wherein $R^1$ is a trisubstituted phenyl selected from the group consisting of 3,4,5-trifluorophenyl and 3,4,5-tricholorophenyl.

25. The pharmaceutical composition according to claim 14, wherein $R^1$ is selected from the group consisting of 2-naphthyl, quinolin-3-yl, 2-methylquinolin-6-yl, benzothiazol-6-yl, 5-indolyl and phenyl.

26. The pharmaceutical composition according to claim 14, wherein $R^1$ is selected from the group consisting of: phenyl, 1-naphthyl, 2-naphthyl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl) phenyl, 3,5-dimethoxyphenyl, 2,4-dichlorophenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5, 6-pentafluorophenyl, 2,5-dimethylphenyl, 4-phenylphenyl, 2-fluoro-3-trifluoromethylphenyl, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyrid-2-yl, pyrid-3-yl, pyrid-4-yl, fluoropyridyls, chloropyridyls, thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetrazol-5-yl, allyl, 2-(cyclohexyl) ethyl, (CH$_3$)$_2$CH=CHCH$_2$CH$_2$CH(CH$_3$)—, C(O)CH$_2$—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl)methyl, (2-methoxyphenyl)methyl, (3-methoxyphenyl)methyl, (3-hydroxyphenyl)methyl, (4-hydroxyphenyl)methyl, (4-methoxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH₃OC(O)CH₂—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH₃CH=CH—, CH₃CH₂CH=CH—, (4-chlorophenyl)C(O)CH₂—, (4-fluorophenyl)C(O)CH₂—, (4-methoxyphenyl)C(O)CH₂—, 4-(fluorophenyl)—NHC(O)CH₂—, 1-phenyl-n-butyl, (phenyl)₂CHNHC(O)CH₂CH₂—, (CH₃)₂NC(O)CH₂—, (phenyl)₂CHNHC(O)CH₂CH₂—, ethylcarbonylmethyl, (2,4-dimethylphenyl)C(O)CH₂—, 4-methoxyphenyl-C(O)CH₂—, phenyl-C(O)CH₂—, CH₃C(O)N(phenyl)—, ethenyl, methylthiomethyl, (CH₃)₃CNHC(O)CH₂—, 4-fluorophenyl-C(O)CH₂—, diphenylmethyl, phenoxymethyl, 3,4-methylenedioxyphenyl-CH₂—, benzo[b]thiophen-3-yl, (CH₃)₃COC(O)NHCH₂—, trans-styryl, H₂NC(O)CH₂CH₂—, 2-trifluoromethylphenyl-C(O)CH₂, phenyl-C(O)NHCH(phenyl)CH₂—, mesityl, CH₃CH(=NHOH)CH₂—, 4-CH₃-phenyl-NHC(O)CH₂CH₂—, C(O)CH(phenyl)CH₂—, (CH₃)₂CHC(O)NHCH(phenyl)—, CH₃CH₂OCH₂—, CH₃OC(O)CH(CH₃)(CH₂)₃—, 2,2,2-trifluoroethyl, 1-(trifluoromethyl)ethyl, 2-CH₃-benzofuran-3-yl, 2-(2,4-dichlorophenoxy)ethyl, SO₂CH₂—, 3-cyclohexyl-n-propyl, CF₃CH₂CH₂CH₂— and N-pyrrolidinyl.

27. The pharmaceutical composition according to claim 14, wherein R² is selected from the group consisting of alkyl, substituted alkyl, alkenyl, cycloalkyl, optionally substituted aryl, optionally substituted heteroaryl and optionally substituted heterocyclic.

28. The pharmaceutical composition according to claim 14, wherein R² is selected from the group consisting of: methyl, ethyl, n-propyl, iso-propyl, n-butyl, iso-butyl, sec-butyl, tert-butyl, —CH₂CH(CH₂CH₃)₂, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH₂-cyclopropyl, —CH₂-cyclohexyl, —CH₂CH₂-cyclopropyl, —CH₂CH₂-cyclohexyl, —CH₂-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH₃)₂NCH₂CH₂CH₂O-benzyl, p-(CH₃)₃COC(O)CH₂O-benzyl, p-(HOOCCH₂O)—benzyl, 2-aminopyrid-6-yl, p-(N-morpholino-CH₂CH₂O)—benzyl, —CH₂CH₂C(O)NH₂, —CH₂-imidazol-4-yl, —CH₂-(3-tetrahydrofuranyl), —CH₂-thiophen-2-yl, —CH₂(1-methyl)cyclopropyl, —CH₂-thiophen-3-yl, thiophen-3-yl, thiophen-2-yl, —CH₂—C(O)O-t-butyl, —CH₂-C(CH₃)₃, —CH₂CH(CH₂CH₃)₂, 2-methylcyclopentyl, cyclohex-2-enyl, —CH[CH(CH₃)₂]COOCH₃, —CH₂CH₂N(CH₃)₂, —CH₂C(CH₃)=CH₂, —CH₂CH=CHCH₃ (cis and trans), —CH₂OH, —CH(OH)CH₃, —CH(O-t-butyl)CH₃, —CH₂OCH₃, —(CH₂)₄NH—Boc, —(CH₂)₄NH₂, —CH₂-pyridyl, pyridyl, —CH₂-naphthyl, —CH₂-(N-morpholino), p-(N-morpholino-CH₂CH₂O)—benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH₂CH₂SCH₃, thien-2-yl, and thien-3-yl.

29. A compound of formula IA:

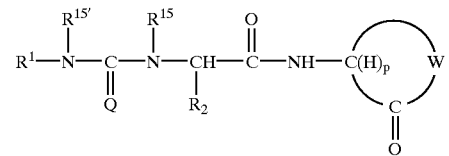

Formula IA

R¹ is selected from the group consisting of:
A) alkyl of from 1 to 20 carbon atoms;
B) alkenyl of from 2 to 10 carbon atoms and 1–2 sites of alkenyl unsaturation;
C) alkynyl of from 2 to 10 carbon atoms and from 1–2 sites of alkynyl unsaturation;
D) cycloalkyl of from 3 to 12 carbon atoms;
E) cycloalkenyl of from 4 to 8 carbon atoms;
F) substituted alkyl of from 1 to 10 carbon atoms, having from 1 to 3 substituents selected from:
  1) alkoxy having the formula alkyl-O— wherein alkyl is as defined in A herein;
  2) substituted alkoxy of the formula substituted alkyl-O— wherein substituted alkyl is as defined in F herein;
  3) cycloalkyl as defined in D herein;
  4) substituted cycloalkyl as defined in I herein;
  5) cycloalkenyl as defined in E herein;
  6) substituted cycloalkenyl as defined in J herein;
  7) acyl selected from alkyl-C(O)—, substituted alkyl-C(O)—, cycloalkyl-C(O)—, substituted cycloalkyl-C(O)—, optionally substituted aryl-C(O)—, optionally substituted heteroaryl-C(O)— and optionally substituted heterocyclic-C(O)— wherein alkyl is defined in A herein; wherein substituted alkyl is defined in F herein; wherein cycloalkyl is defined in D herein; wherein substituted cycloalkyl is defined in I herein; wherein optionally substituted aryl is defined in F25 herein; wherein optionally substituted heteroaryl is defined in F27 herein; and wherein optionally substituted heterocyclic is defined in F29 herein;
  8) acylamino having the formula —C(O)NRRᵇ wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
  9) acyloxy selected from alkyl-C(O)O—, substituted alkyl-C(O)O—, cycloalkyl-C(O)O—, optionally substituted aryl-C(O)O—, optionally substituted heteraryl-C(O)O— and optionally substituted heterocyclic-C(O)O— wherein alkyl is defined in A herein; wherein substituted alkyl is defined in F herein; wherein cycloalkyl is defined in D herein; wherein optionally substituted aryl is defined in F25 herein; wherein optionally substituted heteroaryl is defined in F27 herein ; and wherein optionally substituted heterocyclic is defined in F29 herein;
  10) amino;
  11) substituted amino having the formula —N(R)₂ wherein each R is independently selected from the group consisting of:

a) hydrogen;
b) alkyl as defined in A herein;
c) substituted alkyl as defined in F herein;
d) alkenyl as defined in B herein;
e) substituted alkenyl as defined in G herein;
f) alkynyl as defined in C herein;
g) substituted alkynyl as defined in H herein;
h) optionally substituted aryl as defined in F25 herein;
i) cycloalkyl as defined in D herein;
j) substituted cycloalkyl as defined in I herein;
k) optionally substituted heteroaryl as defined in F27 herein;
l) optionally substituted heterocyclic as defined in F29 herein and wherein one of R can also be hydrogen or R and R together with the nitrogen atom to which they are joined form an optionally substituted heterocyclic as defined in F29 herein;
12) aminoacyl having the formula —NRC(O)R wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein heteroaryl is defined in F27 herein; and wherein optionally substituted heterocyclic is defined in F29 herein;
13) aminoacyloxy having the formula —NRC(O)OR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
14) oxyacylamino having the formula —OC(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
15) cyano;
16) halo selected from fluoro, chloro, bromo and iodo;
17) hydroxy;
18) carboxyl;
19) optionally substituted carboxyalkyl having the formula —C(O)O alkyl and —C(O)O substituted alkyl wherein alkyl is as defined in A and substituted alkyl is as defined in F;
20) keto;
21) thioketo;
22) thiol;
23) thioalkoxy having the formula —S-alkyl, wherein alkyl is defined in A herein;
24) substituted thioalkoxy having the formula —S-substituted alkyl, wherein substituted alkyl is defined in F herein;
25) optionally substituted aryl having 6 to 14 carbon atoms and optionally substituted with 1 to 5 substituents selected from:
a) acyloxy as defined in F9 herein;
b) hydroxy;
c) acyl as defined in F7 herein;
d) alkyl as defined in A herein;
e) alkoxy as defined in F1 herein;
f) alkenyl as defined in B herein;
g) alkynyl as defined in C herein;
h) substituted alkyl as defined in F herein;
i) substituted alkoxy as defined in F2 herein;
j) substituted alkenyl as defined in G herein;
k) substituted alkynyl as defined in H herein;
l) amino;
m) substituted amino as defined in F11 herein;
n) aminoacyl as defined in F12 herein;
o) acylamino as defined in F8 herein;
p) optionally substituted alkaryl in which the alkyl moiety has 1 to 8 carbon atoms and the aryl has 6 to 10 carbon atoms and is optionally substituted as defined in F25 herein;
q) optionally substituted aryl as defined in F25 herein;
r) optionally substituted aryloxy as defined in F26 herein;
s) azido;
t) carboxyl;
u) optionally substituted carboxylalkyl as defined in F19 herein;
v) cyano;
w) halo as defined in F16 herein;
x) nitro;
y) optionally substituted heteroaryl as defined in F27 herein;
z) optionally substituted heterocyclic as defined in F29 herein;
aa) aminoacyloxy as defined in F13 herein;
bb) oxyacylamino as defined in F14 herein;
cc) thioalkoxy as defined in F23 herein;
dd) substituted thioalkoxy as defined in F24 herein;
ee) optionally substituted thioaryloxy having the formula aryl-S— wherein aryl is optionally substituted as defined in F25 herein;
ff) optionally substituted thioheteroaryloxy having the formula heteroaryl-S— wherein heteroaryl is optionally substituted as defined in F27 herein;
gg) —SO-alkyl wherein alkyl is as defined in A herein;
hh) —SO-substituted alkyl wherein substituted alkyl is as defined in F herein;
ii) —SO-optionally substituted aryl wherein optionally substituted aryl is as defined in F25 herein;
jj) —SO— optionally substituted heteroaryl wherein optionally substituted heteroaryl is as defined in F27 herein;
kk) —SO$_2$-alkyl wherein alkyl is as defined in A herein;
ll) —SO$_2$-substituted alkyl wherein substituted alkyl is as defined in F herein;
mm) —SO$_2$-optionally substituted aryl wherein optionally substituted aryl is as defined in F25 herein;
nn) —SO$_2$-optionally substituted heteroaryl wherein optionally substituted heteroaryl is as defined in F27 herein; and
oo) trihalomethyl wherein halo is as defined in F16 herein;
26) optionally substituted aryloxy having the formula aryl-O— wherein aryl is optionally substituted aryl as defined in F25 herein;

27) optionally substituted heteroaryl having 1 to 15 ring carbon atoms and 1 to 4 ring heteroatoms selected from oxygen, nitrogen and sulfur and optionally substituted with 1 to 5 substituents selected from the same group of substituents as defined for optionally substituted aryl in F25 herein;
28) optionally substituted heteroaryloxy having the formula —O-heteroaryl wherein heteroaryl is optionally substituted heteroaryl as defined in F27 herein;
29) optionally substituted saturated or unsaturated heterocyclic from 1 to 15 ring carbon atoms and 1 to 4 ring heteroatoms selected from nitrogen, sulfur and oxygen and optionally substituted with 1 to 5 substituents selected from the same group of substituents as defined for substituted alkyl in F herein;
30) optionally substituted heterocyclooxy having the formula —O-heterocyclic wherein heterocyclic is defined as optionally substituted heterocyclic on F29 hereof;
31) hydroxyamino;
32) alkoxyamino wherein alkoxy is as defined in F1;
33) nitro;
34) —SO-alkyl wherein alkyl is as defined in A herein;
35) —SO-substituted alkyl wherein substituted alkyl is as defined in F herein;
36) —SO-optionally substituted aryl wherein aryl is optionally substituted as defined in F25 herein;
37) —SO-optionally substituted heteroaryl wherein optionally substituted heteroaryl is as defined in F27 herein;
38) —SO$_2$-alkyl wherein alkyl is as defined in A herein;
39) —SO$_2$-substituted alkyl wherein substituted alkyl is as defined in F herein;
40) —SO$_2$-optionally substituted aryl wherein optionally substituted aryl is as defined in F25 herein;
41) —SO$_2$-optionally substituted heteroaryl wherein optionally substituted heteroaryl is as defined in F27 herein;

G) substituted alkenyl having 2 to 10 carbon atoms and having of from 1 to 3 substituents selected from the group consisting of:
1) alkoxy having the formula alkyl-O— wherein alkyl is as defined in A herein;
2) substituted alkoxy of the formula substituted alkyl-O— wherein substituted alkyl is as defined in F herein;
3) cycloalkyl as defined in D herein;
4) substituted cycloalkyl as defined in I herein;
5) cycloalkoxy;
6) substituted cycloalkoxy;
7) acyl as defined in F7 herein;
8) acylamino as defined in F8 herein;
9) acyloxy as defined in F9 herein;
10) amino;
11) substituted amino as defined in F11 herein;
12) aminoacyl as defined in F12 herein;
13) aminoacyloxy as defined in F13 herein;
14) cyano;
15) halo selected from fluoro, cholo, bromo and iodo;
16) hydroxy;
17) carboxyl;
18) optionally substituted carboxyalkyl having the formula —C(O)O-alkyl and —C(O)O-substituted alkyl wherein alkyl is as defined in A and substituted alkyl is as defined in F;
19) keto;
20) thioketo;
21) thiol;
22) thioalkoxy as defined in F23 herein;
23) substituted thioalkoxy as defined in F24 herein;
24) optionally substituted aryl as defined in F25 herein;
25) optionally substituted heteroaryl as defined in F27 herein;
26) optionally substituted saturated or unsaturated heterocyclic as defined in F29 herein;
27) optionally substituted heterocyclooxy as defined in G24 herein;
28) nitro;
29) —SO-alkyl wherein alkyl is as defined in A herein;
30) —SO-substituted alkyl wherein substituted alkyl is as defined in F herein;
31) —SO-aryl wherein optionally substituted aryl is optionally substituted as defined in F25 herein;
32) —SO-optionally substituted heteroaryl wherein optionally substituted heteroaryl is as defined in F27 herein;
33) —SO$_2$-alkyl wherein alkyl is as defined in A herein;
34) —SO$_2$-substituted alkyl wherein substituted alkyl is as defined in F herein;
35) —SO$_2$-optionally substituted aryl wherein optionally substituted aryl is as defined in F25 herein; and
36) —SO$_2$-optionally substituted heteroaryl wherein optionally substituted heteroaryl is as defined in F27 herein;

H) substituted alkynyl having 2 to 10 carbon atoms having 1–2 sites of alkynyl unsaturation and having 1 to 3 substituents selected from the same group of substituents as defined for substituted alkenyl in G herein;
I) substituted cycloalkyl having 3 to 12 carbon atoms and having from 1 to 5 substituents selected from the same group of substituents as defined for substituted alkyl in F herein;
J) substituted cycloalkenyl as defined in E herein having from 1 to 5 substituents selected from the same group of substituents as defined for substituted alkyl in F herein;
K) optionally substituted aryl as defined in F25 herein;
L) optionally substituted heteroaryl as defined in F27 herein; and
M) optionally substituted heterocyclic as defined in F29 herein;

a is an integer from 2 to 6;
$R^{2'}$ is independently selected from the group consisting of:
N) hydrogen;
O) alkyl as defined in A herein;
P) substituted alkyl as defined in F herein;
Q) alkenyl of from 2 to 10 carbon atoms and 1–2 sites of alkenyl unsaturation;
R) substituted alkenyl as defined in G herein;
S) alkynyl of from 2 to 10 carbon atoms and from 1–2 sites of alkynyl unsaturation;
T) substituted alkynyl as defined in H herein;
U) cycloalkyl of from 3 to 12 carbon atoms;
V) optionally substituted aryl as defined in F25 herein;
W) optionally substituted heteroaryl as defined in F27 herein; and
X) optionally substituted heterocyclic as defined in F29 herein;
Q is S and O;

wherein R¹⁵ is independently selected from the group consisting of:
Y) hydrogen,
Z) alkyl as defined in A herein;
AA) substituted alkyl as defined in F herein;
AB) optionally substituted aryl as defined in F25 herein;
AC) optionally substituted heterocyclic as defined in F29 herein;
AD) optionally substituted heteroaryl as defined in F27 herein;
wherein R¹⁵' is independently selected from the group consisting of:
AE) hydrogen,
AF) hydroxyl,
AG) alkyl as defined in A herein;
AH) substituted alkyl as defined in F herein;
AI) optionally substituted aryl as defined in F25 herein;
AJ) optionally substituted heterocyclic as defined in F29 herein;
AK) optionally substituted heteroaryl as defined in F27 herein;
and the moiety:

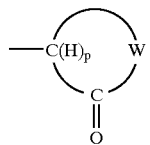

is selected from the group having the formulas:

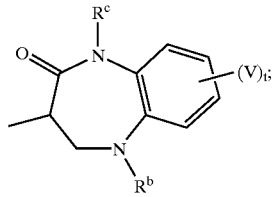

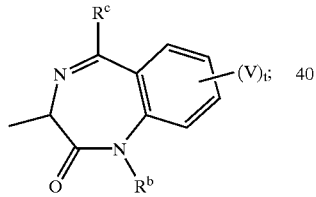

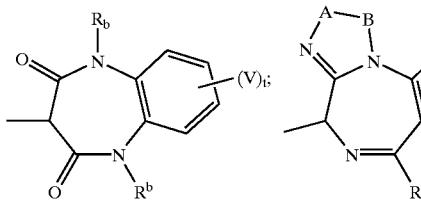

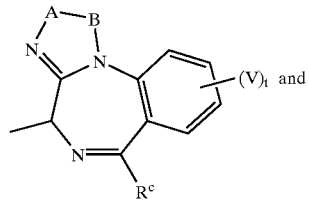

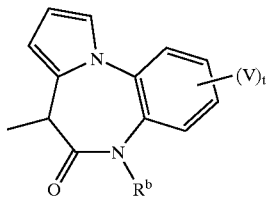

wherein A—B is selected from the group consisting of alkylene, alkenylene, substituted alkylene, substituted alkenylene, and —N═CH—; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, optionally substituted alkaryl, optionally substituted aryl, optionally substituted aryloxy, carboxyl, carboxylalkyl, cyano, halo, nitro, optionally substituted heteroaryl, thioalkoxy, substituted thioalkoxy, and trihalomethyl; R^b is selected from the group consisting of alkyl, substituted alkyl, alkenyl, substituted alkenyl, alkynyl, substituted alkynyl, acyl, optionally substituted aryl, optionally substituted heteroaryl, and optionally substituted heterocyclic; R^c is selected from the group consisting of alkyl, substituted alkyl, alkenyl, substituted alkenyl, optionally substituted aryl, optionally substituted heteroaryl, optionally substituted heterocyclic, cycloalkyl, and substituted cycloalkyl; and t is an integer from 0 to 4; or pharmaceutically salts thereof;

with the following provisos:
when R¹ is trans-cinnamyl, R² is methyl, and R¹⁵ is hydrogen, then W, together with >CH and >C═O, does not form a 2,3-dihydro-1-(3,3-dimethyl-2-oxobutyl)-5-(2-pyridyl)-1H-1,4-benzodiazepin-2-one when R¹ is trans-cinnamyl, R² is methyl, and R¹⁵ is hydrogen, then W, together with >CH and >C═O, does not form a 2,3-dihydro-1-(2-N,N-diethylaminoethyl)-5-(2-pyridyl)-1H-1,4-benzodiazepin-2-one when R¹-N(R¹⁵')C(Q) is (2,5-dimethoxyphenyl) aminocarbonyl and R² is methyl, then W, together with >CH and >C═O, does not form a 2,3-dihydro-1-methyl-5-phenyl-1H-1,4-benzodiazepin-2-one and when Q is S, R¹⁵ and R¹⁵' are hydrogen, and the moiety:

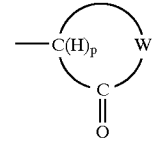

is selected from the group having the formulas:

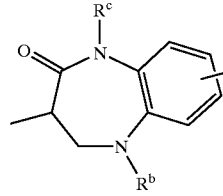

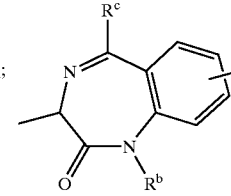

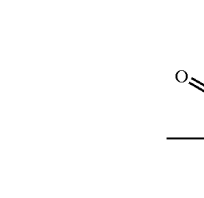

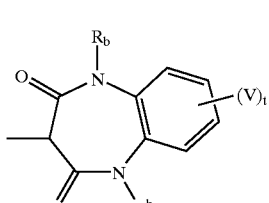

then R¹ is not phenyl.

30. The compound according to claim 29, wherein the moiety:

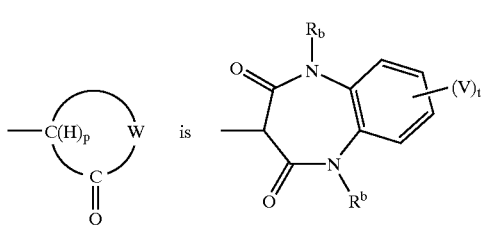

(1)

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

$R_b$ is selected from the group comprising hydrogen, alkyl, substituted alkyl, alkenyl, substituted alkenyl, aryl, heteroaryl, heterocyclic cycloalkyl, and substituted cycloalkyl;

or pharmaceutically acceptable salts thereof.

31. The compound according to claim 29, wherein the moiety:

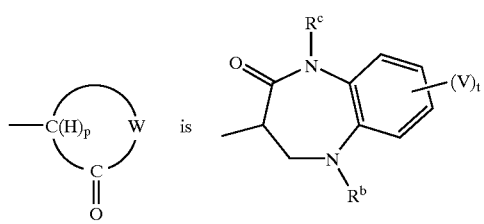

(2)

wherein $R^b$ is selected from the group consisting of alkyl, substituted alkyl as defined in F, alkenyl, substituted alkenyl as defined in G, alkynyl, acyl, optionally substituted aryl as defined in F25, optionally substituted heteroaryl as defined in F27, and optionally substituted heterocyclic as defined in F29;

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

or pharmaceutically acceptable salts thereof.

32. The compound according to claim 29, wherein the moiety:

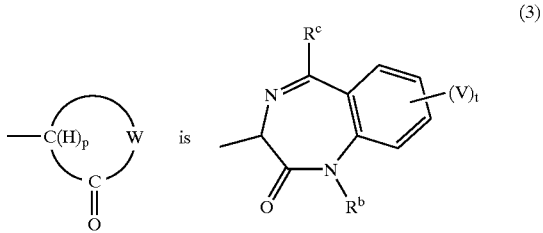

(3)

wherein $R^b$ is selected from the group consisting of alkyl, substituted alkyl as defined in F, alkenyl, substituted alkenyl as defined in G, alkynyl, acyl, optionally substituted aryl as defined in F25, optionally substituted heteroaryl as defined in F27, and optionally substituted heterocyclic as defined in F29;

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

33. The compound according to claim 29, wherein the moiety:

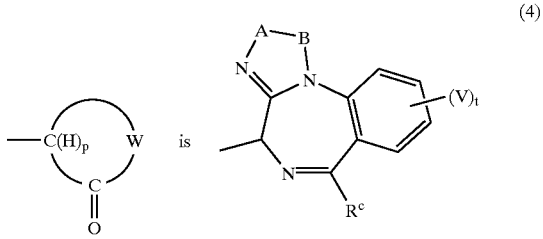

(4)

wherein A—B is selected from the group consisting of alkylene, alkenylene, substituted alkylene, substituted alkenylene and —N═CH—;

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

34. The compound according to claim 29, wherein the moiety:

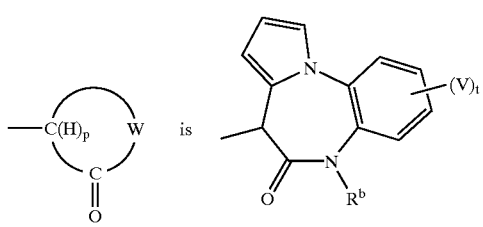

(5)

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

35. The compound according to claim 29, wherein $R^1$ is optionally substituted aryl or optionally substituted heteroaryl.

36. The compound according to claim 29, wherein $R^1$ is selected from the group consisting of:

(a) alkyl, (b) phenyl, (c) a substituted phenyl group of the formula:

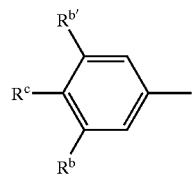

wherein $R^c$ is selected fron the group consisting of acyl, alkyl, alkoxy, alkylalkoxy, azido, cyano, subsstituted amino, halo, hydrogen, nitro, trihalomethyl, thioalkoxy, and wherein $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur, $R^b$ and $R^{b'}$ are independently selected from the group consisting of hydrogen, halo, nitro, cyano, trihalomethyl, alkoxy, and thioalkoxy with the proviso that when $R^c$ is hydrogen, the $R^b$ and $R^{b'}$ are either both hydrogen or both substituents other than hydrogen, (d) 2-naphthyl, (e) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl, (f) heteroaryl, and (g) substituted heteroaryl containing 1 to 3 substituents selected from the group consisting of alkyl, alkoxy, aryl, aryloxy, cyano, halo, nitro, heteroaryl, thioalkoxy, thioaryloxy provided that said substituents are not othro to the heteroaryl attachment to the —NH group.

37. The compound according to claim 29, wherein $R^1$ is selected from the group consisting of mono-, di-, and tri-substituted phenyl groups.

38. The compound according to claim 37, wherein $R^1$ is a monosubstituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)-phenyl, and 4-(1-ethoxy)ethylphenyl.

39. The compound according to claim 37, wherein $R^1$ is a disubstituted phenyl selected from the group consisting of 3,5-dichlorophenyl, 3,5-difluorophenyl, 3,5-di(trifluoromethyl)-phenyl, 3,4-dichlorophenyl, 3,4-difluorophenyl, 3-(trifluoromethyl)-4-chlorophenyl, 3-chloro-4-cyanophenyl, 3-chloro-4-iodophenyl, and 3,4-methylenedioxyphenyl.

40. The compound according to claim 37, wherein $R^1$ is a trisubstituted phenyl selected from the group consisting of 3,4,5-trifluorophenyl and 3,4,5-tricholorophenyl.

41. The compound according to claim 29, wherein $R^1$ is selected from the group consisting of 2-naphthyl, quinolin-3-yl, 2-methylquinolin-6-yl, benzothiazol-6-yl, 5-indolyl and phenyl.

42. The compound according to claim 29, wherein $R^1$ is selected from the group consisting of: phenyl, 1-naphthyl, 2-naphthyl, n-butyl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl)phenyl, 3,5-dimethoxyphenyl, 2,4-dichlorophenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5,6-pentafluorophenyl, 2,5-dimethylphenyl, 4-phenylphenyl, 2-fluoro-3-trifluoromethylphenyl, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyrid-2-yl, pyrid-3-yl, pyrid-4-yl, fluoropyridyls, chloropyridyls, thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetrazol-5-yl, allyl, 2-(cyclohexyl)ethyl, (CH$_3$)$_2$CH=CHCH$_2$CH$_2$CH(CH$_3$)—, C(O)CH$_2$—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl)methyl, (2-methoxyphenyl)methyl, (3-methoxyphenyl)methyl, (3-hydroxyphenyl)methyl, (4-hydroxyphenyl)methyl, (4-methoxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH$_3$OC(O)CH$_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH$_3$CH=CH—, CH$_3$CH$_2$CH=CH—, (4-chlorophenyl)C(O)CH$_2$—, (4-fluorophenyl)C(O)CH$_2$—, (4-methoxyphenyl)C(O)CH$_2$—, 4-(fluorophenyl)—NHC(O)CH$_2$—, 1-phenyl-n-butyl, (phenyl)$_2$CHNHC(O)CH$_2$CH$_2$—, (CH$_3$)$_2$NC(O)CH$_2$—, (phenyl)$_2$CHNHC(O)CH$_2$CH$_2$—, methylcarbonylmethyl, (2,4-dimethylphenyl)C(O)CH$_2$—, 4-methoxyphenyl-C(O)CH$_2$—, phenyl-C(O)CH$_2$—, CH$_3$C(O)N(phenyl)-, ethenyl, methylthiomethyl, (CH$_3$)$_3$CNHC(O)CH$_2$—, 4-fluorophenyl-C(O)CH$_2$—, diphenylmethyl, phenoxymethyl, 3,4-methylenedioxyphenyl-CH$_2$—, benzo[b]thiophen-3-yl, (CH$_3$)$_3$COC(O)NHCH$_2$—, trans-styryl, H$_2$NC(O)CH$_2$CH$_2$—, 2-trifluoromethylphenyl-C(O)CH$_2$, phenylC(O)NHCH(phenyl)CH$_2$—, mesityl, CH$_3$CH(=NHOH)CH$_2$—, 4—CH$_3$-phenyl-NHC(O)CH$_2$CH$_2$—, phenyl-C(O)CH(phenyl)CH$_2$—, (CH$_3$)$_2$CHC(O)NHCH(phenyl)-, CH$_3$CH$_2$OCH$_2$—, CH$_3$OC(O)CH(CH$_3$)(CH$_2$)$_3$—, 2,2,2-trifluoroethyl, 1-(trifluoromethyl)ethyl, 2—CH$_3$-benzofuran-3-yl, 2-(2,4-dichlorophenoxy)ethyl, SO$_2$CH$_2$—, 3-cyclohexyl-n-propyl, CF$_3$CH$_2$CH$_2$CH$_2$— and N-pyrrolidinyl.

43. The compound according to claim 29, wherein R$^2$ is selected from the group consisting of alkyl, substituted alkyl, alkenyl, cycloalkyl, aryl, heteroaryl and heterocyclic.

44. The compound according to claim 29, wherein R$^2$ is selected from the group consisting of methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol-4-yl, —CH$_2$—(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH—Boc, —(CH$_2$)$_4$NH$_2$, —CH$_2$-pyridyl, pyridyl, —CH$_2$-naphthyl, —CH$_2$—(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl, and thien-3-yl.

45. A method for inhibiting β-amyloid peptide release and/or its synthesis in a cell, which method comprises administering to such a cell an amount of a compound or a mixture of compounds effective for inhibiting the cellular release and/or synthesis of β-amyloid peptide, wherein said compounds are represented by the following formula IA:

Formula IA

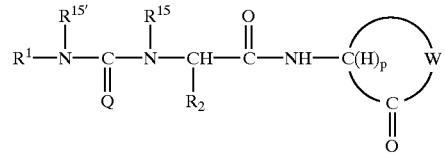

R$^1$ is selected from the group consisting of:
A) alkyl of from 1 to 20 carbon atoms;
B) alkenyl of from 2 to 10 carbon atoms and 1–2 sites of alkenyl unsaturation;
C) alkynyl of from 2 to 10 carbon atoms and from 1–2 sites of alkynyl unsaturation;
D) cycloalkyl of from 3 to 12 carbon atoms;
E) cycloalkenyl of from 4 to 8 carbon atoms;
F) substituted alkyl of from 1 to 10 carbon atoms, having from 1 to 3 substituents selected from:

1) alkoxy having the formula alkyl-O— wherein alkyl is as defined in A herein;
2) substituted alkoxy of the formula substituted alkyl-O— wherein substituted alkyl is as defined in F herein;
3) cycloalkyl as defined in D herein;
4) substituted cycloalkyl as defined in I herein;
5) cycloalkenyl as defined in E herein;
6) substituted cycloalkenyl as defined in J herein;
7) acyl selected from alkyl-C(O)—, substituted alkyl-C(O)—, cycloalkyl-C(O)—, substituted cycloalkyl-C(O)—, optionally substituted aryl-C(O)—, optionally substituted heteroaryl-C(O)— and optionally substituted heterocyclic-C(O)— wherein alkyl is defined in A herein; wherein substituted alkyl is defined in F herein; wherein cycloalkyl is defined in D herein; wherein substituted cycloalkyl is defined in I herein; wherein optionally substituted aryl is defined in F25 herein; wherein optionally substituted heteroaryl is defined in F27 herein; and wherein optionally substituted heterocyclic is defined in F29 herein;
8) acylamino having the formula —C(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
9) acyloxy selected from alkyl-C(O)O—, substituted alkyl-C(O)O—, cycloalkyl-C(O)O—, optionally substituted aryl-C(O)O—, optionally substituted heteraryl-C(O)O— and optionally substituted heterocyclic-C(O)O— wherein alkyl is defined in A herein; wherein substituted alkyl is defined in F herein; wherein cycloalkyl is defined in D herein; wherein optionally substituted aryl is defined in F25 herein; wherein optionally substituted heteroaryl is defined in F27 herein; and wherein optionally substituted heterocyclic is defined in F29 herein;
10) amino;
11) substituted amino having the formula —N(R)$_2$ wherein each R is independently selected from the group consisting of:
    a) hydrogen;
    b) alkyl as defined in A herein;
    c) substituted alkyl as defined in F herein;
    d) alkenyl as defined in B herein;
    e) substituted alkenyl as defined in G herein;
    f) alkynyl as defined in C herein;
    g) substituted alkynyl as defined in H herein;
    h) optionally substituted aryl as defined in F25 herein;
    i) cycloalkyl as defined in D herein;
    j) substituted cycloalkyl as defined in I herein;
    k) optionally substituted heteroaryl as defined in F27 herein;
    l) optionally substituted heterocyclic as defined in F29 herein and
    wherein one of R can also be hydrogen or R and R together with the nitrogen atom to which they are joined form an optionally substituted heterocyclic as defined in F29 herein;
12) aminoacyl having the formula —NRC(O)R wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein heteroaryl is defined in F27 herein; and wherein optionally substituted heterocyclic is defined in F29 herein;
13) aminoacyloxy having the formula —NRC(O)OR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
14) oxyacylamino having the formula —OC(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
15) cyano;
16) halo selected from fluoro, chloro, bromo and iodo;
17) hydroxy;
18) carboxyl;
19) optionally substituted carboxyalkyl having the formula —C(O)O alkyl and —C(O)O substituted alkyl wherein alkyl is as defined in A and substituted alkyl is as defined in F;
20) keto;
21) thioketo;
22) thiol;
23) thioalkoxy having the formula —S-alkyl, wherein alkyl is defined in A herein;
24) substituted thioalkoxy having the formula —S-substituted alkyl, wherein substituted alkyl is defined in F herein;
25) optionally substituted aryl having 6 to 14 carbon atoms and optionally substituted with 1 to 5 substituents selected from:
    a) acyloxy as defined in F9 herein;
    b) hydroxy;
    c) acyl as defined in F7 herein;
    d) alkyl as defined in A herein;
    e) alkoxy as defined in F1 herein;
    f) alkenyl as defined in B herein;
    g) alkynyl as defined in C herein;
    h) substituted alkyl as defined in F herein;
    i) substituted alkoxy as defined in F2 herein;
    j) substituted alkenyl as defined in G herein;
    k) substituted alkynyl as defined in H herein;
    l) amino;
    m) substituted amino as defined in F11 herein;
    n) aminoacyl as defined in F12 herein;
    o) acylamino as defined in F8 herein;
    p) optionally substituted alkaryl in which the alkyl moiety has 1 to 8 carbon atoms and the aryl has 6 to 10 carbon atoms and is optionally substituted as defined in F25 herein;
    q) optionally substituted aryl as defined in F25 herein;

r) optionally substituted aryloxy as defined in F26 herein;
s) azido;
t) carboxyl;
u) optionally substituted carboxylalkyl as defined in F19 herein;
v) cyano;
w) halo as defined in F16 herein;
x) nitro;
y) optionally substituted heteroaryl as defined in F27 herein;
z) optionally substituted heterocyclic as defined in F29 herein;
aa) aminoacyloxy as defined in F13 herein;
bb) oxyacylamino as defined in F14 herein;
cc) thioalkoxy as defined in F23 herein;
dd) substituted thioalkoxy as defined in F24 herein;
ee) optionally substituted thioaryloxy having the formula aryl-S— wherein aryl is optionally substituted as defined in F25 herein;
ff) optionally substituted thioheteroaryloxy having the formula heteroaryl-S— wherein heteroaryl is optionally substituted as defined in F27 herein;
gg) —SO-alkyl wherein alkyl is as defined in A herein;
hh) —SO-substituted alkyl wherein substituted alkyl is as defined in F herein;
ii) —SO-optionally substituted aryl wherein optionally substituted aryl is as defined in F25 herein;
jj) —SO— optionally substituted heteroaryl wherein optionally substituted heteroaryl is as defined in F27 herein;
kk) —SO$_2$— alkyl wherein alkyl is as defined in A herein;
ll) —SO$_2$-substituted alkyl wherein substituted alkyl is as defined in F herein;
mm) —SO$_2$-optionally substituted aryl wherein optionally substituted aryl is as defined in F25 herein;
nn) —SO$_2$-optionally substituted heteroaryl wherein optionally substituted heteroaryl is as defined in F27 herein; and
oo) trihalomethyl wherein halo is as defined in F16 herein;
26) optionally substituted aryloxy having the formula aryl-O— wherein aryl is optionally substituted aryl as defined in F25 herein;
27) optionally substituted heteroaryl having 1 to 15 ring carbon atoms and 1 to 4 ring heteroatoms selected from oxygen, nitrogen and sulfur and optionally substituted with 1 to 5 substituents selected from the same group of substituents as defined for optionally substituted aryl in F25 herein;
28) optionally substituted heteroaryloxy having the formula —O-heteroaryl wherein heteroaryl is optionally substituted heteroaryl as defined in F27 herein;
29) optionally substituted saturated or unsaturated heterocyclic from 1 to 15 ring carbon atoms and 1 to 4 ring heteroatoms selected from nitrogen, sulfur and oxygen and optionally substituted with 1 to 5 substituents selected from the same group of substituents as defined for substituted alkyl in F herein;
30) optionally substituted heterocyclooxy having the formula —O-heterocyclic wherein heterocyclic is defined as optionally substituted heterocyclic on F29 hereof;
31) hydroxyamino;
32) alkoxyamino wherein alkoxy is as defined in F1;
33) nitro;
34) —SO-alkyl wherein alkyl is as defined in A herein;
35) —SO-substituted alkyl wherein substituted alkyl is as defined in F herein;
36) —SO-optionally substituted aryl wherein aryl is optionally substituted as defined in F25 herein;
37) —SO-optionally substituted heteroaryl wherein optionally substituted heteroaryl is as defined in F27 herein;
38) —SO$_2$-alkyl wherein alkyl is as defined in A herein;
39) —SO$_2$-substituted alkyl wherein substituted alkyl is as defined in F herein;
40) —SO$_2$-optionally substituted aryl wherein optionally substituted aryl is as defined in F25 herein;
41) —SO$_2$-optionally substituted heteroaryl wherein optionally substituted heteroaryl is as defined in F27 herein;
G) substituted alkenyl having 2 to 10 carbon atoms and having of from 1 to 3 substituents selected from the group consisting of:
1) alkoxy having the formula alkyl-O— wherein alkyl is as defined in A herein;
2) substituted alkoxy of the formula substituted alkyl-O— wherein substituted alkyl is as defined in F herein;
3) cycloalkyl as defined in D herein;
4) substituted cycloalkyl as defined in I herein;
5) cycloalkoxy;
6) substituted cycloalkoxy;
7) acyl as defined in F7 herein;
8) acylamino as defined in F8 herein;
9) acyloxy as defined in F9 herein;
10) amino;
11) substituted amino as defined in F11 herein;
12) aminoacyl as defined in F12 herein;
13) aminoacyloxy as defined in F13 herein;
14) cyano;
15) halo selected from fluoro, cholo, bromo and iodo;
16) hydroxy;
17) carboxyl;
18) optionally substituted carboxyalkyl having the formula —C(O)O-alkyl and —C(O)O-substituted alkyl wherein alkyl is as defined in A and substituted alkyl is as defined in F;
19) keto;
20) thioketo;
21) thiol;
22) thioalkoxy as defined in F23 herein;
23) substituted thioalkoxy as defined in F24 herein;
24) optionally substituted aryl as defined in F25 herein;
25) optionally substituted heteroaryl as defined in F27 herein;
26) optionally substituted saturated or unsaturated heterocyclic as defined in F29 herein;
27) optionally substituted heterocyclooxy as defined in G24 herein;
28) nitro;
29) —SO-alkyl wherein alkyl is as defined in A herein;
30) —SO-substituted alkyl wherein substituted alkyl is as defined in F herein;
31) —SO-aryl wherein optionally substituted aryl is optionally substituted as defined in F25 herein;
32) —SO-optionally substituted heteroaryl wherein optionally substituted heteroaryl is as defined in F27 herein;

33) —SO₂-alkyl wherein alkyl is as defined in A herein;
34) —SO₂-substituted alkyl wherein substituted alkyl is as defined in F herein;
35) —SO₂-optionally substituted aryl wherein optionally substituted aryl is as defined in F25 herein; and
36) —SO₂-optionally substituted heteroaryl wherein optionally substituted heteroaryl is as defined in F27 herein;
H) substituted alkynyl having 2 to 10 carbon atoms having 1–2 sites of alkynyl unsaturation and having 1 to 3 substituents selected from the same group of substituents as defined for substituted alkenyl in G herein;
I) substituted cycloalkyl having 3 to 12 carbon atoms and having from 1 to 5 substituents selected from the same group of substituents as defined for substituted alkyl in F herein;
J) substituted cycloalkenyl as defined in E herein having from 1 to 5 substituents selected from the same group of substituents as defined for substituted alkyl in F herein;
K) optionally substituted aryl as defined in F25 herein;
L) optionally substituted heteroaryl as defined in F27 herein; and
M) optionally substituted heterocyclic as defined in F29 herein;
a is an integer from 2 to 6;
$R^2$ is independently selected from the group consisting of:
N) hydrogen;
O) alkyl as defined in A herein;
P) substituted alkyl as defined in F herein;
Q) alkenyl of from 2 to 10 carbon atoms and 1–2 sites of alkenyl unsaturation;
R) substituted alkenyl as defined in G herein;
S) alkynyl of from 2 to 10 carbon atoms and from 1–2 sites of alkynyl unsaturation;
T) substituted alkynyl as defined in H herein;
U) cycloalkyl of from 3 to 12 carbon atoms;
V) optionally substituted aryl as defined in F25 herein;
W) optionally substituted heteroaryl as defined in F27 herein; and
X) optionally substituted heterocyclic as defined in F29 herein;
Q is S and O;
wherein $R^{15}$ is independently selected from the group consisting of:
Y) hydrogen,
Z) alkyl as defined in A herein;
AA) substituted alkyl as defined in F herein;
AB) optionally substituted aryl as defined in F25 herein;
AC) optionally substituted heterocyclic as defined in F29 herein;
AD) optionally substituted heteroaryl as defined in F27 herein;
wherein $R^{15}$ is independently selected from the group consisting of:
AE) hydrogen,
AF) hydroxyl,
AG) alkyl as defined in A herein;
AH) substituted alkyl as defined in F herein;
AI) optionally substituted aryl as defined in F25 herein;
AJ) optionally substituted heterocyclic as defined in F29 herein;

AK) optionally substituted heteroaryl as defined in F27 herein;
and the moiety:

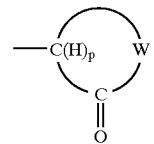

is selected from the group having the formulas:

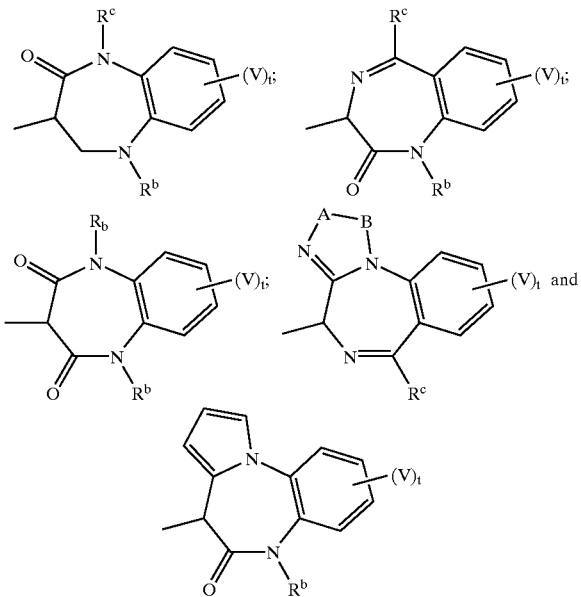

wherein A—B is selected from the group consisting of alkylene, alkenylene, substituted alkylene, substituted alkenylene, and —N═CH—; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, optionally substituted alkaryl, optionally substituted aryl, optionally substituted aryloxy, carboxyl, carboxylalkyl, cyano, halo, nitro, optionally substituted heteroaryl, thioalkoxy, substituted thioalkoxy, and trihalomethyl; $R^b$ is selected from the group consisting of alkyl, substituted alkyl, alkenyl, substituted alkenyl, alkynyl, substituted alkynyl, acyl, optionally substituted aryl, optionally substituted heteroaryl, and optionally substituted heterocyclic; $R^c$ is selected from the group consisting of alkyl, substituted alkyl, alkenyl, substituted alkenyl, optionally substituted aryl, optionally substituted heteroaryl, optionally substituted heterocyclic, cycloalkyl, and substituted cycloalkyl; and t is an integer from 0 to 4;
or pharmaceutically salts thereof;
with the following provisos:
when $R^1$ is trans-cinnamyl, $R^2$ is methyl, and $R^{15}$ is hydrogen, then W, together with >CH and >C═O, does not form a 2,3-dihydro-1-(3,3-dimethyl-2-oxobutyl)-5-(2-pyridyl)-1H-1,4-benzodiazepin-2-one
when $R^1$ is trans-cinnamyl, $R^2$ is methyl, and $R^{15}$ is hydrogen, then W, together with >CH and >C═O, does not form a 2,3dihydro-1-(2-N,N-diethylaminoethyl)-5-(2-pyridyl)-1H-1,4-benzodiazepin-2-one and when $R^1$—N($R^{15'}$)C(Q) is (2,5-dimethoxyphenyl) aminocarbonyl and $R^2$ is methyl, then W, together with >CH and >C=O, does not form a 2,3-dihydro-1-methyl-5-phenyl-1H-1,4-benzodiazepin-2-one.

46. A method for inhibiting β-amyloid peptide release and/or its synthesis in a mammalian subject thereby inhibiting onset of diseases mediated by β-amyloid peptide which method comprises administering to said patient a pharmaceutical composition comprising a pharmaceutically inert carrier and an effective amount of a compound or a mixture of compounds effective for inhibiting the release and/or synthesis of β-amyloid peptide, wherein said compounds are represented by the following formula IA:

Formula IA

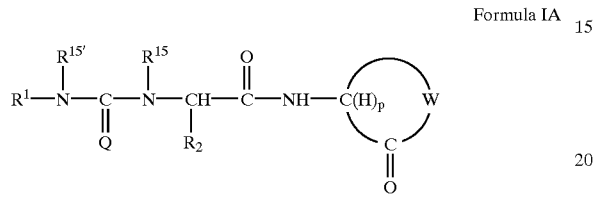

$R^1$ is selected from the group consisting of:
A) alkyl of from 1 to 20 carbon atoms;
B) alkenyl of from 2 to 10 carbon atoms and 1–2 sites of alkenyl unsaturation;
C) alkynyl of from 2 to 10 carbon atoms and from 1–2 sites of alkynyl unsaturation;
D) cycloalkyl of from 3 to 12 carbon atoms;
E) cycloalkenyl of from 4 to 8 carbon atoms;
F) substituted alkyl of from 1 to 10 carbon atoms, having from 1 to 3 substituents selected from:
  1) alkoxy having the formula alkyl-O— wherein alkyl is as defined in A herein;
  2) substituted alkoxy of the formula substituted alkyl-O— wherein substituted alkyl is as defined in F herein;
  3) cycloalkyl as defined in D herein;
  4) substituted cycloalkyl as defined in I herein;
  5) cycloalkenyl as defined in E herein;
  6) substituted cycloalkenyl as defined in J herein;
  7) acyl selected from alkyl-C(O)—, substituted alkyl-C(O)—, cycloalkyl-C(O)—, substituted cycloalkyl-C(O)—, optionally substituted aryl-C(O)—, optionally substituted heteroaryl-C(O)— and optionally substituted heterocyclic-C(O)— wherein alkyl is defined in A herein; wherein substituted alkyl is defined in F herein; wherein cycloalkyl is defined in D herein; wherein substituted cycloalkyl is defined in I herein; wherein optionally substituted aryl is defined in F25 herein; wherein optionally substituted heteroaryl is defined in F27 herein; and wherein optionally substituted heterocyclic is defined in F29 herein;
  8) acylamino having the formula —C(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
  9) acyloxy selected from alkyl-C(O)O—, substituted alkyl-C(O)O—, cycloalkyl-C(O)O—, optionally substituted aryl-C(O)O—, optionally substituted heteraryl-C(O)O— and optionally substituted heterocyclic-C(O)O— wherein alkyl is defined in A herein; wherein substituted alkyl is defined in F herein; wherein cycloalkyl is defined in D herein; wherein optionally substituted aryl is defined in F25 herein; wherein optionally substituted heteroaryl is defined in F27 herein; and wherein optionally substituted heterocyclic is defined in F29 herein;
  10) amino;
  11) substituted amino having the formula —N(R)$_2$ wherein each R is independently selected from the group consisting of:
    a) hydrogen;
    b) alkyl as defined in A herein;
    c) substituted alkyl as defined in F herein;
    d) alkenyl as defined in B herein;
    e) substituted alkenyl as defined in G herein;
    f) alkynyl as defined in C herein;
    g) substituted alkynyl as defined in H herein;
    h) optionally substituted aryl as defined in F25 herein;
    i) cycloalkyl as defined in D herein;
    j) substituted cycloalkyl as defined in I herein;
    k) optionally substituted heteroaryl as defined in F27 herein;
    l) optionally substituted heterocyclic as defined in F29 herein and
    wherein one of R can also be hydrogen or R and R together with the nitrogen atom to which they are joined form an optionally substituted heterocyclic as defined in F29 herein;
  12) aminoacyl having the formula —NRC(O)R wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein heteroaryl is defined in F27 herein; and wherein optionally substituted heterocyclic is defined in F29 herein;
  13) aminoacyloxy having the formula —NRC(O)OR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
  14) oxyacylamino having the formula —OC(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
  15) cyano;
  16) halo selected from fluoro, chloro, bromo and iodo;
  17) hydroxy;
  18) carboxyl;
  19) optionally substituted carboxyalkyl having the formula —C(O)O alkyl and —C(O)O substituted alkyl wherein alkyl is as defined in A and substituted alkyl is as defined in F;
20) keto;
21) thioketo;
22) thiol;
23) thioalkoxy having the formula —S-alkyl, wherein alkyl is defined in A herein;
24) substituted thioalkoxy having the formula —S-substituted alkyl, wherein substituted alkyl is defined in F herein;
25) optionally substituted aryl having 6 to 14 carbon atoms and optionally substituted with 1 to 5 substituents selected from:
  a) acyloxy as defined in F9 herein;
  b) hydroxy;
  c) acyl as defined in F7 herein;
  d) alkyl as defined in A herein;
  e) alkoxy as defined in F1 herein;
  f) alkenyl as defined in B herein;
  g) alkynyl as defined in C herein;
  h) substituted alkyl as defined in F herein;
  i) substituted alkoxy as defined in F2 herein;
  j) substituted alkenyl as defined in G herein;
  k) substituted alkynyl as defined in H herein;
  l) amino;
  m) substituted amino as defined in F11 herein;
  n) aminoacyl as defined in F12 herein;
  o) acylamino as defined in F8 herein;
  p) optionally substituted alkaryl in which the alkyl moiety has 1 to 8 carbon atoms and the aryl has 6 to 10 carbon atoms and is optionally substituted as defined in F25 herein;
  q) optionally substituted aryl as defined in F25 herein;
  r) optionally substituted aryloxy as defined in F26 herein;
  s) azido;
  t) carboxyl;
  u) optionally substituted carboxylalkyl as defined in F19 herein;
  v) cyano;
  w) halo as defined in F16 herein;
  x) nitro;
  y) optionally substituted heteroaryl as defined in F27 herein;
  z) optionally substituted heterocyclic as defined in F29 herein;
  aa) aminoacyloxy as defined in F13 herein;
  bb) oxyacylamino as defined in F14 herein;
  cc) thioalkoxy as defined in F23 herein;
  dd) substituted thioalkoxy as defined in F24 herein;
  ee) optionally substituted thioaryloxy having the formula aryl-S— wherein aryl is optionally substituted as defined in F25 herein;
  ff) optionally substituted thioheteroaryloxy having the formula heteroaryl-S— wherein heteroaryl is optionally substituted as defined in F27 herein;
  gg) —SO-alkyl wherein alkyl is as defined in A herein;
  hh) —SO-substituted alkyl wherein substituted alkyl is as defined in F herein;
  ii) —SO-optionally substituted aryl wherein optionally substituted aryl is as defined in F25 herein;
  jj) —SO— optionally substituted heteroaryl wherein optionally substituted heteroaryl is as defined in F27 herein;
  kk) —SO$_2$— alkyl wherein alkyl is as defined in A herein;
  ll) —SO$_2$— substituted alkyl wherein substituted alkyl is as defined in F herein;
  mm) —SO$_2$-optionally substituted aryl wherein optionally substituted aryl is as defined in F25 herein;
  nn) —SO$_2$-optionally substituted heteroaryl wherein optionally substituted heteroaryl is as defined in F27 herein; and
  oo) trihalomethyl wherein halo is as defined in F16 herein;
26) optionally substituted aryloxy having the formula aryl-O— wherein aryl is optionally substituted aryl as defined in F25 herein;
27) optionally substituted heteroaryl having 1 to 15 ring carbon atoms and 1 to 4 ring heteroatoms selected from oxygen, nitrogen and sulfur and optionally substituted with 1 to 5 substituents selected from the same group of substituents as defined for optionally substituted aryl in F25 herein;
28) optionally substituted heteroaryloxy having the formula —O-heteroaryl wherein heteroaryl is optionally substituted heteroaryl as defined in F27 herein;
29) optionally substituted saturated or unsaturated heterocyclic from 1 to 15 ring carbon atoms and 1 to 4 ring heteroatoms selected from nitrogen, sulfur and oxygen and optionally substituted with 1 to 5 substituents selected from the same group of substituents as defined for substituted alkyl in F herein;
30) optionally substituted heterocyclooxy having the formula —O-heterocyclic wherein heterocyclic is defined as optionally substituted heterocyclic on F29 hereof;
31) hydroxyamino;
32) alkoxyamino wherein alkoxy is as defined in F1;
33) nitro;
34) —SO-alkyl wherein alkyl is as defined in A herein;
35) —SO-substituted alkyl wherein substituted alkyl is as defined in F herein;
36) —SO-optionally substituted aryl wherein aryl is optionally substituted as defined in F25 herein;
37) —SO-optionally substituted heteroaryl wherein optionally substituted heteroaryl is as defined in F27 herein;
38) —SO$_2$-alkyl wherein alkyl is as defined in A herein;
39) —SO$_2$-substituted alkyl wherein substituted alkyl is as defined in F herein;
40) —SO$_2$-optionally substituted aryl wherein optionally substituted aryl is as defined in F25 herein;
41) —SO$_2$-optionally substituted heteroaryl wherein optionally substituted heteroaryl is as defined in F27 herein;
G) substituted alkenyl having 2 to 10 carbon atoms and having of from 1 to 3 substituents selected from the group consisting of:
  1) alkoxy having the formula alkyl-O— wherein alkyl is asdefined in A herein;
  2) substituted alkoxy of the formula substituted alkyl-O— wherein substituted alkyl is as defined in F herein;
  3) cycloalkyl as defined in D herein;
  4) substituted cycloalkyl as defined in I herein;
  5) cycloalkoxy;
  6) substituted cycloalkoxy;
  7) acyl as defined in F7 herein;
  8) acylamino as defined in F8 herein;
  9) acyloxy as defined in F9 herein;

10) amino;
11) substituted amino as defined in F11 herein;
12) aminoacyl as defined in F12 herein;
13) aminoacycloxy as defined in F13 herein;
14) cyano;
15) halo selected from fluoro, cholo, bromo and iodo;
16) hydroxy;
17) carboxyl;
18) optionally substituted carboxyalkyl having the formula —C(O)O-alkyl and —C(O)O-substituted alkyl wherein alkyl is as defined in A and substituted alkyl is as defined in F;
19) keto;
20) thioketo;
21) thiol;
22) thioalkoxy as defined in F23 herein;
23) substituted thioalkoxy as defined in F24 herein;
24) optionally substituted aryl as defined in F25 herein;
25) optionally substituted heteroaryl as defined in F27 herein;
26) optionally substituted saturated or unsaturated heterocyclic as defined in F29 herein;
27) optionally substituted heterocyclooxy as defined in G24 herein;
28) nitro;
29) —SO-alkyl wherein alkyl is as defined in A herein;
30) —SO-substituted alkyl wherein substituted alkyl is as defined in F herein;
31) —SO-aryl wherein optionally substituted aryl is optionally substituted as defined in F25 herein;
32) —SO-optionally substituted heteroaryl wherein optionally substituted heteroaryl is as defined in F27 herein;
33) —SO$_2$-alkyl wherein alkyl is as defined in A herein; —SO$_2$-substituted alkyl wherein substituted alkyl is as defined in F herein;
35) —SO$_2$-optionally substituted aryl wherein optionally substituted aryl is as defined in F25 herein; and
36) —SO$_2$-optionally substituted heteroaryl wherein optionally substituted heteroaryl is as defined in F27 herein;

H) substituted alkynyl having 2 to 10 carbon atoms having 1–2 sites of alkynyl unsaturation and having 1 to 3 substituents selected from the same group of substituents as defined for substituted alkenyl in G herein;

I) substituted cycloalkyl having 3 to 12 carbon atoms and having from 1 to 5 substituents selected from the same group of substituents as defined for substituted alkyl in F herein;

J) substituted cycloalkenyl as defined in E herein having from 1 to 5 substituents selected from the same group of substituents as defined for substituted alkyl in F herein;

K) optionally substituted aryl as defined in F25 herein;
L) optionally substituted heteroaryl as defined in F27 herein; and
M) optionally substituted heterocyclic as defined in F29 herein;

a is an integer from 2 to 6;
R$^{2'}$ is independently selected from the group consisting of:
N) hydrogen;
O) alkyl as defined in A herein;
P) substituted alkyl as defined in F herein;
Q) alkenyl of from 2 to 10 carbon atoms and 1–2 sites of alkenyl unsaturation;

R) substituted alkenyl as defined in G herein;
S) alkynyl of from 2 to 10 carbon atoms and from 1–2 sites of alkynyl unsaturation;
T) substituted alkynyl as defined in H herein;
U) cycloalkyl of from 3 to 12 carbon atoms;
V) optionally substituted aryl as defined in F25 herein;
W) optionally substituted heteroaryl as defined in F27 herein; and
X) optionally substituted heterocyclic as defined in F29 herein;

Q is S and O;
wherein R$^{15}$ is independently selected from the group consisting of:
Y) hydrogen,
Z) alkyl as defined in A herein;
AA) substituted alkyl as defined in F herein;
AB) optionally substituted aryl as defined in F25 herein;
AC) optionally substituted heterocyclic as defined in F29 herein;
AD) optionally substituted heteroaryl as defined in F27 herein; wherein R$^{15'}$ is independently selected from the group consisting of:
AE) hydrogen;
AF) hydroxyl;
AG) alkyl as defined in A herein;
AH) substituted alkyl as defined in F herein;
AI) optionally substituted aryl as defined in F25 herein;
AJ) optionally substituted heterocyclic as defined in F29 herein;
AK) optionally substituted heteroaryl as defined in F27 herein;

and the moiety:

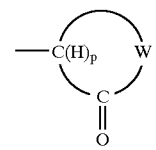

is selected from the group having the formulas:

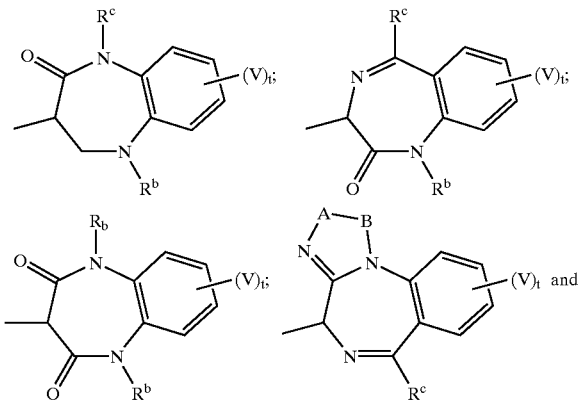

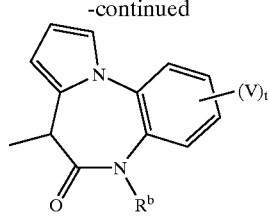

wherein A—B is selected from the group consisting of alkylene, alkenylene, substituted alkylene, substituted alkenylene, and —N═CH—; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, optionally substituted alkaryl, optionally substituted aryl, optionally substituted aryloxy, carboxyl, carboxylalkyl, cyano, halo, nitro, optionally substituted heteroaryl, thioalkoxy, substituted thioalkoxy, and trihalomethyl; $R^b$ is selected from the group consisting of alkyl, substituted alkyl, alkenyl, substituted alkenyl, alkynyl, substituted alkynyl, acyl, optionally substituted aryl, optionally substituted heteroaryl, and optionally substituted heterocyclic; $R^c$ is selected from the group consisting of alkyl, substituted alkyl, alkenyl, substituted alkenyl, optionally substituted aryl, optionally substituted heteroaryl, optionally substituted heterocyclic, cycloalkyl, and substituted cycloalkyl; and t is an integer from 0 to 4;

or pharmaceutically salts thereof;

with the following provisos:

when $R^1$ is trans-cinnamyl, $R^2$ is methyl, and $R^{15}$ is hydrogen, then W, together with >CH and >C═O, does not form a 2,3-dihydro-1-(3,3-dimethyl-2-oxobutyl)-5-(2-pyridyl)-1H-1,4-benzodiazepin-2-one when $R^1$ is trans-cinnamyl, $R^2$ is methyl, and $R^{15}$ is hydrogen, then W, together with >CH and >C═O, does not form a 2,3dihydro-1-(2-N,N-diethylaminoethyl)-5-(2-pyridyl)-1H-1,4-benzodiazepin-2-one and when $R^1$—$N(R^{15'})C(Q)$ is (2,5-dimethoxyphenyl) aminocarbonyl and $R^2$ is methyl, then W, together with >CH and >C═O, does not form a 2,3-dihydro-1-methyl-5-phenyl-1H-1,4-benzodiazepin-2-one.

47. A method for treating a human patient with AD in order to inhibit further deterioration in the condition of that patient, which method comprises administering to said patient a pharmaceutical composition comprising a pharmaceutically inert carrier and a compound or a mixture of compounds in an amount effective for inhibiting further deterioration in the condition of said patient, wherein said compounds are represented by the following formula IA:

Formula IA

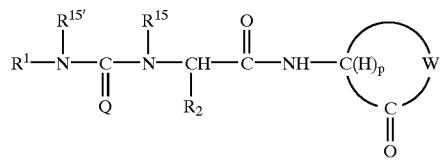

$R^1$ is selected from the group consisting of:
A) alkyl of from 1 to 20 carbon atoms;
B) alkenyl of from 2 to 10 carbon atoms and 1–2 sites of alkenyl unsaturation;
C) alkynyl of from 2 to 10 carbon atoms and from 1–2 sites of alkynyl unsaturation;
D) cycloalkyl of from 3 to 12 carbon atoms;
E) cycloalkenyl of from 4 to 8 carbon atoms;
F) substituted alkyl of from 1 to 10 carbon atoms, having from 1 to 3 substituents selected from:
  1) alkoxy having the formula alkyl-O— wherein alkyl is as defined in A herein;
  2) substituted alkoxy of the formula substituted alkyl-O— wherein substituted alkyl is as defined in F herein;
  3) cycloalkyl as defined in D herein;
  4) substituted cycloalkyl as defined in I herein;
  5) cycloalkenyl as defined in E herein;
  6) substituted cycloalkenyl as defined in J herein;
  7) acyl selected from alkyl-C(O)—, substituted alkyl-C(O)—, cycloalkyl-C(O)—, substituted cycloalkyl-C(O)—, optionally substituted aryl-C(O)—, optionally substituted heteroaryl-C(O)— and optionally substituted heterocyclic-C(O)— wherein alkyl is defined in A herein; wherein substituted alkyl is defined in F herein; wherein cycloalkyl is defined in D herein; wherein substituted cycloalkyl is defined in I herein; wherein optionally substituted aryl is defined in F25 herein; wherein optionally substituted heteroaryl is defined in F27 herein; and wherein optionally substituted heterocyclic is defined in F29 herein;
  8) acylamino having the formula —C(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
  9) acyloxy selected from alkyl-C(O)O—, substituted alkyl-C(O)—, cycloalkyl-C(O)O—, optionally substituted aryl-C(O)O—, optionally substituted heteraryl-C(O)O— and optionally substituted heterocyclic-C(O)O— wherein alkyl is defined in A herein; wherein substituted alkyl is defined in F herein; wherein cycloalkyl is defined in D herein; wherein optionally substituted aryl is defined in F25 herein; wherein optionally substituted heteroaryl is defined in F27 herein; and wherein optionally substituted heterocyclic is defined in F29 herein;
  10) amino;
  11) substituted amino having the formula —$N(R)_2$ wherein each R is independently selected from the group consisting of:
    a) hydrogen;
    b) alkyl as defined in A herein;
    c) substituted alkyl as defined in F herein;
    d) alkenyl as defined in B herein;
    e) substituted alkenyl as defined in G herein;
    f) alkynyl as defined in C herein;
    g) substituted alkynyl as defined in H herein;
    h) optionally substituted aryl as defined in F25 herein;
    i) cycloalkyl as defined in D herein;
    j) substituted cycloalkyl as defined in I herein;
    k) optionally substituted heteroaryl as defined in F27 herein;
    l) optionally substituted heterocyclic as defined in F29 herein and wherein one of R can also be hydrogen or R and R together with the nitrogen atom to which they are joined form an optionally substituted heterocyclic as defined in F29 herein;
12) aminoacyl having the formula —NRC(O)R wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein heteroaryl is defined in F27 herein; and wherein optionally substituted heterocyclic is defined in F29 herein;
13) aminoacyloxy having the formula —NRC(O)OR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
14) oxyacylamino having the formula —OC(O)NRR wherein each R is independently hydrogen, alkyl, substituted alkyl, optionally substituted aryl, optionally substituted heteroaryl, or optionally substituted heterocyclic wherein alkyl is defined in A herein; wherein substituted alkyl is defined in F herein; wherein optionally substituted aryl is defined in F25 herein; wherein optionally substituted heteroaryl is defined in F27 herein; and wherein optionally substituted heterocyclic is defined in F29 herein;
15) cyano;
16) halo selected from fluoro, chloro, bromo and iodo;
17) hydroxy;
18) carboxyl;
19) optionally substituted carboxyalkyl having the formula C(O)O alkyl and —C(O)O substituted alkyl wherein alkyl is as defined in A and substituted alkyl is as defined in F;
20) keto;
21) thioketo;
22) thiol;
23) thioalkoxy having the formula —S-alkyl, wherein alkyl is defined in A herein;
24) substituted thioalkoxy having the formula —S-substituted alkyl, wherein substituted alkyl is defined in F herein;
25) optionally substituted aryl having 6 to 14 carbon atoms and optionally substituted with 1 to 5 substituents selected from:
 a) acyloxy as defined in F9 herein;
 b) hydroxy;
 c) acyl as defined in F7 herein;
 d) alkyl as defined in A herein;
 e) alkoxy as defined in F1 herein;
 f) alkenyl as defined in B herein;
 g) alkynyl as defined in C herein;
 h) substituted alkyl as defined in F herein;
 i) substituted alkoxy as defined in F2 herein;
 j) substituted alkenyl as defined in G herein;
 k) substituted alkynyl as defined in H herein;
 l) amino;
 m) substituted amino as defined in F11 herein;
 n) aminoacyl as defined in F12 herein;
 o) acylamino as defined in F8 herein;
 p) optionally substituted alkaryl in which the alkyl moiety has 1 to 8 carbon atoms and the aryl has 6 to 10 carbon atoms and is optionally substituted as defined in F25 herein;
 q) optionally substituted aryl as defined in F25 herein;
 r) optionally substituted aryloxy as defined in F26 herein;
 s) azido;
 t) carboxyl;
 u) optionally substituted carboxylalkyl as defined in F19 herein;
 v) cyano;
 w) halo as defined in F16 herein;
 x) nitro;
 y) optionally substituted heteroaryl as defined in F27 herein;
 z) optionally substituted heterocyclic as defined in F29 herein;
 aa) aminoacyloxy as defined in F13 herein;
 bb) oxyacylamino as defined in F14 herein;
 cc) thioalkoxy as defined in F23 herein;
 dd) substituted thioalkoxy as defined in F24 herein;
 ee) optionally substituted thioaryloxy having the formula aryl-S— wherein aryl is optionally substituted as defined in F25 herein;
 ff) optionally substituted thioheteroaryloxy having the formula heteroaryl-S— wherein heteroaryl is optionally substituted as defined in F27 herein;
 gg) —SO-alkyl wherein alkyl is as defined in A herein;
 hh) —SO-substituted alkyl wherein substituted alkyl is as defined in F herein;
 ii) —SO-optionally substituted aryl wherein optionally substituted aryl is as defined in F25 herein;
 jj) —SO— optionally substituted heteroaryl wherein optionally substituted heteroaryl is as defined in F27 herein;
 kk) —$SO_2$— alkyl wherein alkyl is as defined in A herein;
 ll) —$SO_2$— substituted alkyl wherein substituted alkyl is as defined in F herein;
 mm) —$SO_2$-optionally substituted aryl wherein optionally substituted aryl is as defined in F25 herein;
 nn) —$SO_2$-optionally substituted heteroaryl wherein optionally substituted heteroaryl is as defined in F27 herein; and
 oo) trihalomethyl wherein halo is as defined in F16 herein;
26) optionally substituted aryloxy having the formula aryl-O— wherein aryl is optionally substituted aryl as defined in F25 herein;
27) optionally substituted heteroaryl having 1 to 15 ring carbon atoms and 1 to 4 ring heteroatoms selected from oxygen, nitrogen and sulfur and optionally substituted with 1 to 5 substituents selected from the same group of substituents as defined for optionally substituted aryl in F25 herein;
28) optionally substituted heteroaryloxy having the formula —O-heteroaryl wherein heteroaryl is optionally substituted heteroaryl as defined in F27 herein;
29) optionally substituted saturated or unsaturated heterocyclic from 1 to 15 ring carbon atoms and 1 to 4 ring heteroatoms selected from nitrogen, sulfur and oxygen and optionally substituted with 1 to 5 substituents selected from the same group of substituents as defined for substituted alkyl in F herein;

30) optionally substituted heterocyclooxy having the formula —O-heterocyclic wherein heterocyclic is defined as optionally substituted heterocyclic on F29 hereof;
31) hydroxyamino;
32) alkoxyamino wherein alkoxy is as defined in F1;
33) nitro;
34) —SO-alkyl wherein alkyl is as defined in A herein;
35) —SO-substituted alkyl wherein substituted alkyl is as defined in F herein;
36) —SO-optionally substituted aryl wherein aryl is optionally substituted as defined in F25 herein;
37) —SO-optionally substituted heteroaryl wherein optionally substituted heteroaryl is as defined in F27 herein;
38) —$SO_2$-alkyl wherein alkyl is as defined in A herein;
39) —$SO_2$-substituted alkyl wherein substituted alkyl is as defined in F herein;
40) —$SO_2$-optionally substituted aryl wherein optionally substituted aryl is as defined in F25 herein;
41) —$SO_2$-optionally substituted heteroaryl wherein optionally substituted heteroaryl is as defined in F27 herein;

G) substituted alkenyl having 2 to 10 carbon atoms and having of from 1 to 3 substituents selected from the group consisting of:
1) alkoxy having the formula alkyl-O— wherein alkyl is as defined in A herein;
2) substituted alkoxy of the formula substituted alkyl-O— wherein substituted alkyl is as defined in F herein;
3) cycloalkyl as defined in D herein;
4) substituted cycloalkyl as defined in I herein;
5) cycloalkoxy;
6) substituted cycloalkoxy;
7) acyl as defined in F7 herein;
8) acylamino as defined in F8 herein;
9) acyloxy as defined in F9 herein;
10) amino;
11) substituted amino as defined in F11 herein;
12) aminoacyl as defined in F12 herein;
13) aminoacyloxy as defined in F13 herein;
14) cyano;
15) halo selected from fluoro, cholo, bromo and iodo;
16) hydroxy;
17) carboxyl;
18) optionally substituted carboxyalkyl having the formula —C(O)O-alkyl and —C(O)O-substituted alkyl wherein alkyl is as defined in A and substituted alkyl is as defined in F;
19) keto;
20) thioketo;
21) thiol;
22) thioalkoxy as defined in F23 herein;
23) substituted thioalkoxy as defined in F24 herein;
24) optionally substituted aryl as defined in F25 herein;
25) optionally substituted heteroaryl as defined in F27 herein;
26) optionally substituted saturated or unsaturated heterocyclic as defined in F29 herein;
27) optionally substituted heterocyclooxy as defined in G24 herein;
28) nitro;
29) —SO-alkyl wherein alkyl is as defined in A herein;
30) —SO-substituted alkyl wherein substituted alkyl is as defined in F herein;
31) —SO-aryl wherein optionally substituted aryl is optionally substituted as defined in F25 herein;
32) —SO-optionally substituted heteroaryl wherein optionally substituted heteroaryl is as defined in F27 herein;
33) —$SO_2$-alkyl wherein alkyl is as defined in A herein;
34) —$SO_2$-substituted alkyl wherein substituted alkyl is as defined in F herein;
35) —$SO_2$-optionally substituted aryl wherein optionally substituted aryl is as defined in F25 herein; and
36) —$SO_2$-optionally substituted heteroaryl wherein optionally substituted heteroaryl is as defined in F27 herein;

H) substituted alkynyl having 2 to 10 carbon atoms having 1–2 sites of alkynyl unsaturation and having 1 to 3 substituents selected from the same group of substituents as defined for substituted alkenyl in G herein;

I) substituted cycloalkyl having 3 to 12 carbon atoms and having from 1 to 5 substituents selected from the same group of substituents as defined for substituted alkyl in F herein;

J) substituted cycloalkenyl as defined in E herein having from 1 to 5 substituents selected from the same group of substituents as defined for substituted alkyl in F herein;

K) optionally substituted aryl as defined in F25 herein;

L) optionally substituted heteroaryl as defined in F27 herein; and

M) optionally substituted heterocyclic as defined in F29 herein;

a is an integer from 2 to 6;

$R^2$ is independently selected from the group consisting of:
N) hydrogen;
O) alkyl as defined in A herein;
P) substituted alkyl as defined in F herein;
Q) alkenyl of from 2 to 10 carbon atoms and 1–2 sites of alkenyl unsaturation;
R) substituted alkenyl as defined in G herein;
S) alkynyl of from 2 to 10 carbon atoms and from 1–2 sites of alkynyl unsaturation;
T) substituted alkynyl as defined in H herein;
U) cycloalkyl of from 3 to 12 carbon atoms;
V) optionally substituted aryl as defined in F25 herein;
W) optionally substituted heteroaryl as defined in F27 herein; and
X) optionally substituted heterocyclic as defined in F29 herein;

Q is S and O;

wherein $R^{15}$ is independently selected from the group consisting of:
Y) hydrogen;
Z) alkyl as defined in A herein;
AA) substituted alkyl as defined in F herein;
AB) optionally substituted aryl as defined in F25 herein;
AC) optionally substituted heterocyclic as defined in F29 herein;
AD) optionally substituted heteroaryl as defined in F27 herein;

wherein $R^{15'}$ is independently selected from the group consisting of:
AE) hydrogen;
AF) hydroxyl;
AG) alkyl as defined in A herein;

AH) substituted alkyl as defined in F herein;
AI) optionally substituted aryl as defined in F25 herein;
AJ) optionally substituted heterocyclic as defined in F29 herein;
AK) optionally substituted heteroaryl as defined in F27 herein;
and the moiety:

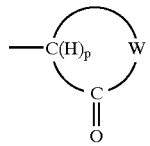

is selected from the group having the formulas:

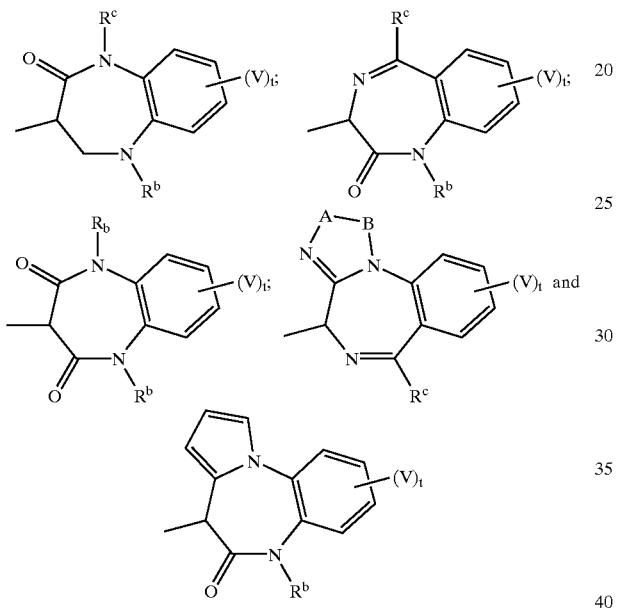

wherein A—B is selected from the group consisting of alkylene, alkenylene, substituted alkylene, substituted alkenylene, and —N=CH—; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, substituted amino, aminoacyl, optionally substituted alkaryl, optionally substituted aryl, optionally substituted aryloxy, carboxyl, carboxyalkyl, cyano, halo, nitro, optionally substituted heteroaryl, thioalkoxy, substituted thioalkoxy, and trihalomethyl; $R^b$ is selected from the group consisting of alkyl, substituted alkyl, alkenyl, substituted alkenyl, alkynyl, substituted alkynyl, acyl, optionally substituted aryl, optionally substituted heteroaryl, and optionally substituted heterocyclic; $R^c$ is selected from the group consisting of alkyl, substituted alkyl, alkenyl, substituted alkenyl, optionally substituted aryl, optionally substituted heteroaryl, optionally substituted heterocyclic, cycloalkyl, and substituted cycloalkyl; and t is an integer from 0 to 4;
or pharmaceutically salts thereof;
with the following provisos:
when $R^1$ is trans-cinnamyl, $R^2$ is methyl, and $R^{15}$ is hydrogen, then W, together with >CH and >C=O, does not form a 2,3-dihydro-1-(3,3-dimethyl-2-oxobutyl)-5-(2-pyridyl)-1H-1,4-benzodiazepin-2-one when $R^1$ is trans-cinnamyl, $R^2$ is methyl, and $R^{15}$ is hydrogen, then W, together with >CH and >C=O, does not form a 2,3dihydro-1-(2-N,N-diethylaminoethyl)-5-(2-pyridyl)-1H-1,4-benzodiazepin-2-one and when $R^1$—N($R^{15'}$)C(Q) is (2,5-dimethoxyphenyl)aminocarbonyl and $R^2$ is methyl, then W, together with >CH and >C=O, does not form a 2,3-dihydro-1-methyl-5-phenyl-1H-1,4-benzodiazepin-2-one.

48. The method according to claims 45, 46, 47, wherein the moiety:

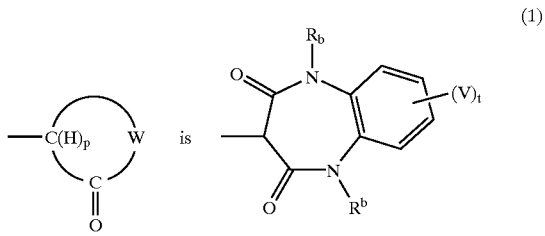

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and
t is an integer from 0 to 4;
$R_b$ is selected from the group comprising hydrogen, alkyl, substituted alkyl, alkenyl, substituted alkenyl, aryl, heteroaryl, heterocyclic cycloalkyl, and substituted cycloalkyl;
or pharmaceutically acceptable salts thereof.

49. The method according to claims 45, 46 or 47, wherein the moiety:

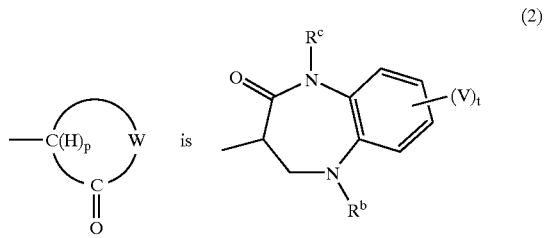

wherein $R^b$ is selected from the group consisting of alkyl, substituted alkyl as defined in F, alkenyl, substituted alkenyl as defined in G, alkynyl, acyl, optionally substituted aryl as defined in F25, optionally substituted heteroaryl as defined in F27, and optionally substituted heterocyclic as defined in F29;

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

or pharmaceutically acceptable salts thereof.

50. The method according to claims 45, 46 or 47, wherein the moiety:

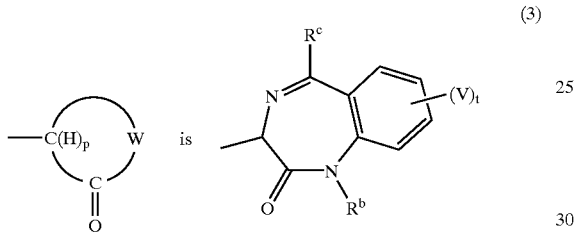

(3)

wherein $R^b$ is selected from the group consisting of alkyl, substituted alkyl as defined in F, alkenyl, substituted alkenyl as defined in G, alkynyl, acyl, optionally substituted aryl as defined in F25, optionally substituted heteroaryl as defined in F27, and optionally substituted heterocyclic as defined in F29;

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F12, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

51. The method according to claims 45, 46 or 47, wherein the moiety:

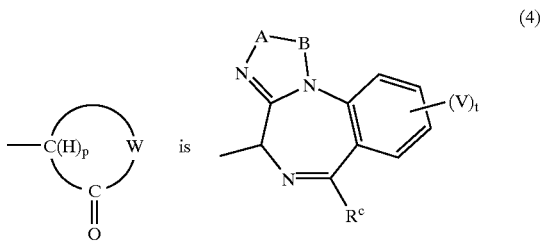

(4)

wherein A—B is selected from the group consisting of alkylene, alkenylene, substituted alkylene, substituted alkenylene and —N=CH—;

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

52. The method according to claims 45, 46 or 47, wherein the moiety:

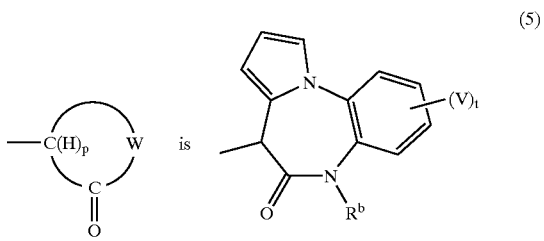

(5)

$R^c$ is selected from the group consisting of alkyl as defined in A, substituted alkyl as defined in F, alkenyl, substituted alkenyl as defined in G, optionally substituted aryl as defined in F25, optionally substituted heteroaryl as defined in F27, optionally substituted heterocyclic as defined in F29, cycloalkyl, and substituted cycloalkyl as defined in I;

each V is independently selected from the group consisting of hydroxy, acyl as defined in F7, acyloxy as defined in F9, alkyl as defined in A, substituted alkyl as defined in F, alkoxy as defined in F1, substituted alkoxy as defined in F2, alkenyl as defined in B, substituted alkenyl as defined in G, alkynyl as defined in C, substituted alkynyl as defined in H, amino, substituted amino as defined in F11, aminoacyl as defined in F12, optionally substituted alkaryl as defined in F25, optionally substituted aryl as defined in F25, optionally substituted aryloxy as defined in F26, carboxyl, carboxyalkyl, cyano, halo, nitro, optionally substituted heteroaryl as defined in F27, thioalkoxy, substituted thioalkoxy as defined in F24, and trihalomethyl; and t is an integer from 0 to 4;

w is an integer from 0 to 3;

or pharmaceutically acceptable salts thereof.

53. The method according to claims 45, 46 or 47, wherein $R^1$ is optionally substituted aryl or optionally substituted heteroaryl.

54. The method according to claims 45, 46 or 47, wherein $R^1$ is selected from the group consisting of:

(a) alkyl;

(b) phenyl;

(c) a substituted phenyl group of the formula:

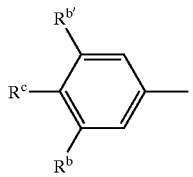

wherein $R^c$ is selected from the group consisting of acyl, alkyl, alkoxy, alkylalkoxy, azido, cyano, substituted amino, halo, hydrogen, nitro, trihalomethyl, thioalkoxy, and wherein $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur, $R^b$ and $R^{b'}$ are independently selected from the group consisting of hydrogen, halo, nitro, cyano, trihalomethyl, alkoxy, and thioalkoxy with the proviso that when $R^c$ is hydrogen, the $R^b$ and $R^{b'}$ are either both hydrogen or both substituents other than hydrogen, (d) 2-naphthyl, (e) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl, (f) heteroaryl, and (g) substituted heteroaryl containing 1 to 3 substituents selected from the group consisting of alkyl, alkoxy, aryl, aryloxy, cyano, halo, nitro, heteroaryl, thioalkoxy, thioaryloxy provided that said substituents are not othro to the heteroaryl attachment to the —NH group.

55. The method according to claims 45, 46 or 47, wherein $R^1$ is selected from the group consisting of mono-, di-, and tri-substituted phenyl groups.

56. The method according to claim 55, wherein $R^1$ is a monosubstituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)-phenyl, and 4-(1-ethoxy) ethylphenyl.

57. The method according to claim 55, wherein $R^1$ is a disubstituted phenyl selected from the group consisting of 3,5-dichlorophenyl, 3,5-difluorophenyl, 3,5-di (trifluoromethyl)-phenyl, 3,4-dichlorophenyl, 3,4-difluorophenyl, 3-(trifluoromethyl)-4-chlorophenyl, 3-chloro4-cyanophenyl, 3-chloro-4-iodophenyl, and 3,4-methylenedioxyphenyl.

58. The method according to claim 55, wherein $R^1$ is a trisubstituted phenyl selected from the group consisting of 3,4,5-trifluorophenyl and 3,4,5-tricholorophenyl.

59. The method according to claim 58, wherein $R^1$ is selected from the group consisting of 2-naphthyl, quinolin-3-yl, 2-methylquinolin-6-yl, benzothiazol-6-yl, 5-indolyl and phenyl.

60. The method according to claim 45, 46 or 47, wherein $R^1$ is selected from the group consisting of: phenyl, 1-naphthyl, 2-naphthyl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl) phenyl, 3,5-dimethoxyphenyl, 2,4-dichlorophenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2-fluoro-6-chlorophenyl, 2,3,4,5,6-pentafluorophenyl, 2,5-dimethylphenyl, 4-phenylphenyl, 2-fluoro-3-trifluoromethylphenyl, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyrid-2-yl, pyrid-3-yl, pyrid-4-yl, fluoropyridyls, chloropyridyls, thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetrazol-5-yl, allyl, 2-(cyclohexyl) ethyl, (CH$_3$)$_2$CH=CHCH$_2$CH$_2$CH(CH$_3$)—, C(O)CH$_2$—, thien-2-yl-methyl, 2-(thien-2-yl)ethyl, 3-(thien-2-yl)-n-propyl, 2-(4-nitrophenyl)ethyl, 2-(4-methoxyphenyl)ethyl, norboran-2-yl, (4-methoxyphenyl)methyl, (2-methoxyphenyl)methyl, (3-methoxyphenyl)methyl, (3-hydroxyphenyl)methyl, (4-hydroxyphenyl)methyl, (4-methoxyphenyl)methyl, (4-methylphenyl)methyl, (4-fluorophenyl)methyl, (4-fluorophenoxy)methyl, (2,4-dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH$_3$OC(O)CH$_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH$_3$CH=CH—, CH$_3$CH$_2$CH=CH—, (4-chlorophenyl)C(O)CH$_2$—, (4-fluorophenyl)C(O)CH$_2$—, (4-methoxyphenyl)C(O)CH$_2$—, 4-(fluorophenyl)—NHC(O)CH$_2$—, 1-phenyl-n-butyl, (phenyl)$_2$CHNHC(O)CH$_2$CH$_2$—, (CH$_3$)$_2$NC(O)CH$_2$—, (phenyl)$_2$CHNHC(O)CH$_2$CH$_2$—, ethylcarbonylmethyl, (2,4-dimethylphenyl)C(O)CH$_2$—, 4-methoxyphenyl-C(O)CH$_2$—, phenyl-C(O)CH$_2$—, CH$_3$C(O)N(phenyl)-, ethenyl, methylthiomethyl, (CH$_3$)$_3$CNHC(O)CH$_2$—, 4-fluorophenyl-C(O)CH$_2$—, diphenylmethyl, phenoxymethyl, 3,4-methylenedioxyphenyl-CH$_2$—, benzo[b]thiophen-3-yl, (CH$_3$)$_3$COC(O)NHCH$_2$—, trans-styryl, H$_2$NC(O)CH$_2$CH$_2$—, 2-trifluoromethylphenyl-C(O)CH$_2$, phenyl-C(O)NHCH(phenyl)CH$_2$—, mesityl, CH$_3$CH(=NHOH)CH$_2$—, 4—CH$_3$-phenyl-NHC(O)CH$_2$CH$_2$—, C(O)CH(phenyl)CH$_2$—, (CH$_3$)$_2$CHC(O)NHCH(phenyl)-, CH$_3$CH$_2$OCH$_2$—, CH$_3$OC(O)CH(CH$_3$)(CH$_2$)$_3$—, 2,2,2-trifluoroethyl, 1-(trifluoromethyl)ethyl, 2—CH$_3$-benzofuran-3-yl, 2-(2,4-dichlorophenoxy)ethyl, SO$_2$CH$_2$—, 3-cyclohexyl-n-propyl, CF$_3$CH$_2$CH$_2$CH$_2$— and N-pyrrolidinyl.

61. The method according to claim 45, 46 or 47, wherein R$^2$ is selected from the group consisting of alkyl, substituted alkyl, alkenyl, cycloalkyl, optionally substituted aryl, optionally substituted heteroaryl and optionally substituted heterocyclic.

62. The method according to claim 45, 46 or 47, wherein R$^2$ is selected from the group consisting of: methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH—Boc, —(CH$_2$)$_4$NH$_2$, —CH$_2$-pyridyl, pyridyl, —CH$_2$-naphthyl, —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl, and thien-3-yl.

63. A compound selected from the group consisting of:

(S)-3-[(N'-(trans-2-phenylcyclopropyl)aminocarbonyl)-L-alaninyl]amino-2,3-dihydro-1-methyl-5-phenyl-1H-1,4-benzodiazepin-2-one (S)-3-[(N'-3,4-dichlorophenyl)aminocarbonyl)-L-alaninyl)amino-2,3-dihydro-1-methyl-5-phenyl-H-1,4-benzodaizepin-2-one (S)-3-[(N'-((2-propenyl)aminocarbonyl)-L-alaninyl)]amino-2,3-dihydro-1-methyl-5-phenyl-1H-1,4-benzodiazepin-2-one (S)-3-[(N'-((R)-(–)-1-(1-naphthyl)ethyl)aminocarbonyl)-L-alaninyl)]amino-2,3-dihydro-1-methyl-5-phenyl-1H-1,4-benzodiazepin-2-one (S)-3[(N'-((2,6-diisopropylphenyl)aminocarbonyl)-L-alaninyl)]amino-2,3-dihydro-1-methyl-5-phenyl-1H-1,4-benzodiazepin-2-one (S)-3-[(N'-((3-[(trifluoromethyl)phenyl)aminocarbonyl)-L-alaninyl)]amino-2,3-dihydro-1-methyl-5-phenyl-1H-1,4-benzodiazepin-2-one (S)-3-[(N'-((phenyl)aminocarbonyl)-L-alaninyl)]amino-2,3 dihydro-1-methyl-5-phenyl-1H-1,4-benzodiazepin-2-one (S)-3-[(N'-((4-ethoxycarbonylphenyl)aminocarbonyl)-L-alaninyl)]amino-2,3-dihydro-1-methyl-5-phenyl-1H-1,4-benzodiazepin-2-one (S)-3-[(N'-((2-bromophenyl)aminocarbonyl)-L-alaninyl)]amino-2,3-dihydro-1-methyl-5-phenyl-1H-1,4-benzodiazepin-one (S)-3-[(N'-((o-tolyl)aminocarbonyl)-L-alaninyl)]amino-2,3-dihydro-1-methyl-5-phenyl-1H-1,4-benzodiazepin-2-one (S)-3-[(N'-((ethyl-6-methylphenyl)aminocarbonyl)-L-alaninyl)]amino-2,3-dihydro-1-methyl-5-phenyl-1H-1,4-benzodiazepin-2-one (S)-3-[(N'-((fluorophenyl)aminocarbonyl)-L-alaninyl)]amino-2,3-dihydro-1-methyl-5-phenyl-1H-1,4-benzodiazepin-2-one (S)-3-[(N'-((2,4-difluorophenyl)aminocarbonyl)-L-alaninyl)]amino-2,3-dihydro-1-methyl-5-phenyl-1H-1,4-benzodiazepin-2-one (S)-3-[(N'-((2-ethoxyphenyl)aminocarbonyl)-L-alaninyl)]amino-2,3-dihydro-1-methyl-5-phenyl-1H-1,4-benzodiazepin-2-one (S)-3-[(N'-((3-acetylphenyl)aminocarbonyl)-L-alaninyl)]amino-2,3-dihydro-1-methyl-5-phenyl-1H-1,4-benzodiazepin-2-one (S)-3-[N'-((3-[(cyano)phenyl)aminocarbonyl)-L-alaninyl)]amino-2,3-dihydro-1-methyl-5-phenyl-1H-1,4-benzodiazepin-2-one (S)-3-[(N'-((phenethyl)aminocarbonyl)-L-alaninyl)]amino-2,3-dihydro-1-methyl-5-phenyl-1H-1,4-benzodiazepin-2-one (S)-3-[(N'-((4-n-butylphenyl)aminocarbonyl)-L-alaninyl)]amino-2,3-dihydro-1-methyl-5-phenyl-1H-1,4-benzodiazepin-2-one (S)-3-[(N'-((octyl)aminocarbonyl)-L-alaninyl)]amino-2,3 dihydro-1-methyl-5-phenyl-1H-1,4-benzodiazepin-2-one (S)-3-[(N'-((4-biphenyl)aminocarbonyl)-L-alaninyl)]amino2,3-hydro-1-methyl-5-phenyl-1H-1,4-benzodiazepin-2-one (S)-3-[(N'-((4-isopropylphenyl)aminocarbonyl)-L-alaninyl)]amino-2,3-dihydro-1-methyl-5-phenyl-1H-1,4-1,4-benzodiazepin-2-one (S)-3-[(N'-((hexyl)aminocarbonyl)-L-alaninyl)]amino-2,3-dihydro-1-methyl-5-phenyl-1H-1,4-benzodiazepin-2-one (S)-3-[(N'-((2-isopropylphenyl)aminocarbonyl)-L-alaninyl)amino-2,3-dihydro-1-methyl-5-phenyl-1H-1-,4-benzodiazepin-2-one (S)-3-[(N'-((2,6-difluorophenyl)aminocarbonyl)-L-alaninyl)]amino-2,3-dihydro-1-methyl-5-phenyl-1H1,4-1,4-benzodiazepin-2-one (S)-3-[(N'-((octadecyl)aminocarbonyl-L-alaninyl)] amino-2,3-dihydro-1-methyl-5-phenyl-1H-1,1,4-benzodiazepin-2-one (S)-3-[(N'-((4-(trifluoromethoxy)phenyl)aminocarbonyl)-L-alaninyl)]amino-2,3-dihydro-1-methyl-5-phenyl-1H-1,4-1,4-benzodiazepin-2-one (S)-3-[(N'-((2,4-dichlorophenyl)aminocarbonyl)-L-alaninyl)]amino-2,3-dihydro-1-methyl-5-phenyl-1H-1,4-benzodiazepin-2-one (S)-3-[(N'-((ethoxycarbonylphenyl)aminocarbonyl)-L-alaninyl)]amino-2,3-dihydro-1-methyl-5-phenyl-1H-1,4-benzodiazepin-2-one (S)-3-[(N'-((4-chlorophenyl)aminocarbonyl)-L-alaninyl)] amino-2,3-dihydro-1-methyl-5-phenyl-1H-4,4-benzodiazepin-2-one (S)-3-[(N'-((4-butoxyphenyl)aminocarbonyl)-L-alaninyl)]amino-2,3-dihydro-1-methyl-phenyl-1H-1,4-benzodiazepin-2-one (S)-3-[(N'-((4-phenoxyphenyl)aminocarbonyl)-L-alaninyl)]amino-2,3-dihydro-1-methyl-5-phenyl-1H-1,4-benzodiazepin-2-one (S)-3-[(N'-((1-naphthyl)aminocarbonyl)-L-alaninyl)] amino 2,3-dihydro-1-methyl-5-phenyl-1H-1,4-benzodiazepin-2-one (S)-3-[(N'-((2-biphenyl)aminocarbonyl)-L-alaninyl)] amino-2,3-dihydro-1-methyl-5-phenyl-1H11,4-benzodiazepin-2-one (S)-3-[(N'-((2-(methylthio)phenyl)aminocarbonyl)-L-alaninyl)]amino-2,3-dihydro-1-methyl-5-phenyl-1H-1,4-benzodiazepin-2-one (S)-3-[(N'-((2-ethyphenyl)aminocarbonyl)-L-alaninyl)] amino-2,3-dihydro-1-methyl-5-phenyl-1H-1,4-benzodiazepin-2-one (S)-3-[(N'-((2-(methoxyphenyl)aminocarbonyl)-L-alaninyl)]amino-2,3-dihydro-1-methyl-5-phenyl-1H-1,4-benzodiazepin-2-one (S)-3-[(N'-((2-(trimethoxyphenyl)aminocarbonyl)-L-alaninyl)]amino-2,3-dihydro-1-methyl-5-phenyl-1H-1,4-benzodiazepin-2-one (S)-3-[(N'-((2-(trimethoxyphenyl)aminocarbonyl)-L-alaninyl)]amino-2,3-dihydro-1-methyl-5-phenyl-1H-1,4-benzodiazepin-2-one (S)-3-[(N'-((2-methyl-6-t-butylphenyl)aminocarbonyl)-L-alaninyl)]amino-2,3-dihydro-1-methyl-5-phenyl-1H-1,4-benzodiazepin-2-one (S)-3-[(N'-((2-(thiophenyl)ethyl)aminocarbonyl)-L-alaninyl)]amino-2,3-dihydro-1-methyl-5-phenyl-1H-1,4-benzodiazepin-2-one and 3-[(N'-3,5-difluorophenyl-acetamido)-L-alaninyl]amino-2,3-dihydro-1-methyl-5-phenyl-1H-1,4-benzodiazepin-2-one.

64. A pharmaceutical composition comprising a pharmaceutically inert carrier and a pharmaceutically effective amount of a compound selected from the group consisting of:

(S)-3-[(N'-(trans-2-phenylcyclopropyl)aminocarbonyl)-L alaninyl)]amino-2,3-dihydro-1-methyl-5-phenyl-1H-1,4-benzodiazepin-2-one (S)-3-[(N'-3,4-dichlorophenyl)aminocarbonyl)-L alaninyl)amino-2,3-dihydro-1-methyl-5-phenyl-H-1,4-benzodaizepin-2-one (S)-3-[(N'-((2-propenyl)aminocarbonyl)-L-alaninyl)] amino-2,3-dihydro-1-methyl-5-phenyl-1H-1,4-benzodiazepin-2-one (S)-3-[(N'-((R)-(−)-1-(1-naphthyl)ethyl)aminocarbonyl)-L-alaninyl)]amino-2,3-dihydro-1-methyl-5-phenyl-1H-1,4-benzodiazepin-2-one (S)-3[(N'-((2,6-diisopropylphenyl)aminocarbonyl)-L-alaninyl)]amino-2,3-dihydro-1-methyl-5-phenyl-1H-1,4-benzodiazepin-2-one (S)-3-[(N'-((3-[(trifluoromethyl)phenyl)aminocarbonyl)-L-alaninyl)]amino-2,3-dihydro-1-methyl-5-phenyl-1H-1,4-benzodiazepin-2-one (S)-3-[(N'-((phenyl)aminocarbonyl)-L-alaninyl)]amino-2,3-dihydro-1-methyl-5-phenyl-1H-1,4-benzodiazepin-2-one (S)-3-[(N'-((4-ethoxycarbonylphenyl)aminocarbonyl)-L-alaninyl)]amino-2,3-dihydro-1-methyl-5-phenyl-1H-1,4-benzodiazepin-2-one (S)-3-[(N'-((2-bromophenyl)aminocarbonyl)-L-alaninyl)] amino-2,3-dihydro-1-methyl-5-phenyl-1H-1,4-benzodiazepin-one (S)-3-[(N'-((o-tolyl)aminocarbonyl)-L-alaninyl)]amino-2,3-dihydro-1-methyl-5-phenyl-1H-1,4-benzodiazepin-2-one (S)-3-[(N'-((ethyl-6-methylphenyl)aminocarbonyl)-L-alaninyl)]amino-2,3-dihydro-1-methyl-5-phenyl-1H-1,4-benzodiazepin-2-one (S)-3-[(N'-((fluorophenyl)aminocarbonyl)-L-alaninyl)] amino-2,3-dihydro-1-methyl-5-phenyl-1H-1,4-benzodiazepin-2-one (S)-3-[(N'-((2,4-difluorophenyl)aminocarbonyl)-L-alaninyl)]amino-2,3-dihydro-1-methyl-5-phenyl-1H-1,4-benzodiazepin-2-one (S)-3-[(N'-((2-ethoxyphenyl)aminocarbonyl)-L-alaninyl)]amino-2,3-dihydro-1-methyl-5-phenyl-1H-1,4-benzodiazepin-2-one (S)-3-[(N'-((3-acetylphenyl)aminocarbonyl)-L-alaninyl)] amino-2,3-dihydro-1-methyl-5-phenyl-1H-1,4-benzodiazepin-2-one (S)-3-[N'-((3-[(cyano)phenyl)aminocarbonyl)-L-alaninyl)]amino-2,3-dihydro-1-methyl-5-phenyl-1H-1,4-benzodiazepin-2-one (S)-3-[(N'-((phenethyl)aminocarbonyl)-L-alaninyl)] amino-2,3-dihydro-1-methyl-5-phenyl-1H-1,4-benzodiazepin-2-one (S)-3-[(N'-((4-n-butylphenyl)aminocarbonyl)-L-alaninyl)]amino-2,3-dihydro-1-methyl-5-phenyl-1H-1,4-benzodiazepin-2-one (S)-3-[(N'-((octyl)aminocarbonyl)-L-alaninyl)]amino-2,3 dihydro-1-methyl-5-1H-1,4-benzodiazepin-2-one (S)-3-[(N'-((4-biphenyl)aminocarbonyl)-L-alaninyl)] amino-2,3-hydro-1-methyl-5-phenyl-1H-1,4-benzodiazepin-2-one (S)-3-[(N'-((4-isopropylphenyl)aminocarbonyl)-L-alaninyl)]amino-2,3-dihydro-1-methyl-5-phenyl-1H-1,4-1,4-benzodiazepin-2-one (S)-3-[(N'-((hexyl)aminocarbonyl)-L-alaninyl)]amino-2,3-dihydro-1-methyl-5-phenyl-1H-1,4-benzodiazepin-2-one (S)-3-[(N'-((2-isopropylphenyl)aminocarbonyl)-L-alaninyl)amino-2,3-dihydro-1-methyl-5-phenyl-1H-1-,4-benzodiazepin-2-one (S)-3-[(N'-((2,6-difluorophenyl)aminocarbonyl)-L-alaninyl)]amino-2,3-dihydro-1-methyl-5-phenyl-1H1,4-1,4-benzodiazepin-2-one (S)-3-[(N'-((octadecyl)aminocarbonyl-L-alaninyl)]amino 2,3-dihydro-1-methyl-5-phenyl-1H-1,1,4-benzodiazepin-2-one (S)-3-[(N'-((4-(trifluoromethoxy)phenyl)aminocarbonyl)-L-alaninyl)]amino-2,3-dihydro-1-methyl-5-phenyl-1H-1,4-1,4-benzodiazepin-2-one (S)-3-[(N'-((2,4-dichlorophenyl)aminocarbonyl)-L-alaninyl)]amino-2,3-dihydro-1-methyl-5-phenyl-1H-1,4-benzodiazepin-2-one (S)-3-[(N'-((ethoxycarbonylphenyl)aminocarbonyl)-L-alaninyl)]amino-2,3-dihydro-1-methyl-5-phenyl-1H-1,4-benzodiazepin-2-one (S)-3-[(N'-((4-chlorophenyl)aminocarbonyl)-L-alaninyl)]amino-2,3-dihydro-1-methyl-5-phenyl-1H-4,4-benzodiazepin-2-one (S)-3-[(N'-((4-butoxyphenyl)aminocarbonyl)-L-alaninyl)]amino-2,3-dihydro-1-methyl-phenyl-1H-1,4-benzodiazepin-2-one (S)-3-[(N'-((4-phenoxyphenyl)aminocarbonyl)-L-alaninyl)]amino-2,3-dihydro-1-methyl-5-phenyl-1H-1,4-benzodiazepin-2-one (S)-3-[(N'-((1-naphthyl)aminocarbonyl)-L-alaninyl)]amino-2,3-dihydro-1-methyl-5-phenyl-1H-1,4-benzodiazepin-2-one (S)-3-[(N'-((2-biphenyl)aminocarbonyl)-L-alaninyl)]amino-2,3-dihydro-1-methyl-5-phenyl-1H11,4-benzodiazepin-2-one (S)-3-[(N'-((2-(methylthio)phenyl)aminocarbonyl)-L-alaninyl)]amino-2,3-dihydro-1-methyl-5-phenyl-1H-1,4-benzodiazepin-2-one (S)-3-[(N'-((2-ethyphenyl)aminocarbonyl)-L-alaninyl)]amino-2,3-dihydro-1-methyl-5-phenyl-1H-1,4-benzodiazepin-2-one (S)-3-[(N'-((2-(methoxyphenyl)aminocarbonyl)-L-alaninyl)]amino-2,3-dihydro-1-methyl-5-phenyl-1H-1,4-benzodiazepin-2-one (S)-3-[(N'-((2-(trimethoxyphenyl)aminocarbonyl)-L-alaninyl)]amino-2,3-dihydro-1-methyl-5-phenyl-1H-1,4-benzodiazepin-2-one (S)-3-[(N'-((2-(trimethoxyphenyl)aminocarbonyl)-L-alaninyl)]amino-2,3-dihydro-1-methyl-5-phenyl-1H-1,4-benzodiazepin-2-one (S)-3-[(N'-((2-methyl-6-t-butylphenyl)aminocarbonyl)-L-alaninyl)]amino-2,3-dihydro-1-methyl-5-phenyl-1H-1,4-benzodiazepin-2-one (S)-3-[(N'-((2-(thiophenyl)ethyl)aminocarbonyl)-L-alaninyl)]amino-2,3-dihydro-1-methyl-5-phenyl-1H-1,4-benzodiazepin-2-one and 3-[(N'-3,5-difluorophenyl-acetamido)-L-alaninyl]amino-2,3-dihydro-1-methyl-5-phenyl-1H-1,4-benzodiazepin-2-one.

65. A method for inhibiting β-amyloid peptide release and/or its synthesis in a cell, which method comprises administering to such a cell an amount of a compound according to claim 63, or a mixture of compounds effective for inhibiting the cellular release and/or synthesis of β-amyloid peptide.

66. A method for inhibiting β-amyloid peptide release and/or its synthesis in a mammalian subject thereby inhibiting onset of diseases mediated by β-amyloid peptide which method comprises administering to said patient a pharmaceutical composition according to claim 64 in an amount effective for inhibiting the release and/or synthesis of β-amyloid peptide.

67. A method for treating a human patient with AD in order to inhibit further deterioration in the condition of that patient, which method comprises administering to said patient a pharmaceutical composition according to claim 64 in an amount effective for inhibiting further deterioration in the condition of said patient.

68. The compound according to claim 29, wherein each $R^{15}$ is H.

69. The compound according to claim 42, wherein each $R^2$ is independently selected from the group consisting of alkyl, susbstituted alkyl, alkenyl, cycloalkyl, optionally substituted aryl, optionally substituted heteroaryl and optionally substituted heterocyclic.

70. The compound according to claim 69, wherein each $R^2$ is independently selected from the group consisting of methyl, ethyl, n-propyl, iso-propyl, n-butyl, iso-butyl, sec-butyl, tert-butyl, —$CH_2CH(CH_2CH_3)_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —$CH_2$-cyclopropyl, —$CH_2$-cyclohexyl, —$CH_2CH_2$-cyclopropyl, —$CH_2CH_2$-cyclohexyl, —$CH_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-$(CH_3)_2NCH_2CH_2CH_2O$-benzyl, p-$(CH_3)_3COC(O)CH_2O$-benzyl, p-$(HOOCCH_2O)$-benzyl, 2-aminopyrid-6-yl, p-(N-morpholino-$CH_2CH_2O$)-benzyl, —$CH_2CH_2C(O)NH_2$, —$CH_2$-imidazol-4-yl, —$CH_2$-(3-tetrahydrofuranyl), —$CH_2$-thiophen-2-yl, —$CH_2$(1-methyl)cyclopropyl, —$CH_2$-thiophen-3-yl, thiophen-3-yl, thiophen-2-yl, —$CH_2$—C(O)O-t-butyl, —$CH_2$—C$(CH_3)_3$, —$CH_2CH(CH_2CH_3)_2$, 2-methylcyclopentyl, cyclohex-2-enyl, —CH[CH$(CH_3)_2$]COOCH$_3$, —$CH_2CH_2N$$(CH_3)_2$, —$CH_2C(CH_3)$=$CH_2$, —$CH_2CH$=$CHCH_3$ (cis and trans), —$CH_2OH$, —$CH(OH)CH_3$, —CH(O-t-butyl)CH$_3$, —$CH_2OCH_3$, —$(CH_2)_4NH$—Boc, —$(CH_2)_4NH_2$, —$CH_2$-pyridyl, pyridyl, —$CH_2$-naphthyl, —$CH_2$—(N-morpholino), p-(N-morpholino-$CH_2CH_2O$)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —$CH_2CH_2SCH_3$, thien-2-yl, and thien-3-yl.

71. The compound according to claim 70, wherein $R^b$ is selected from the group consisting of alkyl, substituted alkyl, cycloalkyl and aryl.

72. The compound according to claim 71, wherein $R^2$ is methyl.

73. The compound according to claim 72, wherein $R^1$ is alkyl.

74. The compound according to claim 73, wherein $R^b$ is alkyl.

75. The compound according to claim 36, wherein $R^1$ is selected from the group consisting of methyl, ethyl, n-propyl, iso-propyl, iso-butyl, sec-butyl, n-butyl and n-pentyl.

76. The pharmaceutical composition according to claim 14, wherein $R^1$ is optionally substituted aryl or optionally substituted heteroaryl.

\* \* \* \* \*